(12) United States Patent
Lisziewicz et al.

(10) Patent No.: US 11,666,644 B2
(45) Date of Patent: Jun. 6, 2023

(54) PEPTIDE VACCINES

(71) Applicant: TREOS BIO LIMITED, London (GB)

(72) Inventors: Julianna Lisziewicz, Balatonalmádi (HU); Levente Molnar, Felsopakony (HU); Eniko Toke, Felsopakony (HU); József Toth, Gyor (HU); Orsolya Lorincz, Budapest (HU); Zsolt Csiszovszki, Budapest (HU); Eszter Somogyi, Balatonalmádi (HU); Katalin Pantya, Budapest (HU); Mónika Megyesi, Mezokeresztes (HU)

(73) Assignee: Treos Bio Limited, London (GB)

( * ) Notice: Subject to any disclaimer, the term of this patent is extended or adjusted under 35 U.S.C. 154(b) by 275 days.

(21) Appl. No.: 17/250,725

(22) PCT Filed: Sep. 3, 2019

(86) PCT No.: PCT/EP2019/073476
§ 371 (c)(1),
(2) Date: Feb. 24, 2021

(87) PCT Pub. No.: WO2020/048990
PCT Pub. Date: Mar. 12, 2020

(65) Prior Publication Data
US 2023/0102031 A1    Mar. 30, 2023

(30) Foreign Application Priority Data

Sep. 4, 2018  (GB) ..................... 1814364
Sep. 4, 2018  (GB) ..................... 1814365
Sep. 4, 2018  (GB) ..................... 1814366
Sep. 4, 2018  (GB) ..................... 1814367

(51) Int. Cl.
*A61K 39/00* (2006.01)
*A61P 35/00* (2006.01)
*A61P 1/00* (2006.01)
*A61K 45/06* (2006.01)

(52) U.S. Cl.
CPC .... *A61K 39/0011* (2013.01); *A61K 39/00115* (2018.08); *A61K 39/001184* (2018.08); *A61K 39/001186* (2018.08); *A61K 39/001189* (2018.08); *A61K 45/06* (2013.01); *A61P 1/00* (2018.01); *A61P 35/00* (2018.01); *A61K 2039/545* (2013.01); *A61K 2039/70* (2013.01); *A61K 2039/828* (2018.08)

(58) Field of Classification Search
CPC .......... A61K 39/00115; A61K 39/001184–89; A61K 39/0011–001198; A61K 2039/828
See application file for complete search history.

(56) References Cited

U.S. PATENT DOCUMENTS

| | | |
|---|---|---|
| 4,235,877 A | 11/1980 | Fullerton |
| 6,346,389 B1 | 2/2002 | Altieri |
| 7,227,002 B1 | 6/2007 | Kufer et al. |
| 7,619,058 B2 | 11/2009 | Kuzushima |
| 7,632,925 B2 | 12/2009 | Kufer et al. |
| 7,820,786 B2 | 10/2010 | Thomson et al. |
| 7,842,294 B2 | 11/2010 | Andersen et al. |
| 7,846,651 B2 | 12/2010 | Kuzushima |
| 7,892,559 B2 | 2/2011 | Straten et al. |
| 7,993,638 B2 | 8/2011 | Cai et al. |
| 8,124,408 B2 | 2/2012 | Cai et al. |
| 8,129,184 B2 | 3/2012 | Yu |
| 8,268,964 B2 | 9/2012 | Scholler et al. |
| 8,309,096 B2 * | 11/2012 | Blais ............ A61K 39/001188 424/277.1 |
| 8,318,174 B2 | 11/2012 | Straten et al. |
| 8,487,076 B1 | 7/2013 | Miyakawa et al. |
| 8,647,629 B2 | 2/2014 | Rammensee et al. |
| 8,956,878 B2 | 2/2015 | Griffiths et al. |
| 9,353,151 B2 | 5/2016 | Miyakawa et al. |
| 9,498,512 B2 | 11/2016 | Rammensee et al. |
| 9,687,539 B2 | 6/2017 | Wang et al. |
| 9,790,562 B2 | 10/2017 | Al-Hendy et al. |
| 10,172,925 B2 | 1/2019 | Nishimura |
| 10,213,497 B2 | 2/2019 | Lisziewicz et al. |
| 10,336,808 B2 | 7/2019 | Scholler et al. |
| 10,434,136 B2 | 10/2019 | Rammensee et al. |

(Continued)

FOREIGN PATENT DOCUMENTS

| CN | 1824678 A | 8/2006 |
|---|---|---|
| CN | 110713546 A | 1/2020 |

(Continued)

OTHER PUBLICATIONS

Shabestarian et al., Asian Pac J Cancer Prev 16(18):8461-65 (Year: 2015).*
Cao et al., BMC Cancer 18:94; DOI 10.1186/s12885-018-4000-y (Year: 2018).*
Liu et al., Int J Cancer 118:1922-29 (Year: 2006).*
Chen et al., PLoS ONE 9(3): e91842. doi:10.1371/journal.pone.0091842 (Year: 2014).*
Smyth et al. Int J Cancer 119:1638-47 (Year: 2006).*
Futawatari et al., World J Gastroenterol 23(46):8200-06 (Year: 2017).*
Jung et al., Anticancer Res 25:2105-12 (Year: 2005).*

(Continued)

*Primary Examiner* — Jessica H Roark
(74) *Attorney, Agent, or Firm* — Goodwin Procter LLP

(57) ABSTRACT

The disclosure relates to polypeptides and pharmaceutical compositions comprising polypeptides that find use in the prevention or treatment of cancer, in particular gastric cancer, lung cancer, melanoma and bladder cancer. The disclosure also relates to methods of inducing a cytotoxic T cell response in a subject or treating cancer by administering pharmaceutical compositions comprising the peptides, and companion diagnostic methods of identifying subjects for treatment. The peptides comprise T cell epitopes that are immunogenic in a high percentage of patients.

23 Claims, 47 Drawing Sheets

Specification includes a Sequence Listing.

(56) References Cited

U.S. PATENT DOCUMENTS

| | | |
|---|---|---|
| 10,973,909 B1 | 4/2021 | Csiszovszki et al. |
| 11,090,332 B2 | 8/2021 | Koos et al. |
| 2004/0054137 A1 | 3/2004 | Thomson et al. |
| 2004/0209324 A1 | 10/2004 | Koren et al. |
| 2005/0100883 A1 | 5/2005 | Wang et al. |
| 2006/0127408 A1 | 6/2006 | Young et al. |
| 2006/0257852 A1 | 11/2006 | Rappuoli et al. |
| 2008/0206270 A1 | 8/2008 | Minev |
| 2009/0285843 A1 | 11/2009 | Simard et al. |
| 2010/0074925 A1 | 3/2010 | Carmon |
| 2010/0099613 A1 | 4/2010 | Buyse et al. |
| 2012/0244145 A1 | 9/2012 | Sampson et al. |
| 2013/0189291 A1 | 7/2013 | Tsunoda et al. |
| 2016/0074489 A1 | 3/2016 | Ichim et al. |
| 2016/0161486 A1 | 6/2016 | Parenteau et al. |
| 2016/0199469 A1 | 7/2016 | Georges et al. |
| 2017/0032082 A1 | 2/2017 | Nguyen et al. |
| 2017/0039314 A1 | 2/2017 | Bremel et al. |
| 2017/0096455 A1 | 4/2017 | Baric et al. |
| 2018/0264094 A1 | 9/2018 | Lisziewicz et al. |
| 2018/0264095 A1 | 9/2018 | Lisziewicz et al. |
| 2019/0240302 A1 | 8/2019 | Lisziewicz et al. |
| 2020/0061173 A1* | 2/2020 | Bouzidi .................. A61P 37/04 |
| 2020/0069786 A1 | 3/2020 | Molnar et al. |
| 2020/0326340 A1 | 10/2020 | Delcommenne |
| 2021/0236611 A1 | 8/2021 | Molnar et al. |
| 2022/0031823 A1 | 2/2022 | Lisziewicz et al. |
| 2022/0072114 A1 | 3/2022 | Lisziewicz et al. |
| 2022/0111024 A1 | 4/2022 | Lisziewicz et al. |

FOREIGN PATENT DOCUMENTS

| | | |
|---|---|---|
| EP | 2042600 A1 | 4/2009 |
| EP | 3369431 A1 | 9/2018 |
| EP | 3370065 A1 | 9/2018 |
| JP | 2016521128 A | 7/2016 |
| WO | WO-9733602 A1 | 9/1997 |
| WO | WO-0018238 A1 | 4/2000 |
| WO | WO-0056365 A1 | 9/2000 |
| WO | WO-0190197 A1 | 11/2001 |
| WO | WO-2006081826 A2 | 8/2006 |
| WO | WO-2007039716 A1 | 4/2007 |
| WO | WO-2008035350 A1 | 3/2008 |
| WO | WO-2009040674 A2 | 4/2009 |
| WO | WO-2010037395 A2 | 4/2010 |
| WO | WO-2012051282 A2 | 4/2012 |
| WO | WO-2014127276 A1 | 8/2014 |
| WO | WO-2014127296 A1 | 8/2014 |
| WO | WO-2014153636 A1 | 10/2014 |
| WO | WO-2014180490 A1 | 11/2014 |
| WO | WO-2015033140 A1 | 3/2015 |
| WO | WO-2015164798 A1 | 10/2015 |
| WO | WO-2016/040900 A1 | 3/2016 |
| WO | WO-2016090177 A1 | 6/2016 |
| WO | WO-2016109880 A1 | 7/2016 |
| WO | WO-2016/170139 A1 | 10/2016 |
| WO | WO-2016172722 A1 | 10/2016 |
| WO | WO-2016176761 A1 | 11/2016 |
| WO | WO-2017011804 A1 | 1/2017 |
| WO | WO-2017083963 A1 | 5/2017 |
| WO | WO-2017162501 A1 | 9/2017 |
| WO | WO-2018067869 A1 | 4/2018 |
| WO | WO-2018102585 A1 | 6/2018 |
| WO | WO-2018138257 A1 | 8/2018 |
| WO | WO-2018158455 A1 | 9/2018 |
| WO | WO-2018158456 A1 | 9/2018 |
| WO | WO-2018158457 A1 | 9/2018 |
| WO | WO-2019010560 A1 | 1/2019 |
| WO | WO-2019090411 A | 5/2019 |
| WO | WO-2019094607 A2 | 5/2019 |
| WO | WO-2019/133853 A1 | 7/2019 |
| WO | WO-2019222760 A1 | 11/2019 |
| WO | WO-2019222762 A1 | 11/2019 |
| WO | WO-2020048990 A1 | 3/2020 |
| WO | WO-2020048992 A1 | 3/2020 |
| WO | WO-2020048995 A1 | 3/2020 |
| WO | WO-2020104923 A1 | 5/2020 |
| WO | WO-2020146431 A1 | 7/2020 |
| WO | WO-2020146434 A2 | 7/2020 |
| WO | WO-2021072535 A1 | 4/2021 |

OTHER PUBLICATIONS

Lian et al., Pathol Res Practice 213:943-48 (Year: 2017).*
Mashino et al., Br. H Cancer 85(5)713-20 (Year: 2001).*
Fujiwara et al., Int'l J Oncol 50:1655-62 (Year: 2017).*
Andersen, M.H., et al., HLA-A24 and survivin: possibilities in therapeutic vaccination against cancer, J Transl Med, 4:38, 2 pages (2006).
Antigenic peptides search results for EpCAM, 1 page, retrieved on Apr. 16, 2021 from <caped.icp.ucl.ac.be/Peptide/search>.
Bachinsky, M.M., et al., Mapping and binding analysis of peptides derived from the tumor-associated antigen survivin for eight HLA alleles, Cancer Immun, 5:6, pp. 1-9 (2005).
Ciesielski, M.J., et al., Therapeutic effect of a T helper cell supported CTL response induced by a survivin peptide vaccine against murine cerebral glioma, Cancer Immunol Immunother, 57(12): 1827-1835 (2008).
Dangi, M., et al., Advanced In Silico Tools for Designing of Antigenic Epitope as Potential Vaccine Candidates Against Coronavirus, In: Bioinformatics: Sequences, Structures, Phylogeny, Springer Nature Singapore Pte Ltd.: 329-357 (2018).
Gross, S., et al., Short Peptide Vaccine Induces CD4+ T Helper Cells in Patients with Different Solid Cancers, Cancer Immunol Res, 4(1): 18-25 (2016).
Hirohashi, Y., et al., The functioning antigens: beyond just as the immunological targets, Cancer Sci 100(5): 798-806 (2009).
Hondowitz, B.D., et al., Discovery of T cell antigens by high-throughput screening of synthetic minigene libraries, PLoS One, 7(1): e29949 (2012).
Kobayashi, J., et al., Comparative study on the immunogenicity between an HLA-A24-restricted cytotoxic T-cell epitope derived from survivin and that from its splice variant survivin-2B in oral cancer patients, J Transl Med, 7:1, pp. 1-11 (2009).
Liu, F., et al., Overexpression of Testes-Specific Protease 50 (TSP50) Predicts Poor Prognosis in Patients with Gastric Cancer, Gastroenterol Res Pract, 2014: 498246 (2014).
Lladser, A., et al., Intradermal DNA electroporation induces survivin-specific CTLs, suppresses angiogenesis and confers protection against mouse melanoma, Cancer Immunol Immunother, 59(1): 81-92 (2010).
MHC-I binding prediction results, IEDB Analysis Resource, pp. 1/1-1/3 retrieved on Apr. 22, 2021 from <tools.iedb.org/mhci/result/>.
Schmitz, M., et al., Generation of survivin-specific CD8+ T effector cells by dendritic cells pulsed with protein or selected peptides, Cancer Res, 60(17): 4845-4849 (2000).
Seliger, B., et al., Molecular mechanisms of HLA class I antigen abnormalities following viral infection and transformation, Int J Cancer, 118(1): 129-138 (2006).
Shi, R., et al., The immunogenicity of a novel cytotoxic T lymphocyte epitope from tumor antigen PL2L60 could be enhanced by 4-chlorophenylalanine substitution at position 1, Cancer Immunol Immunother, 62(11): 1723-1732 (2013).
Somogyi, E., et al., HIV vaccine to induce cytotoxic T cells recognizing conserved HIV-1/2-epitopes derived from the most frequent HLA types of the human population, Immunotherapy, 5(8): 825-828 (2013).
Tantigen search results for EpCAM T cell epitopes, 1 page, retrieved on Apr. 19, 2021 from <http://projects.met-hilab.org/tadb/cgi/searchT.pl>.
Tantigen search results for HILI/PIWIL-2, 1 page, retrieved on Apr. 16, 2021 from <http://projects.met-hilab.org/tadb/cgi/searchT.pl>.
U.S. Appl. No. 16/244,497 Office Action dated Aug. 18, 2021.
U.S. Appl. No. 17/249,362 Office Action dated Sep. 8, 2021.
U.S. Appl. No. 17/645,741 Office Action dated Mar. 2, 2022.

(56) References Cited

OTHER PUBLICATIONS

Voutsas, I.F., et al., Unraveling the role of preexisting immunity in prostate cancer patients vaccinated with a HER-2/neu hybrid peptide, J Immunother Cancer, 4:75, pp. 1-15 (2016).

Wang, Y-Q., et al., Enhancement of survivin-specific anti-tumor immunity by adenovirus prime protein-boost immunity strategy with DDA/MPL adjuvant in a murine melanoma model, Int Immunopharmacol, 17(1): 9-17 (2013).

You, L, et al., Understanding Prediction Systems for HLA-Binding Peptides and T-Cell Epitope Identification. In: Rajapakse, J.C., Schmidt, B., Volkert, G. (Eds) Pattern Recognition in Bioinformatics, 4774: 337-348 (2007).

Yuan, J., et al., Integrated NY-ESO-1 antibody and CD8+ T-cell responses correlate with clinical benefit in advanced melanoma patients treated with ipilimumab, PNAS USA, 108(40): 16723-16728 (2011).

Yuan, J., et al., Safety and immunogenicity of a human and mouse gp100 DNA vaccine in a phase I trial of patients with melanoma, Cancer Immunity, 9:5 (2009).

Zajac, P., et al., MAGE-A antigens and cancer immunotherapy, Front Immunol, 4: 18 (2017).

Zhang, H., et al., DNA and adenovirus tumor vaccine expressing truncated survivin generates specific immune responses and anti-tumor effects in a murine melanoma model, Cancer Immunol Immunother, 61(10): 1857-1867 (2012).

Zhang. X.W., A combination of epitope prediction and molecular docking allows for good identification of MHC class I restricted T-cell epitopes, Comput Biol Chem, 45: 30-35 (2013).

Zheng, L., et al., High Expression of Testes-Specific Protease 50 is Associated with Poor Prognosis in Colorectal Carcinoma, PLoS One, 6(7):e22203 (2011).

Ahmed, S.F., et al., Preliminary identification of potential vaccine targets for the COVID-19 coronavirus (SARS-CoV-2) based on SARS-CoV Immunological studies, Viruses, 12: 254 (2020).

Ali-Khan, N., et al., Overview of proteome analysis, Curr Protoc Protein Sci, Chapter 22: Unit 22.1.1-22.1.19 (2002).

Asahara, S., et al., Phase I/II clinical trial using HLA-A24-restricted peptide vaccine derived from KIF20A for patients with advanced pancreatic cancer, J Transl Med, 11: 291 (2013).

Bagarazzi, M., et al., Immunotherapy Against HPV16/18 Generates Potent $T_H1$ and Cytotoxic Cellular Immune Responses, Sci Transl Med, 4(155): 155ra138 (2012).

Batra, S.K., et al., Epidermal Growth Factor Ligand-independent, Unregulated, Cell-transforming Potential of a Naturally Occurring Human Mutant EGFRvIII Gene, Cell Growth Differ, 6:1251-1259 (1995).

Beatty, G.L., et al., Immune escape mechanisms as a guide for cancer immunotherapy, Clin Cancer Res, 21(4): 687-692 (2015).

Berger, T.G., et al., Circulation and homing of melanoma-reactive T cells to both cutaneous and visceral metastases after vaccination with monocyte-derived dendritic cells, Int J Cancer, 111: 229-237 (2004).

Bigner, S.H., et al., Characterization of the Epidermal Growth Factor Receptor in Human Glioma Cell Lines and Xenografts, Cancer Res, 50: 8017-8022 (1990).

Bioley, G., et al., HLA Class I—Associated Immunodominance Affects CTL Responsiveness to an ESO Recombinant Protein Tumor Antigen Vaccine, Clin Cancer Res, 15(1): 299-306 (2009).

Buonaguro, L., et al., Translating tumor antigens into cancer vaccines, Clin Vaccine Immunol, 18(1): 23-34 (2011).

Butts, C., et al., Randomized Phase IIB Trial of BLP25 Liposome Vaccine in Stage IIIB and IV Non-Small-Cell Lung Cancer, J Clin Oncol, 23(27): 6674-6681 (2005).

Carmon, L., et al., Phase I/II study exploring ImMucin, a pan-major histocompatibility complex, anti-MUC1 signal peptide vaccine, in multiple myeloma patients, Br J Hematol, 169(1):44-56 (2014).

Cathcart, K., et al., A multivalent bcr-abl fusion peptide vaccination trial in patients with chronic Myeloid Leukemia, Blood, 103:1037-1042 (2004).

Celis, E., et al., Identification of potential CTL epitopes of tumor-associated antigen MAGE-1 for five common HLA-A alleles, Mol Immunol, 31(18): 1423-1430 (1994).

Celis, E., et al., Induction of anti-tumor cytotoxic T lymphocytes in normal humans using primary cultures and synthetic peptide epitopes, PNAS USA, 91: 2105-2109 (1994).

Chapuis, A.G., et al., Transferred WT1-reactive CD8+ T cells can mediate antileukemic activity and persist in post-transplant patients, Sci Transl Med, 5(174): 174ra27 (2013).

Chen, Y., et al., Multiple Cancer/Testis Antigens Are Preferentially Expressed in Hormone-Receptor Negative and High-Grade Breast Cancers, PLoS One, 6(3):e17876 (2011).

Chiriva-Internati, M., et al., Identification of AKAP-4 as a New Cancer/Testis Antigen for Detection and Immunotherapy of Prostate Cancer, Prostate, 72(1):12-23 (2012).

Choi, J., et al., The Expression of MAGE and SSX, and Correlation of COX2, VEGF, and Survivin in Colorectal Cancer, Anticancer Res, 32(2): 559-564 (2012).

Chowell, D., et al., Patient HLA class I genotype influences cancer response to checkpoint blockade immunotherapy, Science, 359(6375): 582-587 (2018).

Chu, C.T., et al., Receptor dimerization is not a factor in the signalling activity of a transforming variant epidermal growth factor receptor (EGFRvIII), Biochem J, 324: 855-861 (1997).

Cusi, M.G., et al., Phase I trial of the thymidylate synthase poly-epitope (TSPP) vaccine in advance cancer patients, Cancer Immunol Immunother, 64:1159-1173 (2015).

Durie, BGM, et al., International uniform response criteria for multiple myeloma, Leukemia, 20:1467-1473 (2006).

Eisenhauer, E.A., et al., New response evaluation criteria in solid tumours: Revised RECIST guideline (version 1.1), Euro J Cancer, 45: 228-247 (2009).

Engelhard, V.H., Structure of peptides associated with MHC class I molecules, Curr Opin Immunol, 6(1): 13-23 (1994).

Fenoglio, D., et al., A multi-peptide, dual-adjuvant telomerase vaccine (GX301) is highly immunogenic in patients with prostate and renal cancer, Cancer Immunol Immunother, 62:1041-1052 (2013).

Gerdts, V., et al., Vaccines for porcine epidemic diarrhea virus and other swine coronaviruses, Vet Microbiol, 206: 45-51 (2017).

Goel, S., et al., CDK4/6 inhibition triggers anti-tumor immunity, Nature, 548(7668): 471-475 (2017).

Goossens-Beumer, J., et al., Clinical prognostic value of combined analysis of Aldh1, Survivin, and EpCAM expression in colorectal cancer, Br J Cancer, 110(12): 2935-2944 (2014).

Greenfield, W.W., et al., A phase I dose-escalation clinical trial of a peptide-based human papillomavirus therapeutic vaccine adjuvant for treating with women with biopsy-proven cervical intraepithelial neoplasia 2/3, Oncoimmunol, 10:e1031439 (2015).

Gudmundsdotter, L., et al., Amplified antigen-specific immune responses in HIV-1 infected individuals in a double blind DNA immunization and therapy interruption trial, Vaccine, 29(33):5558-5566 (2011).

Guo, H., et al., Different length peptides bind to HLA-Aw68 similarity at their ends but bulge out in the middle, Nature, 360: 364-366 (1992).

Hartmaier, R.J., et al., Genomic analysis of 63,220 tumors reveals insights into tumor uniqueness and targeted cancer immunotherapy strategies, Genome Med, 9:16 (2017).

HLA Genetics and Nomenclature, 10th International Summer School on Immunogenetics, Stintino, Sardinia: 34 pages (2013).

HLA Nomenclature, (2015) retrieved from http://hla.alleles.org/nomenclature/stats.html on Mar. 17, 2015.

Hodi, F.S., et al., Improved Survival with Ipilimumab in Patients with Metastatic Melanoma, N Engl J Med, 363(8): 711-723 (2010).

Hou. S., et al., Expressions of MAGE-A9 and MAGE-A11 in breast cancer and their expression mechanism, Arch Med Res, 45(1): 44-51 (2014).

Humphrey, P.A., et al., Anti-synthetic peptide antibody reacting at the fusion junction of deletion-mutant epidermal growth factor receptors in human glioblastoma, PNAS, 87: 4207-4211 (1990).

(56) References Cited

OTHER PUBLICATIONS

Kaida, M., et al., Phase 1 Trial of Wilms Tumor 1 (WT1) Peptide Vaccine and Gemcitabine Combination Therapy in Patients With Advanced Pancreatic or Biliary Tract Cancer, J Immunother, 34: 92-99 (2011).
Kakimi, K., et al., A phase I study of vaccination with NY-ESO-1f peptide mixed with Picibanil OK-432 and Montanide ISA-51 in patients with cancers expressing the NY-ESO-1 antigen, Int J Cancer, 129(12): 2836-2846 (2011).
Kalos, M., et al., Adoptive T cell transfer for cancer immunotherapy in the era of synthetic biology, Immunity, 39:49-60 (2013).
Kanojia, D., et al., Sperm-Associated Antigen 9, a Novel Biomarker for Early Detection of Breast Cancer, Cancer Epidemiol Biomarkers Prev, 18(2): 630-639 (2009).
Kantoff, P.W., et al., Overall Survival Analysis of a Phase II Randomized Controlled Trial of a Poxviral-Based PSA-Targeted Immunotherapy in Metastatic Castration-Resistant Prostate Cancer, J Clin Oncol, 28(7): 1099-1105 (2010).
Karkada, M., et al., Therapeutic vaccines and cancer: focus on DPX-0907, Biologies, 8: 27-38 (2014).
Keilholz, U., et al., A clinical and immunologic phase 2 trial of Wilms tumor gene product 1 (WT1) peptide vaccination in patients with AML and MDS, Blood, 113(26): 6541-6548 (2009).
Kenter, G.G., et al., Vaccination against HPV-16 Oncoproteins for Vulvar Intraepithelial Neoplasia, N Engl J Med, 361(19): 1838-1847 (2009).
Kenter, G.K., et al., Phase I immunotherapeutic trial with long peptides spanning the E6 and E7 sequences of high-risk human papillomavirus 16 in end-stage cervical cancer patients shows low toxicity and robust immunogenicity, Clin Cancer Res, 14(1): 169-77 (2008).
Kerkar, S.P., et al., Cellular constituents of immune escape within the tumor microenvironment, Cancer Res, 72(13): 3125-3130 (2012).
Khallouf, H., et al., Therapeutic vaccine strategies against human papillomavirus, Vaccines (Basel), 2(2): 422-62 (2014).
Kissler, S.M., et al. Projecting the transmission dynamics of SARS-CoV-2 through the post-pandemic period, Available at http://nrs.harvard.edu/um-3:HUL.InstRepos:42639308 (31 pgs) (2020).
Kovjazin, R., et al., ImMucin: A novel therapeutic vaccine with promiscuous MHC binding for the treatment of MUC1-expressing tumors, Vaccine, 29(29-30): 4676-4686 (2011).
Krug, L.M., et al., WT1 peptide vaccinations induce CD4 and CD8 T cell Immune responses in patients with mesothelioma and non-small cell lung cancer, Cancer Immunol Immunother, 59(10): 1467-1479 (2010).
Kruger, T., et al., Lessons to be learned from primary renal cell carcinomas: novel tumor antigens and HLA ligands for immunotherapy, Cancer Immunol Immunother, 54: 826-836 (2005).
Lammering, G., et al., Inhibition of the Type III epidermal growth factor receptor variant mutant receptor by dominant-negative EGFR-CD533 enhances malignant glioma cell radiosensitivity, Clin Cancer Res, 10: 6732-6743 (2004).
Lammering, G., et al., Radiation-induced activation of a common variant of EGFR confers enhanced radioresistance, Radiother Oncol, 72: 267-273 (2004).
Lee, et al., In silico identification of vaccine targets for 2019-nCoV, F1000Res, 9:145, pp. 1-14 (2020).
Lee, S., et al., Immunomic analysis of human sarcoma, PNAS, 100(5): 2651-2656 (2003).
Li, J., et al., Thrombocytopenia caused by the development of antibodies to thrombopoietin, Blood, 96(12): 3241-3248 (2001).
Li, M., et al., Expression profile of cancer-testis genes in 121 human colorectal cancer tissue and adjacent normal tissue, Clin Cancer Res, 11(5): 1809-1814 (2005).
Libermann, T.A., et al., Amplification, enhanced expression and possible rearrangement of EGF receptor gene in primary human brain tumors of glial origin, Nature, 313: 144-147 (1985).
Liu, J., et al., Major histocompatibility complex: interaction with peptides, in: eLS, John Wiley & Sons, Ltd: Chichester, a0000922.pub2, pp. 1-12 (2011).
Montgomery, R.B., et al., Expression of oncogenic epidermal growth factor receptor family kinases induces paclitaxel resistance and alters β-tubulin isotype expression, J Biol Chem, 275(23): 17358-17363 (2000).
Nagane, M., et al., A common mutant epidermal growth factor receptor confers enhanced tumorigenicity on human glioblastoma cells by increasing proliferation and reducing apoptosis, Cancer Res, 56: 5079-5086 (1996).
Nicosia, G., et al., Artificial Immune Systems, Third International Conference, ICARIS 2004, Catania, Sicily, Italy, Sep. 13-16, 2004. Lecture Notes in Computer Science, New York: Springer, 3236:189-196 (2004).
Nishikawa, R., et al., A mutant epidermal growth factor receptor common in human glioma confers enhanced tumorgenicity, PNAS USA, 91: 7727-7731 (1994).
Ochoa-Garay, J., et al., The ability of peptides to induce cytotoxic T cells in vitro does not strongly correlate with their affinity for the $H-2L^d$ molecule: implications for vaccine design and immunotherapy, Mol Immunol, 34(3): 273-281 (1997).
Okuno, K., et al., Clinical trial of a 7-peptide cocktail vaccine with oral chemotherapy for patients with metastatic colorectal cancer, Anticancer Res, 34: 3045-3052 (2014).
Padron-Regalado, E., et al., Vaccines for SARS-CoV-2: lessons from other coronavirus strains, Infect Dis Ther, 9: 255-274 (2020).
Paoletti, L.C., Potency of clinical group B streptococcal conjugate vaccines, Vaccine, 19: 2118-2126 (2001).
Pardi, N., et al., mRNA vaccines—a new era in vaccinology, Nat Rev Drug Discov, 19 pages (2018).
Pasini, E., et al., Undifferentiated nasopharyngeal carcinoma from a nonendemic area: Protective role of HLA allele products presenting conserved EBV epitopes, Int J Cancer, 125(6): 1358-1364 (2009).
PCT/EP2018/055230 International Search Report and Written Opinion dated Jun. 8, 2018.
PCT/EP2018/055231 International Search Report and Written Opinion dated Apr. 5, 2018.
PCT/EP2018/055232 International Search Report and Written Opinion dated May 9, 2018.
PCT/EP2019/073476 International Search Report and Written Opinion dated Jan. 23, 2020.
PCT/EP2019/073478 International Search Report and Written Opinion dated Sep. 20, 2019.
PCT/EP2019/073481 International Search Report and Written Opinion dated Dec. 20, 2019.
Phuphanich, S., et al., Phase I trial of a multi-epitope-pulsed dendritic call vaccine for patients with newly diagnosed glioblastoma, Cancer Immunol Immunother, 62(1): 125-135 (2013).
Rahman Oany, et al., Design of an epitope-based peptide vaccine against spike protein of human coronavirus: an in silico approach, Drug Des Devel Ther, 8: 1139-1149 (2014).
Ramakrishnan, R., et al., Chemotherapy enhances tumor cell susceptibility to CTL-mediated killing during cancer immunotherapy in mice, J Clin Invest, 120(4): 1111-1124 (2010).
Rapoport, A.P., et al., Combination immunotherapy after ASCT for multiple myeloma using MAGE-A3/Poly-ICLC immunizations followed by adoptive transfer of vaccine-primed and costimulated autologous T cells, Clin Cancer Res, 20(5): 1355-1365 (2014).
Reche, P.A., et al., Definition of MHC supertypes through clustering of MHC peptide binding repertoires, in Nicosia, G., et al., Eds. ICARIS 2004, LNCS 3239: 189-196( (2004).
Repana, D., et al., The network of cancer genes (NCG): a comprehensive catalogue of known and candidate cancer genes from cancer sequencing screens, Genome Biol, 20(1): 1-12 (2019).
Rosa, D.S., et al., Multiple approaches for increasing the immunogenicity of an epitope-based anti-HIV vaccine, AIDS Res Hum Retroviruses, 31(11): 1077-1088 (2015).
Saini, S., et al., A novel cancer testis antigen, a-kinase anchor protein 4 (AKAP4) is a potential biomarker for breast cancer, PLoS One, 8(2): e57095 (2013).
Sampson, J.H., et al., Immunologic escape after prolonged progression-free survival with epidermal growth factor receptor variant III peptide vaccination in patients with newly diagnosed glioblastoma, J Clin Oncol, 28(31): 4722-4729 (2010).

(56) References Cited

OTHER PUBLICATIONS

Schumacher, T.N., et al., Neoantigens in cancer immunotherapy, Science, 348(6230): 69-74 (2015).
Singh, S.P., et al., Major histocompatibility complex linked databases and prediction tools for designing vaccines, Hum Immunol, 77(3): 295-306 (2015).
Slingluff, C.L., et al., Clinical and Immunologic results of a randomized phase II trial of vaccination using four melanoma peptides either administered in granulocyte-macrophage colony-stimulating factor in adjuvant of pulsed on dendritic cells, J Clin Oncol, 21(21): 4016-4026 (2003).
Slingluff, C.L., et al., Randomized multicenter trial of the effects of melanoma-associated helper peptides and cyclophosphamide on the immunogenicity of a multipeptide melanoma vaccine, J Clin Oncol, 29(21): 2924-2932 (2011).
Snyder, A.S., et al., Genetic basis for clinical response to CTLA-4 blockade in melanoma, N Engl J Med, 371(23): 2189-2199 (2014).
Somogyi, E., et al., Peptide vaccine candidate mimics the heterogeneity of natural SARS-CoV-2 immunity in convalescent humans and induces broad T cell responses in mice models, bioRxiv, pp. 1-39, Oct. 2020.
Song, M., et al., Cancer/testis antigen NT-SAR-35 enhances cell proliferation, migration, and invasion, Int J Oncol, 48(2):569-576 (2016).
Spranger, S., Mechanisms oftumor escape in the context of the T-cell-inflamed and the non-T-cell-inflamed tumor microenvironment, Int Immunol, 28(8): 383-391 (2016).
Tagawa, S.T., et al., Phase I study of intranodal delivery of a plasmid DNA vaccine for patients with stage IV melanoma, Cancer, 98(1):144-154 (2003).
Takedatsu, H., et al., Determination of thrombopoietin-derived peptides recognized by both cellular and humoral immunities in healthy donors and patients with thrombocytopenia, Stem Cells, 23(7): 975-982 (2005).
The UniProt Consortium, UniProt: the universal protein knowledgebase, UniProtKB-Q8N0W7, Nucleic Acids Res. 46:2699 (2018).
Therasse, P., et al., New guidelines to evaluate the response to treatment in solid tumors, J Natl Cancer Inst, 92(3): 205-216 (2000).
Trimble, C.L., et al., Safety, efficacy, and immunogenicity of VGX-3100, a therapeutic synthetic DNA vaccine targeting human papillomavirus 16 and 18 E6 and E7 proteins for cervical intraepithelial neoplasia 2/3: a randomised, double-blind, placebo-controlled phase 2b trial, Lancet, 386(10008): 2078-2088 (2015).
Tsuchida, Y., et al., Response evaluation criteria in solid tumors (RECIST): new guidelines, Med Pediatr Oncol, 37:1-3 (2001).
U.S. Appl. No. 15/910,930 Office Action dated Mar. 25, 2021.
U.S. Appl. No. 15/910,965 Office Action dated May 12, 2021.
U.S. Appl. No. 15/910,988 Office Action dated May 18, 2018.
U.S. Appl. No. 16/559,430 Office Action dated Apr. 27, 2020.
U.S. Appl. No. 16/559,430 Office Action dated Aug. 27, 2020.
U.S. Appl. No. 17/249,362 Office Action dated Apr. 27, 2021.
Valmori, D., et al., Epitope clustering in regions undergoing efficient proteasomal processing defines immunodominant CTL regions of a tumor antigen, Clin Immunol, 122: 163-172 (2007).
Valmori, D., et al., Vaccination with NY-ESO-1 protein and CpG in montanide induces integrated antibody/Th1 responses and CD8 T cells through cross-priming, PNAS USA, 104(21): 8947-8952 (2007).
Van Allen, E.M., et al., Genomic correlates of response to CTLA-4 blockade in metastatic melanoma, Science, 350(6257): 207-211 (2015).
Vitale, M., et al., Effect of tumor cells and tumor microenvironment on NK-cell function, Eur J Immunol, 44: 1582-1592 (2014).
Wada, H., et al., Vaccination with NY-ESO-1 overlapping peptides mixed with picibanil OK-432 and montanide ISA-51 in patients with cancers expressing the NY-ESO-1 antigen, J Immunother, 37(2): 84-92 (2014).
Walter, S., et al., Multipeptide immune response to cancer vaccine IMA901 after single-dose cyclophosphamide associates with longer patient survival, Nat Med, 18(8): 1254-1261 (2012).
Wei, J., et al., Screening of Single-Chain Variable Fragments against TSP50 from a Phage Display Antibody Library and Their Expression as Soluble Proteins, J Biol Med Screen, 11(5): 546-552, (2006).
Weller, M., et al., Rindopepimut with temozolomide for patients with newly diagnosed, EGFRvIII-expressing glioblastoma (ACT IV): a randomised, double-blind, international phase 2 trial, Lancet Oncol, 18(10): 1373-1385 (2017).
Welters, M.J.P., et al., Induction of tumor-specific CD4+ and CD8+ T-cell immunity in cervical cancer patients by a human papillomavirus type 16 E6 and E7 long peptides vaccine, Clin Cancer Res, 14(1): 178-187 (2008).
Welters, M.J.P., et al., Success or failure of vaccination for HPV16-positive vulvar lesions correlates with kinetics and phenotype of induced T-cell responses, PNAS USA, 107(25): 11895-11899 (2010).
Wieczorek, M., et al., Major histocompatibility complex (MHC) class I and MHC class II proteins: conformational plasticity in antigen presentation, Front Immunol, 8: 292 (2017).
Woolhouse, M., et al., Human viruses: discovery and emergence, Philos Trans R Soc London B Biol Sci, 367(1604): 2864-71 (2012).
Wu, F., et al., Severe acute respiratory syndrome coronavirus 2 isolate Wuhan-Hu-1, complete genome, NCBI Reference Sequence: NC_045512.2, (2020).
Yoshitake, Y., et al., Phase II clinical trial of multiple peptide vaccination for advanced head and neck cancer patients revealed induction of immune responses and improved OS, Clin Cancer Res, 21(2): 312-321 (2015).

\* cited by examiner

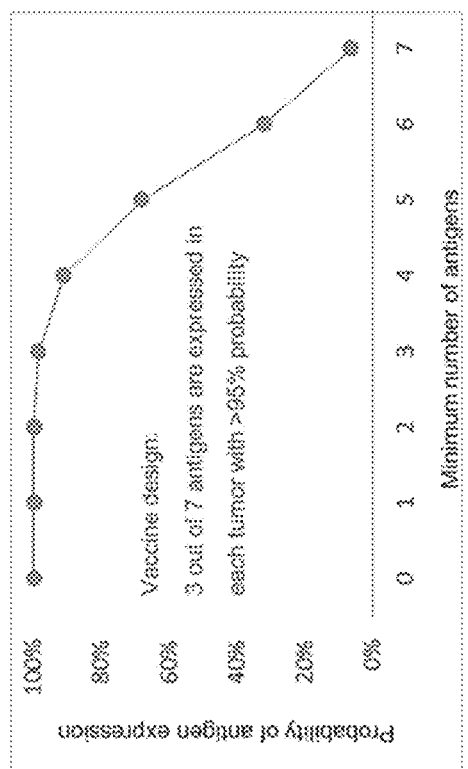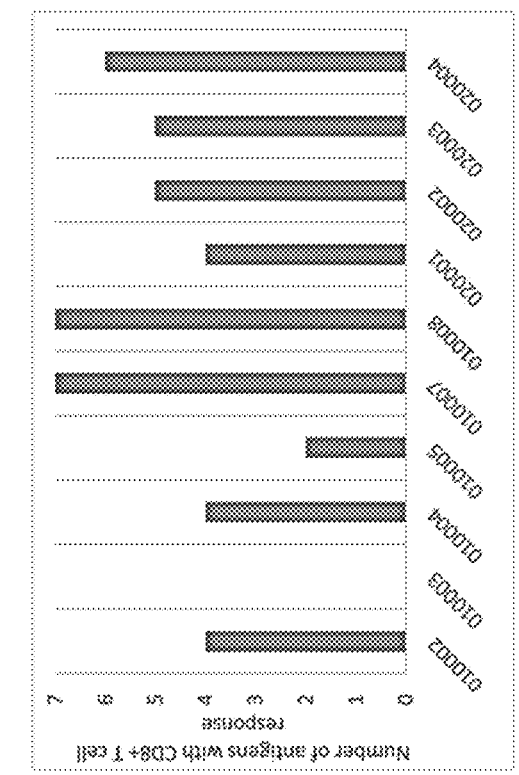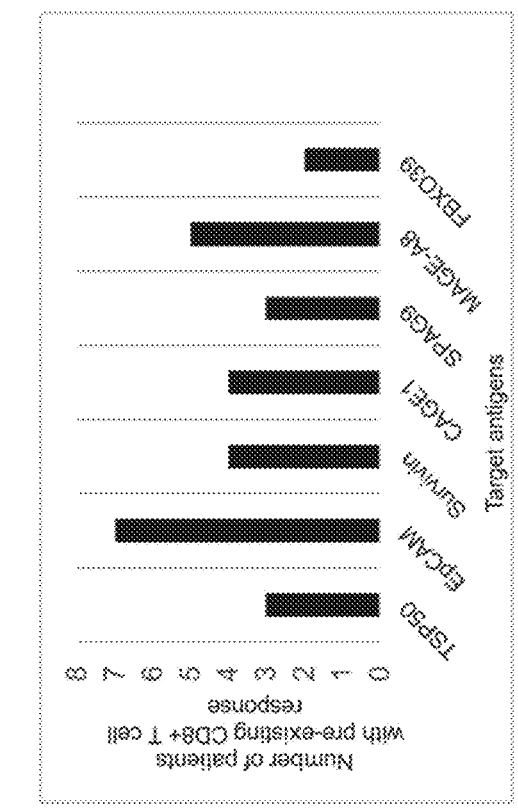
Figure 12

CRC_P3 peptide (30 aa)

EPITOPE (9 aa) MAGE-A8 (9 aa)
YVDEKAPEFSMQGLK DEKVAELVRFLRKY

| PolyPEPI1018 vaccine antigens | Pre-clinical immunogenicity | | Clinical immunogenicity |
|---|---|---|---|
| | Model population (n=433) | CRC cohort (n=37) | OBERTO-101 (n=10) |
| TSP50 | 53% | 62% | 70% |
| EpCAM | 69% | 41% | 90% |
| Survivin | 36% | 32% | 70% |
| Cage | 68% | 81% | 50% |
| SPAG9 | 28% | 3% | 40% |
| FBXO39 | 90% | 100% | 60% |
| MAGE-A8 | 18% | 0% | 60% |
| Any antigen | 98% | 100% | 90% |
| Any 2 antigens | 92% | 92% | 90% |
| Any 3 antigens | 72% | 65% | 80% |

*Lorincz et al. Journal of Clinical Oncology 37, 2019 (suppl; abstr e14298).

Figure 13

Note: In the CAIRO3 trial the PFS1 was m8.5 month (95% CI 6.5-10.3)*
*CAIRO3 trial. Simkens et al. The Lancet 2015

| Antigen | Expression level |
|---|---|
| SURVIVIN | 100% |
| DPPA2 | 100% |
| KK-LC-1 | 80% |
| CAGE-1 | 77% |
| HIWI | 76% |
| TSP50 | 57% |
| 5T4 | 52% |
| MAGE-A3 | 37% |
| MAGE-A1 | 31% |
| MAGE-A2 | 31% |
| MAGE-A10 | 30% |
| PRAME | 20% |
| LAGE-1 | 14% |
| SSX1 | 13% |

Conclusion:
1. 99% of the tumor express ≥3 antigens
2. No biopsy is needed

Figure 17
A
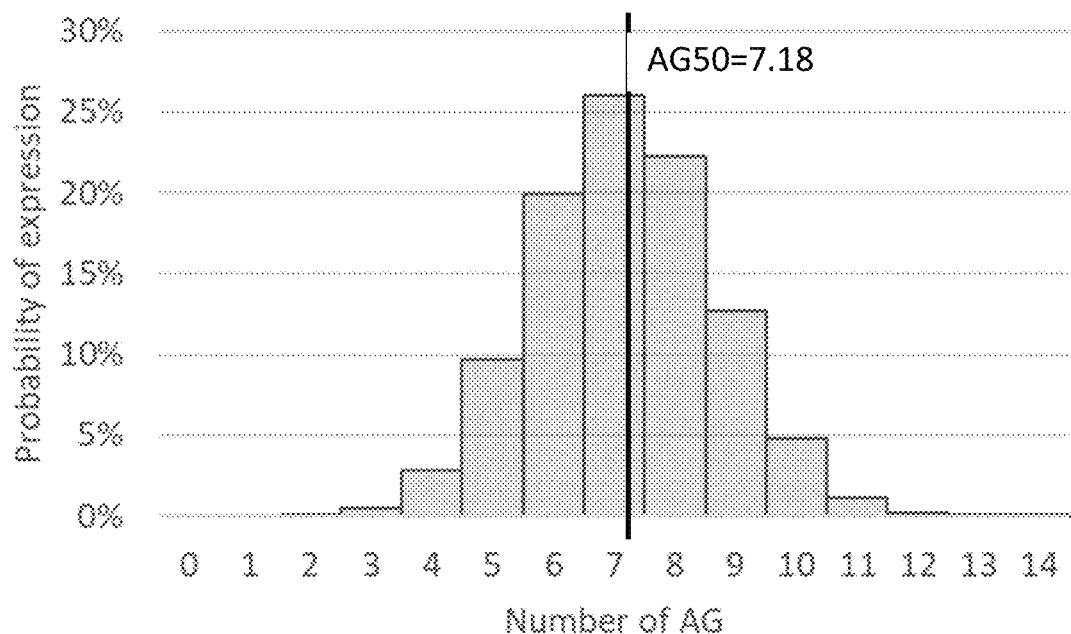
B
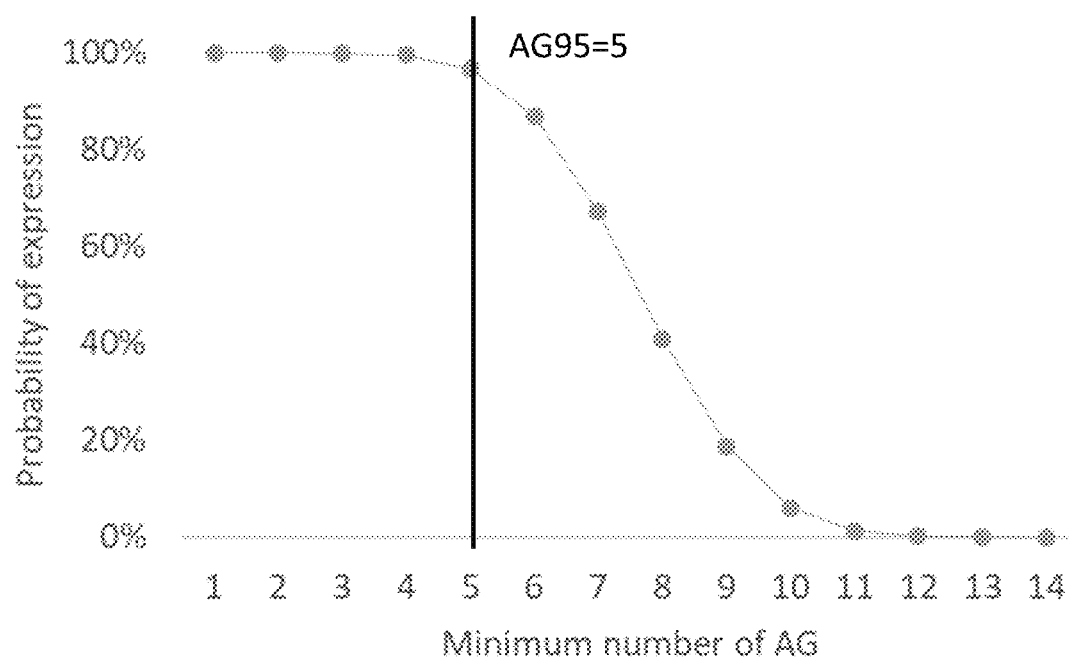

Figure 18
A
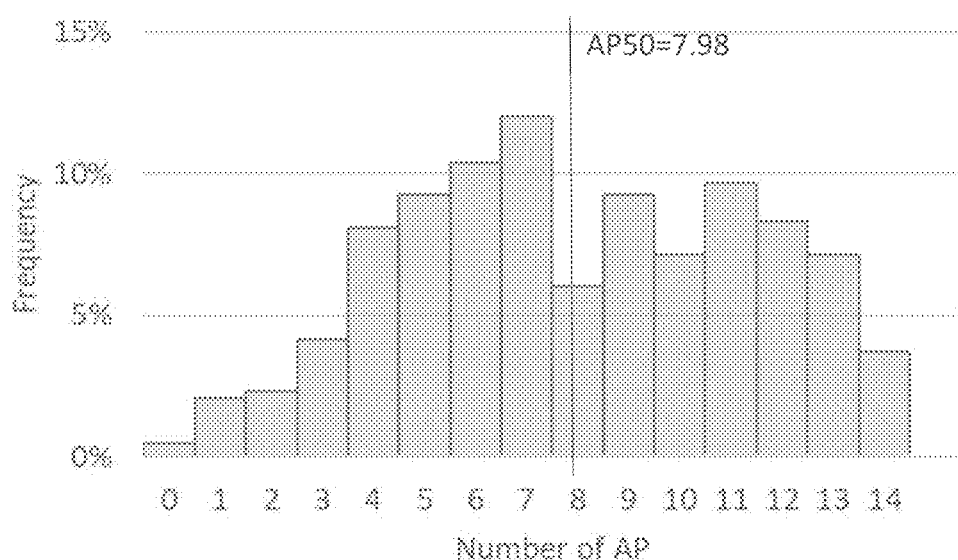
B
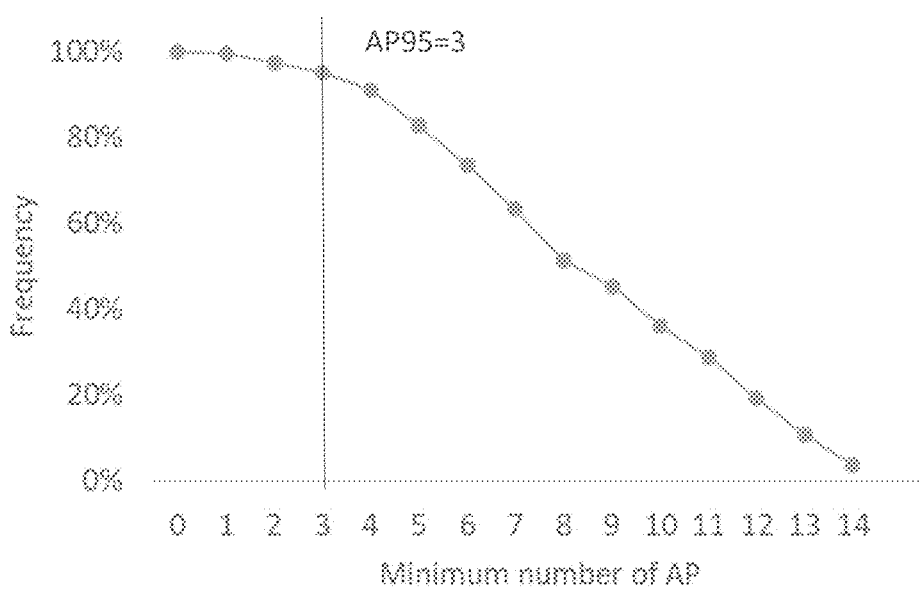

Figure 19
A
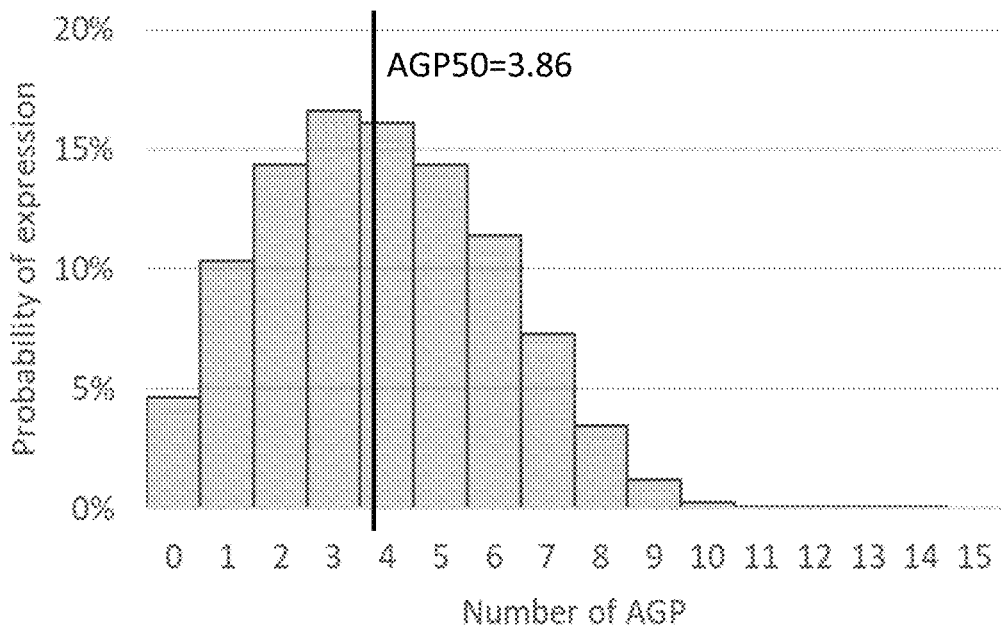
B
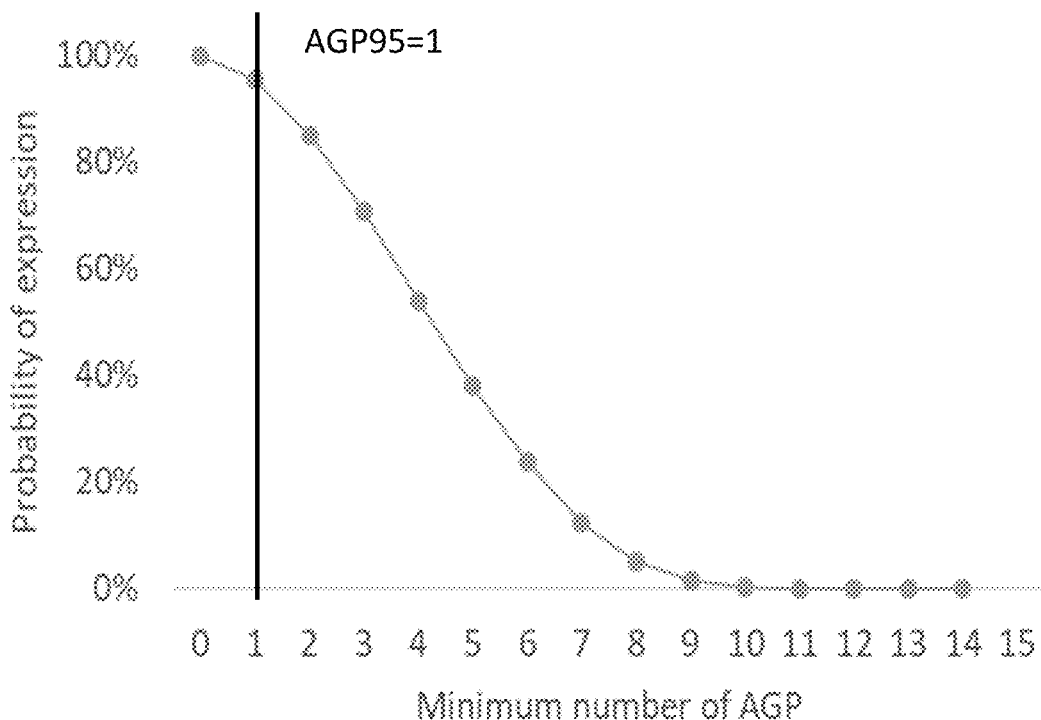

| Antigen | Expression level |
|---|---|
| BRDT | 48% |
| PRAME | 63% |
| NALP4 | 38% |
| MAGE-C2 | 24% |
| MAGE-A12 | 36% |
| NY-SAR-35 | 28% |
| DPPA2 | 30% |
| KK-LC-1 | 35% |
| SURVIVIN | 57% |
| MAGE-A2 | 27% |
| LDHC | 29% |
| MAGE-A3 | 33% |
| MAGE-A1 | 28% |

Conclusion:
1. 99% of the tumor express ≥3 antigens
2. No biopsy is needed

Figure 21
A
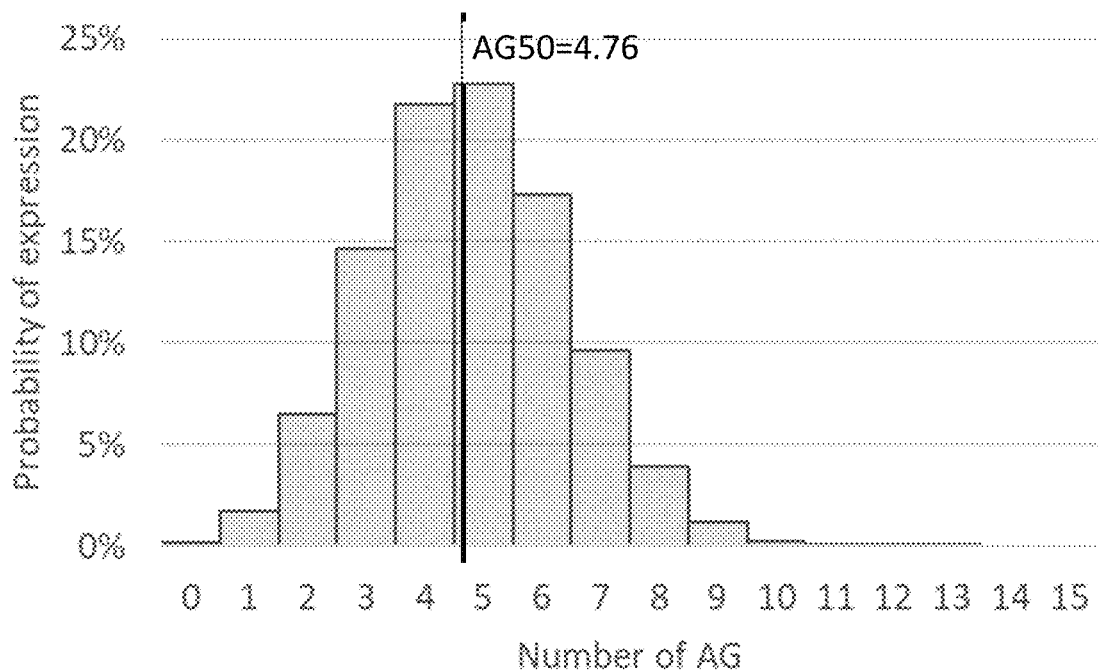
B
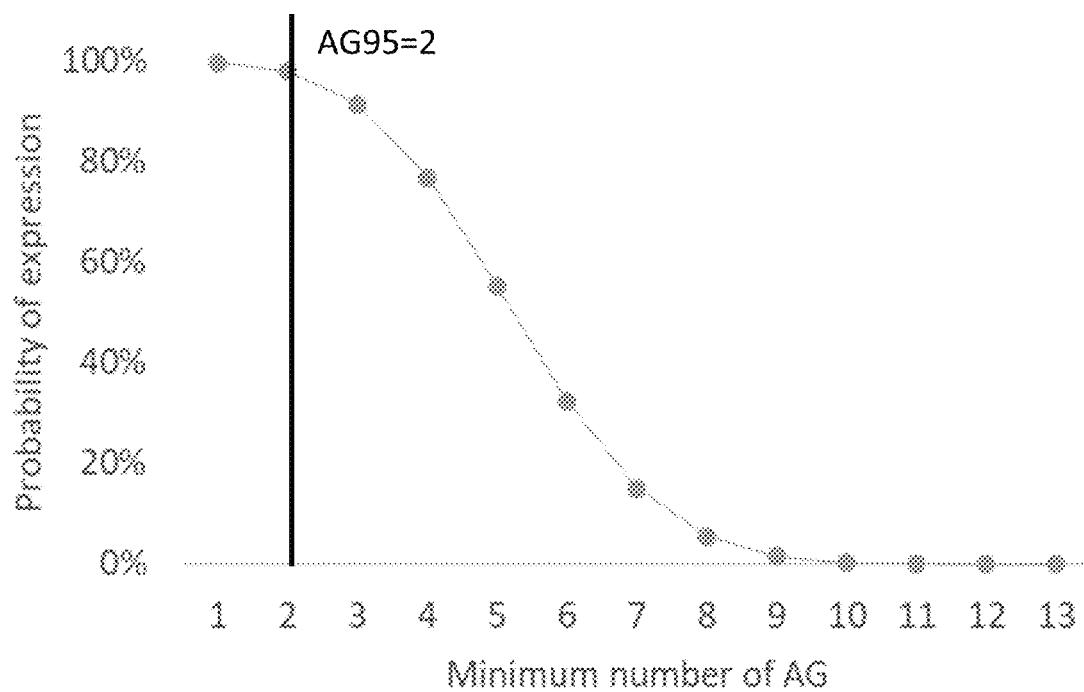

Figure 22
A
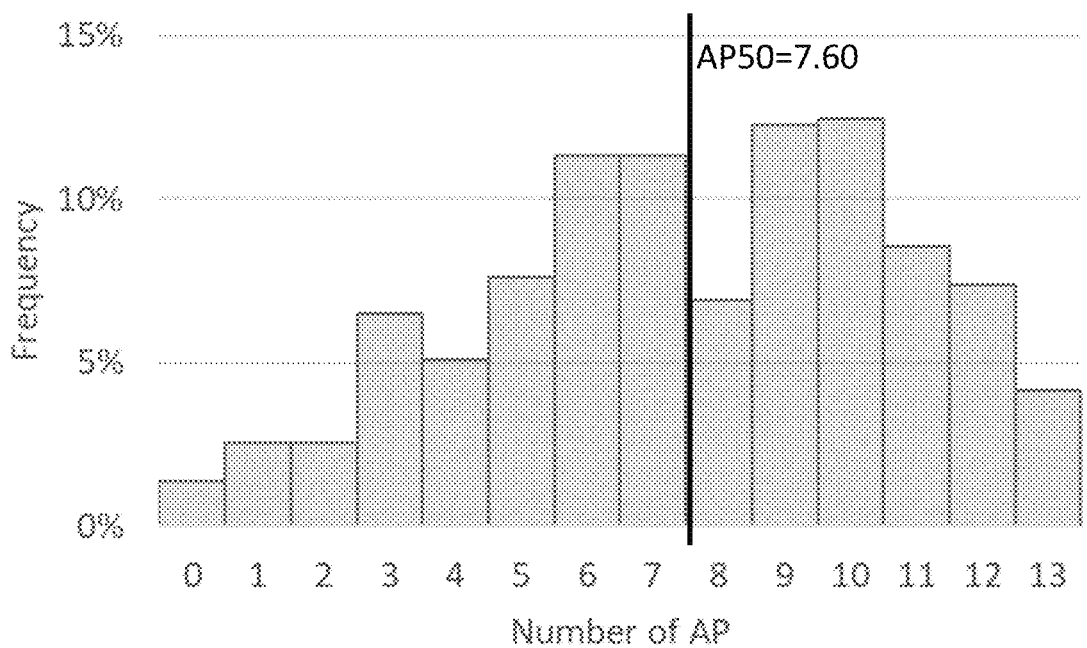
B
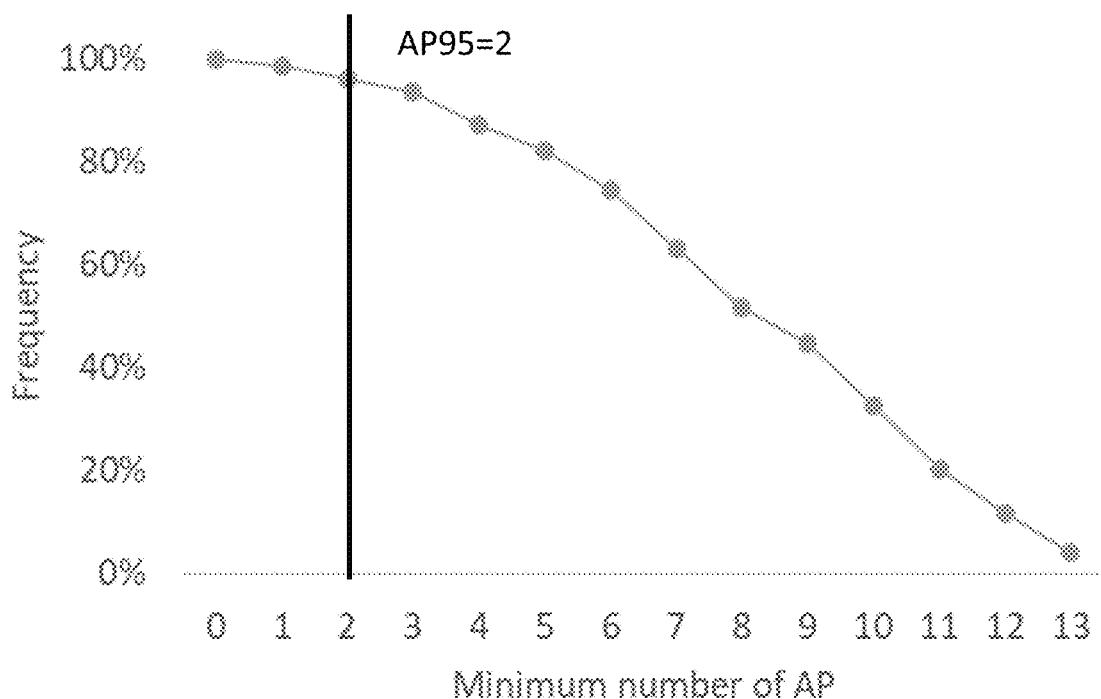

Figure 23
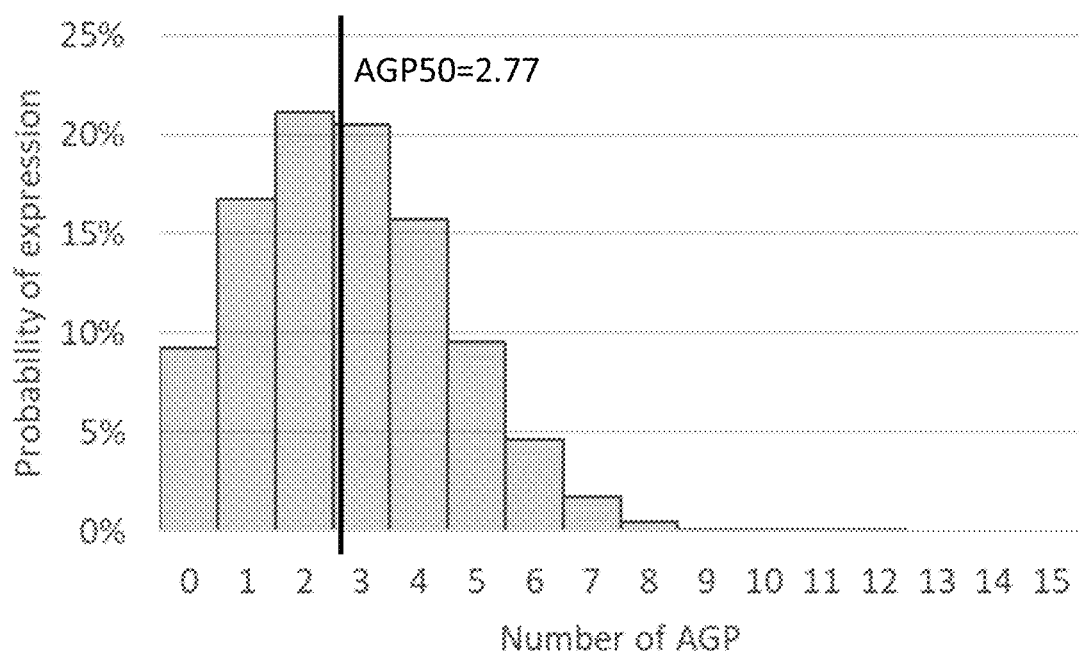
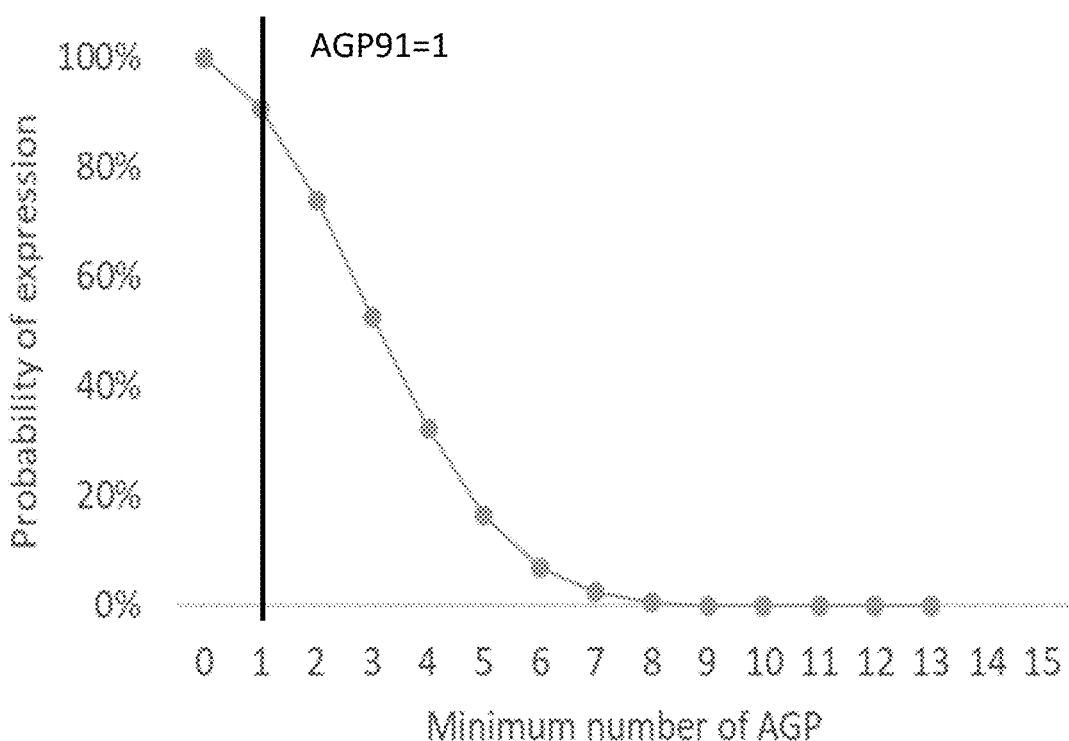

| Antigen | Expression level |
|---|---|
| Survivin | 96% |
| PRAME | 90% |
| MAGE-A6 | 62% |
| MAGE-A2 | 61% |
| MAGE-A3 | 59% |
| MAGE-A11 | 54% |
| MAGE-A12 | 45% |
| MAGE-C1 | 45% |
| MAGE-C2 | 45% |
| MAGE-A10 | 44% |
| Ny-ESO-1 | 38% |
| MAGE-A1 | 37% |
| LAGE-1 | 35% |
| BORIS | 27% |
| SSX-1 | 25% |

Conclusion:
1. 99% of the tumor express ≥3 antigens
2. No biopsy is needed

Figure 25
A
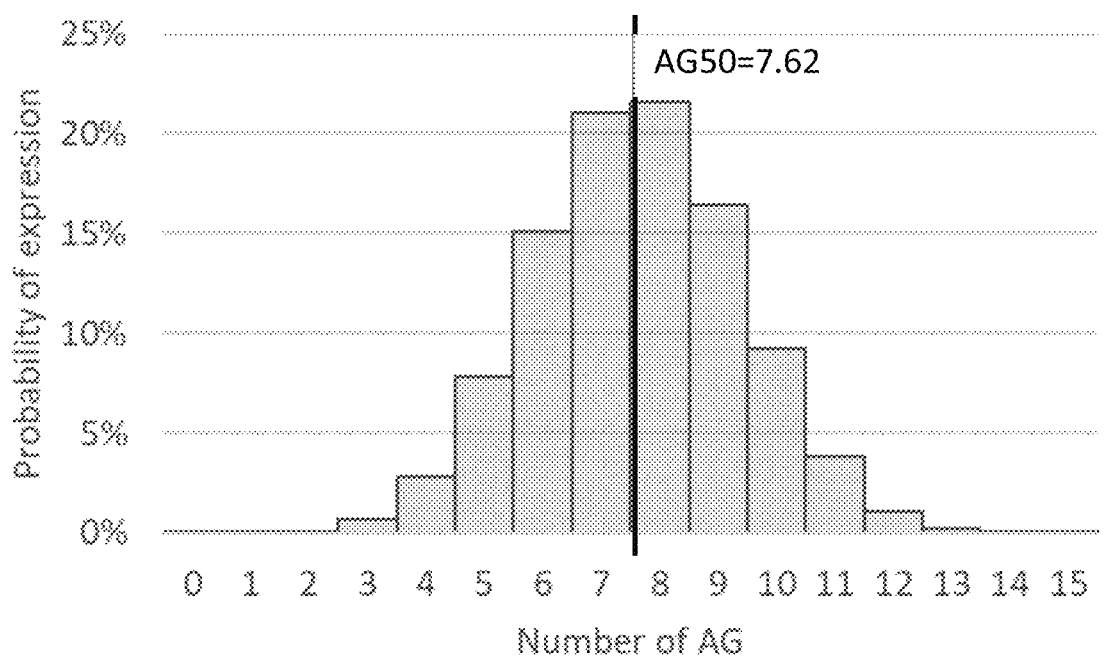
B
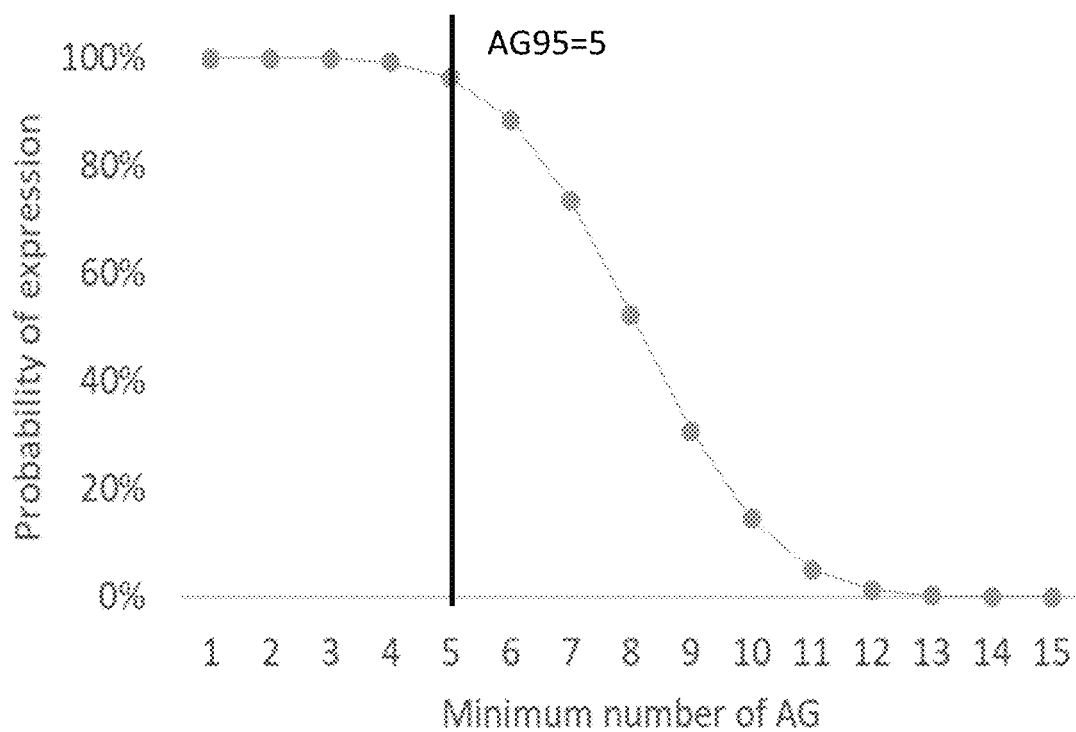

Figure 26
A
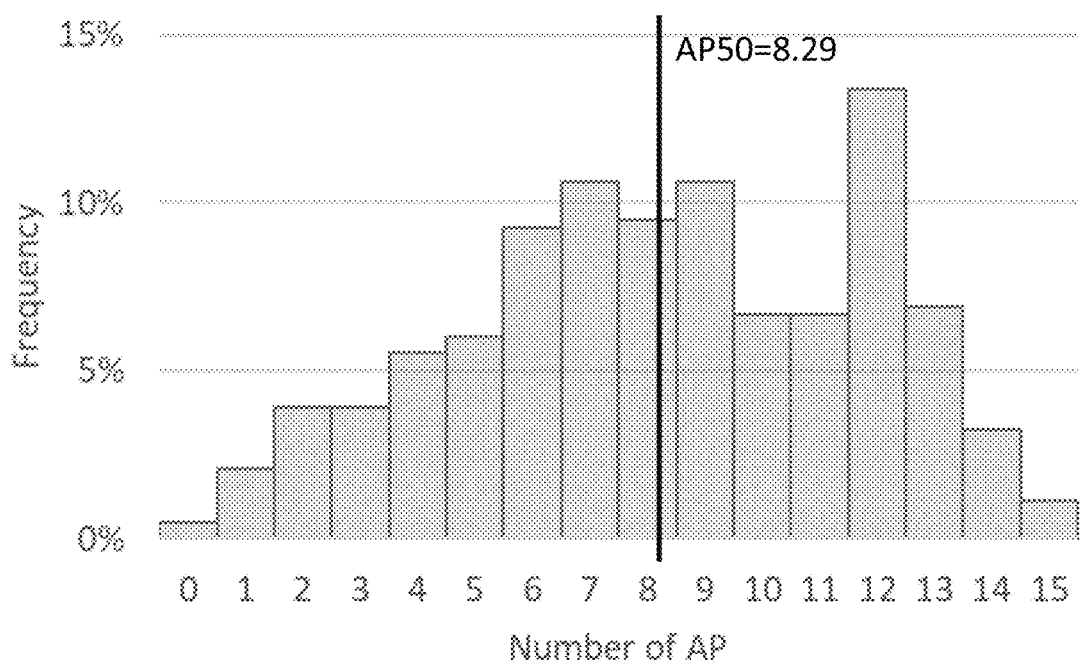
B
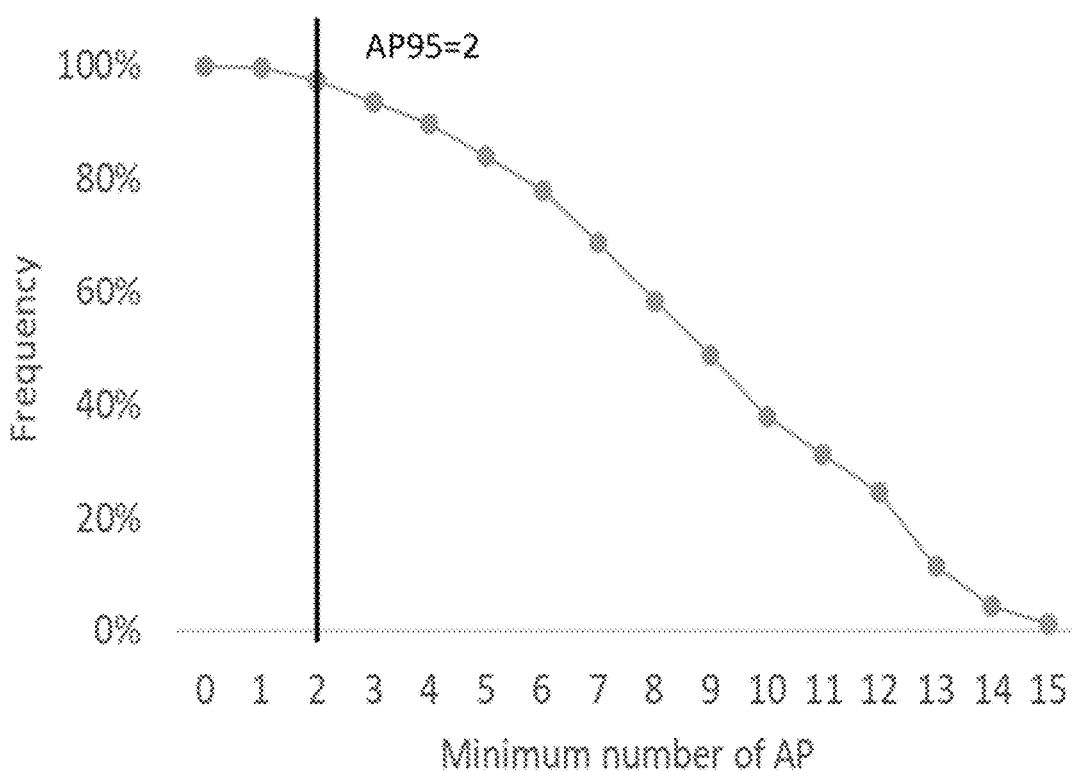

Figure 27
A
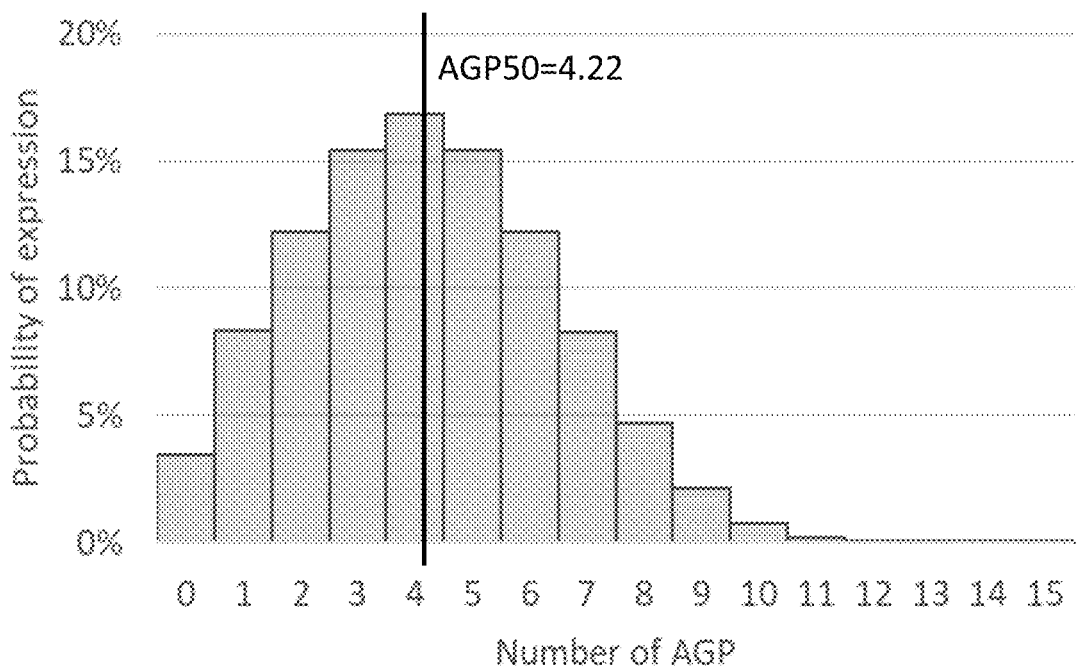
B
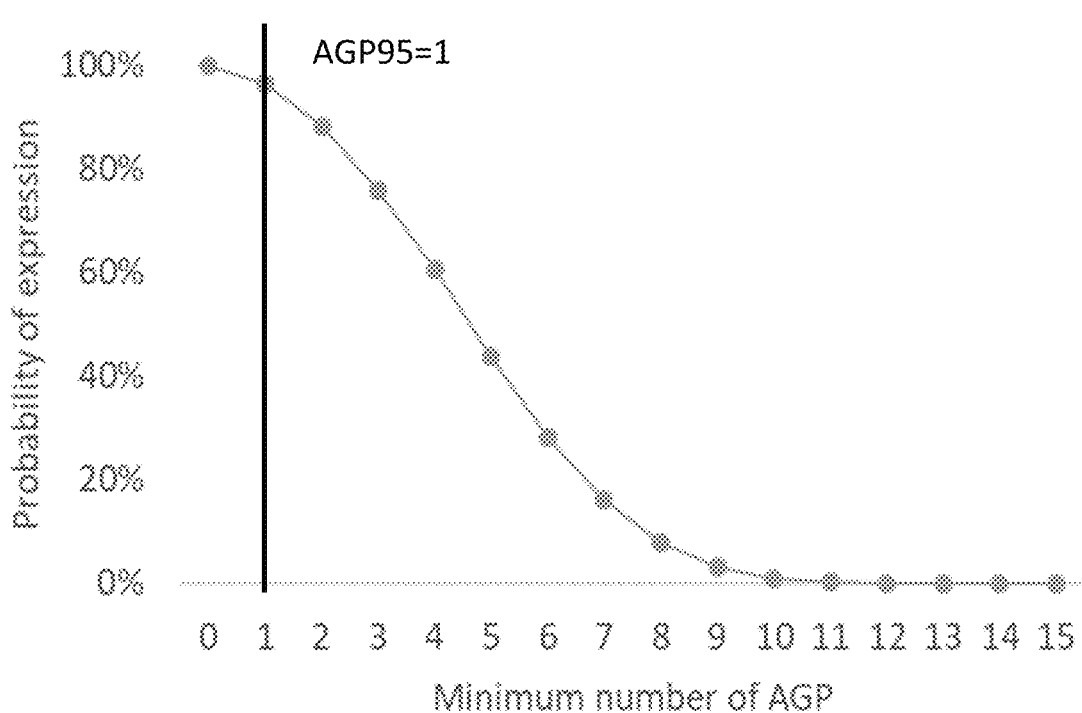

| Antigen | Expression level |
|---|---|
| PIWIL2 | 82% |
| SURVIVIN | 62% |
| MAGE-A9 | 61% |
| MAGE-A8 | 57% |
| EpCAM | 54% |
| CTAGE1 | 53% |
| MAGE-A3 | 42% |
| MAGE-A1 | 34% |
| NY-ESO-1 | 31% |
| LAGE-1 | 30% |
| MAGE-A12 | 29% |
| OY-TES-1 | 28% |
| MAGE-A10 | 28% |
| MAGE-C1 | 27% |
| MAGE-A2 | 25% |
| HAGE | 24% |
| MAGE-C2 | 19% |

Conclusion:
1. 99% of the tumor express ≥3 antigens
2. No biopsy is needed

Figure 29
A
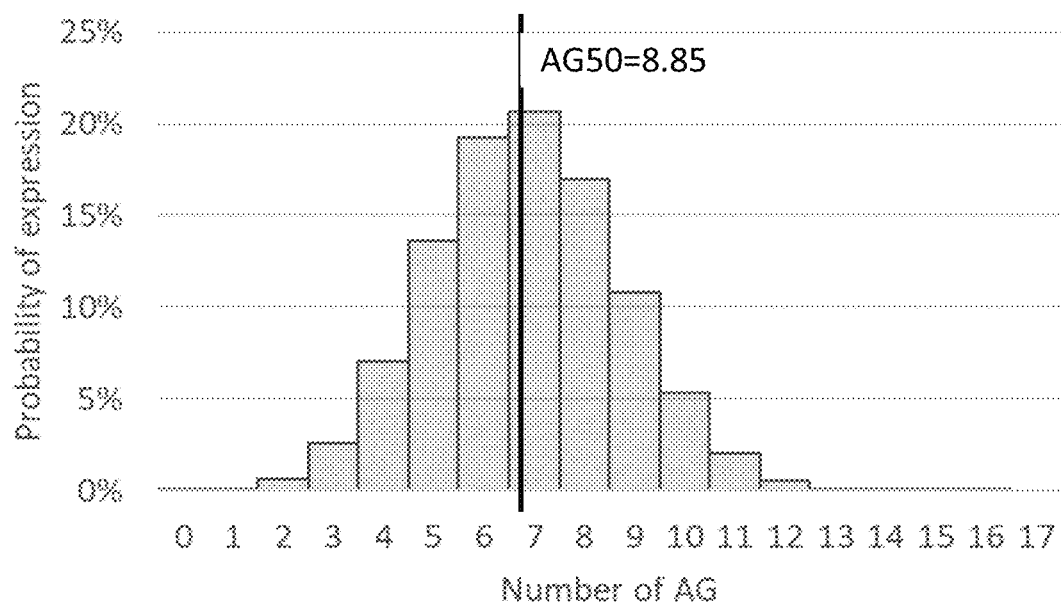
B
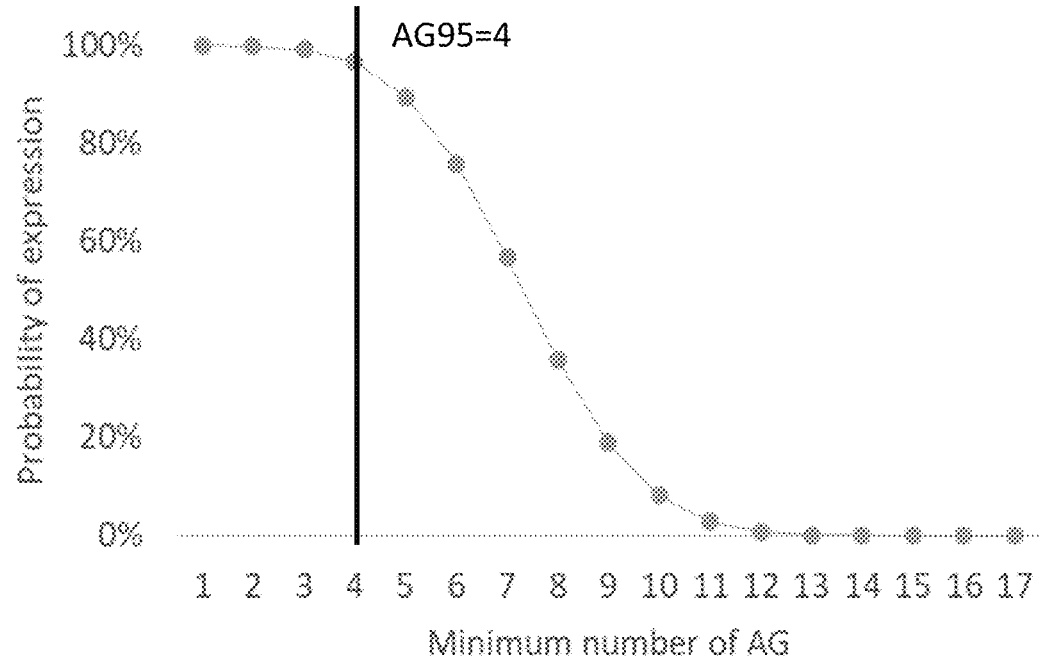

Figure 30
A
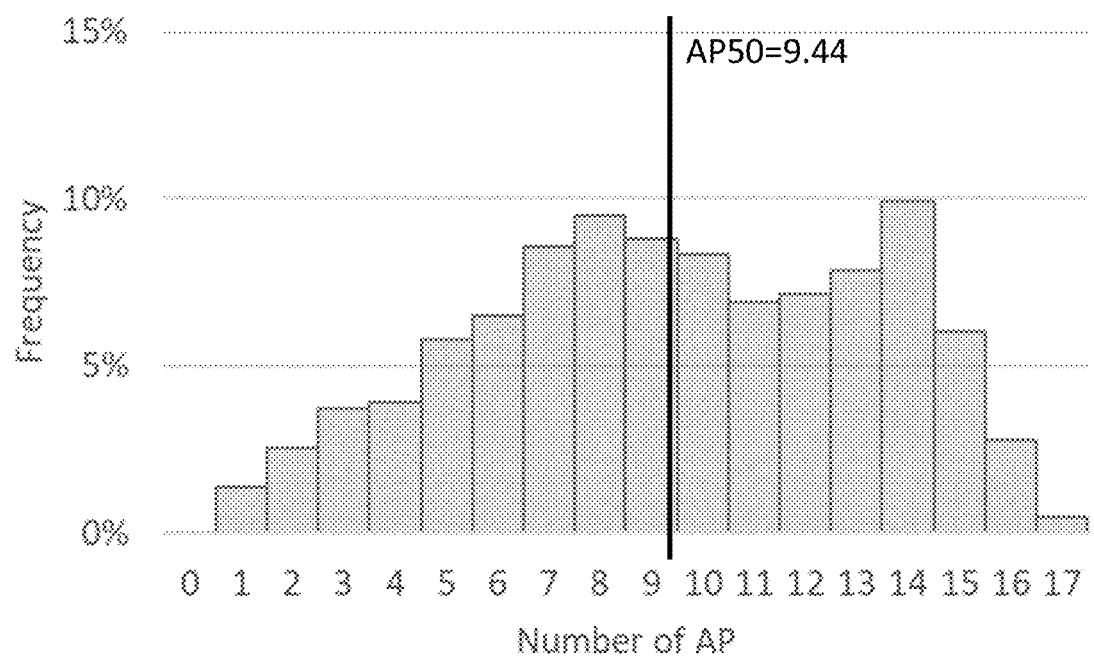
B
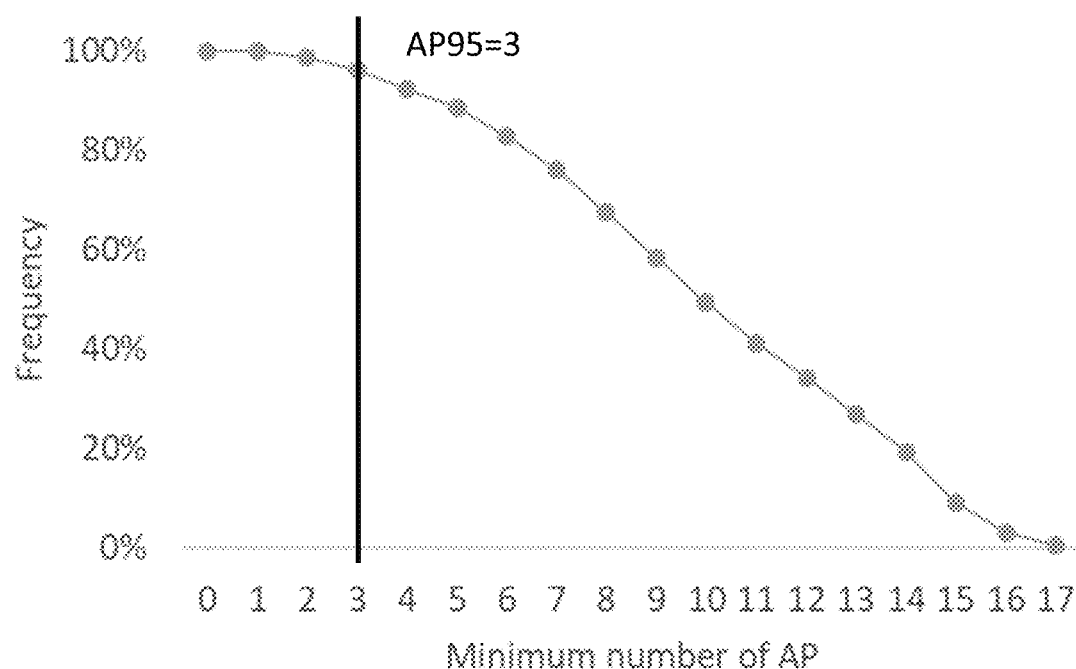

Figure 31
A
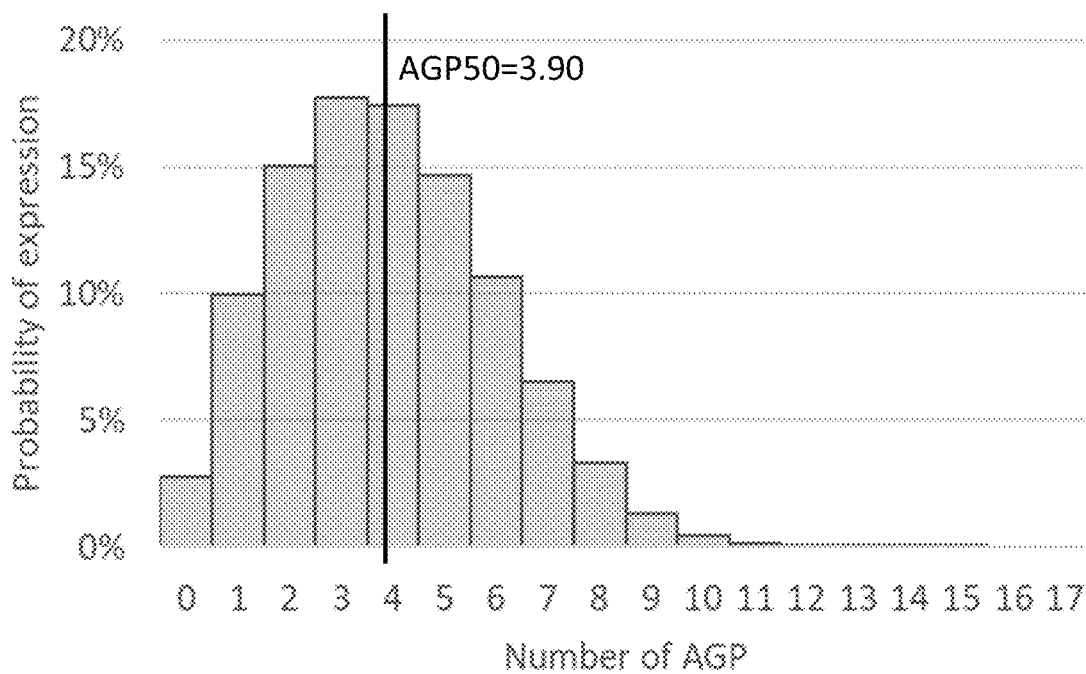
B
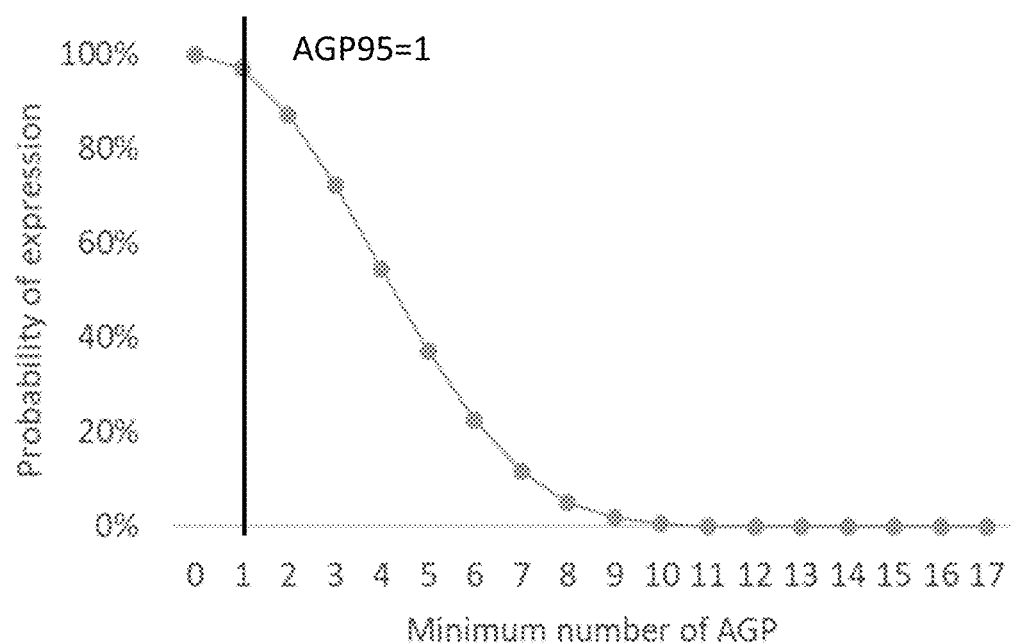

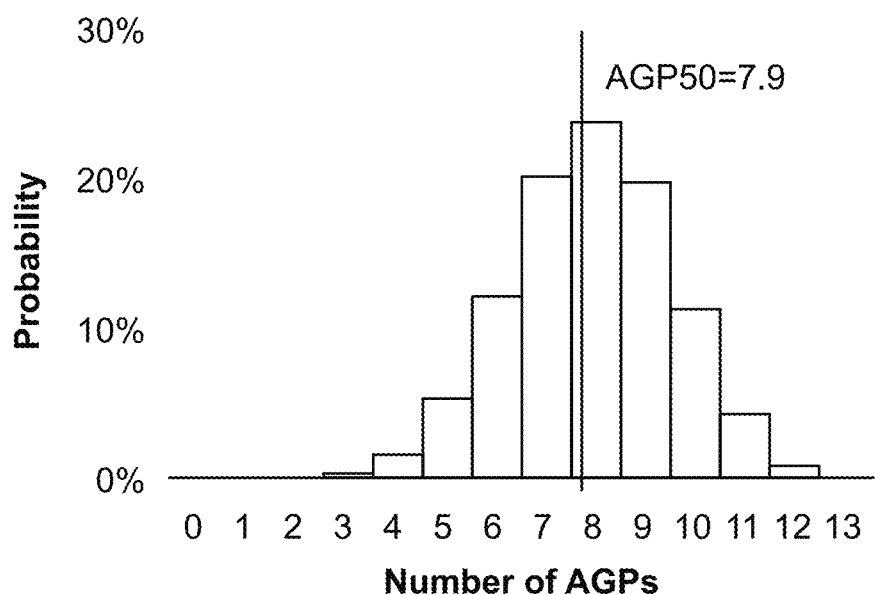
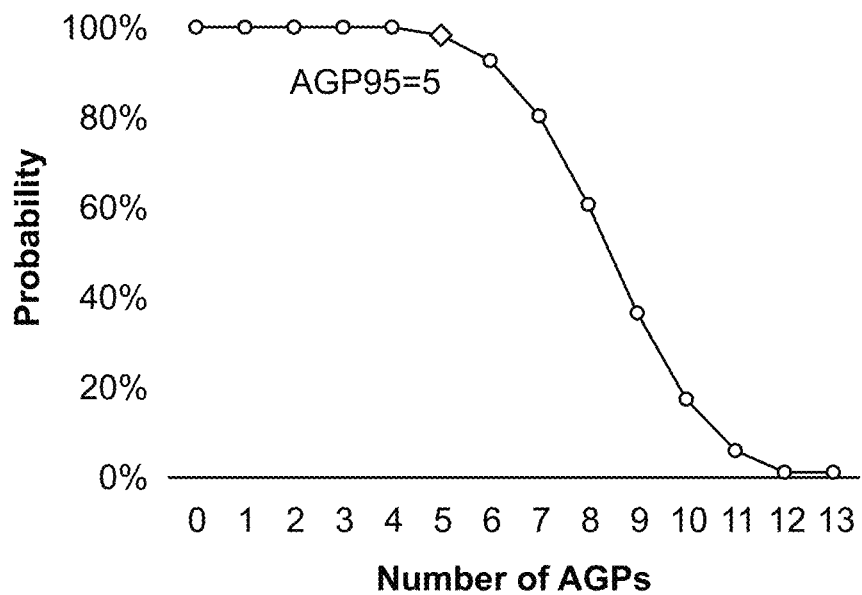
Figure 32

SEQUENCE LISTING

```
<160> NUMBER OF SEQ ID NOS: 394

<210> SEQ ID NO 1
<211> LENGTH: 9
<212> TYPE: PRT
<213> ORGANISM: artificial sequence
<220> FEATURE:
<223> OTHER INFORMATION: MAGE-C1  9mer

<400> SEQUENCE: 1

Lys Met Met Lys Arg Leu Met Thr Val
1               5

<210> SEQ ID NO 2
<211> LENGTH: 9
<212> TYPE: PRT
<213> ORGANISM: artificial sequence
<220> FEATURE:
<223> OTHER INFORMATION: CAGE-1 9mer

<400> SEQUENCE: 2

Lys Met His Ser Leu Leu Ala Leu Met
1               5

<210> SEQ ID NO 3
<211> LENGTH: 9
<212> TYPE: PRT
<213> ORGANISM: artificial sequence
<220> FEATURE:
<223> OTHER INFORMATION: TSP50 9mer

<400> SEQUENCE: 3

Phe Ser Tyr Glu Gln Asp Pro Thr Leu
1               5

<210> SEQ ID NO 4
<211> LENGTH: 9
<212> TYPE: PRT
<213> ORGANISM: artificial sequence
<220> FEATURE:
<223> OTHER INFORMATION: DPPA2 9mer

<400> SEQUENCE: 4

Tyr Leu Arg Leu His Arg His Ala Tyr
1               5
```

```
<210> SEQ ID NO 5
<211> LENGTH: 9
<212> TYPE: PRT
<213> ORGANISM: artificial sequence
<220> FEATURE:
<223> OTHER INFORMATION: HIWI 9mer

<400> SEQUENCE: 5

Leu Gln Tyr Glu Asn Ser Ile Met Leu
1               5

<210> SEQ ID NO 6
<211> LENGTH: 9
<212> TYPE: PRT
<213> ORGANISM: artificial sequence
<220> FEATURE:
<223> OTHER INFORMATION: SURVIVIN 9mer

<400> SEQUENCE: 6

Arg Ala Ile Glu Gln Leu Ala Ala Met
1               5

<210> SEQ ID NO 7
<211> LENGTH: 9
<212> TYPE: PRT
<213> ORGANISM: artificial sequence
<220> FEATURE:
<223> OTHER INFORMATION: HIWI 9mer

<400> SEQUENCE: 7

Phe Val Ala Ser Ile Asn Glu Gly Met
1               5

<210> SEQ ID NO 8
<211> LENGTH: 9
<212> TYPE: PRT
<213> ORGANISM: artificial sequence
<220> FEATURE:
<223> OTHER INFORMATION: TSP50 9mer

<400> SEQUENCE: 8

Thr Thr Met Glu Thr Gln Phe Pro Val
1               5

<210> SEQ ID NO 9
<211> LENGTH: 9
<212> TYPE: PRT
<213> ORGANISM: artificial sequence
<220> FEATURE:
<223> OTHER INFORMATION: 5T4 9mer

<400> SEQUENCE: 9

Leu Ala Ser Asn His Phe Leu Tyr Leu
1               5

<210> SEQ ID NO 10
<211> LENGTH: 9
<212> TYPE: PRT
<213> ORGANISM: artificial sequence
<220> FEATURE:
<223> OTHER INFORMATION: 5T4 9mer

<400> SEQUENCE: 10

Phe Leu Tyr Leu Pro Arg Asp Val Leu
1               5
```

```
<210> SEQ ID NO 11
<211> LENGTH: 9
<212> TYPE: PRT
<213> ORGANISM: artificial sequence
<220> FEATURE:
<223> OTHER INFORMATION: 5T4 9mer

<400> SEQUENCE: 11

Ser Ser Phe Ser Ser Ser Ala Pro Phe
1               5

<210> SEQ ID NO 12
<211> LENGTH: 9
<212> TYPE: PRT
<213> ORGANISM: artificial sequence
<220> FEATURE:
<223> OTHER INFORMATION: MAGE-A2  9mer

<400> SEQUENCE: 12

Phe Ala His Pro Arg Lys Leu Leu Met
1               5

<210> SEQ ID NO 13
<211> LENGTH: 9
<212> TYPE: PRT
<213> ORGANISM: artificial sequence
<220> FEATURE:
<223> OTHER INFORMATION: KK-LC-1 9mer

<400> SEQUENCE: 13

Ser Ser Asn Ser Thr Ala Leu Ala Leu
1               5

<210> SEQ ID NO 14
<211> LENGTH: 9
<212> TYPE: PRT
<213> ORGANISM: artificial sequence
<220> FEATURE:
<223> OTHER INFORMATION: CAGE-1 9mer

<400> SEQUENCE: 14

Ser Thr Asn Ala Leu Ile Gln Pro Val
1               5

<210> SEQ ID NO 15
<211> LENGTH: 9
<212> TYPE: PRT
<213> ORGANISM: artificial sequence
<220> FEATURE:
<223> OTHER INFORMATION: SURVIVIN 9mer

<400> SEQUENCE: 15

Ser Thr Phe Lys Asn Trp Pro Phe Leu
1               5

<210> SEQ ID NO 16
<211> LENGTH: 9
<212> TYPE: PRT
<213> ORGANISM: artificial sequence
<220> FEATURE:
<223> OTHER INFORMATION: MAGE-A2  9mer

<400> SEQUENCE: 16

Phe Ser Thr Thr Ile Asn Tyr Thr Leu
1               5
```

```
<210> SEQ ID NO 17
<211> LENGTH: 9
<212> TYPE: PRT
<213> ORGANISM: artificial sequence
<220> FEATURE:
<223> OTHER INFORMATION: KK-LC-1 9mer

<400> SEQUENCE: 17

Ile Leu Asn Asn Phe Pro His Ser Ile
1               5

<210> SEQ ID NO 18
<211> LENGTH: 9
<212> TYPE: PRT
<213> ORGANISM: artificial sequence
<220> FEATURE:
<223> OTHER INFORMATION: MAGE-A3  9mer

<400> SEQUENCE: 18

Phe Val Gln Glu Asn Tyr Leu Glu Tyr
1               5

<210> SEQ ID NO 19
<211> LENGTH: 9
<212> TYPE: PRT
<213> ORGANISM: artificial sequence
<220> FEATURE:
<223> OTHER INFORMATION: LAGE-1 9mer

<400> SEQUENCE: 19

Ile Thr Met Pro Phe Ser Ser Pro Met
1               5

<210> SEQ ID NO 20
<211> LENGTH: 9
<212> TYPE: PRT
<213> ORGANISM: artificial sequence
<220> FEATURE:
<223> OTHER INFORMATION: MAGE-A3  9mer

<400> SEQUENCE: 20

Ala Ser Ser Ser Leu Gln Leu Val Phe
1               5

<210> SEQ ID NO 21
<211> LENGTH: 9
<212> TYPE: PRT
<213> ORGANISM: artificial sequence
<220> FEATURE:
<223> OTHER INFORMATION: MAGE-A10 9mer

<400> SEQUENCE: 21

Tyr Glu Asp His Phe Pro Leu Leu Phe
1               5

<210> SEQ ID NO 22
<211> LENGTH: 9
<212> TYPE: PRT
<213> ORGANISM: artificial sequence
<220> FEATURE:
<223> OTHER INFORMATION: MAGE-A1  9mer

<400> SEQUENCE: 22

Thr Ser Tyr Val Lys Val Leu Glu Tyr
1               5

<210> SEQ ID NO 23
```

```
<211> LENGTH: 9
<212> TYPE: PRT
<213> ORGANISM: artificial sequence
<220> FEATURE:
<223> OTHER INFORMATION: MAGE-A3  9mer

<400> SEQUENCE: 23

Lys Val Ala Glu Leu Val His Phe Leu
1               5

<210> SEQ ID NO 24
<211> LENGTH: 9
<212> TYPE: PRT
<213> ORGANISM: artificial sequence
<220> FEATURE:
<223> OTHER INFORMATION: KK-LC-1 9mer

<400> SEQUENCE: 24

Asn Thr Asp Asn Asn Leu Ala Val Tyr
1               5

<210> SEQ ID NO 25
<211> LENGTH: 9
<212> TYPE: PRT
<213> ORGANISM: artificial sequence
<220> FEATURE:
<223> OTHER INFORMATION: PRAME 9mer

<400> SEQUENCE: 25

Lys Ala Met Val Gln Ala Trp Pro Phe
1               5

<210> SEQ ID NO 26
<211> LENGTH: 9
<212> TYPE: PRT
<213> ORGANISM: artificial sequence
<220> FEATURE:
<223> OTHER INFORMATION: MAGE-A2  9mer

<400> SEQUENCE: 26

Lys Ala Ser Glu Tyr Leu Gln Leu Val
1               5

<210> SEQ ID NO 27
<211> LENGTH: 9
<212> TYPE: PRT
<213> ORGANISM: artificial sequence
<220> FEATURE:
<223> OTHER INFORMATION: MAGE-A1  9mer

<400> SEQUENCE: 27

Ser Ala Phe Pro Thr Thr Ile Asn Phe
1               5

<210> SEQ ID NO 28
<211> LENGTH: 9
<212> TYPE: PRT
<213> ORGANISM: artificial sequence
<220> FEATURE:
<223> OTHER INFORMATION: SSX1 9mer

<400> SEQUENCE: 28

Met Thr Phe Gly Arg Leu His Arg Ile
1               5

<210> SEQ ID NO 29
<211> LENGTH: 9
```

```
<212> TYPE: PRT
<213> ORGANISM: artificial sequence
<220> FEATURE:
<223> OTHER INFORMATION: MAGE-A1   9mer

<400> SEQUENCE: 29

Arg Ala Leu Ala Glu Thr Ser Tyr Val
1               5

<210> SEQ ID NO 30
<211> LENGTH: 9
<212> TYPE: PRT
<213> ORGANISM: artificial sequence
<220> FEATURE:
<223> OTHER INFORMATION: PRAME 9mer

<400> SEQUENCE: 30

His Val Met Asn Pro Leu Glu Thr Leu
1               5

<210> SEQ ID NO 31
<211> LENGTH: 15
<212> TYPE: PRT
<213> ORGANISM: artificial sequence
<220> FEATURE:
<223> OTHER INFORMATION: DPPA2 15mer

<400> SEQUENCE: 31

Lys Arg Asn Lys Lys Met Met Lys Arg Leu Met Thr Val Glu Lys
1               5                   10                  15

<210> SEQ ID NO 32
<211> LENGTH: 15
<212> TYPE: PRT
<213> ORGANISM: artificial sequence
<220> FEATURE:
<223> OTHER INFORMATION: CAGE-1 15mer

<400> SEQUENCE: 32

Ala Ser Gln Leu Ala Ser Lys Met His Ser Leu Leu Ala Leu Met
1               5                   10                  15

<210> SEQ ID NO 33
<211> LENGTH: 15
<212> TYPE: PRT
<213> ORGANISM: artificial sequence
<220> FEATURE:
<223> OTHER INFORMATION: TSP50 15mer

<400> SEQUENCE: 33

Gly Phe Ser Tyr Glu Gln Asp Pro Thr Leu Arg Asp Pro Glu Ala
1               5                   10                  15

<210> SEQ ID NO 34
<211> LENGTH: 15
<212> TYPE: PRT
<213> ORGANISM: artificial sequence
<220> FEATURE:
<223> OTHER INFORMATION: DPPA2 15mer

<400> SEQUENCE: 34

Lys Ile Glu Val Tyr Leu Arg Leu His Arg His Ala Tyr Pro Glu
1               5                   10                  15

<210> SEQ ID NO 35
<211> LENGTH: 15
<212> TYPE: PRT
```

```
<213> ORGANISM: artificial sequence
<220> FEATURE:
<223> OTHER INFORMATION: HIWI 15mer

<400> SEQUENCE: 35

Gly Phe Thr Thr Ser Ile Leu Gln Tyr Glu Asn Ser Ile Met Leu
1               5                   10                  15

<210> SEQ ID NO 36
<211> LENGTH: 15
<212> TYPE: PRT
<213> ORGANISM: artificial sequence
<220> FEATURE:
<223> OTHER INFORMATION: SURVIVIN 15mer

<400> SEQUENCE: 36

Ala Lys Lys Val Arg Arg Ala Ile Glu Gln Leu Ala Ala Met Asp
1               5                   10                  15

<210> SEQ ID NO 37
<211> LENGTH: 15
<212> TYPE: PRT
<213> ORGANISM: artificial sequence
<220> FEATURE:
<223> OTHER INFORMATION: HIWI 15mer

<400> SEQUENCE: 37

Ser Ile Ala Gly Phe Val Ala Ser Ile Asn Glu Gly Met Thr Arg
1               5                   10                  15

<210> SEQ ID NO 38
<211> LENGTH: 15
<212> TYPE: PRT
<213> ORGANISM: artificial sequence
<220> FEATURE:
<223> OTHER INFORMATION: TSP50 15mer

<400> SEQUENCE: 38

Ser Thr Thr Met Glu Thr Gln Phe Pro Val Ser Glu Gly Lys Val
1               5                   10                  15

<210> SEQ ID NO 39
<211> LENGTH: 15
<212> TYPE: PRT
<213> ORGANISM: artificial sequence
<220> FEATURE:
<223> OTHER INFORMATION: 5T4 15mer

<400> SEQUENCE: 39

Arg Leu Glu Leu Ala Ser Asn His Phe Leu Tyr Leu Pro Arg Asp
1               5                   10                  15

<210> SEQ ID NO 40
<211> LENGTH: 15
<212> TYPE: PRT
<213> ORGANISM: artificial sequence
<220> FEATURE:
<223> OTHER INFORMATION: 5T4 15mer

<400> SEQUENCE: 40

Ser Asn His Phe Leu Tyr Leu Pro Arg Asp Val Leu Ala Gln Leu
1               5                   10                  15

<210> SEQ ID NO 41
<211> LENGTH: 15
<212> TYPE: PRT
<213> ORGANISM: artificial sequence
```

-continued

```
<220> FEATURE:
<223> OTHER INFORMATION: 5T4 15mer

<400> SEQUENCE: 41

Ser Ser Ala Ser Ser Phe Ser Ser Ala Pro Phe Leu Ala Ser
1               5                   10                  15

<210> SEQ ID NO 42
<211> LENGTH: 15
<212> TYPE: PRT
<213> ORGANISM: artificial sequence
<220> FEATURE:
<223> OTHER INFORMATION: MAGE-A2  15mer

<400> SEQUENCE: 42

Arg Glu Asp Ser Val Phe Ala His Pro Arg Lys Leu Leu Met Gln
1               5                   10                  15

<210> SEQ ID NO 43
<211> LENGTH: 15
<212> TYPE: PRT
<213> ORGANISM: artificial sequence
<220> FEATURE:
<223> OTHER INFORMATION: KK-LC-1 15mer

<400> SEQUENCE: 43

Arg Asn Thr Gly Glu Met Ser Ser Asn Ser Thr Ala Leu Ala Leu
1               5                   10                  15

<210> SEQ ID NO 44
<211> LENGTH: 15
<212> TYPE: PRT
<213> ORGANISM: artificial sequence
<220> FEATURE:
<223> OTHER INFORMATION: CAGE-1 15mer

<400> SEQUENCE: 44

Asn Ile Glu Asn Tyr Ser Thr Asn Ala Leu Ile Gln Pro Val Asp
1               5                   10                  15

<210> SEQ ID NO 45
<211> LENGTH: 15
<212> TYPE: PRT
<213> ORGANISM: artificial sequence
<220> FEATURE:
<223> OTHER INFORMATION: SURVIVIN 15mer

<400> SEQUENCE: 45

Lys Asp His Arg Ile Ser Thr Phe Lys Asn Trp Pro Phe Leu Glu
1               5                   10                  15

<210> SEQ ID NO 46
<211> LENGTH: 15
<212> TYPE: PRT
<213> ORGANISM: artificial sequence
<220> FEATURE:
<223> OTHER INFORMATION: MAGE-A2   15mer

<400> SEQUENCE: 46

Ser Phe Ser Thr Thr Ile Asn Tyr Thr Leu Trp Arg Gln Ser Asp
1               5                   10                  15

<210> SEQ ID NO 47
<211> LENGTH: 15
<212> TYPE: PRT
<213> ORGANISM: artificial sequence
<220> FEATURE:
```

```
<223> OTHER INFORMATION: KK-LC-1 15mer

<400> SEQUENCE: 47

Ser Arg Asp Ile Leu Asn Asn Phe Pro His Ser Ile Ala Arg Gln
1               5                   10                  15

<210> SEQ ID NO 48
<211> LENGTH: 15
<212> TYPE: PRT
<213> ORGANISM: artificial sequence
<220> FEATURE:
<223> OTHER INFORMATION: MAGE-A3  15mer

<400> SEQUENCE: 48

Leu Thr Gln His Phe Val Gln Glu Asn Tyr Leu Glu Tyr Arg Gln
1               5                   10                  15

<210> SEQ ID NO 49
<211> LENGTH: 15
<212> TYPE: PRT
<213> ORGANISM: artificial sequence
<220> FEATURE:
<223> OTHER INFORMATION: LAGE-1 15mer

<400> SEQUENCE: 49

Ile Thr Met Pro Phe Ser Ser Pro Met Glu Ala Glu Leu Val Arg
1               5                   10                  15

<210> SEQ ID NO 50
<211> LENGTH: 15
<212> TYPE: PRT
<213> ORGANISM: artificial sequence
<220> FEATURE:
<223> OTHER INFORMATION: MAGE-A3  15mer

<400> SEQUENCE: 50

Lys Ala Ser Ser Ser Leu Gln Leu Val Phe Gly Ile Glu Leu Met
1               5                   10                  15

<210> SEQ ID NO 51
<211> LENGTH: 15
<212> TYPE: PRT
<213> ORGANISM: artificial sequence
<220> FEATURE:
<223> OTHER INFORMATION: MAGE-A10 15mer

<400> SEQUENCE: 51

Arg Asn Tyr Glu Asp His Phe Pro Leu Leu Phe Ser Glu Ala Ser
1               5                   10                  15

<210> SEQ ID NO 52
<211> LENGTH: 15
<212> TYPE: PRT
<213> ORGANISM: artificial sequence
<220> FEATURE:
<223> OTHER INFORMATION: MAGE-A1  15mer

<400> SEQUENCE: 52

Glu Thr Ser Tyr Val Lys Val Leu Glu Tyr Val Ile Lys Val Ser
1               5                   10                  15

<210> SEQ ID NO 53
<211> LENGTH: 15
<212> TYPE: PRT
<213> ORGANISM: artificial sequence
<220> FEATURE:
<223> OTHER INFORMATION: MAGE-A3  15mer
```

```
<400> SEQUENCE: 53

Gln Ala Ala Leu Ser Arg Lys Val Ala Glu Leu Val His Phe Leu
1               5                   10                  15

<210> SEQ ID NO 54
<211> LENGTH: 15
<212> TYPE: PRT
<213> ORGANISM: artificial sequence
<220> FEATURE:
<223> OTHER INFORMATION: KK-LC-1 15mer

<400> SEQUENCE: 54

Ser Asn Thr Asp Asn Asn Leu Ala Val Tyr Asp Leu Ser Arg Asp
1               5                   10                  15

<210> SEQ ID NO 55
<211> LENGTH: 15
<212> TYPE: PRT
<213> ORGANISM: artificial sequence
<220> FEATURE:
<223> OTHER INFORMATION: PRAME 15mer

<400> SEQUENCE: 55

Arg His Ser Gln Thr Leu Lys Ala Met Val Gln Ala Trp Pro Phe
1               5                   10                  15

<210> SEQ ID NO 56
<211> LENGTH: 15
<212> TYPE: PRT
<213> ORGANISM: artificial sequence
<220> FEATURE:
<223> OTHER INFORMATION: MAGE-A2  15mer

<400> SEQUENCE: 56

Ser Lys Ala Ser Glu Tyr Leu Gln Leu Val Phe Gly Ile Glu Val
1               5                   10                  15

<210> SEQ ID NO 57
<211> LENGTH: 15
<212> TYPE: PRT
<213> ORGANISM: artificial sequence
<220> FEATURE:
<223> OTHER INFORMATION: MAGE-A1  15mer

<400> SEQUENCE: 57

Ser Ala Phe Pro Thr Thr Ile Asn Phe Thr Arg Gln Arg Gln Pro
1               5                   10                  15

<210> SEQ ID NO 58
<211> LENGTH: 15
<212> TYPE: PRT
<213> ORGANISM: artificial sequence
<220> FEATURE:
<223> OTHER INFORMATION: SSX1 15mer

<400> SEQUENCE: 58

Gln Val Glu His Pro Gln Met Thr Phe Gly Arg Leu His Arg Ile
1               5                   10                  15

<210> SEQ ID NO 59
<211> LENGTH: 15
<212> TYPE: PRT
<213> ORGANISM: artificial sequence
<220> FEATURE:
<223> OTHER INFORMATION: MAGE-A1  15mer
```

-continued

```
<400> SEQUENCE: 59

Pro Arg Ala Leu Ala Glu Thr Ser Tyr Val Lys Val Leu Glu Tyr
1               5                   10                  15

<210> SEQ ID NO 60
<211> LENGTH: 15
<212> TYPE: PRT
<213> ORGANISM: artificial sequence
<220> FEATURE:
<223> OTHER INFORMATION: PRAME 15mer

<400> SEQUENCE: 60

Asp Gln Leu Leu Arg His Val Met Asn Pro Leu Glu Thr Leu Ser
1               5                   10                  15

<210> SEQ ID NO 61
<211> LENGTH: 30
<212> TYPE: PRT
<213> ORGANISM: artificial sequence
<220> FEATURE:
<223> OTHER INFORMATION: GC1311-01 CAGE-1/DPPA2

<400> SEQUENCE: 61

Ala Ser Gln Leu Ala Ser Lys Met His Ser Leu Leu Ala Leu Met Lys
1               5                   10                  15

Arg Asn Lys Lys Met Met Lys Arg Leu Met Thr Val Glu Lys
            20                  25                  30

<210> SEQ ID NO 62
<211> LENGTH: 30
<212> TYPE: PRT
<213> ORGANISM: artificial sequence
<220> FEATURE:
<223> OTHER INFORMATION: GC1311-02 HIWI/MAGE-A10

<400> SEQUENCE: 62

Gly Phe Thr Thr Ser Ile Leu Gln Tyr Glu Asn Ser Ile Met Leu Arg
1               5                   10                  15

Asn Tyr Glu Asp His Phe Pro Leu Leu Phe Ser Glu Ala Ser
            20                  25                  30

<210> SEQ ID NO 63
<211> LENGTH: 30
<212> TYPE: PRT
<213> ORGANISM: artificial sequence
<220> FEATURE:
<223> OTHER INFORMATION: GC1311-03 MAGE-A2/SURVIVIN

<400> SEQUENCE: 63

Ser Phe Ser Thr Thr Ile Asn Tyr Thr Leu Trp Arg Gln Ser Asp Ala
1               5                   10                  15

Lys Lys Val Arg Arg Ala Ile Glu Gln Leu Ala Ala Met Asp
            20                  25                  30

<210> SEQ ID NO 64
<211> LENGTH: 30
<212> TYPE: PRT
<213> ORGANISM: artificial sequence
<220> FEATURE:
<223> OTHER INFORMATION: GC1311-04 KK-LC-1/SURVIVIN

<400> SEQUENCE: 64

Arg Asn Thr Gly Glu Met Ser Ser Asn Ser Thr Ala Leu Ala Leu Lys
1               5                   10                  15
```

Asp His Arg Ile Ser Thr Phe Lys Asn Trp Pro Phe Leu Glu
            20                  25                  30

<210> SEQ ID NO 65
<211> LENGTH: 30
<212> TYPE: PRT
<213> ORGANISM: artificial sequence
<220> FEATURE:
<223> OTHER INFORMATION: GC1311-05 KK-LC-1/HIWI

<400> SEQUENCE: 65

Ser Arg Asp Ile Leu Asn Asn Phe Pro His Ser Ile Ala Arg Gln Ser
1               5                   10                  15

Ile Ala Gly Phe Val Ala Ser Ile Asn Glu Gly Met Thr Arg
            20                  25                  30

<210> SEQ ID NO 66
<211> LENGTH: 30
<212> TYPE: PRT
<213> ORGANISM: artificial sequence
<220> FEATURE:
<223> OTHER INFORMATION: GC1311-06 MAGE-A2/PRAME

<400> SEQUENCE: 66

Arg Glu Asp Ser Val Phe Ala His Pro Arg Lys Leu Leu Met Gln Asp
1               5                   10                  15

Gln Leu Leu Arg His Val Met Asn Pro Leu Glu Thr Leu Ser
            20                  25                  30

<210> SEQ ID NO 67
<211> LENGTH: 30
<212> TYPE: PRT
<213> ORGANISM: artificial sequence
<220> FEATURE:
<223> OTHER INFORMATION: GC1311-07 5T4/5T4

<400> SEQUENCE: 67

Arg Leu Glu Leu Ala Ser Asn His Phe Leu Tyr Leu Pro Arg Asp Ser
1               5                   10                  15

Asn His Phe Leu Tyr Leu Pro Arg Asp Val Leu Ala Gln Leu
            20                  25                  30

<210> SEQ ID NO 68
<211> LENGTH: 30
<212> TYPE: PRT
<213> ORGANISM: artificial sequence
<220> FEATURE:
<223> OTHER INFORMATION: GC1311-08 5T4/TSP50

<400> SEQUENCE: 68

Ser Ser Ala Ser Ser Phe Ser Ser Ser Ala Pro Phe Leu Ala Ser Ser
1               5                   10                  15

Thr Thr Met Glu Thr Gln Phe Pro Val Ser Glu Gly Lys Val
            20                  25                  30

<210> SEQ ID NO 69
<211> LENGTH: 30
<212> TYPE: PRT
<213> ORGANISM: artificial sequence
<220> FEATURE:
<223> OTHER INFORMATION: GC1311-09 TSP50/MAGE-A1

<400> SEQUENCE: 69

Gly Phe Ser Tyr Glu Gln Asp Pro Thr Leu Arg Asp Pro Glu Ala Pro
1               5                   10                  15

```
Arg Ala Leu Ala Glu Thr Ser Tyr Val Lys Val Leu Glu Tyr
            20                  25                  30

<210> SEQ ID NO 70
<211> LENGTH: 30
<212> TYPE: PRT
<213> ORGANISM: artificial sequence
<220> FEATURE:
<223> OTHER INFORMATION: GC1311-10 KK-LC-1/SSX1

<400> SEQUENCE: 70

Ser Asn Thr Asp Asn Asn Leu Ala Val Tyr Asp Leu Ser Arg Asp Gln
1               5                   10                  15

Val Glu His Pro Gln Met Thr Phe Gly Arg Leu His Arg Ile
            20                  25                  30

<210> SEQ ID NO 71
<211> LENGTH: 30
<212> TYPE: PRT
<213> ORGANISM: artificial sequence
<220> FEATURE:
<223> OTHER INFORMATION: GC1311-11 DPPA2/LAGE-1

<400> SEQUENCE: 71

Lys Ile Glu Val Tyr Leu Arg Leu His Arg His Ala Tyr Pro Glu Ile
1               5                   10                  15

Thr Met Pro Phe Ser Ser Pro Met Glu Ala Glu Leu Val Arg
            20                  25                  30

<210> SEQ ID NO 72
<211> LENGTH: 30
<212> TYPE: PRT
<213> ORGANISM: artificial sequence
<220> FEATURE:
<223> OTHER INFORMATION: GC1311-12 MAGE-A1/MAGE-A3

<400> SEQUENCE: 72

Glu Thr Ser Tyr Val Lys Val Leu Glu Tyr Val Ile Lys Val Ser Leu
1               5                   10                  15

Thr Gln His Phe Val Gln Glu Asn Tyr Leu Glu Tyr Arg Gln
            20                  25                  30

<210> SEQ ID NO 73
<211> LENGTH: 30
<212> TYPE: PRT
<213> ORGANISM: artificial sequence
<220> FEATURE:
<223> OTHER INFORMATION: GC1311-13 MAGE-A3/CAGE-1

<400> SEQUENCE: 73

Gln Ala Ala Leu Ser Arg Lys Val Ala Glu Leu Val His Phe Leu Asn
1               5                   10                  15

Ile Glu Asn Tyr Ser Thr Asn Ala Leu Ile Gln Pro Val Asp
            20                  25                  30

<210> SEQ ID NO 74
<211> LENGTH: 30
<212> TYPE: PRT
<213> ORGANISM: artificial sequence
<220> FEATURE:
<223> OTHER INFORMATION: GC1311-14 PRAME/MAGE-A3

<400> SEQUENCE: 74

Arg His Ser Gln Thr Leu Lys Ala Met Val Gln Ala Trp Pro Phe Lys
```

```
                1               5                  10                    15
Ala  Ser  Ser  Ser  Leu  Gln  Leu  Val  Phe  Gly  Ile  Glu  Leu  Met
                 20                  25                     30
```

<210> SEQ ID NO 75
<211> LENGTH: 30
<212> TYPE: PRT
<213> ORGANISM: artificial sequence
<220> FEATURE:
<223> OTHER INFORMATION: GC1311-15 MAGE-A2/MAGE-A1

<400> SEQUENCE: 75

```
Ser  Lys  Ala  Ser  Glu  Tyr  Leu  Gln  Leu  Val  Phe  Gly  Ile  Glu  Val  Ser
 1                  5                     10                         15

Ala  Phe  Pro  Thr  Thr  Ile  Asn  Phe  Thr  Arg  Gln  Arg  Gln  Pro
                 20                   25                     30
```

<210> SEQ ID NO 76
<211> LENGTH: 298
<212> TYPE: PRT
<213> ORGANISM: Homo sapiens

<400> SEQUENCE: 76

```
Met  Ser  Asp  Ala  Asn  Leu  Asp  Ser  Ser  Lys  Lys  Asn  Phe  Leu  Glu  Gly
 1                  5                     10                         15

Glu  Val  Asp  Asp  Glu  Glu  Ser  Val  Ile  Leu  Thr  Leu  Val  Pro  Val  Lys
                 20                   25                     30

Asp  Asp  Ala  Asn  Met  Glu  Gln  Met  Glu  Pro  Ser  Val  Ser  Ser  Thr  Ser
         35                      40                     45

Asp  Val  Lys  Leu  Glu  Lys  Pro  Lys  Lys  Tyr  Asn  Pro  Gly  His  Leu  Leu
     50                      55                     60

Gln  Thr  Asn  Glu  Gln  Phe  Thr  Ala  Pro  Gln  Lys  Ala  Arg  Cys  Lys  Ile
65                       70                     75                       80

Pro  Ala  Leu  Pro  Leu  Pro  Thr  Ile  Leu  Pro  Pro  Ile  Asn  Lys  Val  Cys
                 85                      90                     95

Arg  Asp  Thr  Leu  Arg  Asp  Trp  Cys  Gln  Gln  Leu  Gly  Leu  Ser  Thr  Asn
             100                     105                    110

Gly  Lys  Lys  Ile  Glu  Val  Tyr  Leu  Arg  Leu  His  Arg  His  Ala  Tyr  Pro
         115                     120                    125

Glu  Gln  Arg  Gln  Asp  Met  Pro  Glu  Met  Ser  Gln  Glu  Thr  Arg  Leu  Gln
     130                     135                    140

Arg  Cys  Ser  Arg  Lys  Arg  Lys  Ala  Val  Thr  Lys  Arg  Ala  Arg  Leu  Gln
145                      150                    155                      160

Arg  Ser  Tyr  Glu  Met  Asn  Glu  Arg  Ala  Glu  Glu  Thr  Asn  Thr  Val  Glu
                 165                    170                    175

Val  Ile  Thr  Ser  Ala  Pro  Gly  Ala  Met  Leu  Ala  Ser  Trp  Ala  Arg  Ile
             180                    185                    190

Ala  Ala  Arg  Ala  Val  Gln  Pro  Lys  Ala  Leu  Asn  Ser  Cys  Ser  Ile  Pro
         195                    200                    205

Val  Ser  Val  Glu  Ala  Phe  Leu  Met  Gln  Ala  Ser  Gly  Val  Arg  Trp  Cys
     210                    215                    220

Val  Val  His  Gly  Arg  Leu  Leu  Ser  Ala  Asp  Thr  Lys  Gly  Trp  Val  Arg
225                      230                    235                      240

Leu  Gln  Phe  His  Ala  Gly  Gln  Ala  Trp  Val  Pro  Thr  Thr  His  Arg  Arg
                 245                    250                    255

Met  Ile  Ser  Leu  Phe  Leu  Pro  Ala  Cys  Ile  Phe  Pro  Ser  Pro  Gly
             260                    265                    270
```

-continued

Ile Glu Asp Asn Met Leu Cys Pro Asp Cys Ala Lys Arg Asn Lys Lys
275 280 285

Met Met Lys Arg Leu Met Thr Val Glu Lys
290 295

<210> SEQ ID NO 77
<211> LENGTH: 777
<212> TYPE: PRT
<213> ORGANISM: Homo sapiens

<400> SEQUENCE: 77

Met Asn Lys Asp Tyr Gln Lys Phe Trp Ser Ser Pro Ser Asp Pro Val
1               5                   10                  15

His Phe Glu Val Asp Thr Ser His Glu Lys Val Glu Ser Met Ser Glu
                20                  25                  30

Ser Asp Thr Met Asn Val Ser Asn Leu Ser Gln Gly Val Met Leu Ser
            35                  40                  45

His Ser Pro Ile Cys Met Glu Thr Thr Gly Thr Thr Cys Asp Leu Pro
        50                  55                  60

Gln Asn Glu Ile Lys Asn Phe Glu Arg Glu Asn Glu Tyr Glu Ser Thr
65                  70                  75                  80

Leu Cys Glu Asp Ala Tyr Gly Thr Leu Asp Asn Leu Leu Asn Asp Asn
                85                  90                  95

Asn Ile Glu Asn Tyr Ser Thr Asn Ala Leu Ile Gln Pro Val Asp Thr
                100                 105                 110

Ile Ser Ile Ser Ser Leu Arg Gln Phe Glu Thr Val Cys Lys Phe His
            115                 120                 125

Trp Val Glu Ala Phe Asp Asp Glu Met Thr Glu Lys Pro Glu Phe Gln
        130                 135                 140

Ser Gln Val Tyr Asn Tyr Ala Lys Asp Asn Asn Ile Lys Gln Asp Ser
145                 150                 155                 160

Phe Lys Glu Glu Asn Pro Met Glu Thr Ser Val Ser Ala Asn Thr Asp
                165                 170                 175

Gln Leu Gly Asn Glu Tyr Phe Arg Gln Pro Pro Pro Arg Ser Pro Pro
                180                 185                 190

Leu Ile His Cys Ser Gly Glu Met Leu Lys Phe Thr Glu Lys Ser Leu
            195                 200                 205

Ala Lys Ser Ile Ala Lys Glu Ser Ala Leu Asn Pro Ser Gln Pro Pro
        210                 215                 220

Ser Phe Leu Cys Lys Thr Ala Val Pro Ser Lys Glu Ile Gln Asn Tyr
225                 230                 235                 240

Gly Glu Ile Pro Glu Met Ser Val Ser Tyr Glu Lys Glu Val Thr Ala
                245                 250                 255

Glu Gly Val Glu Arg Pro Glu Ile Val Ser Thr Trp Ser Ser Ala Gly
                260                 265                 270

Ile Ser Trp Arg Ser Glu Ala Cys Arg Glu Asn Cys Glu Met Pro Asp
            275                 280                 285

Trp Glu Gln Ser Ala Glu Ser Leu Gln Pro Val Gln Glu Asp Met Ala
        290                 295                 300

Leu Asn Glu Val Leu Gln Lys Leu Lys His Thr Asn Arg Lys Gln Glu
305                 310                 315                 320

Val Arg Ile Gln Glu Leu Gln Cys Ser Asn Leu Tyr Leu Glu Lys Arg
                325                 330                 335

Val Lys Glu Leu Gln Met Lys Ile Thr Lys Gln Gln Val Phe Ile Asp

```
              340             345             350
Val Ile Asn Lys Leu Lys Glu Asn Val Glu Glu Leu Ile Glu Asp Lys
            355                 360                 365
Tyr Lys Ile Ile Leu Glu Lys Asn Asp Thr Lys Lys Thr Leu Gln Asn
        370                 375                 380
Leu Glu Glu Val Leu Ala Asn Thr Gln Lys His Leu Gln Glu Ser Arg
385                 390                 395                 400
Asn Asp Lys Glu Met Leu Gln Leu Gln Phe Lys Lys Ile Lys Ala Asn
                405                 410                 415
Tyr Val Cys Leu Gln Glu Arg Tyr Met Thr Glu Met Gln Gln Lys Asn
            420                 425                 430
Lys Ser Val Ser Gln Tyr Leu Glu Met Asp Lys Thr Leu Ser Lys Lys
        435                 440                 445
Glu Glu Glu Val Glu Arg Leu Gln Leu Lys Lys Glu Leu Glu Lys
        450                 455                 460
Ala Thr Ala Ser Ala Leu Asp Leu Leu Lys Arg Glu Lys Glu Ala Gln
465                 470                 475                 480
Glu Gln Glu Phe Leu Ser Leu Gln Glu Phe Gln Lys Leu Glu Lys
                485                 490                 495
Glu Asn Leu Glu Glu Arg Gln Lys Leu Lys Ser Arg Leu Glu Lys Leu
            500                 505                 510
Leu Thr Gln Val Arg Asn Leu Gln Phe Met Ser Glu Asn Glu Arg Thr
        515                 520                 525
Lys Asn Ile Lys Leu Gln Gln Gln Ile Asn Glu Val Lys Asn Glu Asn
        530                 535                 540
Ala Lys Leu Lys Gln Gln Val Ala Arg Ser Glu Glu Gln Asn Tyr Val
545                 550                 555                 560
Pro Lys Phe Glu Thr Ala Gln Leu Lys Asp Gln Leu Glu Glu Val Leu
                565                 570                 575
Lys Ser Asp Ile Thr Lys Asp Thr Lys Thr Thr His Ser Asn Leu Leu
            580                 585                 590
Pro Asp Cys Ser Pro Cys Glu Glu Arg Leu Asn Pro Ala Asp Ile Lys
        595                 600                 605
Arg Ala Ser Gln Leu Ala Ser Lys Met His Ser Leu Leu Ala Leu Met
        610                 615                 620
Val Gly Leu Leu Thr Cys Gln Asp Ile Ile Asn Ser Asp Ala Glu His
625                 630                 635                 640
Phe Lys Glu Ser Glu Lys Val Ser Asp Ile Met Leu Gln Lys Leu Lys
                645                 650                 655
Ser Leu His Leu Lys Lys Lys Thr Leu Asp Lys Glu Val Ile Asp Cys
            660                 665                 670
Asp Ser Asp Glu Ala Lys Ser Ile Arg Asp Val Pro Thr Leu Leu Gly
        675                 680                 685
Ala Lys Leu Asp Lys Tyr His Ser Leu Asn Glu Glu Leu Asp Phe Leu
        690                 695                 700
Val Thr Ser Tyr Glu Glu Ile Ile Glu Cys Ala Asp Gln Arg Leu Ala
705                 710                 715                 720
Ile Ser His Ser Gln Ile Ala His Leu Glu Glu Arg Asn Lys His Leu
                725                 730                 735
Glu Asp Leu Ile Arg Lys Pro Arg Glu Lys Ala Arg Lys Pro Arg Ser
            740                 745                 750
Lys Ser Leu Glu Asn His Pro Lys Ser Met Thr Met Met Pro Ala Leu
        755                 760                 765
```

```
Phe Lys Glu Asn Arg Asn Asp Leu Asp
    770                 775
```

<210> SEQ ID NO 78
<211> LENGTH: 385
<212> TYPE: PRT
<213> ORGANISM: Homo sapiens

<400> SEQUENCE: 78

```
Met Gly Arg Trp Cys Gln Thr Val Ala Arg Gly Gln Arg Pro Arg Thr
1               5                   10                  15

Ser Ala Pro Ser Arg Ala Gly Ala Leu Leu Leu Leu Leu Leu Leu Leu
            20                  25                  30

Arg Ser Ala Gly Cys Trp Gly Ala Gly Glu Ala Pro Gly Ala Leu Ser
        35                  40                  45

Thr Ala Asp Pro Ala Asp Gln Ser Val Gln Cys Val Pro Lys Ala Thr
    50                  55                  60

Cys Pro Ser Ser Arg Pro Arg Leu Leu Trp Gln Thr Pro Thr Thr Gln
65                  70                  75                  80

Thr Leu Pro Ser Thr Thr Met Glu Thr Gln Phe Pro Val Ser Glu Gly
                85                  90                  95

Lys Val Asp Pro Tyr Arg Ser Cys Gly Phe Ser Tyr Glu Gln Asp Pro
            100                 105                 110

Thr Leu Arg Asp Pro Glu Ala Val Ala Arg Arg Trp Pro Trp Met Val
        115                 120                 125

Ser Val Arg Ala Asn Gly Thr His Ile Cys Ala Gly Thr Ile Ile Ala
130                 135                 140

Ser Gln Trp Val Leu Thr Val Ala His Cys Leu Ile Trp Arg Asp Val
145                 150                 155                 160

Ile Tyr Ser Val Arg Val Gly Ser Pro Trp Ile Asp Gln Met Thr Gln
                165                 170                 175

Thr Ala Ser Asp Val Pro Val Leu Gln Val Ile Met His Ser Arg Tyr
            180                 185                 190

Arg Ala Gln Arg Phe Trp Ser Trp Val Gly Gln Ala Asn Asp Ile Gly
        195                 200                 205

Leu Leu Lys Leu Lys Gln Glu Leu Lys Tyr Ser Asn Tyr Val Arg Pro
    210                 215                 220

Ile Cys Leu Pro Gly Thr Asp Tyr Val Leu Lys Asp His Ser Arg Cys
225                 230                 235                 240

Thr Val Thr Gly Trp Gly Leu Ser Lys Ala Asp Gly Met Trp Pro Gln
                245                 250                 255

Phe Arg Thr Ile Gln Glu Lys Glu Val Ile Ile Leu Asn Asn Lys Glu
            260                 265                 270

Cys Asp Asn Phe Tyr His Asn Phe Thr Lys Ile Pro Thr Leu Val Gln
        275                 280                 285

Ile Ile Lys Ser Gln Met Met Cys Ala Glu Asp Thr His Arg Glu Lys
    290                 295                 300

Phe Cys Tyr Glu Leu Thr Gly Glu Pro Leu Val Cys Ser Met Glu Gly
305                 310                 315                 320

Thr Trp Tyr Leu Val Gly Leu Val Ser Trp Gly Ala Gly Cys Gln Lys
                325                 330                 335

Ser Glu Ala Pro Pro Ile Tyr Leu Gln Val Ser Ser Tyr Gln His Trp
            340                 345                 350

Ile Trp Asp Cys Leu Asn Gly Gln Ala Leu Ala Leu Pro Ala Pro Ser
```

355                 360                 365
Arg Thr Leu Leu Leu Ala Leu Pro Leu Pro Leu Ser Leu Leu Ala Ala
    370                 375                 380

Leu
385

<210> SEQ ID NO 79
<211> LENGTH: 861
<212> TYPE: PRT
<213> ORGANISM: Homo sapiens

<400> SEQUENCE: 79

Met Thr Gly Arg Ala Arg Ala Arg Ala Arg Gly Arg Ala Arg Gly Gln
1               5                   10                  15

Glu Thr Ala Gln Leu Val Gly Ser Thr Ala Ser Gln Gln Pro Gly Tyr
            20                  25                  30

Ile Gln Pro Arg Pro Gln Pro Pro Ala Glu Gly Glu Leu Phe Gly
        35                  40                  45

Arg Gly Arg Gln Arg Gly Thr Ala Gly Gly Thr Ala Lys Ser Gln Gly
50                  55                  60

Leu Gln Ile Ser Ala Gly Phe Gln Glu Leu Ser Leu Ala Glu Arg Gly
65                  70                  75                  80

Gly Arg Arg Arg Asp Phe His Asp Leu Gly Val Asn Thr Arg Gln Asn
                85                  90                  95

Leu Asp His Val Lys Glu Ser Lys Thr Gly Ser Ser Gly Ile Ile Val
            100                 105                 110

Arg Leu Ser Thr Asn His Phe Arg Leu Thr Ser Arg Pro Gln Trp Ala
        115                 120                 125

Leu Tyr Gln Tyr His Ile Asp Tyr Asn Pro Leu Met Glu Ala Arg Arg
    130                 135                 140

Leu Arg Ser Ala Leu Leu Phe Gln His Glu Asp Leu Ile Gly Lys Cys
145                 150                 155                 160

His Ala Phe Asp Gly Thr Ile Leu Phe Leu Pro Lys Arg Leu Gln Gln
                165                 170                 175

Lys Val Thr Glu Val Phe Ser Lys Thr Arg Asn Gly Glu Asp Val Arg
            180                 185                 190

Ile Thr Ile Thr Leu Thr Asn Glu Leu Pro Pro Thr Ser Pro Thr Cys
        195                 200                 205

Leu Gln Phe Tyr Asn Ile Ile Phe Arg Arg Leu Leu Lys Ile Met Asn
    210                 215                 220

Leu Gln Gln Ile Gly Arg Asn Tyr Tyr Asn Pro Asn Asp Pro Ile Asp
225                 230                 235                 240

Ile Pro Ser His Arg Leu Val Ile Trp Pro Gly Phe Thr Thr Ser Ile
                245                 250                 255

Leu Gln Tyr Glu Asn Ser Ile Met Leu Cys Thr Asp Val Ser His Lys
            260                 265                 270

Val Leu Arg Ser Glu Thr Val Leu Asp Phe Met Phe Asn Phe Tyr His
        275                 280                 285

Gln Thr Glu Glu His Lys Phe Gln Glu Gln Val Ser Lys Glu Leu Ile
    290                 295                 300

Gly Leu Val Val Leu Thr Lys Tyr Asn Asn Lys Thr Tyr Arg Val Asp
305                 310                 315                 320

Asp Ile Asp Trp Asp Gln Asn Pro Lys Ser Thr Phe Lys Lys Ala Asp
                325                 330                 335

Gly Ser Glu Val Ser Phe Leu Glu Tyr Tyr Arg Lys Gln Tyr Asn Gln
            340                 345                 350

Glu Ile Thr Asp Leu Lys Gln Pro Val Leu Val Ser Gln Pro Lys Arg
            355                 360                 365

Arg Arg Gly Pro Gly Thr Leu Pro Gly Pro Ala Met Leu Ile Pro
        370                 375                 380

Glu Leu Cys Tyr Leu Thr Gly Leu Thr Asp Lys Met Arg Asn Asp Phe
385                 390                 395                 400

Asn Val Met Lys Asp Leu Ala Val His Thr Arg Leu Thr Pro Glu Gln
            405                 410                 415

Arg Gln Arg Glu Val Gly Arg Leu Ile Asp Tyr Ile His Lys Asn Asp
            420                 425                 430

Asn Val Gln Arg Glu Leu Arg Asp Trp Gly Leu Ser Phe Asp Ser Asn
            435                 440                 445

Leu Leu Ser Phe Ser Gly Arg Ile Leu Gln Thr Glu Lys Ile His Gln
450                 455                 460

Gly Gly Lys Thr Phe Asp Tyr Asn Pro Gln Phe Ala Asp Trp Ser Lys
465                 470                 475                 480

Glu Thr Arg Gly Ala Pro Leu Ile Ser Val Lys Pro Leu Asp Asn Trp
            485                 490                 495

Leu Leu Ile Tyr Thr Arg Arg Asn Tyr Glu Ala Ala Asn Ser Leu Ile
            500                 505                 510

Gln Asn Leu Phe Lys Val Thr Pro Ala Met Gly Met Gln Met Arg Lys
            515                 520                 525

Ala Ile Met Ile Glu Val Asp Asp Arg Thr Glu Ala Tyr Leu Arg Val
            530                 535                 540

Leu Gln Gln Lys Val Thr Ala Asp Thr Gln Ile Val Val Cys Leu Leu
545                 550                 555                 560

Ser Ser Asn Arg Lys Asp Lys Tyr Asp Ala Ile Lys Lys Tyr Leu Cys
            565                 570                 575

Thr Asp Cys Pro Thr Pro Ser Gln Cys Val Val Ala Arg Thr Leu Gly
            580                 585                 590

Lys Gln Gln Thr Val Met Ala Ile Ala Thr Lys Ile Ala Leu Gln Met
            595                 600                 605

Asn Cys Lys Met Gly Gly Glu Leu Trp Arg Val Asp Ile Pro Leu Lys
            610                 615                 620

Leu Val Met Ile Val Gly Ile Asp Cys Tyr His Asp Met Thr Ala Gly
625                 630                 635                 640

Arg Arg Ser Ile Ala Gly Phe Val Ala Ser Ile Asn Glu Gly Met Thr
            645                 650                 655

Arg Trp Phe Ser Arg Cys Ile Phe Gln Asp Arg Gly Gln Glu Leu Val
            660                 665                 670

Asp Gly Leu Lys Val Cys Leu Gln Ala Ala Leu Arg Ala Trp Asn Ser
            675                 680                 685

Cys Asn Glu Tyr Met Pro Ser Arg Ile Ile Val Tyr Arg Asp Gly Val
            690                 695                 700

Gly Asp Gly Gln Leu Lys Thr Leu Val Asn Tyr Glu Val Pro Gln Phe
705                 710                 715                 720

Leu Asp Cys Leu Lys Ser Ile Gly Arg Gly Tyr Asn Pro Arg Leu Thr
            725                 730                 735

Val Ile Val Val Lys Lys Arg Val Asn Thr Arg Phe Phe Ala Gln Ser
            740                 745                 750

Gly Gly Arg Leu Gln Asn Pro Leu Pro Gly Thr Val Ile Asp Val Glu

```
                755                 760                 765
Val Thr Arg Pro Glu Trp Tyr Asp Phe Phe Ile Val Ser Gln Ala Val
770                 775                 780

Arg Ser Gly Ser Val Ser Pro Thr His Tyr Asn Val Ile Tyr Asp Asn
785                 790                 795                 800

Ser Gly Leu Lys Pro Asp His Ile Gln Arg Leu Thr Tyr Lys Leu Cys
                805                 810                 815

His Ile Tyr Tyr Asn Trp Pro Gly Val Ile Arg Val Pro Ala Pro Cys
                820                 825                 830

Gln Tyr Ala His Lys Leu Ala Phe Leu Val Gly Gln Ser Ile His Arg
                835                 840                 845

Glu Pro Asn Leu Ser Leu Ser Asn Arg Leu Tyr Tyr Leu
850                 855                 860

<210> SEQ ID NO 80
<211> LENGTH: 142
<212> TYPE: PRT
<213> ORGANISM: Homo sapiens

<400> SEQUENCE: 80

Met Gly Ala Pro Thr Leu Pro Pro Ala Trp Gln Pro Phe Leu Lys Asp
1               5                   10                  15

His Arg Ile Ser Thr Phe Lys Asn Trp Pro Phe Leu Glu Gly Cys Ala
                20                  25                  30

Cys Thr Pro Glu Arg Met Ala Glu Ala Gly Phe Ile His Cys Pro Thr
            35                  40                  45

Glu Asn Glu Pro Asp Leu Ala Gln Cys Phe Phe Cys Phe Lys Glu Leu
50                  55                  60

Glu Gly Trp Glu Pro Asp Asp Asp Pro Ile Glu Glu His Lys Lys His
65                  70                  75                  80

Ser Ser Gly Cys Ala Phe Leu Ser Val Lys Lys Gln Phe Glu Glu Leu
                85                  90                  95

Thr Leu Gly Glu Phe Leu Lys Leu Asp Arg Glu Arg Ala Lys Asn Lys
                100                 105                 110

Ile Ala Lys Glu Thr Asn Asn Lys Lys Lys Glu Phe Glu Glu Thr Ala
            115                 120                 125

Lys Lys Val Arg Arg Ala Ile Glu Gln Leu Ala Ala Met Asp
        130                 135                 140

<210> SEQ ID NO 81
<211> LENGTH: 420
<212> TYPE: PRT
<213> ORGANISM: Homo sapiens

<400> SEQUENCE: 81

Met Pro Gly Gly Cys Ser Arg Gly Pro Ala Ala Gly Asp Gly Arg Leu
1               5                   10                  15

Arg Leu Ala Arg Leu Ala Leu Val Leu Leu Gly Trp Val Ser Ser Ser
                20                  25                  30

Ser Pro Thr Ser Ser Ala Ser Ser Phe Ser Ser Ser Ala Pro Phe Leu
            35                  40                  45

Ala Ser Ala Val Ser Ala Gln Pro Pro Leu Pro Asp Gln Cys Pro Ala
50                  55                  60

Leu Cys Glu Cys Ser Glu Ala Ala Arg Thr Val Lys Cys Val Asn Arg
65                  70                  75                  80

Asn Leu Thr Glu Val Pro Thr Asp Leu Pro Ala Tyr Val Arg Asn Leu
```

85                  90                  95
Phe Leu Thr Gly Asn Gln Leu Ala Val Leu Pro Ala Gly Ala Phe Ala
            100                 105                 110

Arg Arg Pro Pro Leu Ala Glu Leu Ala Ala Leu Asn Leu Ser Gly Ser
        115                 120                 125

Arg Leu Asp Glu Val Arg Ala Gly Ala Phe Glu His Leu Pro Ser Leu
    130                 135                 140

Arg Gln Leu Asp Leu Ser His Asn Pro Leu Ala Asp Leu Ser Pro Phe
145                 150                 155                 160

Ala Phe Ser Gly Ser Asn Ala Ser Val Ser Ala Pro Ser Pro Leu Val
                165                 170                 175

Glu Leu Ile Leu Asn His Ile Val Pro Pro Glu Asp Glu Arg Gln Asn
            180                 185                 190

Arg Ser Phe Glu Gly Met Val Val Ala Ala Leu Ala Gly Arg Ala
        195                 200                 205

Leu Gln Gly Leu Arg Arg Leu Glu Leu Ala Ser Asn His Phe Leu Tyr
    210                 215                 220

Leu Pro Arg Asp Val Leu Ala Gln Leu Pro Ser Leu Arg His Leu Asp
225                 230                 235                 240

Leu Ser Asn Asn Ser Leu Val Ser Leu Thr Tyr Val Ser Phe Arg Asn
                245                 250                 255

Leu Thr His Leu Glu Ser Leu His Leu Glu Asp Asn Ala Leu Lys Val
            260                 265                 270

Leu His Asn Gly Thr Leu Ala Glu Leu Gln Gly Leu Pro His Ile Arg
        275                 280                 285

Val Phe Leu Asp Asn Asn Pro Trp Val Cys Asp Cys His Met Ala Asp
    290                 295                 300

Met Val Thr Trp Leu Lys Glu Thr Glu Val Val Gln Gly Lys Asp Arg
305                 310                 315                 320

Leu Thr Cys Ala Tyr Pro Glu Lys Met Arg Asn Arg Val Leu Leu Glu
                325                 330                 335

Leu Asn Ser Ala Asp Leu Asp Cys Asp Pro Ile Leu Pro Pro Ser Leu
            340                 345                 350

Gln Thr Ser Tyr Val Phe Leu Gly Ile Val Leu Ala Leu Ile Gly Ala
        355                 360                 365

Ile Phe Leu Leu Val Leu Tyr Leu Asn Arg Lys Gly Ile Lys Lys Trp
    370                 375                 380

Met His Asn Ile Arg Asp Ala Cys Arg Asp His Met Glu Gly Tyr His
385                 390                 395                 400

Tyr Arg Tyr Glu Ile Asn Ala Asp Pro Arg Leu Thr Asn Leu Ser Ser
                405                 410                 415

Asn Ser Asp Val
            420

<210> SEQ ID NO 82
<211> LENGTH: 509
<212> TYPE: PRT
<213> ORGANISM: Homo sapiens

<400> SEQUENCE: 82

Met Glu Arg Arg Arg Leu Trp Gly Ser Ile Gln Ser Arg Tyr Ile Ser
1               5                   10                  15

Met Ser Val Trp Thr Ser Pro Arg Arg Leu Val Glu Leu Ala Gly Gln
            20                  25                  30

-continued

```
Ser Leu Leu Lys Asp Glu Ala Leu Ala Ile Ala Ala Leu Glu Leu Leu
         35                  40                  45

Pro Arg Glu Leu Phe Pro Pro Leu Phe Met Ala Ala Phe Asp Gly Arg
 50                  55                  60

His Ser Gln Thr Leu Lys Ala Met Val Gln Ala Trp Pro Phe Thr Cys
 65                  70                  75                  80

Leu Pro Leu Gly Val Leu Met Lys Gly Gln His Leu His Leu Glu Thr
                 85                  90                  95

Phe Lys Ala Val Leu Asp Gly Leu Asp Val Leu Leu Ala Gln Glu Val
                100                 105                 110

Arg Pro Arg Arg Trp Lys Leu Gln Val Leu Asp Leu Arg Lys Asn Ser
            115                 120                 125

His Gln Asp Phe Trp Thr Val Trp Ser Gly Asn Arg Ala Ser Leu Tyr
        130                 135                 140

Ser Phe Pro Glu Pro Glu Ala Ala Gln Pro Met Thr Lys Lys Arg Lys
145                 150                 155                 160

Val Asp Gly Leu Ser Thr Glu Ala Glu Gln Pro Phe Ile Pro Val Glu
                165                 170                 175

Val Leu Val Asp Leu Phe Leu Lys Glu Gly Ala Cys Asp Glu Leu Phe
            180                 185                 190

Ser Tyr Leu Ile Glu Lys Val Lys Arg Lys Asn Val Leu Arg Leu
        195                 200                 205

Cys Cys Lys Lys Leu Lys Ile Phe Ala Met Pro Met Gln Asp Ile Lys
    210                 215                 220

Met Ile Leu Lys Met Val Gln Leu Asp Ser Ile Glu Asp Leu Glu Val
225                 230                 235                 240

Thr Cys Thr Trp Lys Leu Pro Thr Leu Ala Lys Phe Ser Pro Tyr Leu
                245                 250                 255

Gly Gln Met Ile Asn Leu Arg Arg Leu Leu Leu Ser His Ile His Ala
            260                 265                 270

Ser Ser Tyr Ile Ser Pro Glu Lys Glu Glu Gln Tyr Ile Ala Gln Phe
        275                 280                 285

Thr Ser Gln Phe Leu Ser Leu Gln Cys Leu Gln Ala Leu Tyr Val Asp
    290                 295                 300

Ser Leu Phe Phe Leu Arg Gly Arg Leu Asp Gln Leu Leu Arg His Val
305                 310                 315                 320

Met Asn Pro Leu Glu Thr Leu Ser Ile Thr Asn Cys Arg Leu Ser Glu
                325                 330                 335

Gly Asp Val Met His Leu Ser Gln Ser Pro Ser Val Ser Gln Leu Ser
            340                 345                 350

Val Leu Ser Leu Ser Gly Val Met Leu Thr Asp Val Ser Pro Glu Pro
        355                 360                 365

Leu Gln Ala Leu Leu Glu Arg Ala Ser Ala Thr Leu Gln Asp Leu Val
    370                 375                 380

Phe Asp Glu Cys Gly Ile Thr Asp Asp Gln Leu Leu Ala Leu Leu Pro
385                 390                 395                 400

Ser Leu Ser His Cys Ser Gln Leu Thr Thr Leu Ser Phe Tyr Gly Asn
                405                 410                 415

Ser Ile Ser Ile Ser Ala Leu Gln Ser Leu Leu Gln His Leu Ile Gly
            420                 425                 430

Leu Ser Asn Leu Thr His Val Leu Tyr Pro Val Pro Leu Glu Ser Tyr
        435                 440                 445

Glu Asp Ile His Gly Thr Leu His Leu Glu Arg Leu Ala Tyr Leu His
```

```
            450                 455                 460
Ala Arg Leu Arg Glu Leu Leu Cys Glu Leu Gly Arg Pro Ser Met Val
465                 470                 475                 480

Trp Leu Ser Ala Asn Pro Cys Pro His Cys Gly Asp Arg Thr Phe Tyr
                485                 490                 495

Asp Pro Glu Pro Ile Leu Cys Pro Cys Phe Met Pro Asn
            500                 505

<210> SEQ ID NO 83
<211> LENGTH: 113
<212> TYPE: PRT
<213> ORGANISM: Homo sapiens

<400> SEQUENCE: 83

Met Asn Phe Tyr Leu Leu Leu Ala Ser Ser Ile Leu Cys Ala Leu Ile
1               5                   10                  15

Val Phe Trp Lys Tyr Arg Arg Phe Gln Arg Asn Thr Gly Glu Met Ser
                20                  25                  30

Ser Asn Ser Thr Ala Leu Ala Leu Val Arg Pro Ser Ser Ser Gly Leu
            35                  40                  45

Ile Asn Ser Asn Thr Asp Asn Asn Leu Ala Val Tyr Asp Leu Ser Arg
    50                  55                  60

Asp Ile Leu Asn Asn Phe Pro His Ser Ile Ala Arg Gln Lys Arg Ile
65                  70                  75                  80

Leu Val Asn Leu Ser Met Val Glu Asn Lys Leu Val Glu Leu Glu His
                85                  90                  95

Thr Leu Leu Ser Lys Gly Phe Arg Gly Ala Ser Pro His Arg Lys Ser
            100                 105                 110

Thr

<210> SEQ ID NO 84
<211> LENGTH: 314
<212> TYPE: PRT
<213> ORGANISM: Homo sapiens

<400> SEQUENCE: 84

Met Pro Leu Glu Gln Arg Ser Gln His Cys Lys Pro Glu Glu Gly Leu
1               5                   10                  15

Glu Ala Arg Gly Glu Ala Leu Gly Leu Val Gly Ala Gln Ala Pro Ala
                20                  25                  30

Thr Glu Glu Gln Gln Thr Ala Ser Ser Ser Thr Leu Val Glu Val
            35                  40                  45

Thr Leu Gly Glu Val Pro Ala Ala Asp Ser Pro Ser Pro Pro His Ser
    50                  55                  60

Pro Gln Gly Ala Ser Ser Phe Ser Thr Thr Ile Asn Tyr Thr Leu Trp
65                  70                  75                  80

Arg Gln Ser Asp Glu Gly Ser Ser Asn Gln Glu Glu Glu Gly Pro Arg
                85                  90                  95

Met Phe Pro Asp Leu Glu Ser Glu Phe Gln Ala Ala Ile Ser Arg Lys
            100                 105                 110

Met Val Glu Leu Val His Phe Leu Leu Leu Lys Tyr Arg Ala Arg Glu
        115                 120                 125

Pro Val Thr Lys Ala Glu Met Leu Glu Ser Val Leu Arg Asn Cys Gln
    130                 135                 140

Asp Phe Phe Pro Val Ile Phe Ser Lys Ala Ser Glu Tyr Leu Gln Leu
145                 150                 155                 160
```

```
Val Phe Gly Ile Glu Val Val Glu Val Val Pro Ile Ser His Leu Tyr
                165                 170                 175

Ile Leu Val Thr Cys Leu Gly Leu Ser Tyr Asp Gly Leu Leu Gly Asp
            180                 185                 190

Asn Gln Val Met Pro Lys Thr Gly Leu Leu Ile Ile Val Leu Ala Ile
        195                 200                 205

Ile Ala Ile Glu Gly Asp Cys Ala Pro Glu Glu Lys Ile Trp Glu Glu
    210                 215                 220

Leu Ser Met Leu Glu Val Phe Glu Gly Arg Glu Asp Ser Val Phe Ala
225                 230                 235                 240

His Pro Arg Lys Leu Leu Met Gln Asp Leu Val Gln Glu Asn Tyr Leu
                245                 250                 255

Glu Tyr Arg Gln Val Pro Gly Ser Asp Pro Ala Cys Tyr Glu Phe Leu
            260                 265                 270

Trp Gly Pro Arg Ala Leu Ile Glu Thr Ser Tyr Val Lys Val Leu His
        275                 280                 285

His Thr Leu Lys Ile Gly Gly Glu Pro His Ile Ser Tyr Pro Pro Leu
    290                 295                 300

His Glu Arg Ala Leu Arg Glu Gly Glu Glu
305                 310

<210> SEQ ID NO 85
<211> LENGTH: 314
<212> TYPE: PRT
<213> ORGANISM: Homo sapiens

<400> SEQUENCE: 85

Met Pro Leu Glu Gln Arg Ser Gln His Cys Lys Pro Glu Glu Gly Leu
1               5                   10                  15

Glu Ala Arg Gly Glu Ala Leu Gly Leu Val Gly Ala Gln Ala Pro Ala
            20                  25                  30

Thr Glu Glu Gln Glu Ala Ala Ser Ser Ser Thr Leu Val Glu Val
        35                  40                  45

Thr Leu Gly Glu Val Pro Ala Ala Glu Ser Pro Asp Pro Pro Gln Ser
50                  55                  60

Pro Gln Gly Ala Ser Ser Leu Pro Thr Thr Met Asn Tyr Pro Leu Trp
65                  70                  75                  80

Ser Gln Ser Tyr Glu Asp Ser Ser Asn Gln Glu Glu Glu Gly Pro Ser
                85                  90                  95

Thr Phe Pro Asp Leu Glu Ser Glu Phe Gln Ala Ala Leu Ser Arg Lys
            100                 105                 110

Val Ala Glu Leu Val His Phe Leu Leu Leu Lys Tyr Arg Ala Arg Glu
        115                 120                 125

Pro Val Thr Lys Ala Glu Met Leu Gly Ser Val Val Gly Asn Trp Gln
    130                 135                 140

Tyr Phe Phe Pro Val Ile Phe Ser Lys Ala Ser Ser Ser Leu Gln Leu
145                 150                 155                 160

Val Phe Gly Ile Glu Leu Met Glu Val Asp Pro Ile Gly His Leu Tyr
                165                 170                 175

Ile Phe Ala Thr Cys Leu Gly Leu Ser Tyr Asp Gly Leu Leu Gly Asp
            180                 185                 190

Asn Gln Ile Met Pro Lys Ala Gly Leu Leu Ile Ile Val Leu Ala Ile
        195                 200                 205

Ile Ala Arg Glu Gly Asp Cys Ala Pro Glu Glu Lys Ile Trp Glu Glu
```

```
                210                 215                 220
Leu Ser Val Leu Glu Val Phe Glu Gly Arg Glu Asp Ser Ile Leu Gly
225                 230                 235                 240

Asp Pro Lys Lys Leu Leu Thr Gln His Phe Val Gln Glu Asn Tyr Leu
                245                 250                 255

Glu Tyr Arg Gln Val Pro Gly Ser Asp Pro Ala Cys Tyr Glu Phe Leu
            260                 265                 270

Trp Gly Pro Arg Ala Leu Val Glu Thr Ser Tyr Val Lys Val Leu His
        275                 280                 285

His Met Val Lys Ile Ser Gly Pro His Ile Ser Tyr Pro Pro Leu
    290                 295                 300

His Glu Trp Val Leu Arg Glu Gly Glu Glu
305                 310

<210> SEQ ID NO 86
<211> LENGTH: 210
<212> TYPE: PRT
<213> ORGANISM: Homo sapiens

<400> SEQUENCE: 86

Met Gln Ala Glu Gly Gln Gly Thr Gly Gly Ser Thr Gly Asp Ala Asp
1               5                   10                  15

Gly Pro Gly Gly Pro Gly Ile Pro Asp Gly Pro Gly Gly Asn Ala Gly
            20                  25                  30

Gly Pro Gly Glu Ala Gly Ala Thr Gly Gly Arg Gly Pro Arg Gly Ala
        35                  40                  45

Gly Ala Ala Arg Ala Ser Gly Pro Arg Gly Gly Ala Pro Arg Gly Pro
    50                  55                  60

His Gly Gly Ala Ala Ser Ala Gln Asp Gly Arg Cys Pro Cys Gly Ala
65                  70                  75                  80

Arg Arg Pro Asp Ser Arg Leu Leu Gln Leu His Ile Thr Met Pro Phe
                85                  90                  95

Ser Ser Pro Met Glu Ala Glu Leu Val Arg Arg Ile Leu Ser Arg Asp
            100                 105                 110

Ala Ala Pro Leu Pro Arg Pro Gly Ala Val Leu Lys Asp Phe Thr Val
        115                 120                 125

Ser Gly Asn Leu Leu Phe Met Ser Val Arg Asp Gln Asp Arg Glu Gly
    130                 135                 140

Ala Gly Arg Met Arg Val Val Gly Trp Gly Leu Gly Ser Ala Ser Pro
145                 150                 155                 160

Glu Gly Gln Lys Ala Arg Asp Leu Arg Thr Pro Lys His Lys Val Ser
                165                 170                 175

Glu Gln Arg Pro Gly Thr Pro Gly Pro Pro Pro Glu Gly Ala Gln
            180                 185                 190

Gly Asp Gly Cys Arg Gly Val Ala Phe Asn Val Met Phe Ser Ala Pro
        195                 200                 205

His Ile
    210

<210> SEQ ID NO 87
<211> LENGTH: 369
<212> TYPE: PRT
<213> ORGANISM: Homo sapiens

<400> SEQUENCE: 87

Met Pro Arg Ala Pro Lys Arg Gln Arg Cys Met Pro Glu Glu Asp Leu
```

```
            1               5                  10                 15
         Gln Ser Gln Ser Glu Thr Gln Gly Leu Glu Gly Ala Gln Ala Pro Leu
                         20                 25                 30

Ala Val Glu Glu Asp Ala Ser Ser Thr Ser Thr Ser Ser Ser Ser Phe
                         35                 40                 45

Pro Ser Ser Phe Pro Ser Ser Ser Ser Ser Ser Ser Ser Cys Tyr
                         50                 55                 60

Pro Leu Ile Pro Ser Thr Pro Glu Glu Val Ser Ala Asp Asp Glu Thr
          65                 70                 75                 80

Pro Asn Pro Pro Gln Ser Ala Gln Ile Ala Cys Ser Ser Pro Ser Val
                         85                 90                 95

Val Ala Ser Leu Pro Leu Asp Gln Ser Asp Glu Gly Ser Ser Ser Gln
                        100                105                110

Lys Glu Glu Ser Pro Ser Thr Leu Gln Val Leu Pro Asp Ser Glu Ser
                        115                120                125

Leu Pro Arg Ser Glu Ile Asp Glu Lys Val Thr Asp Leu Val Gln Phe
                        130                135                140

Leu Leu Phe Lys Tyr Gln Met Lys Glu Pro Ile Thr Lys Ala Glu Ile
         145                150                155                160

Leu Glu Ser Val Ile Arg Asn Tyr Glu Asp His Phe Pro Leu Leu Phe
                        165                170                175

Ser Glu Ala Ser Glu Cys Met Leu Leu Val Phe Gly Ile Asp Val Lys
                        180                185                190

Glu Val Asp Pro Thr Gly His Ser Phe Val Leu Val Thr Ser Leu Gly
                        195                200                205

Leu Thr Tyr Asp Gly Met Leu Ser Asp Val Gln Ser Met Pro Lys Thr
                        210                215                220

Gly Ile Leu Ile Leu Ile Leu Ser Ile Ile Phe Ile Glu Gly Tyr Cys
         225                230                235                240

Thr Pro Glu Glu Val Ile Trp Glu Ala Leu Asn Met Met Gly Leu Tyr
                        245                250                255

Asp Gly Met Glu His Leu Ile Tyr Gly Glu Pro Arg Lys Leu Leu Thr
                        260                265                270

Gln Asp Trp Val Gln Glu Asn Tyr Leu Glu Tyr Arg Gln Val Pro Gly
                        275                280                285

Ser Asp Pro Ala Arg Tyr Glu Phe Leu Trp Gly Pro Arg Ala His Ala
                        290                295                300

Glu Ile Arg Lys Met Ser Leu Leu Lys Phe Leu Ala Lys Val Asn Gly
         305                310                315                320

Ser Asp Pro Arg Ser Phe Pro Leu Trp Tyr Glu Glu Ala Leu Lys Asp
                        325                330                335

Glu Glu Glu Arg Ala Gln Asp Arg Ile Ala Thr Thr Asp Asp Thr Thr
                        340                345                350

Ala Met Ala Ser Ala Ser Ser Ser Ala Thr Gly Ser Phe Ser Tyr Pro
                        355                360                365

Glu
```

<210> SEQ ID NO 88
<211> LENGTH: 309
<212> TYPE: PRT
<213> ORGANISM: Homo sapiens

<400> SEQUENCE: 88

Met Ser Leu Glu Gln Arg Ser Leu His Cys Lys Pro Glu Glu Ala Leu

```
1               5                   10                  15
Glu Ala Gln Gln Glu Ala Leu Gly Leu Val Cys Val Gln Ala Ala Thr
            20                  25                  30

Ser Ser Ser Ser Pro Leu Val Leu Gly Thr Leu Glu Glu Val Pro Thr
            35                  40                  45

Ala Gly Ser Thr Asp Pro Pro Gln Ser Pro Gln Gly Ala Ser Ala Phe
50                  55                  60

Pro Thr Thr Ile Asn Phe Thr Arg Gln Arg Gln Pro Ser Glu Gly Ser
65                  70                  75                  80

Ser Ser Arg Glu Glu Glu Gly Pro Ser Thr Ser Cys Ile Leu Glu Ser
                85                  90                  95

Leu Phe Arg Ala Val Ile Thr Lys Lys Val Ala Asp Leu Val Gly Phe
            100                 105                 110

Leu Leu Leu Lys Tyr Arg Ala Arg Glu Pro Val Thr Lys Ala Glu Met
            115                 120                 125

Leu Glu Ser Val Ile Lys Asn Tyr Lys His Cys Phe Pro Glu Ile Phe
        130                 135                 140

Gly Lys Ala Ser Glu Ser Leu Gln Leu Val Phe Gly Ile Asp Val Lys
145                 150                 155                 160

Glu Ala Asp Pro Thr Gly His Ser Tyr Val Leu Val Thr Cys Leu Gly
                165                 170                 175

Leu Ser Tyr Asp Gly Leu Leu Gly Asp Asn Gln Ile Met Pro Lys Thr
            180                 185                 190

Gly Phe Leu Ile Ile Val Leu Val Met Ile Ala Met Glu Gly Gly His
            195                 200                 205

Ala Pro Glu Glu Glu Ile Trp Glu Glu Leu Ser Val Met Glu Val Tyr
210                 215                 220

Asp Gly Arg Glu His Ser Ala Tyr Gly Glu Pro Arg Lys Leu Leu Thr
225                 230                 235                 240

Gln Asp Leu Val Gln Glu Lys Tyr Leu Glu Tyr Arg Gln Val Pro Asp
                245                 250                 255

Ser Asp Pro Ala Arg Tyr Glu Phe Leu Trp Gly Pro Arg Ala Leu Ala
            260                 265                 270

Glu Thr Ser Tyr Val Lys Val Leu Glu Tyr Val Ile Lys Val Ser Ala
            275                 280                 285

Arg Val Arg Phe Phe Phe Pro Ser Leu Arg Glu Ala Ala Leu Arg Glu
            290                 295                 300

Glu Glu Glu Gly Val
305

<210> SEQ ID NO 89
<211> LENGTH: 188
<212> TYPE: PRT
<213> ORGANISM: Homo sapiens

<400> SEQUENCE: 89

Met Asn Gly Asp Asp Thr Phe Ala Lys Arg Pro Arg Asp Asp Ala Lys
1               5                   10                  15

Ala Ser Glu Lys Arg Ser Lys Ala Phe Asp Asp Ile Ala Thr Tyr Phe
            20                  25                  30

Ser Lys Lys Glu Trp Lys Lys Met Lys Tyr Ser Glu Lys Ile Ser Tyr
            35                  40                  45

Val Tyr Met Lys Arg Asn Tyr Lys Ala Met Thr Lys Leu Gly Phe Lys
50                  55                  60
```

```
Val Thr Leu Pro Pro Phe Met Cys Asn Lys Gln Ala Thr Asp Phe Gln
 65                  70                  75                  80

Gly Asn Asp Phe Asp Asn Asp His Asn Arg Arg Ile Gln Val Glu His
                 85                  90                  95

Pro Gln Met Thr Phe Gly Arg Leu His Arg Ile Ile Pro Lys Ile Met
            100                 105                 110

Pro Lys Lys Pro Ala Glu Asp Glu Asn Asp Ser Lys Gly Val Ser Glu
        115                 120                 125

Ala Ser Gly Pro Gln Asn Asp Gly Lys Gln Leu His Pro Pro Gly Lys
    130                 135                 140

Ala Asn Ile Ser Glu Lys Ile Asn Lys Arg Ser Gly Pro Lys Arg Gly
145                 150                 155                 160

Lys His Ala Trp Thr His Arg Leu Arg Glu Arg Lys Gln Leu Val Ile
                165                 170                 175

Tyr Glu Glu Ile Ser Asp Pro Glu Glu Asp Asp Glu
            180                 185

<210> SEQ ID NO 90
<211> LENGTH: 9
<212> TYPE: PRT
<213> ORGANISM: artificial sequence
<220> FEATURE:
<223> OTHER INFORMATION: BRDT 9mer

<400> SEQUENCE: 90

Phe Ala Ala Asp Val Arg Leu Met Phe
1               5

<210> SEQ ID NO 91
<211> LENGTH: 9
<212> TYPE: PRT
<213> ORGANISM: artificial sequence
<220> FEATURE:
<223> OTHER INFORMATION: PRAME 9mer

<400> SEQUENCE: 91

Lys Ala Met Val Gln Ala Trp Pro Phe
1               5

<210> SEQ ID NO 92
<211> LENGTH: 9
<212> TYPE: PRT
<213> ORGANISM: artificial sequence
<220> FEATURE:
<223> OTHER INFORMATION: BRDT 9mer

<400> SEQUENCE: 92

Phe Ser Trp Pro Phe Gln Arg Pro Val
1               5

<210> SEQ ID NO 93
<211> LENGTH: 9
<212> TYPE: PRT
<213> ORGANISM: artificial sequence
<220> FEATURE:
<223> OTHER INFORMATION: NALP4 9mer

<400> SEQUENCE: 93

Tyr Ser Ser Phe Val Phe Asn Leu Phe
1               5

<210> SEQ ID NO 94
<211> LENGTH: 9
```

```
<212> TYPE: PRT
<213> ORGANISM: artificial sequence
<220> FEATURE:
<223> OTHER INFORMATION: NALP4 9mer

<400> SEQUENCE: 94

Arg Ala Met Glu Ala Phe Asn Leu Val
1               5

<210> SEQ ID NO 95
<211> LENGTH: 9
<212> TYPE: PRT
<213> ORGANISM: artificial sequence
<220> FEATURE:
<223> OTHER INFORMATION: NALP4 9mer

<400> SEQUENCE: 95

Phe Val Ile Asp Ser Phe Glu Glu Leu
1               5

<210> SEQ ID NO 96
<211> LENGTH: 9
<212> TYPE: PRT
<213> ORGANISM: artificial sequence
<220> FEATURE:
<223> OTHER INFORMATION: MAGE-A12 9mer

<400> SEQUENCE: 96

Lys Met Ala Glu Leu Val His Phe Leu
1               5

<210> SEQ ID NO 97
<211> LENGTH: 9
<212> TYPE: PRT
<213> ORGANISM: artificial sequence
<220> FEATURE:
<223> OTHER INFORMATION: MAGE-A2  9mer

<400> SEQUENCE: 97

Phe Ala His Pro Arg Lys Leu Leu Met
1               5

<210> SEQ ID NO 98
<211> LENGTH: 9
<212> TYPE: PRT
<213> ORGANISM: artificial sequence
<220> FEATURE:
<223> OTHER INFORMATION: SURVIVIN 9mer

<400> SEQUENCE: 98

Arg Ala Ile Glu Gln Leu Ala Ala Met
1               5

<210> SEQ ID NO 99
<211> LENGTH: 9
<212> TYPE: PRT
<213> ORGANISM: artificial sequence
<220> FEATURE:
<223> OTHER INFORMATION: PRAME 9mer

<400> SEQUENCE: 99

Tyr Ile Ala Gln Phe Thr Ser Gln Phe
1               5

<210> SEQ ID NO 100
<211> LENGTH: 9
<212> TYPE: PRT
```

-continued

```
<213> ORGANISM: artificial sequence
<220> FEATURE:
<223> OTHER INFORMATION: PRAME 9mer

<400> SEQUENCE: 100

His Val Met Asn Pro Leu Glu Thr Leu
1               5

<210> SEQ ID NO 101
<211> LENGTH: 9
<212> TYPE: PRT
<213> ORGANISM: artificial sequence
<220> FEATURE:
<223> OTHER INFORMATION: MAGE-A12 9mer

<400> SEQUENCE: 101

Phe Gln Asp Phe Phe Pro Val Ile Phe
1               5

<210> SEQ ID NO 102
<211> LENGTH: 9
<212> TYPE: PRT
<213> ORGANISM: artificial sequence
<220> FEATURE:
<223> OTHER INFORMATION: PRAME 9mer

<400> SEQUENCE: 102

Leu Leu Arg His Val Met Asn Pro Leu
1               5

<210> SEQ ID NO 103
<211> LENGTH: 9
<212> TYPE: PRT
<213> ORGANISM: artificial sequence
<220> FEATURE:
<223> OTHER INFORMATION: DPPA2 9mer

<400> SEQUENCE: 103

Lys Met Met Lys Arg Leu Met Thr Val
1               5

<210> SEQ ID NO 104
<211> LENGTH: 9
<212> TYPE: PRT
<213> ORGANISM: artificial sequence
<220> FEATURE:
<223> OTHER INFORMATION: NY-SAR-35 9mer

<400> SEQUENCE: 104

Phe Val Leu Ala Asn Gly His Ile Leu
1               5

<210> SEQ ID NO 105
<211> LENGTH: 9
<212> TYPE: PRT
<213> ORGANISM: artificial sequence
<220> FEATURE:
<223> OTHER INFORMATION: BRDT 9mer

<400> SEQUENCE: 105

Met Leu Ala Lys Lys His Phe Ser Tyr
1               5

<210> SEQ ID NO 106
<211> LENGTH: 9
<212> TYPE: PRT
<213> ORGANISM: artificial sequence
```

```
<220> FEATURE:
<223> OTHER INFORMATION: LDHC 9mer

<400> SEQUENCE: 106

Ser Val Met Asp Leu Val Gly Ser Ile
1               5

<210> SEQ ID NO 107
<211> LENGTH: 9
<212> TYPE: PRT
<213> ORGANISM: artificial sequence
<220> FEATURE:
<223> OTHER INFORMATION: LDHC 9mer

<400> SEQUENCE: 107

Met Met Asp Leu Gln His Gly Ser Leu
1               5

<210> SEQ ID NO 108
<211> LENGTH: 9
<212> TYPE: PRT
<213> ORGANISM: artificial sequence
<220> FEATURE:
<223> OTHER INFORMATION: MAGE-A2  9mer

<400> SEQUENCE: 108

Phe Ser Thr Thr Ile Asn Tyr Thr Leu
1               5

<210> SEQ ID NO 109
<211> LENGTH: 9
<212> TYPE: PRT
<213> ORGANISM: artificial sequence
<220> FEATURE:
<223> OTHER INFORMATION: MAGE-C2  9mer

<400> SEQUENCE: 109

Met Ala Ser Glu Ser Leu Ser Val Met
1               5

<210> SEQ ID NO 110
<211> LENGTH: 9
<212> TYPE: PRT
<213> ORGANISM: artificial sequence
<220> FEATURE:
<223> OTHER INFORMATION: MAGE-C2  9mer

<400> SEQUENCE: 110

Phe Val Tyr Gly Glu Pro Arg Glu Leu
1               5

<210> SEQ ID NO 111
<211> LENGTH: 9
<212> TYPE: PRT
<213> ORGANISM: artificial sequence
<220> FEATURE:
<223> OTHER INFORMATION: MAGE-C2  9mer

<400> SEQUENCE: 111

Ser Val Met Ser Ser Asn Val Ser Phe
1               5

<210> SEQ ID NO 112
<211> LENGTH: 9
<212> TYPE: PRT
<213> ORGANISM: artificial sequence
<220> FEATURE:
```

```
<223> OTHER INFORMATION: MAGE-A3  9mer

<400> SEQUENCE: 112

Phe Val Gln Glu Asn Tyr Leu Glu Tyr
1               5

<210> SEQ ID NO 113
<211> LENGTH: 9
<212> TYPE: PRT
<213> ORGANISM: artificial sequence
<220> FEATURE:
<223> OTHER INFORMATION: MAGE-A12 9mer

<400> SEQUENCE: 113

Lys Ala Ser Glu Tyr Leu Gln Leu Val
1               5

<210> SEQ ID NO 114
<211> LENGTH: 9
<212> TYPE: PRT
<213> ORGANISM: artificial sequence
<220> FEATURE:
<223> OTHER INFORMATION: SURVIVIN 9mer

<400> SEQUENCE: 114

Ser Thr Phe Lys Asn Trp Pro Phe Leu
1               5

<210> SEQ ID NO 115
<211> LENGTH: 9
<212> TYPE: PRT
<213> ORGANISM: artificial sequence
<220> FEATURE:
<223> OTHER INFORMATION: DPPA2 9mer

<400> SEQUENCE: 115

Tyr Leu Arg Leu His Arg His Ala Tyr
1               5

<210> SEQ ID NO 116
<211> LENGTH: 9
<212> TYPE: PRT
<213> ORGANISM: artificial sequence
<220> FEATURE:
<223> OTHER INFORMATION: MAGE-A3  9mer

<400> SEQUENCE: 116

Ala Ser Ser Ser Leu Gln Leu Val Phe
1               5

<210> SEQ ID NO 117
<211> LENGTH: 9
<212> TYPE: PRT
<213> ORGANISM: artificial sequence
<220> FEATURE:
<223> OTHER INFORMATION: KK-LC-1 9mer

<400> SEQUENCE: 117

Ser Ser Asn Ser Thr Ala Leu Ala Leu
1               5

<210> SEQ ID NO 118
<211> LENGTH: 9
<212> TYPE: PRT
<213> ORGANISM: artificial sequence
<220> FEATURE:
<223> OTHER INFORMATION: MAGE-C2  9mer
```

```
<400> SEQUENCE: 118

Phe Ser Thr Ser Ser Ser Leu Ile Leu
1               5

<210> SEQ ID NO 119
<211> LENGTH: 9
<212> TYPE: PRT
<213> ORGANISM: artificial sequence
<220> FEATURE:
<223> OTHER INFORMATION: MAGE-A1  9mer

<400> SEQUENCE: 119

Arg Ala Leu Ala Glu Thr Ser Tyr Val
1               5

<210> SEQ ID NO 120
<211> LENGTH: 15
<212> TYPE: PRT
<213> ORGANISM: artificial sequence
<220> FEATURE:
<223> OTHER INFORMATION: BRDT 15mer

<400> SEQUENCE: 120

Asp Ala Tyr Lys Phe Ala Ala Asp Val Arg Leu Met Phe Met Asn
1               5                   10                  15

<210> SEQ ID NO 121
<211> LENGTH: 15
<212> TYPE: PRT
<213> ORGANISM: artificial sequence
<220> FEATURE:
<223> OTHER INFORMATION: PRAME 15mer

<400> SEQUENCE: 121

Arg His Ser Gln Thr Leu Lys Ala Met Val Gln Ala Trp Pro Phe
1               5                   10                  15

<210> SEQ ID NO 122
<211> LENGTH: 15
<212> TYPE: PRT
<213> ORGANISM: artificial sequence
<220> FEATURE:
<223> OTHER INFORMATION: BRDT 15mer

<400> SEQUENCE: 122

Asp Leu Trp Lys His Ser Phe Ser Trp Pro Phe Gln Arg Pro Val
1               5                   10                  15

<210> SEQ ID NO 123
<211> LENGTH: 15
<212> TYPE: PRT
<213> ORGANISM: artificial sequence
<220> FEATURE:
<223> OTHER INFORMATION: NALP4 15mer

<400> SEQUENCE: 123

Gln Ser Thr Thr Ser Val Tyr Ser Ser Phe Val Phe Asn Leu Phe
1               5                   10                  15

<210> SEQ ID NO 124
<211> LENGTH: 15
<212> TYPE: PRT
<213> ORGANISM: artificial sequence
<220> FEATURE:
<223> OTHER INFORMATION: NALP4 15mer
```

```
<400> SEQUENCE: 124

Lys Arg Ala Met Glu Ala Phe Asn Leu Val Arg Glu Ser Glu Gln
1               5                   10                  15

<210> SEQ ID NO 125
<211> LENGTH: 15
<212> TYPE: PRT
<213> ORGANISM: artificial sequence
<220> FEATURE:
<223> OTHER INFORMATION: NALP4 15mer

<400> SEQUENCE: 125

Phe Val Ile Asp Ser Phe Glu Glu Leu Gln Gly Gly Leu Asn Glu
1               5                   10                  15

<210> SEQ ID NO 126
<211> LENGTH: 15
<212> TYPE: PRT
<213> ORGANISM: artificial sequence
<220> FEATURE:
<223> OTHER INFORMATION: MAGE-A12 15mer

<400> SEQUENCE: 126

Gln Val Ala Leu Ser Arg Lys Met Ala Glu Leu Val His Phe Leu
1               5                   10                  15

<210> SEQ ID NO 127
<211> LENGTH: 15
<212> TYPE: PRT
<213> ORGANISM: artificial sequence
<220> FEATURE:
<223> OTHER INFORMATION: MAGE-A2   15mer

<400> SEQUENCE: 127

Arg Glu Asp Ser Val Phe Ala His Pro Arg Lys Leu Leu Met Gln
1               5                   10                  15

<210> SEQ ID NO 128
<211> LENGTH: 15
<212> TYPE: PRT
<213> ORGANISM: artificial sequence
<220> FEATURE:
<223> OTHER INFORMATION: SURVIVIN 15mer

<400> SEQUENCE: 128

Ala Lys Lys Val Arg Arg Ala Ile Glu Gln Leu Ala Ala Met Asp
1               5                   10                  15

<210> SEQ ID NO 129
<211> LENGTH: 15
<212> TYPE: PRT
<213> ORGANISM: artificial sequence
<220> FEATURE:
<223> OTHER INFORMATION: PRAME 15mer

<400> SEQUENCE: 129

Lys Glu Glu Gln Tyr Ile Ala Gln Phe Thr Ser Gln Phe Leu Ser
1               5                   10                  15

<210> SEQ ID NO 130
<211> LENGTH: 15
<212> TYPE: PRT
<213> ORGANISM: artificial sequence
<220> FEATURE:
<223> OTHER INFORMATION: PRAME 15mer

<400> SEQUENCE: 130
```

Asp Gln Leu Leu Arg His Val Met Asn Pro Leu Glu Thr Leu Ser
1               5                   10                  15

<210> SEQ ID NO 131
<211> LENGTH: 15
<212> TYPE: PRT
<213> ORGANISM: artificial sequence
<220> FEATURE:
<223> OTHER INFORMATION: MAGE-A12 15mer

<400> SEQUENCE: 131

Arg Asn Phe Gln Asp Phe Phe Pro Val Ile Phe Ser Lys Ala Ser
1               5                   10                  15

<210> SEQ ID NO 132
<211> LENGTH: 15
<212> TYPE: PRT
<213> ORGANISM: artificial sequence
<220> FEATURE:
<223> OTHER INFORMATION: PRAME 15mer

<400> SEQUENCE: 132

Arg Gly Arg Leu Asp Gln Leu Leu Arg His Val Met Asn Pro Leu
1               5                   10                  15

<210> SEQ ID NO 133
<211> LENGTH: 15
<212> TYPE: PRT
<213> ORGANISM: artificial sequence
<220> FEATURE:
<223> OTHER INFORMATION: DPPA2 15mer

<400> SEQUENCE: 133

Lys Arg Asn Lys Lys Met Met Lys Arg Leu Met Thr Val Glu Lys
1               5                   10                  15

<210> SEQ ID NO 134
<211> LENGTH: 15
<212> TYPE: PRT
<213> ORGANISM: artificial sequence
<220> FEATURE:
<223> OTHER INFORMATION: NY-SAR-35 15mer

<400> SEQUENCE: 134

Ser Ser Tyr Phe Val Leu Ala Asn Gly His Ile Leu Pro Asn Ser
1               5                   10                  15

<210> SEQ ID NO 135
<211> LENGTH: 15
<212> TYPE: PRT
<213> ORGANISM: artificial sequence
<220> FEATURE:
<223> OTHER INFORMATION: BRDT 15mer

<400> SEQUENCE: 135

Ile Leu Lys Glu Met Leu Ala Lys Lys His Phe Ser Tyr Ala Trp
1               5                   10                  15

<210> SEQ ID NO 136
<211> LENGTH: 15
<212> TYPE: PRT
<213> ORGANISM: artificial sequence
<220> FEATURE:
<223> OTHER INFORMATION: LDHC 15mer

<400> SEQUENCE: 136

Ser Val Met Asp Leu Val Gly Ser Ile Leu Lys Asn Leu Arg Arg
1               5                   10                  15

<210> SEQ ID NO 137
<211> LENGTH: 15
<212> TYPE: PRT
<213> ORGANISM: artificial sequence
<220> FEATURE:
<223> OTHER INFORMATION: LDHC 15mer

<400> SEQUENCE: 137

Lys Leu Lys Gly Glu Met Met Asp Leu Gln His Gly Ser Leu Phe
1               5                   10                  15

<210> SEQ ID NO 138
<211> LENGTH: 15
<212> TYPE: PRT
<213> ORGANISM: artificial sequence
<220> FEATURE:
<223> OTHER INFORMATION: MAGE-A2  15mer

<400> SEQUENCE: 138

Ser Ser Phe Ser Thr Thr Ile Asn Tyr Thr Leu Trp Arg Gln Ser
1               5                   10                  15

<210> SEQ ID NO 139
<211> LENGTH: 15
<212> TYPE: PRT
<213> ORGANISM: artificial sequence
<220> FEATURE:
<223> OTHER INFORMATION: MAGE-C2  15mer

<400> SEQUENCE: 139

Met Ala Ser Glu Ser Leu Ser Val Met Ser Ser Asn Val Ser Phe
1               5                   10                  15

<210> SEQ ID NO 140
<211> LENGTH: 15
<212> TYPE: PRT
<213> ORGANISM: artificial sequence
<220> FEATURE:
<223> OTHER INFORMATION: MAGE-C2  15mer

<400> SEQUENCE: 140

Glu His Phe Val Tyr Gly Glu Pro Arg Glu Leu Leu Thr Lys Val
1               5                   10                  15

<210> SEQ ID NO 141
<211> LENGTH: 15
<212> TYPE: PRT
<213> ORGANISM: artificial sequence
<220> FEATURE:
<223> OTHER INFORMATION: MAGE-C2  15mer

<400> SEQUENCE: 141

Ser Glu Ser Leu Ser Val Met Ser Ser Asn Val Ser Phe Ser Glu
1               5                   10                  15

<210> SEQ ID NO 142
<211> LENGTH: 15
<212> TYPE: PRT
<213> ORGANISM: artificial sequence
<220> FEATURE:
<223> OTHER INFORMATION: MAGE-A3  15mer

<400> SEQUENCE: 142

Leu Thr Gln His Phe Val Gln Glu Asn Tyr Leu Glu Tyr Arg Gln

```
                1               5                      10                      15
```

<210> SEQ ID NO 143
<211> LENGTH: 15
<212> TYPE: PRT
<213> ORGANISM: artificial sequence
<220> FEATURE:
<223> OTHER INFORMATION: MAGE-A12 15mer

<400> SEQUENCE: 143

```
Ser Lys Ala Ser Glu Tyr Leu Gln Leu Val Phe Gly Ile Glu Val
1               5                   10                  15
```

<210> SEQ ID NO 144
<211> LENGTH: 15
<212> TYPE: PRT
<213> ORGANISM: artificial sequence
<220> FEATURE:
<223> OTHER INFORMATION: SURVIVIN 15mer

<400> SEQUENCE: 144

```
Lys Asp His Arg Ile Ser Thr Phe Lys Asn Trp Pro Phe Leu Glu
1               5                   10                  15
```

<210> SEQ ID NO 145
<211> LENGTH: 15
<212> TYPE: PRT
<213> ORGANISM: artificial sequence
<220> FEATURE:
<223> OTHER INFORMATION: DPPA2 15mer

<400> SEQUENCE: 145

```
Lys Ile Glu Val Tyr Leu Arg Leu His Arg His Ala Tyr Pro Glu
1               5                   10                  15
```

<210> SEQ ID NO 146
<211> LENGTH: 15
<212> TYPE: PRT
<213> ORGANISM: artificial sequence
<220> FEATURE:
<223> OTHER INFORMATION: MAGE-A3   15mer

<400> SEQUENCE: 146

```
Lys Ala Ser Ser Ser Leu Gln Leu Val Phe Gly Ile Glu Leu Met
1               5                   10                  15
```

<210> SEQ ID NO 147
<211> LENGTH: 15
<212> TYPE: PRT
<213> ORGANISM: artificial sequence
<220> FEATURE:
<223> OTHER INFORMATION: KK-LC-1 15mer

<400> SEQUENCE: 147

```
Arg Asn Thr Gly Glu Met Ser Ser Asn Ser Thr Ala Leu Ala Leu
1               5                   10                  15
```

<210> SEQ ID NO 148
<211> LENGTH: 15
<212> TYPE: PRT
<213> ORGANISM: artificial sequence
<220> FEATURE:
<223> OTHER INFORMATION: MAGE-C2   15mer

<400> SEQUENCE: 148

```
Ser Ser Phe Ser Thr Ser Ser Ser Leu Ile Leu Gly Gly Pro Glu
1               5                   10                  15
```

```
<210> SEQ ID NO 149
<211> LENGTH: 15
<212> TYPE: PRT
<213> ORGANISM: artificial sequence
<220> FEATURE:
<223> OTHER INFORMATION: MAGE-A1  15mer

<400> SEQUENCE: 149

Pro Arg Ala Leu Ala Glu Thr Ser Tyr Val Lys Val Leu Glu Tyr
1               5                   10                  15

<210> SEQ ID NO 150
<211> LENGTH: 30
<212> TYPE: PRT
<213> ORGANISM: artificial sequence
<220> FEATURE:
<223> OTHER INFORMATION: LC821-01  BRDT/SURVIVIN

<400> SEQUENCE: 150

Asp Ala Tyr Lys Phe Ala Ala Asp Val Arg Leu Met Phe Met Asn Ala
1               5                   10                  15

Lys Lys Val Arg Arg Ala Ile Glu Gln Leu Ala Ala Met Asp
            20                  25                  30

<210> SEQ ID NO 151
<211> LENGTH: 30
<212> TYPE: PRT
<213> ORGANISM: artificial sequence
<220> FEATURE:
<223> OTHER INFORMATION: LC821-02  PRAME/MAGE-A2

<400> SEQUENCE: 151

Arg His Ser Gln Thr Leu Lys Ala Met Val Gln Ala Trp Pro Phe Arg
1               5                   10                  15

Glu Asp Ser Val Phe Ala His Pro Arg Lys Leu Leu Met Gln
            20                  25                  30

<210> SEQ ID NO 152
<211> LENGTH: 30
<212> TYPE: PRT
<213> ORGANISM: artificial sequence
<220> FEATURE:
<223> OTHER INFORMATION: LC821-03  BRDT/MAGE-A12

<400> SEQUENCE: 152

Asp Leu Trp Lys His Ser Phe Ser Trp Pro Phe Gln Arg Pro Val Ser
1               5                   10                  15

Lys Ala Ser Glu Tyr Leu Gln Leu Val Phe Gly Ile Glu Val
            20                  25                  30

<210> SEQ ID NO 153
<211> LENGTH: 30
<212> TYPE: PRT
<213> ORGANISM: artificial sequence
<220> FEATURE:
<223> OTHER INFORMATION: LC821-04  PRAME/LDHC

<400> SEQUENCE: 153

Asp Gln Leu Leu Arg His Val Met Asn Pro Leu Glu Thr Leu Ser Ser
1               5                   10                  15

Val Met Asp Leu Val Gly Ser Ile Leu Lys Asn Leu Arg Arg
            20                  25                  30
```

-continued

```
<210> SEQ ID NO 154
<211> LENGTH: 30
<212> TYPE: PRT
<213> ORGANISM: artificial sequence
<220> FEATURE:
<223> OTHER INFORMATION: LC821-05  NALP4/SURVIVIN

<400> SEQUENCE: 154

Gln Ser Thr Thr Ser Val Tyr Ser Ser Phe Val Phe Asn Leu Phe Lys
1               5                   10                  15

Asp His Arg Ile Ser Thr Phe Lys Asn Trp Pro Phe Leu Glu
            20                  25                  30

<210> SEQ ID NO 155
<211> LENGTH: 30
<212> TYPE: PRT
<213> ORGANISM: artificial sequence
<220> FEATURE:
<223> OTHER INFORMATION: LC821-06 MAGE-C2/NALP4

<400> SEQUENCE: 155

Ser Ser Phe Ser Thr Ser Ser Leu Ile Leu Gly Gly Pro Glu Phe
1               5                   10                  15

Val Ile Asp Ser Phe Glu Glu Leu Gln Gly Gly Leu Asn Glu
            20                  25                  30

<210> SEQ ID NO 156
<211> LENGTH: 30
<212> TYPE: PRT
<213> ORGANISM: artificial sequence
<220> FEATURE:
<223> OTHER INFORMATION: LC821-07 MAGE-A2/NALP4

<400> SEQUENCE: 156

Ser Ser Phe Ser Thr Thr Ile Asn Tyr Thr Leu Trp Arg Gln Ser Lys
1               5                   10                  15

Arg Ala Met Glu Ala Phe Asn Leu Val Arg Glu Ser Glu Gln
            20                  25                  30

<210> SEQ ID NO 157
<211> LENGTH: 30
<212> TYPE: PRT
<213> ORGANISM: artificial sequence
<220> FEATURE:
<223> OTHER INFORMATION: LC821-08 NY-SAR-35/MAGE-A12

<400> SEQUENCE: 157

Ser Ser Tyr Phe Val Leu Ala Asn Gly His Ile Leu Pro Asn Ser Arg
1               5                   10                  15

Asn Phe Gln Asp Phe Phe Pro Val Ile Phe Ser Lys Ala Ser
            20                  25                  30

<210> SEQ ID NO 158
<211> LENGTH: 30
<212> TYPE: PRT
<213> ORGANISM: artificial sequence
<220> FEATURE:
<223> OTHER INFORMATION: LC821-09 MAGE-C2/PRAME

<400> SEQUENCE: 158

Met Ala Ser Glu Ser Leu Ser Val Met Ser Ser Asn Val Ser Phe Lys
1               5                   10                  15

Glu Glu Gln Tyr Ile Ala Gln Phe Thr Ser Gln Phe Leu Ser
            20                  25                  30
```

<210> SEQ ID NO 159
<211> LENGTH: 30
<212> TYPE: PRT
<213> ORGANISM: artificial sequence
<220> FEATURE:
<223> OTHER INFORMATION: LC821-10 PRAME/MAGE-A3

<400> SEQUENCE: 159

Arg Gly Arg Leu Asp Gln Leu Leu Arg His Val Met Asn Pro Leu Leu
1               5                   10                  15

Thr Gln His Phe Val Gln Glu Asn Tyr Leu Glu Tyr Arg Gln
            20                  25                  30

<210> SEQ ID NO 160
<211> LENGTH: 30
<212> TYPE: PRT
<213> ORGANISM: artificial sequence
<220> FEATURE:
<223> OTHER INFORMATION: LC821-11 MAGE-C2/LDHC

<400> SEQUENCE: 160

Ser Glu Ser Leu Ser Val Met Ser Ser Asn Val Ser Phe Ser Glu Lys
1               5                   10                  15

Leu Lys Gly Glu Met Met Asp Leu Gln His Gly Ser Leu Phe
            20                  25                  30

<210> SEQ ID NO 161
<211> LENGTH: 30
<212> TYPE: PRT
<213> ORGANISM: artificial sequence
<220> FEATURE:
<223> OTHER INFORMATION: LC821-12 MAGE-A12/MAGE-A1

<400> SEQUENCE: 161

Gln Val Ala Leu Ser Arg Lys Met Ala Glu Leu Val His Phe Leu Pro
1               5                   10                  15

Arg Ala Leu Ala Glu Thr Ser Tyr Val Lys Val Leu Glu Tyr
            20                  25                  30

<210> SEQ ID NO 162
<211> LENGTH: 30
<212> TYPE: PRT
<213> ORGANISM: artificial sequence
<220> FEATURE:
<223> OTHER INFORMATION: LC821-13 MAGE-C2/BRDT

<400> SEQUENCE: 162

Glu His Phe Val Tyr Gly Glu Pro Arg Glu Leu Leu Thr Lys Val Ile
1               5                   10                  15

Leu Lys Glu Met Leu Ala Lys Lys His Phe Ser Tyr Ala Trp
            20                  25                  30

<210> SEQ ID NO 163
<211> LENGTH: 30
<212> TYPE: PRT
<213> ORGANISM: artificial sequence
<220> FEATURE:
<223> OTHER INFORMATION: LC821-14 DPPA2/MAGE-A3

<400> SEQUENCE: 163

Lys Ile Glu Val Tyr Leu Arg Leu His Arg His Ala Tyr Pro Glu Lys
1               5                   10                  15

Ala Ser Ser Ser Leu Gln Leu Val Phe Gly Ile Glu Leu Met
            20                  25                  30

<210> SEQ ID NO 164
<211> LENGTH: 30
<212> TYPE: PRT
<213> ORGANISM: artificial sequence
<220> FEATURE:
<223> OTHER INFORMATION: LC821-15 KK-LC-1/DPPA2

<400> SEQUENCE: 164

Arg Asn Thr Gly Glu Met Ser Ser Asn Ser Thr Ala Leu Ala Leu Lys
1               5                   10                  15

Arg Asn Lys Lys Met Met Lys Arg Leu Met Thr Val Glu Lys
            20                  25                  30

<210> SEQ ID NO 165
<211> LENGTH: 947
<212> TYPE: PRT
<213> ORGANISM: Homo sapiens

<400> SEQUENCE: 165

Met Ser Leu Pro Ser Arg Gln Thr Ala Ile Ile Val Asn Pro Pro Pro
1               5                   10                  15

Pro Glu Tyr Ile Asn Thr Lys Lys Asn Gly Arg Leu Thr Asn Gln Leu
            20                  25                  30

Gln Tyr Leu Gln Lys Val Val Leu Lys Asp Leu Trp Lys His Ser Phe
        35                  40                  45

Ser Trp Pro Phe Gln Arg Pro Val Asp Ala Val Lys Leu Gln Leu Pro
    50                  55                  60

Asp Tyr Tyr Thr Ile Ile Lys Asn Pro Met Asp Leu Asn Thr Ile Lys
65                  70                  75                  80

Lys Arg Leu Glu Asn Lys Tyr Tyr Ala Lys Ala Ser Glu Cys Ile Glu
                85                  90                  95

Asp Phe Asn Thr Met Phe Ser Asn Cys Tyr Leu Tyr Asn Lys Pro Gly
            100                 105                 110

Asp Asp Ile Val Leu Met Ala Gln Ala Leu Glu Lys Leu Phe Met Gln
        115                 120                 125

Lys Leu Ser Gln Met Pro Gln Glu Glu Gln Val Val Gly Val Lys Glu
    130                 135                 140

Arg Ile Lys Lys Gly Thr Gln Gln Asn Ile Ala Val Ser Ser Ala Lys
145                 150                 155                 160

Glu Lys Ser Ser Pro Ser Ala Thr Gly Lys Val Phe Lys Gln Gln Glu
                165                 170                 175

Ile Pro Ser Val Phe Pro Lys Thr Ser Ile Ser Pro Leu Asn Val Val
            180                 185                 190

Gln Gly Ala Ser Val Asn Ser Ser Ser Gln Thr Ala Ala Gln Val Thr
        195                 200                 205

Lys Gly Val Lys Arg Lys Ala Asp Thr Thr Thr Pro Ala Thr Ser Ala
    210                 215                 220

Val Lys Ala Ser Ser Glu Phe Ser Pro Thr Phe Thr Glu Lys Ser Val
225                 230                 235                 240

Ala Leu Pro Pro Ile Lys Glu Asn Met Pro Lys Asn Val Leu Pro Asp
                245                 250                 255

Ser Gln Gln Gln Tyr Asn Val Val Lys Thr Val Lys Val Thr Glu Gln
            260                 265                 270

Leu Arg His Cys Ser Glu Ile Leu Lys Glu Met Leu Ala Lys Lys His
        275                 280                 285

```
Phe Ser Tyr Ala Trp Pro Phe Tyr Asn Pro Val Asp Val Asn Ala Leu
        290                 295                 300

Gly Leu His Asn Tyr Tyr Asp Val Val Lys Asn Pro Met Asp Leu Gly
305                 310                 315                 320

Thr Ile Lys Glu Lys Met Asp Asn Gln Glu Tyr Lys Asp Ala Tyr Lys
                    325                 330                 335

Phe Ala Ala Asp Val Arg Leu Met Phe Met Asn Cys Tyr Lys Tyr Asn
                340                 345                 350

Pro Pro Asp His Glu Val Val Thr Met Ala Arg Met Leu Gln Asp Val
            355                 360                 365

Phe Glu Thr His Phe Ser Lys Ile Pro Ile Glu Pro Val Glu Ser Met
370                 375                 380

Pro Leu Cys Tyr Ile Lys Thr Asp Ile Thr Glu Thr Thr Gly Arg Glu
385                 390                 395                 400

Asn Thr Asn Glu Ala Ser Ser Glu Gly Asn Ser Ser Asp Asp Ser Glu
                405                 410                 415

Asp Glu Arg Val Lys Arg Leu Ala Lys Leu Gln Glu Gln Leu Lys Ala
            420                 425                 430

Val His Gln Gln Leu Gln Val Leu Ser Gln Val Pro Phe Arg Lys Leu
        435                 440                 445

Asn Lys Lys Lys Glu Lys Ser Lys Lys Glu Lys Lys Lys Glu Lys Val
450                 455                 460

Asn Asn Ser Asn Glu Asn Pro Arg Lys Met Cys Glu Gln Met Arg Leu
465                 470                 475                 480

Lys Glu Lys Ser Lys Arg Asn Gln Pro Lys Lys Arg Lys Gln Gln Phe
                485                 490                 495

Ile Gly Leu Lys Ser Glu Asp Glu Asp Asn Ala Lys Pro Met Asn Tyr
                500                 505                 510

Asp Glu Lys Arg Gln Leu Ser Leu Asn Ile Asn Lys Leu Pro Gly Asp
            515                 520                 525

Lys Leu Gly Arg Val Val His Ile Ile Gln Ser Arg Glu Pro Ser Leu
530                 535                 540

Ser Asn Ser Asn Pro Asp Glu Ile Glu Ile Asp Phe Glu Thr Leu Lys
545                 550                 555                 560

Ala Ser Thr Leu Arg Glu Leu Glu Lys Tyr Val Ser Ala Cys Leu Arg
                565                 570                 575

Lys Arg Pro Leu Lys Pro Pro Ala Lys Lys Ile Met Met Ser Lys Glu
                580                 585                 590

Glu Leu His Ser Gln Lys Lys Gln Glu Leu Glu Lys Arg Leu Leu Asp
            595                 600                 605

Val Asn Asn Gln Leu Asn Ser Arg Lys Arg Gln Thr Lys Ser Asp Lys
610                 615                 620

Thr Gln Pro Ser Lys Ala Val Glu Asn Val Ser Arg Leu Ser Glu Ser
625                 630                 635                 640

Ser Ser Ser Ser Ser Ser Ser Glu Ser Glu Ser Ser Ser Ser Ser Asp
                645                 650                 655

Leu Ser Ser Ser Asp Ser Ser Asp Ser Glu Ser Glu Met Phe Pro Lys
                660                 665                 670

Phe Thr Glu Val Lys Pro Asn Asp Ser Pro Ser Lys Glu Asn Val Lys
            675                 680                 685

Lys Met Lys Asn Glu Cys Ile Pro Pro Glu Gly Arg Thr Gly Val Thr
690                 695                 700

Gln Ile Gly Tyr Cys Val Gln Asp Thr Thr Ser Ala Asn Thr Thr Leu
```

```
705                 710                 715                 720
Val His Gln Thr Thr Pro Ser His Val Met Pro Asn His His Gln
                725                 730                 735
Leu Ala Phe Asn Tyr Gln Glu Leu Glu His Leu Gln Thr Val Lys Asn
                740                 745                 750
Ile Ser Pro Leu Gln Ile Leu Pro Pro Ser Gly Asp Ser Glu Gln Leu
                755                 760                 765
Ser Asn Gly Ile Thr Val Met His Pro Ser Gly Asp Ser Asp Thr Thr
                770                 775                 780
Met Leu Glu Ser Glu Cys Gln Ala Pro Val Gln Lys Asp Ile Lys Ile
785                 790                 795                 800
Lys Asn Ala Asp Ser Trp Lys Ser Leu Gly Lys Pro Val Lys Pro Ser
                805                 810                 815
Gly Val Met Lys Ser Ser Asp Glu Leu Phe Asn Gln Phe Arg Lys Ala
                820                 825                 830
Ala Ile Glu Lys Glu Val Lys Ala Arg Thr Gln Glu Leu Ile Arg Lys
                835                 840                 845
His Leu Glu Gln Asn Thr Lys Glu Leu Lys Ala Ser Gln Glu Asn Gln
                850                 855                 860
Arg Asp Leu Gly Asn Gly Leu Thr Val Glu Ser Phe Ser Asn Lys Ile
865                 870                 875                 880
Gln Asn Lys Cys Ser Gly Glu Glu Gln Lys Glu His Gln Gln Ser Ser
                885                 890                 895
Glu Ala Gln Asp Lys Ser Lys Leu Trp Leu Leu Lys Asp Arg Asp Leu
                900                 905                 910
Ala Arg Gln Lys Glu Gln Glu Arg Arg Arg Glu Ala Met Val Gly
                915                 920                 925
Thr Ile Asp Met Thr Leu Gln Ser Asp Ile Met Thr Met Phe Glu Asn
                930                 935                 940
Asn Phe Asp
945

<210> SEQ ID NO 166
<211> LENGTH: 509
<212> TYPE: PRT
<213> ORGANISM: Homo sapiens

<400> SEQUENCE: 166

Met Glu Arg Arg Arg Leu Trp Gly Ser Ile Gln Ser Arg Tyr Ile Ser
1               5                   10                  15
Met Ser Val Trp Thr Ser Pro Arg Arg Leu Val Glu Leu Ala Gly Gln
                20                  25                  30
Ser Leu Leu Lys Asp Glu Ala Leu Ala Ile Ala Ala Leu Glu Leu Leu
                35                  40                  45
Pro Arg Glu Leu Phe Pro Pro Leu Phe Met Ala Ala Phe Asp Gly Arg
                50                  55                  60
His Ser Gln Thr Leu Lys Ala Met Val Gln Ala Trp Pro Phe Thr Cys
65                  70                  75                  80
Leu Pro Leu Gly Val Leu Met Lys Gly Gln His Leu His Leu Glu Thr
                85                  90                  95
Phe Lys Ala Val Leu Asp Gly Leu Asp Val Leu Leu Ala Gln Glu Val
                100                 105                 110
Arg Pro Arg Arg Trp Lys Leu Gln Val Leu Asp Leu Arg Lys Asn Ser
                115                 120                 125
```

```
His Gln Asp Phe Trp Thr Val Trp Ser Gly Asn Arg Ala Ser Leu Tyr
    130                 135                 140
Ser Phe Pro Glu Pro Glu Ala Ala Gln Pro Met Thr Lys Lys Arg Lys
145                 150                 155                 160
Val Asp Gly Leu Ser Thr Glu Ala Glu Gln Pro Phe Ile Pro Val Glu
                165                 170                 175
Val Leu Val Asp Leu Phe Leu Lys Glu Gly Ala Cys Asp Glu Leu Phe
            180                 185                 190
Ser Tyr Leu Ile Glu Lys Val Lys Arg Lys Lys Asn Val Leu Arg Leu
        195                 200                 205
Cys Cys Lys Lys Leu Lys Ile Phe Ala Met Pro Met Gln Asp Ile Lys
    210                 215                 220
Met Ile Leu Lys Met Val Gln Leu Asp Ser Ile Glu Asp Leu Glu Val
225                 230                 235                 240
Thr Cys Thr Trp Lys Leu Pro Thr Leu Ala Lys Phe Ser Pro Tyr Leu
                245                 250                 255
Gly Gln Met Ile Asn Leu Arg Arg Leu Leu Leu Ser His Ile His Ala
                260                 265                 270
Ser Ser Tyr Ile Ser Pro Glu Lys Glu Glu Gln Tyr Ile Ala Gln Phe
        275                 280                 285
Thr Ser Gln Phe Leu Ser Leu Gln Cys Leu Gln Ala Leu Tyr Val Asp
    290                 295                 300
Ser Leu Phe Phe Leu Arg Gly Arg Leu Asp Gln Leu Leu Arg His Val
305                 310                 315                 320
Met Asn Pro Leu Glu Thr Leu Ser Ile Thr Asn Cys Arg Leu Ser Glu
                325                 330                 335
Gly Asp Val Met His Leu Ser Gln Ser Pro Ser Val Ser Gln Leu Ser
                340                 345                 350
Val Leu Ser Leu Ser Gly Val Met Leu Thr Asp Val Ser Pro Glu Pro
        355                 360                 365
Leu Gln Ala Leu Leu Glu Arg Ala Ser Ala Thr Leu Gln Asp Leu Val
    370                 375                 380
Phe Asp Glu Cys Gly Ile Thr Asp Asp Gln Leu Leu Ala Leu Leu Pro
385                 390                 395                 400
Ser Leu Ser His Cys Ser Gln Leu Thr Thr Leu Ser Phe Tyr Gly Asn
                405                 410                 415
Ser Ile Ser Ile Ser Ala Leu Gln Ser Leu Leu Gln His Leu Ile Gly
                420                 425                 430
Leu Ser Asn Leu Thr His Val Leu Tyr Pro Val Pro Leu Glu Ser Tyr
        435                 440                 445
Glu Asp Ile His Gly Thr Leu His Leu Glu Arg Leu Ala Tyr Leu His
    450                 455                 460
Ala Arg Leu Arg Glu Leu Leu Cys Glu Leu Gly Arg Pro Ser Met Val
465                 470                 475                 480
Trp Leu Ser Ala Asn Pro Cys Pro His Cys Gly Asp Arg Thr Phe Tyr
                485                 490                 495
Asp Pro Glu Pro Ile Leu Cys Pro Cys Phe Met Pro Asn
                500                 505
```

<210> SEQ ID NO 167
<211> LENGTH: 994
<212> TYPE: PRT
<213> ORGANISM: Homo sapiens

<400> SEQUENCE: 167

-continued

```
Met Ala Ala Ser Phe Phe Ser Asp Phe Gly Leu Met Trp Tyr Leu Glu
1               5                   10                  15

Glu Leu Lys Lys Glu Glu Phe Arg Lys Phe Lys Glu His Leu Lys Gln
            20                  25                  30

Met Thr Leu Gln Leu Glu Leu Lys Gln Ile Pro Trp Thr Glu Val Lys
        35                  40                  45

Lys Ala Ser Arg Glu Glu Leu Ala Asn Leu Leu Ile Lys His Tyr Glu
    50                  55                  60

Glu Gln Gln Ala Trp Asn Ile Thr Leu Arg Ile Phe Gln Lys Met Asp
65                  70                  75                  80

Arg Lys Asp Leu Cys Met Lys Val Met Arg Glu Arg Thr Gly Tyr Thr
                85                  90                  95

Lys Thr Tyr Gln Ala His Ala Lys Gln Lys Phe Ser Arg Leu Trp Ser
            100                 105                 110

Ser Lys Ser Val Thr Glu Ile His Leu Tyr Phe Glu Glu Val Lys
        115                 120                 125

Gln Glu Glu Cys Asp His Leu Asp Arg Leu Phe Ala Pro Lys Glu Ala
130                 135                 140

Gly Lys Gln Pro Arg Thr Val Ile Ile Gln Gly Pro Gln Gly Ile Gly
145                 150                 155                 160

Lys Thr Thr Leu Leu Met Lys Leu Met Met Ala Trp Ser Asp Asn Lys
                165                 170                 175

Ile Phe Arg Asp Arg Phe Leu Tyr Thr Phe Tyr Phe Cys Cys Arg Glu
            180                 185                 190

Leu Arg Glu Leu Pro Pro Thr Ser Leu Ala Asp Leu Ile Ser Arg Glu
        195                 200                 205

Trp Pro Asp Pro Ala Ala Pro Ile Thr Glu Ile Val Ser Gln Pro Glu
    210                 215                 220

Arg Leu Leu Phe Val Ile Asp Ser Phe Glu Glu Leu Gln Gly Gly Leu
225                 230                 235                 240

Asn Glu Pro Asp Ser Asp Leu Cys Gly Asp Leu Met Glu Lys Arg Pro
                245                 250                 255

Val Gln Val Leu Leu Ser Ser Leu Leu Arg Lys Lys Met Leu Pro Glu
            260                 265                 270

Ala Ser Leu Leu Ile Ala Ile Lys Pro Val Cys Pro Lys Glu Leu Arg
        275                 280                 285

Asp Gln Val Thr Ile Ser Glu Ile Tyr Gln Pro Arg Gly Phe Asn Glu
    290                 295                 300

Ser Asp Arg Leu Val Tyr Phe Cys Cys Phe Lys Asp Pro Lys Arg
305                 310                 315                 320

Ala Met Glu Ala Phe Asn Leu Val Arg Glu Ser Glu Gln Leu Phe Ser
                325                 330                 335

Ile Cys Gln Ile Pro Leu Leu Cys Trp Ile Leu Cys Thr Ser Leu Lys
            340                 345                 350

Gln Glu Met Gln Lys Gly Lys Asp Leu Ala Leu Thr Cys Gln Ser Thr
        355                 360                 365

Thr Ser Val Tyr Ser Ser Phe Val Phe Asn Leu Phe Thr Pro Glu Gly
    370                 375                 380

Ala Glu Gly Pro Thr Pro Gln Thr Gln His Gln Leu Lys Ala Leu Cys
385                 390                 395                 400

Ser Leu Ala Ala Glu Gly Met Trp Thr Asp Thr Phe Glu Phe Cys Glu
                405                 410                 415
```

```
Asp Asp Leu Arg Arg Asn Gly Val Val Asp Ala Asp Ile Pro Ala Leu
            420                 425                 430

Leu Gly Thr Lys Ile Leu Leu Lys Tyr Gly Glu Arg Glu Ser Ser Tyr
        435                 440                 445

Val Phe Leu His Val Cys Ile Gln Glu Phe Cys Ala Ala Leu Phe Tyr
    450                 455                 460

Leu Leu Lys Ser His Leu Asp His Pro His Pro Ala Val Arg Cys Val
465                 470                 475                 480

Gln Glu Leu Leu Val Ala Asn Phe Glu Lys Ala Arg Arg Ala His Trp
                485                 490                 495

Ile Phe Leu Gly Cys Phe Leu Thr Gly Leu Leu Asn Lys Lys Glu Gln
            500                 505                 510

Glu Lys Leu Asp Ala Phe Phe Gly Phe Gln Leu Ser Gln Glu Ile Lys
        515                 520                 525

Gln Gln Ile His Gln Cys Leu Lys Ser Leu Gly Glu Arg Gly Asn Pro
    530                 535                 540

Gln Gly Gln Val Asp Ser Leu Ala Ile Phe Tyr Cys Leu Phe Glu Met
545                 550                 555                 560

Gln Asp Pro Ala Phe Val Lys Gln Ala Val Asn Leu Leu Gln Glu Ala
                565                 570                 575

Asn Phe His Ile Ile Asp Asn Val Asp Leu Val Val Ser Ala Tyr Cys
            580                 585                 590

Leu Lys Tyr Cys Ser Ser Leu Arg Lys Leu Cys Phe Ser Val Gln Asn
        595                 600                 605

Val Phe Lys Lys Glu Asp Glu His Ser Thr Ser Asp Tyr Ser Leu
    610                 615                 620

Ile Cys Trp His His Ile Cys Ser Val Leu Thr Thr Ser Gly His Leu
625                 630                 635                 640

Arg Glu Leu Gln Val Gln Asp Ser Thr Leu Ser Glu Ser Thr Phe Val
                645                 650                 655

Thr Trp Cys Asn Gln Leu Arg His Pro Ser Cys Arg Leu Gln Lys Leu
            660                 665                 670

Gly Ile Asn Asn Val Ser Phe Ser Gly Gln Ser Val Leu Leu Phe Glu
        675                 680                 685

Val Leu Phe Tyr Gln Pro Asp Leu Lys Tyr Leu Ser Phe Thr Leu Thr
    690                 695                 700

Lys Leu Ser Arg Asp Asp Ile Arg Ser Leu Cys Asp Ala Leu Asn Tyr
705                 710                 715                 720

Pro Ala Gly Asn Val Lys Glu Leu Ala Leu Val Asn Cys His Leu Ser
                725                 730                 735

Pro Ile Asp Cys Glu Val Leu Ala Gly Leu Leu Thr Asn Asn Lys Lys
            740                 745                 750

Leu Thr Tyr Leu Asn Val Ser Cys Asn Gln Leu Asp Thr Gly Val Pro
        755                 760                 765

Leu Leu Cys Glu Ala Leu Cys Ser Pro Asp Thr Val Leu Val Tyr Leu
    770                 775                 780

Met Leu Ala Phe Cys His Leu Ser Glu Gln Cys Cys Glu Tyr Ile Ser
785                 790                 795                 800

Glu Met Leu Leu Arg Asn Lys Ser Val Arg Tyr Leu Asp Leu Ser Ala
                805                 810                 815

Asn Val Leu Lys Asp Glu Gly Leu Lys Thr Leu Cys Glu Ala Leu Lys
            820                 825                 830

His Pro Asp Cys Cys Leu Asp Ser Leu Cys Leu Val Lys Cys Phe Ile
```

```
              835                 840                 845
Thr Ala Ala Gly Cys Glu Asp Leu Ala Ser Ala Leu Ile Ser Asn Gln
850                 855                 860

Asn Leu Lys Ile Leu Gln Ile Gly Cys Asn Glu Ile Gly Asp Val Gly
865                 870                 875                 880

Val Gln Leu Leu Cys Arg Ala Leu Thr His Thr Asp Cys Arg Leu Glu
                885                 890                 895

Ile Leu Gly Leu Glu Glu Cys Gly Leu Thr Ser Thr Cys Cys Lys Asp
                900                 905                 910

Leu Ala Ser Val Leu Thr Cys Ser Lys Thr Leu Gln Gln Leu Asn Leu
                915                 920                 925

Thr Leu Asn Thr Leu Asp His Thr Gly Val Val Leu Cys Glu Ala
930                 935                 940

Leu Arg His Pro Glu Cys Ala Leu Gln Val Leu Gly Leu Arg Lys Thr
945                 950                 955                 960

Asp Phe Asp Glu Glu Thr Gln Ala Leu Leu Thr Ala Glu Glu Arg
                965                 970                 975

Asn Pro Asn Leu Thr Ile Thr Asp Asp Cys Asp Thr Ile Thr Arg Val
                980                 985                 990

Glu Ile

<210> SEQ ID NO 168
<211> LENGTH: 314
<212> TYPE: PRT
<213> ORGANISM: Homo sapiens

<400> SEQUENCE: 168

Met Pro Leu Glu Gln Arg Ser Gln His Cys Lys Pro Glu Glu Gly Leu
1               5                   10                  15

Glu Ala Gln Gly Glu Ala Leu Gly Leu Val Gly Ala Gln Ala Pro Ala
                20                  25                  30

Thr Glu Glu Gln Glu Thr Ala Ser Ser Ser Thr Leu Val Glu Val
                35                  40                  45

Thr Leu Arg Glu Val Pro Ala Ala Glu Ser Pro Ser Pro Pro His Ser
50                  55                  60

Pro Gln Gly Ala Ser Thr Leu Pro Thr Thr Ile Asn Tyr Thr Leu Trp
65                  70                  75                  80

Ser Gln Ser Asp Glu Gly Ser Ser Asn Glu Gln Glu Gly Pro Ser
                85                  90                  95

Thr Phe Pro Asp Leu Glu Thr Ser Phe Gln Val Ala Leu Ser Arg Lys
                100                 105                 110

Met Ala Glu Leu Val His Phe Leu Leu Leu Lys Tyr Arg Ala Arg Glu
                115                 120                 125

Pro Phe Thr Lys Ala Glu Met Leu Gly Ser Val Ile Arg Asn Phe Gln
                130                 135                 140

Asp Phe Phe Pro Val Ile Phe Ser Lys Ala Ser Glu Tyr Leu Gln Leu
145                 150                 155                 160

Val Phe Gly Ile Glu Val Val Glu Val Val Arg Ile Gly His Leu Tyr
                165                 170                 175

Ile Leu Val Thr Cys Leu Gly Leu Ser Tyr Asp Gly Leu Leu Gly Asp
                180                 185                 190

Asn Gln Ile Val Pro Lys Thr Gly Leu Leu Ile Ile Val Leu Ala Ile
                195                 200                 205

Ile Ala Lys Glu Gly Asp Cys Ala Pro Glu Glu Lys Ile Trp Glu Glu
```

Leu Ser Val Leu Glu Ala Ser Asp Gly Arg Glu Asp Ser Val Phe Ala
225                 230                 235                 240

His Pro Arg Lys Leu Leu Thr Gln Asp Leu Val Gln Glu Asn Tyr Leu
            245                 250                 255

Glu Tyr Arg Gln Val Pro Gly Ser Asp Pro Ala Cys Tyr Glu Phe Leu
                260                 265                 270

Trp Gly Pro Arg Ala Leu Val Glu Thr Ser Tyr Val Lys Val Leu His
            275                 280                 285

His Leu Leu Lys Ile Ser Gly Gly Pro His Ile Ser Tyr Pro Pro Leu
            290                 295                 300

His Glu Trp Ala Phe Arg Glu Gly Glu Glu
305                 310

<210> SEQ ID NO 169
<211> LENGTH: 314
<212> TYPE: PRT
<213> ORGANISM: Homo sapiens

<400> SEQUENCE: 169

Met Pro Leu Glu Gln Arg Ser Gln His Cys Lys Pro Glu Glu Gly Leu
1               5                   10                  15

Glu Ala Arg Gly Glu Ala Leu Gly Leu Val Gly Ala Gln Ala Pro Ala
            20                  25                  30

Thr Glu Glu Gln Gln Thr Ala Ser Ser Ser Thr Leu Val Glu Val
            35                  40                  45

Thr Leu Gly Glu Val Pro Ala Ala Asp Ser Pro Ser Pro Pro His Ser
50                  55                  60

Pro Gln Gly Ala Ser Ser Phe Ser Thr Thr Ile Asn Tyr Thr Leu Trp
65                  70                  75                  80

Arg Gln Ser Asp Glu Gly Ser Ser Asn Gln Glu Glu Glu Gly Pro Arg
                85                  90                  95

Met Phe Pro Asp Leu Glu Ser Glu Phe Gln Ala Ala Ile Ser Arg Lys
            100                 105                 110

Met Val Glu Leu Val His Phe Leu Leu Leu Lys Tyr Arg Ala Arg Glu
            115                 120                 125

Pro Val Thr Lys Ala Glu Met Leu Glu Ser Val Leu Arg Asn Cys Gln
            130                 135                 140

Asp Phe Phe Pro Val Ile Phe Ser Lys Ala Ser Glu Tyr Leu Gln Leu
145                 150                 155                 160

Val Phe Gly Ile Glu Val Val Glu Val Val Pro Ile Ser His Leu Tyr
                165                 170                 175

Ile Leu Val Thr Cys Leu Gly Leu Ser Tyr Asp Gly Leu Leu Gly Asp
            180                 185                 190

Asn Gln Val Met Pro Lys Thr Gly Leu Leu Ile Ile Val Leu Ala Ile
            195                 200                 205

Ile Ala Ile Glu Gly Asp Cys Ala Pro Glu Glu Lys Ile Trp Glu Glu
210                 215                 220

Leu Ser Met Leu Glu Val Phe Glu Gly Arg Glu Asp Ser Val Phe Ala
225                 230                 235                 240

His Pro Arg Lys Leu Leu Met Gln Asp Leu Val Gln Glu Asn Tyr Leu
            245                 250                 255

Glu Tyr Arg Gln Val Pro Gly Ser Asp Pro Ala Cys Tyr Glu Phe Leu
                260                 265                 270

```
Trp Gly Pro Arg Ala Leu Ile Glu Thr Ser Tyr Val Lys Val Leu His
        275                 280                 285

His Thr Leu Lys Ile Gly Gly Glu Pro His Ile Ser Tyr Pro Pro Leu
    290                 295                 300

His Glu Arg Ala Leu Arg Glu Gly Glu Glu
305                 310

<210> SEQ ID NO 170
<211> LENGTH: 142
<212> TYPE: PRT
<213> ORGANISM: Homo sapiens

<400> SEQUENCE: 170

Met Gly Ala Pro Thr Leu Pro Pro Ala Trp Gln Pro Phe Leu Lys Asp
1               5                   10                  15

His Arg Ile Ser Thr Phe Lys Asn Trp Pro Phe Leu Glu Gly Cys Ala
            20                  25                  30

Cys Thr Pro Glu Arg Met Ala Glu Ala Gly Phe Ile His Cys Pro Thr
        35                  40                  45

Glu Asn Glu Pro Asp Leu Ala Gln Cys Phe Phe Cys Phe Lys Glu Leu
    50                  55                  60

Glu Gly Trp Glu Pro Asp Asp Asp Pro Ile Glu Glu His Lys Lys His
65                  70                  75                  80

Ser Ser Gly Cys Ala Phe Leu Ser Val Lys Lys Gln Phe Glu Glu Leu
                85                  90                  95

Thr Leu Gly Glu Phe Leu Lys Leu Asp Arg Glu Arg Ala Lys Asn Lys
            100                 105                 110

Ile Ala Lys Glu Thr Asn Asn Lys Lys Lys Glu Phe Glu Glu Thr Ala
        115                 120                 125

Lys Lys Val Arg Arg Ala Ile Glu Gln Leu Ala Ala Met Asp
        130                 135                 140

<210> SEQ ID NO 171
<211> LENGTH: 298
<212> TYPE: PRT
<213> ORGANISM: Homo sapiens

<400> SEQUENCE: 171

Met Ser Asp Ala Asn Leu Asp Ser Ser Lys Lys Asn Phe Leu Glu Gly
1               5                   10                  15

Glu Val Asp Asp Glu Glu Ser Val Ile Leu Thr Leu Pro Val Lys
            20                  25                  30

Asp Asp Ala Asn Met Glu Gln Met Glu Pro Ser Val Ser Ser Thr Ser
        35                  40                  45

Asp Val Lys Leu Glu Lys Pro Lys Lys Tyr Asn Pro Gly His Leu Leu
    50                  55                  60

Gln Thr Asn Glu Gln Phe Thr Ala Pro Gln Lys Ala Arg Cys Lys Ile
65                  70                  75                  80

Pro Ala Leu Pro Leu Pro Thr Ile Leu Pro Ile Asn Lys Val Cys
                85                  90                  95

Arg Asp Thr Leu Arg Asp Trp Cys Gln Gln Leu Gly Leu Ser Thr Asn
            100                 105                 110

Gly Lys Lys Ile Glu Val Tyr Leu Arg Leu His Arg His Ala Tyr Pro
        115                 120                 125

Glu Gln Arg Gln Asp Met Pro Glu Met Ser Gln Glu Thr Arg Leu Gln
    130                 135                 140
```

```
Arg Cys Ser Arg Lys Arg Lys Ala Val Thr Lys Arg Ala Arg Leu Gln
145                 150                 155                 160

Arg Ser Tyr Glu Met Asn Glu Arg Ala Glu Glu Thr Asn Thr Val Glu
            165                 170                 175

Val Ile Thr Ser Ala Pro Gly Ala Met Leu Ala Ser Trp Ala Arg Ile
            180                 185                 190

Ala Ala Arg Ala Val Gln Pro Lys Ala Leu Asn Ser Cys Ser Ile Pro
            195                 200                 205

Val Ser Val Glu Ala Phe Leu Met Gln Ala Ser Gly Val Arg Trp Cys
            210                 215                 220

Val Val His Gly Arg Leu Leu Ser Ala Asp Thr Lys Gly Trp Val Arg
225                 230                 235                 240

Leu Gln Phe His Ala Gly Gln Ala Trp Val Pro Thr Thr His Arg Arg
            245                 250                 255

Met Ile Ser Leu Phe Leu Leu Pro Ala Cys Ile Phe Pro Ser Pro Gly
            260                 265                 270

Ile Glu Asp Asn Met Leu Cys Pro Asp Cys Ala Lys Arg Asn Lys Lys
            275                 280                 285

Met Met Lys Arg Leu Met Thr Val Glu Lys
            290                 295

<210> SEQ ID NO 172
<211> LENGTH: 255
<212> TYPE: PRT
<213> ORGANISM: Homo sapiens

<400> SEQUENCE: 172

Met Ser Ser His Arg Lys Ala Lys Gly Arg Asn Arg Arg Ser His
1               5                   10                  15

Arg Ala Met Arg Val Ala His Leu Glu Leu Ala Thr Tyr Glu Leu Ala
                20                  25                  30

Ala Thr Glu Ser Asn Pro Glu Ser Ser His Pro Gly Tyr Glu Ala Ala
            35                  40                  45

Met Ala Asp Arg Pro Gln Pro Gly Trp Arg Glu Ser Leu Lys Met Arg
        50                  55                  60

Val Ser Lys Pro Phe Gly Met Leu Met Leu Ser Ile Trp Ile Leu Leu
65                  70                  75                  80

Phe Val Cys Tyr Tyr Leu Ser Tyr Tyr Leu Cys Ser Gly Ser Ser Tyr
                85                  90                  95

Phe Val Leu Ala Asn Gly His Ile Leu Pro Asn Ser Glu Asn Ala His
            100                 105                 110

Gly Gln Ser Leu Glu Glu Asp Ser Ala Leu Glu Ala Leu Leu Asn Phe
        115                 120                 125

Phe Phe Pro Thr Thr Cys Asn Leu Arg Glu Asn Gln Val Ala Lys Pro
    130                 135                 140

Cys Asn Glu Leu Gln Asp Leu Ser Glu Ser Glu Cys Leu Arg His Lys
145                 150                 155                 160

Cys Cys Phe Ser Ser Ser Gly Thr Thr Ser Phe Lys Cys Phe Ala Pro
                165                 170                 175

Phe Arg Asp Val Pro Lys Gln Met Met Gln Met Phe Gly Leu Gly Ala
            180                 185                 190

Ile Ser Leu Ile Leu Val Cys Leu Pro Ile Tyr Cys Arg Ser Leu Phe
        195                 200                 205

Trp Arg Ser Glu Pro Ala Asp Asp Leu Gln Arg Gln Asp Asn Arg Val
    210                 215                 220
```

```
Val Thr Gly Leu Lys Lys Gln Arg Arg Lys Arg Lys Ser Glu
225                 230                 235                 240

Met Leu Gln Lys Ala Ala Arg Gly Arg Glu Glu His Gly Asp Glu
            245                 250                 255
```

<210> SEQ ID NO 173
<211> LENGTH: 332
<212> TYPE: PRT
<213> ORGANISM: Homo sapiens

<400> SEQUENCE: 173

```
Met Ser Thr Val Lys Glu Gln Leu Ile Glu Lys Leu Ile Glu Asp Asp
1               5                   10                  15

Glu Asn Ser Gln Cys Lys Ile Thr Ile Val Gly Thr Gly Ala Val Gly
                20                  25                  30

Met Ala Cys Ala Ile Ser Ile Leu Leu Lys Asp Leu Ala Asp Glu Leu
            35                  40                  45

Ala Leu Val Asp Val Ala Leu Asp Lys Leu Lys Gly Glu Met Met Asp
        50                  55                  60

Leu Gln His Gly Ser Leu Phe Phe Ser Thr Ser Lys Ile Thr Ser Gly
65                  70                  75                  80

Lys Asp Tyr Ser Val Ser Ala Asn Ser Arg Ile Val Ile Val Thr Ala
                85                  90                  95

Gly Ala Arg Gln Gln Glu Gly Glu Thr Arg Leu Ala Leu Val Gln Arg
            100                 105                 110

Asn Val Ala Ile Met Lys Ser Ile Ile Pro Ala Ile Val His Tyr Ser
        115                 120                 125

Pro Asp Cys Lys Ile Leu Val Val Ser Asn Pro Val Asp Ile Leu Thr
130                 135                 140

Tyr Ile Val Trp Lys Ile Ser Gly Leu Pro Val Thr Arg Val Ile Gly
145                 150                 155                 160

Ser Gly Cys Asn Leu Asp Ser Ala Arg Phe Arg Tyr Leu Ile Gly Glu
                165                 170                 175

Lys Leu Gly Val His Pro Thr Ser Cys His Gly Trp Ile Ile Gly Glu
            180                 185                 190

His Gly Asp Ser Ser Val Pro Leu Trp Ser Gly Val Asn Val Ala Gly
        195                 200                 205

Val Ala Leu Lys Thr Leu Asp Pro Lys Leu Gly Thr Asp Ser Asp Lys
210                 215                 220

Glu His Trp Lys Asn Ile His Lys Gln Val Ile Gln Ser Ala Tyr Glu
225                 230                 235                 240

Ile Ile Lys Leu Lys Gly Tyr Thr Ser Trp Ala Ile Gly Leu Ser Val
                245                 250                 255

Met Asp Leu Val Gly Ser Ile Leu Lys Asn Leu Arg Arg Val His Pro
            260                 265                 270

Val Ser Thr Met Val Lys Gly Leu Tyr Gly Ile Lys Glu Glu Leu Phe
        275                 280                 285

Leu Ser Ile Pro Cys Val Leu Gly Arg Asn Gly Val Ser Asp Val Val
    290                 295                 300

Lys Ile Asn Leu Asn Ser Glu Glu Glu Ala Leu Phe Lys Lys Ser Ala
305                 310                 315                 320

Glu Thr Leu Trp Asn Ile Gln Lys Asp Leu Ile Phe
                325                 330
```

```
<210> SEQ ID NO 174
<211> LENGTH: 373
<212> TYPE: PRT
<213> ORGANISM: Homo sapiens

<400> SEQUENCE: 174

Met Pro Pro Val Pro Gly Val Pro Phe Arg Asn Val Asp Asn Asp Ser
1               5                   10                  15

Pro Thr Ser Val Glu Leu Glu Asp Trp Val Asp Ala Gln His Pro Thr
            20                  25                  30

Asp Glu Glu Glu Glu Ala Ser Ser Ala Ser Ser Thr Leu Tyr Leu
        35                  40                  45

Val Phe Ser Pro Ser Ser Phe Ser Thr Ser Ser Ser Leu Ile Leu Gly
50                  55                  60

Gly Pro Glu Glu Glu Val Pro Ser Gly Val Ile Pro Asn Leu Thr
65                  70                  75                  80

Glu Ser Ile Pro Ser Ser Pro Pro Gln Gly Pro Pro Gln Gly Pro Ser
                85                  90                  95

Gln Ser Pro Leu Ser Ser Cys Cys Ser Ser Phe Ser Trp Ser Ser Phe
            100                 105                 110

Ser Glu Glu Ser Ser Ser Gln Lys Gly Glu Asp Thr Gly Thr Cys Gln
        115                 120                 125

Gly Leu Pro Asp Ser Glu Ser Ser Phe Thr Tyr Thr Leu Asp Glu Lys
130                 135                 140

Val Ala Glu Leu Val Glu Phe Leu Leu Leu Lys Tyr Glu Ala Glu Glu
145                 150                 155                 160

Pro Val Thr Glu Ala Glu Met Leu Met Ile Val Ile Lys Tyr Lys Asp
                165                 170                 175

Tyr Phe Pro Val Ile Leu Lys Arg Ala Arg Glu Phe Met Glu Leu Leu
            180                 185                 190

Phe Gly Leu Ala Leu Ile Glu Val Gly Pro Asp His Phe Cys Val Phe
        195                 200                 205

Ala Asn Thr Val Gly Leu Thr Asp Glu Gly Ser Asp Asp Glu Gly Met
210                 215                 220

Pro Glu Asn Ser Leu Leu Ile Ile Ile Leu Ser Val Ile Phe Ile Lys
225                 230                 235                 240

Gly Asn Cys Ala Ser Glu Glu Val Ile Trp Glu Val Leu Asn Ala Val
                245                 250                 255

Gly Val Tyr Ala Gly Arg Glu His Phe Val Tyr Gly Glu Pro Arg Glu
            260                 265                 270

Leu Leu Thr Lys Val Trp Val Gln Gly His Tyr Leu Glu Tyr Arg Glu
        275                 280                 285

Val Pro His Ser Ser Pro Pro Tyr Tyr Glu Phe Leu Trp Gly Pro Arg
290                 295                 300

Ala His Ser Glu Ser Ile Lys Lys Val Leu Glu Phe Leu Ala Lys
305                 310                 315                 320

Leu Asn Asn Thr Val Pro Ser Ser Phe Pro Ser Trp Tyr Lys Asp Ala
                325                 330                 335

Leu Lys Asp Val Glu Glu Arg Val Gln Ala Thr Ile Asp Thr Ala Asp
            340                 345                 350

Asp Ala Thr Val Met Ala Ser Glu Ser Leu Ser Val Met Ser Ser Asn
        355                 360                 365

Val Ser Phe Ser Glu
    370
```

<210> SEQ ID NO 175
<211> LENGTH: 314
<212> TYPE: PRT
<213> ORGANISM: Homo sapiens

<400> SEQUENCE: 175

Met Pro Leu Glu Gln Arg Ser Gln His Cys Lys Pro Glu Glu Gly Leu
1               5                   10                  15

Glu Ala Arg Gly Glu Ala Leu Gly Leu Val Gly Ala Gln Ala Pro Ala
            20                  25                  30

Thr Glu Glu Gln Glu Ala Ala Ser Ser Ser Thr Leu Val Glu Val
        35                  40                  45

Thr Leu Gly Glu Val Pro Ala Ala Glu Ser Pro Asp Pro Pro Gln Ser
    50                  55                  60

Pro Gln Gly Ala Ser Ser Leu Pro Thr Thr Met Asn Tyr Pro Leu Trp
65                  70                  75                  80

Ser Gln Ser Tyr Glu Asp Ser Ser Asn Gln Glu Glu Glu Gly Pro Ser
                85                  90                  95

Thr Phe Pro Asp Leu Glu Ser Glu Phe Gln Ala Ala Leu Ser Arg Lys
            100                 105                 110

Val Ala Glu Leu Val His Phe Leu Leu Leu Lys Tyr Arg Ala Arg Glu
        115                 120                 125

Pro Val Thr Lys Ala Glu Met Leu Gly Ser Val Val Gly Asn Trp Gln
    130                 135                 140

Tyr Phe Phe Pro Val Ile Phe Ser Lys Ala Ser Ser Ser Leu Gln Leu
145                 150                 155                 160

Val Phe Gly Ile Glu Leu Met Glu Val Asp Pro Ile Gly His Leu Tyr
                165                 170                 175

Ile Phe Ala Thr Cys Leu Gly Leu Ser Tyr Asp Gly Leu Leu Gly Asp
            180                 185                 190

Asn Gln Ile Met Pro Lys Ala Gly Leu Leu Ile Ile Val Leu Ala Ile
        195                 200                 205

Ile Ala Arg Glu Gly Asp Cys Ala Pro Glu Glu Lys Ile Trp Glu Glu
    210                 215                 220

Leu Ser Val Leu Glu Val Phe Glu Gly Arg Glu Asp Ser Ile Leu Gly
225                 230                 235                 240

Asp Pro Lys Lys Leu Leu Thr Gln His Phe Val Gln Glu Asn Tyr Leu
                245                 250                 255

Glu Tyr Arg Gln Val Pro Gly Ser Asp Pro Ala Cys Tyr Glu Phe Leu
            260                 265                 270

Trp Gly Pro Arg Ala Leu Val Glu Thr Ser Tyr Val Lys Val Leu His
        275                 280                 285

His Met Val Lys Ile Ser Gly Gly Pro His Ile Ser Tyr Pro Pro Leu
    290                 295                 300

His Glu Trp Val Leu Arg Glu Gly Glu Glu
305                 310

<210> SEQ ID NO 176
<211> LENGTH: 113
<212> TYPE: PRT
<213> ORGANISM: Homo sapiens

<400> SEQUENCE: 176

Met Asn Phe Tyr Leu Leu Leu Ala Ser Ser Ile Leu Cys Ala Leu Ile
1               5                   10                  15

```
Val Phe Trp Lys Tyr Arg Arg Phe Gln Arg Asn Thr Gly Glu Met Ser
                20                  25                  30

Ser Asn Ser Thr Ala Leu Ala Leu Val Arg Pro Ser Ser Ser Gly Leu
            35                  40                  45

Ile Asn Ser Asn Thr Asp Asn Asn Leu Ala Val Tyr Asp Leu Ser Arg
        50                  55                  60

Asp Ile Leu Asn Asn Phe Pro His Ser Ile Ala Arg Gln Lys Arg Ile
 65                  70                  75                  80

Leu Val Asn Leu Ser Met Val Glu Asn Lys Leu Val Glu Leu Glu His
                 85                  90                  95

Thr Leu Leu Ser Lys Gly Phe Arg Gly Ala Ser Pro His Arg Lys Ser
                100                 105                 110

Thr
```

<210> SEQ ID NO 177
<211> LENGTH: 309
<212> TYPE: PRT
<213> ORGANISM: Homo sapiens

<400> SEQUENCE: 177

```
Met Ser Leu Glu Gln Arg Ser Leu His Cys Lys Pro Glu Glu Ala Leu
 1               5                  10                  15

Glu Ala Gln Gln Glu Ala Leu Gly Leu Val Cys Val Gln Ala Ala Thr
                20                  25                  30

Ser Ser Ser Ser Pro Leu Val Leu Gly Thr Leu Glu Glu Val Pro Thr
            35                  40                  45

Ala Gly Ser Thr Asp Pro Pro Gln Ser Pro Gln Gly Ala Ser Ala Phe
        50                  55                  60

Pro Thr Thr Ile Asn Phe Thr Arg Gln Arg Gln Pro Ser Glu Gly Ser
 65                  70                  75                  80

Ser Ser Arg Glu Glu Glu Gly Pro Ser Thr Ser Cys Ile Leu Glu Ser
                 85                  90                  95

Leu Phe Arg Ala Val Ile Thr Lys Lys Val Ala Asp Leu Val Gly Phe
                100                 105                 110

Leu Leu Leu Lys Tyr Arg Ala Arg Glu Pro Val Thr Lys Ala Glu Met
                115                 120                 125

Leu Glu Ser Val Ile Lys Asn Tyr Lys His Cys Phe Pro Glu Ile Phe
                130                 135                 140

Gly Lys Ala Ser Glu Ser Leu Gln Leu Val Phe Gly Ile Asp Val Lys
145                 150                 155                 160

Glu Ala Asp Pro Thr Gly His Ser Tyr Val Leu Val Thr Cys Leu Gly
                165                 170                 175

Leu Ser Tyr Asp Gly Leu Leu Gly Asp Asn Gln Ile Met Pro Lys Thr
                180                 185                 190

Gly Phe Leu Ile Ile Val Leu Val Met Ile Ala Met Glu Gly Gly His
                195                 200                 205

Ala Pro Glu Glu Glu Ile Trp Glu Glu Leu Ser Val Met Glu Val Tyr
                210                 215                 220

Asp Gly Arg Glu His Ser Ala Tyr Gly Glu Pro Arg Lys Leu Leu Thr
225                 230                 235                 240

Gln Asp Leu Val Gln Glu Lys Tyr Leu Glu Tyr Arg Gln Val Pro Asp
                245                 250                 255

Ser Asp Pro Ala Arg Tyr Glu Phe Leu Trp Gly Pro Arg Ala Leu Ala
                260                 265                 270
```

```
Glu Thr Ser Tyr Val Lys Val Leu Glu Tyr Val Ile Lys Val Ser Ala
            275                 280                 285

Arg Val Arg Phe Phe Phe Pro Ser Leu Arg Glu Ala Ala Leu Arg Glu
        290                 295                 300

Glu Glu Glu Gly Val
305

<210> SEQ ID NO 178
<211> LENGTH: 9
<212> TYPE: PRT
<213> ORGANISM: artificial sequence
<220> FEATURE:
<223> OTHER INFORMATION: PRAME 9mer

<400> SEQUENCE: 178

Tyr Leu His Ala Arg Leu Arg Glu Leu
1               5

<210> SEQ ID NO 179
<211> LENGTH: 9
<212> TYPE: PRT
<213> ORGANISM: artificial sequence
<220> FEATURE:
<223> OTHER INFORMATION: MAGE-A2  9mer

<400> SEQUENCE: 179

Phe Ala His Pro Arg Lys Leu Leu Met
1               5

<210> SEQ ID NO 180
<211> LENGTH: 9
<212> TYPE: PRT
<213> ORGANISM: artificial sequence
<220> FEATURE:
<223> OTHER INFORMATION: PRAME 9mer

<400> SEQUENCE: 180

Lys Ala Met Val Gln Ala Trp Pro Phe
1               5

<210> SEQ ID NO 181
<211> LENGTH: 9
<212> TYPE: PRT
<213> ORGANISM: artificial sequence
<220> FEATURE:
<223> OTHER INFORMATION: MAGE-C1  9mer

<400> SEQUENCE: 181

Phe Ser Tyr Thr Leu Leu Ser Leu Phe
1               5

<210> SEQ ID NO 182
<211> LENGTH: 9
<212> TYPE: PRT
<213> ORGANISM: artificial sequence
<220> FEATURE:
<223> OTHER INFORMATION: Survivin 9mer

<400> SEQUENCE: 182

Arg Ala Ile Glu Gln Leu Ala Ala Met
1               5

<210> SEQ ID NO 183
<211> LENGTH: 9
<212> TYPE: PRT
<213> ORGANISM: artificial sequence
```

```
<220> FEATURE:
<223> OTHER INFORMATION: MAGE-C1  9mer

<400> SEQUENCE: 183

Phe Ser Ser Thr Leu Val Ser Leu Phe
1               5

<210> SEQ ID NO 184
<211> LENGTH: 9
<212> TYPE: PRT
<213> ORGANISM: artificial sequence
<220> FEATURE:
<223> OTHER INFORMATION: MAGE-A2  9mer

<400> SEQUENCE: 184

Phe Ser Thr Thr Ile Asn Tyr Thr Leu
1               5

<210> SEQ ID NO 185
<211> LENGTH: 9
<212> TYPE: PRT
<213> ORGANISM: artificial sequence
<220> FEATURE:
<223> OTHER INFORMATION: MAGE-A12 9mer

<400> SEQUENCE: 185

Lys Met Ala Glu Leu Val His Phe Leu
1               5

<210> SEQ ID NO 186
<211> LENGTH: 9
<212> TYPE: PRT
<213> ORGANISM: artificial sequence
<220> FEATURE:
<223> OTHER INFORMATION: MAGE-C1  9mer

<400> SEQUENCE: 186

Tyr Val Phe Val Asn Thr Leu Asp Leu
1               5

<210> SEQ ID NO 187
<211> LENGTH: 9
<212> TYPE: PRT
<213> ORGANISM: artificial sequence
<220> FEATURE:
<223> OTHER INFORMATION: MAGE-C1  9mer

<400> SEQUENCE: 187

Phe Ser Tyr Thr Leu Ala Ser Leu Leu
1               5

<210> SEQ ID NO 188
<211> LENGTH: 9
<212> TYPE: PRT
<213> ORGANISM: artificial sequence
<220> FEATURE:
<223> OTHER INFORMATION: PRAME 9mer

<400> SEQUENCE: 188

Tyr Ile Ala Gln Phe Thr Ser Gln Phe
1               5

<210> SEQ ID NO 189
<211> LENGTH: 9
<212> TYPE: PRT
<213> ORGANISM: artificial sequence
<220> FEATURE:
```

<223> OTHER INFORMATION: MAGE-C1 9mer

<400> SEQUENCE: 189

Met Thr Ser Ser Phe Ser Ser Thr Leu
1               5

<210> SEQ ID NO 190
<211> LENGTH: 9
<212> TYPE: PRT
<213> ORGANISM: artificial sequence
<220> FEATURE:
<223> OTHER INFORMATION: PRAME 9mer

<400> SEQUENCE: 190

His Val Met Asn Pro Leu Glu Thr Leu
1               5

<210> SEQ ID NO 191
<211> LENGTH: 9
<212> TYPE: PRT
<213> ORGANISM: artificial sequence
<220> FEATURE:
<223> OTHER INFORMATION: Ny-ESO-1 9mer

<400> SEQUENCE: 191

Arg Leu Leu Glu Phe Tyr Leu Ala Met
1               5

<210> SEQ ID NO 192
<211> LENGTH: 9
<212> TYPE: PRT
<213> ORGANISM: artificial sequence
<220> FEATURE:
<223> OTHER INFORMATION: MAGE-C2 9mer

<400> SEQUENCE: 192

Met Ala Ser Glu Ser Leu Ser Val Met
1               5

<210> SEQ ID NO 193
<211> LENGTH: 9
<212> TYPE: PRT
<213> ORGANISM: artificial sequence
<220> FEATURE:
<223> OTHER INFORMATION: MAGE-C2 9mer

<400> SEQUENCE: 193

Phe Val Tyr Gly Glu Pro Arg Glu Leu
1               5

<210> SEQ ID NO 194
<211> LENGTH: 9
<212> TYPE: PRT
<213> ORGANISM: artificial sequence
<220> FEATURE:
<223> OTHER INFORMATION: MAGE-A6 9mer

<400> SEQUENCE: 194

Phe Val Gln Glu Asn Tyr Leu Glu Tyr
1               5

<210> SEQ ID NO 195
<211> LENGTH: 9
<212> TYPE: PRT
<213> ORGANISM: artificial sequence
<220> FEATURE:
<223> OTHER INFORMATION: BORIS 9mer

<400> SEQUENCE: 195

Phe Thr Ser Ser Arg Met Ser Ser Phe
1               5

<210> SEQ ID NO 196
<211> LENGTH: 9
<212> TYPE: PRT
<213> ORGANISM: artificial sequence
<220> FEATURE:
<223> OTHER INFORMATION: LAGE-1  9mer

<400> SEQUENCE: 196

Phe Thr Val Ser Gly Asn Leu Leu Phe
1               5

<210> SEQ ID NO 197
<211> LENGTH: 9
<212> TYPE: PRT
<213> ORGANISM: artificial sequence
<220> FEATURE:
<223> OTHER INFORMATION: MAGE-A2  9mer

<400> SEQUENCE: 197

Lys Ala Ser Glu Tyr Leu Gln Leu Val
1               5

<210> SEQ ID NO 198
<211> LENGTH: 9
<212> TYPE: PRT
<213> ORGANISM: artificial sequence
<220> FEATURE:
<223> OTHER INFORMATION: Survivin 9mer

<400> SEQUENCE: 198

Ser Thr Phe Lys Asn Trp Pro Phe Leu
1               5

<210> SEQ ID NO 199
<211> LENGTH: 9
<212> TYPE: PRT
<213> ORGANISM: artificial sequence
<220> FEATURE:
<223> OTHER INFORMATION: MAGE-A11 9mer

<400> SEQUENCE: 199

His Ser Tyr Val Leu Val Thr Ser Leu
1               5

<210> SEQ ID NO 200
<211> LENGTH: 9
<212> TYPE: PRT
<213> ORGANISM: artificial sequence
<220> FEATURE:
<223> OTHER INFORMATION: SSX-1 9mer

<400> SEQUENCE: 200

Met Thr Phe Gly Arg Leu His Arg Ile
1               5

<210> SEQ ID NO 201
<211> LENGTH: 9
<212> TYPE: PRT
<213> ORGANISM: artificial sequence
<220> FEATURE:
<223> OTHER INFORMATION: MAGE-A3  9mer

```
<400> SEQUENCE: 201

Ala Ser Ser Ser Leu Gln Leu Val Phe
1               5

<210> SEQ ID NO 202
<211> LENGTH: 9
<212> TYPE: PRT
<213> ORGANISM: artificial sequence
<220> FEATURE:
<223> OTHER INFORMATION: MAGE-C2 9mer

<400> SEQUENCE: 202

Phe Ser Thr Ser Ser Ser Leu Ile Leu
1               5

<210> SEQ ID NO 203
<211> LENGTH: 9
<212> TYPE: PRT
<213> ORGANISM: artificial sequence
<220> FEATURE:
<223> OTHER INFORMATION: MAGE-A3  9mer

<400> SEQUENCE: 203

Lys Val Ala Glu Leu Val His Phe Leu
1               5

<210> SEQ ID NO 204
<211> LENGTH: 9
<212> TYPE: PRT
<213> ORGANISM: artificial sequence
<220> FEATURE:
<223> OTHER INFORMATION: MAGE-A11 9mer

<400> SEQUENCE: 204

Ala Met Asp Ala Ile Phe Gly Ser Leu
1               5

<210> SEQ ID NO 205
<211> LENGTH: 9
<212> TYPE: PRT
<213> ORGANISM: artificial sequence
<220> FEATURE:
<223> OTHER INFORMATION: MAGE-A10 9mer

<400> SEQUENCE: 205

Tyr Glu Asp His Phe Pro Leu Leu Phe
1               5

<210> SEQ ID NO 206
<211> LENGTH: 9
<212> TYPE: PRT
<213> ORGANISM: artificial sequence
<220> FEATURE:
<223> OTHER INFORMATION: MAGE-A11 9mer

<400> SEQUENCE: 206

Tyr Ala Gly Arg Glu His Phe Leu Phe
1               5

<210> SEQ ID NO 207
<211> LENGTH: 9
<212> TYPE: PRT
<213> ORGANISM: artificial sequence
<220> FEATURE:
<223> OTHER INFORMATION: MAGE-A1   9mer

<400> SEQUENCE: 207
```

Arg Ala Leu Ala Glu Thr Ser Tyr Val
1               5

<210> SEQ ID NO 208
<211> LENGTH: 15
<212> TYPE: PRT
<213> ORGANISM: artificial sequence
<220> FEATURE:
<223> OTHER INFORMATION: PRAME 15mer

<400> SEQUENCE: 208

Leu Glu Arg Leu Ala Tyr Leu His Ala Arg Leu Arg Glu Leu Leu
1               5                   10                  15

<210> SEQ ID NO 209
<211> LENGTH: 15
<212> TYPE: PRT
<213> ORGANISM: artificial sequence
<220> FEATURE:
<223> OTHER INFORMATION: PRAME 15mer

<400> SEQUENCE: 209

Glu Asp Ser Val Phe Ala His Pro Arg Lys Leu Leu Met Gln Asp
1               5                   10                  15

<210> SEQ ID NO 210
<211> LENGTH: 15
<212> TYPE: PRT
<213> ORGANISM: artificial sequence
<220> FEATURE:
<223> OTHER INFORMATION: MAGE-C1  15mer

<400> SEQUENCE: 210

Arg His Ser Gln Thr Leu Lys Ala Met Val Gln Ala Trp Pro Phe
1               5                   10                  15

<210> SEQ ID NO 211
<211> LENGTH: 15
<212> TYPE: PRT
<213> ORGANISM: artificial sequence
<220> FEATURE:
<223> OTHER INFORMATION: MAGE-C1  15mer

<400> SEQUENCE: 211

Ser Phe Ser Tyr Thr Leu Leu Ser Leu Phe Gln Ser Ser Pro Glu
1               5                   10                  15

<210> SEQ ID NO 212
<211> LENGTH: 15
<212> TYPE: PRT
<213> ORGANISM: artificial sequence
<220> FEATURE:
<223> OTHER INFORMATION: Survivin 15mer

<400> SEQUENCE: 212

Thr Ala Lys Lys Val Arg Arg Ala Ile Glu Gln Leu Ala Ala Met
1               5                   10                  15

<210> SEQ ID NO 213
<211> LENGTH: 15
<212> TYPE: PRT
<213> ORGANISM: artificial sequence
<220> FEATURE:
<223> OTHER INFORMATION: MAGE-C1  15mer

<400> SEQUENCE: 213

Ser Pro Ser Phe Ser Ser Thr Leu Val Ser Leu Phe Gln Ser Ser
1               5                   10                  15

<210> SEQ ID NO 214
<211> LENGTH: 15
<212> TYPE: PRT
<213> ORGANISM: artificial sequence
<220> FEATURE:
<223> OTHER INFORMATION: MAGE-A2  15mer

<400> SEQUENCE: 214

Ser Ser Phe Ser Thr Thr Ile Asn Tyr Thr Leu Trp Arg Gln Ser
1               5                   10                  15

<210> SEQ ID NO 215
<211> LENGTH: 15
<212> TYPE: PRT
<213> ORGANISM: artificial sequence
<220> FEATURE:
<223> OTHER INFORMATION: MAGE-A12 15mer

<400> SEQUENCE: 215

Gln Val Ala Leu Ser Arg Lys Met Ala Glu Leu Val His Phe Leu
1               5                   10                  15

<210> SEQ ID NO 216
<211> LENGTH: 15
<212> TYPE: PRT
<213> ORGANISM: artificial sequence
<220> FEATURE:
<223> OTHER INFORMATION: MAGE-C1  15mer

<400> SEQUENCE: 216

Asp Asp Ser Tyr Val Phe Val Asn Thr Leu Asp Leu Thr Ser Glu
1               5                   10                  15

<210> SEQ ID NO 217
<211> LENGTH: 15
<212> TYPE: PRT
<213> ORGANISM: artificial sequence
<220> FEATURE:
<223> OTHER INFORMATION: MAGE-C1  15mer

<400> SEQUENCE: 217

Phe Ser Tyr Thr Leu Ala Ser Leu Leu Gln Ser Ser His Glu Ser
1               5                   10                  15

<210> SEQ ID NO 218
<211> LENGTH: 15
<212> TYPE: PRT
<213> ORGANISM: artificial sequence
<220> FEATURE:
<223> OTHER INFORMATION: PRAME 15mer

<400> SEQUENCE: 218

Lys Glu Glu Gln Tyr Ile Ala Gln Phe Thr Ser Gln Phe Leu Ser
1               5                   10                  15

<210> SEQ ID NO 219
<211> LENGTH: 15
<212> TYPE: PRT
<213> ORGANISM: artificial sequence
<220> FEATURE:
<223> OTHER INFORMATION: MAGE-C1  15mer

<400> SEQUENCE: 219

Gln Ile Pro Met Thr Ser Ser Phe Ser Ser Thr Leu Leu Ser Ile

```
1               5                   10                  15
```

<210> SEQ ID NO 220
<211> LENGTH: 15
<212> TYPE: PRT
<213> ORGANISM: artificial sequence
<220> FEATURE:
<223> OTHER INFORMATION: PRAME 15mer

<400> SEQUENCE: 220

```
Asp Gln Leu Leu Arg His Val Met Asn Pro Leu Glu Thr Leu Ser
1               5                   10                  15
```

<210> SEQ ID NO 221
<211> LENGTH: 15
<212> TYPE: PRT
<213> ORGANISM: artificial sequence
<220> FEATURE:
<223> OTHER INFORMATION: Ny-ESO-1 15mer

<400> SEQUENCE: 221

```
Arg Gly Pro Glu Ser Arg Leu Leu Glu Phe Tyr Leu Ala Met Pro
1               5                   10                  15
```

<210> SEQ ID NO 222
<211> LENGTH: 15
<212> TYPE: PRT
<213> ORGANISM: artificial sequence
<220> FEATURE:
<223> OTHER INFORMATION: MAGE-C2 15mer

<400> SEQUENCE: 222

```
Met Ala Ser Glu Ser Leu Ser Val Met Ser Ser Asn Val Ser Phe
1               5                   10                  15
```

<210> SEQ ID NO 223
<211> LENGTH: 15
<212> TYPE: PRT
<213> ORGANISM: artificial sequence
<220> FEATURE:
<223> OTHER INFORMATION: MAGE-C2 15mer

<400> SEQUENCE: 223

```
Arg Glu His Phe Val Tyr Gly Glu Pro Arg Glu Leu Leu Thr Lys
1               5                   10                  15
```

<210> SEQ ID NO 224
<211> LENGTH: 15
<212> TYPE: PRT
<213> ORGANISM: artificial sequence
<220> FEATURE:
<223> OTHER INFORMATION: MAGE-A6 15mer

<400> SEQUENCE: 224

```
Gln Tyr Phe Val Gln Glu Asn Tyr Leu Glu Tyr Arg Gln Val Pro
1               5                   10                  15
```

<210> SEQ ID NO 225
<211> LENGTH: 15
<212> TYPE: PRT
<213> ORGANISM: artificial sequence
<220> FEATURE:
<223> OTHER INFORMATION: BORIS 15mer

<400> SEQUENCE: 225

```
Met Phe Thr Ser Ser Arg Met Ser Ser Phe Asn Arg His Met Lys
1               5                   10                  15
```

```
<210> SEQ ID NO 226
<211> LENGTH: 15
<212> TYPE: PRT
<213> ORGANISM: artificial sequence
<220> FEATURE:
<223> OTHER INFORMATION: LAGE-1 15mer

<400> SEQUENCE: 226

Asp Phe Thr Val Ser Gly Asn Leu Leu Phe Met Ser Val Arg Asp
1               5                   10                  15

<210> SEQ ID NO 227
<211> LENGTH: 15
<212> TYPE: PRT
<213> ORGANISM: artificial sequence
<220> FEATURE:
<223> OTHER INFORMATION: MAGE-A2 15mer

<400> SEQUENCE: 227

Ser Lys Ala Ser Glu Tyr Leu Gln Leu Val Phe Gly Ile Glu Val
1               5                   10                  15

<210> SEQ ID NO 228
<211> LENGTH: 15
<212> TYPE: PRT
<213> ORGANISM: artificial sequence
<220> FEATURE:
<223> OTHER INFORMATION: Survivin 15mer

<400> SEQUENCE: 228

Lys Asp His Arg Ile Ser Thr Phe Lys Asn Trp Pro Phe Leu Glu
1               5                   10                  15

<210> SEQ ID NO 229
<211> LENGTH: 15
<212> TYPE: PRT
<213> ORGANISM: artificial sequence
<220> FEATURE:
<223> OTHER INFORMATION: MAGE-A11 15mer

<400> SEQUENCE: 229

Ser His Ser Tyr Val Leu Val Thr Ser Leu Asn Leu Ser Tyr Asp
1               5                   10                  15

<210> SEQ ID NO 230
<211> LENGTH: 15
<212> TYPE: PRT
<213> ORGANISM: artificial sequence
<220> FEATURE:
<223> OTHER INFORMATION: SSX-1 15mer

<400> SEQUENCE: 230

Gln Val Glu His Pro Gln Met Thr Phe Gly Arg Leu His Arg Ile
1               5                   10                  15

<210> SEQ ID NO 231
<211> LENGTH: 15
<212> TYPE: PRT
<213> ORGANISM: artificial sequence
<220> FEATURE:
<223> OTHER INFORMATION: MAGE-A3 15mer

<400> SEQUENCE: 231

Lys Ala Ser Ser Ser Leu Gln Leu Val Phe Gly Ile Glu Leu Met
1               5                   10                  15
```

```
<210> SEQ ID NO 232
<211> LENGTH: 15
<212> TYPE: PRT
<213> ORGANISM: artificial sequence
<220> FEATURE:
<223> OTHER INFORMATION: MAGE-C2 15mer

<400> SEQUENCE: 232

Ser Ser Phe Ser Thr Ser Ser Ser Leu Ile Leu Gly Gly Pro Glu
1               5                   10                  15

<210> SEQ ID NO 233
<211> LENGTH: 15
<212> TYPE: PRT
<213> ORGANISM: artificial sequence
<220> FEATURE:
<223> OTHER INFORMATION: MAGE-A3  15mer

<400> SEQUENCE: 233

Gln Ala Ala Leu Ser Arg Lys Val Ala Glu Leu Val His Phe Leu
1               5                   10                  15

<210> SEQ ID NO 234
<211> LENGTH: 15
<212> TYPE: PRT
<213> ORGANISM: artificial sequence
<220> FEATURE:
<223> OTHER INFORMATION: MAGE-A11 15mer

<400> SEQUENCE: 234

Ser Pro Thr Ala Met Asp Ala Ile Phe Gly Ser Leu Ser Asp Glu
1               5                   10                  15

<210> SEQ ID NO 235
<211> LENGTH: 15
<212> TYPE: PRT
<213> ORGANISM: artificial sequence
<220> FEATURE:
<223> OTHER INFORMATION: MAGE-A10 15mer

<400> SEQUENCE: 235

Arg Asn Tyr Glu Asp His Phe Pro Leu Leu Phe Ser Glu Ala Ser
1               5                   10                  15

<210> SEQ ID NO 236
<211> LENGTH: 15
<212> TYPE: PRT
<213> ORGANISM: artificial sequence
<220> FEATURE:
<223> OTHER INFORMATION: MAGE-A11 15mer

<400> SEQUENCE: 236

Tyr Ala Gly Arg Glu His Phe Leu Phe Gly Glu Pro Lys Arg Leu
1               5                   10                  15

<210> SEQ ID NO 237
<211> LENGTH: 15
<212> TYPE: PRT
<213> ORGANISM: artificial sequence
<220> FEATURE:
<223> OTHER INFORMATION: MAGE-A1  15mer

<400> SEQUENCE: 237

Pro Arg Ala Leu Ala Glu Thr Ser Tyr Val Lys Val Leu Glu Tyr
1               5                   10                  15
```

-continued

```
<210> SEQ ID NO 238
<211> LENGTH: 30
<212> TYPE: PRT
<213> ORGANISM: artificial sequence
<220> FEATURE:
<223> OTHER INFORMATION: MC621-01 PRAME/PRAME

<400> SEQUENCE: 238

Leu Glu Arg Leu Ala Tyr Leu His Ala Arg Leu Arg Glu Leu Leu Asp
1               5                   10                  15

Gln Leu Leu Arg His Val Met Asn Pro Leu Glu Thr Leu Ser
            20                  25                  30

<210> SEQ ID NO 239
<211> LENGTH: 30
<212> TYPE: PRT
<213> ORGANISM: artificial sequence
<220> FEATURE:
<223> OTHER INFORMATION: MC621-02 Survivin/MAGE-A2

<400> SEQUENCE: 239

Thr Ala Lys Lys Val Arg Arg Ala Ile Glu Gln Leu Ala Ala Met Glu
1               5                   10                  15

Asp Ser Val Phe Ala His Pro Arg Lys Leu Leu Met Gln Asp
            20                  25                  30

<210> SEQ ID NO 240
<211> LENGTH: 30
<212> TYPE: PRT
<213> ORGANISM: artificial sequence
<220> FEATURE:
<223> OTHER INFORMATION: MC621-03 PRAME/MAGE-A3

<400> SEQUENCE: 240

Arg His Ser Gln Thr Leu Lys Ala Met Val Gln Ala Trp Pro Phe Lys
1               5                   10                  15

Ala Ser Ser Ser Leu Gln Leu Val Phe Gly Ile Glu Leu Met
            20                  25                  30

<210> SEQ ID NO 241
<211> LENGTH: 30
<212> TYPE: PRT
<213> ORGANISM: artificial sequence
<220> FEATURE:
<223> OTHER INFORMATION: MC621-04 MAGE-C1 /MAGE-A2

<400> SEQUENCE: 241

Asp Asp Ser Tyr Val Phe Val Asn Thr Leu Asp Leu Thr Ser Glu Ser
1               5                   10                  15

Ser Phe Ser Thr Thr Ile Asn Tyr Thr Leu Trp Arg Gln Ser
            20                  25                  30

<210> SEQ ID NO 242
<211> LENGTH: 30
<212> TYPE: PRT
<213> ORGANISM: artificial sequence
<220> FEATURE:
<223> OTHER INFORMATION: MC621-05 MAGE-C1 /MAGE-A2

<400> SEQUENCE: 242

Ser Phe Ser Tyr Thr Leu Leu Ser Leu Phe Gln Ser Ser Pro Glu Ser
1               5                   10                  15

Lys Ala Ser Glu Tyr Leu Gln Leu Val Phe Gly Ile Glu Val
            20                  25                  30
```

<210> SEQ ID NO 243
<211> LENGTH: 30
<212> TYPE: PRT
<213> ORGANISM: artificial sequence
<220> FEATURE:
<223> OTHER INFORMATION: MC621-06 MAGE-A11/MAGE-C1

<400> SEQUENCE: 243

Ser His Ser Tyr Val Leu Val Thr Ser Leu Asn Leu Ser Tyr Asp Ser
1               5                   10                  15

Pro Ser Phe Ser Ser Thr Leu Val Ser Leu Phe Gln Ser Ser
            20                  25                  30

<210> SEQ ID NO 244
<211> LENGTH: 30
<212> TYPE: PRT
<213> ORGANISM: artificial sequence
<220> FEATURE:
<223> OTHER INFORMATION: MC621-07 LAGE-1 /MAGE-C2

<400> SEQUENCE: 244

Asp Phe Thr Val Ser Gly Asn Leu Leu Phe Met Ser Val Arg Asp Met
1               5                   10                  15

Ala Ser Glu Ser Leu Ser Val Met Ser Ser Asn Val Ser Phe
            20                  25                  30

<210> SEQ ID NO 245
<211> LENGTH: 30
<212> TYPE: PRT
<213> ORGANISM: artificial sequence
<220> FEATURE:
<223> OTHER INFORMATION: MC621-08 BORIS/MAGE-A12

<400> SEQUENCE: 245

Met Phe Thr Ser Ser Arg Met Ser Ser Phe Asn Arg His Met Lys Gln
1               5                   10                  15

Val Ala Leu Ser Arg Lys Met Ala Glu Leu Val His Phe Leu
            20                  25                  30

<210> SEQ ID NO 246
<211> LENGTH: 30
<212> TYPE: PRT
<213> ORGANISM: artificial sequence
<220> FEATURE:
<223> OTHER INFORMATION: MC621-09 MAGE-C2/MAGE-C1

<400> SEQUENCE: 246

Ser Ser Phe Ser Thr Ser Ser Ser Leu Ile Leu Gly Gly Pro Glu Phe
1               5                   10                  15

Ser Tyr Thr Leu Ala Ser Leu Leu Gln Ser Ser His Glu Ser
            20                  25                  30

<210> SEQ ID NO 247
<211> LENGTH: 30
<212> TYPE: PRT
<213> ORGANISM: artificial sequence
<220> FEATURE:
<223> OTHER INFORMATION: MC621-10 Survivin/MAGE-C1

<400> SEQUENCE: 247

Lys Asp His Arg Ile Ser Thr Phe Lys Asn Trp Pro Phe Leu Glu Gln
1               5                   10                  15

Ile Pro Met Thr Ser Ser Phe Ser Ser Thr Leu Leu Ser Ile
            20                  25                  30

```
<210> SEQ ID NO 248
<211> LENGTH: 30
<212> TYPE: PRT
<213> ORGANISM: artificial sequence
<220> FEATURE:
<223> OTHER INFORMATION: MC621-11 Ny-ESO-1/MAGE-A10

<400> SEQUENCE: 248

Arg Gly Pro Glu Ser Arg Leu Leu Glu Phe Tyr Leu Ala Met Pro Arg
1               5                   10                  15

Asn Tyr Glu Asp His Phe Pro Leu Leu Phe Ser Glu Ala Ser
            20                  25                  30

<210> SEQ ID NO 249
<211> LENGTH: 30
<212> TYPE: PRT
<213> ORGANISM: artificial sequence
<220> FEATURE:
<223> OTHER INFORMATION: MC621-12 MAGE-A3 /MAGE-A6

<400> SEQUENCE: 249

Gln Ala Ala Leu Ser Arg Lys Val Ala Glu Leu Val His Phe Leu Gln
1               5                   10                  15

Tyr Phe Val Gln Glu Asn Tyr Leu Glu Tyr Arg Gln Val Pro
            20                  25                  30

<210> SEQ ID NO 250
<211> LENGTH: 30
<212> TYPE: PRT
<213> ORGANISM: artificial sequence
<220> FEATURE:
<223> OTHER INFORMATION: MC621-13 MAGE-A11 /MAGE-A1

<400> SEQUENCE: 250

Ser Pro Thr Ala Met Asp Ala Ile Phe Gly Ser Leu Ser Asp Glu Pro
1               5                   10                  15

Arg Ala Leu Ala Glu Thr Ser Tyr Val Lys Val Leu Glu Tyr
            20                  25                  30

<210> SEQ ID NO 251
<211> LENGTH: 30
<212> TYPE: PRT
<213> ORGANISM: artificial sequence
<220> FEATURE:
<223> OTHER INFORMATION: MC621-14 MAGE-C2/MAGE-A11

<400> SEQUENCE: 251

Arg Glu His Phe Val Tyr Gly Glu Pro Arg Glu Leu Leu Thr Lys Tyr
1               5                   10                  15

Ala Gly Arg Glu His Phe Leu Phe Gly Glu Pro Lys Arg Leu
            20                  25                  30

<210> SEQ ID NO 252
<211> LENGTH: 30
<212> TYPE: PRT
<213> ORGANISM: artificial sequence
<220> FEATURE:
<223> OTHER INFORMATION: MC621-15 SSX-1/PRAME

<400> SEQUENCE: 252

Gln Val Glu His Pro Gln Met Thr Phe Gly Arg Leu His Arg Ile Lys
1               5                   10                  15

Glu Glu Gln Tyr Ile Ala Gln Phe Thr Ser Gln Phe Leu Ser
```

<210> SEQ ID NO 253
<211> LENGTH: 509
<212> TYPE: PRT
<213> ORGANISM: Homo sapiens

<400> SEQUENCE: 253

```
Met Glu Arg Arg Arg Leu Trp Gly Ser Ile Gln Ser Arg Tyr Ile Ser
1               5                   10                  15

Met Ser Val Trp Thr Ser Pro Arg Arg Leu Val Glu Leu Ala Gly Gln
                20                  25                  30

Ser Leu Leu Lys Asp Glu Ala Leu Ala Ile Ala Ala Leu Glu Leu Leu
            35                  40                  45

Pro Arg Glu Leu Phe Pro Pro Leu Phe Met Ala Ala Phe Asp Gly Arg
        50                  55                  60

His Ser Gln Thr Leu Lys Ala Met Val Gln Ala Trp Pro Phe Thr Cys
65                  70                  75                  80

Leu Pro Leu Gly Val Leu Met Lys Gly Gln His Leu His Leu Glu Thr
                85                  90                  95

Phe Lys Ala Val Leu Asp Gly Leu Asp Val Leu Leu Ala Gln Glu Val
            100                 105                 110

Arg Pro Arg Arg Trp Lys Leu Gln Val Leu Asp Leu Arg Lys Asn Ser
        115                 120                 125

His Gln Asp Phe Trp Thr Val Trp Ser Gly Asn Arg Ala Ser Leu Tyr
130                 135                 140

Ser Phe Pro Glu Pro Glu Ala Ala Gln Pro Met Thr Lys Lys Arg Lys
145                 150                 155                 160

Val Asp Gly Leu Ser Thr Glu Ala Glu Gln Pro Phe Ile Pro Val Glu
                165                 170                 175

Val Leu Val Asp Leu Phe Leu Lys Glu Gly Ala Cys Asp Glu Leu Phe
            180                 185                 190

Ser Tyr Leu Ile Glu Lys Val Lys Arg Lys Lys Asn Val Leu Arg Leu
        195                 200                 205

Cys Cys Lys Lys Leu Lys Ile Phe Ala Met Pro Met Gln Asp Ile Lys
    210                 215                 220

Met Ile Leu Lys Met Val Gln Leu Asp Ser Ile Glu Asp Leu Glu Val
225                 230                 235                 240

Thr Cys Thr Trp Lys Leu Pro Thr Leu Ala Lys Phe Ser Pro Tyr Leu
                245                 250                 255

Gly Gln Met Ile Asn Leu Arg Arg Leu Leu Ser His Ile His Ala
            260                 265                 270

Ser Ser Tyr Ile Ser Pro Glu Lys Glu Glu Gln Tyr Ile Ala Gln Phe
        275                 280                 285

Thr Ser Gln Phe Leu Ser Leu Gln Cys Leu Gln Ala Leu Tyr Val Asp
    290                 295                 300

Ser Leu Phe Phe Leu Arg Gly Arg Leu Asp Gln Leu Leu Arg His Val
305                 310                 315                 320

Met Asn Pro Leu Glu Thr Leu Ser Ile Thr Asn Cys Arg Leu Ser Glu
                325                 330                 335

Gly Asp Val Met His Leu Ser Gln Ser Pro Ser Val Ser Gln Leu Ser
            340                 345                 350

Val Leu Ser Leu Ser Gly Val Met Leu Thr Asp Val Ser Pro Glu Pro
        355                 360                 365
```

```
Leu Gln Ala Leu Leu Glu Arg Ala Ser Ala Thr Leu Gln Asp Leu Val
    370                 375                 380

Phe Asp Glu Cys Gly Ile Thr Asp Asp Gln Leu Leu Ala Leu Leu Pro
385                 390                 395                 400

Ser Leu Ser His Cys Ser Gln Leu Thr Thr Leu Ser Phe Tyr Gly Asn
                405                 410                 415

Ser Ile Ser Ile Ser Ala Leu Gln Ser Leu Leu Gln His Leu Ile Gly
                420                 425                 430

Leu Ser Asn Leu Thr His Val Leu Tyr Pro Val Pro Leu Glu Ser Tyr
            435                 440                 445

Glu Asp Ile His Gly Thr Leu His Leu Glu Arg Leu Ala Tyr Leu His
    450                 455                 460

Ala Arg Leu Arg Glu Leu Leu Cys Glu Leu Gly Arg Pro Ser Met Val
465                 470                 475                 480

Trp Leu Ser Ala Asn Pro Cys His Cys Gly Asp Arg Thr Phe Tyr
                485                 490                 495

Asp Pro Glu Pro Ile Leu Cys Pro Cys Phe Met Pro Asn
                500                 505
```

<210> SEQ ID NO 254
<211> LENGTH: 314
<212> TYPE: PRT
<213> ORGANISM: Homo sapiens

<400> SEQUENCE: 254

```
Met Pro Leu Glu Gln Arg Ser Gln His Cys Lys Pro Glu Glu Gly Leu
1               5                   10                  15

Glu Ala Arg Gly Glu Ala Leu Gly Leu Val Gly Ala Gln Ala Pro Ala
                20                  25                  30

Thr Glu Gln Gln Thr Ala Ser Ser Ser Thr Leu Val Glu Val
            35                  40                  45

Thr Leu Gly Glu Val Pro Ala Ala Asp Ser Pro Ser Pro Pro His Ser
    50                  55                  60

Pro Gln Gly Ala Ser Ser Phe Ser Thr Thr Ile Asn Tyr Thr Leu Trp
65                  70                  75                  80

Arg Gln Ser Asp Glu Gly Ser Ser Asn Gln Glu Glu Gly Pro Arg
                85                  90                  95

Met Phe Pro Asp Leu Glu Ser Glu Phe Gln Ala Ala Ile Ser Arg Lys
                100                 105                 110

Met Val Glu Leu Val His Phe Leu Leu Leu Lys Tyr Arg Ala Arg Glu
                115                 120                 125

Pro Val Thr Lys Ala Glu Met Leu Glu Ser Val Leu Arg Asn Cys Gln
                130                 135                 140

Asp Phe Phe Pro Val Ile Phe Ser Lys Ala Ser Glu Tyr Leu Gln Leu
145                 150                 155                 160

Val Phe Gly Ile Glu Val Val Glu Val Pro Ile Ser His Leu Tyr
                165                 170                 175

Ile Leu Val Thr Cys Leu Gly Leu Ser Tyr Asp Gly Leu Leu Gly Asp
                180                 185                 190

Asn Gln Val Met Pro Lys Thr Gly Leu Leu Ile Ile Val Leu Ala Ile
            195                 200                 205

Ile Ala Ile Glu Gly Asp Cys Ala Pro Glu Glu Lys Ile Trp Glu Glu
    210                 215                 220

Leu Ser Met Leu Glu Val Phe Glu Gly Arg Glu Asp Ser Val Phe Ala
225                 230                 235                 240
```

His Pro Arg Lys Leu Leu Met Gln Asp Leu Val Gln Glu Asn Tyr Leu
            245                 250                 255

Glu Tyr Arg Gln Val Pro Gly Ser Asp Pro Ala Cys Tyr Glu Phe Leu
            260                 265                 270

Trp Gly Pro Arg Ala Leu Ile Glu Thr Ser Tyr Val Lys Val Leu His
            275                 280                 285

His Thr Leu Lys Ile Gly Gly Glu Pro His Ile Ser Tyr Pro Pro Leu
            290                 295                 300

His Glu Arg Ala Leu Arg Glu Gly Glu Glu
305                 310

<210> SEQ ID NO 255
<211> LENGTH: 1142
<212> TYPE: PRT
<213> ORGANISM: Homo sapiens

<400> SEQUENCE: 255

Met Gly Asp Lys Asp Met Pro Thr Ala Gly Met Pro Ser Leu Leu Gln
1               5                   10                  15

Ser Ser Ser Glu Ser Pro Gln Ser Cys Pro Glu Gly Glu Asp Ser Gln
            20                  25                  30

Ser Pro Leu Gln Ile Pro Gln Ser Ser Pro Glu Ser Asp Asp Thr Leu
            35                  40                  45

Tyr Pro Leu Gln Ser Pro Gln Ser Arg Ser Glu Gly Glu Asp Ser Ser
        50                  55                  60

Asp Pro Leu Gln Arg Pro Pro Glu Gly Lys Asp Ser Gln Ser Pro Leu
65                  70                  75                  80

Gln Ile Pro Gln Ser Ser Pro Glu Gly Asp Asp Thr Gln Ser Pro Leu
            85                  90                  95

Gln Asn Ser Gln Ser Ser Pro Glu Gly Lys Asp Ser Leu Ser Pro Leu
            100                 105                 110

Glu Ile Ser Gln Ser Pro Pro Gly Glu Asp Val Gln Ser Pro Leu
            115                 120                 125

Gln Asn Pro Ala Ser Ser Phe Phe Ser Ser Ala Leu Leu Ser Ile Phe
            130                 135                 140

Gln Ser Ser Pro Glu Ser Thr Gln Ser Pro Phe Glu Gly Phe Pro Gln
145                 150                 155                 160

Ser Val Leu Gln Ile Pro Val Ser Ala Ala Ser Ser Ser Thr Leu Val
            165                 170                 175

Ser Ile Phe Gln Ser Ser Pro Glu Ser Thr Gln Ser Pro Phe Glu Gly
            180                 185                 190

Phe Pro Gln Ser Pro Leu Gln Ile Pro Val Ser Arg Ser Phe Ser Ser
            195                 200                 205

Thr Leu Leu Ser Ile Phe Gln Ser Ser Pro Glu Arg Thr Gln Ser Thr
210                 215                 220

Phe Glu Gly Phe Ala Gln Ser Pro Leu Gln Ile Pro Val Ser Pro Ser
225                 230                 235                 240

Ser Ser Ser Thr Leu Leu Ser Leu Phe Gln Ser Phe Ser Glu Arg Thr
            245                 250                 255

Gln Ser Thr Phe Glu Gly Phe Ala Gln Ser Ser Leu Gln Ile Pro Val
            260                 265                 270

Ser Pro Ser Phe Ser Ser Thr Leu Val Ser Leu Phe Gln Ser Ser Pro
            275                 280                 285

Glu Arg Thr Gln Ser Thr Phe Glu Gly Phe Pro Gln Ser Pro Leu Gln

```
            290                 295                 300
Ile Pro Val Ser Ser Ser Ser Ser Thr Leu Leu Ser Leu Phe Gln
305                 310                 315                 320

Ser Ser Pro Glu Arg Thr His Ser Thr Phe Glu Gly Phe Pro Gln Ser
                325                 330                 335

Leu Leu Gln Ile Pro Met Thr Ser Ser Phe Ser Ser Thr Leu Leu Ser
                340                 345                 350

Ile Phe Gln Ser Ser Pro Glu Ser Ala Gln Ser Thr Phe Glu Gly Phe
                355                 360                 365

Pro Gln Ser Pro Leu Gln Ile Pro Gly Ser Pro Ser Phe Ser Ser Thr
            370                 375                 380

Leu Leu Ser Leu Phe Gln Ser Ser Pro Glu Arg Thr His Ser Thr Phe
385                 390                 395                 400

Glu Gly Phe Pro Gln Ser Pro Leu Gln Ile Pro Met Thr Ser Ser Phe
                405                 410                 415

Ser Ser Thr Leu Leu Ser Ile Leu Gln Ser Ser Pro Glu Ser Ala Gln
                420                 425                 430

Ser Ala Phe Glu Gly Phe Pro Gln Ser Pro Leu Gln Ile Pro Val Ser
            435                 440                 445

Ser Ser Phe Ser Tyr Thr Leu Leu Ser Leu Phe Gln Ser Ser Pro Glu
            450                 455                 460

Arg Thr His Ser Thr Phe Glu Gly Phe Pro Gln Ser Pro Leu Gln Ile
465                 470                 475                 480

Pro Val Ser Ser Ser Ser Ser Ser Thr Leu Leu Ser Leu Phe Gln
                485                 490                 495

Ser Ser Pro Glu Cys Thr Gln Ser Thr Phe Glu Gly Phe Pro Gln Ser
                500                 505                 510

Pro Leu Gln Ile Pro Gln Ser Pro Pro Glu Gly Glu Asn Thr His Ser
            515                 520                 525

Pro Leu Gln Ile Val Pro Ser Leu Pro Glu Trp Glu Asp Ser Leu Ser
            530                 535                 540

Pro His Tyr Phe Pro Gln Ser Pro Pro Gln Gly Glu Asp Ser Leu Ser
545                 550                 555                 560

Pro His Tyr Phe Pro Gln Ser Pro Pro Gln Gly Glu Asp Ser Leu Ser
                565                 570                 575

Pro His Tyr Phe Pro Gln Ser Pro Gln Gly Glu Asp Ser Leu Ser Pro
            580                 585                 590

His Tyr Phe Pro Gln Ser Pro Pro Gln Gly Glu Asp Ser Met Ser Pro
            595                 600                 605

Leu Tyr Phe Pro Gln Ser Pro Leu Gln Gly Glu Glu Phe Gln Ser Ser
            610                 615                 620

Leu Gln Ser Pro Val Ser Ile Cys Ser Ser Thr Pro Ser Ser Leu
625                 630                 635                 640

Pro Gln Ser Phe Pro Glu Ser Ser Gln Ser Pro Pro Glu Gly Pro Val
                645                 650                 655

Gln Ser Pro Leu His Ser Pro Gln Ser Pro Pro Glu Gly Met His Ser
            660                 665                 670

Gln Ser Pro Leu Gln Ser Pro Glu Ser Ala Pro Glu Gly Glu Asp Ser
            675                 680                 685

Leu Ser Pro Leu Gln Ile Pro Gln Ser Pro Leu Glu Gly Glu Asp Ser
            690                 695                 700

Leu Ser Ser Leu His Phe Pro Gln Ser Pro Pro Glu Trp Glu Asp Ser
705                 710                 715                 720
```

```
Leu Ser Pro Leu His Phe Pro Gln Phe Pro Gln Gly Glu Asp Phe
                725                 730                 735

Gln Ser Ser Leu Gln Ser Pro Val Ser Ile Cys Ser Ser Thr Ser
            740                 745                 750

Leu Ser Leu Pro Gln Ser Phe Pro Glu Ser Pro Gln Ser Pro Pro Glu
        755                 760                 765

Gly Pro Ala Gln Ser Pro Leu Gln Arg Pro Val Ser Ser Phe Phe Ser
770                 775                 780

Tyr Thr Leu Ala Ser Leu Leu Gln Ser Ser His Glu Ser Pro Gln Ser
785                 790                 795                 800

Pro Pro Glu Gly Pro Ala Gln Ser Pro Leu Gln Ser Pro Val Ser Ser
            805                 810                 815

Phe Pro Ser Ser Thr Ser Ser Ser Leu Ser Gln Ser Ser Pro Val Ser
            820                 825                 830

Ser Phe Pro Ser Ser Thr Ser Ser Ser Leu Ser Lys Ser Ser Pro Glu
            835                 840                 845

Ser Pro Leu Gln Ser Pro Val Ile Ser Phe Ser Ser Ser Thr Ser Leu
    850                 855                 860

Ser Pro Phe Ser Glu Glu Ser Ser Pro Val Asp Glu Tyr Thr Ser
865                 870                 875                 880

Ser Ser Asp Thr Leu Leu Glu Ser Asp Ser Leu Thr Asp Ser Glu Ser
                885                 890                 895

Leu Ile Glu Ser Glu Pro Leu Phe Thr Tyr Thr Leu Asp Glu Lys Val
                900                 905                 910

Asp Glu Leu Ala Arg Phe Leu Leu Lys Tyr Gln Val Lys Gln Pro
            915                 920                 925

Ile Thr Lys Ala Glu Met Leu Thr Asn Val Ile Ser Arg Tyr Thr Gly
    930                 935                 940

Tyr Phe Pro Val Ile Phe Arg Lys Ala Arg Glu Phe Ile Glu Ile Leu
945                 950                 955                 960

Phe Gly Ile Ser Leu Arg Glu Val Asp Pro Asp Asp Ser Tyr Val Phe
                965                 970                 975

Val Asn Thr Leu Asp Leu Thr Ser Glu Gly Cys Leu Ser Asp Glu Gln
                980                 985                 990

Gly Met Ser Gln Asn Arg Leu Leu Ile Leu Ile Leu Ser Ile Ile Phe
            995                 1000                1005

Ile Lys Gly Thr Tyr Ala Ser Glu Glu Val Ile Trp Asp Val Leu
    1010                1015                1020

Ser Gly Ile Gly Val Arg Ala Gly Arg Glu His Phe Ala Phe Gly
    1025                1030                1035

Glu Pro Arg Glu Leu Leu Thr Lys Val Trp Val Gln Glu His Tyr
    1040                1045                1050

Leu Glu Tyr Arg Glu Val Pro Asn Ser Ser Pro Pro Arg Tyr Glu
    1055                1060                1065

Phe Leu Trp Gly Pro Arg Ala His Ser Glu Val Ile Lys Arg Lys
    1070                1075                1080

Val Val Glu Phe Leu Ala Met Leu Lys Asn Thr Val Pro Ile Thr
    1085                1090                1095

Phe Pro Ser Ser Tyr Lys Asp Ala Leu Lys Asp Val Glu Glu Arg
    1100                1105                1110

Ala Gln Ala Ile Ile Asp Thr Thr Asp Asp Ser Thr Ala Thr Glu
    1115                1120                1125
```

<210> SEQ ID NO 256
<211> LENGTH: 142
<212> TYPE: PRT
<213> ORGANISM: Homo sapiens

<400> SEQUENCE: 256

Met Gly Ala Pro Thr Leu Pro Pro Ala Trp Gln Pro Phe Leu Lys Asp
1               5                   10                  15

His Arg Ile Ser Thr Phe Lys Asn Trp Pro Phe Leu Glu Gly Cys Ala
            20                  25                  30

Cys Thr Pro Glu Arg Met Ala Glu Ala Gly Phe Ile His Cys Pro Thr
        35                  40                  45

Glu Asn Glu Pro Asp Leu Ala Gln Cys Phe Phe Cys Phe Lys Glu Leu
    50                  55                  60

Glu Gly Trp Glu Pro Asp Asp Pro Ile Glu Glu His Lys Lys His Ser
65                  70                  75                  80

Ser Ser Gly Cys Ala Phe Leu Ser Val Lys Lys Gln Phe Glu Glu Leu
                85                  90                  95

Thr Leu Gly Glu Phe Leu Lys Leu Asp Arg Glu Arg Ala Lys Asn Lys
            100                 105                 110

Ile Ala Lys Glu Thr Asn Asn Lys Lys Lys Glu Phe Glu Glu Thr Ala
        115                 120                 125

Lys Lys Val Arg Arg Ala Ile Glu Gln Leu Ala Ala Met Asp
    130                 135                 140

<210> SEQ ID NO 257
<211> LENGTH: 314
<212> TYPE: PRT
<213> ORGANISM: Homo sapiens

<400> SEQUENCE: 257

Met Pro Leu Glu Gln Arg Ser Gln His Cys Lys Pro Glu Glu Gly Leu
1               5                   10                  15

Glu Ala Gln Gly Glu Ala Leu Gly Leu Val Gly Ala Gln Ala Pro Ala
            20                  25                  30

Thr Glu Glu Gln Glu Thr Ala Ser Ser Ser Thr Leu Val Glu Val
        35                  40                  45

Thr Leu Arg Glu Val Pro Ala Ala Glu Ser Pro Ser Pro His Ser
    50                  55                  60

Pro Gln Gly Ala Ser Thr Leu Pro Thr Thr Ile Asn Tyr Thr Leu Trp
65                  70                  75                  80

Ser Gln Ser Asp Glu Gly Ser Ser Asn Glu Glu Gln Glu Gly Pro Ser
                85                  90                  95

Thr Phe Pro Asp Leu Glu Thr Ser Phe Gln Val Ala Leu Ser Arg Lys
            100                 105                 110

Met Ala Glu Leu Val His Phe Leu Leu Leu Lys Tyr Arg Ala Arg Glu
        115                 120                 125

Pro Phe Thr Lys Ala Glu Met Leu Gly Ser Val Ile Arg Asn Phe Gln
    130                 135                 140

Asp Phe Phe Pro Val Ile Phe Ser Lys Ala Ser Glu Tyr Leu Gln Leu
145                 150                 155                 160

Val Phe Gly Ile Glu Val Val Glu Val Val Arg Ile Gly His Leu Tyr
                165                 170                 175

```
Ile Leu Val Thr Cys Leu Gly Leu Ser Tyr Asp Gly Leu Gly Asp
            180                 185                 190

Asn Gln Ile Val Pro Lys Thr Gly Leu Leu Ile Val Leu Ala Ile
        195                 200                 205

Ile Ala Lys Glu Gly Asp Cys Ala Pro Glu Glu Lys Ile Trp Glu Glu
    210                 215                 220

Leu Ser Val Leu Glu Ala Ser Asp Gly Arg Glu Asp Ser Val Phe Ala
225                 230                 235                 240

His Pro Arg Lys Leu Leu Thr Gln Asp Leu Val Gln Glu Asn Tyr Leu
                245                 250                 255

Glu Tyr Arg Gln Val Pro Gly Ser Asp Pro Ala Cys Tyr Glu Phe Leu
            260                 265                 270

Trp Gly Pro Arg Ala Leu Val Glu Thr Ser Tyr Val Lys Val Leu His
        275                 280                 285

His Leu Leu Lys Ile Ser Gly Pro His Ile Ser Tyr Pro Pro Leu
    290                 295                 300

His Glu Trp Ala Phe Arg Glu Gly Glu Glu
305                 310
```

<210> SEQ ID NO 258
<211> LENGTH: 180
<212> TYPE: PRT
<213> ORGANISM: Homo sapiens

<400> SEQUENCE: 258

```
Met Gln Ala Glu Gly Arg Gly Thr Gly Gly Ser Thr Gly Asp Ala Asp
1               5                   10                  15

Gly Pro Gly Gly Pro Gly Ile Pro Asp Gly Pro Gly Gly Asn Ala Gly
            20                  25                  30

Gly Pro Gly Glu Ala Gly Ala Thr Gly Gly Arg Gly Pro Arg Gly Ala
        35                  40                  45

Gly Ala Ala Arg Ala Ser Gly Pro Gly Gly Ala Pro Arg Gly Pro
    50                  55                  60

His Gly Gly Ala Ala Ser Gly Leu Asn Gly Cys Cys Arg Cys Gly Ala
65                  70                  75                  80

Arg Gly Pro Glu Ser Arg Leu Leu Glu Phe Tyr Leu Ala Met Pro Phe
                85                  90                  95

Ala Thr Pro Met Glu Ala Glu Leu Ala Arg Arg Ser Leu Ala Gln Asp
            100                 105                 110

Ala Pro Pro Leu Pro Val Pro Gly Val Leu Leu Lys Glu Phe Thr Val
        115                 120                 125

Ser Gly Asn Ile Leu Thr Ile Arg Leu Thr Ala Ala Asp His Arg Gln
    130                 135                 140

Leu Gln Leu Ser Ile Ser Ser Cys Leu Gln Gln Leu Ser Leu Leu Met
145                 150                 155                 160

Trp Ile Thr Gln Cys Phe Leu Pro Val Phe Leu Ala Gln Pro Pro Ser
                165                 170                 175

Gly Gln Arg Arg
            180
```

<210> SEQ ID NO 259
<211> LENGTH: 373
<212> TYPE: PRT
<213> ORGANISM: Homo sapiens

<400> SEQUENCE: 259

```
Met Pro Pro Val Pro Gly Val Pro Phe Arg Asn Val Asp Asn Asp Ser
1               5                   10                  15

Pro Thr Ser Val Glu Leu Glu Asp Trp Val Asp Ala Gln His Pro Thr
            20                  25                  30

Asp Glu Glu Glu Glu Ala Ser Ser Ala Ser Ser Thr Leu Tyr Leu
        35                  40                  45

Val Phe Ser Pro Ser Ser Phe Ser Thr Ser Ser Leu Ile Leu Gly
    50                  55                  60

Gly Pro Glu Glu Glu Val Pro Ser Gly Val Ile Pro Asn Leu Thr
65                  70                  75                  80

Glu Ser Ile Pro Ser Ser Pro Pro Gln Gly Pro Gln Gly Pro Ser
                85                  90                  95

Gln Ser Pro Leu Ser Ser Cys Cys Ser Ser Phe Ser Trp Ser Ser Phe
            100                 105                 110

Ser Glu Glu Ser Ser Ser Gln Lys Gly Glu Asp Thr Gly Thr Cys Gln
            115                 120                 125

Gly Leu Pro Asp Ser Glu Ser Ser Phe Thr Tyr Thr Leu Asp Glu Lys
            130                 135                 140

Val Ala Glu Leu Val Glu Phe Leu Leu Leu Lys Tyr Glu Ala Glu Glu
145                 150                 155                 160

Pro Val Thr Glu Ala Glu Met Leu Met Ile Val Ile Lys Tyr Lys Asp
                165                 170                 175

Tyr Phe Pro Val Ile Leu Lys Arg Ala Arg Glu Phe Met Glu Leu Leu
                180                 185                 190

Phe Gly Leu Ala Leu Ile Glu Val Gly Pro Asp His Phe Cys Val Phe
            195                 200                 205

Ala Asn Thr Val Gly Leu Thr Asp Glu Gly Ser Asp Asp Glu Gly Met
210                 215                 220

Pro Glu Asn Ser Leu Leu Ile Ile Ile Leu Ser Val Ile Phe Ile Lys
225                 230                 235                 240

Gly Asn Cys Ala Ser Glu Glu Val Ile Trp Glu Val Leu Asn Ala Val
                245                 250                 255

Gly Val Tyr Ala Gly Arg Glu His Phe Val Tyr Gly Glu Pro Arg Glu
            260                 265                 270

Leu Leu Thr Lys Val Trp Val Gln Gly His Tyr Leu Glu Tyr Arg Glu
            275                 280                 285

Val Pro His Ser Ser Pro Pro Tyr Tyr Glu Phe Leu Trp Gly Pro Arg
            290                 295                 300

Ala His Ser Glu Ser Ile Lys Lys Lys Val Leu Glu Phe Leu Ala Lys
305                 310                 315                 320

Leu Asn Asn Thr Val Pro Ser Ser Phe Pro Ser Trp Tyr Lys Asp Ala
                325                 330                 335

Leu Lys Asp Val Glu Glu Arg Val Gln Ala Thr Ile Asp Thr Ala Asp
            340                 345                 350

Asp Ala Thr Val Met Ala Ser Glu Ser Leu Ser Val Met Ser Ser Asn
            355                 360                 365

Val Ser Phe Ser Glu
            370

<210> SEQ ID NO 260
<211> LENGTH: 314
<212> TYPE: PRT
<213> ORGANISM: Homo sapiens

<400> SEQUENCE: 260
```

Met Pro Leu Glu Gln Arg Ser Gln His Cys Lys Pro Glu Glu Gly Leu
1               5                   10                  15

Glu Ala Arg Gly Glu Ala Leu Gly Leu Val Gly Ala Gln Ala Pro Ala
            20                  25                  30

Thr Glu Gln Glu Ala Ala Ser Ser Ser Thr Leu Val Glu Val
            35                  40                  45

Thr Leu Gly Glu Val Pro Ala Ala Glu Ser Pro Asp Pro Pro Gln Ser
        50                  55                  60

Pro Gln Gly Ala Ser Ser Leu Pro Thr Thr Met Asn Tyr Pro Leu Trp
65                  70                  75                  80

Ser Gln Ser Tyr Glu Asp Ser Ser Asn Gln Glu Glu Glu Gly Pro Ser
                85                  90                  95

Thr Phe Pro Asp Leu Glu Ser Glu Phe Gln Ala Ala Leu Ser Arg Lys
            100                 105                 110

Val Ala Lys Leu Val His Phe Leu Leu Leu Lys Tyr Arg Ala Arg Glu
        115                 120                 125

Pro Val Thr Lys Ala Glu Met Leu Gly Ser Val Val Gly Asn Trp Gln
    130                 135                 140

Tyr Phe Phe Pro Val Ile Phe Ser Lys Ala Ser Asp Ser Leu Gln Leu
145                 150                 155                 160

Val Phe Gly Ile Glu Leu Met Glu Val Asp Pro Ile Gly His Val Tyr
                165                 170                 175

Ile Phe Ala Thr Cys Leu Gly Leu Ser Tyr Asp Gly Leu Leu Gly Asp
            180                 185                 190

Asn Gln Ile Met Pro Lys Thr Gly Phe Leu Ile Ile Ile Leu Ala Ile
        195                 200                 205

Ile Ala Lys Glu Gly Asp Cys Ala Pro Glu Glu Lys Ile Trp Glu Glu
    210                 215                 220

Leu Ser Val Leu Glu Val Phe Glu Gly Arg Glu Asp Ser Ile Phe Gly
225                 230                 235                 240

Asp Pro Lys Lys Leu Leu Thr Gln Tyr Phe Val Gln Glu Asn Tyr Leu
                245                 250                 255

Glu Tyr Arg Gln Val Pro Gly Ser Asp Pro Ala Cys Tyr Glu Phe Leu
            260                 265                 270

Trp Gly Pro Arg Ala Leu Ile Glu Thr Ser Tyr Val Lys Val Leu His
        275                 280                 285

His Met Val Lys Ile Ser Gly Gly Pro Arg Ile Ser Tyr Pro Leu Leu
    290                 295                 300

His Glu Trp Ala Leu Arg Glu Gly Glu Glu
305                 310

<210> SEQ ID NO 261
<211> LENGTH: 663
<212> TYPE: PRT
<213> ORGANISM: Homo sapiens

<400> SEQUENCE: 261

Met Ala Ala Thr Glu Ile Ser Val Leu Ser Glu Gln Phe Thr Lys Ile
1               5                   10                  15

Lys Glu Leu Glu Leu Met Pro Glu Lys Gly Leu Lys Glu Glu Lys
            20                  25                  30

Asp Gly Val Cys Arg Glu Lys Asp His Arg Ser Pro Ser Glu Leu Glu
        35                  40                  45

Ala Glu Arg Thr Ser Gly Ala Phe Gln Asp Ser Val Leu Glu Glu Glu

-continued

```
            50                  55                  60
Val Glu Leu Val Leu Ala Pro Ser Glu Glu Ser Glu Lys Tyr Ile Leu
 65                  70                  75                  80

Thr Leu Gln Thr Val His Phe Thr Ser Glu Ala Val Glu Leu Gln Asp
                     85                  90                  95

Met Ser Leu Leu Ser Ile Gln Gln Glu Gly Val Gln Val Val Val
                100                 105                 110

Gln Gln Pro Gly Pro Gly Leu Leu Trp Leu Glu Glu Gly Pro Arg Gln
            115                 120                 125

Ser Leu Gln Gln Cys Val Ala Ile Ser Ile Gln Gln Glu Leu Tyr Ser
            130                 135                 140

Pro Gln Glu Met Glu Val Leu Gln Phe His Ala Leu Glu Glu Asn Val
145                 150                 155                 160

Met Val Ala Ser Glu Asp Ser Lys Leu Ala Val Ser Leu Ala Glu Thr
                165                 170                 175

Thr Gly Leu Ile Lys Leu Glu Glu Gln Glu Lys Asn Gln Leu Leu
                180                 185                 190

Ala Glu Arg Thr Lys Glu Gln Leu Phe Phe Val Glu Thr Met Ser Gly
            195                 200                 205

Asp Glu Arg Ser Asp Glu Ile Val Leu Thr Val Ser Asn Ser Asn Val
210                 215                 220

Glu Glu Gln Glu Asp Gln Pro Thr Ala Gly Gln Ala Asp Ala Glu Lys
225                 230                 235                 240

Ala Lys Ser Thr Lys Asn Gln Arg Lys Thr Lys Gly Ala Lys Gly Thr
                245                 250                 255

Phe His Cys Asp Val Cys Met Phe Thr Ser Ser Arg Met Ser Ser Phe
                260                 265                 270

Asn Arg His Met Lys Thr His Thr Ser Glu Lys Pro His Leu Cys His
            275                 280                 285

Leu Cys Leu Lys Thr Phe Arg Thr Val Thr Leu Leu Arg Asn His Val
            290                 295                 300

Asn Thr His Thr Gly Thr Arg Pro Tyr Lys Cys Asn Asp Cys Asn Met
305                 310                 315                 320

Ala Phe Val Thr Ser Gly Glu Leu Val Arg His Arg Arg Tyr Lys His
                325                 330                 335

Thr His Glu Lys Pro Phe Lys Cys Ser Met Cys Lys Tyr Ala Ser Val
                340                 345                 350

Glu Ala Ser Lys Leu Lys Arg His Val Arg Ser His Thr Gly Glu Arg
            355                 360                 365

Pro Phe Gln Cys Cys Gln Cys Ser Tyr Ala Ser Arg Asp Thr Tyr Lys
            370                 375                 380

Leu Lys Arg His Met Arg Thr His Ser Gly Glu Lys Pro Tyr Glu Cys
385                 390                 395                 400

His Ile Cys His Thr Arg Phe Thr Gln Ser Gly Thr Met Lys Ile His
                405                 410                 415

Ile Leu Gln Lys His Gly Glu Asn Val Pro Lys Tyr Gln Cys Pro His
            420                 425                 430

Cys Ala Thr Ile Ile Ala Arg Lys Ser Asp Leu Arg Val His Met Arg
            435                 440                 445

Asn Leu His Ala Tyr Ser Ala Ala Glu Leu Lys Cys Arg Tyr Cys Ser
            450                 455                 460

Ala Val Phe His Glu Arg Tyr Ala Leu Ile Gln His Gln Lys Thr His
465                 470                 475                 480
```

```
Lys Asn Glu Lys Arg Phe Lys Cys Lys His Cys Ser Tyr Ala Cys Lys
                485                 490                 495

Gln Glu Arg His Met Thr Ala His Ile Arg Thr His Thr Gly Glu Lys
            500                 505                 510

Pro Phe Thr Cys Leu Ser Cys Asn Lys Cys Phe Arg Gln Lys Gln Leu
        515                 520                 525

Leu Asn Ala His Phe Arg Lys Tyr His Asp Ala Asn Phe Ile Pro Thr
    530                 535                 540

Val Tyr Lys Cys Ser Lys Cys Gly Lys Gly Phe Ser Arg Trp Ile Asn
545                 550                 555                 560

Leu His Arg His Ser Glu Lys Cys Gly Ser Gly Glu Ala Lys Ser Ala
                565                 570                 575

Ala Ser Gly Lys Gly Arg Arg Thr Arg Lys Arg Lys Gln Thr Ile Leu
            580                 585                 590

Lys Glu Ala Thr Lys Gly Gln Lys Glu Ala Ala Lys Gly Trp Lys Glu
        595                 600                 605

Ala Ala Asn Gly Asp Glu Ala Ala Glu Glu Ala Ser Thr Thr Lys
    610                 615                 620

Gly Glu Gln Phe Pro Gly Glu Met Phe Pro Val Ala Cys Arg Glu Thr
625                 630                 635                 640

Thr Ala Arg Val Lys Glu Glu Val Asp Glu Gly Val Thr Cys Glu Met
                645                 650                 655

Leu Leu Asn Thr Met Asp Lys
                660

<210> SEQ ID NO 262
<211> LENGTH: 210
<212> TYPE: PRT
<213> ORGANISM: Homo sapiens

<400> SEQUENCE: 262

Met Gln Ala Glu Gly Gln Gly Thr Gly Gly Ser Thr Gly Asp Ala Asp
1               5                   10                  15

Gly Pro Gly Gly Pro Gly Ile Pro Asp Gly Pro Gly Gly Asn Ala Gly
            20                  25                  30

Gly Pro Gly Glu Ala Gly Ala Thr Gly Gly Arg Gly Pro Arg Gly Ala
        35                  40                  45

Gly Ala Ala Arg Ala Ser Gly Pro Arg Gly Ala Pro Arg Gly Pro
    50                  55                  60

His Gly Gly Ala Ala Ser Ala Gln Asp Gly Arg Cys Pro Cys Gly Ala
65                  70                  75                  80

Arg Arg Pro Asp Ser Arg Leu Leu Gln Leu His Ile Thr Met Pro Phe
                85                  90                  95

Ser Ser Pro Met Glu Ala Glu Leu Val Arg Arg Ile Leu Ser Arg Asp
            100                 105                 110

Ala Ala Pro Leu Pro Arg Pro Gly Ala Val Leu Lys Asp Phe Thr Val
        115                 120                 125

Ser Gly Asn Leu Leu Phe Met Ser Val Arg Asp Gln Asp Arg Glu Gly
    130                 135                 140

Ala Gly Arg Met Arg Val Val Gly Trp Gly Leu Gly Ser Ala Ser Pro
145                 150                 155                 160

Glu Gly Gln Lys Ala Arg Asp Leu Arg Thr Pro Lys His Lys Val Ser
                165                 170                 175

Glu Gln Arg Pro Gly Thr Pro Gly Pro Pro Pro Glu Gly Ala Gln
```

```
                180                 185                 190
Gly Asp Gly Cys Arg Gly Val Ala Phe Asn Val Met Phe Ser Ala Pro
            195                 200                 205
His Ile
    210

<210> SEQ ID NO 263
<211> LENGTH: 429
<212> TYPE: PRT
<213> ORGANISM: Homo sapiens

<400> SEQUENCE: 263

Met Glu Thr Gln Phe Arg Arg Gly Gly Leu Gly Cys Ser Pro Ala Ser
1               5                   10                  15

Ile Lys Arg Lys Lys Lys Arg Glu Asp Ser Gly Asp Phe Gly Leu Gln
            20                  25                  30

Val Ser Thr Met Phe Ser Glu Asp Asp Phe Gln Ser Thr Glu Arg Ala
        35                  40                  45

Pro Tyr Gly Pro Gln Leu Gln Trp Ser Gln Asp Leu Pro Arg Val Gln
    50                  55                  60

Val Phe Arg Glu Gln Ala Asn Leu Glu Asp Arg Ser Pro Arg Arg Thr
65                  70                  75                  80

Gln Arg Ile Thr Gly Gly Glu Gln Val Leu Trp Gly Pro Ile Thr Gln
                85                  90                  95

Ile Phe Pro Thr Val Arg Pro Ala Asp Leu Thr Arg Val Ile Met Pro
            100                 105                 110

Leu Glu Gln Arg Ser Gln His Cys Lys Pro Glu Gly Leu Gln Ala
        115                 120                 125

Gln Glu Glu Asp Leu Gly Leu Val Gly Ala Gln Ala Leu Gln Ala Glu
    130                 135                 140

Glu Gln Glu Ala Ala Phe Phe Ser Ser Thr Leu Asn Val Gly Thr Leu
145                 150                 155                 160

Glu Glu Leu Pro Ala Ala Glu Ser Pro Ser Pro Gln Ser Pro Gln
                165                 170                 175

Glu Glu Ser Phe Ser Pro Thr Ala Met Asp Ala Ile Phe Gly Ser Leu
            180                 185                 190

Ser Asp Glu Gly Ser Gly Ser Gln Glu Lys Glu Gly Pro Ser Thr Ser
        195                 200                 205

Pro Asp Leu Ile Asp Pro Glu Ser Phe Ser Gln Asp Ile Leu His Asp
    210                 215                 220

Lys Ile Ile Asp Leu Val His Leu Leu Leu Arg Lys Tyr Arg Val Lys
225                 230                 235                 240

Gly Leu Ile Thr Lys Ala Glu Met Leu Gly Ser Val Ile Lys Asn Tyr
                245                 250                 255

Glu Asp Tyr Phe Pro Glu Ile Phe Arg Glu Ala Ser Val Cys Met Gln
            260                 265                 270

Leu Leu Phe Gly Ile Asp Val Lys Glu Val Asp Pro Thr Ser His Ser
        275                 280                 285

Tyr Val Leu Val Thr Ser Leu Asn Leu Ser Tyr Asp Gly Ile Gln Cys
    290                 295                 300

Asn Glu Gln Ser Met Pro Lys Ser Gly Leu Leu Ile Ile Val Leu Gly
305                 310                 315                 320

Val Ile Phe Met Glu Gly Asn Cys Ile Pro Glu Glu Val Met Trp Glu
                325                 330                 335
```

```
Val Leu Ser Ile Met Gly Val Tyr Ala Gly Arg Glu His Phe Leu Phe
            340                 345                 350

Gly Glu Pro Lys Arg Leu Leu Thr Gln Asn Trp Val Gln Glu Lys Tyr
        355                 360                 365

Leu Val Tyr Arg Gln Val Pro Gly Thr Asp Pro Ala Cys Tyr Glu Phe
    370                 375                 380

Leu Trp Gly Pro Arg Ala His Ala Glu Thr Ser Lys Met Lys Val Leu
385                 390                 395                 400

Glu Tyr Ile Ala Asn Ala Asn Gly Arg Asp Pro Thr Ser Tyr Pro Ser
            405                 410                 415

Leu Tyr Glu Asp Ala Leu Arg Glu Glu Gly Glu Gly Val
        420                 425

<210> SEQ ID NO 264
<211> LENGTH: 188
<212> TYPE: PRT
<213> ORGANISM: Homo sapiens

<400> SEQUENCE: 264

Met Asn Gly Asp Asp Thr Phe Ala Lys Arg Pro Arg Asp Asp Ala Lys
1               5                   10                  15

Ala Ser Glu Lys Arg Ser Lys Ala Phe Asp Asp Ile Ala Thr Tyr Phe
            20                  25                  30

Ser Lys Lys Glu Trp Lys Lys Met Lys Tyr Ser Glu Lys Ile Ser Tyr
        35                  40                  45

Val Tyr Met Lys Arg Asn Tyr Lys Ala Met Thr Lys Leu Gly Phe Lys
50                  55                  60

Val Thr Leu Pro Pro Phe Met Cys Asn Lys Gln Ala Thr Asp Phe Gln
65                  70                  75                  80

Gly Asn Asp Phe Asp Asn Asp His Asn Arg Arg Ile Gln Val Glu His
            85                  90                  95

Pro Gln Met Thr Phe Gly Arg Leu His Arg Ile Ile Pro Lys Ile Met
        100                 105                 110

Pro Lys Lys Pro Ala Glu Asp Glu Asn Asp Ser Lys Gly Val Ser Glu
    115                 120                 125

Ala Ser Gly Pro Gln Asn Asp Gly Lys Gln Leu His Pro Pro Gly Lys
    130                 135                 140

Ala Asn Ile Ser Glu Lys Ile Asn Lys Arg Ser Gly Pro Lys Arg Gly
145                 150                 155                 160

Lys His Ala Trp Thr His Arg Leu Arg Glu Arg Lys Gln Leu Val Ile
                165                 170                 175

Tyr Glu Glu Ile Ser Asp Pro Glu Glu Asp Asp Glu
            180                 185

<210> SEQ ID NO 265
<211> LENGTH: 314
<212> TYPE: PRT
<213> ORGANISM: Homo sapiens

<400> SEQUENCE: 265

Met Pro Leu Glu Gln Arg Ser Gln His Cys Lys Pro Glu Glu Gly Leu
1               5                   10                  15

Glu Ala Arg Gly Glu Ala Leu Gly Leu Val Gly Ala Gln Ala Pro Ala
            20                  25                  30

Thr Glu Glu Gln Glu Ala Ala Ser Ser Ser Ser Thr Leu Val Glu Val
        35                  40                  45
```

```
Thr Leu Gly Glu Val Pro Ala Ala Glu Ser Pro Asp Pro Pro Gln Ser
 50                  55                  60

Pro Gln Gly Ala Ser Ser Leu Pro Thr Thr Met Asn Tyr Pro Leu Trp
 65                  70                  75                  80

Ser Gln Ser Tyr Glu Asp Ser Ser Asn Gln Glu Glu Glu Gly Pro Ser
                 85                  90                  95

Thr Phe Pro Asp Leu Glu Ser Glu Phe Gln Ala Ala Leu Ser Arg Lys
            100                 105                 110

Val Ala Glu Leu Val His Phe Leu Leu Leu Lys Tyr Arg Ala Arg Glu
        115                 120                 125

Pro Val Thr Lys Ala Glu Met Leu Gly Ser Val Gly Asn Trp Gln
130                 135                 140

Tyr Phe Phe Pro Val Ile Phe Ser Lys Ala Ser Ser Ser Leu Gln Leu
145                 150                 155                 160

Val Phe Gly Ile Glu Leu Met Glu Val Asp Pro Ile Gly His Leu Tyr
                165                 170                 175

Ile Phe Ala Thr Cys Leu Gly Leu Ser Tyr Asp Gly Leu Leu Gly Asp
            180                 185                 190

Asn Gln Ile Met Pro Lys Ala Gly Leu Leu Ile Ile Val Leu Ala Ile
        195                 200                 205

Ile Ala Arg Glu Gly Asp Cys Ala Pro Glu Glu Lys Ile Trp Glu Glu
210                 215                 220

Leu Ser Val Leu Glu Val Phe Glu Gly Arg Glu Asp Ser Ile Leu Gly
225                 230                 235                 240

Asp Pro Lys Lys Leu Leu Thr Gln His Phe Val Gln Glu Asn Tyr Leu
                245                 250                 255

Glu Tyr Arg Gln Val Pro Gly Ser Asp Pro Ala Cys Tyr Glu Phe Leu
            260                 265                 270

Trp Gly Pro Arg Ala Leu Val Glu Thr Ser Tyr Val Lys Val Leu His
        275                 280                 285

His Met Val Lys Ile Ser Gly Gly Pro His Ile Ser Tyr Pro Pro Leu
290                 295                 300

His Glu Trp Val Leu Arg Glu Gly Glu Glu
305                 310

<210> SEQ ID NO 266
<211> LENGTH: 369
<212> TYPE: PRT
<213> ORGANISM: Homo sapiens

<400> SEQUENCE: 266

Met Pro Arg Ala Pro Lys Arg Gln Arg Cys Met Pro Glu Glu Asp Leu
 1               5                  10                  15

Gln Ser Gln Ser Glu Thr Gln Gly Leu Glu Gly Ala Gln Ala Pro Leu
                20                  25                  30

Ala Val Glu Glu Asp Ala Ser Ser Thr Ser Thr Ser Ser Ser Phe
            35                  40                  45

Pro Ser Ser Phe Pro Ser Ser Ser Ser Ser Ser Ser Cys Tyr
 50                  55                  60

Pro Leu Ile Pro Ser Thr Pro Glu Glu Val Ser Ala Asp Asp Glu Thr
 65                  70                  75                  80

Pro Asn Pro Pro Gln Ser Ala Gln Ile Ala Cys Ser Ser Pro Ser Val
                 85                  90                  95

Val Ala Ser Leu Pro Leu Asp Gln Ser Asp Glu Gly Ser Ser Ser Gln
            100                 105                 110
```

```
Lys Glu Glu Ser Pro Ser Thr Leu Gln Val Leu Pro Asp Ser Glu Ser
            115                 120                 125

Leu Pro Arg Ser Glu Ile Asp Glu Lys Val Thr Asp Leu Val Gln Phe
        130                 135                 140

Leu Leu Phe Lys Tyr Gln Met Lys Glu Pro Ile Thr Lys Ala Glu Ile
145                 150                 155                 160

Leu Glu Ser Val Ile Arg Asn Tyr Glu Asp His Phe Pro Leu Leu Phe
                165                 170                 175

Ser Glu Ala Ser Glu Cys Met Leu Leu Val Phe Gly Ile Asp Val Lys
            180                 185                 190

Glu Val Asp Pro Thr Gly His Ser Phe Val Leu Val Thr Ser Leu Gly
        195                 200                 205

Leu Thr Tyr Asp Gly Met Leu Ser Asp Val Gln Ser Met Pro Lys Thr
210                 215                 220

Gly Ile Leu Ile Leu Ile Leu Ser Ile Ile Phe Ile Glu Gly Tyr Cys
225                 230                 235                 240

Thr Pro Glu Glu Val Ile Trp Glu Ala Leu Asn Met Met Gly Leu Tyr
                245                 250                 255

Asp Gly Met Glu His Leu Ile Tyr Gly Glu Pro Arg Lys Leu Leu Thr
            260                 265                 270

Gln Asp Trp Val Gln Glu Asn Tyr Leu Glu Tyr Arg Gln Val Pro Gly
        275                 280                 285

Ser Asp Pro Ala Arg Tyr Glu Phe Leu Trp Gly Pro Arg Ala His Ala
290                 295                 300

Glu Ile Arg Lys Met Ser Leu Leu Lys Phe Leu Ala Lys Val Asn Gly
305                 310                 315                 320

Ser Asp Pro Arg Ser Phe Pro Leu Trp Tyr Glu Glu Ala Leu Lys Asp
                325                 330                 335

Glu Glu Glu Arg Ala Gln Asp Arg Ile Ala Thr Thr Asp Asp Thr Thr
            340                 345                 350

Ala Met Ala Ser Ala Ser Ser Ser Ala Thr Gly Ser Phe Ser Tyr Pro
        355                 360                 365

Glu

<210> SEQ ID NO 267
<211> LENGTH: 309
<212> TYPE: PRT
<213> ORGANISM: Homo sapiens

<400> SEQUENCE: 267

Met Ser Leu Glu Gln Arg Ser Leu His Cys Lys Pro Glu Glu Ala Leu
1               5                   10                  15

Glu Ala Gln Gln Glu Ala Leu Gly Leu Val Cys Val Gln Ala Ala Thr
            20                  25                  30

Ser Ser Ser Ser Pro Leu Val Leu Gly Thr Leu Glu Glu Val Pro Thr
        35                  40                  45

Ala Gly Ser Thr Asp Pro Pro Gln Ser Pro Gln Gly Ala Ser Ala Phe
    50                  55                  60

Pro Thr Thr Ile Asn Phe Thr Arg Gln Arg Gln Pro Ser Glu Gly Ser
65                  70                  75                  80

Ser Ser Arg Glu Glu Glu Gly Pro Ser Thr Ser Cys Ile Leu Glu Ser
                85                  90                  95

Leu Phe Arg Ala Val Ile Thr Lys Lys Val Ala Asp Leu Val Gly Phe
            100                 105                 110
```

Leu Leu Leu Lys Tyr Arg Ala Arg Glu Pro Val Thr Lys Ala Glu Met
            115                 120                 125

Leu Glu Ser Val Ile Lys Asn Tyr Lys His Cys Phe Pro Glu Ile Phe
130                 135                 140

Gly Lys Ala Ser Glu Ser Leu Gln Leu Val Phe Gly Ile Asp Val Lys
145                 150                 155                 160

Glu Ala Asp Pro Thr Gly His Ser Tyr Val Leu Val Thr Cys Leu Gly
                165                 170                 175

Leu Ser Tyr Asp Gly Leu Leu Gly Asp Asn Gln Ile Met Pro Lys Thr
            180                 185                 190

Gly Phe Leu Ile Ile Val Leu Val Met Ile Ala Met Glu Gly Gly His
            195                 200                 205

Ala Pro Glu Glu Glu Ile Trp Glu Glu Leu Ser Val Met Glu Val Tyr
210                 215                 220

Asp Gly Arg Glu His Ser Ala Tyr Gly Glu Pro Arg Lys Leu Leu Thr
225                 230                 235                 240

Gln Asp Leu Val Gln Glu Lys Tyr Leu Glu Tyr Arg Gln Val Pro Asp
                245                 250                 255

Ser Asp Pro Ala Arg Tyr Glu Phe Leu Trp Gly Pro Arg Ala Leu Ala
            260                 265                 270

Glu Thr Ser Tyr Val Lys Val Leu Glu Tyr Val Ile Lys Val Ser Ala
            275                 280                 285

Arg Val Arg Phe Phe Phe Pro Ser Leu Arg Glu Ala Ala Leu Arg Glu
            290                 295                 300

Glu Glu Glu Gly Val
305

<210> SEQ ID NO 268
<211> LENGTH: 9
<212> TYPE: PRT
<213> ORGANISM: artificial sequence
<220> FEATURE:
<223> OTHER INFORMATION: PIWIL2 9mer

<400> SEQUENCE: 268

Phe Val Ala Ser Ile Asn Leu Thr Leu
1               5

<210> SEQ ID NO 269
<211> LENGTH: 9
<212> TYPE: PRT
<213> ORGANISM: artificial sequence
<220> FEATURE:
<223> OTHER INFORMATION: PIWIL2 9mer

<400> SEQUENCE: 269

Phe Tyr Asp Pro Thr Ser Ala Met Val
1               5

<210> SEQ ID NO 270
<211> LENGTH: 9
<212> TYPE: PRT
<213> ORGANISM: artificial sequence
<220> FEATURE:
<223> OTHER INFORMATION: PIWIL2 9mer

<400> SEQUENCE: 270

Phe Gln Met Pro His Gln Glu Ile Val
1               5

```
<210> SEQ ID NO 271
<211> LENGTH: 9
<212> TYPE: PRT
<213> ORGANISM: artificial sequence
<220> FEATURE:
<223> OTHER INFORMATION: CTAGE1 9mer

<400> SEQUENCE: 271

Phe Leu Leu Thr Ser Phe Pro Thr Phe
1               5

<210> SEQ ID NO 272
<211> LENGTH: 9
<212> TYPE: PRT
<213> ORGANISM: artificial sequence
<220> FEATURE:
<223> OTHER INFORMATION: MAGE-A9 9mer

<400> SEQUENCE: 272

Phe Met Phe Gln Glu Ala Leu Lys Leu
1               5

<210> SEQ ID NO 273
<211> LENGTH: 9
<212> TYPE: PRT
<213> ORGANISM: artificial sequence
<220> FEATURE:
<223> OTHER INFORMATION: EpCAM 9mer

<400> SEQUENCE: 273

Arg Thr Tyr Trp Ile Ile Ile Glu Leu
1               5

<210> SEQ ID NO 274
<211> LENGTH: 9
<212> TYPE: PRT
<213> ORGANISM: artificial sequence
<220> FEATURE:
<223> OTHER INFORMATION: OY-TES-1 9mer

<400> SEQUENCE: 274

Met Ile Met Glu Asn Ile Gln Glu Leu
1               5

<210> SEQ ID NO 275
<211> LENGTH: 9
<212> TYPE: PRT
<213> ORGANISM: artificial sequence
<220> FEATURE:
<223> OTHER INFORMATION: MAGE-A9 9mer

<400> SEQUENCE: 275

Ser Ser Ile Ser Val Tyr Tyr Thr Leu
1               5

<210> SEQ ID NO 276
<211> LENGTH: 9
<212> TYPE: PRT
<213> ORGANISM: artificial sequence
<220> FEATURE:
<223> OTHER INFORMATION: NY-ESO-1 9mer

<400> SEQUENCE: 276

Arg Leu Leu Glu Phe Tyr Leu Ala Met
1               5
```

```
<210> SEQ ID NO 277
<211> LENGTH: 9
<212> TYPE: PRT
<213> ORGANISM: artificial sequence
<220> FEATURE:
<223> OTHER INFORMATION: SURVIVIN 9mer

<400> SEQUENCE: 277

Arg Ala Ile Glu Gln Leu Ala Ala Met
1               5

<210> SEQ ID NO 278
<211> LENGTH: 9
<212> TYPE: PRT
<213> ORGANISM: artificial sequence
<220> FEATURE:
<223> OTHER INFORMATION: MAGE-C1 9mer

<400> SEQUENCE: 278

Phe Ser Tyr Thr Leu Leu Ser Leu Phe
1               5

<210> SEQ ID NO 279
<211> LENGTH: 9
<212> TYPE: PRT
<213> ORGANISM: artificial sequence
<220> FEATURE:
<223> OTHER INFORMATION: CTAGE1 9mer

<400> SEQUENCE: 279

Phe Leu Phe Gly Gly Asn Asn Phe Ile
1               5

<210> SEQ ID NO 280
<211> LENGTH: 9
<212> TYPE: PRT
<213> ORGANISM: artificial sequence
<220> FEATURE:
<223> OTHER INFORMATION: EpCAM 9mer

<400> SEQUENCE: 280

Tyr Val Asp Glu Lys Ala Pro Glu Phe
1               5

<210> SEQ ID NO 281
<211> LENGTH: 9
<212> TYPE: PRT
<213> ORGANISM: artificial sequence
<220> FEATURE:
<223> OTHER INFORMATION: MAGE-A2 9mer

<400> SEQUENCE: 281

Phe Ala His Pro Arg Lys Leu Leu Met
1               5

<210> SEQ ID NO 282
<211> LENGTH: 9
<212> TYPE: PRT
<213> ORGANISM: artificial sequence
<220> FEATURE:
<223> OTHER INFORMATION: MAGE-C1 9mer

<400> SEQUENCE: 282

Tyr Val Phe Val Asn Thr Leu Asp Leu
1               5

<210> SEQ ID NO 283
```

```
<211> LENGTH: 9
<212> TYPE: PRT
<213> ORGANISM: artificial sequence
<220> FEATURE:
<223> OTHER INFORMATION: LAGE-1 9mer

<400> SEQUENCE: 283

Phe Thr Val Ser Gly Asn Leu Leu Phe
1               5

<210> SEQ ID NO 284
<211> LENGTH: 9
<212> TYPE: PRT
<213> ORGANISM: artificial sequence
<220> FEATURE:
<223> OTHER INFORMATION: MAGE-A3 9mer

<400> SEQUENCE: 284

Phe Val Gln Glu Asn Tyr Leu Glu Tyr
1               5

<210> SEQ ID NO 285
<211> LENGTH: 9
<212> TYPE: PRT
<213> ORGANISM: artificial sequence
<220> FEATURE:
<223> OTHER INFORMATION: MAGE-A8 9mer

<400> SEQUENCE: 285

Ala Ile Trp Glu Ala Leu Ser Val Met
1               5

<210> SEQ ID NO 286
<211> LENGTH: 9
<212> TYPE: PRT
<213> ORGANISM: artificial sequence
<220> FEATURE:
<223> OTHER INFORMATION: HAGE 9mer

<400> SEQUENCE: 286

Leu Gln Met Ser Asn Phe Val Asn Leu
1               5

<210> SEQ ID NO 287
<211> LENGTH: 9
<212> TYPE: PRT
<213> ORGANISM: artificial sequence
<220> FEATURE:
<223> OTHER INFORMATION: MAGE-A8 9mer

<400> SEQUENCE: 287

Lys Val Ala Glu Leu Val Arg Phe Leu
1               5

<210> SEQ ID NO 288
<211> LENGTH: 9
<212> TYPE: PRT
<213> ORGANISM: artificial sequence
<220> FEATURE:
<223> OTHER INFORMATION: MAGE-A3 9mer

<400> SEQUENCE: 288

Ala Ser Ser Ser Leu Gln Leu Val Phe
1               5

<210> SEQ ID NO 289
<211> LENGTH: 9
```

-continued

```
<212> TYPE: PRT
<213> ORGANISM: artificial sequence
<220> FEATURE:
<223> OTHER INFORMATION: SURVIVIN 9mer

<400> SEQUENCE: 289

Ser Thr Phe Lys Asn Trp Pro Phe Leu
1               5

<210> SEQ ID NO 290
<211> LENGTH: 9
<212> TYPE: PRT
<213> ORGANISM: artificial sequence
<220> FEATURE:
<223> OTHER INFORMATION: MAGE-A2 9mer

<400> SEQUENCE: 290

Phe Ser Thr Thr Ile Asn Tyr Thr Leu
1               5

<210> SEQ ID NO 291
<211> LENGTH: 9
<212> TYPE: PRT
<213> ORGANISM: artificial sequence
<220> FEATURE:
<223> OTHER INFORMATION: MAGE-A3 9mer

<400> SEQUENCE: 291

Lys Val Ala Glu Leu Val His Phe Leu
1               5

<210> SEQ ID NO 292
<211> LENGTH: 9
<212> TYPE: PRT
<213> ORGANISM: artificial sequence
<220> FEATURE:
<223> OTHER INFORMATION: MAGE-A1 9mer

<400> SEQUENCE: 292

Thr Ser Tyr Val Lys Val Leu Glu Tyr
1               5

<210> SEQ ID NO 293
<211> LENGTH: 9
<212> TYPE: PRT
<213> ORGANISM: artificial sequence
<220> FEATURE:
<223> OTHER INFORMATION: MAGE-C2 9mer

<400> SEQUENCE: 293

Met Ala Ser Glu Ser Leu Ser Val Met
1               5

<210> SEQ ID NO 294
<211> LENGTH: 9
<212> TYPE: PRT
<213> ORGANISM: artificial sequence
<220> FEATURE:
<223> OTHER INFORMATION: MAGE-C2 9mer

<400> SEQUENCE: 294

Phe Val Tyr Gly Glu Pro Arg Glu Leu
1               5

<210> SEQ ID NO 295
<211> LENGTH: 9
<212> TYPE: PRT
```

```
<213> ORGANISM: artificial sequence
<220> FEATURE:
<223> OTHER INFORMATION: MAGE-A10 9mer

<400> SEQUENCE: 295

Tyr Glu Asp His Phe Pro Leu Leu Phe
1               5

<210> SEQ ID NO 296
<211> LENGTH: 9
<212> TYPE: PRT
<213> ORGANISM: artificial sequence
<220> FEATURE:
<223> OTHER INFORMATION: MAGE-A12 9mer

<400> SEQUENCE: 296

Lys Ala Ser Glu Tyr Leu Gln Leu Val
1               5

<210> SEQ ID NO 297
<211> LENGTH: 9
<212> TYPE: PRT
<213> ORGANISM: artificial sequence
<220> FEATURE:
<223> OTHER INFORMATION: LAGE-1 9mer

<400> SEQUENCE: 297

Leu Gln Leu His Ile Thr Met Pro Phe
1               5

<210> SEQ ID NO 298
<211> LENGTH: 15
<212> TYPE: PRT
<213> ORGANISM: artificial sequence
<220> FEATURE:
<223> OTHER INFORMATION: PIWIL2 15mer

<400> SEQUENCE: 298

Phe Val Ala Ser Ile Asn Leu Thr Leu Thr Lys Trp Tyr Ser Arg
1               5                   10                  15

<210> SEQ ID NO 299
<211> LENGTH: 15
<212> TYPE: PRT
<213> ORGANISM: artificial sequence
<220> FEATURE:
<223> OTHER INFORMATION: PIWIL2 15mer

<400> SEQUENCE: 299

Arg Asn Phe Tyr Asp Pro Thr Ser Ala Met Val Leu Gln Gln His
1               5                   10                  15

<210> SEQ ID NO 300
<211> LENGTH: 15
<212> TYPE: PRT
<213> ORGANISM: artificial sequence
<220> FEATURE:
<223> OTHER INFORMATION: PIWIL2 15mer

<400> SEQUENCE: 300

Tyr Ser Arg Val Val Phe Gln Met Pro His Gln Glu Ile Val Asp
1               5                   10                  15

<210> SEQ ID NO 301
<211> LENGTH: 15
<212> TYPE: PRT
<213> ORGANISM: artificial sequence
```

```
<220> FEATURE:
<223> OTHER INFORMATION: CTAGE1 15mer

<400> SEQUENCE: 301

Gln Asn Tyr Ile Asp Gln Phe Leu Leu Thr Ser Phe Pro Thr Phe
1               5                   10                  15

<210> SEQ ID NO 302
<211> LENGTH: 15
<212> TYPE: PRT
<213> ORGANISM: artificial sequence
<220> FEATURE:
<223> OTHER INFORMATION: MAGE-A9 15mer

<400> SEQUENCE: 302

Glu Phe Met Phe Gln Glu Ala Leu Lys Leu Lys Val Ala Glu Leu
1               5                   10                  15

<210> SEQ ID NO 303
<211> LENGTH: 15
<212> TYPE: PRT
<213> ORGANISM: artificial sequence
<220> FEATURE:
<223> OTHER INFORMATION: EpCAM 15mer

<400> SEQUENCE: 303

Arg Thr Tyr Trp Ile Ile Ile Glu Leu Lys His Lys Ala Arg Glu
1               5                   10                  15

<210> SEQ ID NO 304
<211> LENGTH: 15
<212> TYPE: PRT
<213> ORGANISM: artificial sequence
<220> FEATURE:
<223> OTHER INFORMATION: OY-TES-1 15mer

<400> SEQUENCE: 304

Glu Ser Thr Pro Met Ile Met Glu Asn Ile Gln Glu Leu Ile Arg
1               5                   10                  15

<210> SEQ ID NO 305
<211> LENGTH: 15
<212> TYPE: PRT
<213> ORGANISM: artificial sequence
<220> FEATURE:
<223> OTHER INFORMATION: MAGE-A9 15mer

<400> SEQUENCE: 305

Ser Ser Ile Ser Val Tyr Tyr Thr Leu Trp Ser Gln Phe Asp Glu
1               5                   10                  15

<210> SEQ ID NO 306
<211> LENGTH: 15
<212> TYPE: PRT
<213> ORGANISM: artificial sequence
<220> FEATURE:
<223> OTHER INFORMATION: NY-ESO-1 15mer

<400> SEQUENCE: 306

Arg Gly Pro Glu Ser Arg Leu Leu Glu Phe Tyr Leu Ala Met Pro
1               5                   10                  15

<210> SEQ ID NO 307
<211> LENGTH: 15
<212> TYPE: PRT
<213> ORGANISM: artificial sequence
<220> FEATURE:
```

```
<223> OTHER INFORMATION: SURVIVIN 15mer

<400> SEQUENCE: 307

Ala Lys Lys Val Arg Arg Ala Ile Glu Gln Leu Ala Ala Met Asp
1               5                   10                  15

<210> SEQ ID NO 308
<211> LENGTH: 15
<212> TYPE: PRT
<213> ORGANISM: artificial sequence
<220> FEATURE:
<223> OTHER INFORMATION: MAGE-C1 15mer

<400> SEQUENCE: 308

Ser Ser Phe Ser Tyr Thr Leu Leu Ser Leu Phe Gln Ser Ser Pro
1               5                   10                  15

<210> SEQ ID NO 309
<211> LENGTH: 15
<212> TYPE: PRT
<213> ORGANISM: artificial sequence
<220> FEATURE:
<223> OTHER INFORMATION: CTAGE1 15mer

<400> SEQUENCE: 309

Ser Phe Val Leu Phe Leu Phe Gly Gly Asn Asn Phe Ile Gln Asn
1               5                   10                  15

<210> SEQ ID NO 310
<211> LENGTH: 15
<212> TYPE: PRT
<213> ORGANISM: artificial sequence
<220> FEATURE:
<223> OTHER INFORMATION: EpCAM 15mer

<400> SEQUENCE: 310

Gln Thr Leu Ile Tyr Tyr Val Asp Glu Lys Ala Pro Glu Phe Ser
1               5                   10                  15

<210> SEQ ID NO 311
<211> LENGTH: 15
<212> TYPE: PRT
<213> ORGANISM: artificial sequence
<220> FEATURE:
<223> OTHER INFORMATION: MAGE-A2 15mer

<400> SEQUENCE: 311

Arg Glu Asp Ser Val Phe Ala His Pro Arg Lys Leu Leu Met Gln
1               5                   10                  15

<210> SEQ ID NO 312
<211> LENGTH: 15
<212> TYPE: PRT
<213> ORGANISM: artificial sequence
<220> FEATURE:
<223> OTHER INFORMATION: MAGE-C1 15mer

<400> SEQUENCE: 312

Asp Asp Ser Tyr Val Phe Val Asn Thr Leu Asp Leu Thr Ser Glu
1               5                   10                  15

<210> SEQ ID NO 313
<211> LENGTH: 15
<212> TYPE: PRT
<213> ORGANISM: artificial sequence
<220> FEATURE:
<223> OTHER INFORMATION: LAGE-1 15mer
```

```
<400> SEQUENCE: 313

Asp Phe Thr Val Ser Gly Asn Leu Leu Phe Met Ser Val Arg Asp
1               5                   10                  15

<210> SEQ ID NO 314
<211> LENGTH: 15
<212> TYPE: PRT
<213> ORGANISM: artificial sequence
<220> FEATURE:
<223> OTHER INFORMATION: MAGE-A3 15mer

<400> SEQUENCE: 314

Leu Thr Gln His Phe Val Gln Glu Asn Tyr Leu Glu Tyr Arg Gln
1               5                   10                  15

<210> SEQ ID NO 315
<211> LENGTH: 15
<212> TYPE: PRT
<213> ORGANISM: artificial sequence
<220> FEATURE:
<223> OTHER INFORMATION: MAGE-A8 15mer

<400> SEQUENCE: 315

Glu Glu Ala Ile Trp Glu Ala Leu Ser Val Met Gly Leu Tyr Asp
1               5                   10                  15

<210> SEQ ID NO 316
<211> LENGTH: 15
<212> TYPE: PRT
<213> ORGANISM: artificial sequence
<220> FEATURE:
<223> OTHER INFORMATION: HAGE 15mer

<400> SEQUENCE: 316

Asn Asp Leu Gln Met Ser Asn Phe Val Asn Leu Lys Asn Ile Thr
1               5                   10                  15

<210> SEQ ID NO 317
<211> LENGTH: 15
<212> TYPE: PRT
<213> ORGANISM: artificial sequence
<220> FEATURE:
<223> OTHER INFORMATION: MAGE-A8 15mer

<400> SEQUENCE: 317

Glu Lys Val Ala Glu Leu Val Arg Phe Leu Leu Arg Lys Tyr Gln
1               5                   10                  15

<210> SEQ ID NO 318
<211> LENGTH: 15
<212> TYPE: PRT
<213> ORGANISM: artificial sequence
<220> FEATURE:
<223> OTHER INFORMATION: MAGE-A3 15mer

<400> SEQUENCE: 318

Lys Ala Ser Ser Ser Leu Gln Leu Val Phe Gly Ile Glu Leu Met
1               5                   10                  15

<210> SEQ ID NO 319
<211> LENGTH: 15
<212> TYPE: PRT
<213> ORGANISM: artificial sequence
<220> FEATURE:
<223> OTHER INFORMATION: SURVIVIN 15mer
```

-continued

```
<400> SEQUENCE: 319

Lys Asp His Arg Ile Ser Thr Phe Lys Asn Trp Pro Phe Leu Glu
1               5                   10                  15

<210> SEQ ID NO 320
<211> LENGTH: 15
<212> TYPE: PRT
<213> ORGANISM: artificial sequence
<220> FEATURE:
<223> OTHER INFORMATION: MAGE-A2 15mer

<400> SEQUENCE: 320

Ser Ser Phe Ser Thr Thr Ile Asn Tyr Thr Leu Trp Arg Gln Ser
1               5                   10                  15

<210> SEQ ID NO 321
<211> LENGTH: 15
<212> TYPE: PRT
<213> ORGANISM: artificial sequence
<220> FEATURE:
<223> OTHER INFORMATION: MAGE-A3 15mer

<400> SEQUENCE: 321

Gln Ala Ala Leu Ser Arg Lys Val Ala Glu Leu Val His Phe Leu
1               5                   10                  15

<210> SEQ ID NO 322
<211> LENGTH: 15
<212> TYPE: PRT
<213> ORGANISM: artificial sequence
<220> FEATURE:
<223> OTHER INFORMATION: MAGE-A1 15mer

<400> SEQUENCE: 322

Glu Thr Ser Tyr Val Lys Val Leu Glu Tyr Val Ile Lys Val Ser
1               5                   10                  15

<210> SEQ ID NO 323
<211> LENGTH: 15
<212> TYPE: PRT
<213> ORGANISM: artificial sequence
<220> FEATURE:
<223> OTHER INFORMATION: MAGE-C2 15mer

<400> SEQUENCE: 323

Met Ala Ser Glu Ser Leu Ser Val Met Ser Ser Asn Val Ser Phe
1               5                   10                  15

<210> SEQ ID NO 324
<211> LENGTH: 15
<212> TYPE: PRT
<213> ORGANISM: artificial sequence
<220> FEATURE:
<223> OTHER INFORMATION: MAGE-C2 15mer

<400> SEQUENCE: 324

Arg Glu His Phe Val Tyr Gly Glu Pro Arg Glu Leu Leu Thr Lys
1               5                   10                  15

<210> SEQ ID NO 325
<211> LENGTH: 15
<212> TYPE: PRT
<213> ORGANISM: artificial sequence
<220> FEATURE:
<223> OTHER INFORMATION: MAGE-A10 15mer

<400> SEQUENCE: 325
```

Arg Asn Tyr Glu Asp His Phe Pro Leu Leu Phe Ser Glu Ala Ser
1               5                   10                  15

<210> SEQ ID NO 326
<211> LENGTH: 15
<212> TYPE: PRT
<213> ORGANISM: artificial sequence
<220> FEATURE:
<223> OTHER INFORMATION: MAGE-A12 15mer

<400> SEQUENCE: 326

Lys Ala Ser Glu Tyr Leu Gln Leu Val Phe Gly Ile Glu Val Val
1               5                   10                  15

<210> SEQ ID NO 327
<211> LENGTH: 15
<212> TYPE: PRT
<213> ORGANISM: artificial sequence
<220> FEATURE:
<223> OTHER INFORMATION: LAGE-1 15mer

<400> SEQUENCE: 327

Asp Ser Arg Leu Leu Gln Leu His Ile Thr Met Pro Phe Ser Ser
1               5                   10                  15

<210> SEQ ID NO 328
<211> LENGTH: 30
<212> TYPE: PRT
<213> ORGANISM: artificial sequence
<220> FEATURE:
<223> OTHER INFORMATION: BLV1411-01 MAGE-C1/PIWIL2

<400> SEQUENCE: 328

Asp Asp Ser Tyr Val Phe Val Asn Thr Leu Asp Leu Thr Ser Glu Arg
1               5                   10                  15

Asn Phe Tyr Asp Pro Thr Ser Ala Met Val Leu Gln Gln His
            20                  25                  30

<210> SEQ ID NO 329
<211> LENGTH: 30
<212> TYPE: PRT
<213> ORGANISM: artificial sequence
<220> FEATURE:
<223> OTHER INFORMATION: BLV1411-02 MAGE-A9/OY-TES-1

<400> SEQUENCE: 329

Glu Phe Met Phe Gln Glu Ala Leu Lys Leu Lys Val Ala Glu Leu Glu
1               5                   10                  15

Ser Thr Pro Met Ile Met Glu Asn Ile Gln Glu Leu Ile Arg
            20                  25                  30

<210> SEQ ID NO 330
<211> LENGTH: 30
<212> TYPE: PRT
<213> ORGANISM: artificial sequence
<220> FEATURE:
<223> OTHER INFORMATION: BLV1411-03 PIWIL2/MAGE-A1

<400> SEQUENCE: 330

Tyr Ser Arg Val Val Phe Gln Met Pro His Gln Glu Ile Val Asp Glu
1               5                   10                  15

Thr Ser Tyr Val Lys Val Leu Glu Tyr Val Ile Lys Val Ser
            20                  25                  30

```
<210> SEQ ID NO 331
<211> LENGTH: 30
<212> TYPE: PRT
<213> ORGANISM: artificial sequence
<220> FEATURE:
<223> OTHER INFORMATION: BLV1411-04 CTAGE1/MAGE-A2

<400> SEQUENCE: 331

Gln Asn Tyr Ile Asp Gln Phe Leu Leu Thr Ser Phe Pro Thr Phe Arg
1               5                   10                  15

Glu Asp Ser Val Phe Ala His Pro Arg Lys Leu Leu Met Gln
            20                  25                  30

<210> SEQ ID NO 332
<211> LENGTH: 30
<212> TYPE: PRT
<213> ORGANISM: artificial sequence
<220> FEATURE:
<223> OTHER INFORMATION: BLV1411-05 HAGE/EpCAM

<400> SEQUENCE: 332

Asn Asp Leu Gln Met Ser Asn Phe Val Asn Leu Lys Asn Ile Thr Arg
1               5                   10                  15

Thr Tyr Trp Ile Ile Ile Glu Leu Lys His Lys Ala Arg Glu
            20                  25                  30

<210> SEQ ID NO 333
<211> LENGTH: 30
<212> TYPE: PRT
<213> ORGANISM: artificial sequence
<220> FEATURE:
<223> OTHER INFORMATION: BLV1411-06 MAGE-A9/MAGE-A8

<400> SEQUENCE: 333

Ser Ser Ile Ser Val Tyr Tyr Thr Leu Trp Ser Gln Phe Asp Glu Glu
1               5                   10                  15

Lys Val Ala Glu Leu Val Arg Phe Leu Leu Arg Lys Tyr Gln
            20                  25                  30

<210> SEQ ID NO 334
<211> LENGTH: 30
<212> TYPE: PRT
<213> ORGANISM: artificial sequence
<220> FEATURE:
<223> OTHER INFORMATION: BLV1411-07 NY-ESO-1/MAGE-A10

<400> SEQUENCE: 334

Arg Gly Pro Glu Ser Arg Leu Leu Glu Phe Tyr Leu Ala Met Pro Arg
1               5                   10                  15

Asn Tyr Glu Asp His Phe Pro Leu Leu Phe Ser Glu Ala Ser
            20                  25                  30

<210> SEQ ID NO 335
<211> LENGTH: 30
<212> TYPE: PRT
<213> ORGANISM: artificial sequence
<220> FEATURE:
<223> OTHER INFORMATION: BLV1411-08 CTAGE1/MAGE-A8

<400> SEQUENCE: 335

Ser Phe Val Leu Phe Leu Phe Gly Gly Asn Asn Phe Ile Gln Asn Glu
1               5                   10                  15

Glu Ala Ile Trp Glu Ala Leu Ser Val Met Gly Leu Tyr Asp
            20                  25                  30
```

```
<210> SEQ ID NO 336
<211> LENGTH: 30
<212> TYPE: PRT
<213> ORGANISM: artificial sequence
<220> FEATURE:
<223> OTHER INFORMATION: BLV1411-09 EpCAM/MAGE-C2

<400> SEQUENCE: 336

Gln Thr Leu Ile Tyr Tyr Val Asp Glu Lys Ala Pro Glu Phe Ser Arg
1               5                   10                  15

Glu His Phe Val Tyr Gly Glu Pro Arg Glu Leu Leu Thr Lys
            20                  25                  30

<210> SEQ ID NO 337
<211> LENGTH: 30
<212> TYPE: PRT
<213> ORGANISM: artificial sequence
<220> FEATURE:
<223> OTHER INFORMATION: BLV1411-10 MAGE-C1/MAGE-A12

<400> SEQUENCE: 337

Ser Ser Phe Ser Tyr Thr Leu Leu Ser Leu Phe Gln Ser Ser Pro Lys
1               5                   10                  15

Ala Ser Glu Tyr Leu Gln Leu Val Phe Gly Ile Glu Val Val
            20                  25                  30

<210> SEQ ID NO 338
<211> LENGTH: 30
<212> TYPE: PRT
<213> ORGANISM: artificial sequence
<220> FEATURE:
<223> OTHER INFORMATION: BLV1411-11 PIWIL2/LAGE-1

<400> SEQUENCE: 338

Phe Val Ala Ser Ile Asn Leu Thr Leu Thr Lys Trp Tyr Ser Arg Asp
1               5                   10                  15

Phe Thr Val Ser Gly Asn Leu Leu Phe Met Ser Val Arg Asp
            20                  25                  30

<210> SEQ ID NO 339
<211> LENGTH: 30
<212> TYPE: PRT
<213> ORGANISM: artificial sequence
<220> FEATURE:
<223> OTHER INFORMATION: BLV1411-12 MAGE-A3/MAGE-A3

<400> SEQUENCE: 339

Leu Thr Gln His Phe Val Gln Glu Asn Tyr Leu Glu Tyr Arg Gln Lys
1               5                   10                  15

Ala Ser Ser Ser Leu Gln Leu Val Phe Gly Ile Glu Leu Met
            20                  25                  30

<210> SEQ ID NO 340
<211> LENGTH: 30
<212> TYPE: PRT
<213> ORGANISM: artificial sequence
<220> FEATURE:
<223> OTHER INFORMATION: BLV1411-13 MAGE-A2/LAGE-1

<400> SEQUENCE: 340

Ser Ser Phe Ser Thr Thr Ile Asn Tyr Thr Leu Trp Arg Gln Ser Asp
1               5                   10                  15

Ser Arg Leu Leu Gln Leu His Ile Thr Met Pro Phe Ser Ser
            20                  25                  30
```

<210> SEQ ID NO 341
<211> LENGTH: 30
<212> TYPE: PRT
<213> ORGANISM: artificial sequence
<220> FEATURE:
<223> OTHER INFORMATION: BLV1411-14 SURVIVIN/MAGE-C2

<400> SEQUENCE: 341

Ala Lys Lys Val Arg Arg Ala Ile Glu Gln Leu Ala Ala Met Asp Met
1               5                   10                  15

Ala Ser Glu Ser Leu Ser Val Met Ser Ser Asn Val Ser Phe
            20                  25                  30

<210> SEQ ID NO 342
<211> LENGTH: 30
<212> TYPE: PRT
<213> ORGANISM: artificial sequence
<220> FEATURE:
<223> OTHER INFORMATION: BLV1411-15 MAGE-A3/SURVIVIN

<400> SEQUENCE: 342

Gln Ala Ala Leu Ser Arg Lys Val Ala Glu Leu Val His Phe Leu Lys
1               5                   10                  15

Asp His Arg Ile Ser Thr Phe Lys Asn Trp Pro Phe Leu Glu
            20                  25                  30

<210> SEQ ID NO 343
<211> LENGTH: 973
<212> TYPE: PRT
<213> ORGANISM: Homo sapiens

<400> SEQUENCE: 343

Met Asp Pro Phe Arg Pro Ser Phe Arg Gly Gln Ser Pro Ile His Pro
1               5                   10                  15

Ser Gln Cys Gln Ala Val Arg Met Pro Gly Cys Trp Pro Gln Ala Ser
            20                  25                  30

Lys Pro Leu Asp Pro Ala Leu Gly Arg Gly Ala Pro Ala Gly Arg Gly
        35                  40                  45

His Val Phe Gly Lys Pro Glu Glu Pro Ser Thr Gln Arg Gly Pro Ala
    50                  55                  60

Gln Arg Glu Ser Val Gly Leu Val Ser Met Phe Arg Gly Leu Gly Ile
65                  70                  75                  80

Glu Thr Val Ser Lys Thr Pro Leu Lys Arg Glu Met Leu Pro Ser Gly
                85                  90                  95

Arg Gly Ile Leu Gly Arg Gly Leu Ser Ala Asn Leu Val Arg Lys Asp
            100                 105                 110

Arg Glu Glu Leu Ser Pro Thr Phe Trp Asp Pro Lys Val Leu Ala Ala
        115                 120                 125

Gly Asp Ser Lys Met Ala Glu Thr Ser Val Gly Trp Ser Arg Thr Leu
    130                 135                 140

Gly Arg Gly Ser Ser Asp Ala Ser Leu Leu Pro Leu Gly Arg Ala Ala
145                 150                 155                 160

Gly Gly Ile Ser Arg Glu Val Asp Lys Pro Pro Cys Thr Phe Ser Thr
                165                 170                 175

Pro Ser Arg Gly Pro Pro Gln Leu Ser Ser Pro Ala Leu Pro Gln
            180                 185                 190

Ser Pro Leu His Ser Pro Asp Arg Pro Leu Val Leu Thr Val Glu His
        195                 200                 205

```
Lys Glu Lys Glu Leu Ile Val Lys Gln Gly Ser Lys Gly Thr Pro Gln
            210                 215                 220

Ser Leu Gly Leu Asn Leu Val Lys Ile Gln Cys His Asn Glu Ala Val
225                 230                 235                 240

Tyr Gln Tyr His Val Thr Phe Ser Pro Asn Val Glu Cys Lys Ser Met
                245                 250                 255

Arg Phe Gly Met Leu Lys Asp His Gln Ala Val Thr Gly Asn Val Thr
                260                 265                 270

Ala Phe Asp Gly Ser Ile Leu Tyr Leu Pro Val Lys Leu Gln Gln Val
            275                 280                 285

Leu Glu Leu Lys Ser Gln Arg Lys Thr Asp Ser Ala Glu Ile Ser Ile
290                 295                 300

Lys Ile Gln Met Thr Lys Ile Leu Glu Pro Cys Ser Asp Leu Cys Ile
305                 310                 315                 320

Pro Phe Tyr Asn Val Val Phe Arg Arg Val Met Lys Leu Leu Asp Met
                325                 330                 335

Lys Leu Val Gly Arg Asn Phe Tyr Asp Pro Thr Ser Ala Met Val Leu
            340                 345                 350

Gln Gln His Arg Leu Gln Ile Trp Pro Gly Tyr Ala Ala Ser Ile Arg
            355                 360                 365

Arg Thr Asp Gly Gly Leu Phe Leu Leu Ala Asp Val Ser His Lys Val
    370                 375                 380

Ile Arg Asn Asp Cys Val Leu Asp Val Met His Ala Ile Tyr Gln Gln
385                 390                 395                 400

Asn Lys Glu His Phe Gln Asp Glu Cys Thr Lys Leu Leu Val Gly Asn
                405                 410                 415

Ile Val Ile Thr Arg Tyr Asn Asn Arg Thr Tyr Arg Ile Asp Asp Val
            420                 425                 430

Asp Trp Asn Lys Thr Pro Lys Asp Ser Phe Thr Met Ser Asp Gly Lys
            435                 440                 445

Glu Ile Thr Phe Leu Glu Tyr Tyr Ser Lys Asn Tyr Gly Ile Thr Val
    450                 455                 460

Lys Glu Glu Asp Gln Pro Leu Leu Ile His Arg Pro Ser Glu Arg Gln
465                 470                 475                 480

Asp Asn His Gly Met Leu Leu Lys Gly Glu Ile Leu Leu Pro Glu
                485                 490                 495

Leu Ser Phe Met Thr Gly Ile Pro Glu Lys Met Lys Lys Asp Phe Arg
            500                 505                 510

Ala Met Lys Asp Leu Ala Gln Ile Asn Leu Ser Pro Lys Gln His
            515                 520                 525

His Ser Ala Leu Glu Cys Leu Leu Gln Arg Ile Ala Lys Asn Glu Ala
530                 535                 540

Ala Thr Asn Glu Leu Met Arg Trp Gly Leu Arg Leu Gln Lys Asp Val
545                 550                 555                 560

His Lys Ile Glu Gly Arg Val Leu Pro Met Glu Arg Ile Asn Leu Lys
                565                 570                 575

Asn Thr Ser Phe Ile Thr Ser Gln Glu Leu Asn Trp Val Lys Glu Val
            580                 585                 590

Thr Arg Asp Pro Ser Ile Leu Thr Ile Pro Met His Phe Trp Ala Leu
    595                 600                 605

Phe Tyr Pro Lys Arg Ala Met Asp Gln Ala Arg Glu Leu Val Asn Met
    610                 615                 620
```

Leu Glu Lys Ile Ala Gly Pro Ile Gly Met Arg Met Ser Pro Pro Ala
625                 630                 635                 640

Trp Val Glu Leu Lys Asp Asp Arg Ile Glu Thr Tyr Val Arg Thr Ile
            645                 650                 655

Gln Ser Thr Leu Gly Ala Glu Gly Lys Ile Gln Met Val Val Cys Ile
            660                 665                 670

Ile Met Gly Pro Arg Asp Asp Leu Tyr Gly Ala Ile Lys Lys Leu Cys
            675                 680                 685

Cys Val Gln Ser Pro Val Pro Ser Gln Val Val Asn Val Arg Thr Ile
            690                 695                 700

Gly Gln Pro Thr Arg Leu Arg Ser Val Ala Gln Lys Ile Leu Leu Gln
705                 710                 715                 720

Ile Asn Cys Lys Leu Gly Gly Glu Leu Trp Gly Val Asp Ile Pro Leu
            725                 730                 735

Lys Gln Leu Met Val Ile Gly Met Asp Val Tyr His Asp Pro Ser Arg
            740                 745                 750

Gly Met Arg Ser Val Val Gly Phe Val Ala Ser Ile Asn Leu Thr Leu
            755                 760                 765

Thr Lys Trp Tyr Ser Arg Val Val Phe Gln Met Pro His Gln Glu Ile
770                 775                 780

Val Asp Ser Leu Lys Leu Cys Leu Val Gly Ser Leu Lys Lys Phe Tyr
785                 790                 795                 800

Glu Val Asn His Cys Leu Pro Glu Lys Ile Val Val Tyr Arg Asp Gly
            805                 810                 815

Val Ser Asp Gly Gln Leu Lys Thr Val Ala Asn Tyr Glu Ile Pro Gln
            820                 825                 830

Leu Gln Lys Cys Phe Glu Ala Phe Glu Asn Tyr Gln Pro Lys Met Val
            835                 840                 845

Val Phe Val Val Gln Lys Lys Ile Ser Thr Asn Leu Tyr Leu Ala Ala
850                 855                 860

Pro Gln Asn Phe Val Thr Pro Thr Pro Gly Thr Val Val Asp His Thr
865                 870                 875                 880

Ile Thr Ser Cys Glu Trp Val Asp Phe Tyr Leu Leu Ala His His Val
            885                 890                 895

Arg Gln Gly Cys Gly Ile Pro Thr His Tyr Val Cys Val Leu Asn Thr
            900                 905                 910

Ala Asn Leu Ser Pro Asp His Met Gln Arg Leu Thr Phe Lys Leu Cys
            915                 920                 925

His Met Tyr Trp Asn Trp Pro Gly Thr Ile Arg Val Pro Ala Pro Cys
930                 935                 940

Lys Tyr Ala His Lys Leu Ala Phe Leu Ser Gly His Ile Leu His His
945                 950                 955                 960

Glu Pro Ala Ile Gln Leu Cys Glu Asn Leu Phe Phe Leu
            965                 970

<210> SEQ ID NO 344
<211> LENGTH: 74
<212> TYPE: PRT
<213> ORGANISM: Homo sapiens

<400> SEQUENCE: 344

Met Phe Val Ile Ile Ser Leu His Asn Cys Val Val Ile Ser Phe Val
1               5                   10                  15

Leu Phe Leu Phe Gly Gly Asn Asn Phe Ile Gln Asn Phe Tyr Leu Pro
            20                  25                  30

Gln Asn Tyr Ile Asp Gln Phe Leu Leu Thr Ser Phe Pro Thr Phe Thr
                35                  40                  45

Ser Val Gly Val Leu Ile Val Leu Val Leu Cys Ser Ala Phe Leu Leu
 50                  55                  60

Leu Trp Gln Gly Glu Gly Val Asn Leu Arg
 65                  70

<210> SEQ ID NO 345
<211> LENGTH: 315
<212> TYPE: PRT
<213> ORGANISM: Homo sapiens

<400> SEQUENCE: 345

Met Ser Leu Glu Gln Arg Ser Pro His Cys Lys Pro Asp Glu Asp Leu
 1               5                  10                  15

Glu Ala Gln Gly Glu Asp Leu Gly Leu Met Gly Ala Gln Glu Pro Thr
                20                  25                  30

Gly Glu Glu Glu Thr Thr Ser Ser Asp Ser Lys Glu Glu
                35                  40                  45

Val Ser Ala Ala Gly Ser Ser Ser Pro Pro Gln Ser Pro Gln Gly Gly
 50                  55                  60

Ala Ser Ser Ile Ser Val Tyr Tyr Thr Leu Trp Ser Gln Phe Asp
 65                  70                  75                  80

Glu Gly Ser Ser Gln Glu Glu Glu Pro Ser Ser Ser Val Asp
                85                  90                  95

Pro Ala Gln Leu Glu Phe Met Phe Gln Glu Ala Leu Lys Leu Lys Val
                100                 105                 110

Ala Glu Leu Val His Phe Leu Leu His Lys Tyr Arg Val Lys Glu Pro
                115                 120                 125

Val Thr Lys Ala Glu Met Leu Glu Ser Val Ile Lys Asn Tyr Lys Arg
                130                 135                 140

Tyr Phe Pro Val Ile Phe Gly Lys Ala Ser Glu Phe Met Gln Val Ile
145                 150                 155                 160

Phe Gly Thr Asp Val Lys Glu Val Asp Pro Ala Gly His Ser Tyr Ile
                165                 170                 175

Leu Val Thr Ala Leu Gly Leu Ser Cys Asp Ser Met Leu Gly Asp Gly
                180                 185                 190

His Ser Met Pro Lys Ala Ala Leu Leu Ile Ile Val Leu Gly Val Ile
                195                 200                 205

Leu Thr Lys Asp Asn Cys Ala Pro Glu Val Ile Trp Glu Ala Leu
                210                 215                 220

Ser Val Met Gly Val Tyr Val Gly Lys Glu His Met Phe Tyr Gly Glu
225                 230                 235                 240

Pro Arg Lys Leu Leu Thr Gln Asp Trp Val Gln Glu Asn Tyr Leu Glu
                245                 250                 255

Tyr Arg Gln Val Pro Gly Ser Asp Pro Ala His Tyr Glu Phe Leu Trp
                260                 265                 270

Gly Ser Lys Ala His Ala Glu Thr Ser Tyr Glu Lys Val Ile Asn Tyr
                275                 280                 285

Leu Val Met Leu Asn Ala Arg Glu Pro Ile Cys Tyr Pro Ser Leu Tyr
                290                 295                 300

Glu Glu Val Leu Gly Glu Glu Gln Glu Gly Val
305                 310                 315

```
<210> SEQ ID NO 346
<211> LENGTH: 314
<212> TYPE: PRT
<213> ORGANISM: Homo sapiens

<400> SEQUENCE: 346

Met Ala Pro Pro Gln Val Leu Ala Phe Gly Leu Leu Leu Ala Ala Ala
1               5                   10                  15

Thr Ala Thr Phe Ala Ala Ala Gln Glu Glu Cys Val Cys Glu Asn Tyr
            20                  25                  30

Lys Leu Ala Val Asn Cys Phe Val Asn Asn Asn Arg Gln Cys Gln Cys
        35                  40                  45

Thr Ser Val Gly Ala Gln Asn Thr Val Ile Cys Ser Lys Leu Ala Ala
    50                  55                  60

Lys Cys Leu Val Met Lys Ala Glu Met Asn Gly Ser Lys Leu Gly Arg
65                  70                  75                  80

Arg Ala Lys Pro Glu Gly Ala Leu Gln Asn Asn Asp Gly Leu Tyr Asp
                85                  90                  95

Pro Asp Cys Asp Glu Ser Gly Leu Phe Lys Ala Lys Gln Cys Asn Gly
            100                 105                 110

Thr Ser Met Cys Trp Cys Val Asn Thr Ala Gly Val Arg Arg Thr Asp
        115                 120                 125

Lys Asp Thr Glu Ile Thr Cys Ser Glu Arg Val Arg Thr Tyr Trp Ile
    130                 135                 140

Ile Ile Glu Leu Lys His Lys Ala Arg Glu Lys Pro Tyr Asp Ser Lys
145                 150                 155                 160

Ser Leu Arg Thr Ala Leu Gln Lys Glu Ile Thr Thr Arg Tyr Gln Leu
                165                 170                 175

Asp Pro Lys Phe Ile Thr Ser Ile Leu Tyr Glu Asn Asn Val Ile Thr
            180                 185                 190

Ile Asp Leu Val Gln Asn Ser Ser Gln Lys Thr Gln Asn Asp Val Asp
        195                 200                 205

Ile Ala Asp Val Ala Tyr Tyr Phe Glu Lys Asp Val Lys Gly Glu Ser
    210                 215                 220

Leu Phe His Ser Lys Lys Met Asp Leu Thr Val Asn Gly Glu Gln Leu
225                 230                 235                 240

Asp Leu Asp Pro Gly Gln Thr Leu Ile Tyr Tyr Val Asp Glu Lys Ala
                245                 250                 255

Pro Glu Phe Ser Met Gln Gly Leu Lys Ala Gly Val Ile Ala Val Ile
            260                 265                 270

Val Val Val Val Ile Ala Val Val Ala Gly Ile Val Val Leu Val Ile
        275                 280                 285

Ser Arg Lys Lys Arg Met Ala Lys Tyr Glu Lys Ala Glu Ile Lys Glu
    290                 295                 300

Met Gly Glu Met His Arg Glu Leu Asn Ala
305                 310

<210> SEQ ID NO 347
<211> LENGTH: 543
<212> TYPE: PRT
<213> ORGANISM: Homo sapiens

<400> SEQUENCE: 347

Met Arg Lys Pro Ala Ala Gly Phe Leu Pro Ser Leu Leu Lys Val Leu
1               5                   10                  15

Leu Leu Pro Leu Ala Pro Ala Ala Ala Gln Asp Ser Thr Gln Ala Ser
```

-continued

```
               20                  25                  30
Thr Pro Gly Ser Pro Leu Ser Pro Thr Glu Tyr Glu Arg Phe Phe Ala
           35                  40                  45
Leu Leu Thr Pro Thr Trp Lys Ala Glu Thr Cys Arg Leu Arg Ala
 50                  55                  60
Thr His Gly Cys Arg Asn Pro Thr Leu Val Gln Leu Asp Gln Tyr Glu
 65                  70                  75                  80
Asn His Gly Leu Val Pro Asp Gly Ala Val Cys Ser Asn Leu Pro Tyr
                   85                  90                  95
Ala Ser Trp Phe Glu Ser Phe Cys Gln Phe Thr His Tyr Arg Cys Ser
               100                 105                 110
Asn His Val Tyr Tyr Ala Lys Arg Val Leu Cys Ser Gln Pro Val Ser
               115                 120                 125
Ile Leu Ser Pro Asn Thr Leu Lys Glu Ile Glu Ala Ser Ala Glu Val
               130                 135                 140
Ser Pro Thr Thr Met Thr Ser Pro Ile Ser Pro His Phe Thr Val Thr
145                 150                 155                 160
Glu Arg Gln Thr Phe Gln Pro Trp Pro Glu Arg Leu Ser Asn Asn Val
               165                 170                 175
Glu Glu Leu Leu Gln Ser Ser Leu Ser Leu Gly Gly Gln Glu Gln Ala
               180                 185                 190
Pro Glu His Lys Gln Glu Gln Gly Val Glu His Arg Gln Glu Pro Thr
               195                 200                 205
Gln Glu His Lys Gln Glu Glu Gly Gln Lys Gln Glu Gln Gln Glu Glu
               210                 215                 220
Glu Gln Glu Glu Glu Gly Lys Gln Glu Glu Gly Gln Gly Thr Lys Glu
225                 230                 235                 240
Gly Arg Glu Ala Val Ser Gln Leu Gln Thr Asp Ser Glu Pro Lys Phe
               245                 250                 255
His Ser Glu Ser Leu Ser Ser Asn Pro Ser Ser Phe Ala Pro Arg Val
               260                 265                 270
Arg Glu Val Glu Ser Thr Pro Met Ile Met Glu Asn Ile Gln Glu Leu
               275                 280                 285
Ile Arg Ser Ala Gln Glu Ile Asp Glu Met Asn Glu Ile Tyr Asp Glu
               290                 295                 300
Asn Ser Tyr Trp Arg Asn Gln Asn Pro Gly Ser Leu Leu Gln Leu Pro
305                 310                 315                 320
His Thr Glu Ala Leu Leu Val Leu Cys Tyr Ser Ile Val Glu Asn Thr
               325                 330                 335
Cys Ile Ile Thr Pro Thr Ala Lys Ala Trp Lys Tyr Met Glu Glu Glu
               340                 345                 350
Ile Leu Gly Phe Gly Lys Ser Val Cys Asp Ser Leu Gly Arg Arg His
               355                 360                 365
Met Ser Thr Cys Ala Leu Cys Asp Phe Cys Ser Leu Lys Leu Glu Gln
               370                 375                 380
Cys His Ser Glu Ala Ser Leu Gln Arg Gln Gln Cys Asp Thr Ser His
385                 390                 395                 400
Lys Thr Pro Phe Val Ser Pro Leu Leu Ala Ser Gln Ser Leu Ser Ile
                   405                 410                 415
Gly Asn Gln Val Gly Ser Pro Glu Ser Gly Arg Phe Tyr Gly Leu Asp
               420                 425                 430
Leu Tyr Gly Gly Leu His Met Asp Phe Trp Cys Ala Arg Leu Ala Thr
               435                 440                 445
```

```
Lys Gly Cys Glu Asp Val Arg Val Ser Gly Trp Leu Gln Thr Glu Phe
    450                 455                 460

Leu Ser Phe Gln Asp Gly Asp Phe Pro Thr Lys Ile Cys Asp Thr Asp
465                 470                 475                 480

Tyr Ile Gln Tyr Pro Asn Tyr Cys Ser Phe Lys Ser Gln Cys Leu
                485                 490                 495

Met Arg Asn Arg Asn Arg Lys Val Ser Arg Met Arg Cys Leu Gln Asn
            500                 505                 510

Glu Thr Tyr Ser Ala Leu Ser Pro Gly Lys Ser Glu Asp Val Val Leu
            515                 520                 525

Arg Trp Ser Gln Glu Phe Ser Thr Leu Thr Leu Gly Gln Phe Gly
            530                 535                 540

<210> SEQ ID NO 348
<211> LENGTH: 180
<212> TYPE: PRT
<213> ORGANISM: Homo sapiens

<400> SEQUENCE: 348

Met Gln Ala Glu Gly Arg Gly Thr Gly Gly Ser Thr Gly Asp Ala Asp
1               5                   10                  15

Gly Pro Gly Gly Pro Gly Ile Pro Asp Gly Pro Gly Gly Asn Ala Gly
                20                  25                  30

Gly Pro Gly Glu Ala Gly Ala Thr Gly Gly Arg Gly Pro Arg Gly Ala
            35                  40                  45

Gly Ala Ala Arg Ala Ser Gly Pro Gly Gly Gly Ala Pro Arg Gly Pro
50                  55                  60

His Gly Gly Ala Ala Ser Gly Leu Asn Gly Cys Cys Arg Cys Gly Ala
65                  70                  75                  80

Arg Gly Pro Glu Ser Arg Leu Leu Glu Phe Tyr Leu Ala Met Pro Phe
                85                  90                  95

Ala Thr Pro Met Glu Ala Glu Leu Ala Arg Arg Ser Leu Ala Gln Asp
                100                 105                 110

Ala Pro Pro Leu Pro Val Pro Gly Val Leu Leu Lys Glu Phe Thr Val
            115                 120                 125

Ser Gly Asn Ile Leu Thr Ile Arg Leu Thr Ala Ala Asp His Arg Gln
130                 135                 140

Leu Gln Leu Ser Ile Ser Ser Cys Leu Gln Gln Leu Ser Leu Leu Met
145                 150                 155                 160

Trp Ile Thr Gln Cys Phe Leu Pro Val Phe Leu Ala Gln Pro Pro Ser
                165                 170                 175

Gly Gln Arg Arg
            180

<210> SEQ ID NO 349
<211> LENGTH: 142
<212> TYPE: PRT
<213> ORGANISM: Homo sapiens

<400> SEQUENCE: 349

Met Gly Ala Pro Thr Leu Pro Pro Ala Trp Gln Pro Phe Leu Lys Asp
1               5                   10                  15

His Arg Ile Ser Thr Phe Lys Asn Trp Pro Phe Leu Glu Gly Cys Ala
                20                  25                  30

Cys Thr Pro Glu Arg Met Ala Glu Ala Gly Phe Ile His Cys Pro Thr
            35                  40                  45
```

-continued

```
Glu Asn Glu Pro Asp Leu Ala Gln Cys Phe Phe Cys Phe Lys Glu Leu
         50                  55                  60

Glu Gly Trp Glu Pro Asp Asp Pro Ile Glu His Lys Lys His
 65                  70                  75                  80

Ser Ser Gly Cys Ala Phe Leu Ser Val Lys Lys Gln Phe Glu Glu Leu
                 85                  90                  95

Thr Leu Gly Glu Phe Leu Lys Leu Asp Arg Glu Arg Ala Lys Asn Lys
            100                 105                 110

Ile Ala Lys Glu Thr Asn Asn Lys Lys Glu Phe Glu Glu Thr Ala
        115                 120                 125

Lys Lys Val Arg Arg Ala Ile Glu Gln Leu Ala Ala Met Asp
130                 135                 140

<210> SEQ ID NO 350
<211> LENGTH: 1142
<212> TYPE: PRT
<213> ORGANISM: Homo sapiens

<400> SEQUENCE: 350

Met Gly Asp Lys Asp Met Pro Thr Ala Gly Met Pro Ser Leu Leu Gln
 1               5                  10                  15

Ser Ser Ser Glu Ser Pro Gln Ser Cys Pro Glu Gly Glu Asp Ser Gln
             20                  25                  30

Ser Pro Leu Gln Ile Pro Gln Ser Pro Glu Ser Asp Asp Thr Leu
         35                  40                  45

Tyr Pro Leu Gln Ser Pro Gln Ser Arg Ser Gly Glu Asp Ser Ser
 50                  55                  60

Asp Pro Leu Gln Arg Pro Pro Glu Gly Lys Asp Ser Gln Ser Pro Leu
 65                  70                  75                  80

Gln Ile Pro Gln Ser Ser Pro Glu Gly Asp Asp Thr Gln Ser Pro Leu
                 85                  90                  95

Gln Asn Ser Gln Ser Ser Pro Glu Gly Lys Asp Ser Leu Ser Pro Leu
            100                 105                 110

Glu Ile Ser Gln Ser Pro Pro Glu Gly Glu Asp Val Gln Ser Pro Leu
        115                 120                 125

Gln Asn Pro Ala Ser Ser Phe Phe Ser Ser Ala Leu Leu Ser Ile Phe
130                 135                 140

Gln Ser Ser Pro Glu Ser Thr Gln Ser Pro Phe Glu Gly Phe Pro Gln
145                 150                 155                 160

Ser Val Leu Gln Ile Pro Val Ser Ala Ala Ser Ser Thr Leu Val
                165                 170                 175

Ser Ile Phe Gln Ser Ser Pro Glu Ser Thr Gln Ser Pro Phe Glu Gly
            180                 185                 190

Phe Pro Gln Ser Pro Leu Gln Ile Pro Val Ser Arg Ser Phe Ser Ser
        195                 200                 205

Thr Leu Leu Ser Ile Phe Gln Ser Ser Pro Glu Arg Thr Gln Ser Thr
210                 215                 220

Phe Glu Gly Phe Ala Gln Ser Pro Leu Gln Ile Pro Val Ser Pro Ser
225                 230                 235                 240

Ser Ser Ser Thr Leu Leu Ser Leu Phe Gln Ser Phe Ser Glu Arg Thr
                245                 250                 255

Gln Ser Thr Phe Glu Gly Phe Ala Gln Ser Ser Leu Gln Ile Pro Val
            260                 265                 270

Ser Pro Ser Phe Ser Ser Thr Leu Val Ser Leu Phe Gln Ser Ser Pro
```

```
              275                 280                 285
Glu Arg Thr Gln Ser Thr Phe Glu Gly Phe Pro Gln Ser Pro Leu Gln
290                 295                 300
Ile Pro Val Ser Ser Ser Ser Ser Thr Leu Leu Ser Leu Phe Gln
305                 310                 315                 320
Ser Ser Pro Glu Arg Thr His Ser Thr Phe Glu Gly Phe Pro Gln Ser
                325                 330                 335
Leu Leu Gln Ile Pro Met Thr Ser Ser Phe Ser Ser Thr Leu Leu Ser
                340                 345                 350
Ile Phe Gln Ser Ser Pro Glu Ser Ala Gln Ser Thr Phe Glu Gly Phe
            355                 360                 365
Pro Gln Ser Pro Leu Gln Ile Pro Gly Ser Pro Ser Phe Ser Ser Thr
        370                 375                 380
Leu Leu Ser Leu Phe Gln Ser Ser Pro Glu Arg Thr His Ser Thr Phe
385                 390                 395                 400
Glu Gly Phe Pro Gln Ser Pro Leu Gln Ile Pro Met Thr Ser Ser Phe
                405                 410                 415
Ser Ser Thr Leu Leu Ser Ile Leu Gln Ser Ser Pro Glu Ser Ala Gln
                420                 425                 430
Ser Ala Phe Glu Gly Phe Pro Gln Ser Pro Leu Gln Ile Pro Val Ser
            435                 440                 445
Ser Ser Phe Ser Tyr Thr Leu Leu Ser Leu Phe Gln Ser Ser Pro Glu
        450                 455                 460
Arg Thr His Ser Thr Phe Glu Gly Phe Pro Gln Ser Pro Leu Gln Ile
465                 470                 475                 480
Pro Val Ser Ser Ser Ser Ser Ser Thr Leu Leu Ser Leu Phe Gln
                485                 490                 495
Ser Ser Pro Glu Cys Thr Gln Ser Thr Phe Glu Gly Phe Pro Gln Ser
                500                 505                 510
Pro Leu Gln Ile Pro Gln Ser Pro Pro Glu Gly Glu Asn Thr His Ser
            515                 520                 525
Pro Leu Gln Ile Val Pro Ser Leu Pro Glu Trp Glu Asp Ser Leu Ser
        530                 535                 540
Pro His Tyr Phe Pro Gln Ser Pro Pro Gln Gly Glu Asp Ser Leu Ser
545                 550                 555                 560
Pro His Tyr Phe Pro Gln Ser Pro Gln Gly Glu Asp Ser Leu Ser
                565                 570                 575
Pro His Tyr Phe Pro Gln Ser Pro Gln Gly Glu Asp Ser Leu Ser Pro
                580                 585                 590
His Tyr Phe Pro Gln Ser Pro Pro Gln Gly Glu Asp Ser Met Ser Pro
            595                 600                 605
Leu Tyr Phe Pro Gln Ser Pro Leu Gln Gly Glu Glu Phe Gln Ser Ser
        610                 615                 620
Leu Gln Ser Pro Val Ser Ile Cys Ser Ser Ser Thr Pro Ser Ser Leu
625                 630                 635                 640
Pro Gln Ser Phe Pro Glu Ser Ser Gln Ser Pro Pro Glu Gly Pro Val
                645                 650                 655
Gln Ser Pro Leu His Ser Pro Gly Ser Pro Pro Glu Gly Met His Ser
                660                 665                 670
Gln Ser Pro Leu Gln Ser Pro Glu Ser Ala Pro Glu Gly Glu Asp Ser
            675                 680                 685
Leu Ser Pro Leu Gln Ile Pro Gln Ser Pro Leu Glu Gly Glu Asp Ser
        690                 695                 700
```

```
Leu Ser Ser Leu His Phe Pro Gln Ser Pro Glu Trp Glu Asp Ser
705                 710                 715                 720

Leu Ser Pro Leu His Phe Pro Gln Phe Pro Gln Gly Glu Asp Phe
            725                 730                 735

Gln Ser Ser Leu Gln Ser Pro Val Ser Ile Cys Ser Ser Thr Ser
                740                 745                 750

Leu Ser Leu Pro Gln Ser Phe Pro Glu Ser Pro Gln Ser Pro Glu
            755                 760                 765

Gly Pro Ala Gln Ser Pro Leu Gln Arg Pro Val Ser Ser Phe Phe Ser
770                 775                 780

Tyr Thr Leu Ala Ser Leu Leu Gln Ser Ser His Glu Ser Pro Gln Ser
785                 790                 795                 800

Pro Pro Glu Gly Pro Ala Gln Ser Pro Leu Gln Ser Pro Val Ser Ser
                805                 810                 815

Phe Pro Ser Ser Thr Ser Ser Ser Leu Ser Gln Ser Ser Pro Val Ser
                820                 825                 830

Ser Phe Pro Ser Ser Thr Ser Ser Ser Leu Ser Lys Ser Ser Pro Glu
            835                 840                 845

Ser Pro Leu Gln Ser Pro Val Ile Ser Phe Ser Ser Ser Thr Ser Leu
850                 855                 860

Ser Pro Phe Ser Glu Glu Ser Ser Ser Pro Val Asp Glu Tyr Thr Ser
865                 870                 875                 880

Ser Ser Asp Thr Leu Leu Glu Ser Asp Ser Leu Thr Asp Ser Glu Ser
                885                 890                 895

Leu Ile Glu Ser Glu Pro Leu Phe Thr Tyr Thr Leu Asp Glu Lys Val
                900                 905                 910

Asp Glu Leu Ala Arg Phe Leu Leu Lys Tyr Gln Val Lys Gln Pro
            915                 920                 925

Ile Thr Lys Ala Glu Met Leu Thr Asn Val Ile Ser Arg Tyr Thr Gly
    930                 935                 940

Tyr Phe Pro Val Ile Phe Arg Lys Ala Arg Glu Phe Ile Glu Ile Leu
945                 950                 955                 960

Phe Gly Ile Ser Leu Arg Glu Val Asp Pro Asp Ser Tyr Val Phe
                965                 970                 975

Val Asn Thr Leu Asp Leu Thr Ser Glu Gly Cys Leu Ser Asp Glu Gln
                980                 985                 990

Gly Met Ser Gln Asn Arg Leu Leu Ile Leu Ile Leu Ser Ile Ile Phe
            995                 1000                1005

Ile Lys Gly Thr Tyr Ala Ser Glu Glu Val Ile Trp Asp Val Leu
1010                1015                1020

Ser Gly Ile Gly Val Arg Ala Gly Arg Glu His Phe Ala Phe Gly
1025                1030                1035

Glu Pro Arg Glu Leu Leu Thr Lys Val Trp Val Gln Glu His Tyr
1040                1045                1050

Leu Glu Tyr Arg Glu Val Pro Asn Ser Ser Pro Arg Tyr Glu
1055                1060                1065

Phe Leu Trp Gly Pro Arg Ala His Ser Glu Val Ile Lys Arg Lys
1070                1075                1080

Val Val Glu Phe Leu Ala Met Leu Lys Asn Thr Val Pro Ile Thr
1085                1090                1095

Phe Pro Ser Ser Tyr Lys Asp Ala Leu Lys Asp Val Glu Glu Arg
1100                1105                1110
```

Ala Gln Ala Ile Ile Asp Thr Thr Asp Asp Ser Thr Ala Thr Glu
    1115                1120                1125

Ser Ala Ser Ser Ser Val Met Ser Pro Ser Phe Ser Ser Glu
    1130                1135                1140

<210> SEQ ID NO 351
<211> LENGTH: 314
<212> TYPE: PRT
<213> ORGANISM: Homo sapiens

<400> SEQUENCE: 351

Met Pro Leu Glu Gln Arg Ser Gln His Cys Lys Pro Glu Glu Gly Leu
1               5                   10                  15

Glu Ala Arg Gly Glu Ala Leu Gly Leu Val Gly Ala Gln Ala Pro Ala
            20                  25                  30

Thr Glu Gln Gln Thr Ala Ser Ser Ser Thr Leu Val Glu Val
        35                  40                  45

Thr Leu Gly Glu Val Pro Ala Ala Asp Ser Pro Ser Pro Pro His Ser
50                  55                  60

Pro Gln Gly Ala Ser Ser Phe Ser Thr Thr Ile Asn Tyr Thr Leu Trp
65                  70                  75                  80

Arg Gln Ser Asp Glu Gly Ser Ser Asn Gln Glu Glu Glu Gly Pro Arg
                85                  90                  95

Met Phe Pro Asp Leu Glu Ser Glu Phe Gln Ala Ala Ile Ser Arg Lys
            100                 105                 110

Met Val Glu Leu Val His Phe Leu Leu Leu Lys Tyr Arg Ala Arg Glu
        115                 120                 125

Pro Val Thr Lys Ala Glu Met Leu Glu Ser Val Leu Arg Asn Cys Gln
130                 135                 140

Asp Phe Phe Pro Val Ile Phe Ser Lys Ala Ser Glu Tyr Leu Gln Leu
145                 150                 155                 160

Val Phe Gly Ile Glu Val Val Glu Val Val Pro Ile Ser His Leu Tyr
                165                 170                 175

Ile Leu Val Thr Cys Leu Gly Leu Ser Tyr Asp Gly Leu Leu Gly Asp
            180                 185                 190

Asn Gln Val Met Pro Lys Thr Gly Leu Leu Ile Ile Val Leu Ala Ile
        195                 200                 205

Ile Ala Ile Glu Gly Asp Cys Ala Pro Glu Glu Lys Ile Trp Glu Glu
210                 215                 220

Leu Ser Met Leu Glu Val Phe Glu Gly Arg Glu Asp Ser Val Phe Ala
225                 230                 235                 240

His Pro Arg Lys Leu Leu Met Gln Asp Leu Val Gln Glu Asn Tyr Leu
                245                 250                 255

Glu Tyr Arg Gln Val Pro Gly Ser Asp Pro Ala Cys Tyr Glu Phe Leu
            260                 265                 270

Trp Gly Pro Arg Ala Leu Ile Glu Thr Ser Tyr Val Lys Val Leu His
        275                 280                 285

His Thr Leu Lys Ile Gly Gly Glu Pro His Ile Ser Tyr Pro Pro Leu
290                 295                 300

His Glu Arg Ala Leu Arg Glu Gly Glu Glu
305                 310

<210> SEQ ID NO 352
<211> LENGTH: 210
<212> TYPE: PRT
<213> ORGANISM: Homo sapiens

<400> SEQUENCE: 352

```
Met Gln Ala Glu Gly Gln Gly Thr Gly Ser Thr Gly Asp Ala Asp
1               5                   10                  15

Gly Pro Gly Gly Pro Gly Ile Pro Asp Gly Pro Gly Gly Asn Ala Gly
                20                  25                  30

Gly Pro Gly Glu Ala Gly Ala Thr Gly Gly Arg Gly Pro Arg Gly Ala
            35                  40                  45

Gly Ala Ala Arg Ala Ser Gly Pro Arg Gly Gly Ala Pro Arg Gly Pro
        50                  55                  60

His Gly Gly Ala Ala Ser Ala Gln Asp Gly Arg Cys Pro Cys Gly Ala
65                  70                  75                  80

Arg Arg Pro Asp Ser Arg Leu Leu Gln Leu His Ile Thr Met Pro Phe
                85                  90                  95

Ser Ser Pro Met Glu Ala Glu Leu Val Arg Arg Ile Leu Ser Arg Asp
                100                 105                 110

Ala Ala Pro Leu Pro Arg Pro Gly Ala Val Leu Lys Asp Phe Thr Val
            115                 120                 125

Ser Gly Asn Leu Leu Phe Met Ser Val Arg Asp Gln Asp Arg Glu Gly
        130                 135                 140

Ala Gly Arg Met Arg Val Val Gly Trp Gly Leu Gly Ser Ala Ser Pro
145                 150                 155                 160

Glu Gly Gln Lys Ala Arg Asp Leu Arg Thr Pro Lys His Lys Val Ser
                165                 170                 175

Glu Gln Arg Pro Gly Thr Pro Gly Pro Pro Pro Glu Gly Ala Gln
            180                 185                 190

Gly Asp Gly Cys Arg Gly Val Ala Phe Asn Val Met Phe Ser Ala Pro
        195                 200                 205

His Ile
    210
```

<210> SEQ ID NO 353
<211> LENGTH: 314
<212> TYPE: PRT
<213> ORGANISM: Homo sapiens

<400> SEQUENCE: 353

```
Met Pro Leu Glu Gln Arg Ser Gln His Cys Lys Pro Glu Glu Gly Leu
1               5                   10                  15

Glu Ala Arg Gly Glu Ala Leu Gly Leu Val Gly Ala Gln Ala Pro Ala
                20                  25                  30

Thr Glu Glu Gln Glu Ala Ala Ser Ser Ser Thr Leu Val Glu Val
            35                  40                  45

Thr Leu Gly Glu Val Pro Ala Ala Glu Ser Pro Asp Pro Pro Gln Ser
        50                  55                  60

Pro Gln Gly Ala Ser Ser Leu Pro Thr Thr Met Asn Tyr Pro Leu Trp
65                  70                  75                  80

Ser Gln Ser Tyr Glu Asp Ser Ser Asn Gln Glu Glu Glu Gly Pro Ser
                85                  90                  95

Thr Phe Pro Asp Leu Glu Ser Glu Phe Gln Ala Ala Leu Ser Arg Lys
            100                 105                 110

Val Ala Glu Leu Val His Phe Leu Leu Leu Lys Tyr Arg Ala Arg Glu
        115                 120                 125

Pro Val Thr Lys Ala Glu Met Leu Gly Ser Val Val Gly Asn Trp Gln
130                 135                 140
```

Tyr Phe Phe Pro Val Ile Phe Ser Lys Ala Ser Ser Ser Leu Gln Leu
145                 150                 155                 160

Val Phe Gly Ile Glu Leu Met Glu Val Asp Pro Ile Gly His Leu Tyr
            165                 170                 175

Ile Phe Ala Thr Cys Leu Gly Leu Ser Tyr Asp Gly Leu Leu Gly Asp
            180                 185                 190

Asn Gln Ile Met Pro Lys Ala Gly Leu Leu Ile Ile Val Leu Ala Ile
            195                 200                 205

Ile Ala Arg Glu Gly Asp Cys Ala Pro Glu Glu Lys Ile Trp Glu Glu
210                 215                 220

Leu Ser Val Leu Glu Val Phe Glu Gly Arg Glu Asp Ser Ile Leu Gly
225                 230                 235                 240

Asp Pro Lys Lys Leu Leu Thr Gln His Phe Val Gln Glu Asn Tyr Leu
            245                 250                 255

Glu Tyr Arg Gln Val Pro Gly Ser Asp Pro Ala Cys Tyr Glu Phe Leu
            260                 265                 270

Trp Gly Pro Arg Ala Leu Val Glu Thr Ser Tyr Val Lys Val Leu His
            275                 280                 285

His Met Val Lys Ile Ser Gly Gly Pro His Ile Ser Tyr Pro Pro Leu
            290                 295                 300

His Glu Trp Val Leu Arg Glu Gly Glu Glu
305                 310

<210> SEQ ID NO 354
<211> LENGTH: 318
<212> TYPE: PRT
<213> ORGANISM: Homo sapiens

<400> SEQUENCE: 354

Met Leu Leu Gly Gln Lys Ser Gln Arg Tyr Lys Ala Glu Glu Gly Leu
1               5                   10                  15

Gln Ala Gln Gly Glu Ala Pro Gly Leu Met Asp Val Gln Ile Pro Thr
            20                  25                  30

Ala Glu Glu Gln Lys Ala Ala Ser Ser Ser Thr Leu Ile Met Gly
            35                  40                  45

Thr Leu Glu Glu Val Thr Asp Ser Gly Ser Pro Ser Pro Gln Ser
50                  55                  60

Pro Glu Gly Ala Ser Ser Leu Thr Val Thr Asp Ser Thr Leu Trp
65                  70                  75                  80

Ser Gln Ser Asp Glu Gly Ser Ser Asn Glu Glu Glu Gly Pro Ser
            85                  90                  95

Thr Ser Pro Asp Pro Ala His Leu Glu Ser Leu Phe Arg Glu Ala Leu
            100                 105                 110

Asp Glu Lys Val Ala Glu Leu Val Arg Phe Leu Leu Arg Lys Tyr Gln
            115                 120                 125

Ile Lys Glu Pro Val Thr Lys Ala Glu Met Leu Glu Ser Val Ile Lys
            130                 135                 140

Asn Tyr Lys Asn His Phe Pro Asp Ile Phe Ser Lys Ala Ser Glu Cys
145                 150                 155                 160

Met Gln Val Ile Phe Gly Ile Asp Val Lys Glu Val Asp Pro Ala Gly
            165                 170                 175

His Ser Tyr Ile Leu Val Thr Cys Leu Gly Leu Ser Tyr Asp Gly Leu
            180                 185                 190

Leu Gly Asp Asp Gln Ser Thr Pro Lys Thr Gly Leu Leu Ile Ile Val

```
                  195                 200                 205
Leu Gly Met Ile Leu Met Glu Gly Ser Arg Ala Pro Glu Glu Ala Ile
210                 215                 220

Trp Glu Ala Leu Ser Val Met Gly Leu Tyr Asp Gly Arg Glu His Ser
225                 230                 235                 240

Val Tyr Trp Lys Leu Arg Lys Leu Leu Thr Gln Glu Trp Val Gln Glu
                245                 250                 255

Asn Tyr Leu Glu Tyr Arg Gln Ala Pro Gly Ser Asp Pro Val Arg Tyr
                260                 265                 270

Glu Phe Leu Trp Gly Pro Arg Ala Leu Ala Glu Thr Ser Tyr Val Lys
                275                 280                 285

Val Leu Glu His Val Val Arg Val Asn Ala Arg Val Arg Ile Ser Tyr
                290                 295                 300

Pro Ser Leu His Glu Glu Ala Leu Gly Glu Glu Lys Gly Val
305                 310                 315

<210> SEQ ID NO 355
<211> LENGTH: 648
<212> TYPE: PRT
<213> ORGANISM: Homo sapiens

<400> SEQUENCE: 355

Met Ser His His Gly Gly Ala Pro Lys Ala Ser Thr Trp Val Val Ala
1               5                   10                  15

Ser Arg Arg Ser Ser Thr Val Ser Arg Ala Pro Glu Arg Arg Pro Ala
                20                  25                  30

Glu Glu Leu Asn Arg Thr Gly Pro Glu Gly Tyr Ser Val Gly Arg Gly
                35                  40                  45

Gly Arg Trp Arg Gly Thr Ser Arg Pro Pro Glu Ala Val Ala Ala Gly
50                  55                  60

His Glu Glu Leu Pro Leu Cys Phe Ala Leu Lys Ser His Phe Val Gly
65                  70                  75                  80

Ala Val Ile Gly Arg Gly Gly Ser Lys Ile Lys Asn Ile Gln Ser Thr
                85                  90                  95

Thr Asn Thr Thr Ile Gln Ile Ile Gln Glu Gln Pro Glu Ser Leu Val
                100                 105                 110

Lys Ile Phe Gly Ser Lys Ala Met Gln Thr Lys Ala Lys Ala Val Ile
                115                 120                 125

Asp Asn Phe Val Lys Lys Leu Glu Glu Asn Tyr Asn Ser Glu Cys Gly
                130                 135                 140

Ile Asp Thr Ala Phe Gln Pro Ser Val Gly Lys Asp Gly Ser Thr Asp
145                 150                 155                 160

Asn Asn Val Val Ala Gly Asp Arg Pro Leu Ile Asp Trp Asp Gln Ile
                165                 170                 175

Arg Glu Glu Gly Leu Lys Trp Gln Lys Thr Lys Trp Ala Asp Leu Pro
                180                 185                 190

Pro Ile Lys Lys Asn Phe Tyr Lys Glu Ser Thr Ala Thr Ser Ala Met
                195                 200                 205

Ser Lys Val Glu Ala Asp Ser Trp Arg Lys Glu Asn Phe Asn Ile Thr
                210                 215                 220

Trp Asp Asp Leu Lys Asp Gly Glu Lys Arg Pro Ile Pro Asn Pro Thr
225                 230                 235                 240

Cys Thr Phe Asp Asp Ala Phe Gln Cys Tyr Pro Glu Val Met Glu Asn
                245                 250                 255
```

```
Ile Lys Lys Ala Gly Phe Gln Lys Pro Thr Pro Ile Gln Ser Gln Ala
            260                 265                 270

Trp Pro Ile Val Leu Gln Gly Ile Asp Leu Ile Gly Val Ala Gln Thr
            275                 280                 285

Gly Thr Gly Lys Thr Leu Cys Tyr Leu Met Pro Gly Phe Ile His Leu
            290                 295                 300

Val Leu Gln Pro Ser Leu Lys Gly Gln Arg Asn Arg Pro Gly Met Leu
305                 310                 315                 320

Val Leu Thr Pro Thr Arg Glu Leu Ala Leu Gln Val Glu Gly Glu Cys
                325                 330                 335

Cys Lys Tyr Ser Tyr Lys Gly Leu Arg Ser Val Cys Val Tyr Gly Gly
                340                 345                 350

Gly Asn Arg Asp Glu Gln Ile Glu Glu Leu Lys Lys Gly Val Asp Ile
            355                 360                 365

Ile Ile Ala Thr Pro Gly Arg Leu Asn Asp Leu Gln Met Ser Asn Phe
            370                 375                 380

Val Asn Leu Lys Asn Ile Thr Tyr Leu Val Leu Asp Glu Ala Asp Lys
385                 390                 395                 400

Met Leu Asp Met Gly Phe Glu Pro Gln Ile Met Lys Ile Leu Leu Asp
                405                 410                 415

Val Arg Pro Asp Arg Gln Thr Val Met Thr Ser Ala Thr Trp Pro His
                420                 425                 430

Ser Val His Arg Leu Ala Gln Ser Tyr Leu Lys Glu Pro Met Ile Val
            435                 440                 445

Tyr Val Gly Thr Leu Asp Leu Val Ala Val Ser Val Lys Gln Asn
            450                 455                 460

Ile Ile Val Thr Thr Glu Glu Lys Trp Ser His Met Gln Thr Phe
465                 470                 475                 480

Leu Gln Ser Met Ser Ser Thr Asp Lys Val Ile Val Phe Val Ser Arg
                485                 490                 495

Lys Ala Val Ala Asp His Leu Ser Ser Asp Leu Ile Leu Gly Asn Ile
            500                 505                 510

Ser Val Glu Ser Leu His Gly Asp Arg Glu Gln Arg Asp Arg Glu Lys
            515                 520                 525

Ala Leu Glu Asn Phe Lys Thr Gly Lys Val Arg Ile Leu Ile Ala Thr
            530                 535                 540

Asp Leu Ala Ser Arg Gly Leu Asp Val His Asp Val Thr His Val Tyr
545                 550                 555                 560

Asn Phe Asp Phe Pro Arg Asn Ile Glu Glu Tyr Val His Arg Ile Gly
                565                 570                 575

Arg Thr Gly Arg Ala Gly Arg Thr Gly Val Ser Ile Thr Thr Leu Thr
            580                 585                 590

Arg Asn Asp Trp Arg Val Ala Ser Glu Leu Ile Asn Ile Leu Glu Arg
595                 600                 605

Ala Asn Gln Ser Ile Pro Glu Glu Leu Val Ser Met Ala Glu Arg Phe
            610                 615                 620

Lys Ala His Gln Gln Lys Arg Glu Met Glu Arg Lys Met Glu Arg Pro
625                 630                 635                 640

Gln Gly Arg Pro Lys Lys Phe His
                645

<210> SEQ ID NO 356
<211> LENGTH: 309
<212> TYPE: PRT
```

<213> ORGANISM: Homo sapiens

<400> SEQUENCE: 356

Met Ser Leu Glu Gln Arg Ser Leu His Cys Lys Pro Glu Glu Ala Leu
1               5                   10                  15

Glu Ala Gln Gln Glu Ala Leu Gly Leu Val Cys Val Gln Ala Ala Thr
            20                  25                  30

Ser Ser Ser Ser Pro Leu Val Leu Gly Thr Leu Glu Glu Val Pro Thr
        35                  40                  45

Ala Gly Ser Thr Asp Pro Pro Gln Ser Pro Gln Gly Ala Ser Ala Phe
    50                  55                  60

Pro Thr Thr Ile Asn Phe Thr Arg Gln Arg Gln Pro Ser Glu Gly Ser
65                  70                  75                  80

Ser Ser Arg Glu Glu Glu Gly Pro Ser Thr Ser Cys Ile Leu Glu Ser
                85                  90                  95

Leu Phe Arg Ala Val Ile Thr Lys Lys Val Ala Asp Leu Val Gly Phe
            100                 105                 110

Leu Leu Leu Lys Tyr Arg Ala Arg Glu Pro Val Thr Lys Ala Glu Met
        115                 120                 125

Leu Glu Ser Val Ile Lys Asn Tyr Lys His Cys Phe Pro Glu Ile Phe
    130                 135                 140

Gly Lys Ala Ser Glu Ser Leu Gln Leu Val Phe Gly Ile Asp Val Lys
145                 150                 155                 160

Glu Ala Asp Pro Thr Gly His Ser Tyr Val Leu Val Thr Cys Leu Gly
                165                 170                 175

Leu Ser Tyr Asp Gly Leu Leu Gly Asp Asn Gln Ile Met Pro Lys Thr
            180                 185                 190

Gly Phe Leu Ile Ile Val Leu Val Met Ile Ala Met Glu Gly Gly His
        195                 200                 205

Ala Pro Glu Glu Glu Ile Trp Glu Glu Leu Ser Val Met Glu Val Tyr
    210                 215                 220

Asp Gly Arg Glu His Ser Ala Tyr Gly Glu Pro Arg Lys Leu Leu Thr
225                 230                 235                 240

Gln Asp Leu Val Gln Glu Lys Tyr Leu Glu Tyr Arg Gln Val Pro Asp
                245                 250                 255

Ser Asp Pro Ala Arg Tyr Glu Phe Leu Trp Gly Pro Arg Ala Leu Ala
            260                 265                 270

Glu Thr Ser Tyr Val Lys Val Leu Glu Tyr Val Ile Lys Val Ser Ala
        275                 280                 285

Arg Val Arg Phe Phe Phe Pro Ser Leu Arg Glu Ala Ala Leu Arg Glu
    290                 295                 300

Glu Glu Glu Gly Val
305

<210> SEQ ID NO 357
<211> LENGTH: 373
<212> TYPE: PRT
<213> ORGANISM: Homo sapiens

<400> SEQUENCE: 357

Met Pro Pro Val Pro Gly Val Pro Phe Arg Asn Val Asp Asn Asp Ser
1               5                   10                  15

Pro Thr Ser Val Glu Leu Glu Asp Trp Val Asp Ala Gln His Pro Thr
            20                  25                  30

Asp Glu Glu Glu Glu Glu Ala Ser Ser Ala Ser Ser Thr Leu Tyr Leu

```
                35                  40                  45
Val Phe Ser Pro Ser Ser Phe Ser Thr Ser Ser Leu Ile Leu Gly
 50                  55                  60

Gly Pro Glu Glu Glu Val Pro Ser Gly Val Ile Pro Asn Leu Thr
 65                  70                  75                  80

Glu Ser Ile Pro Ser Pro Pro Gln Gly Pro Gln Gly Pro Ser
                 85                  90                  95

Gln Ser Pro Leu Ser Ser Cys Cys Ser Ser Phe Ser Trp Ser Ser Phe
                100                 105                 110

Ser Glu Glu Ser Ser Ser Gln Lys Gly Glu Asp Thr Gly Thr Cys Gln
                115                 120                 125

Gly Leu Pro Asp Ser Glu Ser Ser Phe Thr Tyr Thr Leu Asp Glu Lys
                130                 135                 140

Val Ala Glu Leu Val Glu Phe Leu Leu Leu Lys Tyr Glu Ala Glu Glu
145                 150                 155                 160

Pro Val Thr Glu Ala Glu Met Leu Met Ile Val Ile Lys Tyr Lys Asp
                165                 170                 175

Tyr Phe Pro Val Ile Leu Lys Arg Ala Arg Glu Phe Met Glu Leu Leu
                180                 185                 190

Phe Gly Leu Ala Leu Ile Glu Val Gly Pro Asp His Phe Cys Val Phe
                195                 200                 205

Ala Asn Thr Val Gly Leu Thr Asp Glu Gly Ser Asp Asp Glu Gly Met
210                 215                 220

Pro Glu Asn Ser Leu Leu Ile Ile Leu Ser Val Ile Phe Ile Lys
225                 230                 235                 240

Gly Asn Cys Ala Ser Glu Val Ile Trp Glu Val Leu Asn Ala Val
                245                 250                 255

Gly Val Tyr Ala Gly Arg Glu His Phe Val Tyr Gly Glu Pro Arg Glu
                260                 265                 270

Leu Leu Thr Lys Val Trp Val Gln Gly His Tyr Leu Gly Tyr Arg Glu
                275                 280                 285

Val Pro His Ser Ser Pro Pro Tyr Tyr Glu Phe Leu Trp Gly Pro Arg
290                 295                 300

Ala His Ser Glu Ser Ile Lys Lys Lys Val Leu Glu Phe Leu Ala Lys
305                 310                 315                 320

Leu Asn Asn Thr Val Pro Ser Ser Phe Pro Ser Trp Tyr Lys Asp Ala
                325                 330                 335

Leu Lys Asp Val Glu Glu Arg Val Gln Ala Thr Ile Asp Thr Ala Asp
                340                 345                 350

Asp Ala Thr Val Met Ala Ser Glu Ser Leu Ser Val Met Ser Ser Asn
                355                 360                 365

Val Ser Phe Ser Glu
    370

<210> SEQ ID NO 358
<211> LENGTH: 369
<212> TYPE: PRT
<213> ORGANISM: Homo sapiens

<400> SEQUENCE: 358

Met Pro Arg Ala Pro Lys Arg Gln Arg Cys Met Pro Glu Glu Asp Leu
1               5                   10                  15

Gln Ser Gln Ser Glu Thr Gln Gly Leu Glu Gly Ala Gln Ala Pro Leu
                20                  25                  30
```

```
Ala Val Glu Glu Asp Ala Ser Ser Thr Ser Thr Ser Ser Phe
            35                  40                  45

Pro Ser Ser Phe Pro Ser Ser Ser Ser Ser Ser Ser Cys Tyr
    50                  55                  60

Pro Leu Ile Pro Ser Thr Pro Glu Glu Val Ser Ala Asp Asp Glu Thr
65                  70                  75                  80

Pro Asn Pro Pro Gln Ser Ala Gln Ile Ala Cys Ser Ser Pro Ser Val
                85                  90                  95

Val Ala Ser Leu Pro Leu Asp Gln Ser Asp Glu Gly Ser Ser Ser Gln
            100                 105                 110

Lys Glu Glu Ser Pro Ser Thr Leu Gln Val Leu Pro Asp Ser Glu Ser
            115                 120                 125

Leu Pro Arg Ser Glu Ile Asp Glu Lys Val Thr Asp Leu Val Gln Phe
    130                 135                 140

Leu Leu Phe Lys Tyr Gln Met Lys Glu Pro Ile Thr Lys Ala Glu Ile
145                 150                 155                 160

Leu Glu Ser Val Ile Arg Asn Tyr Glu Asp His Phe Pro Leu Leu Phe
                165                 170                 175

Ser Glu Ala Ser Glu Cys Met Leu Leu Val Phe Gly Ile Asp Val Lys
            180                 185                 190

Glu Val Asp Pro Thr Gly His Ser Phe Val Leu Val Thr Ser Leu Gly
            195                 200                 205

Leu Thr Tyr Asp Gly Met Leu Ser Asp Val Gln Ser Met Pro Lys Thr
    210                 215                 220

Gly Ile Leu Ile Leu Ile Leu Ser Ile Ile Phe Ile Glu Gly Tyr Cys
225                 230                 235                 240

Thr Pro Glu Glu Val Ile Trp Glu Ala Leu Asn Met Met Gly Leu Tyr
                245                 250                 255

Asp Gly Met Glu His Leu Ile Tyr Gly Glu Pro Arg Lys Leu Leu Thr
            260                 265                 270

Gln Asp Trp Val Gln Glu Asn Tyr Leu Glu Tyr Arg Gln Val Pro Gly
            275                 280                 285

Ser Asp Pro Ala Arg Tyr Glu Phe Leu Trp Gly Pro Arg Ala His Ala
    290                 295                 300

Glu Ile Arg Lys Met Ser Leu Leu Lys Phe Leu Ala Lys Val Asn Gly
305                 310                 315                 320

Ser Asp Pro Arg Ser Phe Pro Leu Trp Tyr Glu Ala Leu Lys Asp
                325                 330                 335

Glu Glu Arg Ala Gln Asp Arg Ile Ala Thr Thr Asp Asp Thr Thr
            340                 345                 350

Ala Met Ala Ser Ala Ser Ser Ala Thr Gly Ser Phe Ser Tyr Pro
            355                 360                 365

Glu

<210> SEQ ID NO 359
<211> LENGTH: 314
<212> TYPE: PRT
<213> ORGANISM: Homo sapiens

<400> SEQUENCE: 359

Met Pro Leu Glu Gln Arg Ser Gln His Cys Lys Pro Glu Glu Gly Leu
1               5                   10                  15

Glu Ala Gln Gly Glu Ala Leu Gly Leu Val Gly Ala Gln Ala Pro Ala
            20                  25                  30
```

```
Thr Glu Glu Gln Glu Thr Ala Ser Ser Ser Thr Leu Val Glu Val
         35                  40                  45

Thr Leu Arg Glu Val Pro Ala Ala Glu Ser Pro Ser Pro Pro His Ser
 50                  55                  60

Pro Gln Gly Ala Ser Thr Leu Pro Thr Thr Ile Asn Tyr Thr Leu Trp
 65                  70                  75                  80

Ser Gln Ser Asp Glu Gly Ser Ser Asn Glu Gln Glu Gly Pro Ser
             85                  90                  95

Thr Phe Pro Asp Leu Glu Thr Ser Phe Gln Val Ala Leu Ser Arg Lys
             100                 105                 110

Met Ala Glu Leu Val His Phe Leu Leu Lys Tyr Arg Ala Arg Glu
         115                 120                 125

Pro Phe Thr Lys Ala Glu Met Leu Gly Ser Val Ile Arg Asn Phe Gln
         130                 135                 140

Asp Phe Phe Pro Val Ile Phe Ser Lys Ala Ser Glu Tyr Leu Gln Leu
145                 150                 155                 160

Val Phe Gly Ile Glu Val Val Glu Val Val Arg Ile Gly His Leu Tyr
                 165                 170                 175

Ile Leu Val Thr Cys Leu Gly Leu Ser Tyr Asp Gly Leu Leu Gly Asp
             180                 185                 190

Asn Gln Ile Val Pro Lys Thr Gly Leu Leu Ile Ile Val Leu Ala Ile
         195                 200                 205

Ile Ala Lys Glu Gly Asp Cys Ala Pro Glu Glu Lys Ile Trp Glu Glu
 210                 215                 220

Leu Ser Val Leu Glu Ala Ser Asp Gly Arg Glu Asp Ser Val Phe Ala
225                 230                 235                 240

His Pro Arg Lys Leu Leu Thr Gln Asp Leu Val Gln Glu Asn Tyr Leu
                 245                 250                 255

Glu Tyr Arg Gln Val Pro Gly Ser Asp Pro Ala Cys Tyr Glu Phe Leu
             260                 265                 270

Trp Gly Pro Arg Ala Leu Val Glu Thr Ser Tyr Val Lys Val Leu His
         275                 280                 285

His Leu Leu Lys Ile Ser Gly Gly Pro His Ile Ser Tyr Pro Pro Leu
 290                 295                 300

His Glu Trp Ala Phe Arg Glu Gly Glu Glu
305                 310

<210> SEQ ID NO 360
<211> LENGTH: 20
<212> TYPE: PRT
<213> ORGANISM: artificial sequence
<220> FEATURE:
<223> OTHER INFORMATION: POC01_P1 AKAP4

<400> SEQUENCE: 360

Asn Ser Leu Gln Lys Gln Leu Gln Ala Val Leu Gln Trp Ile Ala Ala
1               5                   10                  15

Ser Gln Phe Asn
            20

<210> SEQ ID NO 361
<211> LENGTH: 20
<212> TYPE: PRT
<213> ORGANISM: artificial sequence
<220> FEATURE:
<223> OTHER INFORMATION: POC01_P2 BORIS

<400> SEQUENCE: 361
```

-continued

Ser Gly Asp Glu Arg Ser Asp Glu Ile Val Leu Thr Val Ser Asn Ser
1               5                   10                  15

Asn Val Glu Glu
            20

<210> SEQ ID NO 362
<211> LENGTH: 20
<212> TYPE: PRT
<213> ORGANISM: artificial sequence
<220> FEATURE:
<223> OTHER INFORMATION: POC01_P3 SPAG9

<400> SEQUENCE: 362

Val Gln Lys Glu Asp Gly Arg Val Gln Ala Phe Gly Trp Ser Leu Pro
1               5                   10                  15

Gln Lys Tyr Lys
            20

<210> SEQ ID NO 363
<211> LENGTH: 20
<212> TYPE: PRT
<213> ORGANISM: artificial sequence
<220> FEATURE:
<223> OTHER INFORMATION: POC01_P4 OY-TES-1

<400> SEQUENCE: 363

Glu Val Glu Ser Thr Pro Met Ile Met Glu Asn Ile Gln Glu Leu Ile
1               5                   10                  15

Arg Ser Ala Gln
            20

<210> SEQ ID NO 364
<211> LENGTH: 20
<212> TYPE: PRT
<213> ORGANISM: artificial sequence
<220> FEATURE:
<223> OTHER INFORMATION: POC01_P5 SP17

<400> SEQUENCE: 364

Ala Tyr Phe Glu Ser Leu Leu Glu Lys Arg Glu Lys Thr Asn Phe Asp
1               5                   10                  15

Pro Ala Glu Trp
            20

<210> SEQ ID NO 365
<211> LENGTH: 20
<212> TYPE: PRT
<213> ORGANISM: artificial sequence
<220> FEATURE:
<223> OTHER INFORMATION: POC01_P6 WT1

<400> SEQUENCE: 365

Pro Ser Gln Ala Ser Ser Gly Gln Ala Arg Met Phe Pro Asn Ala Pro
1               5                   10                  15

Tyr Leu Pro Ser
            20

<210> SEQ ID NO 366
<211> LENGTH: 20
<212> TYPE: PRT
<213> ORGANISM: artificial sequence
<220> FEATURE:
<223> OTHER INFORMATION: POC01_P7 HIWI

```
<400> SEQUENCE: 366

Arg Arg Ser Ile Ala Gly Phe Val Ala Ser Ile Asn Glu Gly Met Thr
1               5                   10                  15

Arg Trp Phe Ser
            20

<210> SEQ ID NO 367
<211> LENGTH: 20
<212> TYPE: PRT
<213> ORGANISM: artificial sequence
<220> FEATURE:
<223> OTHER INFORMATION: POC01_P8 PRAME

<400> SEQUENCE: 367

Met Gln Asp Ile Lys Met Ile Leu Lys Met Val Gln Leu Asp Ser Ile
1               5                   10                  15

Glu Asp Leu Glu
            20

<210> SEQ ID NO 368
<211> LENGTH: 20
<212> TYPE: PRT
<213> ORGANISM: artificial sequence
<220> FEATURE:
<223> OTHER INFORMATION: POC01_P9 AKAP-3

<400> SEQUENCE: 368

Ala Asn Ser Val Val Ser Asp Met Met Val Ser Ile Met Lys Thr Leu
1               5                   10                  15

Lys Ile Gln Val
            20

<210> SEQ ID NO 369
<211> LENGTH: 20
<212> TYPE: PRT
<213> ORGANISM: artificial sequence
<220> FEATURE:
<223> OTHER INFORMATION: POC01_P10 MAGE-A4

<400> SEQUENCE: 369

Arg Glu Ala Leu Ser Asn Lys Val Asp Glu Leu Ala His Phe Leu Leu
1               5                   10                  15

Arg Lys Tyr Arg
            20

<210> SEQ ID NO 370
<211> LENGTH: 20
<212> TYPE: PRT
<213> ORGANISM: artificial sequence
<220> FEATURE:
<223> OTHER INFORMATION: POC01_P11 MAGE-A9

<400> SEQUENCE: 370

Glu Thr Ser Tyr Glu Lys Val Ile Asn Tyr Leu Val Met Leu Asn Ala
1               5                   10                  15

Arg Glu Pro Ile
            20

<210> SEQ ID NO 371
<211> LENGTH: 20
<212> TYPE: PRT
<213> ORGANISM: artificial sequence
<220> FEATURE:
<223> OTHER INFORMATION: POC01_P12a MAGE-A10
```

-continued

<400> SEQUENCE: 371

Asp Val Lys Glu Val Asp Pro Thr Gly His Ser Phe Val Leu Val Thr
1               5                   10                  15

Ser Leu Gly Leu
            20

<210> SEQ ID NO 372
<211> LENGTH: 20
<212> TYPE: PRT
<213> ORGANISM: artificial sequence
<220> FEATURE:
<223> OTHER INFORMATION: POC01_P12b BAGE

<400> SEQUENCE: 372

Ser Ala Gln Leu Leu Gln Ala Arg Leu Met Lys Glu Glu Ser Pro Val
1               5                   10                  15

Val Ser Trp Arg
            20

<210> SEQ ID NO 373
<211> LENGTH: 20
<212> TYPE: PRT
<213> ORGANISM: artificial sequence
<220> FEATURE:
<223> OTHER INFORMATION: PBRC01_cP1 FSIP1

<400> SEQUENCE: 373

Ile Ser Asp Thr Lys Asp Tyr Phe Met Ser Lys Thr Leu Gly Ile Gly
1               5                   10                  15

Arg Leu Lys Arg
            20

<210> SEQ ID NO 374
<211> LENGTH: 20
<212> TYPE: PRT
<213> ORGANISM: artificial sequence
<220> FEATURE:
<223> OTHER INFORMATION: PBRC01_cP2 SPAG9

<400> SEQUENCE: 374

Phe Asp Arg Asn Thr Glu Ser Leu Phe Glu Glu Leu Ser Ser Ala Gly
1               5                   10                  15

Ser Gly Leu Ile
            20

<210> SEQ ID NO 375
<211> LENGTH: 20
<212> TYPE: PRT
<213> ORGANISM: artificial sequence
<220> FEATURE:
<223> OTHER INFORMATION: PBRC01_cP3 AKAP4

<400> SEQUENCE: 375

Ser Gln Lys Met Asp Met Ser Asn Ile Val Leu Met Leu Ile Gln Lys
1               5                   10                  15

Leu Leu Asn Glu
            20

<210> SEQ ID NO 376
<211> LENGTH: 20
<212> TYPE: PRT
<213> ORGANISM: artificial sequence
<220> FEATURE:

```
<223> OTHER INFORMATION: PBRC01_cP4 BORIS

<400> SEQUENCE: 376

Ser Ala Val Phe His Glu Arg Tyr Ala Leu Ile Gln His Gln Lys Thr
1               5                   10                  15

His Lys Asn Glu
            20

<210> SEQ ID NO 377
<211> LENGTH: 20
<212> TYPE: PRT
<213> ORGANISM: artificial sequence
<220> FEATURE:
<223> OTHER INFORMATION: PBRC01_cP5 MAGE-A11

<400> SEQUENCE: 377

Asp Val Lys Glu Val Asp Pro Thr Ser His Ser Tyr Val Leu Val Thr
1               5                   10                  15

Ser Leu Asn Leu
            20

<210> SEQ ID NO 378
<211> LENGTH: 20
<212> TYPE: PRT
<213> ORGANISM: artificial sequence
<220> FEATURE:
<223> OTHER INFORMATION: PBRC01_cP6 NY-SAR-35

<400> SEQUENCE: 378

Glu Asn Ala His Gly Gln Ser Leu Glu Glu Asp Ser Ala Leu Glu Ala
1               5                   10                  15

Leu Leu Asn Phe
            20

<210> SEQ ID NO 379
<211> LENGTH: 20
<212> TYPE: PRT
<213> ORGANISM: artificial sequence
<220> FEATURE:
<223> OTHER INFORMATION: PBRC01_cP7 HOM-TES-85

<400> SEQUENCE: 379

Met Ala Ser Phe Arg Lys Leu Thr Leu Ser Glu Lys Val Pro Pro Asn
1               5                   10                  15

His Pro Ser Arg
            20

<210> SEQ ID NO 380
<211> LENGTH: 20
<212> TYPE: PRT
<213> ORGANISM: artificial sequence
<220> FEATURE:
<223> OTHER INFORMATION: PBRC01_cP8 NY-BR-1

<400> SEQUENCE: 380

Lys Arg Ala Ser Gln Tyr Ser Gly Gln Leu Lys Val Leu Ile Ala Glu
1               5                   10                  15

Asn Thr Met Leu
            20

<210> SEQ ID NO 381
<211> LENGTH: 20
<212> TYPE: PRT
<213> ORGANISM: artificial sequence
```

```
<220> FEATURE:
<223> OTHER INFORMATION: PBRC01_cP9 MAGE-A9

<400> SEQUENCE: 381

Val Asp Pro Ala Gln Leu Glu Phe Met Phe Gln Glu Ala Leu Lys Leu
1               5                   10                  15

Lys Val Ala Glu
            20

<210> SEQ ID NO 382
<211> LENGTH: 20
<212> TYPE: PRT
<213> ORGANISM: artificial sequence
<220> FEATURE:
<223> OTHER INFORMATION: PBRC01_cP10 SCP-1

<400> SEQUENCE: 382

Glu Tyr Glu Arg Glu Glu Thr Arg Gln Val Tyr Met Asp Leu Asn Asn
1               5                   10                  15

Asn Ile Glu Lys
            20

<210> SEQ ID NO 383
<211> LENGTH: 20
<212> TYPE: PRT
<213> ORGANISM: artificial sequence
<220> FEATURE:
<223> OTHER INFORMATION: PBRC01_cP11 MAGE-A1

<400> SEQUENCE: 383

Pro Glu Ile Phe Gly Lys Ala Ser Glu Ser Leu Gln Leu Val Phe Gly
1               5                   10                  15

Ile Asp Val Lys
            20

<210> SEQ ID NO 384
<211> LENGTH: 20
<212> TYPE: PRT
<213> ORGANISM: artificial sequence
<220> FEATURE:
<223> OTHER INFORMATION: PBRC01_cP12 MAGE-C2

<400> SEQUENCE: 384

Asp Ser Glu Ser Ser Phe Thr Tyr Thr Leu Asp Glu Lys Val Ala Glu
1               5                   10                  15

Leu Val Glu Phe
            20

<210> SEQ ID NO 385
<211> LENGTH: 30
<212> TYPE: PRT
<213> ORGANISM: artificial sequence
<220> FEATURE:
<223> OTHER INFORMATION: crc_P3 peptide 30aa

<400> SEQUENCE: 385

Tyr Val Asp Glu Lys Ala Pro Glu Phe Ser Met Gln Gly Leu Lys Asp
1               5                   10                  15

Glu Lys Val Ala Glu Leu Val Arg Phe Leu Leu Arg Lys Tyr
            20                  25                  30

<210> SEQ ID NO 386
<211> LENGTH: 9
<212> TYPE: PRT
```

```
<213> ORGANISM: Homo sapiens

<400> SEQUENCE: 386

Ser Val Ala Ser Thr Ile Thr Gly Val
1               5

<210> SEQ ID NO 387
<211> LENGTH: 9
<212> TYPE: PRT
<213> ORGANISM: Homo sapiens

<400> SEQUENCE: 387

Val Met Ala Gly Asp Ile Tyr Ser Val
1               5

<210> SEQ ID NO 388
<211> LENGTH: 9
<212> TYPE: PRT
<213> ORGANISM: Homo sapiens

<400> SEQUENCE: 388

Ala Leu Ala Asp Gly Val Gln Lys Val
1               5

<210> SEQ ID NO 389
<211> LENGTH: 9
<212> TYPE: PRT
<213> ORGANISM: Homo sapiens

<400> SEQUENCE: 389

Leu Leu Gly Ala Thr Cys Met Phe Val
1               5

<210> SEQ ID NO 390
<211> LENGTH: 9
<212> TYPE: PRT
<213> ORGANISM: Homo sapiens

<400> SEQUENCE: 390

Ser Val Phe Ala Gly Val Val Gly Val
1               5

<210> SEQ ID NO 391
<211> LENGTH: 9
<212> TYPE: PRT
<213> ORGANISM: Homo sapiens

<400> SEQUENCE: 391

Ala Leu Phe Asp Gly Asp Pro His Leu
1               5

<210> SEQ ID NO 392
<211> LENGTH: 9
<212> TYPE: PRT
<213> ORGANISM: Homo sapiens

<400> SEQUENCE: 392

Tyr Val Asp Pro Val Ile Thr Ser Ile
1               5

<210> SEQ ID NO 393
<211> LENGTH: 9
<212> TYPE: PRT
<213> ORGANISM: Homo sapiens
```

```
<400> SEQUENCE: 393

Ser Thr Ala Pro Pro Val His Asn Val
1               5

<210> SEQ ID NO 394
<211> LENGTH: 9
<212> TYPE: PRT
<213> ORGANISM: Homo sapiens

<400> SEQUENCE: 394

Leu Ala Ala Leu Pro His Ser Cys Leu
1               5
```

PEPTIDE VACCINES

CROSS-REFERENCE

This application is the U.S. National Stage entry of International Application No. PCT/EP2019/073476, filed on Sep. 3, 2019, which claims the benefit of and priority to UK Application No. 1814367.7, filed on Sep. 4, 2018, UK Application No. 1814366.9, filed Sep. 4, 2018, UK Application No. 1814365.1, filed Sep. 4, 2018, UK Application No. 1814364.4, filed Sep. 4, 2018, each of which are incorporated herein by reference in their entireties.

SEQUENCE LISTING

The instant application contains a Sequence Listing which has been filed electronically in ASCII format and is hereby incorporated by reference in its entirety. Said ASCII copy, created Apr. 21, 2021, is named TBL_007_SL.txt and is 283,286 bytes in size.

FIELD

The disclosure relates to polypeptides and vaccines that find use in the prevention or treatment of cancer, in particular cancers that express certain antigens expressed in gastric cancers, lung cancers, melanomas and bladder cancers.

BACKGROUND

Cancer is killing millions of people worldwide, because existing drugs do not enable effective prevention or treatment. Current checkpoint inhibitor immunotherapies that re-activate existing immune responses can provide clinical benefit for a fraction of cancer patients. Current cancer vaccines that induce new immune responses are poorly immunogenic and fail to benefit most patients.

Recent analyses of 63,220 unique tumors revealed that cancer vaccines need to be generated specifically for each patient because extensive inter-individual tumor genomic heterogeneity (Hartmaier et al. *Genome Medicine* 2017 9:16). Using state of art technologies it is currently not feasible to scale HLA-specific cancer vaccines to large populations.

SUMMARY

In antigen presenting cells (APC) protein antigens, including tumour associated antigens (TAA), are processed into peptides. These peptides bind to HLA molecules and are presented on the cell surface as peptide-HLA complexes to T cells. Different individuals express different HLA molecules, and different HLA molecules present different peptides. The inventors have demonstrated that an epitope that binds to a single HLA class I allele expressed in a subject is essential, but not sufficient to induce tumor specific T cell responses. Instead tumour specific T cell responses are optimally activated when an epitope is recognised and presented by the HLA molecules encoded by at least three HLA class I genes of an individual (WO/2018/158456, WO/2018/158457, WO/2018/158455, EP 3370065 and EP 3369431). Based on this discovery the inventors have identified the T cell epitopes from certain gastric and/or lung and/or melanoma and/or bladder cancer associated-polypeptide antigens (tumor specific antigens (TSA) and/or cancer testis antigens (CTA)) that are capable of binding to at least three class I HLA in a high proportion of individuals. These T cell epitopes, or fragments of the antigens comprising the T cell epitopes, are useful for inducing specific immune responses against tumor cells expressing these antigens and for treating or preventing cancer.

In a first aspect the disclosure provides a polypeptide that comprises a fragment of up to 50 consecutive amino acids of
(a) a gastric cancer-associated antigen selected from DPPA2, CAGE-1, TSP50, HIWI, SURVIVIN, 5T4, PRAME, KK-LC-1, MAGE-A2, MAGE-A3, LAGE-1, MAGE-A10, MAGE-A1 and SSX1, wherein the fragment comprises an amino acid sequence selected from any one of SEQ ID NOs: 1 to 30;
(b) a lung cancer-associated antigen selected from BRDT, PRAME, NALP4, MAGE-A12, MAGE-A2, SURVIVIN, DPPA2, NY-SAR-35, LDHC, MAGE-C2, MAGE-A3, KK-LC-1 and MAGE-A1, wherein the fragment comprises an amino acid sequence selected from any one of SEQ ID NOs: 90 to 119;
(c) a melanoma-associated antigen selected from PRAME, MAGE-A2, MAGE-C1, SURVIVIN, MAGE-A12, Ny-ESO-1, MAGE-C2, MAGE-A6, BORIS, LAGE-1, MAGE-A11, SSX-1, MAGE-A3, MAGE-A10 and MAGE-A1, wherein the fragment comprises an amino acid sequence selected from any one of SEQ ID NOs: 178 to 207; and/or
(d) a bladder cancer-associated antigen selected from PIWIL2, CTAGE1, MAGE-A9, EpCAM, OY-TES-1, NY-ESO-1, SURVIVIN, MAGE-C1, MAGE-A2, LAGE-1, MAGE-A3, MAGE-A8, HAGE, MAGE-A1, MAGE-C2, MAGE-A10 and MAGE-A12, wherein the fragment comprises an amino acid sequence selected from any one of SEQ ID NOs: 268 to 297.

In some specific cases the disclosure provides a polypeptide that
(a) is a fragment of a gastric cancer-associated antigen selected from DPPA2, CAGE-1, TSP50, HIWI, SURVIVIN, 5T4, PRAME, KK-LC-1, MAGE-A2, MAGE-A3, LAGE-1, MAGE-A10, MAGE-A1 and SSX1, wherein the fragment comprises an amino acid sequence selected from any one of SEQ ID NOs: 1 to 30; or
(b) comprises or consists of two or more fragments of one or more gastric cancer associated antigens selected from DPPA2, CAGE-1, TSP50, HIWI, SURVIVIN, 5T4, PRAME, KK-LC-1, MAGE-A2, MAGE-A3, LAGE-1, MAGE-A10, MAGE-A1 and SSX1, wherein each fragment comprises a different amino acid sequence selected from any one of SEQ ID NOs: 1 to 30, optionally wherein the fragments overlap or are arranged end to end in the polypeptide; or
(c) is a fragment of a lung cancer-associated antigen selected from BRDT, PRAME, NALP4, MAGE-A12, MAGE-A2, SURVIVIN, DPPA2, NY-SAR-35, LDHC, MAGE-C2, MAGE-A3, KK-LC-1 and MAGE-A1, wherein the fragment comprises an amino acid sequence selected from any one of SEQ ID NOs: 90 to 119; or
(d) comprises or consists of two or more fragments of one or more lung cancer associated antigens selected from BRDT, PRAME, NALP4, MAGE-A12, MAGE-A2, SURVIVIN, DPPA2, NY-SAR-35, LDHC, MAGE-C2, MAGE-A3, KK-LC-1 and MAGE-A1, wherein each fragment comprises a different amino acid sequence selected from any one of SEQ ID NOs: 90 to 119, optionally wherein the fragments overlap or are arranged end to end in the polypeptide; or (e) is a fragment of a melanoma-associated antigen selected from PRAME, MAGE-A2, MAGE-C1, SURVIVIN, MAGE-A12, Ny-ESO-1, MAGE-C2, MAGE-A6, BORIS, LAGE-1, MAGE-A11, SSX-1, MAGE-A3, MAGE-A10 and MAGE-A1, wherein the fragment comprises an amino acid sequence selected from any one of SEQ ID NOs: 178 to 207; or (f) comprises or consists of two or more fragments of one or more melanoma associated antigens selected from PRAME, MAGE-A2, MAGE-C1, SURVIVIN, MAGE-A12, Ny-ESO-1, MAGE-C2, MAGE-A6, BORIS, LAGE-1, MAGE-A11, SSX-1, MAGE-A3, MAGE-A10 and MAGE-A1, wherein each fragment comprises a different amino acid sequence selected from any one of SEQ ID NOs: 178 to 207, optionally wherein the fragments overlap or are arranged end to end in the polypeptide; or (g) is a fragment of a bladder cancer-associated antigen selected from PIWIL2, CTAGE1, MAGE-A9, EpCAM, OY-TES-1, NY-ESO-1, SURVIVIN, MAGE-C1, MAGE-A2, LAGE-1, MAGE-A3, MAGE-A8, HAGE, MAGE-A1, MAGE-C2, MAGE-A10 and MAGE-A12, wherein the fragment comprises an amino acid sequence selected from any one of SEQ ID NOs: 268 to 297; or (h) comprises or consists of two or more fragments of one or more bladder cancer associated antigens selected from PIWIL2, CTAGE1, MAGE-A9, EpCAM, OY-TES-1, NY-ESO-1, SURVIVIN, MAGE-C1, MAGE-A2, LAGE-1, MAGE-A3, MAGE-A8, HAGE, MAGE-A1, MAGE-C2, MAGE-A10 and MAGE-A12, wherein each fragment comprises a different amino acid sequence selected from any one of SEQ ID NOs: 268 to 297, optionally wherein the fragments overlap or are arranged end to end in the polypeptide.

In some specific cases the polypeptide comprises or consists of fragments of at least two different cancer-associated antigens, wherein the cancer-associated antigens are selected from (a) DPPA2, CAGE-1, TSP50, HIWI, SURVIVIN, 5T4, PRAME, KK-LC-1, MAGE-A2, MAGE-A3, LAGE-1, MAGE-A10, MAGE-A1 and SSX1 and wherein each fragment comprises a different amino acid sequence selected from SEQ ID NOs: 1 to 30; and/or (b) BRDT, PRAME, NALP4, MAGE-A12, MAGE-A2, SURVIVIN, DPPA2, NY-SAR-35, LDHC, MAGE-C2, MAGE-A3, KK-LC-1 and MAGE-A1; and wherein each fragment comprises a different amino acid sequence selected from SEQ ID NOs: 90 to 119; and/or (c) PRAME, MAGE-A2, MAGE-C1, SURVIVIN, MAGE-A12, Ny-ESO-1, MAGE-C2, MAGE-A6, BORIS, LAGE-1, MAGE-A11, SSX-1, MAGE-A3, MAGE-A10 and MAGE-A1; and wherein each fragment comprises a different amino acid sequence selected from SEQ ID NOs: 178 to 207 and/or (d) PIWIL2, CTAGE1, MAGE-A9, EpCAM, OY-TES-1, NY-ESO-1, SURVIVIN, MAGE-C1, MAGE-A2, LAGE-1, MAGE-A3, MAGE-A8, HAGE, MAGE-A1, MAGE-C2, MAGE-A10 and MAGE-A12; and wherein each fragment comprises a different amino acid sequence selected from SEQ ID NOs: 268 to 297.

In some cases the polypeptide comprises or consists of one or more amino acid sequences selected from SEQ ID NOs: 31 to 60, 90 to 119, 178 to 207 and/or 268 to 297.

In some cases the polypeptide comprises or consists of one or more amino acid sequences selected from SEQ ID NOs: 61 to 75, 120 to 149, 208 to 237, and/or 298 to 327.

In a further aspect the disclosure provides a panel of two or more polypeptides as described above, wherein each peptide comprises or consists of a different amino acid sequence selected from SEQ ID NOs: 1 to 30; and/or SEQ ID NOs: 31 to 60; and/or SEQ ID NOs: 61 to 75; or selected from SEQ ID NOs: 90 to 119; and/or SEQ ID NOs: 120 to 149; and/or SEQ ID NOs: 150 to 164; or selected from SEQ ID NOs: 178 to 207; and/or SEQ ID NOs: 208 to 237; and/or SEQ ID NOs: 238 to 252; or selected from SEQ ID NOs: 268 to 297; and/or SEQ ID NOs: 298 to 327; and/or SEQ ID NOs: 328 to 342.

In a further aspect the disclosure provides a pharmaceutical composition or kit having one or more polypeptides or panels of peptides as described above as active ingredients, or having a polypeptide comprising at least two amino acid sequences selected from SEQ ID NOs: 1 to 30; SEQ ID NOs: 31 to 60; and/or SEQ ID NOs: 61-75; and/or SEQ ID NOs: 90 to 119; SEQ ID NOs: 120 to 149; and/or SEQ ID NOs: 150 to 164; and/or SEQ ID NOs: 178 to 207; and/or SEQ ID NOs: 208 to 237; and/or SEQ ID NOs: 238 to 252; and/or SEQ ID NOs: 268 to 297; and/or SEQ ID NOs: 298 to 327; and/or SEQ ID NOs: 328 to 342 as an active ingredient.

In a further aspect the disclosure provides a method of inducing immune responses, (e.g. vaccination, providing immunotherapy or inducing a CD8+ T cell response in a subject), the method comprising administering to the subject a pharmaceutical composition, kit or the panel of polypeptides as described above. The method may be a method of treating cancer, such as gastric cancer, lung cancer, melanoma and bladder cancer.

In further aspects, the disclosure provides the pharmaceutical composition, kit or panel of polypeptides described above for use in a method of inducing immune responses or for use in a method of treating cancer, optionally gastric cancer, lung cancer, melanoma and bladder cancer; and use of a peptide or a panel of peptides as described above in the manufacture of a medicament for inducing immune responses or for treating cancer, optionally gastric cancer, lung cancer, melanoma and bladder cancer.

In a further aspect the disclosure provides a method of identifying a human subject who will likely have a CD8+ T cell response to administration of a pharmaceutical composition as described above, the method comprising (i) determining that the active ingredient polypeptide(s) of the pharmaceutical composition comprise a sequence that is a T cell epitope capable of binding to at least three HLA class I of the subject; and (ii) identifying the subject as likely to have a CD8+ T cell response to administration of the pharmaceutical composition.

In a further aspect the disclosure provides a method of identifying a subject who will likely have a clinical response to a method of treatment as described above, the method comprising (i) determining that the active ingredient polypeptide(s) comprise two or more different amino acid sequences each of which is a. a T cell epitope capable of binding to at least three HLA class I of the subject; and b. a fragment of a cancer-associated antigen expressed by cancer cells of the subject; and (ii) identifying the subject as likely to have a clinical response to the method of treatment.

In a further aspect the disclosure provides a method of determining the likelihood that a specific human subject will have a clinical response to a method of treatment described above, wherein one or more of the following factors corresponds to a higher likelihood of a clinical response:
  (a) presence in the active ingredient polypeptide(s) of a higher number of amino acid sequences and/or different amino acid sequences that are each a T cell epitope capable of binding to at least three HLA class I of the subject;
  (b) a higher number of target polypeptide antigens, comprising at least one amino acid sequence that is both
     A. comprised in an active ingredient polypeptide; and
     B. a T cell epitope capable of binding to at least three HLA class I of the subject; optionally wherein the target polypeptide antigens are expressed in the subject, further optionally wherein the target polypeptides antigens are in one or more samples obtained from the subject;
  (c) a higher probability that the subject expresses target polypeptide antigens, optionally a threshold number of the target polypeptide antigens and/or optionally target polypeptide antigens that have been determined to comprise at least one amino acid sequence that is both
     A. comprised in in an active ingredient polypeptide; and
     B. a T cell epitope capable of binding to at least three HLA class I of the subject; and/or
  (d) a higher number of target polypeptide antigens that the subject is predicted to express, optionally a higher number of target polypeptide antigens that the subject expresses with a threshold probability, and/or optionally the target polypeptide antigens that have been determined to comprise at least one amino acid sequence that is both
     A. comprised in in an active ingredient polypeptide; and
     B. a T cell epitope capable of binding to at least three HLA class I of the subject.

In some cases the cancer-associated antigens may be a gastric cancer antigen selected from DPPA2, CAGE-1, TSP50, HIWI, SURVIVIN, 5T4, PRAME, KK-LC-1, MAGE-A2, MAGE-A3, LAGE-1, MAGE-A10, MAGE-A1, SSX1, a lung cancer antigen selected from BRDT, PRAME, NALP4, MAGE-A12, MAGE-A2, SURVIVIN, DPPA2NY-SAR-35, LDHC, MAGE-C2, MAGE-A3, KK-LC-1, MAGE-A1, a melanoma antigen selected from PRAME, MAGE-A2, MAGE-C1, SURVIVIN, MAGE-A12, Ny-ESO-1, MAGE-C2, MAGE-A6, BORIS, LAGE-1, MAGE-A11, SSX-1, MAGE-A3, MAGE-A10, MAGE-A1, and/or a bladder cancer antigen selected from PIWIL2, CTAGE1, MAGE-A9, EpCAM, OY-TES-1, NY-ESO-1, SURVIVIN, MAGE-C1, MAGE-A2, LAGE-1, MAGE-A3, MAGE-A8 and HAGE, MAGE-A1, MAGE-C2, MAGE-A10 and MAGE A12. In some cases the methods above comprise the step of determining that one or more cancer-associated antigens is expressed by cancer cells of the subject. The cancer-associated antigen(s) may be present in one or more samples obtained from the subject.

In some cases administration of the pharmaceutical composition or the active ingredient polypeptides of the kit may then be selected as a method of treatment for the subject. The subject may further be treated by administration of the pharmaceutical composition or the active ingredient polypeptides.

In a further aspect the disclosure provides a method of treatment as described above, wherein the subject has been identified as likely to have a clinical response or as having above a threshold minimum likelihood of having a clinical response to the treatment by the method described above.

In a further aspect the disclosure provides a method of identifying a human subject who will likely not have a clinical response to a method of treatment as described above, the method comprising
  (i) determining that the active ingredient polypeptide(s) of the pharmaceutical composition do not comprise two or more different amino acid sequences each of which is a T cell epitope capable of binding to at least three HLA class I of the subject; and
  (ii) identifying the subject as likely not to have a clinical response to the method of treatment.

The methods described above may comprise the step of determining the HLA class I and/or class II genotype of the subject.

The present disclosure includes methods of treating a human subject likely to respond to a polypeptide(s) or pharmaceutical composition comprising the polypeptide(s) of the current disclosure comprising: (a) determining that a polypeptide(s) or pharmaceutical composition comprising the polypeptide(s) comprises an amino acid sequence that is a T cell epitope capable of binding to at least three HLA class I molecules of the human subject; and (b) administering to the human subject the polypeptide or pharmaceutical composition. In certain embodiments, the method further comprises using population expression data for each antigen to determine the likelihood that the human subject will have a CD8+ T cell response that targets one or more polypeptide antigens that are expressed by cancer cells of the human subject, wherein the antigen: (a) is selected from gastric cancer antigens DPPA2, CAGE-1, TSP50, HIWI, SURVIVIN, 5T4, PRAME, KK-LC-1, MAGE-A2, MAGE-A3, LAGE-1, MAGE-A10, MAGE-A1 SSX1, and/or lung cancer antigens BRDT, PRAME, NALP4, MAGE-A12, MAGE-A2, SURVIVIN, DPPA2, NY-SAR-35, LDHC, MAGE-C2, MAGE-A3, KK-LC-1, MAGE-A1, and/or melanoma cancer antigens PRAME, MAGE-A2, MAGE-C1, SURVIVIN, MAGE-A12, Ny-ESO-1, MAGE-C2, MAGE-A6, BORIS, LAGE-1, MAGE-A11, SSX-1, MAGE-A3, MAGE-A10, MAGE-A1, and/or bladder cancer antigens PIWIL2, CTAGE1, MAGE-A9, EpCAM, OY-TES-1, NY-ESO-1, SURVIVIN, MAGE-C1, MAGE-A2, LAGE-1, MAGE-A3, MAGE-A8 and HAGE, MAGE-A1, MAGE-C2, MAGE-A10 and MAGE-A12; and (b) comprises an amino acid sequence that is a fragment of an active ingredient peptide of the pharmaceutical composition, and a T cell epitope capable of binding to at least three HLA class I molecules of the human subject.

The present disclosure includes methods of treating a human subject likely to respond to a polypeptide(s) or pharmaceutical composition comprising the polypeptide(s) of the current disclosure comprising: (a) determining that a polypeptide(s) or pharmaceutical composition comprising the polypeptide(s) comprise two or more different amino acid sequences each of which is a T cell epitope capable of binding to at least three HLA class I molecules of the human subject; and a fragment of a cancer-associated antigen expressed by cancer cells of the human subject, optionally wherein the cancer-associated antigen is present in a sample obtained from the human subject; and (b) administering to the human subject the polypeptide or pharmaceutical composition.

The present disclosure includes methods of treating a human subject likely to respond to a polypeptide(s) or pharmaceutical composition comprising the polypeptide(s)

of the current disclosure comprising determining any one of the following: (a) presence in a polypeptide(s) or pharmaceutical composition comprising the polypeptide(s) of a higher number of amino acid sequences and/or different amino acid sequences that are each a T cell epitope capable of binding to at least three HLA class I of the human subject; (b) a higher number of target polypeptide antigens in the human subject or a sample from the human subject, comprising at least one amino acid sequence that is both comprised in an active ingredient polypeptide, and a T cell epitope capable of binding to at least three HLA class I of the human subject; (c) a higher probability that the human subject expresses target polypeptide antigens, optionally a threshold number of the target polypeptide antigens and/or optionally target polypeptide antigens that have been determined to comprise at least one amino acid sequence that is both comprised in in an active ingredient polypeptide, and a T cell epitope capable of binding to at least three HLA class I of the human subject; and/or (d) a higher number of target polypeptide antigens that the human subject is predicted to express, optionally a higher number of target polypeptide antigens that the human subject expresses with a threshold probability, and/or optionally the target polypeptide antigens that have been determined to comprise at least one amino acid sequence that is both comprised in in an active ingredient polypeptide, and a T cell epitope capable of binding to at least three HLA class I of the human subject; and (e) administering to the human subject the polypeptide or pharmaceutical composition. In certain embodiments, the method further comprises identifying which polypeptide antigens targeted by the polypeptide(s) or pharmaceutical composition comprising the polypeptide(s) comprise an amino acid sequence that is both comprised in an active ingredient polypeptide, and a T cell epitope capable of binding to at least three HLA class I of the human subject using population expression data for each antigen identified to determine the probability that the human subject expresses one or more of the antigens identified that together comprise at least two different amino acid sequences; and administering to the human subject the polypeptide or pharmaceutical composition. In certain embodiments, the at least two different amino acid sequences are comprised in the amino acid sequence of two different polypeptide antigens targeted by the active ingredient polypeptide(s).

The disclosure will now be described in more detail, by way of example and not limitation, and by reference to the accompanying drawings. Many equivalent modifications and variations will be apparent, to those skilled in the art when given this disclosure. Accordingly, the exemplary embodiments of the disclosure set forth are considered to be illustrative and not limiting. Various changes to the described embodiments may be made without departing from the scope of the disclosure. All documents cited herein, whether supra or infra, are expressly incorporated by reference in their entirety.

The present disclosure includes the combination of the aspects and preferred features described except where such a combination is clearly impermissible or is stated to be expressly avoided. As used in this specification and the appended claims, the singular forms "a", "an", and "the" include plural referents unless the content clearly dictates otherwise. Thus, for example, reference to "a peptide" includes two or more such peptides.

Section headings are used herein for convenience only and are not to be construed as limiting in any way.

DESCRIPTION OF THE FIGURES

FIG. 3
Distribution of HLA class I PEPI3+ compared to CD8+ T cell responses measured by a state of art assay among peptide pools used in the CD8+ T cell response assays. A: HLA class I restricted PEPI3+s. The 90% Overall Percent of Agreement (OPA) among the T cell responses and PEPI3+ peptides demonstrate the utility of the invented peptides for prediction of vaccine induced T cell response set of individuals (p<0.001). B: Class I HLA restricted epitopes (PEPI1+). The OPA between predicted epitopes and CD8+ T cell responses was 25% (not statistically significant). True positive (TP), both peptide and T cell responses were detected (shaded); True negative (TN): neither peptides nor T cell responses were detected (shaded); False negative (FN), only T cell responses were detected; False positive (FP), only peptide were detected.

FIG. 4
Correlation between PEPI Test predicted CD4 peptides and T-cell reactivity measured with peptide pools in patients treated with SLP vaccine. A: ≥3 HLA class II allele-binding PEPIs; B: single HLA class II allele-binding epitopes. Gray: true positive (TP) and true negative (TN) responses; White: false negative (FN) and false positive (FP) responses. TP: both peptide and T cell responses were detected; TN: neither peptides nor T cell responses were detected; FN: only T cell responses were detected; FP: only peptides were detected.

Figure 1:
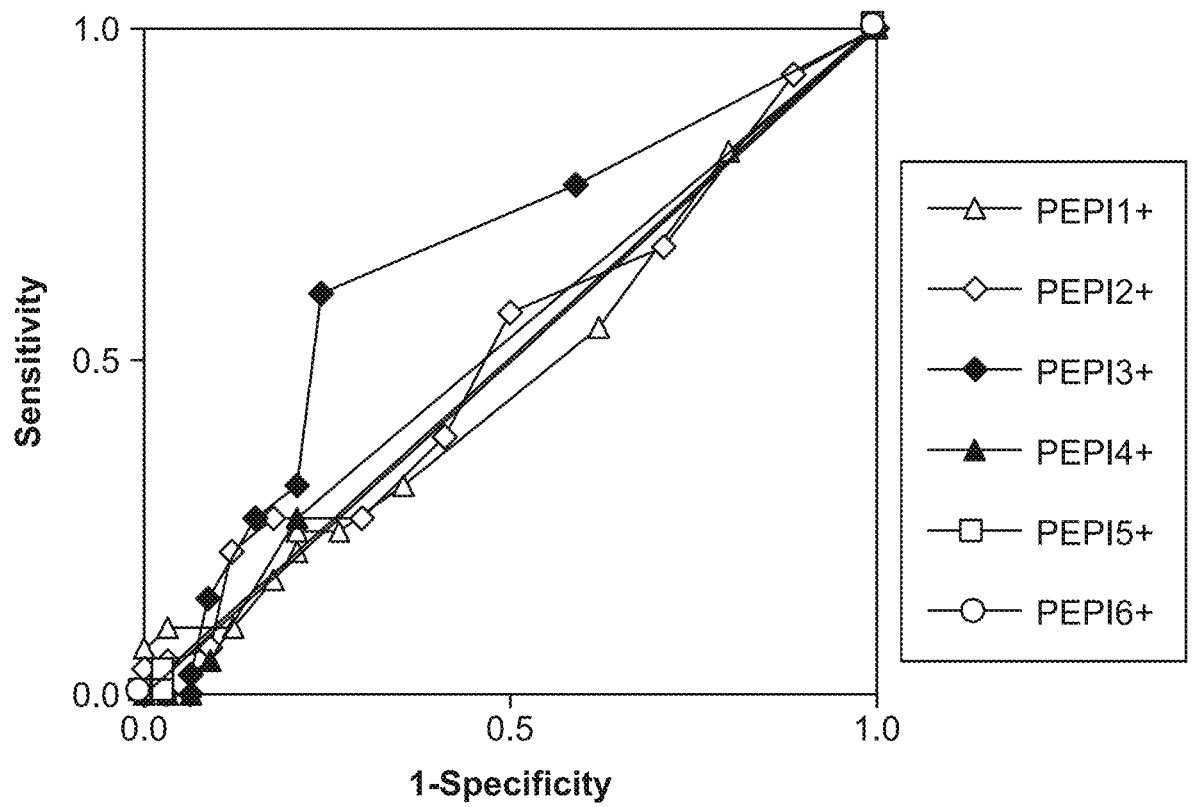
FIG. 1
ROC curve of HLA restricted PEPI biomarkers.

HLA Class I allele binding properties of TUMAPs of IMA901 peptide vaccine for 2,915 common alleles. (A) and for the Class I genotype (6 alleles) of 51 HLA-A*02+ RCC patients. Percentages at the bottom indicate the proportion of HLAs the TUMAPs can bind to. Lines in darker grey indicate binding HLA alleles. (B) Probability indicates the proportion of patients who can present the indicated number of TUMAPs with their three or more HLAs. AP indicates number of antigens which can generate at least one PEPI. In this case, since both the antigens and the predicted PEPIs are 9mers, AP=TUMAP=PEPI.

FIG. 9

Correlation between immune response measured for any TUMAP and immune response against expressed antigen on the tumor (AGP)

FIG. 10

Correlation study between immune response rates (IRR) and PEPI Score, between objective response rates (ORR) and MultiPEPI Scores and between objective response rates (ORR) and MultiAg PEPI Scores. A: Preliminary experiment to explore the relationship between PEPI Score and immune response rate of therapeutic vaccines ($r^2=0.7$, p=0.001) B: IRR—PEPI Score plot. ($r^2=0.47$, p=0.001). C: MultiPEPI Score and clinical response rate of therapeutic vaccines ($r^2=0.75$, p=0.001). D: ORRs plotted against the MultiPEPI Score ($r^2=0.12$, p=0.124). E: ORRs plotted against the MultiAg PEPI Score for vaccines with multiple antigens ($r^2=0.64$; p=0.009). F: ORRs plotted against the MultiPEPI Score for vaccines with multiple antigens ($r^2=0.87$; p=0.0002). G: ORRs plotted against the MultiPEPI Score in patients with target antigen positive disease ($r^2=0.56$ and p=0.005). Dark grey dashed lines indicate the 95% confidence interval; grey dashed line indicates the trendline.

FIG. 11

OBERTO trial design (NCT03391232)

FIG. 12

Antigen expression in CRC cohort of OBERTO trial (n=10). A: Expression frequencies of PolyPEPI1018 source antigens determined based on 2391 biopsies. B: PolyPEPI1018 vaccine design specified as 3 out of 7 TSAs are expressed in CRC tumors with above 95% probability. C: In average, 4 out of the 10 patients had pre-existing immune responses against each target antigens, referring to the real expression of the TSAs in the tumors of the patients. D: 7 out of the 10 patients had pre-existing immune responses against minimum of 1 TSA, in average against 3 different TSAs.

FIG. 13

Immunogenicity of PolyPEPI1018 in CRC patients confirms proper target antigen and target peptide selection. Upper part: target peptide selection and peptide design of PolyPEPI1018 vaccine composition. Two 15mers from CRC specific CTA (TSA) selected to contain 9mer PEPI3+ predominant in representative Model population. Table: PolyPEPI1018 vaccine has been retrospectively tested during a preclinical study in a CRC cohort and was proven to be immunogenic in all tested individuals for at least one antigen by generating PEPI3+s. Clinical immune responses were measured specific for at least one antigen in 90% of patients, and multi-antigen immune responses were also found in 90% of patients against at least 2, and in 80% of patients against at least 3 antigens as tested with IFNy fluorospot assay specifically measured for the vaccine-comprising peptides.

FIG. 14

Clinical response for PolyPEPI1018 treatment. A: Swimmer plot of clinical responses of OBERTO trial (NCT03391232). B: Association progression free survival (PFS) and AGP count. C: Association tumour volume and AGP count.

FIG. 15

Peptide hotspot analysis example: PRAME antigen hotspot on 433 patients of the Model Population. On the y axis are the 433 patients of the Model Population, on the x axis is the amino acid sequence of the PRAME antigen (CTA). Each data point represents a PEPI presented by ≥3 HLA class I of one patient starting at the specified amino acid position. The two most frequent PEPIs (called bestEPIs) of the PRAME antigen are highlighted in dark gray (peptide hotspots=PEPI Hotspots).

FIG. 16

CTA Expression Curve calculated by analyzing expression frequency data of tumor specific antigens (CTAs) in human gastric cancer tissues. (No cell line data were included.)

FIG. 17

Antigen expression distribution for gastric cancer based on the calculation of multi-antigen responses from expression frequencies of the selected 14 different CTAs. A: non-cumulative distribution to calculate the expected value for the number of expressed antigens (AG50). This value shows that probably 7.18 vaccine antigens will be expressed by gastric tumor cells. B: cumulative distribution curve of the minimum number of expressed antigens (CTA expression curve). This shows that minimum 5 vaccine antigens will be expressed with 95% probability in gastric cancer cell (AG95).

FIG. 18

PEPI representing antigens: gastric cancer vaccine-specific CTA antigens with ≥1 PEPI, called as "AP") distribution within the Model Population (n=433) for gastric cancer vaccine. A: non-cumulative distribution of AP where the average number of APs is: AP50=7.98, meaning that in average almost 8 CTAs will have PEPIs in the Model Population. B: cumulative distribution curve of the minimum number of APs in the Model Population (n=433). This shows that at least three vaccine antigen will have PEPIs in 95% of the Model Population (n=433) (AP95=3).

FIG. 19

PEPI represented expressed antigen (gastric cancer vaccine-specific CTA antigens expressed by the tumor, for which ≥1 PEPI is predicted, called as "AGP") distribution within the model population (n=433) calculated with CTA expression rates for gastric cancer. A: non-cumulative distribution of AGP where the expected value for number expressed CTAs represented by PEPI is AGP50=3.86. AGP50 is a measure of the effectiveness of the disclosed gastric cancer vaccine in attacking gastric tumor in an unselected patient population. AGP50=3.86 means that at least 3 CTAs from the vaccine will probably be expressed by the gastric tumor cells and present PEPIs in the Model Population. B: cumulative distribution curve of the minimum number of AGPs in the Model Population (n=433) shows that at least 1 of the vaccine CTAs will present PEPIs in 95% of the population and the remaining 5% of the population will likely have no AGP at all (AGP95=1).

FIG. 20

CTA Expression Curve calculated by analyzing expression frequency data of tumor specific antigens (CTAs) in human lung cancer tissues. (No cell line data were included.)

FIG. 21

Antigen expression distribution for lung cancer based on the calculation of multi-antigen responses from expression frequencies of the selected 13 different CTAs. A: non-cumulative distribution to calculate the expected value for the number of expressed antigens (AG50). This value shows that probably 4.76 vaccine antigens will be expressed by lung tumor cells. B: cumulative distribution curve of the minimum number of expressed antigens (CTA expression curve). This shows that minimum 2 vaccine antigens will be expressed with 95% probability in lung cancer cell (AG95).

FIG. 22

PEPI representing antigens: lung cancer vaccine-specific CTA antigens with ≥1 PEPI, called as "AP") distribution within the Model Population (n=433) for lung cancer vaccine. A: non-cumulative distribution of AP where the average number of APs is: AP50=7.6, meaning that in average almost 8 CTAs will have PEPIs in the Model Population. B: cumulative distribution curve of the minimum number of APs in the Model Population (n=433). This shows that at least two vaccine antigen will have PEPIs in 95% of the Model Population (n=433) (AP95=2).

FIG. 23

PEPI represented expressed antigen (lung cancer vaccine-specific CTA antigens expressed by the tumor, for which ≥1 PEPI is predicted, called as "AGP") distribution within the model population (n=433) calculated with CTA expression rates for lung cancer. A: non-cumulative distribution of AGP where the expected value for number expressed CTAs represented by PEPI is AGP50=2.77. AGP50 is a measure of the effectiveness of the disclosed lung cancer vaccine in attacking lung tumor in an unselected patient population. AGP50=2.77 means that at least 3 CTAs from the vaccine will probably be expressed by the lung tumor cells and present PEPIs in the Model Population. B: cumulative distribution curve of the minimum number of AGPs in the Model Population (n=433) shows that at least 1 of the vaccine CTAs will present PEPIs in 91% of the population and the remaining 9% of the population will likely have no AGP at all (AGP95=0).

FIG. 24

CTA Expression Curve calculated by analyzing expression frequency data of tumor specific antigens (CTAs) in human melanoma. (No cell line data were included.)

FIG. 25

Antigen expression distribution for melanoma based on the calculation of multi-antigen responses from expression frequencies of the selected 15 different CTAs. A: non-cumulative distribution to calculate the expected value for the number of expressed antigens (AG50). This value shows that probably 7.62 vaccine antigens will be expressed by gastric tumor cells. B: cumulative distribution curve of the minimum number of expressed antigens (CTA expression curve). This shows that minimum 5 vaccine antigens will be expressed with 95% probability in melanoma cell (AG95).

FIG. 26

PEPI representing antigens: melanoma vaccine-specific CTA antigens with ≥1 PEPI, called as "AP") distribution within the Model Population (n=433) for melanoma vaccine. A: non-cumulative distribution of AP where the average number of APs is: AP50=8.29, meaning that in average 8 CTAs will have PEPIs in the Model Population. B: cumulative distribution curve of the minimum number of APs in the Model Population (n=433). This shows that at least three vaccine antigen will have PEPIs in 95% of the Model Population (n=433) (AP95=2).

FIG. 27

PEPI represented expressed antigen (melanoma vaccine-specific CTA antigens expressed by the tumor, for which ≥1 PEPI is predicted, called as "AGP") distribution within the model population (n=433) calculated with CTA expression rates for melanoma. A: non-cumulative distribution of AGP where the expected value for number expressed CTAs represented by PEPI is AGP50=4.22. AGP50 is a measure of the effectiveness of the disclosed melanoma vaccine in attacking gastric tumor in an unselected patient population. AGP50=4.22 means that at least 3 CTAs from the vaccine will probably be expressed by the gastric tumor cells and present PEPIs in the Model Population. B: cumulative distribution curve of the minimum number of AGPs in the Model Population (n=433) shows that at least 1 of the vaccine CTAs will present PEPIs in 95% of the population and the remaining 5% of the population will likely have no AGP at all (AGP95=1).

FIG. 28

CTA Expression Curve calculated by analyzing expression frequency data of tumor specific antigens (CTAs) in human bladder cancer tissues. (No cell line data were included.)

FIG. 29

Antigen expression distribution for bladder cancer based on the calculation of multi-antigen responses from expression frequencies of the selected 17 different CTAs. A: non-cumulative distribution to calculate the expected value for the number of expressed antigens (AG50). This value shows that probably 8.85 vaccine antigens will be expressed by bladder tumor cells. B: cumulative distribution curve of the minimum number of expressed antigens (CTA expression curve). This shows that minimum 4 vaccine antigens will be expressed with 95% probability in bladder cancer cell (AG95).

FIG. 30

PEPI representing antigens: bladder cancer vaccine-specific CTA antigens with ≥1 PEPI, called as "AP") distribution within the Model Population (n=433) for bladder cancer vaccine. A: non-cumulative distribution of AP where the average number of APs is: AP50=9.44, meaning that in average almost 8 CTAs will have PEPIs in the Model Population. B: cumulative distribution curve of the minimum number of APs in the Model Population (n=433). This shows that at least three vaccine antigen will have PEPIs in 95% of the Model Population (n=433) (AP95=3).

FIG. 31

PEPI represented expressed antigen (bladder cancer vaccine-specific CTA antigens expressed by the tumor, for which ≥1 PEPI is predicted, called as "AGP") distribution within the model population (n=433) calculated with CTA expression rates for bladder cancer. A: non-cumulative distribution of AGP where the expected value for number expressed CTAs represented by PEPI is AGP50=3.90. AGP50 is a measure of the effectiveness of the disclosed bladder cancer vaccine in attacking bladder tumor in an unselected patient population. AGP50=3.90 means that at least 3 CTAs from the vaccine will probably be expressed by the bladder tumor cells and present PEPIs in the Model Population. B: cumulative distribution curve of the minimum number of AGPs in the Model Population (n=433) shows that at least 1 of the vaccine CTAs will present PEPIs in 95% of the population and the remaining 5% of the population will likely have no AGP at all (AGP95=1).

FIG. 32

Probability of vaccine antigen expression in the Patient-A's tumor cells. There is over 95% probability that 5 out of the 13 target antigens in the vaccine regimen is expressed in the patient's tumor. Consequently, the 13 peptide vaccines together can induce immune responses against at least 5 ovarian cancer antigens with 95% probability (AGP95). It has 84% probability that each peptide will induce immune responses in the Patient-A. AGP50 is the mean (expected value)=7.9 (it is a measure of the effectiveness of the vaccine in attacking the tumor of Patient-A).

FIG. 33

Treatment schedule of Patient-A.

FIG. 34

T cell responses of patient-A. A. Left: Vaccine peptide-specific T cell responses (20-mers). right: CD8+ cytotoxic T cell responses (9-mers). Predicted T cell responses are confirmed by bioassay.

FIG. 35

MRI findings of Patient-A treated with personalised (PIT) vaccine. This late stage, heavily pretreated ovarian cancer patient had an unexpected objective response after the PIT vaccine treatment. These MRI findings suggest that PIT vaccine in combination with chemotherapy significantly reduced her tumor burden.

FIG. 36

Probability of vaccine antigen expression in the Patient-B's tumor cells and treatment schedule of Patent-B. A: There is over 95% probability that 4 out of the 13 target antigens in the vaccine is expressed in the patient's tumor. B: Consequently, the 12 peptide vaccines together can induce immune responses against at least 4 breast cancer antigens with 95% probability (AGP95). It has 84% probability that each peptide will induce immune responses in the Patient-B. AGP50=6.45; it is a measure of the effectiveness of the vaccine in attacking the tumor of Patient-B. C: Treatment schedule of Patient-B.

FIG. 37

T cell responses of Patient-A. Left: Vaccine peptide-specific T cell responses (20-mers) of P. Right: Kinetic of vaccine-specific CD8+ cytotoxic T cell responses (9-mers). Predicted T cell responses are confirmed by bioassay.

FIG. 38

Treatment schedule of Patient-C.

FIG. 39

T cell responses of Patient-C. A: Vaccine peptide-specific T cell responses (20-mers). B: Vaccine peptide-specific CD8+ T cell responses (9-mers). C-D: Kinetics of vaccine-specific CD4+ T cells and CD8+ cytotoxic T cell responses (9-mers), respectively. Long lasting immune responses both CD4 and CD 8 T cell specific are present after 14 months.

FIG. 40

Treatment schedule of Patient-D.

FIG. 41

Immune responses of Patient-D for PIT treatment. A: CD4+ specific T cell responses (20mer) and B: CD8+ T cell specific T cell responses (9mer). 0.5-4 months refer to the timespan following the last vaccination until PBMC sample collection.

FIG. 42

Schematic showing exemplary positions of amino acids in overlapping HLA class I- and HLA class-II binding epitopes in a 30-mer peptide.

DESCRIPTION OF THE SEQUENCES

SEQ ID NOs: 1 to 30 set forth 9 mer T cell epitopes described in Table 20a.
SEQ ID NOs: 31 to 60 set forth 15 mer T cell epitopes described in Table 20a.
SEQ ID NOs: 61 to 75 set forth gastric cancer vaccine peptides described in Table 21a.
SEQ ID NOs: 76 to 89 set forth gastric cancer associated antigens.
SEQ ID NOs: 90 to 119 set forth 9 mer T cell epitopes described in Table 20b.
SEQ ID NOs: 120 to 149 set forth 15 mer T cell epitopes described in Table 20b.
SEQ ID NOs: 150 to 164 set forth lung cancer vaccine peptides described in Table 21b.
SEQ ID NOs: 165 to 177 set forth lung cancer associated antigens.
SEQ ID NOs: 178 to 207 set forth 9 mer T cell epitopes described in Table 20c.
SEQ ID NOs: 208 to 237 set forth 15 mer T cell epitopes described in Table 20c.
SEQ ID NOs: 238 to 252 set forth melanoma vaccine peptides described in Table 21c.
SEQ ID NOs: 253 to 267 set forth melanoma associated antigens.
SEQ ID NOs: 268 to 297 set forth 9 mer T cell epitopes described in Table 20d.
SEQ ID NOs: 298 to 327 set forth 15 mer T cell epitopes described in Table 20d.
SEQ ID NOs: 328 to 342 set forth bladder cancer vaccine peptides described in Table 21d.
SEQ ID NOs: 343 to 359 set forth bladder cancer associated antigens.
SEQ ID NOs: 360 to 372 set forth sequences of personalized vaccine of Patient-A and are described in Table 22.
SEQ ID NOs: 373 to 384 set forth sequences of personalized vaccine of Patient-B and are described in Table 24.
SEQ ID NO: 385 sets forth the 30 amino acid CRC_P3 peptide, FIG. 13.
SEQ ID NOs: 386 to 394 set forth the 9mer sequences shown in FIG. 8.

DETAILED DESCRIPTION

HLA Genotypes

HLAs are encoded by the most polymorphic genes of the human genome. Each person has a maternal and a paternal allele for the three HLA class I molecules (HLA-A*, HLA-B*, HLA-C*) and four HLA class II molecules (HLA-DP*, HLA-DQ*, HLA-DRB1*, HLA-DRB3*/4*/5*). Practically, each person expresses a different combination of 6 HLA class I and 8 HLA class II molecules that present different epitopes from the same protein antigen. The function of HLA molecules is to regulate T cell responses.

The nomenclature used to designate the amino acid sequence of the HLA molecule is as follows: gene name*allele:protein number, which, for instance, can look like: HLA-A*02:25. In this example, "02" refers to the allele. In most instances, alleles are defined by serotypes—meaning that the proteins of a given allele will not react with each other in serological assays. Protein numbers ("25" in the example above) are assigned consecutively as the protein is discovered. A new protein number is assigned for any protein with a different amino acid sequence determining the binding specificity to non-self antigenic peptides (e.g. even a one amino acid change in sequence is considered a different protein number). Further information on the nucleic acid sequence of a given locus may be appended to the HLA nomenclature, but such information is not required for the methods described herein.

The HLA class I genotype or HLA class II genotype of an individual may refer to the actual amino acid sequence of each class I or class II HLA of an individual, or may refer to the nomenclature, as described above, that designates, minimally, the allele and protein number of each HLA gene. In some embodiments, the HLA genotype of an individual is obtained or determined by assaying a biological sample from the individual. The biological sample typically contains subject DNA. The biological sample may be, for example, a blood, serum, plasma, saliva, urine, expiration, cell or tissue sample. In some embodiments the biological sample is a saliva sample. In some embodiments the biological sample is a buccal swab sample. An HLA genotype may be obtained or determined using any suitable method. For example, the sequence may be determined via sequencing the HLA gene loci using methods and protocols known in the art. In some embodiments, the HLA genotype is determined using sequence specific primer (SSP) technologies. In some embodiments, the HLA genotype is determined using sequence specific oligonucleotide (SSO) technologies. In some embodiments, the HLA genotype is determined using sequence based typing (SBT) technologies. In some embodiments, the HLA genotype is determined using next generation sequencing. Alternatively, the HLA set of an individual may be stored in a database and accessed using methods known in the art.

Some subjects may have two HLA alleles that encode the same HLA molecule (for example, two copies for HLA-A*02:25 in case of homozygosity). The HLA molecules encoded by these alleles bind all of the same T cell epitopes. For the purposes of this disclosure "binding to at least two HLA molecules of the subject" as used herein includes binding to the HLA molecules encoded by two identical HLA alleles in a single subject. In other words, "binding to at least two HLA molecules of the subject" and the like could otherwise be expressed as "binding to the HLA molecules encoded by at least two HLA alleles of the subject".

HLA-Epitope Binding

A given HLA of a subject will only present to T cells a limited number of different peptides produced by the processing of protein antigens in an APC. As used herein, "display" or "present", when used in relation to HLA, references the binding between a peptide (epitope) and an HLA. In this regard, to "display" or "present" a peptide is synonymous with "binding" a peptide.

As used herein, the term "epitope" or "T cell epitope" refers to a sequence of contiguous amino acids contained within a protein antigen that possess a binding affinity for (is capable of binding to) one or more HLAs. An epitope is HLA- and antigen-specific (HLA-epitope pairs, predicted with known methods), but not subject specific. An epitope, a T cell epitope, a polypeptide, a fragment of a polypeptide or a composition comprising a polypeptide or a fragment thereof is "immunogenic" for a specific human subject if it is capable of inducing a T cell response (a cytotoxic T cell response or a helper T cell response) in that subject. In some cases the helper T cell response is a Th1-type helper T cell response. In some cases an epitope, a T cell epitope, a polypeptide, a fragment of a polypeptide or a composition comprising a polypeptide or a fragment thereof is "immunogenic" for a specific human subject if it is more likely to induce a T cell response or immune response in the subject than a different T cell epitope (or in some cases two different T cell epitopes each) capable of binding to just one HLA molecule of the subject.

The terms "T cell response" and "immune response" are used herein interchangeably, and refer to the activation of T cells and/or the induction of one or more effector functions following recognition of one or more HLA-epitope binding pairs. In some cases an "immune response" includes an antibody response, because HLA class II molecules stimulate helper T cell responses that are involved in inducing both long lasting CTL responses and antibody responses. Effector functions include cytotoxicity, cytokine production and proliferation. According to the present disclosure, an epitope, a T cell epitope, or a fragment of a polypeptide is immunogenic for a specific subject if it is capable of binding to at least two, or in some cases at least three, class I or at least two, or in some cases at least three or at least four class II HLAs of the subject.

The term "personal epitope", or "PEPI" as used herein distinguishes a subject-specific epitope from an HLA specific epitope. A "PEPI" is a fragment of a polypeptide consisting of a sequence of contiguous amino acids of the polypeptide that is a T cell epitope capable of binding to one or more HLA class I molecules of a specific human subject. In other cases a "PEPI" is a fragment of a polypeptide consisting of a sequence of contiguous amino acids of the polypeptide that is a T cell epitope capable of binding to one or more HLA class II molecules of a specific human subject. In other words a "PEPI" is a T cell epitope that is recognised by the HLA set of a specific individual, and is consequently specific to the subject in addition to the HLA and the antigen. In contrast to an "epitope", which is specific only to HLA and the antigen, PEPIs are specific to an individual because different individuals have different HLA molecules which each bind to different T cell epitopes. This subject specificity of the PEPIs allows to make personalized cancer vaccines.

"PEPI1" as used herein refers to a peptide, or a fragment of a polypeptide, that can bind to one HLA class I molecule (or, in specific contexts, HLA class II molecule) of an individual. "PEPI1+" refers to a peptide, or a fragment of a polypeptide, that can bind to one or more HLA class I (or II) molecule of an individual.

"PEPI2" refers to a peptide, or a fragment of a polypeptide, that can bind to two HLA class I (or II) molecules of an individual. "PEPI2+" refers to a peptide, or a fragment of a polypeptide, that can bind to two or more HLA class I (or II) molecules of an individual, i.e. a fragment identified according to a method of the disclosure.

"PEPI3" refers to a peptide, or a fragment of a polypeptide, that can bind to three HLA class I (or II) molecules of an individual. "PEPI3+" refers to a peptide, or a fragment of a polypeptide, that can bind to three or more HLA class I (or II) molecules of an individual.

"PEPI4" refers to a peptide, or a fragment of a polypeptide, that can bind to four HLA class I (or II) molecules of an individual. "PEPI4+" refers to a peptide, or a fragment of a polypeptide, that can bind to four or more HLA class I (or II) molecules of an individual.

"PEPI5" refers to a peptide, or a fragment of a polypeptide, that can bind to five HLA class I (or II) molecules of an individual. "PEPI5+" refers to a peptide, or a fragment of a polypeptide, that can bind to five or more HLA class I (or II) molecules of an individual.

"PEPI6" refers to a peptide, or a fragment of a polypeptide, that can bind to all six HLA class I (or six HLA class II) molecules of an individual.

Generally speaking, epitopes presented by HLA class I molecules are about nine amino acids long and epitopes presented by HLA class II molecules are about fifteen amino acids long. For the purposes of this disclosure, however, an epitope may be more or less than nine (for HLA Class I) or fifteen (for HLA Class II) amino acids long, as long as the epitope is capable of binding HLA. For example, an epitope that is capable of binding to class I HLA may be between 7, or 8 or 9 and 9 or 10 or 11 amino acids long. An epitope that is capable of binding to a class II HLA may be between 13, or 14 or 15 and 15 or 16 or 17 amino acids long.

Using techniques known in the art, it is possible to determine the epitopes that will bind to a known HLA. Any suitable method may be used, provided that the same method is used to determine multiple HLA-epitope binding pairs that are directly compared. For example, biochemical analysis may be used. It is also possible to use lists of epitopes known to be bound by a given HLA. It is also possible to use predictive or modelling software to determine which epitopes may be bound by a given HLA. Examples are provided in Table 1. In some cases a T cell epitope is capable of binding to a given HLA if it has an IC50 or predicted IC50 of less than 5000 nM, less than 2000 nM, less than 1000 nM, or less than 500 nM.

TABLE 1

Example software for determining epitope-HLA binding

| EPITOPE PREDICTION TOOLS | WEB ADDRESS |
|---|---|
| BIMAS, NIH | bimas.cit.nih.gov/molbio/hla_bind/ |
| PPAPROC, Tubingen Univ. | |
| MHCPred, Edward Jenner Inst, of Vaccine Res. | |
| EpiJen, Edward Jenner Inst, of Vaccine Res. | ddg-pharmfac.net/epijen/EpiJen/EpiJen.htm |
| NetMHC, Center for Biological Sequence Analysis | cbs.dtu.dk/services/NetMHC/ |
| SVMHC, Tubingen Univ. | abi.inf.uni-tuebingen.de/Services/SVMHC/ |
| SYFPEITHI, Biomedical Informatics, Heidelberg | syfpeithi.de/bin/MHCServer.dll/EpitopePrediction.htm |
| ETK EPITOOLKIT, Tubingen Univ. | etk.informatik.uni-tuebingen.de/epipred/ |
| PREDEP, Hebrew Univ. Jerusalem | margalit.huji.ac.il/Teppred/mhc-bind/index.html |
| RANKPEP, MIF Bioinformatics | bio.dfci.harvard.edu/RANKPEP/ |
| IEDB, Immune Epitope Database | tools.immuneepitope.org/main/html/tcell_tools.html |
| EPITOPE DATABASES | WEB ADDRESS |
| MHCBN, Institute of Microbial Technology, Chandigarh, INDIA | imtech.res.in/raghava/mhcbn/ |
| SYFPEITHI, Biomedical Informatics, Heidelberg | syfpeithi.de/ |
| Anti Jen, Edward Jenner Inst, of Vaccine Res. | ddg-pharmfac.net/antijen/AntiJen/antijenhomepage.htm |
| EPIMHC database of MHC ligands, MIF Bioinformatics | immunax.dfci.harvard.edu/epimhc/ |
| IEDB, Immune Epitope Database | iedb.org/ |

HLA molecules regulate T cell responses. Until recently, the triggering of an immune response to individual epitopes was thought to be determined by recognition of the epitope by the product of single HLA allele, i.e. HLA-restricted epitopes. However, HLA-restricted epitopes induce T cell responses in only a fraction of individuals. Peptides that activate a T cell response in one individual are inactive in others despite HLA allele matching. Therefore, it was previously unknown how an individual's HLA molecules present the antigen-derived epitopes that positively activate T cell responses.

The inventors discovered that multiple HLA expressed by an individual need to present the same peptide in order to trigger a T cell response. Therefore the fragments of a polypeptide antigen (epitopes) that are immunogenic for a specific individual (PEPIs) are those that can bind to multiple class I (activate CD8+ T cells eg, cytotoxic T cells) or class II (activate CD4+ T cells, eg. helper T cells or CD4+ killer cells) HLAs expressed by that individual. This discovery is described in PCT/EP2018/055231, PCT/EP2018/055232, PCT/EP2018/055230, EP 3370065 and EP 3369431.

Polypeptides

The disclosure relates to polypeptides that are derived from CTAs and that are immunogenic for a high proportion of the human population.

As used herein, the term "polypeptide" refers to a full-length protein, a portion of a protein, or a peptide characterized as a string of amino acids. As used herein, the term "peptide" refers to a short polypeptide comprising between 2, or 3, or 4, or 5, or 6, or 7, or 8, or 9, or 10, or 11, or 12, or 13, or 14, or 15 and 10, or 11, or 12, or 13, or 14, or 15, or 20, or 25, or 30, or 35, or 40, or 45, or 50 or 55 or 60 amino acids. The polypeptides are typically about 9 to 50 or 15 to 40 or 20 to 30 amino acids long.

The terms "fragment" or "fragment of a polypeptide" as used herein refer to a string of amino acids or an amino acid sequence typically of reduced length relative to the or a reference polypeptide and comprising, over the common portion, an amino acid sequence identical to the reference polypeptide. Such a fragment according to the disclosure may be, where appropriate, included in a larger polypeptide of which it is a constituent. In some cases the fragment may comprise the full length of the polypeptide, for example where the whole polypeptide, such as a 9 amino acid peptide, is a single T cell epitope. In some cases the fragments referred to herein may be between 2, or 3, or 4, or 5 or 6 or 7 or 8 or 9 and 20, or 25, or 30, or 35, or 40, or 45, or 50 amino acids.

In some embodiments the peptides of the disclosure may comprise or consist of one or more fragments of one or more CTAs. CTAs are not typically expressed beyond embryonic development in healthy cells. In healthy adults, CTA expression is limited to male germ cells that do not express HLAs and cannot present antigens to T cells. Therefore, CTAs are considered expressional neoantigens when expressed in cancer cells.

CTAs are a good choice for cancer vaccine targets because their expression is (i) specific for tumor cells, (ii) more frequent in metastases than in primary tumors and (iii) conserved among metastases of the same patient (Gajewski ed. Targeted Therapeutics in Melanoma. Springer New York. 2012).

The peptides of the disclosure may comprise or consist of one or more fragments of one or more gastric cancer-associated antigens selected from DPPA2 (SEQ ID NO: 76, Q7Z7J5.1), CAGE-1 (SEQ ID NO: 77, Q8TC20.1), TSP50 (SEQ ID NO: 78, Q9UI38.1), HIWI (SEQ ID NO: 79, Q96J94.1), SURVIVIN (SEQ ID NO: 80, 015392.1), 5T4 (SEQ ID NO: 81, Q13641.1), PRAME (SEQ ID NO:82, P78395.1), KK-LC-1 (SEQ ID NO 83, Q5H943.1), MAGE-A2 (SEQ ID NO: 84, P43356.1), MAGE-A3 (SEQ ID NO: 85, P43357.1), LAGE-1 (SEQ ID NO: 86, 075638.1), MAGE-A10 (SEQ ID NO: 87, P43363.1), MAGE-A1 (SEQ ID NO: 88, P43355.1) and SSX1 (SEQ ID NO: 89, Q16384.1); and/or one or more lung cancer-associated antigens selected from BRDT (SEQ ID NO: 165, Q58F21.1), PRAME (SEQ ID NO: 166, P78395.1), NALP4 (SEQ ID NO: 167, Q96MN2.1), MAGE-A12 (SEQ ID NO: 168, P43365.1), MAGE-A2 (SEQ ID NO: 169, P43356.1), SURVIVIN (SEQ ID NO: 170, O15392.1), DPPA2 (SEQ ID NO:171, Q7Z7J5.1), NY-SAR-35 (SEQ ID NO 172, Q8N0W7.1), LDHC (SEQ ID NO: 173, P07864.1), MAGE-C2 (SEQ ID NO: 174, Q9UBF1.1), MAGE-A3 (SEQ ID NO: 175, P43357.1), KK-LC-1 (SEQ ID NO: 176, Q5H943.1) and MAGE-A1 (SEQ ID NO: 177, P43355.1); and/or one or more melanoma cancer-associated antigens selected from PRAME (SEQ ID NO: 253, P78395.1), MAGE-A2 (SEQ ID NO: 254, P43356.1), MAGE-C1 (SEQ ID NO: 255, P43355.1), SURVIVIN (SEQ ID NO: 256, 015392.1), MAGE-A12 (SEQ ID NO: 257, P43365.1), Ny-ESO-1 (SEQ ID NO: 258, P78358.1), MAGE-C2 (SEQ ID NO:259, Q9UBF1.1), MAGE-A6 (SEQ ID NO 260, P43360.1), BORIS (SEQ ID NO: 261, Q8NI51.1), LAGE-1 (SEQ ID NO: 262, 075638.1), MAGE-A11 (SEQ ID NO: 263, P43364.1), SSX-1 (SEQ ID NO: 264, Q16384.1), MAGE-A3 (SEQ ID NO: 265, P43357.1) MAGE-A10 (SEQ ID NO: 266, P43363.1) and MAGE-A1 (SEQ ID NO: 267, P43355.1); and/or one or more bladder cancer-associated antigens selected from PIWIL2 (SEQ ID NO: 343, Q8TC59.1), CTAGE1 (SEQ ID NO: 344, Q96RT6.1), MAGE-A9 (SEQ ID NO: 345, P43362.1), EpCAM (SEQ ID NO: 346, P16422.1), OY-TES-1 (SEQ ID NO: 347, Q8NEB7.1), NY-ESO-1 (SEQ ID NO: 348, P78358.1), SURVIVIN (SEQ ID NO:349, 015392.1), MAGE-C1 (SEQ ID NO 350, 060732.1), MAGE-A2 (SEQ ID NO: 351, P43356.1), LAGE-1 (SEQ ID NO: 352, 075638.1), MAGE-A3 (SEQ ID NO: 353, P43357.1), MAGE-A8 (SEQ ID NO: 354, P43361.1), HAGE (SEQ ID NO: 355, Q9NXZ2.1), MAGE-A1 (SEQ ID NO: 356, P43355.1), MAGE-C2 (SEQ ID NO: 357, Q9UBF1.1), MAGE-A10 (SEQ ID NO: 358, P43363.1), and MAGE-A12 (SEQ ID NO: 359, P43365.1).

In some cases the amino acid sequence is flanked at the N and/or C terminus by additional amino acids that are not part of the sequence of the target polypeptide antigen, in other words that are not the same sequence of consecutive amino acids found adjacent to the selected fragments in the target polypeptide antigen. In some cases the sequence is flanked by up to 41 or 35 or 30 or 25 or 20 or 15 or 10, or 9 or 8 or 7 or 6 or 5 or 4 or 3 or 2 or 1 additional amino acid at the N and/or C terminus or between target polypeptide fragments. In other cases each polypeptide either consists of a fragment of a target polypeptide antigen, or consists of two or more such fragments arranged end to end (arranged sequentially in the peptide end to end) or overlapping in a single peptide (where two or more of the fragments comprise partially overlapping sequences, for example where two PEPIs in the same polypeptide are within 50 amino acids of each other). Typically each polypeptide may comprise at least one fragment of a target polypeptide antigen wherein the fragment comprises an amino acid sequence that is a T cell epitope capable of binding to at least three or at least four HLA class II alleles in some subjects or a high proportion of subjects or the maximum proportion of subjects.

Figure 42:
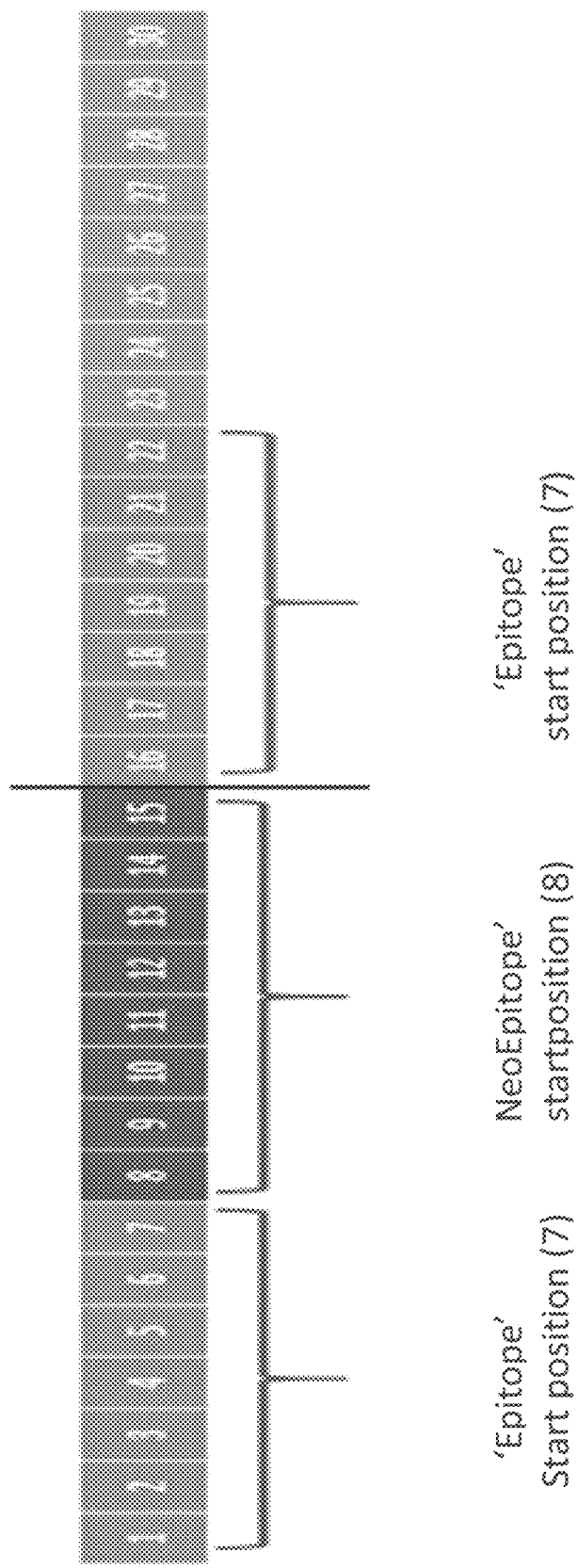

When fragments of different polypeptides or from different regions of the same polypeptide are joined together in an engineered peptide there is the potential for neoepitopes to be generated around the join or junction (FIG. 42). Such neoepitopes encompass at least one amino acid from each fragment on either side of the join or junction, and may be referred to herein as junctional amino acid sequences. The neoepitopes may induce undesired T cell responses against healthy cells (autoimmunity). The polypeptides may be designed, or the polypeptides may be screened, to avoid, eliminate or minimise neoepitopes that correspond to a fragment of a protein expressed in normal healthy human cells and/or neoepitopes that are capable of binding to at least two, or in some cases at least three, or at least four HLA class I molecules of the subject, or in some cases at least two, or at least three or four or five HLA class II molecules of the subject. In some cases the peptide is designed, or the polypeptide screened, to eliminate polypeptides having a junctional neoepitope that is capable of binding in more than a threshold percentage of human subjects in an intent-to-treat population, to at least two HLA class I molecules expressed by individual subjects of the population. In some cases the threshold is 20%, or 15%, or 10%, or 5%, or 2%, or 1%, or 0.5% of said population. Alignment may be determined using known methods such as BLAST algorithms. Software for performing BLAST analyses is publicly available through the National Center for Biotechnology Information (ncbi.nlm.nih.gov/).

The presence in a vaccine or immunotherapy composition of at least two polypeptide fragments (epitopes) that can bind to at least three HLA class I of an individual (≥2 PEPI3+) is predictive for a clinical response. In other words, if ≥2 PEPI3+ can be identified within the active ingredient polypeptide(s) of a vaccine or immunotherapy composition, then an individual is a likely clinical responder. The at least two multiple HLA-binding PEPIs of the composition polypeptides may both target a single antigen (e.g a polypeptide vaccine comprising two multiple HLA-binding PEPIs derived from a single tumor associated antigen targeted by the vaccine) or may target different antigens (e.g. a polypeptide vaccine comprising one multiple HLA-binding PEPI derived from one tumor associated antigen and a second multiple HLA-binding PEPI derived from a different tumor associated antigen).

Without wishing to be bound by theory, the inventors believe that one reason for the increased likelihood of deriving clinical benefit from a vaccine/immunotherapy comprising at least two multiple-HLA binding PEPIs, is that diseased cell populations, such as cancer or tumor cells or cells infected by viruses or pathogens such as HIV, are often heterogenous both within and between effected subjects. A specific cancer patient, for example, may or may not express or overexpress a particular cancer associated target polypeptide antigen of a vaccine, or their cancer may comprise heterogeneous cell populations, some of which (over-)express the antigen and some of which do not. In addition, the likelihood of developing resistance is decreased when more multiple HLA-binding PEPIs are included or targeted by a vaccine/immunotherapy because a patient is less likely to develop resistance to the composition through mutation of the target PEPI(s).

Currently most vaccines and immunotherapy compositions target only a single polypeptide antigen. However according to the present disclosure it is in some cases beneficial to provide a pharmaceutical composition that targets two or more different polypeptide antigens. For example, most cancers or tumors are heterogeneous, meaning that different cancer or tumor cells of a subject (over-) express different antigens. The tumour cells of different cancer patients also express different combinations of tumour-associated antigens. The anti-cancer immunogenic compositions that are most likely to be effective are those that target multiple antigens expressed by the tumor, and therefore more cancer or tumor cells, in an individual human subject or in a population.

The beneficial effect of combining multiple bestEPIs in a single treatment (administration of one or more pharmaceutical compositions that together comprise multiple PEPIs), can be illustrated by the personalised vaccine polypeptides described in Example 21 below. Exemplary CTA expression probabilities in ovarian cancer are as follows: BAGE: 30%; MAGE A9: 37%; MAGE A4: 34%; MAGE A10: 52%. If patient-A were treated with a vaccine comprising PEPIs in only BAGE and MAGE A9, then the probability of having a mAGP (multiple expressed antigens with PEPI) would be 11%. If patent-A were treated with a vaccine comprising only PEPIs for the MAGE A4 and MAGE A10 CTAs, then the probability of having a multiAGP would be 19%. However if a vaccine contained all 4 of these CTAs (BAGE, MAGE A9, MAGE A4 and MAGE A10), then the probability of having a mAGP would be 50%. In other words the effect would be greater than the combined probabilities of mAGP for both two-PEPI treatments (probability mAGP for BAGE/MAGE+probability mAGP for MAGE A4 and MAGE A10). Patient-A's PIT vaccine described in Example 21 contains a further 9 PEPIs, and thus, the probability of having a mAGP is over 99.95%.

Likewise exemplary CTA expression probabilities in breast cancer are as follows: MAGE C2: 21%; MAGE A1: 37%; SPC1: 38%; MAGE A9: 44%. Treatment of patient-B with a vaccine comprising PEPIs in only MAGE C2: 21% and MAGE A1 has a mAGP probability of 7%. Treatment of patient-B with a vaccine comprising PEPIs in only SPC1: 38%; MAGE A9 has a mAGP probability of 11%. Treatment of patient-B with a vaccine comprising PEPIs in MAGE C2: 21%; MAGE A1: 37%; SPC1: 38%; MAGE A9 has a mAGP probability of 44% (44>7+11). Patient's PIT vaccine described in Example 21 contains a further 8 PEPIs, and thus, the probability of having a mAGP is over 99.93%.

Accordingly in some cases, the polypeptide or panel of polypeptides of the disclosure or an active ingredient polypeptide of a pharmaceutical composition or kit of the disclosure may comprise or consist of any combination of at least 1, 2, 3, 4, 5, 6, 7, 8, 9, 10, 11, 12, 13, 14, 15, 16, 17, 18, 19, 20, 21, 22, 23, 24 or 25 fragments of at least 1, 2, 3, 4, 5, 6, 7, 8, 9, 10, 11, 12, 13, 14, 15, 16, 17, 18, 19, 20, 21, 22, 23, 24 or 25 or more of the cancer associated antigens, or CTAs, such as the CTA discussed above. In some cases each fragment may comprise or consist of a different target epitope having an amino acid sequence selected from SEQ ID NOs: 1-30, SEQ ID NOs: 31-60, SEQ ID NOs: 90 to 119, SEQ ID NOs: 120 to 149, SEQ ID NOs: 178 to 207, SEQ ID NOs: 208 to 237, SEQ ID NOs: 268 to 297, and/or SEQ ID NOs: 298 to 327; or selected from SEQ ID NOs: 1 to 2, or to 3, or 4, or 5, or 6, or 7, or 8, or 9, or 10, or 11, or 12, or 13, or 14, or 15, or 16, or 17, or 18, or 19, or 20, or 21, or 22, or 23, or 24, or 25, or 26, or 27, or 28, or 29; or SEQ ID NOs: 31 to 32, or to 33, or 34, or 35, or 36, or 37, or 38, or 39, or 40, or 41 to 42, or to 43, or to 44, or to 45, or to 46, or to 47, or to 48, or to 49, or 50, or 51, or 52, or 53, or 54, or 55, or 56, or 57, or 58, or 59; or selected from SEQ ID NOs: 90 to 91, or to 92, or 93 or 94, or 95, or 96, or 97, or 98, or 99, or 100, or 101, or 102, or 103, or 104, or 105, or 106, or 107, or 108, or 109, or 110, or 111, or 112, or 113, or 114, or 115, or 116, or 117, or 118; or SEQ ID NOs: 120 to 121, or to 122, or 123, or 124, or 125, or 126, or 127, or 128, or 129; or 130; or 131; or 132; or 133; or 134; or 135; or 136; or 137; or 138; or 139; or 140; or 141; or 142; or 143; or 144; or 145; or 146; or 147; or 148; or 149; or selected from SEQ ID NOs: 178 to 179, or to 180, or 181, or 182, or 183, or 184, or 185, or 186, or 187, or 188, or 189, or 190, or 191, or 192, or 193, or 194, or 195, or 196, or 197, or 198, or 199, or 200, or 201, or 202, or 203, or 204, or 205, or 206; or SEQ ID NOs: 208 to 209, or 210, or 211, or 212, or 213, or 214, or 215, or 216, or 217, or 218, or 219, or 220, or 221, or 222, or 223, or 224, or 225, or 226, or 227, or 228, or 229, or 230, or 231, or 232, or 233, or 234, or 235, or 236; or selected from SEQ ID NOs: 268 to 269, or to 270, or 271, or 272, or 273, or 274, or 275, or 276, or 277, or 278, or 279, or 280, or 281, or 282, or 283, or 284, or 285, or 286, or 287, or 288, or 289, or 290, or 291, or 292, or 293, or 294, or 295, or 296; or selected from SEQ ID NOs: 298 to 299, or to 300, or 301, or 302, or 303, or 304, or 305, or 306, or 307, or 308, or 309, or 310, or 311, or 312, or 313, or 314, or 315, or 316, or 317, or 318, or 319, or 320, or 321, or 322, or 323, or 324, or 325, or 326; or selected from any of these groups of sequences but excluding any specific combinations of sequences that are within 50-60 amino acids of each other in any one or more of the antigens of SEQ ID NOs: 76 to 89, 165 to 177, 253 to 267 and/or 343 to 359, such as any combination of SEQ ID NOs: 3 and 8; SEQ ID NOs: 9 and 10; SEQ ID NOs: 12 and 16; SEQ ID NOs: 13, 18 and 25; SEQ ID NOs: 21 and 24; SEQ ID NOs: 23 and 30; SEQ ID NOs: 93 and 94; SEQ ID NOs: 99, 100 and 102; SEQ ID NOs: 109 and 111; SEQ ID NOs: 96, 101 and 113; SEQ ID NOs: 188 and 190; and/or SEQ ID NOs: 201 and 203; SEQ ID NOs: 268 and 270; SEQ ID NOs: 271 and 281; SEQ ID NOs: 272 and 275; and/or SEQ ID NOs: 288 and 291. In some cases each fragment may comprise or consist of a different amino acid sequence selected from SEQ ID NOs: 60 or 61 to 75; SEQ ID NOs: 150 to 164; SEQ ID NOs: 238 to 252; and/or SEQ ID NOs: 328 to 342.

In some cases the disclosure provides a panel of any two or more of the peptides or groups of peptides described above. For example the panel may comprise 2, 3, 4, 5, 6, 7, 8, 9, 10, 11, 12, 13, 14, 15, 16, 17, 18, 19, 20, 21, 22, 23, 24, 25 or more such peptides.

Pharmaceutical Compositions, Methods of Treatment and Modes of Administration

In some aspects the disclosure relates to a pharmaceutical composition, kit, or panels of polypeptides as described above having one or more polypeptides as active ingredient(s). These may be for use in a method of inducing an immune response, treating, vaccinating or providing immunotherapy to a subject, and the pharmaceutical composition may be a vaccine or immunotherapy composition. Such a treatment comprises administering one or more polypeptides or pharmaceutical compositions that together comprise all of the active ingredient polypeptides of the treatment to the subject. Multiple polypeptides or pharmaceutical compositions may be administered together or sequentially, for example all of the pharmaceutical compositions or polypeptides may be administered to the subject within a period of 1 year, or 6 months, or 3 months, or 60 or 50 or 40 or 30 days.

The term "active ingredient" as used herein refers to a polypeptide that is intended to induce an immune response and may include a polypeptide product of a vaccine or immunotherapy composition that is produced in vivo after administration to a subject. For a DNA or RNA immunotherapy composition, the polypeptide may be produced in vivo by the cells of a subject to whom the composition is administered. For a cell-based composition, the polypeptide may be processed and/or presented by cells of the composition, for example autologous dendritic cells or antigen presenting cells pulsed with the polypeptide or comprising an expression construct encoding the polypeptide. The pharmaceutical composition may comprise a polynucleotide or cell encoding one or more active ingredient polypeptides.

The composition/kit may optionally further comprise at least one pharmaceutically acceptable diluent, carrier, or preservative and/or additional polypeptides that do not comprise any PEPIs. The polypeptides may be engineered or non-naturally occurring. The kit may comprise one or more separate containers each containing one or more of the active ingredient peptides. The composition/kit may be a personalised medicine to prevent, diagnose, alleviate, treat, or cure a disease of an individual, such as a cancer.

The immunogenic or pharmaceutical compositions or kits described herein may comprise, in addition to one or more immunogenic peptides, a pharmaceutically acceptable excipient, carrier, diluent, buffer, stabiliser, preservative, adjuvant or other materials well known to those skilled in the art. Such materials are preferably non-toxic and preferably do not interfere with the pharmaceutical activity of the active ingredient(s). The pharmaceutical carrier or diluent may be, for example, water containing solutions. The precise nature of the carrier or other material may depend on the route of administration, e.g. oral, intravenous, cutaneous or subcutaneous, nasal, intramuscular, intradermal, and intraperitoneal routes.

The pharmaceutical compositions of the disclosure may comprise one or more "pharmaceutically acceptable carriers". These are typically large, slowly metabolized macromolecules such as proteins, saccharides, polylactic acids, polyglycolic acids, polymeric amino acids, amino acid copolymers, sucrose (Paoletti et al., 2001, Vaccine, 19:2118), trehalose (WO 00/56365), lactose and lipid aggregates (such as oil droplets or liposomes). Such carriers are well known to those of ordinary skill in the art. The pharmaceutical compositions may also contain diluents, such as water, saline, glycerol, etc. Additionally, auxiliary substances, such as wetting or emulsifying agents, pH buffering substances, and the like, may be present. Sterile pyrogen-free, phosphate buffered physiologic saline is a typical carrier (Gennaro, 2000, Remington: The Science and Practice of Pharmacy, 20th edition, ISBN:0683306472).

The pharmaceutical compositions of the disclosure may be lyophilized or in aqueous form, i.e. solutions or suspensions. Liquid formulations of this type allow the compositions to be administered direct from their packaged form, without the need for reconstitution in an aqueous medium, and are thus ideal for injection. The pharmaceutical compositions may be presented in vials, or they may be presented in ready filled syringes. The syringes may be supplied with or without needles. A syringe will include a single dose, whereas a vial may include a single dose or multiple doses.

Liquid formulations of the disclosure are also suitable for reconstituting other medicaments from a lyophilized form. Where a pharmaceutical composition is to be used for such extemporaneous reconstitution, the disclosure provides a kit, which may comprise two vials, or may comprise one ready-filled syringe and one vial, with the contents of the syringe being used to reconstitute the contents of the vial prior to injection.

The pharmaceutical compositions of the disclosure may include an antimicrobial, particularly when packaged in a multiple dose format. Antimicrobials may be used, such as 2-phenoxyethanol or parabens (methyl, ethyl, propyl parabens). Any preservative is preferably present at low levels. Preservative may be added exogenously and/or may be a component of the bulk antigens which are mixed to form the composition (e.g. present as a preservative in pertussis antigens).

The pharmaceutical compositions of the disclosure may comprise detergent e.g. Tween (polysorbate), DMSO (dimethyl sulfoxide), DMF (dimethylformamide). Detergents are generally present at low levels, e.g. <0.01%, but may also be used at higher levels, e.g. 0.01-50%.

The pharmaceutical compositions of the disclosure may include sodium salts (e.g. sodium chloride) and free phosphate ions in solution (e.g. by the use of a phosphate buffer).

In certain embodiments, the pharmaceutical composition may be encapsulated in a suitable vehicle either to deliver the peptides into antigen presenting cells or to increase the stability. As will be appreciated by a skilled artisan, a variety of vehicles are suitable for delivering a pharmaceutical composition of the disclosure. Non-limiting examples of suitable structured fluid delivery systems may include nanoparticles, liposomes, microemulsions, micelles, dendrimers and other phospholipid-containing systems. Methods of incorporating pharmaceutical compositions into delivery vehicles are known in the art.

In order to increase the immunogenicity of the composition, the pharmacological compositions may comprise one or more adjuvants and/or cytokines.

Suitable adjuvants include an aluminum salt such as aluminum hydroxide or aluminum phosphate, but may also be a salt of calcium, iron or zinc, or may be an insoluble suspension of acylated tyrosine, or acylated sugars, or may be cationically or anionically derivatised saccharides, polyphosphazenes, biodegradable microspheres, monophosphoryl lipid A (MPL), lipid A derivatives (e.g. of reduced toxicity), 3-O-deacylated MPL [3D-MPL], quil A, Saponin, QS21, Freund's Incomplete Adjuvant (Difco Laboratories, Detroit, Mich.), Merck Adjuvant 65 (Merck and Company, Inc., Rahway, N.J.), AS-2 (Smith-Kline Beecham, Philadelphia, Pa.), CpG oligonucleotides, bioadhesives and mucoadhesives, microparticles, liposomes, polyoxyethylene ether formulations, polyoxyethylene ester formulations, muramyl peptides or imidazoquinolone compounds (e.g. imiquamod and its homologues). Human immunomodulators suitable for use as adjuvants in the disclosure include cytokines such as interleukins (e.g. IL-1, IL-2, IL-4, IL-5, IL-6, IL-7, IL-12, etc), macrophage colony stimulating factor (M-CSF), tumour necrosis factor (TNF), granulocyte, macrophage colony stimulating factor (GM-CSF) may also be used as adjuvants.

In some embodiments, the compositions comprise an adjuvant selected from the group consisting of Montanide ISA-51 (Seppic, Inc., Fairfield, N.J., United States of America), QS-21 (Aquila Biopharmaceuticals, Inc., Lexington, Mass., United States of America), GM-CSF, cyclophosamide, bacillus Calmette-Guerin (BCG), corynbacterium parvum, levamisole, azimezone, isoprinisone, dinitrochlorobenezene (DNCB), keyhole limpet hemocyanins (KLH), Freunds adjuvant (complete and incomplete), mineral gels, aluminum hydroxide (Alum), lysolecithin, pluronic polyols, polyanions, oil emulsions, dinitrophenol, diphtheria toxin (DT).

By way of example, the cytokine may be selected from the group consisting of a transforming growth factor (TGF) such as but not limited to TGF-α and TGF-β; insulin-like growth factor-I and/or insulin-like growth factor-II; erythropoietin (EPO); an osteoinductive factor; an interferon such as but not limited to interferon-α, -β, and -γ; a colony stimulating factor (CSF) such as but not limited to macrophage-CSF (M-CSF); granulocyte-macrophage-CSF (GM-CSF); and granulocyte-CSF (G-CSF). In some embodiments, the cytokine is selected from the group consisting of nerve growth factors such as NGF-β; platelet-growth factor; a transforming growth factor (TGF) such as but not limited to TGF-α and TGF-β; insulin-like growth factor-I and insulin-like growth factor-II; erythropoietin (EPO); an osteoinductive factor; an interferon (IFN) such as but not limited to IFN-α, IFN-β, and IFN-γ; a colony stimulating factor (CSF) such as macrophage-CSF (M-CSF); granulocyte-macrophage-CSF (GM-CSF); and granulocyte-CSF (G-CSF); an interleukin (Il) such as but not limited to IL-1, IL-1.alpha., IL-2, IL-3, IL-4, IL-5, IL-6, IL-7, IL-8, IL-9, IL-10, IL-11, IL-12; IL-13, IL-14, IL-15, IL-16, IL-17, IL-18; LIF; kit-ligand or FLT-3; angiostatin; thrombospondin; endostatin; a tumor necrosis factor (TNF); and LT.

It is expected that an adjuvant or cytokine can be added in an amount of about 0.01 mg to about 10 mg per dose, preferably in an amount of about 0.2 mg to about 5 mg per dose. Alternatively, the adjuvant or cytokine may be at a concentration of about 0.01 to 50%, preferably at a concentration of about 2% to 30%.

In certain aspects, the pharmaceutical compositions of the disclosure are prepared by physically mixing the adjuvant and/or cytokine with the peptides of the disclosure under appropriate sterile conditions in accordance with known techniques to produce the final product.

Examples of suitable compositions of the invented polypeptide fragments and methods of administration are provided in Esseku and Adeyeye (2011) and Van den Mooter G. (2006). Vaccine and immunotherapy composition preparation is generally described in Vaccine Design ("The subunit and adjuvant approach" (eds Powell M. F. & Newman M. J. (1995) Plenum Press New York). Encapsulation within liposomes, which is also envisaged, is described by Fullerton, U.S. Pat. No. 4,235,877.

In some embodiments, the compositions disclosed herein are prepared as a nucleic acid vaccine. In some embodiments, the nucleic acid vaccine is a DNA vaccine. In some embodiments, DNA vaccines, or gene vaccines, comprise a plasmid with a promoter and appropriate transcription and translation control elements and a nucleic acid sequence encoding one or more polypeptides of the disclosure. In some embodiments, the plasmids also include sequences to enhance, for example, expression levels, intracellular targeting, or proteasomal processing. In some embodiments, DNA vaccines comprise a viral vector containing a nucleic acid sequence encoding one or more polypeptides of the disclosure. In additional aspects, the compositions disclosed herein comprise one or more nucleic acids encoding peptides determined to have immunoreactivity with a biological sample. For example, in some embodiments, the compositions comprise one or more nucleotide sequences encoding 1, 2, 3, 4, 5, 6, 7, 8, 9, 10, 11, 12, 13, 14, 15, 16, 17, 18, 19, 20, or more peptides comprising a fragment that is a T cell epitope capable of binding to at least three HLA class I molecules and/or at least three HLA class II molecules of a patient. In some embodiments, the peptides are derived from an antigen that is expressed in cancer. In some embodiments the DNA or gene vaccine also encodes immunomodulatory molecules to manipulate the resulting immune responses, such as enhancing the potency of the vaccine, stimulating the immune system or reducing immunosuppression. Strategies for enhancing the immunogenicity of DNA or gene vaccines include encoding of xenogeneic versions of antigens, fusion of antigens to molecules that activate T cells or trigger associative recognition, priming with DNA vectors followed by boosting with viral vector, and utilization of immunomodulatory molecules. In some embodiments, the DNA vaccine is introduced by a needle, a gene gun, an aerosol injector, with patches, via microneedles, by abrasion, among other forms. In some forms the DNA vaccine is incorporated into liposomes or other forms of nanobodies. In some embodiments, the DNA vaccine includes a delivery system selected from the group consisting of a transfection agent; protamine; a protamine liposome; a polysaccharide particle; a cationic nanoemulsion; a cationic polymer; a cationic polymer liposome; a cationic nanoparticle; a cationic lipid and cholesterol nanoparticle; a cationic lipid, cholesterol, and PEG nanoparticle; a dendrimer nanoparticle. In some embodiments, the DNA vaccines is administered by inhalation or ingestion. In some embodiments, the DNA vaccine is introduced into the blood, the thymus, the pancreas, the skin, the muscle, a tumor, or other sites.

In some embodiments, the compositions disclosed herein are prepared as an RNA vaccine. In some embodiments, the RNA is non-replicating mRNA or virally derived, self-amplifying RNA. In some embodiments, the non-replicating mRNA encodes the peptides disclosed herein and contains 5' and 3' untranslated regions (UTRs). In some embodiments, the virally derived, self-amplifying RNA encodes not only the peptides disclosed herein but also the viral replication machinery that enables intracellular RNA amplification and abundant protein expression. In some embodiments, the RNA is directly introduced into the individual. In some embodiments, the RNA is chemically synthesized or transcribed in vitro. In some embodiments, the mRNA is produced from a linear DNA template using a T7, a T3, or an Sp6 phage RNA polymerase, and the resulting product contains an open reading frame that encodes the peptides disclosed herein, flanking UTRs, a 5' cap, and a poly(A) tail. In some embodiments, various versions of 5' caps are added during or after the transcription reaction using a vaccinia virus capping enzyme or by incorporating synthetic cap or anti-reverse cap analogues. In some embodiments, an optimal length of the poly(A) tail is added to mRNA either directly from the encoding DNA template or by using poly(A) polymerase. The RNA encodes one or more peptides comprising a fragment that is a T cell epitope capable of binding to at least three HLA class I and/or at least three HLA class II molecules of a patient. In some embodiments, the fragments are derived from an antigen that is expressed in cancer. In some embodiments, the RNA includes signals to enhance stability and translation. In some embodiments, the RNA also includes unnatural nucleotides to increase the half-life or modified nucleosides to change the immunostimulatory profile. In some embodiments, the RNAs is introduced by a needle, a gene gun, an aerosol injector, with patches, via microneedles, by abrasion, among other forms. In some forms the RNA vaccine is incorporated into liposomes or other forms of nanobodies that facilitate cellular uptake of RNA and protect it from degradation. In some embodiments, the RNA vaccine includes a delivery system selected from the group consisting of a transfection agent; protamine; a protamine liposome; a polysaccharide particle; a cationic nanoemulsion; a cationic polymer; a cationic polymer liposome; a cationic nanoparticle; a cationic lipid and cholesterol nanoparticle; a cationic lipid, cholesterol, and PEG nanoparticle; a dendrimer nanoparticle; and/or naked mRNA; naked mRNA with in vivo electroporation; protamine-complexed mRNA; mRNA associated with a positively charged oil-in-water cationic nanoemulsion; mRNA associated with a chemically modified dendrimer and complexed with polyethylene glycol (PEG)-lipid; protamine-complexed mRNA in a PEG-lipid nanoparticle; mRNA associated with a cationic polymer such as polyethylenimine (PEI); mRNA associated with a cationic polymer such as PEI and a lipid component; mRNA associated with a polysaccharide (for example, chitosan) particle or gel; mRNA in a cationic lipid nanoparticle (for example, 1,2-dioleoyloxy-3-trimethylammoniumpropane (DOTAP) or dioleoylphosphatidylethanolamine (DOPE) lipids); mRNA complexed with cationic lipids and cholesterol; or mRNA complexed with cationic lipids, cholesterol and PEG-lipid. In some embodiments, the RNA vaccine is administered by inhalation or ingestion. In some embodiments, the RNA is introduced into the blood, the thymus, the pancreas, the skin, the muscle, a tumor, or other sites, and/or by an intradermal, intramuscular, subcutaneous, intranasal, intranodal, intravenous, intrasplenic, intratumoral or other delivery route.

Polynucleotide or oligonucleotide components may be naked nucleotide sequences or be in combination with cationic lipids, polymers or targeting systems. They may be delivered by any available technique. For example, the polynucleotide or oligonucleotide may be introduced by needle injection, preferably intradermally, subcutaneously or intramuscularly. Alternatively, the polynucleotide or oligonucleotide may be delivered directly across the skin using a delivery device such as particle-mediated gene delivery. The polynucleotide or oligonucleotide may be administered topically to the skin, or to mucosal surfaces for example by intranasal, oral, or intrarectal administration.

Uptake of polynucleotide or oligonucleotide constructs may be enhanced by several known transfection techniques, for example those including the use of transfection agents. Examples of these agents include cationic agents, for example, calcium phosphate and DEAE-Dextran and lipofectants, for example, lipofectam and transfectam. The dosage of the polynucleotide or oligonucleotide to be administered can be altered.

Administration is typically in a "prophylactically effective amount" or a "therapeutically effective amount" (as the case may be, although prophylaxis may be considered therapy), this being sufficient to result in a clinical response or to show clinical benefit to the individual, e.g. an effective amount to prevent or delay onset of the disease or condition, to ameliorate one or more symptoms, to induce or prolong remission, or to delay relapse or recurrence.

The dose may be determined according to various parameters, especially according to the substance used; the age, weight and condition of the individual to be treated; the route of administration; and the required regimen. The amount of antigen in each dose is selected as an amount which induces an immune response. A physician will be able to determine the required route of administration and dosage for any particular individual. The dose may be provided as a single dose or may be provided as multiple doses, for example taken at regular intervals, for example 2, 3 or 4 doses administered hourly. Typically peptides, polynucleotides or oligonucleotides are typically administered in the range of 1 pg to 1 mg, more typically 1 pg to g for particle mediated delivery and 1 µg to 1 mg, more typically 1-100 µg, more typically 5-50 µg for other routes. Generally, it is expected that each dose will comprise 0.01-3 mg of antigen. An optimal amount for a particular vaccine can be ascertained by studies involving observation of immune responses in subjects.

Examples of the techniques and protocols mentioned above can be found in Remington's Pharmaceutical Sciences, 20th Edition, 2000, pub. Lippincott, Williams & Wilkins.

In some cases in accordance with the disclosure, more than one peptide or composition of peptides is administered. Two or more pharmaceutical compositions may be administered together/simultaneously and/or at different times or sequentially. Thus, the disclosure includes sets of pharmaceutical compositions and uses thereof. The use of combination of different peptides, optionally targeting different antigens, is important to overcome the challenges of genetic heterogeneity of tumors and HLA heterogeneity of individuals. The use of peptides of the disclosure in combination expands the group of individuals who can experience clinical benefit from vaccination. Multiple pharmaceutical compositions of peptides of the disclosure, manufactured for use in one regimen, may define a drug product.

Routes of administration include but are not limited to intranasal, oral, subcutaneous, intradermal, and intramuscular. The subcutaneous administration is particularly preferred. Subcutaneous administration may for example be by injection into the abdomen, lateral and anterior aspects of upper arm or thigh, scapular area of back, or upper ventrodorsal gluteal area.

The compositions of the disclosure may also be administered in one, or more doses, as well as, by other routes of administration. For example, such other routes include, intracutaneously, intravenously, intravascularly, intraarterially, intraperitnoeally, intrathecally, intratracheally, intracardially, intralobally, intramedullarly, intrapulmonarily, and intravaginally. Depending on the desired duration of the treatment, the compositions according to the disclosure may be administered once or several times, also intermittently, for instance on a monthly basis for several months or years and in different dosages.

Solid dosage forms for oral administration include capsules, tablets, caplets, pills, powders, pellets, and granules. In such solid dosage forms, the active ingredient is ordinarily combined with one or more pharmaceutically acceptable excipients, examples of which are detailed above. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof.

One or more compositions of the disclosure may be administered, or the methods and uses for treatment according to the disclosure may be performed, alone or in combination with other pharmacological compositions or treatments, for example chemotherapy and/or immunotherapy and/or vaccine. The other therapeutic compositions or treatments may for example be one or more of those discussed herein, and may be administered either simultaneously or sequentially with (before or after) the composition or treatment of the disclosure.

In some cases the treatment may be administered in combination with checkpoint blockade therapy, co-stimulatory antibodies, chemotherapy and/or radiotherapy, targeted therapy or monoclonal antibody therapy. It has been demonstrated that chemotherapy sensitizes tumors to be killed by tumor specific cytotoxic T cells induced by vaccination (Ramakrishnan et al. *J Clin Invest.* 2010; 120(4):1111-1124). Examples for checkpoint inhibitors are CTLA-4 inhibitor, Ipilimumab and programmed cell death-1/programmed cell death ligand-1 (PD-1/PD-L1) signaling inhibitors, Nibolumab, Pembrolizumab, Atezolizumab and Durvalumab. Examples of chemotherapy agents include alkylating agents including nitrogen mustards such as mechlorethamine (HN2), cyclophosphamide, ifosfamide, melphalan (L-sarcolysin) and chlorambucil; anthracyclines; epothilones; nitrosoureas such as carmustine (BCNU), lomustine (CCNU), semustine (methyl-CCNU) and streptozocin (streptozotocin); triazenes such as decarbazine (DTIC; dimethyltriazenoimidazole-carboxamide; ethylenimines/methylmelamines such as hexamethylmelamine, thiotepa; alkyl sulfonates such as busulfan; Antimetabolites including folic acid analogues such as methotrexate (amethopterin); alkylating agents, antimetabolites, pyrimidine analogs such as fluorouracil (5-fluorouracil; 5-FU), floxuridine (fluorodeoxyuridine; FUdR) and cytarabine (cytosine arabinoside); purine analogues and related inhibitors such as mercaptopurine (6-mercaptopurine; 6-MP), thioguanine (6-thioguanine; TG) and pentostatin (2'-deoxycoformycin); epipodophylotoxins; enzymes such as L-asparaginase; biological response modifiers such as IFNα, IL-2, G-CSF and GM-CSF; platinum coordination complexes such as cisplatin (cis-DDP), oxaliplatin and carboplatin; anthracenediones such as mitoxantrone and anthracycline; substituted urea such as hydroxyurea; methylhydrazine derivatives including procarbazine (N-methylhydrazine, MIH) and procarbazine; adrenocortical suppressants such as mitotane (o,p'-DDD) and aminoglutethimide; taxol and analogues/derivatives; hormones and agonists/antagonists including adrenocorticosteroid antagonists such as prednisone and equivalents, dexamethasone and aminoglutethimide, progestin such as hydroxyprogesterone caproate, medroxyprogesterone acetate and megestrol acetate, estrogen such as diethylstilbestrol and ethinyl estradiol equivalents, antiestrogen such as tamoxifen, androgens including testosterone propionate and fluoxymesterone/equivalents, antiandrogens such as flutamide, gonadotropin-releasing hormone analogs and leuprolide and non-steroidal antiandrogens such as flutamide; natural products including *vinca* alkaloids such as vinblastine (VLB) and vincristine, epipodophyllotoxins such as etoposide and teniposide, antibiotics such as dactinomycin (actinomycin D), daunorubicin (daunomycin; rubidomycin), doxorubicin, bleomycin, plicamycin (mithramycin) and mitomycin (mitomycin C), enzymes such as L-asparaginase, and biological response modifiers such as interferon alphenomes.

In some cases the method of treatment is a method of vaccination or a method of providing immunotherapy. As used herein, "immunotherapy" is the prevention or treatment of a disease or condition by inducing or enhancing an immune response in an individual. In certain embodiments, immunotherapy refers to a therapy that comprises the administration of one or more drugs to an individual to elicit T cell responses. In a specific embodiment, immunotherapy refers to a therapy that comprises the administration or expression of polypeptides that contain one or more PEPIs to an individual to elicit a T cell response to recognize and kill cells that display the one or more PEPIs on their cell surface in conjunction with a class I HLAs. In another specific embodiment, immunotherapy comprises the administration of one or more PEPIs to an individual to elicit a cytotoxic T cell response against cells that display tumor associated antigens (TAAs), tumor specific antigens (TSA) or cancer testis antigens (CTAs) comprising the one or more PEPIs on their cell surface. In another embodiment, immunotherapy refers to a therapy that comprises the administration or expression of polypeptides that contain one or more PEPIs presented by class II HLAs to an individual to elicit a CD4+ T helper or CD4+ killer cell response to provide co-stimulation to cytotoxic T cells that recognize and kill diseased cells that display the one or more PEPIs on their cell surface in conjunction with a class I HLAs. In still another specific embodiment, immunotherapy refers to a therapy that comprises administration of one or more drugs to an individual that re-activate existing T cells to kill target cells. The theory is that the cytotoxic T cell response will eliminate the cells displaying the one or more PEPIs, thereby improving the clinical condition of the individual. In some instances, immunotherapy may be used to treat tumors. In other instances, immunotherapy may be used to treat intracellular pathogen-based diseases or disorders.

In some cases the disclosure relates to the treatment of cancer or the treatment of solid tumors. In some cases the treatment is of gastric cancer, lung cancer, melanoma and/or bladder cancer. In other cases the treatment may be of any other cancer or solid tumor that expresses a target tumor associated antigen of the present peptides as described herein, or any cancer in which such target polypeptide antigens are expressed in some or a high percentage of subjects. The treatment may be of cancers or malignant or benign tumors of any cell, tissue, or organ type. The cancer may or may not be metastatic. Exemplary cancers include carcinomas, sarcomas, lymphomas, leukemias, germ cell tumors, or blastomas. The cancer may or may not be a hormone related or dependent cancer (e.g., an estrogen or androgen related cancer). The cancer may or may not be one that is associated with or caused by a viral infection and/or viral TAAs.

Selection of Polypeptides and Patients

Specific polypeptide antigens, and particularly short peptides derived from such antigens that are commonly used in vaccination and immunotherapy, induce immune responses in only a fraction of human subjects. The polypeptides of the present disclosure are specifically selected to induce immune responses in a high proportion of the general population, but they may not be effective in all individuals due to HLA genotype heterogeneity. HLA genotype population heterogeneity means that the immune or clinical response rate to the vaccines described herein will differ between different human subpopulations. In some cases the vaccines described herein are for use to treat a specific or target subpopulation, for example an Asian population, or a Vietnamese, Chinese, and/or Japanese population.

The disclosure also provides a method of identifying a human subject who will likely have a CD8+ or cytotoxic T cell response to administration of a pharmaceutical composition comprising a peptide of the disclosure (likely responders), or of predicting the likelihood that a subject will have a cytotoxic T cell response.

As provided herein T cell epitope presentation by multiple HLAs of an individual is generally needed to trigger a T cell response. The best predictor of a cytotoxic T cell response to a given polypeptide, as determined by the inventors, is the presence of at least one T cell epitope that is presented by three or more HLA class I of an individual (≥1 PEPI3+). Accordingly the presence within the active ingredient peptides of a pharmaceutical composition of one or more T cell epitopes that is capable of binding to at least three HLA of a subject is predictive for the subject having a cytotoxic T cell response to administration of the pharmaceutical composition. The subject is a likely immune responder.

In some cases the T cell epitope that is capable of binding to at least three HLA class I of the subject has the amino acid sequence of any one of SEQ ID NOs: 1 to 30. In other cases the T cell epitope may have a different amino acid sequence within the one or more peptides of the pharmaceutical composition.

The inventors have further discovered that the presence in a vaccine or immunotherapy composition of at least two epitopes that can bind to at least three HLA of an individual is predictive for a clinical response. In other words, if an individual has a total of ≥2 PEPI3+ within the active ingredient polypeptide(s) of a vaccine or immunotherapy composition, and these PEPI3+s are derived from antigen sequences that are in fact expressed in the individual (for example, target tumor cells of the individual express the target tumor-associated antigens), then the individual is a likely clinical responder (i.e. a clinically relevant immune responder).

Accordingly some aspects of the disclosure relate to a method of identifying a subject who will likely have a clinical response to a method of treatment according to the disclosure, or of predicting the likelihood that a subject will have a clinical response. A "clinical response" or "clinical benefit" as used herein may be the prevention or a delay in the onset of a disease or condition, the amelioration of one or more symptoms, the induction or prolonging of remission, or the delay of a relapse or recurrence or deterioration, or any other improvement or stabilisation in the disease status of a subject. Where appropriate, a "clinical response" may correlate to "disease control" or an "objective response" as defined by the Response Evaluation Criteria In Solid Tumors (RECIST) guidelines.

In some embodiments the method comprises determining that one or more cancer-associated antigens selected from gastric cancer antigens DPPA2, CAGE-1, TSP50, HIWI, SURVIVIN, 5T4, PRAME, KK-LC-1, MAGE-A2, MAGE-A3, LAGE-1, MAGE-A10, MAGE-A1 SSX1, and/or lung cancer antigens BRDT, PRAME, NALP4, MAGE-A12, MAGE-A2, SURVIVIN, DPPA2, NY-SAR-35, LDHC, MAGE-C2, MAGE-A3, KK-LC-1, MAGE-A1, and/or melanoma cancer antigens PRAME, MAGE-A2, MAGE-C1, SURVIVIN, MAGE-A12, Ny-ESO-1, MAGE-C2, MAGE-A6, BORIS, LAGE-1, MAGE-A11, SSX-1, MAGE-A3, MAGE-A10, MAGE-A1, and/or bladder cancer antigens PIWIL2, CTAGE1, MAGE-A9, EpCAM, OY-TES-1, NY-ESO-1, SURVIVIN, MAGE-C1, MAGE-A2, LAGE-1, MAGE-A3, MAGE-A8 and HAGE, MAGE-A1, MAGE-C2, MAGE-A10 and MAGE-A12 is expressed by a cancer. For example expression of the cancer associated antigen may be detected in a sample obtained from the subject, for example a tumor biopsy, using methods that are known in the art.

The inventors have discovered that it is not sufficient that a vaccine or immunotherapy composition targets an antigen that is expressed by cancer or tumor cells of a patient, nor that the target sequences of that antigen can bind to HLA class I of the patient (HLA restricted epitopes). The composition is likely effective only in patients that both express the target antigen and have three or more different HLA class I molecules that bind to the same sequence T cell epitope of the target antigen. Moreover, as described above, at least two epitopes that binds to at least 3 HLAs of the patient are generally needed to induce a clinically relevant immune response.

Therefore the method further comprises determining that the active ingredient peptide(s) of the pharmaceutical composition comprise two or more different amino acid sequences each of which is a) a fragment of a cancer-associated antigen expressed by cancer cells of the subject, determined as described above; and b) a T cell epitope capable of binding to at least three HLA class I molecules of the subject.

In some cases the likelihood that a subject will have a clinical response to a peptide vaccine or immunotherapy composition, such as those described herein, can be determined without knowing whether the target antigens are expressed in cancer or tumor cells of the subject and/or without determining the HLA class I genotype of the subject. Known antigen expression frequencies in the disease (e.g. MAGE-A3 in a tumor type like gastric cancer, lung cancer, melanoma or bladder cancer) and/or known frequencies for HLA class I and class II genotype of subjects in the target population (e.g ethnic population, general population, diseased population) may be used instead. Moreover by combining peptides that target the most frequently presented PEPIs across the population (BestEPIs) in multiple frequently expressed target antigens in the disease, as identified and described herein, it is possible to design a cancer vaccine regime that is effective for a high proportion of patients. However, using the companion diagnostic methods described herein to pre-select patients who are most likely to have a clinical response will increase clinical response rates amongst treated patients.

The likelihood that a subject will respond to treatment is increased by (i) the presence of more multiple HLA-binding PEPIs in the active ingredient polypeptides; (ii) the presence of PEPIs in more target polypeptide antigens; and (iii) expression of the target polypeptide antigens in the subject or in diseased cells of the subject. In some cases expression of the target polypeptide antigens in the subject may be known, for example if target polypeptide antigens are in a sample obtained from the subject. In other cases, the probability that a specific subject, or diseased cells of a specific subject, (over-)express a specific or any combination of target polypeptide antigens may be determined using population expression frequency data, e.g. probability of expression of an antigen in gastric cancer, lung cancer, melanoma or bladder cancer. The population expression frequency data may relate to a subject- and/or disease-matched population or the intent-to-treat population. For example, the frequency or probability of expression of a particular cancer-associated antigen in a particular cancer or subject having a particular cancer, for example gastric cancer, can be determined by detecting the antigen in tumor, e.g. gastric cancer tumor samples. In some cases such expression frequencies may be determined from published figures and scientific publications. In some cases a method of the disclosure comprises a step of determining the expression frequency of a relevant target polypeptide antigen in a relevant population.

Disclosed is a range of pharmacodynamic biomarkers to predict the activity/effect of vaccines in individual human subjects as well as in populations of human subjects. These biomarkers expedite more effective vaccine development and also decrease the development cost and may be used to assess and compare different compositions. Exemplary biomarkers are as follows.

AG95 or AG50—potency of a vaccine: The number of antigens in a cancer vaccine that a specific tumor type expresses with 95% or 50% probability. AG95 and AG50 are indicators of the vaccine's potency, and are independent of the immunogenicity of the vaccine antigens. AG95 and AG50 are calculated from the tumor antigen expression rate data. Such data may be obtained from experiments published in peer reviewed scientific journals. Technically, AG95 and AG50 are determined from the binomial distribution of antigens in the vaccine, and takes into account all possible variations and expression rates.

PEPI3+ count—immunogenicity of a vaccine in a subject: Vaccine-derived PEPI3+ are personal epitopes that bind to at least 3 HLAs of a subject and induce T cell responses. PEPI3+ can be determined using the PEPI3+ Test in subjects whose complete 4-digit HLA genotype is known.

AP count—antigenicity of a vaccine in a subject: Number of vaccine antigens with PEPI3+. Vaccines contain sequences from target polypeptide antigens expressed by diseased cells. AP count is the number of antigens in the vaccine that contain PEPI3+, and the AP count represents the number of antigens in the vaccine that can induce T cell responses in a subject. AP count characterizes the vaccine-antigen specific T cell responses of the subject since it depends only on the HLA genotype of the subject and is independent of the subject's disease, age, and medication. The correct value is between 0 (no PEPI presented by the antigen) and maximum number of antigens (all antigens present PEPIs).

AP50—antigenicity of a vaccine in a population: The mean number of vaccine antigens with a PEPI in a population. The AP50 is suitable for the characterization of vaccine-antigen specific T cell responses in a given population since it depends on the HLA genotype of subjects in a population.

AGP count—effectiveness of a vaccine in a subject: Number of vaccine antigens expressed in the tumor with PEPI. The AGP count indicates the number of tumor antigens that vaccine recognizes and induces a T cell response against (hit the target). The AGP count depends on the vaccine-antigen expression rate in the subject's tumor and the HLA genotype of the subject. The correct value is between 0 (no PEPI presented by expressed antigen) and maximum number of antigens (all antigens are expressed and present a PEPI).

AGP50—effectiveness of a cancer vaccine in a population: The mean number of vaccine antigens expressed in the indicated tumor with PEPI (i.e., AGP) in a population. The AGP50 indicates the mean number of tumor antigens that the T cell responses induced by the vaccine can recognize. AGP50 is dependent on the expression rate of the antigens in the indicated tumor type and the immunogenicity of the antigens in the target population. AGP50 can estimate a vaccine's effectiveness in different populations and can be used to compare different vaccines in the same population. The computation of AGP50 is similar to that used for AG50, except the expression is weighted by the occurrence of the PEPI3+ in the subject on the expressed vaccine antigens. In a theoretical population, where each subject has a PEPI from each vaccine antigen, the AGP50 will be equal to AG50. In another theoretical population, where no subject has a PEPI from any vaccine antigen, the AGP50 will be 0. In general, the following statement is valid: $0 \leq AGP50 \leq AG50$.

mAGP—a candidate biomarker for the selection of likely responders: Likelihood that a cancer vaccine induces T cell responses against multiple antigens expressed in the indicated tumor. mAGP is calculated from the expression rates of vaccine-antigens in the tumor and the presence of vaccine derived PEPIs in the subject. Technically, based on the AGP distribution, the mAGP is the sum of probabilities of the multiple AGP ($\geq 2$ AGPs).

The results of a prediction as set out above may be used to inform a physician's decisions concerning treatment of the subject. Accordingly, in some cases the method of the disclosure predicts that a subject will have or is likely to have a T cell response and/or a clinical response to a treatment as described herein, and the method further comprises selecting the treatment for the human subject. In some cases a subject is selected for treatment if their likelihood of a response targeted at a predefined number of target polypeptide antigens, optionally wherein the target polypeptide antigens are (predicted to be) expressed, is above a predetermined threshold. In some cases the number of target polypeptide antigens or epitopes is two. In some cases the number of target polypeptide antigens or epitopes is three, or four, or five, or six, or seven, or eight, or nine, or ten. The method may further comprise administering the treatment to the human subject. Alternatively, the method may predict that the subject will not have an immune response and/or a clinical response and further comprise selecting a different treatment for the subject.

Further Embodiments of the Disclosure—(1A)—Gastric Cancer

1. A pharmaceutical composition comprising one or more peptides, wherein each peptide comprises a different one of the amino acid sequence of any one of SEQ ID NOs: 61 to 75.
2. The pharmaceutical composition of item 1, comprising 2 or more peptides, 3 or more peptides, 4 or more peptides, 5 or more peptides, 6 or more peptides, 7 or more peptides, 8 or more peptides, 9 or more peptides, 10 or more peptides, 11 or more peptides, or 12 or more peptides.
3. The pharmaceutical composition of item 1, further comprising at least one additional peptide comprising a fragment of an antigen selected from DPPA2, CAGE-1, TSP50, HIWI, SURVIVIN, 5T4, PRAME, KK-LC-1, MAGE-A2, MAGE-A3, LAGE-1, MAGE-A10, MAGE-A1 and SSX1.
4. The pharmaceutical composition of item 3, wherein the fragment of an antigen comprises an amino acid sequence selected from any one of SEQ ID NOs: 1 to 30.
5. The pharmaceutical composition of item 3, wherein the fragment of an antigen comprises an amino acid sequence selected from any one of SEQ ID NOs: 31-60.
6. The pharmaceutical composition of item 1, further comprising a pharmaceutically acceptable adjuvant, diluent, carrier, preservative, or combination thereof.
7. The pharmaceutical composition of item 6, wherein the adjuvant is selected from the group consisting of Montanide ISA-51, QS-21, GM-CSF, cyclophosamide, bacillus Calmette-Guerin (BCG), corynbacterium parvum, levamisole, azimezone, isoprinisone, dinitrochlorobenezene (DNCB), keyhole limpet hemocyanins (KLH), Freunds adjuvant (complete), Freunds adjuvant (incomplete), mineral gels, aluminum hydroxide (Alum), lysolecithin, pluronic polyols, polyanions, oil emulsions, dinitrophenol, diphtheria toxin (DT), and combinations thereof.

8. A pharmaceutical composition comprising one or more nucleic acid molecules encoding one or more peptides, wherein each peptide comprises a different one of the amino acid sequence of any one of SEQ ID NOs:61 to 75.

9. The pharmaceutical composition of item 8, wherein the one or more nucleic acid molecules encode 2 or more peptides, 3 or more peptides, 4 or more peptides, 5 or more peptides, 6 or more peptides, 7 or more peptides, 8 or more peptides, 9 or more peptides, 10 or more peptides, 11 or more peptides, or 12 or more peptides.

10. The pharmaceutical composition of item 8, wherein the one or more nucleic acid molecules encode at least one additional peptide comprising a fragment of an antigen selected from DPPA2, CAGE-1, TSP50, HIWI, SURVIVIN, 5T4, PRAME, KK-LC-1, MAGE-A2, MAGE-A3, LAGE-1, MAGE-A10, MAGE-A1 and SSX1.

11. The pharmaceutical composition of item 10, wherein the fragment of an antigen comprises an amino acid sequence selected from any one of SEQ ID NOs: 1 to 30.

12. The pharmaceutical composition of item 10, wherein the fragment of an antigen comprises an amino acid sequence selected from any one of SEQ ID NOs:31-60.

13. The pharmaceutical composition of item 8, further comprising a pharmaceutically acceptable adjuvant, diluent, carrier, preservative, or combination thereof.

14. The pharmaceutical composition of item 13, wherein the adjuvant is selected from the group consisting of Montanide ISA-51, QS-21, GM-CSF, cyclophosamide, bacillus Calmette-Guerin (BCG), corynbacterium parvum, levamisole, azimezone, isoprinisone, dinitrochlorobenezene (DNCB), keyhole limpet hemocyanins (KLH), Freunds adjuvant (complete), Freunds adjuvant (incomplete), mineral gels, aluminum hydroxide (Alum), lysolecithin, pluronic polyols, polyanions, oil emulsions, dinitrophenol, diphtheria toxin (DT), and combinations thereof.

15. A method of identifying and treating a human subject having cancer who will likely have a clinical response to administration of a pharmaceutical composition according to item 1, the method comprising
    (i) assaying a biological sample of the subject to determine HLA genotype of the subject;
    (ii) determining that the pharmaceutical composition comprises two or more sequences that are a T cell epitope capable of binding to at least three HLA class I molecules of the subject;
    (iii) determining the probability that a tumor of the subject expresses one or more antigen corresponding to the T cell epitopes identified in step (ii) using population expression data for each antigen, to identify the likelihood of the subject to have a clinical response to administration of the pharmaceutical composition; and
    (iv) administering the composition of item 1 to the identified subject.

16. The method of item 15, wherein the subject has gastric cancer.

17. The method of item 15, wherein the pharmaceutical composition comprises 2 or more peptides, 3 or more peptides, 4 or more peptides, 5 or more peptides, 6 or more peptides, 7 or more peptides, 8 or more peptides, 9 or more peptides, 10 or more peptides, 11 or more peptides, or 12 or more peptides.

18. The method of item 15, wherein the pharmaceutical composition further comprises at least one additional peptide comprising a fragment of an antigen selected from DPPA2, CAGE-1, TSP50, HIWI, SURVIVIN, 5T4, PRAME, KK-LC-1, MAGE-A2, MAGE-A3, LAGE-1, MAGE-A10, MAGE-A1 and SSX1.

19. The method of item 18, wherein the fragment of an antigen comprises an amino acid sequence selected from any one of SEQ ID NOs: 1 to 30.

20. The method of item 18, wherein the fragment of an antigen comprises an amino acid sequence selected from any one of SEQ ID NOs: 31-60.

21. The method of item 15, wherein the pharmaceutical composition further comprises a pharmaceutically acceptable adjuvant, diluent, carrier, preservative, or combination thereof.

22. The method of item 21, wherein the adjuvant is selected from the group consisting of Montanide ISA-51, QS-21, GM-CSF, cyclophosamide, bacillus Calmette-Guerin (BCG), corynbacterium parvum, levamisole, azimezone, isoprinisone, dinitrochlorobenezene (DNCB), keyhole limpet hemocyanins (KLH), Freunds adjuvant (complete), Freunds adjuvant (incomplete), mineral gels, aluminum hydroxide (Alum), lysolecithin, pluronic polyols, polyanions, oil emulsions, dinitrophenol, diphtheria toxin (DT), and combinations thereof.

23. The method of item 15, further comprising administering a chemotherapeutic agent, a checkpoint inhibitor, a targeted therapy, radiation therapy, another immunotherapy, neoadjuvant therapy or combination thereof to the identified subject.

24. The method of item 15, further comprising prior to the administering step,
    (i) assaying a tumor sample from the subject to determine that the three or more peptides of the pharmaceutical composition comprise two or more different amino acid sequences each of which is
       a. a fragment of a cancer-associated antigen expressed by cancer cells of the subject as determined in step (i); and
       b. a T cell epitope capable of binding to at least three HLA class I molecules of the subject; and
    (ii) confirming the subject as likely to have a clinical response to the method of treatment.

25. A method of identifying and treating a human subject having cancer who will likely have an immune response to administration of a pharmaceutical composition according to item 1, the method comprising
    (i) assaying a biological sample of the subject to determine HLA genotype of the subject;
    (ii) determining that the pharmaceutical composition comprises one or more sequences that are a T cell epitope capable of binding to at least three HLA class I molecules of the subject; and
    (iii) administering the composition of item 1 to the identified subject.

26. A kit comprising:
    a. a first pharmaceutical composition comprising one or more peptides, wherein each peptide comprises a different one of the amino acid sequence of any one of SEQ ID NOs: 61 to 75; and
    b. a second different pharmaceutical composition comprising one or more peptides, wherein each peptide comprises a different one of the amino acid sequence of any one of SEQ ID NOs: 61 to 75.

27. A pharmaceutical composition comprising: a nucleic acid molecule expressing two or more polypeptides, each polypeptide comprising a fragment of up to 50 consecutive amino acids of an antigen selected from DPPA2, CAGE-1, TSP50, HIWI, SURVIVIN, 5T4, PRAME, KK-LC-1, MAGE-A2, MAGE-A3, LAGE-1, MAGE-A10, MAGE-A1 and SSX1, wherein each fragment comprises a different amino acid sequence selected from any one of SEQ ID NOs: 1 to 30.

Further Embodiments of the
Disclosure—(1B)—Lung Cancer

1. A pharmaceutical composition comprising one or more peptides, wherein each peptide comprises a different one of the amino acid sequence of any one of SEQ ID NOs: 150 to 164.
2. The pharmaceutical composition of item 1, comprising 2 or more peptides, 3 or more peptides, 4 or more peptides, 5 or more peptides, 6 or more peptides, 7 or more peptides, 8 or more peptides, 9 or more peptides, 10 or more peptides, 11 or more peptides, or 12 or more peptides.
3. The pharmaceutical composition of item 1, further comprising at least one additional peptide comprising a fragment of an antigen selected from BRDT, PRAME, NALP4, MAGE-A12, MAGE-A2, SURVIVIN, DPPA2, NY-SAR-35, LDHC, MAGE-C2, MAGE-A3, KK-LC-1 and MAGE-A1.
4. The pharmaceutical composition of item 3, wherein the fragment of an antigen comprises an amino acid sequence selected from any one of SEQ ID NOs: 90 to 119.
5. The pharmaceutical composition of item 3, wherein the fragment of an antigen comprises an amino acid sequence selected from any one of SEQ ID NOs: 120 to 149.
6. The pharmaceutical composition of item 1, further comprising a pharmaceutically acceptable adjuvant, diluent, carrier, preservative, or combination thereof.
7. The pharmaceutical composition of item 6, wherein the adjuvant is selected from the group consisting of Montanide ISA-51, QS-21, GM-CSF, cyclophosamide, bacillus Calmette-Guerin (BCG), corynbacterium parvum, levamisole, azimezone, isoprinisone, dinitrochlorobenezene (DNCB), keyhole limpet hemocyanins (KLH), Freunds adjuvant (complete), Freunds adjuvant (incomplete), mineral gels, aluminum hydroxide (Alum), lysolecithin, pluronic polyols, polyanions, oil emulsions, dinitrophenol, diphtheria toxin (DT), and combinations thereof.
8. A pharmaceutical composition comprising one or more nucleic acid molecules encoding one or more peptides, wherein each peptide comprises a different one of the amino acid sequence of any one of SEQ ID NOs: 150 to 164.
9. The pharmaceutical composition of item 8, wherein the one or more nucleic acid molecules encode 2 or more peptides, 3 or more peptides, 4 or more peptides, 5 or more peptides, 6 or more peptides, 7 or more peptides, 8 or more peptides, 9 or more peptides, 10 or more peptides, 11 or more peptides, or 12 or more peptides.
10. The pharmaceutical composition of item 8, wherein the one or more nucleic acid molecules encode at least one additional peptide comprising a fragment of an antigen selected from BRDT, PRAME, NALP4, MAGE-A12, MAGE-A2, SURVIVIN, DPPA2, NY-SAR-35, LDHC, MAGE-C2, MAGE-A3, KK-LC-1 and MAGE-A1.
11. The pharmaceutical composition of item 10, wherein the fragment of an antigen comprises an amino acid sequence selected from any one of SEQ ID NOs: 90 to 119.
12. The pharmaceutical composition of item 10, wherein the fragment of an antigen comprises an amino acid sequence selected from any one of SEQ ID NOs: 120 to 149.
13. The pharmaceutical composition of item 8, further comprising a pharmaceutically acceptable adjuvant, diluent, carrier, preservative, or combination thereof.
14. The pharmaceutical composition of item 13, wherein the adjuvant is selected from the group consisting of Montanide ISA-51, QS-21, GM-CSF, cyclophosamide, bacillus Calmette-Guerin (BCG), corynbacterium parvum, levamisole, azimezone, isoprinisone, dinitrochlorobenezene (DNCB), keyhole limpet hemocyanins (KLH), Freunds adjuvant (complete), Freunds adjuvant (incomplete), mineral gels, aluminum hydroxide (Alum), lysolecithin, pluronic polyols, polyanions, oil emulsions, dinitrophenol, diphtheria toxin (DT), and combinations thereof.
15. A method of identifying and treating a human subject having cancer who will likely have a clinical response to administration of a pharmaceutical composition according to item 1, the method comprising
  (i) assaying a biological sample of the subject to determine HLA genotype of the subject;
  (ii) determining that the pharmaceutical composition comprises two or more sequences that are a T cell epitope capable of binding to at least three HLA class I molecules of the subject;
  (iii) determining the probability that a tumor of the subject expresses one or more antigen corresponding to the T cell epitopes identified in step (ii) using population expression data for each antigen, to identify the likelihood of the subject to have a clinical response to administration of the pharmaceutical composition; and
  (iv) administering the composition of item 1 to the identified subject.
16. The method of item 15, wherein the subject has lung cancer.
17. The method of item 15, wherein the pharmaceutical composition comprises 2 or more peptides, 3 or more peptides, 4 or more peptides, 5 or more peptides, 6 or more peptides, 7 or more peptides, 8 or more peptides, 9 or more peptides, 10 or more peptides, 11 or more peptides, or 12 or more peptides.
18. The method of item 15, wherein the pharmaceutical composition further comprises comprising at least one additional peptide comprising a fragment of an antigen selected from BRDT, PRAME, NALP4, MAGE-A12, MAGE-A2, SURVIVIN, DPPA2, NY-SAR-35, LDHC, MAGE-C2, MAGE-A3, KK-LC-1 and MAGE-A1.
19. The method of item 18, wherein the fragment of an antigen comprises an amino acid sequence selected from any one of SEQ ID NOs: 90 to 119.
20. The method of item 18, wherein the fragment of an antigen comprises an amino acid sequence selected from any one of SEQ ID NOs: 120 to 149.
21. The method of item 15, wherein the pharmaceutical composition further comprises a pharmaceutically acceptable adjuvant, diluent, carrier, preservative, or combination thereof.
22. The method of item 21, wherein the adjuvant is selected from the group consisting of Montanide ISA-51, QS-21, GM-CSF, cyclophosamide, bacillus Calmette-Guerin (BCG), corynbacterium parvum, levamisole, azimezone, isoprinisone, dinitrochlorobenezene (DNCB), keyhole limpet hemocyanins (KLH), Freunds adjuvant (complete), Freunds adjuvant (incomplete), mineral gels, aluminum hydroxide (Alum), lysolecithin, pluronic polyols, polyanions, oil emulsions, dinitrophenol, diphtheria toxin (DT), and combinations thereof.

23. The method of item 15, further comprising administering a chemotherapeutic agent, a checkpoint inhibitor, a targeted therapy, radiation therapy, another immunotherapy, neoadjuvant therapy or combination thereof to the identified subject.

24. The method of item 15, further comprising prior to the administering step,
   (i) assaying a tumor sample from the subject to determine that the three or more peptides of the pharmaceutical composition comprise two or more different amino acid sequences each of which is
      a. a fragment of a cancer-associated antigen expressed by cancer cells of the subject as determined in step (i); and
      b. a T cell epitope capable of binding to at least three HLA class I molecules of the subject; and
   (ii) confirming the subject as likely to have a clinical response to the method of treatment.

25. A method of identifying and treating a human subject having cancer who will likely have an immune response to administration of a pharmaceutical composition according to item 1, the method comprising
   (i) assaying a biological sample of the subject to determine HLA genotype of the subject;
   (ii) determining that the pharmaceutical composition comprises one or more sequences that are a T cell epitope capable of binding to at least three HLA class I molecules of the subject; and
   (iii) administering the composition of item 1 to the identified subject.

26. A kit comprising:
   a. a first pharmaceutical composition comprising one or more peptides, wherein each peptide comprises a different one of the amino acid sequence of any one of SEQ ID NOs: 150 to 164; and
   b. a second different pharmaceutical composition comprising one or more peptides, wherein each peptide comprises a different one of the amino acid sequence of any one of SEQ ID NOs: 150 to 164.

27. A pharmaceutical composition comprising: a nucleic acid molecule expressing two or more polypeptides, each polypeptide comprising a fragment of up to 50 consecutive amino acids of an antigen selected from BRDT, PRAME, NALP4, MAGE-A12, MAGE-A2, SURVIVIN, DPPA2, NY-SAR-35, LDHC, MAGE-C2, MAGE-A3, KK-LC-1 and MAGE-A1, wherein each fragment comprises a different amino acid sequence selected from any one of SEQ ID NOs: 90 to 119.

Further Embodiments of the
Disclosure—(IC)—Melanoma

1. A pharmaceutical composition comprising one or more peptides, wherein each peptide comprises a different one of the amino acid sequence of any one of SEQ ID NOs: 238 to 252.

2. The pharmaceutical composition of item 1, comprising 2 or more peptides, 3 or more peptides, 4 or more peptides, 5 or more peptides, 6 or more peptides, 7 or more peptides, 8 or more peptides, 9 or more peptides, 10 or more peptides, 11 or more peptides, or 12 or more peptides.

3. The pharmaceutical composition of item 1, further comprising at least one additional peptide comprising a fragment of an antigen selected from PRAME, MAGE-A2, MAGE-C1, SURVIVIN, MAGE-A12, Ny-ESO-1, MAGE-C2, MAGE-A6, BORIS, LAGE-1, MAGE-A11, SSX-1, MAGE-A3, MAGE-A10 and MAGE-A1.

4. The pharmaceutical composition of item 3, wherein the fragment of an antigen comprises an amino acid sequence selected from any one of SEQ ID NOs: 178 to 207.

5. The pharmaceutical composition of item 3, wherein the fragment of an antigen comprises an amino acid sequence selected from any one of SEQ ID NOs: 208 to 237.

6. The pharmaceutical composition of item 1, further comprising a pharmaceutically acceptable adjuvant, diluent, carrier, preservative, or combination thereof.

7. The pharmaceutical composition of item 6, wherein the adjuvant is selected from the group consisting of Montanide ISA-51, QS-21, GM-CSF, cyclophosamide, bacillus Calmette-Guerin (BCG), corynbacterium parvum, levamisole, azimezone, isoprinisone, dinitrochlorobenezene (DNCB), keyhole limpet hemocyanins (KLH), Freunds adjuvant (complete), Freunds adjuvant (incomplete), mineral gels, aluminum hydroxide (Alum), lysolecithin, pluronic polyols, polyanions, oil emulsions, dinitrophenol, diphtheria toxin (DT), and combinations thereof.

8. A pharmaceutical composition comprising one or more nucleic acid molecules encoding one or more peptides, wherein each peptide comprises a different one of the amino acid sequence of any one of SEQ ID NOs:61 to 75.

9. The pharmaceutical composition of item 8, wherein the one or more nucleic acid molecules encode 2 or more peptides, 3 or more peptides, 4 or more peptides, 5 or more peptides, 6 or more peptides, 7 or more peptides, 8 or more peptides, 9 or more peptides, 10 or more peptides, 11 or more peptides, or 12 or more peptides.

10. The pharmaceutical composition of item 8, wherein the one or more nucleic acid molecules encode at least one additional peptide comprising a fragment of an antigen selected from PRAME, MAGE-A2, MAGE-C1, SURVIVIN, MAGE-A12, Ny-ESO-1, MAGE-C2, MAGE-A6, BORIS, LAGE-1, MAGE-A11, SSX-1, MAGE-A3, MAGE-A10 and MAGE-A1.

11. The pharmaceutical composition of item 10, wherein the fragment of an antigen comprises an amino acid sequence selected from any one of SEQ ID NOs: 178 to 207.

12. The pharmaceutical composition of item 10, wherein the fragment of an antigen comprises an amino acid sequence selected from any one of SEQ ID NOs: 208 to 237.

13. The pharmaceutical composition of item 8, further comprising a pharmaceutically acceptable adjuvant, diluent, carrier, preservative, or combination thereof.

14. The pharmaceutical composition of item 13, wherein the adjuvant is selected from the group consisting of Montanide ISA-51, QS-21, GM-CSF, cyclophosamide, bacillus Calmette-Guerin (BCG), corynbacterium parvum, levamisole, azimezone, isoprinisone, dinitrochlorobenezene (DNCB), keyhole limpet hemocyanins (KLH), Freunds adjuvant (complete), Freunds adjuvant (incomplete), mineral gels, aluminum hydroxide (Alum), lysolecithin, pluronic polyols, polyanions, oil emulsions, dinitrophenol, diphtheria toxin (DT), and combinations thereof.

15. A method of identifying and treating a human subject having cancer who will likely have a clinical response to administration of a pharmaceutical composition according to item 1, the method comprising (i) assaying a biological sample of the subject to determine HLA genotype of the subject;
(ii) determining that the pharmaceutical composition comprises two or more sequences that are a T cell epitope capable of binding to at least three HLA class I molecules of the subject;
(iii) determining the probability that a tumor of the subject expresses one or more antigen corresponding to the T cell epitopes identified in step (ii) using population expression data for each antigen, to identify the likelihood of the subject to have a clinical response to administration of the pharmaceutical composition; and
(iv) administering the composition of item 1 to the identified subject.

16. The method of item 15, wherein the subject has melanoma.
17. The method of item 15, wherein the pharmaceutical composition comprises 2 or more peptides, 3 or more peptides, 4 or more peptides, 5 or more peptides, 6 or more peptides, 7 or more peptides, 8 or more peptides, 9 or more peptides, 10 or more peptides, 11 or more peptides, or 12 or more peptides.
18. The method of item 15, wherein the pharmaceutical composition further comprises at least one additional peptide comprising a fragment of an antigen selected from PRAME, MAGE-A2, MAGE-C1, SURVIVIN, MAGE-A12, Ny-ESO-1, MAGE-C2, MAGE-A6, BORIS, LAGE-1, MAGE-A11, SSX-1, MAGE-A3, MAGE-A10 and MAGE-A1.
19. The method of item 18, wherein the fragment of an antigen comprises an amino acid sequence selected from any one of SEQ ID NOs:178 to 207.
20. The method of item 18, wherein the fragment of an antigen comprises an amino acid sequence selected from any one of SEQ ID NOs:208 to 237.
21. The method of item 15, wherein the pharmaceutical composition further comprises a pharmaceutically acceptable adjuvant, diluent, carrier, preservative, or combination thereof.
22. The method of item 21, wherein the adjuvant is selected from the group consisting of Montanide ISA-51, QS-21, GM-CSF, cyclophosamide, bacillus Calmette-Guerin (BCG), corynbacterium parvum, levamisole, azimezone, isoprinisone, dinitrochlorobenezene (DNCB), keyhole limpet hemocyanins (KLH), Freunds adjuvant (complete), Freunds adjuvant (incomplete), mineral gels, aluminum hydroxide (Alum), lysolecithin, pluronic polyols, polyanions, oil emulsions, dinitrophenol, diphtheria toxin (DT), and combinations thereof.
23. The method of item 15, further comprising administering a chemotherapeutic agent, a checkpoint inhibitor, a targeted therapy, radiation therapy, another immunotherapy, neoadjuvant therapy or combination thereof to the identified subject.
24. The method of item 15, further comprising prior to the administering step,
(iii) assaying a tumor sample from the subject to determine that the three or more peptides of the pharmaceutical composition comprise two or more different amino acid sequences each of which is
c. a fragment of a cancer-associated antigen expressed by cancer cells of the subject as determined in step (i); and
d. a T cell epitope capable of binding to at least three HLA class I molecules of the subject; and
(iv) confirming the subject as likely to have a clinical response to the method of treatment.

25. A method of identifying and treating a human subject having cancer who will likely have an immune response to administration of a pharmaceutical composition according to item 1, the method comprising
(i) assaying a biological sample of the subject to determine HLA genotype of the subject;
(ii) determining that the pharmaceutical composition comprises one or more sequences that are a T cell epitope capable of binding to at least three HLA class I molecules of the subject; and
(iii) administering the composition of item 1 to the identified subject.
26. A kit comprising:
a. a first pharmaceutical composition comprising one or more peptides, wherein each peptide comprises a different one of the amino acid sequence of any one of SEQ ID NOs: 238 to 267; and
b. a second different pharmaceutical composition comprising one or more peptides, wherein each peptide comprises a different one of the amino acid sequence of any one of SEQ ID NOs: 238 to 267.
27. A pharmaceutical composition comprising: a nucleic acid molecule expressing two or more polypeptides, each polypeptide comprising a fragment of up to 50 consecutive amino acids of an antigen selected from PRAME, MAGE-A2, MAGE-C1, SURVIVIN, MAGE-A12, Ny-ESO-1, MAGE-C2, MAGE-A6, BORIS, LAGE-1, MAGE-A11, SSX-1, MAGE-A3, MAGE-A10 and MAGE-A1, wherein each fragment comprises a different amino acid sequence selected from any one of SEQ ID NOs:178 to 207.

Further Embodiments of the Disclosure—(1D)—Bladder Cancer

1. A pharmaceutical composition comprising one or more peptides, wherein each peptide comprises a different one of the amino acid sequence of any one of SEQ ID NOs: 328 to 342.
2. The pharmaceutical composition of item 1, comprising 2 or more peptides, 3 or more peptides, 4 or more peptides, 5 or more peptides, 6 or more peptides, 7 or more peptides, 8 or more peptides, 9 or more peptides, 10 or more peptides, 11 or more peptides, or 12 or more peptides.
3. The pharmaceutical composition of item 1, further comprising at least one additional peptide comprising a fragment of an antigen selected from PIWIL2, CTAGE1, MAGE-A9, EpCAM, OY-TES-1, NY-ESO-1, SURVIVIN, MAGE-C1, MAGE-A2, LAGE-1, MAGE-A3, MAGE-A8, HAGE, MAGE-A1, MAGE-C2, MAGE-A10 and MAGE-A12.
4. The pharmaceutical composition of item 3, wherein the fragment of an antigen comprises an amino acid sequence selected from any one of SEQ ID NOs: 268 to 297.
5. The pharmaceutical composition of item 3, wherein the fragment of an antigen comprises an amino acid sequence selected from any one of SEQ ID NOs: 298 to 327.
6. The pharmaceutical composition of item 1, further comprising a pharmaceutically acceptable adjuvant, diluent, carrier, preservative, or combination thereof.
7. The pharmaceutical composition of item 6, wherein the adjuvant is selected from the group consisting of Montanide ISA-51, QS-21, GM-CSF, cyclophosamide, bacillus Calmette-Guerin (BCG), corynbacterium parvum, levamisole, azimezone, isoprinisone, dinitrochlorobenezene (DNCB), keyhole limpet hemocyanins (KLH), Freunds adjuvant (complete), Freunds adjuvant (incomplete), mineral gels, aluminum hydroxide (Alum), lysolecithin, pluronic polyols, polyanions, oil emulsions, dinitrophenol, diphtheria toxin (DT), and combinations thereof.
8. A pharmaceutical composition comprising one or more nucleic acid molecules encoding one or more peptides, wherein each peptide comprises a different one of the amino acid sequence of any one of SEQ ID NOs: 328 to 342.
9. The pharmaceutical composition of item 8, wherein the one or more nucleic acid molecules encode 2 or more peptides, 3 or more peptides, 4 or more peptides, 5 or more peptides, 6 or more peptides, 7 or more peptides, 8 or more peptides, 9 or more peptides, 10 or more peptides, 11 or more peptides, or 12 or more peptides.
10. The pharmaceutical composition of item 8, wherein the one or more nucleic acid molecules encode at least one additional peptide comprising a fragment of an antigen selected from PIWIL2, CTAGE1, MAGE-A9, EpCAM, OY-TES-1, NY-ESO-1, SURVIVIN, MAGE-C1, MAGE-A2, LAGE-1, MAGE-A3, MAGE-A8, HAGE, MAGE-A1, MAGE-C2, MAGE-A10 and MAGE-A12.
11. The pharmaceutical composition of item 10, wherein the fragment of an antigen comprises an amino acid sequence selected from any one of SEQ ID NOs: 268 to 297.
12. The pharmaceutical composition of item 10, wherein the fragment of an antigen comprises an amino acid sequence selected from any one of SEQ ID NOs: 298 to 327.
13. The pharmaceutical composition of item 8, further comprising a pharmaceutically acceptable adjuvant, diluent, carrier, preservative, or combination thereof.
14. The pharmaceutical composition of item 13, wherein the adjuvant is selected from the group consisting of Montanide ISA-51, QS-21, GM-CSF, cyclophosamide, bacillus Calmette-Guerin (BCG), corynbacterium parvum, levamisole, azimezone, isoprinisone, dinitrochlorobenezene (DNCB), keyhole limpet hemocyanins (KLH), Freunds adjuvant (complete), Freunds adjuvant (incomplete), mineral gels, aluminum hydroxide (Alum), lysolecithin, pluronic polyols, polyanions, oil emulsions, dinitrophenol, diphtheria toxin (DT), and combinations thereof.
15. A method of identifying and treating a human subject having cancer who will likely have a clinical response to administration of a pharmaceutical composition according to item 1, the method comprising
   (i) assaying a biological sample of the subject to determine HLA genotype of the subject;
   (ii) determining that the pharmaceutical composition comprises two or more sequences that are a T cell epitope capable of binding to at least three HLA class I molecules of the subject;
   (iii) determining the probability that a tumor of the subject expresses one or more antigen corresponding to the T cell epitopes identified in step (ii) using population expression data for each antigen, to identify the likelihood of the subject to have a clinical response to administration of the pharmaceutical composition; and
   (iv) administering the composition of item 1 to the identified subject.
16. The method of item 15, wherein the subject has bladder cancer.
17. The method of item 15, wherein the pharmaceutical composition comprises 2 or more peptides, 3 or more peptides, 4 or more peptides, 5 or more peptides, 6 or more peptides, 7 or more peptides, 8 or more peptides, 9 or more peptides, 10 or more peptides, 11 or more peptides, or 12 or more peptides.
18. The method of item 15, wherein the pharmaceutical composition further comprises comprising at least one additional peptide comprising a fragment of an antigen selected from PIWIL2, CTAGE1, MAGE-A9, EpCAM, OY-TES-1, NY-ESO-1, SURVIVIN, MAGE-C1, MAGE-A2, LAGE-1, MAGE-A3, MAGE-A8, HAGE, MAGE-A1, MAGE-C2, MAGE-A10 and MAGE-A12.
19. The method of item 18, wherein the fragment of an antigen comprises an amino acid sequence selected from any one of SEQ ID NOs: 268 to 297.
20. The method of item 18, wherein the fragment of an antigen comprises an amino acid sequence selected from any one of SEQ ID NOs: 298 to 327.
21. The method of item 15, wherein the pharmaceutical composition further comprises a pharmaceutically acceptable adjuvant, diluent, carrier, preservative, or combination thereof.
22. The method of item 21, wherein the adjuvant is selected from the group consisting of Montanide ISA-51, QS-21, GM-CSF, cyclophosamide, bacillus Calmette-Guerin (BCG), corynbacterium parvum, levamisole, azimezone, isoprinisone, dinitrochlorobenezene (DNCB), keyhole limpet hemocyanins (KLH), Freunds adjuvant (complete), Freunds adjuvant (incomplete), mineral gels, aluminum hydroxide (Alum), lysolecithin, pluronic polyols, polyanions, oil emulsions, dinitrophenol, diphtheria toxin (DT), and combinations thereof.
23. The method of item 15, further comprising administering a chemotherapeutic agent, a checkpoint inhibitor, a targeted therapy, radiation therapy, another immunotherapy, neoadjuvant therapy or combination thereof to the identified subject.
24. The method of item 15, further comprising prior to the administering step,
   (v) assaying a tumor sample from the subject to determine that the three or more peptides of the pharmaceutical composition comprise two or more different amino acid sequences each of which is
      e. a fragment of a cancer-associated antigen expressed by cancer cells of the subject as determined in step (i); and
      f. a T cell epitope capable of binding to at least three HLA class I molecules of the subject; and
   (vi) confirming the subject as likely to have a clinical response to the method of treatment.
25. A method of identifying and treating a human subject having cancer who will likely have an immune response to administration of a pharmaceutical composition according to item 1, the method comprising
   (i) assaying a biological sample of the subject to determine HLA genotype of the subject;
   (ii) determining that the pharmaceutical composition comprises one or more sequences that are a T cell epitope capable of binding to at least three HLA class I molecules of the subject; and
   (iii) administering the composition of item 1 to the identified subject.
26. A kit comprising:
   a. a first pharmaceutical composition comprising one or more peptides, wherein each peptide comprises a different one of the amino acid sequence of any one of SEQ ID NOs: 328 to 342; and
   b. a second different pharmaceutical composition comprising one or more peptides, wherein each peptide comprises a different one of the amino acid sequence of any one of SEQ ID NOs: 328 to 342.
27. A pharmaceutical composition comprising: a nucleic acid molecule expressing two or more polypeptides, each polypeptide comprising a fragment of up to 50 consecutive amino acids of an antigen selected from PIWIL2, CTAGE1, MAGE-A9, EpCAM, OY-TES-1, NY-ESO-1, SURVIVIN, MAGE-C1, MAGE-A2, LAGE-1, MAGE-A3, MAGE-A8, HAGE, MAGE-A1, MAGE-C2, MAGE-A10 and MAGE-A12, wherein each fragment comprises a different amino acid sequence selected from any one of SEQ ID NOs: 268 to 297.

Further Embodiments of the Disclosure—(2B)—Lung

1. A polypeptide that comprises a fragment of up to 50 consecutive amino acids of a lung cancer-associated antigen selected from BRDT, PRAME, NALP4, MAGE-A12, MAGE-A2, SURVIVIN, DPPA2, NY-SAR-35, LDHC, MAGE-C2, MAGE-A3, KK-LC-1 and MAGE-A1, wherein the fragment comprises an amino acid sequence selected from any one of SEQ ID NOs: 90 to 119, optionally wherein the fragment is flanked at the N and/or C terminus by additional amino acids that are not part of the sequence of the lung cancer-associated antigen.
2. The polypeptide of item 1, wherein the polypeptide
    a. is a fragment of a lung cancer-associated antigen selected from BRDT, PRAME, NALP4, MAGE-A12, MAGE-A2, SURVIVIN, DPPA2, NY-SAR-35, LDHC, MAGE-C2, MAGE-A3, KK-LC-1 and MAGE-A1, wherein the fragment comprises an amino acid sequence selected from any one of SEQ ID NOs: 90 to 119; or
    b. comprises or consists of two or more fragments of one or more lung cancer associated antigens selected from BRDT, PRAME, NALP4, MAGE-A12, MAGE-A2, SURVIVIN, DPPA2, NY-SAR-35, LDHC, MAGE-C2, MAGE-A3, KK-LC-1 and MAGE-A1, wherein each fragment comprises a different amino acid sequence selected from any one of SEQ ID NOs: 90 to 119, optionally wherein the fragments overlap or are arranged end to end in the polypeptide.
3. The polypeptide according to item 1 or item 2, wherein the polypeptide comprises or consists of fragments of at least two different cancer-associated antigens, wherein the cancer-associated antigens are selected from BRDT, PRAME, NALP4, MAGE-A12, MAGE-A2, SURVIVIN, DPPA2, NY-SAR-35, LDHC, MAGE-C2, MAGE-A3, KK-LC-1 and MAGE-A1; and wherein each fragment comprises a different amino acid sequence selected from SEQ ID NOs: 90 to 119.
4. The polypeptide according to any one of items 1 to 3, comprising or consisting of one or more amino acid sequences selected from SEQ ID NOs: 120 to 149.
5. The polypeptide according to any one of items 1 to 4 comprising or consisting of the amino acid sequence of any one of SEQ ID NOs: 150 to 164.
6. A panel of two or more polypeptides according to any one of items 1 to 5, wherein each polypeptide comprises a different amino acid sequence selected from SEQ ID NOs: 90 to 119.
7. A pharmaceutical composition or kit comprising one or more polypeptides according to any one of items 1 to 5, or a panel of polypeptides according to item 6, or a polypeptide comprising at least two amino acid sequences selected SEQ ID NOs: 90 to 119, or one or more polynucleic acids or vectors encoding said one or more polypeptides.
8. A method of vaccination, providing immunotherapy or inducing a cytotoxic T cell response in a subject, the method comprising administering to the subject a pharmaceutical composition or the peptides, polynucleic acids or vectors of a kit according to item 7.
9. The method of item 8 that is a method of treating cancer, optionally lung cancer.
10. A method of identifying a human subject who will likely have a cytotoxic T cell response to administration of a pharmaceutical composition or the peptides, polynucleic acids or vectors of a kit according to item 7, the method comprising
    (i) determining that the active ingredient polypeptide(s) of the pharmaceutical composition or kit comprise a sequence that is a T cell epitope capable of binding to at least three HLA class I molecules of the subject; and
    (ii) identifying the subject as likely to have a cytotoxic T cell response to administration of the pharmaceutical composition or the peptides, polynucleic acids or vectors of the kit.
11. The method of item 10 further comprising using population expression data for each antigen that
    (a) is selected from BRDT, PRAME, NALP4, MAGE-A12, MAGE-A2, SURVIVIN, DPPA2, NY-SAR-35, LDHC, MAGE-C2, MAGE-A3, KK-LC-1 and MAGE-A1; and
    (b) comprises an amino acid sequence that is
        i. a fragment of an active ingredient peptide of the pharmaceutical composition; and
        ii. a T cell epitope capable of binding to at least three HLA class I molecules of the subject;
    to determine the likelihood that the subject will have a CD8+ T cell response that targets one or more polypeptide antigens that are expressed by cancer cells of the subject.
12. A method of identifying a subject who will likely have a clinical response to a method of treatment according to item 9, the method comprising
    (i) determining that the active ingredient polypeptide(s) of the pharmaceutical composition comprise two or more different amino acid sequences each of which is
        a. a T cell epitope capable of binding to at least three HLA class I molecules of the subject; and
        b. a fragment of a cancer-associated antigen expressed by cancer cells of the subject, optionally wherein the cancer-associated antigen is present in a sample obtained from the subject; and
    (ii) identifying the subject as likely to have a clinical response to the method of treatment.
13. A method of determining the likelihood that a specific human subject will have a clinical response to a method of treatment according to item 9, wherein one or more of the following factors corresponds to a higher likelihood of a clinical response:
    (a) presence in the active ingredient polypeptide(s) of a higher number of amino acid sequences and/or different amino acid sequences that are each a T cell epitope capable of binding to at least three HLA class I of the subject;
    (b) a higher number of target polypeptide antigens, comprising at least one amino acid sequence that is both
        A. comprised in an active ingredient polypeptide; and
        B. a T cell epitope capable of binding to at least three HLA class I of the subject; optionally wherein the target polypeptide antigens are expressed in the subject, further optionally wherein the target polypeptides antigens are in one or more samples obtained from the subject;
(c) a higher probability that the subject expresses target polypeptide antigens, optionally a threshold number of the target polypeptide antigens and/or optionally target polypeptide antigens that have been determined to comprise at least one amino acid sequence that is both
  A. comprised in in an active ingredient polypeptide; and
  B. a T cell epitope capable of binding to at least three HLA class I of the subject; and/or
(d) a higher number of target polypeptide antigens that the subject is predicted to express, optionally a higher number of target polypeptide antigens that the subject expresses with a threshold probability, and/or optionally the target polypeptide antigens that have been determined to comprise at least one amino acid sequence that is both
  A. comprised in in an active ingredient polypeptide; and
  B. a T cell epitope capable of binding to at least three HLA class I of the subject.

14. The method of item 13, wherein the method comprises
  (i) identifying which polypeptide antigens targeted by the active ingredient polypeptide(s) comprise an amino acid sequence that is both
    A. comprised in an active ingredient polypeptide; and
    B. a T cell epitope capable of binding to at least three HLA class I of the subject;
  (ii) using population expression data for each antigen identified in step (i) to determine the probability that the subject expresses one or more of the antigens identified in step (i) that together comprise at least two different amino acid sequences of step (i); and
  (iii) determining the likelihood that the subject will have a clinical response to administration of the pharmaceutical composition, kit or panel of polypeptides, wherein a higher probability determined in step (ii) corresponds to a more likely clinical response.

15. The method of item 14, wherein the at least two different amino acid sequences are comprised in the amino acid sequence of two different polypeptide antigens targeted by the active ingredient polypeptide(s).

16. The method of any one of items 12 to 15 further comprising selecting or recommending administration of the pharmaceutical composition or the peptides, polynucleic acids or vectors of the kit as a method of treatment for the subject, and optionally further treating the subject by administering the pharmaceutical composition or the peptides, polynucleic acids or vectors of the kit.

17. A method of treatment according to item 9, wherein the subject has been identified as likely to have a clinical response or as having above a threshold minimum likelihood of having a clinical response to the treatment by a method according to any one of items 12 to 15.

18. The method of any one of items 8, 9, 16 and 17 wherein the treatment is administered in combination with chemotherapy, targeted therapy or a checkpoint inhibitor.

19. A method of identifying a human subject who will likely not have a clinical response to a method of treatment according to item 9, the method comprising
  (i) determining that the active ingredient peptide(s) of the pharmaceutical composition do not comprise two or more different amino acid sequences each of which is a T cell epitope capable of binding to at least three HLA class I molecules of the subject; and
  (ii) identifying the subject as likely not to have a clinical response to the method of treatment.

Further Embodiments of the Disclosure—(3B)—Melanoma

1. A polypeptide that comprises a fragment of up to 50 consecutive amino acids of a melanoma-associated antigen selected from PRAME, MAGE-A2, MAGE-C1, SURVIVIN, MAGE-A12, Ny-ESO-1, MAGE-C2, MAGE-A6, BORIS, LAGE-1, MAGE-A11, SSX-1, MAGE-A3, MAGE-A10 and MAGE-A1, wherein the fragment comprises an amino acid sequence selected from any one of SEQ ID NOs: 178 to 207, optionally wherein the fragment is flanked at the N and/or C terminus by additional amino acids that are not part of the sequence of the melanoma-associated antigen.

2. The polypeptide of item 1, wherein the polypeptide
  c. is a fragment of a melanoma-associated antigen selected from PRAME, MAGE-A2, MAGE-C1, SURVIVIN, MAGE-A12, Ny-ESO-1, MAGE-C2, MAGE-A6, BORIS, LAGE-1, MAGE-A11, SSX-1, MAGE-A3, MAGE-A10 and MAGE-A1, wherein the fragment comprises an amino acid sequence selected from any one of SEQ ID NOs: 178 to 207; or
  d. comprises or consists of two or more fragments of one or more melanoma associated antigens selected from PRAME, MAGE-A2, MAGE-C1, SURVIVIN, MAGE-A12, Ny-ESO-1, MAGE-C2, MAGE-A6, BORIS, LAGE-1, MAGE-A11, SSX-1, MAGE-A3, MAGE-A10 and MAGE-A1, wherein each fragment comprises a different amino acid sequence selected from any one of SEQ ID NOs: 178 to 207, optionally wherein the fragments overlap or are arranged end to end in the polypeptide.

3. The polypeptide according to item 1 or item 2, wherein the polypeptide comprises or consists of fragments of at least two different cancer-associated antigens, wherein the cancer-associated antigens are selected from PRAME, MAGE-A2, MAGE-C1, SURVIVIN, MAGE-A12, Ny-ESO-1, MAGE-C2, MAGE-A6, BORIS, LAGE-1, MAGE-A11, SSX-1, MAGE-A3, MAGE-A10 and MAGE-A1; and wherein each fragment comprises a different amino acid sequence selected from SEQ ID NOs: 178 to 207.

4. The polypeptide according to any one of items 1 to 3, comprising or consisting of one or more amino acid sequences selected from SEQ ID NOs: 208 to 237.

5. The polypeptide according to any one of items 1 to 4 comprising or consisting of the amino acid sequence of any one of SEQ ID NOs: 238 to 252.

6. A panel of two or more polypeptides according to any one of items 1 to 5, wherein each polypeptide comprises a different amino acid sequence selected from SEQ ID NOs: 178 to 207.

7. A pharmaceutical composition or kit comprising one or more polypeptides according to any one of items 1 to 5, or a panel of polypeptides according to item 6, or a polypeptide comprising at least two amino acid sequences selected SEQ ID NOs: 178 to 207, or one or more polynucleic acids or vectors encoding said one or more polypeptides.

8. A method of vaccination, providing immunotherapy or inducing a cytotoxic T cell response in a subject, the method comprising administering to the subject a pharmaceutical composition or the peptides, polynucleic acids or vectors of a kit according to item 7.
9. The method of item 8 that is a method of treating cancer, optionally melanoma.
10. A method of identifying a human subject who will likely have a cytotoxic T cell response to administration of a pharmaceutical composition or the peptides, polynucleic acids or vectors of a kit according to item 7, the method comprising
    (i) determining that the active ingredient polypeptide(s) of the pharmaceutical composition or kit comprise a sequence that is a T cell epitope capable of binding to at least three HLA class I molecules of the subject; and
    (iii) identifying the subject as likely to have a cytotoxic T cell response to administration of the pharmaceutical composition or the peptides, polynucleic acids or vectors of the kit.
11. The method of item 10 further comprising using population expression data for each antigen that
    (a) is selected from PRAME, MAGE-A2, MAGE-C1, SURVIVIN, MAGE-A12, Ny-ESO-1, MAGE-C2, MAGE-A6, BORIS, LAGE-1, MAGE-A11, SSX-1, MAGE-A3, MAGE-A10 and MAGE-A1; and
    (b) comprises an amino acid sequence that is
        i. a fragment of an active ingredient peptide of the pharmaceutical composition; and
        ii. a T cell epitope capable of binding to at least three HLA class I molecules of the subject;
    to determine the likelihood that the subject will have a CD8+ T cell response that targets one or more polypeptide antigens that are expressed by cancer cells of the subject.
12. A method of identifying a subject who will likely have a clinical response to a method of treatment according to item 9, the method comprising
    (i) determining that the active ingredient polypeptide(s) of the pharmaceutical composition comprise two or more different amino acid sequences each of which is
        c. a T cell epitope capable of binding to at least three HLA class I molecules of the subject; and
        d. a fragment of a cancer-associated antigen expressed by cancer cells of the subject, optionally wherein the cancer-associated antigen is present in a sample obtained from the subject; and
    (ii) identifying the subject as likely to have a clinical response to the method of treatment.
13. A method of determining the likelihood that a specific human subject will have a clinical response to a method of treatment according to item 9, wherein one or more of the following factors corresponds to a higher likelihood of a clinical response:
    (a) presence in the active ingredient polypeptide(s) of a higher number of amino acid sequences and/or different amino acid sequences that are each a T cell epitope capable of binding to at least three HLA class I of the subject;
    (b) a higher number of target polypeptide antigens, comprising at least one amino acid sequence that is both
        A. comprised in an active ingredient polypeptide; and
        B. a T cell epitope capable of binding to at least three HLA class I of the subject; optionally wherein the target polypeptide antigens are expressed in the subject, further optionally wherein the target polypeptides antigens are in one or more samples obtained from the subject;
    (c) a higher probability that the subject expresses target polypeptide antigens, optionally a threshold number of the target polypeptide antigens and/or optionally target polypeptide antigens that have been determined to comprise at least one amino acid sequence that is both
        A. comprised in in an active ingredient polypeptide; and
        B. a T cell epitope capable of binding to at least three HLA class I of the subject; and/or
    (d) a higher number of target polypeptide antigens that the subject is predicted to express, optionally a higher number of target polypeptide antigens that the subject expresses with a threshold probability, and/or optionally the target polypeptide antigens that have been determined to comprise at least one amino acid sequence that is both
        A. comprised in in an active ingredient polypeptide; and
        B. a T cell epitope capable of binding to at least three HLA class I of the subject.
14. The method of item 13, wherein the method comprises
    (iv) identifying which polypeptide antigens targeted by the active ingredient polypeptide(s) comprise an amino acid sequence that is both
        A. comprised in an active ingredient polypeptide; and
        B. a T cell epitope capable of binding to at least three HLA class I of the subject;
    (v) using population expression data for each antigen identified in step (i) to determine the probability that the subject expresses one or more of the antigens identified in step (i) that together comprise at least two different amino acid sequences of step (i); and
    (vi) determining the likelihood that the subject will have a clinical response to administration of the pharmaceutical composition, kit or panel of polypeptides, wherein a higher probability determined in step (ii) corresponds to a more likely clinical response.
15. The method of item 14, wherein the at least two different amino acid sequences are comprised in the amino acid sequence of two different polypeptide antigens targeted by the active ingredient polypeptide(s).
16. The method of any one of items 12 to 15 further comprising selecting or recommending administration of the pharmaceutical composition or the peptides, polynucleic acids or vectors of the kit as a method of treatment for the subject, and optionally further treating the subject by administering the pharmaceutical composition or the peptides, polynucleic acids or vectors of the kit.
17. A method of treatment according to item 9, wherein the subject has been identified as likely to have a clinical response or as having above a threshold minimum likelihood of having a clinical response to the treatment by a method according to any one of items 12 to 15.
18. The method of any one of items 8, 9, 16 and 17 wherein the treatment is administered in combination with chemotherapy, targeted therapy or a checkpoint inhibitor.
19. A method of identifying a human subject who will likely not have a clinical response to a method of treatment according to item 9, the method comprising
    (i) determining that the active ingredient peptide(s) of the pharmaceutical composition do not comprise two or more different amino acid sequences each of which is a T cell epitope capable of binding to at least three HLA class I molecules of the subject; and
    (ii) identifying the subject as likely not to have a clinical response to the method of treatment.

Further Embodiments of the Disclosure—(4B)—Bladder

1. A polypeptide that comprises a fragment of up to 50 consecutive amino acids of a bladder cancer-associated antigen selected from PIWIL2, CTAGE1, MAGE-A9, EpCAM, OY-TES-1, NY-ESO-1, SURVIVIN, MAGE-C1, MAGE-A2, LAGE-1, MAGE-A3, MAGE-A8, HAGE, MAGE-A1, MAGE-C2, MAGE-A10 and MAGE-A12, wherein the fragment comprises an amino acid sequence selected from any one of SEQ ID NOs: 268 to 297, optionally wherein the fragment is flanked at the N and/or C terminus by additional amino acids that are not part of the sequence of the bladder cancer-associated antigen.

2. The polypeptide of item 1, wherein the polypeptide
   e. is a fragment of a bladder cancer-associated antigen selected from PIWIL2, CTAGE1, MAGE-A9, EpCAM, OY-TES-1, NY-ESO-1, SURVIVIN, MAGE-C1, MAGE-A2, LAGE-1, MAGE-A3, MAGE-A8, HAGE, MAGE-A1, MAGE-C2, MAGE-A10 and MAGE-A12, wherein the fragment comprises an amino acid sequence selected from any one of SEQ ID NOs: 268 to 297; or
   f. comprises or consists of two or more fragments of one or more bladder cancer associated antigens selected from PIWIL2, CTAGE1, MAGE-A9, EpCAM, OY-TES-1, NY-ESO-1, SURVIVIN, MAGE-C1, MAGE-A2, LAGE-1, MAGE-A3, MAGE-A8, HAGE, MAGE-A1, MAGE-C2, MAGE-A10 and MAGE-A12, wherein each fragment comprises a different amino acid sequence selected from any one of SEQ ID NOs: 268 to 297, optionally wherein the fragments overlap or are arranged end to end in the polypeptide.

3. The polypeptide according to item 1 or item 2, wherein the polypeptide comprises or consists of fragments of at least two different cancer-associated antigens, wherein the cancer-associated antigens are selected from PIWIL2, CTAGE1, MAGE-A9, EpCAM, OY-TES-1, NY-ESO-1, SURVIVIN, MAGE-C1, MAGE-A2, LAGE-1, MAGE-A3, MAGE-A8, HAGE, MAGE-A1, MAGE-C2, MAGE-A10 and MAGE-A12; and wherein each fragment comprises a different amino acid sequence selected from SEQ ID NOs: 268 to 297.

4. The polypeptide according to any one of items 1 to 3, comprising or consisting of one or more amino acid sequences selected from SEQ ID NOs: 298 to 327.

5. The polypeptide according to any one of items 1 to 4 comprising or consisting of the amino acid sequence of any one of SEQ ID NOs: 328 to 342.

6. A panel of two or more polypeptides according to any one of items 1 to 5, wherein each polypeptide comprises a different amino acid sequence selected from SEQ ID NOs: 268 to 297.

7. A pharmaceutical composition or kit comprising one or more polypeptides according to any one of items 1 to 5, or a panel of polypeptides according to item 6, or a polypeptide comprising at least two amino acid sequences selected SEQ ID NOs: 268 to 297, or one or more polynucleic acids or vectors encoding said one or more polypeptides.

8. A method of vaccination, providing immunotherapy or inducing a cytotoxic T cell response in a subject, the method comprising administering to the subject a pharmaceutical composition or the peptides, polynucleic acids or vectors of a kit according to item 7.

9. The method of item 8 that is a method of treating cancer, optionally bladder cancer.

10. A method of identifying a human subject who will likely have a cytotoxic T cell response to administration of a pharmaceutical composition or the peptides, polynucleic acids or vectors of a kit according to item 7, the method comprising
    (i) determining that the active ingredient polypeptide(s) of the pharmaceutical composition or kit comprise a sequence that is a T cell epitope capable of binding to at least three HLA class I molecules of the subject; and
    (iv) identifying the subject as likely to have a cytotoxic T cell response to administration of the pharmaceutical composition or the peptides, polynucleic acids or vectors of the kit.

11. The method of item 10 further comprising using population expression data for each antigen that
    (a) is selected PIWIL2, CTAGE1, MAGE-A9, EpCAM, OY-TES-1, NY-ESO-1, SURVIVIN, MAGE-C1, MAGE-A2, LAGE-1, MAGE-A3, MAGE-A8, HAGE, MAGE-A1, MAGE-C2, MAGE-A10 and MAGE-A12; and
    (b) comprises an amino acid sequence that is
        i. a fragment of an active ingredient peptide of the pharmaceutical composition; and
        ii. a T cell epitope capable of binding to at least three HLA class I molecules of the subject;
    to determine the likelihood that the subject will have a CD8+ T cell response that targets one or more polypeptide antigens that are expressed by cancer cells of the subject.

12. A method of identifying a subject who will likely have a clinical response to a method of treatment according to item 9, the method comprising
    (i) determining that the active ingredient polypeptide(s) of the pharmaceutical composition comprise two or more different amino acid sequences each of which is
        e. a T cell epitope capable of binding to at least three HLA class I molecules of the subject; and
        f. a fragment of a cancer-associated antigen expressed by cancer cells of the subject, optionally wherein the cancer-associated antigen is present in a sample obtained from the subject; and
    (ii) identifying the subject as likely to have a clinical response to the method of treatment.

13. A method of determining the likelihood that a specific human subject will have a clinical response to a method of treatment according to item 9, wherein one or more of the following factors corresponds to a higher likelihood of a clinical response:
    (a) presence in the active ingredient polypeptide(s) of a higher number of amino acid sequences and/or different amino acid sequences that are each a T cell epitope capable of binding to at least three HLA class I of the subject;
    (b) a higher number of target polypeptide antigens, comprising at least one amino acid sequence that is both
        A. comprised in an active ingredient polypeptide; and
        B. a T cell epitope capable of binding to at least three HLA class I of the subject; optionally wherein the target polypeptide antigens are expressed in the subject, further optionally wherein the target polypeptides antigens are in one or more samples obtained from the subject;
    (c) a higher probability that the subject expresses target polypeptide antigens, optionally a threshold number of the target polypeptide antigens and/or optionally target polypeptide antigens that have been determined to comprise at least one amino acid sequence that is both A. comprised in in an active ingredient polypeptide; and
B. a T cell epitope capable of binding to at least three HLA class I of the subject; and/or
(d) a higher number of target polypeptide antigens that the subject is predicted to express, optionally a higher number of target polypeptide antigens that the subject expresses with a threshold probability, and/or optionally the target polypeptide antigens that have been determined to comprise at least one amino acid sequence that is both
A. comprised in in an active ingredient polypeptide; and
B. a T cell epitope capable of binding to at least three HLA class I of the subject.
14. The method of item 13, wherein the method comprises
(vii) identifying which polypeptide antigens targeted by the active ingredient polypeptide(s) comprise an amino acid sequence that is both
A. comprised in an active ingredient polypeptide; and
B. a T cell epitope capable of binding to at least three HLA class I of the subject; (viii) using population expression data for each antigen identified in step (i) to determine the probability that the subject expresses one or more of the antigens identified in step (i) that together comprise at least two different amino acid sequences of step (i); and
(ix) determining the likelihood that the subject will have a clinical response to administration of the pharmaceutical composition, kit or panel of polypeptides, wherein a higher probability determined in step (ii) corresponds to a more likely clinical response.
15. The method of item 14, wherein the at least two different amino acid sequences are comprised in the amino acid sequence of two different polypeptide antigens targeted by the active ingredient polypeptide(s).
16. The method of any one of items 12 to 15 further comprising selecting or recommending administration of the pharmaceutical composition or the peptides, polynucleic acids or vectors of the kit as a method of treatment for the subject, and optionally further treating the subject by administering the pharmaceutical composition or the peptides, polynucleic acids or vectors of the kit.
17. A method of treatment according to item 9, wherein the subject has been identified as likely to have a clinical response or as having above a threshold minimum likelihood of having a clinical response to the treatment by a method according to any one of items 12 to 15.
18. The method of any one of items 8, 9, 16 and 17 wherein the treatment is administered in combination with chemotherapy, targeted therapy or a checkpoint inhibitor.
19. A method of identifying a human subject who will likely not have a clinical response to a method of treatment according to item 9, the method comprising
(i) determining that the active ingredient peptide(s) of the pharmaceutical composition do not comprise two or more different amino acid sequences each of which is a T cell epitope capable of binding to at least three HLA class I molecules of the subject; and
(ii) identifying the subject as likely not to have a clinical response to the method of treatment.

EXAMPLES

Example 1—HLA-Epitope Binding Prediction Process and Validation

Predicted binding between particular HLA and epitopes (9 mer peptides) was based on the Immune Epitope Database tool for epitope prediction (iedb.org).

The HLA I-epitope binding prediction process was validated by comparison with HLA class I-epitope pairs determined by laboratory experiments. A dataset was compiled of HLA I-epitope pairs reported in peer reviewed publications or public immunological databases.

The rate of agreement with the experimentally determined dataset was determined (Table 2). The binding HLA I-epitope pairs of the dataset were correctly predicted with a 93% probability. Coincidentally the non-binding HLA I-epitope pairs were also correctly predicted with a 93% probability.

TABLE 2

Analytical specificity and sensitivity of the HLA-epitope binding prediction process.

| HLA-epitope pairs | True epitopes (n = 327) (Binder match) | False epitopes (n = 100) (Non-binder match) |
|---|---|---|
| HIV | 91% (32) | 82% (14) |
| Viral | 100% (35) | 100% (11) |
| Tumor | 90% (172) | 94% (32) |
| Other (fungi, bacteria, etc.) | 100% (65) | 95% (36) |
| All | 93% (304) | 93% (93) |

The accuracy of the prediction of multiple HLA binding epitopes was also determined (Table 3). Based on the analytical specificity and sensitivity using the 93% probability for both true positive and true negative prediction and 7% (=100%-93%) probability for false positive and false negative prediction, the probability of the existence of a multiple HLA binding epitope in a person can be calculated. The probability of multiple HLA binding to an epitope shows the relationship between the number of HLAs binding an epitope and the expected minimum number of real binding. Per PEPI definition three is the expected minimum number of HLA to bind an epitope (bold).

TABLE 3

Accuracy of multiple HLA binding epitopes predictions.

| Expected minimum number of real HLA binding | Predicted number of HLAs binding to an epitope | | | | | | |
|---|---|---|---|---|---|---|---|
| | 0 | 1 | 2 | 3 | 4 | 5 | 6 |
| 1 | 35% | 95% | 100% | 100% | 100% | 100% | 100% |
| 2 | 6% | 29% | 90% | 99% | 100% | 100% | 100% |
| 3 | 1% | 4% | 22% | 84% | 98% | 100% | 100% |
| 4 | 0% | 0% | 2% | 16% | 78% | 96% | 99% |
| 5 | 0% | 0% | 0% | 1% | 10% | 71% | 94% |
| 6 | 0% | 0% | 0% | 0% | 0% | 5% | 65% |

The validated HLA-epitope binding prediction process was used to determine all HLA-epitope binding pairs described in the Examples below.

Example 2—Epitope Presentation by Multiple HLA Predicts Cytotoxic T Lymphocyte (CTL) Response This study investigates whether the presentation of one or more epitopes of a polypeptide antigen by one or more HLA class I molecule of an individual is predictive for a CTL response.

The study was carried out by retrospective analysis of six clinical trials, conducted on 71 cancer patients and 9 HIV-infected patients (Table 4). Patients from these studies were treated with an HPV vaccine, three different NY-ESO-1 specific cancer vaccines, one HIV-1 vaccine and a CTLA-4 specific monoclonal antibody (Ipilimumab) that was shown to reactivate CTLs against NY-ESO-1 antigen in melanoma patients. All of these clinical trials measured antigen specific CD8+ CTL responses (immunogenicity) in the study subjects after vaccination. In some cases, correlation between CTL responses and clinical responses were reported.

No patient was excluded from the retrospective study for any reason other than data availability. The 157 patient datasets (Table 4) were randomized with a standard random number generator to create two independent cohorts for training and evaluation studies. In some cases the cohorts contained multiple datasets from the same patient, resulting in a training cohort of 76 datasets from 48 patients and a test/validation cohort of 81 datasets from 51 patients.

all 6 (PEPI6) HLA class I molecules of each patient was determined and the number of HLA bound were used as classifiers for the reported CTL responses. The true positive rate (sensitivity) and true negative rate (specificity) were determined from the training dataset for each classifier (number of HLA bound) separately.

ROC analysis was performed for each classifier. In a ROC curve, the true positive rate (Sensitivity) was plotted in function of the false positive rate (1−Specificity) for different cut-off points (FIG. 1). Each point on the ROC curve represents a sensitivity/specificity pair corresponding to a particular decision threshold (epitope (PEPI) count). The area under the ROC curve (AUC) is a measure of how well the classifier can distinguish between two diagnostic groups (CTL responder or non-responder).

The analysis unexpectedly revealed that predicted epitope presentation by multiple class I HLAs of a subject (PEPI2+,

TABLE 4

Summary of patient datasets

| Clinical trial | Immunotherapy | Target Antigen | Disease | # Patients* | # Data sets (# antigen × # patient) | Immunoassay performed in the clinical trials** | HLA genotyping method |
|---|---|---|---|---|---|---|---|
| 1 | VGX-3100 | HPV16-E6 HPV16-E7 HPV18-E6 HPV18-E7 HPV16/18 | Cervical cancer | 17/18 | 5 × 17 | IFN-γ ELISPOT | High Resolution SBT |
| 2 | HIVIS vaccine | HIV-1 Gag HIV-1 RT | AIDS | 9/12 | 2 × 9 | IFN-γ ELISPOT | Low-Medium Resolution SSO |
| 3 | rNY-ESO-1 | NY-ESO-1 | Breast-and ovarian cancers, melanoma and sarcoma | 18/18 | 1 × 18 | In vitro and Ex vivo IFN-γ ELISPOT | High Resolution SBT |
| 4 | Ipilimumab | NY-ESO-1 | Metastatic melanoma | 19/20 | 1 × 19 | ICS after T-cell stimulation | Low to medium resolution typing, SSP of genomic DNA, high resolution sequencing |
| 5 | NY-ESO-1f | NY-ESO-1 (91-110) | Esophageal-, non-small-cell lung- and gastric cancer | 10/10 | 1 × 10 | ICS after T-cell stimulation | SSO probing and SSP of genomic DNA |
| 6 | NY-ESO-1 overlapping peptides | NY-ESO-1 (79-173) | Esophageal- and lung cancer, malignant melanoma | 7/9 | 1 × 7 | ICS after T-cell stimulation | SSO probing and SSP of genomic DNA |
| Total | 6 | 7 | | 80 | 157 | | |

The reported CD8+ T cell responses of the training dataset were compared with the HLA class I restriction profile of epitopes (9 mers) of the vaccine antigens. The antigen sequences and the HLA class I genotype of each patient were obtained from publicly available protein sequence databases or peer reviewed publications and the HLA I-epitope binding prediction process was blinded to patients' clinical CD8+ T cell response data where CD8+ T cells are IFN-γ producing CTL specific for vaccine peptides (9 mers). The number of epitopes from each antigen predicted to bind to at least 1 (PEPI1+), or at least 2 (PEPI2+), or at least 3 (PEPI3+), or at least 4 (PEPI4+), or at least 5 (PEPI5+), or PEPI3+, PEPI4+, PEPI5+, or PEPI6), was in every case a better predictor of the CD8+ T cell response or CTL response than epitope presentation by merely one or more HLA class I (PEPI1+, AUC=0.48, Table 5).

TABLE 5

Determination of diagnostic value of the PEPI biomarker by ROC analysis

| Classifiers | AUC |
|---|---|
| PEPI1+ | 0.48 |
| PEPI2+ | 0.51 |

TABLE 5-continued

Determination of diagnostic value of the
PEPI biomarker by ROC analysis

| Classifiers | AUC |
|---|---|
| PEPI3+ | 0.65 |
| PEPI4+ | 0.52 |
| PEPI5+ | 0.5 |
| PEPI6+ | 0.5 |

The CTL response of an individual was best predicted by considering the epitopes of an antigen that could be presented by at least 3 HLA class I alleles of an individual (PEPI3+, AUC=0.65, Table 5). The threshold count of PEPI3+(number of antigen-specific epitopes presented by 3 or more HLA of an individual) that best predicted a positive CTL response was 1 (Table 6). In other words, at least one antigen-derived epitope is presented by at least 3 HLA class I of a subject (≥1 PEPI3+), then the antigen can trigger at least one CTL clone, and the subject is a likely CTL responder. Using the ≥1 PEPI3+ threshold to predict likely CTL responders ("≥1 PEPI3+ test") provided 76% true positive rate (diagnostic sensitivity) (Table 6).

TABLE 6

Determination of the ≥1 PEPI3+ threshold to predict likely
CTL responders in the training dataset.

| | PEPI3+ Count | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Sensitivity: | 0.76 | 0.60 | 0.31 | 0.26 | 0.14 | 0.02 | 0 | 0 | 0 | 0 | 0 | 0 |
| 1-Specificity: | 0.59 | 0.24 | 0.21 | 0.15 | 0.09 | 0.06 | 0.06 | 0.03 | 0.03 | 0.03 | 0.03 | 0.03 |

Example 3—Retrospective Validation of the 1 PEPI3+ Threshold as Novel Biomarker for PEPI Test In a retrospective analysis, the test cohort of 81 datasets from 51 patients was used to validate the ≥1 PEPI3+ threshold to predict an antigen-specific CD8+ T cell response or CTL response. For each dataset in the test cohort it was determined whether the ≥1 PEPI3+ threshold was met (at least one antigen-derived epitope presented by at least three class I HLA of the individual). This was compared with the experimentally determined CD8+ T cell responses (CTL responses) reported from the clinical trials (Table 7).

The retrospective validation demonstrated that a PEPI3+ peptide induces CD8+ T cell response (CTL response) in an individual with 84% probability. 84% is the same value that was determined in the analytical validation of the PEPI3+ prediction, epitopes that binds to at least 3 HLAs of an individual (Table 3). These data provide strong evidences that immune responses are induced by PEPIs in individuals.

TABLE 7

Diagnostic performance characteristics of
the ≥ 1 PEPI3+ test (n = 81).

| Performance characteristic | | Description | Result |
|---|---|---|---|
| Positive predictive value | 100% [A/(A + B)] | The likelihood that an individual that meets the ≥ 1 PEPI3+ threshold has antigen-specific CTL responses after treatment with immunotherapy. | 84% |
| Sensitivity | 100% [A/(A + C)] | The proportion of subjects with antigen-specific CTL responses after treatment with immunotherapy who meet the ≥ 1 PEPI3+ threshold. | 75% |
| Specificity | 100% [D/(B + D)] | The proportion of subjects without antigen-specific CTL responses after treatment with immunotherapy who do not meet the ≥ 1 PEPI3+ threshold. | 55% |
| Negative predictive value (NPV) | 100% [D/(C + D)] | The likelihood that an individual who does not meet the ≥ 1 PEPI3+ threshold does not have antigen-specific CTL responses after treatment with immunotherapy. | 42% |
| Overall percent agreement (OPA) | 100% [(A + D)/N] | The percentage of predictions based on the ≥ 1 PEPI3+ threshold that match the experimentally determined result, whether positive or negative. | 70% |
| Fisher's exact (p) | | | 0.01 |

Figure 2:
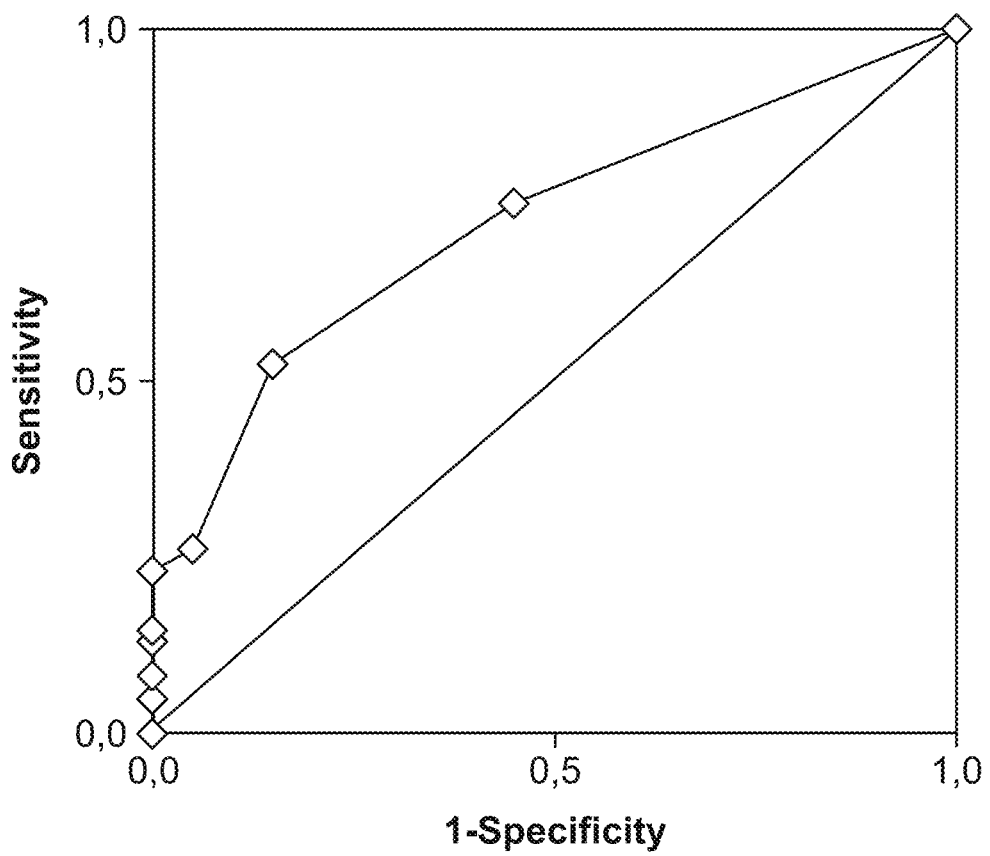
FIG. 2
ROC curve of ≥1 PEPI3+ Test for the determination of the diagnostic accuracy. AUC=0.73 classifies a fair diagnostic value for the PEPI biomarker.

ROC analysis determined the diagnostic accuracy, using the PEPI3+ count as cut-off values (FIG. 2). The AUC value=0.73. For ROC analysis an AUC of 0.7 to 0.8 is generally considered as fair diagnostic value.

A PEPI3+ count of at least 1 (≥1 PEPI3+) best predicted a CTL response in the test dataset (Table 8). This result confirmed the threshold determined during the training (Table 5).

TABLE 8

Confirmation of the ≥1 PEPI3+ threshold to predict likely CTL responders in the test/validation dataset.

| | PEPI3+ Count | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Sensitivity: | 0.75 | 0.5 | 0.26 | 0.23 | 0.15 | 0.13 | 0.08 | 0.05 | 0 | 0 | 0 | 0 |
| 1-Specificity: | 0.45 | 0.15 | 0.05 | 0 | 0 | 0 | 0 | 0 | 0 | 0 | 0 | 0 |

Example 4—Clinical Validation of the 1 PEPI3+ Threshold as Novel Biomarker for PEPI Test The PEPI3+ biomarker-based vaccine design has been tested first time in a phase I clinical trial in metastatic colorectal cancer (mCRC) patients in the OBERTO phase I/II clinical trial (NCT03391232). In this study, we evaluated the safety, tolerability and immunogenicity of a single or multiple dose(s) of PolyPEPI1018 as an add-on to maintenance therapy in subjects with mCRC. PolyPEPI1018 is a peptide vaccine containing 12 unique epitopes derived from 7 conserved TSAs frequently expressed in mCRC (WO2018158455 A1). These epitopes were designed to bind to at least three autologous HLA alleles that are more likely to induce T-cell responses than epitopes presented by a single HLA (See Examples 2 & 3). mCRC patients in the first line setting received the vaccine (dose: 0.2 mg/peptide) just after the transition to maintenance therapy with a fluoropyrimidine and bevacizumab. Vaccine-specific T-cell responses were first predicted by identification of PEPI3+-s in silico (using the patient's complete HLA genotype and antigen expression rate specifically for CRC) and then measured by ELISpot after one cycle of vaccination (phase I part of the trial).

Seventy datasets from 10 patients (Phase 1 cohort and dataset of OBERTO trial) was used to prospectively validate that PEPI3+ biomarker predicts antigen-specific CTL responses. For each dataset, predicted PEPI3+-s were determined in silico and compared to the vaccine-specific immune responses measured by ELISPOT assay from the patients' blood. Diagnostic characteristics (positive predictive value, negative predictive value, overall percent agreement) determined this way were then compared with the retrospective validation results described in Example 3.

The overall percent agreement was 64%, with high positive predictive value of 79%, representing 79% probability that the patient with predicted PEPI3+ will produce CD8 T cell specific immune response against the analyzed antigen. Clinical trial data were significantly correlated with the retrospective trial results (p=0.01) and provides evidence for the PEPI3+ calculation with PEPI test to predict antigen-specific T cell responses based on the complete HLA-genotype of patients (Table 9).

TABLE 9

Prospective validation of the ≥ 1 PEPI3+ and PEPI test

| Parameter | Definition | Retrospective validation n = 81* | Prospective validation (OBERTO) n = 70** |
|---|---|---|---|
| PPV Positive Predictive Value | The likelihood that an individual with a positive PEPI test result has antigen-specific T cell responses | 84% | 79% |
| NPV Negative Predictive Value | The likelihood that an individual with a negative PEPI test result does not have antigen-specific T cell responses | 42% | 51% |
| OPA Overall Percent Agreement | The percentage of results that are true results, whether positive or negative | 70% | 64% |
| Fisher's exact probability test (p) | | 0.01 | 0.01 |

*51 patients; 6 clinical trials; 81 dataset
**10 patients; Treos phase I clinical trial (OBERTO); 70 datasets

Example 5—the ≥1 PEPI3+ Test Predicts CD8+ T Cell Reactivities

Supporting data were obtained to show that the ≥1 PEPI3+ correlates with clinical immunogenicity data but the state-of-art mono-HLA specific epitope determination does not show correlation with vaccine-specific immunogenicity.

The ≥1 PEPI3+ calculation was compared with a state-of-art method for predicting a specific human subject's CTL response to peptide antigens.

The HLA genotypes of 28 cervical cancer and VIN-3 patients that received HPV-16 synthetic long peptide vaccine (LPV) in two different clinical trials were determined from DNA samples. The LPV consists of long peptides covering the HPV-16 viral oncoproteins E6 and E7. The amino acid sequence of the LPV was obtained from M. J. Welters, et al. Induction of tumor-specific CD4+ and CD8+ T-cell immunity in cervical cancer patients by a human papillomavirus type 16 E6 and E7 long peptides vaccine. *Clin Cancer Res* 14, 178-187 (2008)., G. G. Kenter, et al. Vaccination against HPV-16 oncoproteins for vulvar intraepithelial neoplasia. *N Engl J Med* 361, 1838-1847 (2009). M. J. Welters, et al. Success or failure of vaccination for HPV16-positive vulvar lesions correlates with kinetics and phenotype of induced T-cell responses. *Proc Natl Acad Sci USA* 107, 11895-11899 (2010). The publications also report the T cell responses of each vaccinated patient to pools of overlapping peptides of the vaccine. 25 (20 having VIN-3 and 5 having cervical cancer) patients had immune response data available, and 25 had clinical response data available.

For each patient, epitopes (9 mers) of the LPV that are presented by at least three patient class I HLA (PEPI3+s) were identified and their distribution among the peptide pools was determined. Peptides that comprised at least one PEPI3+(≥1 PEPI3+) were predicted to induce a CD8+ T cell response. Peptides that comprised no PEPI3+ were predicted not to induce a CD8+ T cell response.

Figure 3A:
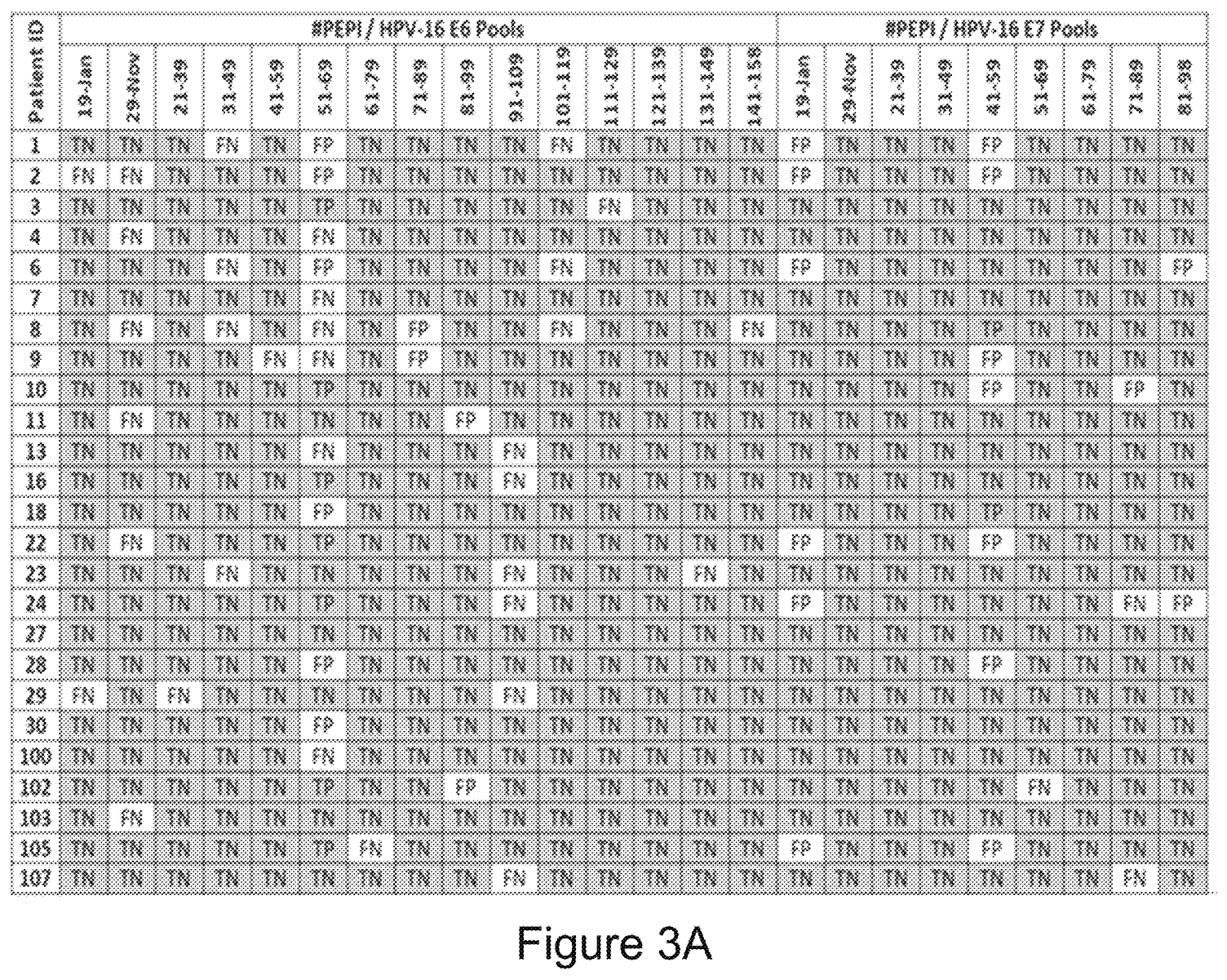

The ≥1 PEPI3+ threshold correctly predicted 529 out of 555 negative CD8+ T cell responses (95% true negative (TN) rate) and 9 out of 45 positive CD8+ T cell responses (20% true positive (TP) rate) measured after vaccination (FIG. 3A). Overall, the agreement between the ≥1 PEPI3+ threshold and experimentally determined CD8+ T cell reactivity was 90% ($p<0.001$).

Figure 3B:
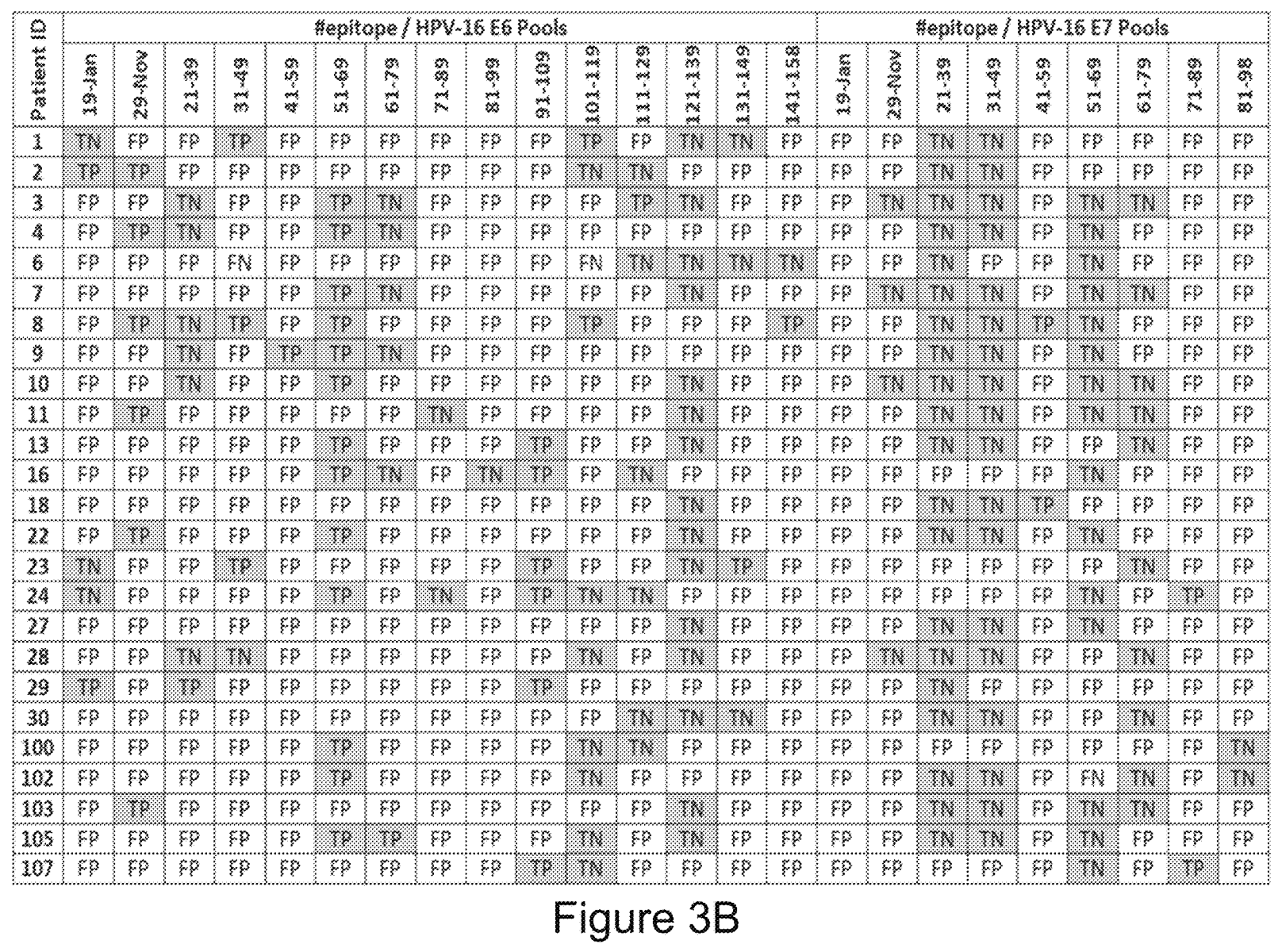

For each patient the distribution among the peptide pools of epitopes that are presented by at least one patient class I HLA (≥1 PEPI1+, HLA restricted epitope prediction, prior art method) was also determined. Forty-two HLA class I-binding epitopes predicted 45 CD8+ T cell responses (93% TP rate). In contrast, of the 555 negative T cell responses, only 105 were ruled out by HLA-binding epitopes (19% TN rate) (FIG. 3B). Overall, the agreement between a single HLA class I allele-binding epitope and CD8+ T cell response was 25%, which was not statistically significant.

Example 6—Prediction of HLA Class II Restricted CD4+ Helper T Cell Epitopes

Figure 4:
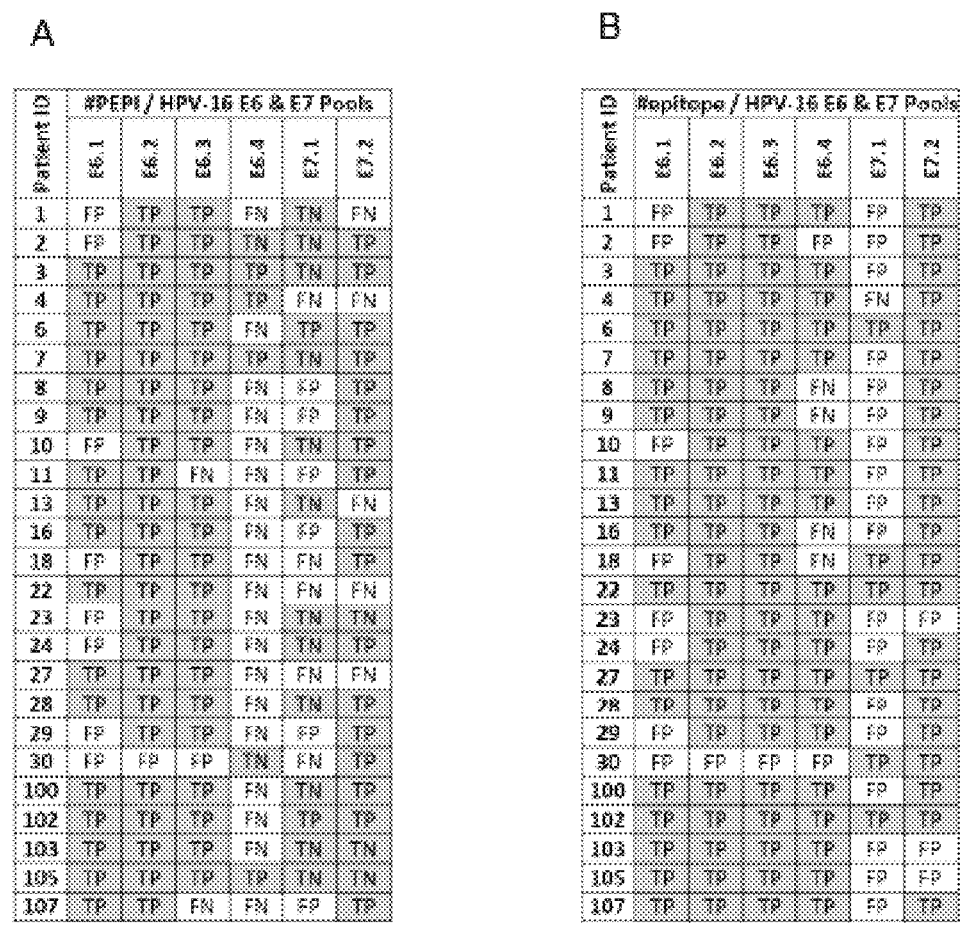

The 28 cervical cancer and VIN-3 patients that received the HPV-16 synthetic long peptide vaccine (LPV) in two different clinical trials (as detailed in Example 5) were investigated for CD4+ T helper responses following LPV vaccination (FIG. 4). The TP rate of the prediction of HLA class II restricted epitopes was 95%, since the State of Art tool predicted 112 positive responses (positive CD4+ T cell reactivity to a peptide pool for a person's HLA class II alleles) out of 117. The TN rate was 0% since it could rule out 0 of 33 negative T cell responses. Overall, the agreement between HLA-restricted class II PEPI prediction and CD4+ T cell reactivity was 75% (not significant).

The HLA class II-binding PEPI3+-s predicted 86 of 117 positive CD4+ T-cell responses (73% TP rate) and ruled out 17 of 33 negative T cell responses (52% TN rate). Overall, the agreement between HLA class II PEPI3+-s and CD4+ T-cell response was 69% ($p=0.005$)(FIG. 4A).

Figure 5:
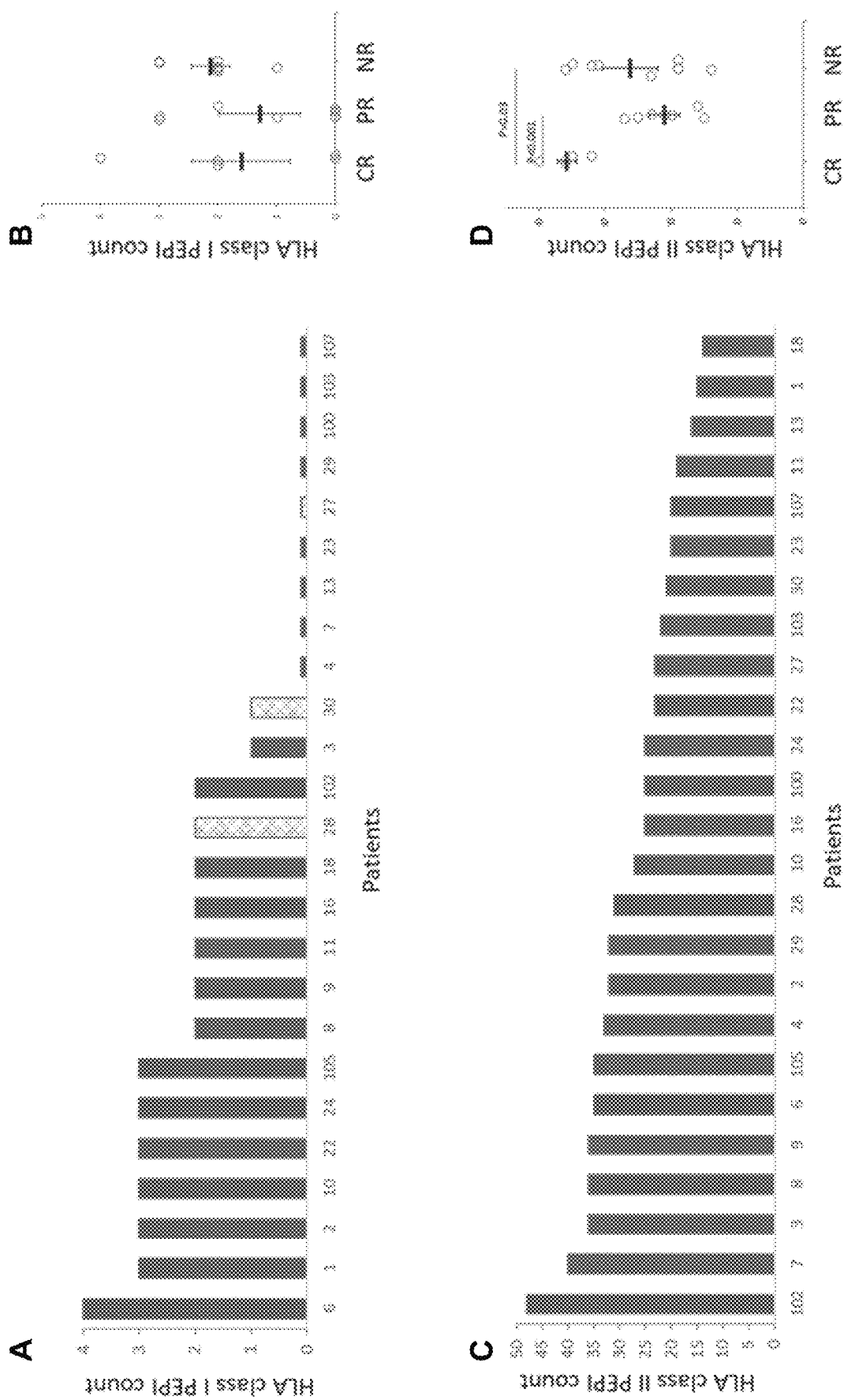
FIG. 5
Multiple HLA binding peptides that define the HPV-16 LPV vaccine specific T cell response set of 20 VIN-3 and 5 cervical cancer patients. PEPI counts were compared to clinical responses after treatment with LPV. Predicted CD8+ T cell responders according to HLA class I PEPIs (A) and CD4+ T cell responders according to HLA class II PEPIs (B). Correlation between HLA class I (C) and class II (D) PEPI count and clinical response at 3 months follow-up in VIN-3 patients. Predicted T cell responders: PEPI count ≥1. Gray column, patient with HPV16 E6- and/or E7-specific T cell response; Dashed column, patient without T cell responses. CR, complete clinical responder; PR, partial clinical responder; NR, clinical non-responder.

Example 7—the ≥1 PEPI3+ Test Predicts T Cell Responses to Full Length LPV Polypeptides Using the same studies reported in Examples 5 and 6, the ≥1 PEPI3+ test was used to predict patient CD8+ and CD4+ T cell responses to the full length E6 and E7 polypeptide antigens of the LPV vaccine. Results were compared to the experimentally determined responses reported. The test correctly predicted the CD8+ T cell reactivity (PEPI3+) of 11 out of 15 VIN-3 patients with positive CD8+ T cell reactivity test results (sensitivity 70%, PPV 85%) and of 2 out of 5 cervical cancer patients (sensitivity 40%, PPV 100%) (FIG. 5A). The CD4+ T cell reactivities (PEPI3+) were correctly predicted 100% both of VIN-3 and cervical cancer patients (FIG. 5B).

Class I and class II HLA restricted PEPI3+ count was also observed to correlate with the reported clinical benefit to LPV vaccinated patients. Patients with higher PEPI3+ counts had either complete or partial response already after 3 months. There was also a correlation between the number of PEPIs and clinical response in VIN-3 patients for HLA class II PEPIs but not HLA class I PEPIs, confirming the post-hoc analysis results from the clinical trial (FIGS. 5C and 5D).

Example 8—Case Study, PEPI3+ Correlation with Vaccine-Specific Immunogenicity

Figure 6:
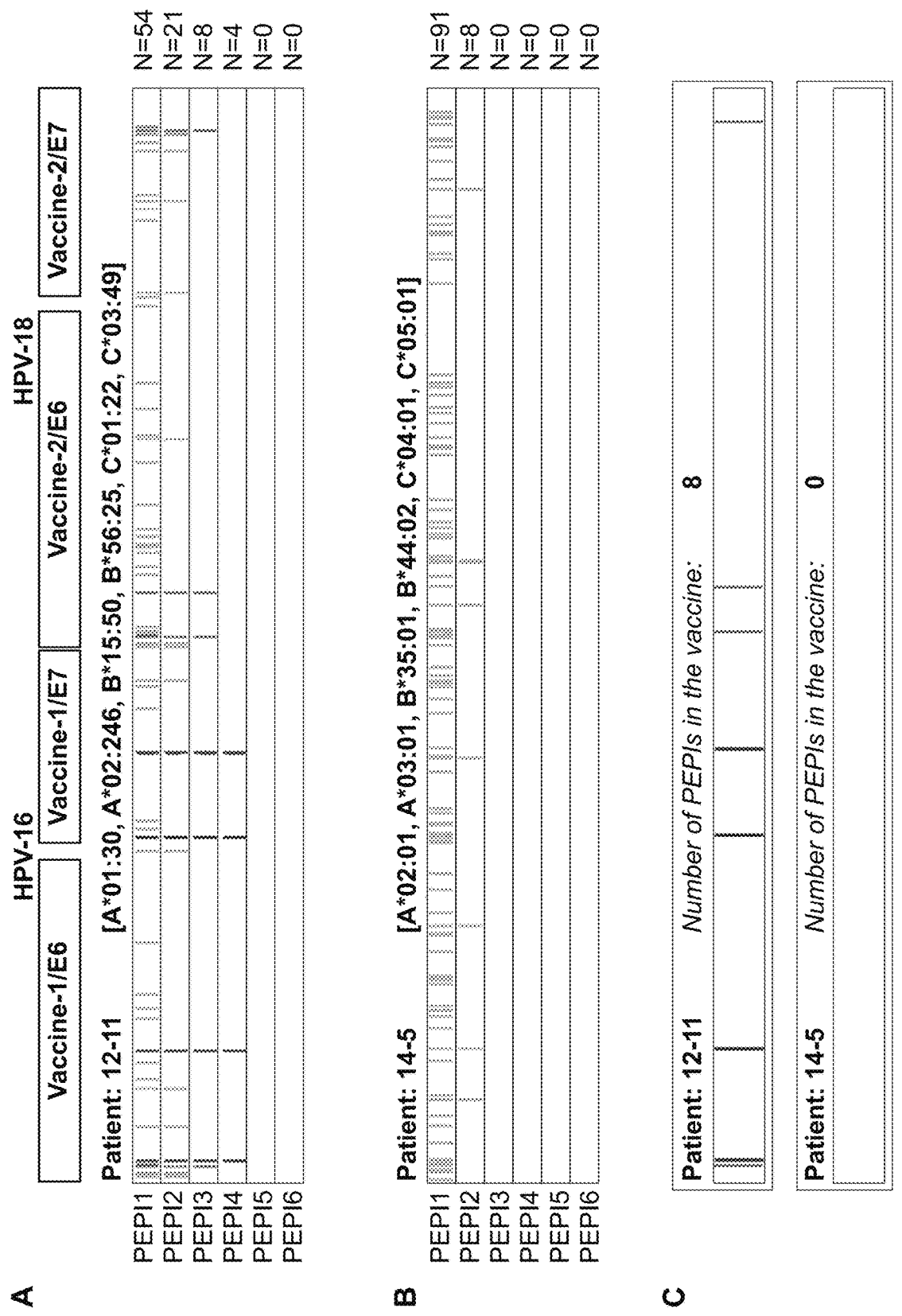
FIG. 6
The multiple HLA class I binding peptides that define the HPV vaccine specific T cell response set of 2 patients. A: Four HPV antigens in the HPV vaccine. Boxes represent the length of the amino acid sequences from the N terminus to the C terminus. B: Process to identify the multiple HLA binding peptides of two patients: HLA sequences of the patients labelled as 4-digit HLA genotype right from the patient's ID. The location of the $1^{st}$ amino acid of the 54 and 91 epitopes that can bind to the patient 12-11 and patient 14-5 HLAs (PEPI1+) respectively are depicted with lines. PEPI2 represents the peptides selected from PEPI1+s that can bind to multiple HLAs of a patient (PEPI2+). PEPI3 represent peptides that can bind to ≥3 HLAs of a patient (PEPI3+). PEPI4 represent peptides that can bind to ≥4 HLAs of a patient (PEPI4+). PEPI5 represent peptides that can bind to ≥5 HLAs of a patient (PEPI5+). PEPI6 represent peptides that can bind to 6 HLAs of a patient (PEPI6). C: The DNA vaccine specific PEPI3+ set of two patients characterizes their vaccine specific T cell responses.

"Vaccine-1" is an HPV16 based DNA vaccine containing full length E6 and E7 antigens with a linker in between. "Vaccine-2" is an HPV18 based DNA vaccine containing full length E6 and E7 antigens with a linker in between (FIG. 6A). A Phase II clinical trial investigated the T cell responses of 17 HPV-infected patients with cervical cancer who were vaccinated with both Vaccine-1" and "Vaccine-2" ("Vaccine-3" vaccination, Bagarazzi et al. Science Translational Medicine. 2012; 4(155):155ra138.).

FIG. 6B shows for two illustrative patients (patient 12-11 and patient 14-5) the position of each epitope (9 mer) presented by at least 1 (PEPI1+), at least 2 (PEPI2+), at least 3 (PEPI3+), at least 4 (PEPI4+), at least 5 (PEPI5+), or all 6 (PEPI6) class I HLA of these patients within the full length sequence of the two HPV-16 and two HPV-18 antigens.

Patient 12-11 had an overall PEPI1+ count of 54 for the combined vaccines (54 epitopes presented by one or more class I HLA). Patient 14-5 had a PEPI1+ count of 91. Therefore patient 14-5 has a higher PEPI1+ count than patient 12-11 with respect to the four HPV antigens. The PEPI1+s represent the distinct vaccine antigen specific HLA restricted epitope sets of patients 12-11 and 14-5. Only 27 PEPI1+s were common between these two patients.

For the PEPI3+ counts (number of epitopes presented by three or more patient class I HLA), the results for patients 12-11 and 14-5 were reversed. Patient 12-11 had a PEPI3+ count of 8, including at least one PEPI3+ in each of the four HPV16/18 antigens. Patient 14-5 had a PEPI3+ count of 0 (FIG. 6C).

The reported immune responses of these two patients matched the PEPI3+ counts, not the PEPI1+ counts. Patient 12-11 developed immune responses to each of the four antigens post-vaccination as measured by ELISpot, whilst patient 14-5 did not develop immune responses to any of the four antigens of the vaccines. A similar pattern was observed when the PEPI1+ and PEPI3+ sets of all 17 patients in the trial were compared. There was no correlation between the PEPI1+ count and the experimentally determined T cell responses reported from the clinical trial. However, correlation between the T cell immunity predicted by the 1 PEPI3+ test and the reported T cell immunity was observed. The ≥1 PEPI3+ test predicted the immune responders to HPV DNA vaccine.

Moreover, the diversity of the patient's PEPI3+ set resembled the diversity of T cell responses generally found in cancer vaccine trials. Patients 12-3 and 12-6, similar to patient 14-5, did not have PEPI3+s predicting that the HPV vaccine could not trigger T cell immunity. All other patients had at least one PEPI3 predicting the likelihood that the HPV vaccine can trigger T cell immunity. 11 patients had multiple PEPI3+ predicting that the HPV vaccine likely triggers polyclonal T cell responses. Patients 15-2 and 15-3 could mount high magnitude T cell immunity to E6 of both HPV, but poor immunity to E7. Other patients 15-1 and 12-11 had the same magnitude response to E7 of HPV18 and HPV16, respectively.

Example 9—Design of a Model Population for Conducting in Silico Trials and Identifying Candidate Precision Vaccine Targets for Large Population An in silico human trial cohort of 433 subjects with complete 4-digit HLA class I Follow genotype (2×HLA- A*xx:xx; 2×HLA-B*xx:xx; 2×HLA-C*xx:xx) and demographic Copy information was compiled. This Model Population has subjects with mixed ethnicity having a total of 152 different HLA alleles that are representative for >85% of presently known allele G-groups.

A database of a "Big Population" containing 7,189 subjects characterized with 4-digit HLA genotype and demographic information was also established. The Big Population has 328 different HLA class I alleles. The HLA allele distribution of the Model Population significantly correlated with the Big Population (Table 10) (Pearson p<0.001). Therefore the 433 patient Model Population is representative for a 16 times larger population.

The Model Population is representative for 85% of the human race as given by HLA diversity as well as HLA frequency.

TABLE 10

Statistical analysis of HLA distributions in "Model Population" vs. "Big Population".

| Group name 1 | Group name 2 | Pearson R value | Correlation | P Value |
|---|---|---|---|---|
| 433 Model Population | 7,189 Big Population | 0.89 | Strong | P < 0.001 |

Figure 7:
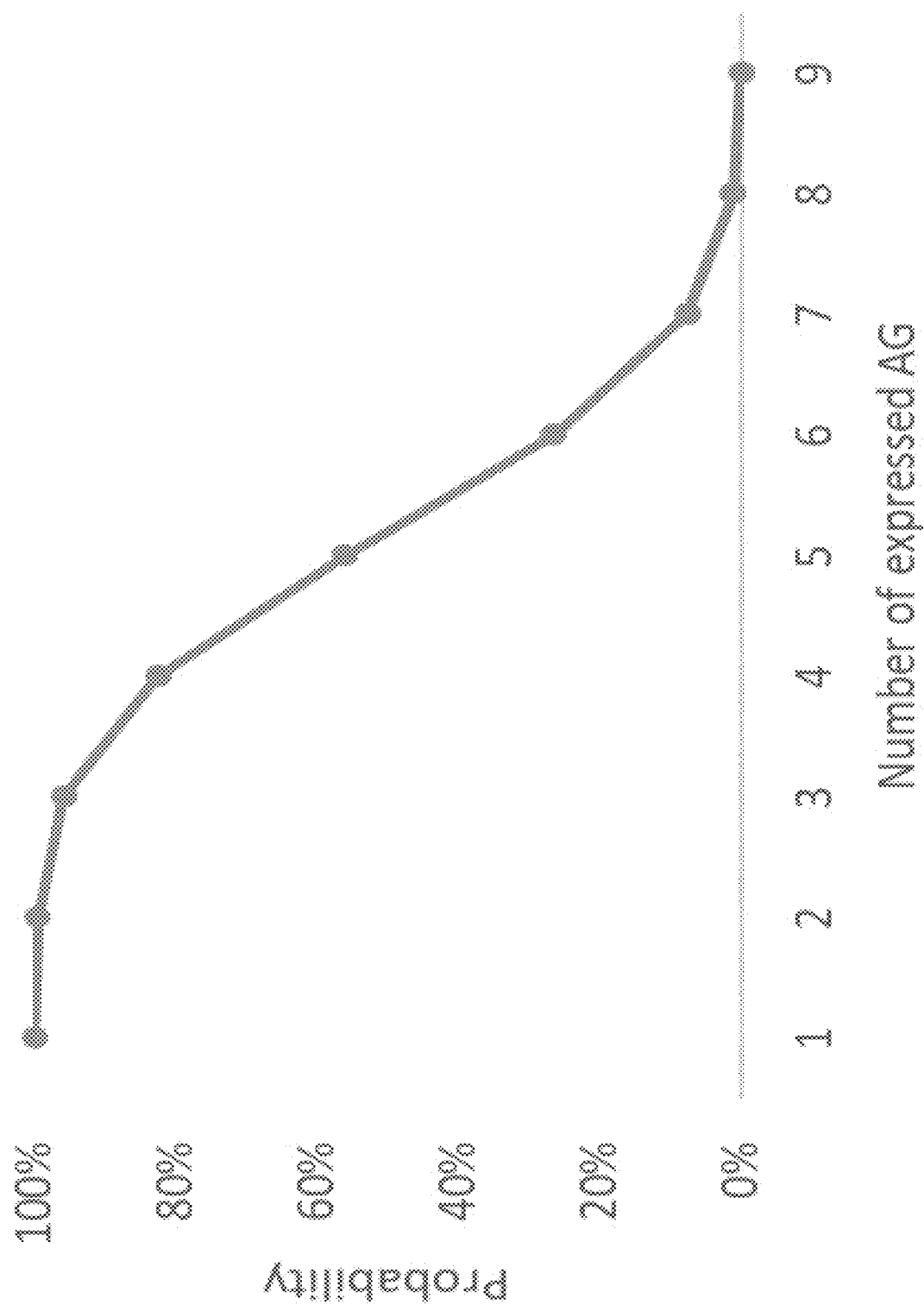
FIG. 7
TSA expression probability targeted by IMA901 vaccine.

Example 10—in Silico Trial Based on the Identification of Multiple HLA Binding Epitopes in a Multi-Peptide Vaccine IMA901 Predict the Reported Clinical Trial Immune Response Rate Probability of Targeting Multiple Antigens in the Tumor of RCC Patients IMA901 is a therapeutic vaccine for renal cell cancer (RCC) comprising 9 peptides derived from tumor-associated antigens (TUMAPs). It was demonstrated that TUMAPs are naturally presented in human cancer tissue, they are overexpressed antigens shared by a subset of patients with the given cancer entity (Table 11). We estimated the probability that a TSA is expressed in a subject treated with IMA901 vaccine using available data from the scientific literature (FIG. 7). We used the Bayesian convention assuming that the expression probabilities follow a Beta-distribution.

We defined AG50 as the number of TSAs (AG) in the cancer vaccine that a specific tumor type expresses with 50% probability. The AG50 modelling of cancer vaccines assumes that each AG produces an effect proportional to the expression rate of the AG in the tumor type (if each AG in the vaccine is immunogenic).

For IMA901 vaccine targeting 9 antigens (9 TUMAPs), the AG50 value is 4.7, meaning that about half of the antigens are overexpressed in 50% of patients' tumor. Moreover, the probability of targeting 2 expressed antigens is 100% and 3 antigens is 96%. These results suggest high potency of IMA901 vaccine based on target antigen selection.

TABLE 11

Overexpression of TAAs in RCC tumors selected for IMA901 vaccine

| TAA (AG) | Published expression rate in RCC tumors* | Estimated expression rate (95% CI) |
|---|---|---|
| ADF-001 | 5/11[1] | 46% (21%, 72%) |
| ADF-002 | 5/11 | 46% (21%, 72%) |
| APO-001 | 9/11[1] | 77% (52%, 95%) |
| CCN-001 | 4/11 | 38% (15%, 65%) |
| GUC-001 | 0/2[2] | 25% (1%, 71%) |
| K67-001 | 2/2 | 75% (29%, 99%) |
| MET-001 | 11/11 | 92% (74%, 100%) |
| MUC-001 | 0/11 | 8% (0%, 26%) |
| RGS-001 | 7/11 | 62% (35%, 85%) |

*expression is defined as overexpression in tumors compared to healthy tissues provided in the source publications
[1]Walter S et al, Multipeptide immune response to cancer vaccine IMA901 after single-dose cyclophosphamide associates with longer patient survival, Nature Medicine, (2012), 18, 1254-1261
[2]Krüger T et al, Lessons to be learned from primary renal cell carcinomas, Cancer Immunol, Immunother, 2005, 54, 826-836

Probability of Inducing Immune Responses Against Multiple Antigens in the Tumor of RCC Patients A total of 96 HLA-A*02+ subjects with advanced RCC were treated with IMA901 in two independent clinical studies (Phase I and Phase II) (Walter S et al, Multipeptide immune response to cancer vaccine IMA901 after single-dose cyclophosphamide associates with longer patient survival, Nature Medicine, (2012), 18, 1254-1261). Each of the 9 peptides in IMA901 have been identified as HLA-A*02-restricted epitopes. Based on currently accepted standards, all 9 peptides are strong candidates to boost T cell responses against renal cancer since their presence has been detected in renal cancer patients, and because the trial patients were specifically selected to have at least one HLA molecule (HLA-A*02) capable of presenting each of the peptides. Despite this restriction the immune response rate of the phase I and phase II clinical trials measured for at least one peptide of the vaccine was 74% and 64%, respectively.

Figure 8:
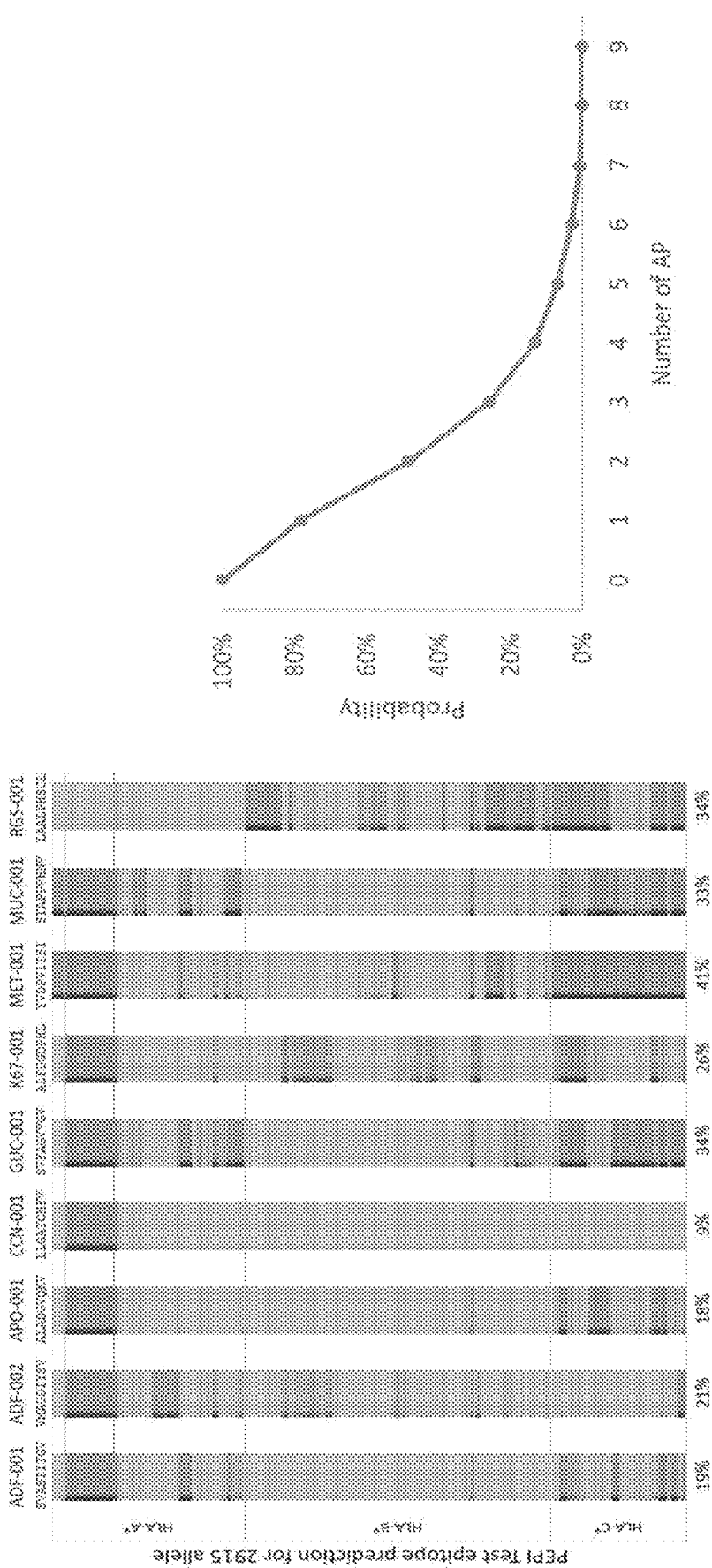
FIG. 8

We analyzed by in silico prediction the HLA binding properties of each TUMAP in IMA901 and found that 8 out of the 9 TUMAPs can bind to many HLA-A*02 alleles confirming the identification process (FIG. 8). However, we found that each TUMAP can bind to many other HLA-B* and HLA-C* alleles (FIG. 8A).

Since the complete 4-digit HLA genotype of subjects who participated in IMA901 clinical trials were not available, we used the genotype data of 51 HLA-A*02 selected RCC subjects from another clinical trial, to characterize the immunogenicity of IMA901 vaccine (REF: Chowell D, Morris L G T, Grigg C M, Weber J K, Samstein R M, et al. Patient HLA class I genotype influences cancer response to checkpoint blockade immunotherapy. Science. 2018; 359 (6375): 582-587.). As presented on FIG. 8B, only few TUMAPs are able to bind to multiple HLAs of the same subject. The most immunogenic peptide in this context turned to be MET-001 capable of generating PEPI in 35% of RCC patients. However, CCN-001 could not generate PEPI in any of the patients, in agreement with FIG. 8A; CCN-001 can bind only to HLA-A*02 alleles. Based on FIG. 8A, MUC-001 is theoretically able to bind other alleles, too (both HLA-B and HLA-C), however those alleles were not present in the patients of our model population, therefore this peptide could not generate PEPI, either.

The immunogenicity of IMA901 vaccine determined in the 2 clinical trials was compared with the PEPI response rate determined using the PEPI test in our RCC model population. We found 67% (CI95 53-78%) immune response to at least one peptide of the IMA901 vaccine. According to PEPI test, 33% (CI95 22-47%) of these HLA-A*02+ subjects did not have 3 HLAs binding to any TUMAPs. Interestingly, IMA901 did not induce T cell responses in 25% and 36% of HLA-A*02 selected subjects in the Phase I and Phase II clinical trials, respectively. Furthermore, PEPI test predicted 30% (CI95 19-43%) of subjects with 1 PEPI to one TUMAP, and 37% (CI95 25-51%) have ≥2 PEPIs to at least two IMA901 peptides, which is in agreement with the average 40% and 27% immune response to 1 or ≥2 TUMAPs in both clinical trials (Table 12). The differences between the immunogenicity found in the 3 cohorts can be explained by the differences in the HLA genotype of the study subjects as well as the potential errors in measuring T cell responses and in determining PEPIs with the PEPI test (see Example 1). The phase I and phase II study results show the variability of the immune response rates of the same vaccine in different trial cohorts. However, the agreements between PEPI response rates and immunogenicity of peptide vaccines are determined by the host HLA sequences.

TABLE 12

Immunogenicity of IMA901 vaccine is determined by the host HLA genotype (multiple HLAs)

| Immune responses to TUMAPs | Phase I (n = 27)* | Phase II (n = 61)* | Phase I + II (n = 88) | RCC model population (n = 51)** (CI95%) |
|---|---|---|---|---|
| No peptide | 25% | 36% | 33% | 33% (22-47%) |
| ≥1 peptide | 74% | 64% | 67% | 67% (53-78%) |
| 1 peptide | 44% | 38% | 40% | 30% (19-43%) |
| ≥2 peptides | 29% | 26% | 27% | 37% (25-51%) |

*reported immunological data for the trials conducted with IMA901 vaccine (REF: Walter Nat Med 2012);
**Predicted by PEPI test Similarly to the AG50, we defined AP50 as the average number of antigens with PEPI of a vaccine which shows how the vaccine can induce immune response against the antigens targeted by the composition (cancer vaccine specific immune response). AP, therefore is depending of the HLA heterogeneity of the analyzed population and is independent on the expression of the antigen on the tumor. The IMA901 composition can induce immune response against an average of 1.06 vaccine antigens (AP50=1.06) meaning that in the HLA-A*02 selected RCC model population it can induce immune response against at least one vaccine antigen. This result is far less compared to the designed intention of immunogenicity (HLA-matched patients treated with 9 peptides).

Comparison of Immunogenicity and Clinical Response of TUMAPs in the IMA901 Peptide Vaccine An immune response induced by a vaccine against a single antigen might not be sufficient for clinical activity, as the given antigen might not be expressed in the patient. Therefore, we defined AGP as the immune response which targets an expressed antigen, taking into account both the immunogenicity and expression probability of the vaccine antigen on the tumor, presented above. AGP depends on the antigen (AG) expression rate in the indicated tumor and the HLA genotype of subjects capable to make PEPI (P) in the study population.

Figure 9:
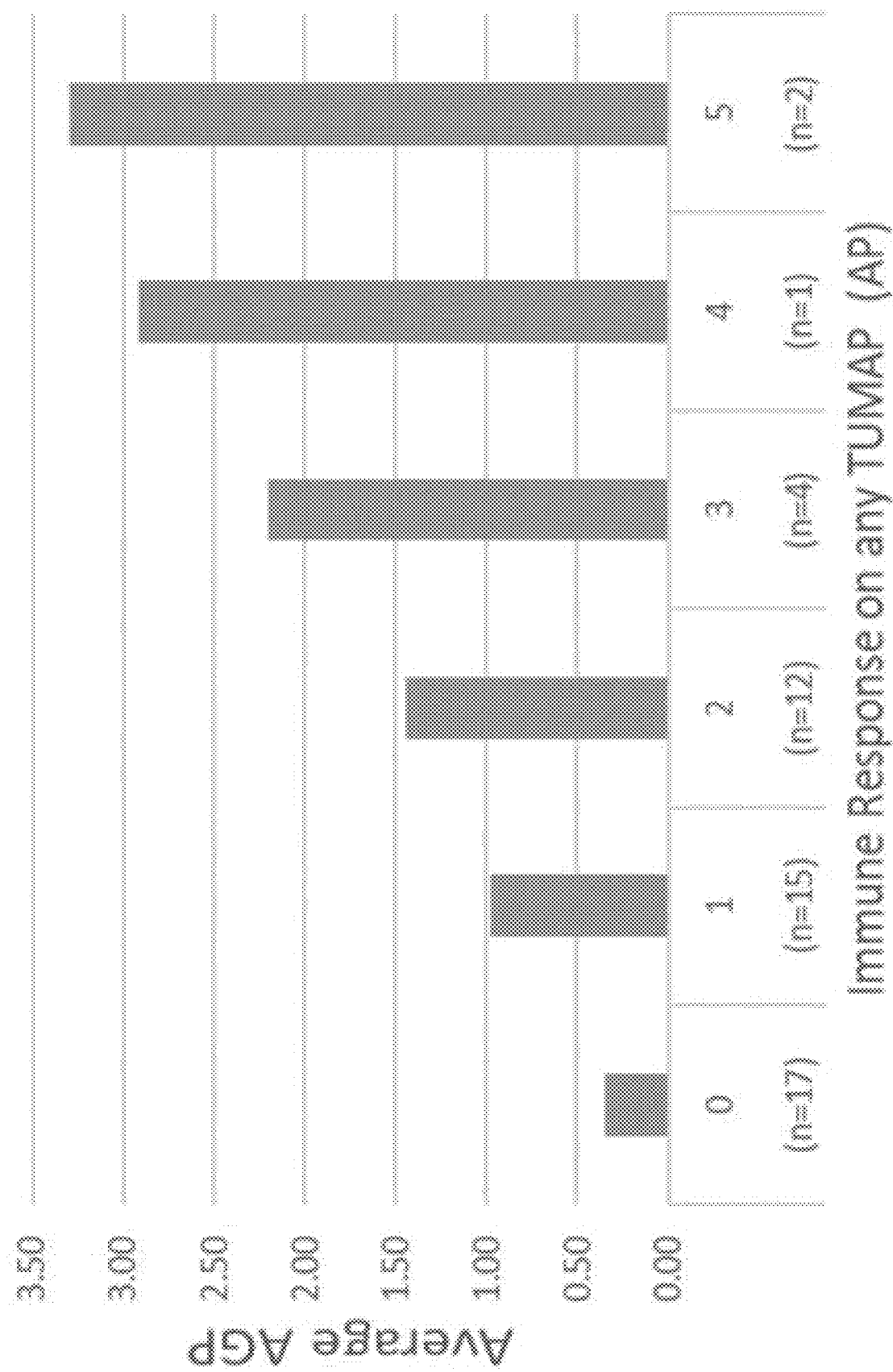

Therefore, we investigated the correlation between immune responses against different number of antigens (TUMAPs) and the immune responses against likely expressed antigens (AGP). We found that an immune response elicited by one peptide (1 TUMAP) corresponds to 0.98 AGP, meaning that there is 98% probability that the immune response induced by any peptide of the IMA901 vaccine will target an expressed antigen on the tumor (FIG. 9). However, immune responses elicited by 2 or 3 TUMAPs correspond to only 1.44 and 2.21 AGP, respectively. 0.35 AGP corresponding to 0 TUMAP indicates the cumulated error of PEPI test prediction (see Example 1).

To characterize the potency of a cancer vaccine we defined AGP50, a parameter showing the number of antigens that the vaccine induced CTLs can recognize in a tumor with 50% probability. The computation is similar to the AG50 but in addition to the expression, the occurrence of the PEPI presentation on certain vaccine antigen is also considered. AGP50 for IMA901 vaccine for the RCC model population is 1.10.

In a retrospective analysis, IMA901 clinical trial investigators found that significantly more subjects who responded to multiple TUMAPs of IMA901 experienced disease control (DC, stable disease or partial response) compared with subjects who had no response or responded to only 1 TUMAP (Table 13). Since the presence of PEPIs accurately predicted the responders to TUMAPs, we investigated the relationship between disease control rate in the TUMAP responder subpopulation and AGP. Similarly, to the investigators we analyzed the percentage of patients who are likely to have immune response against an expressed antigen (i.e.: ≥1 AGP) for the subpopulations predicted to have immune response to 0, 1 or 2 TUMAPs using our RCC model population. Interestingly, percentage of patients with 1 AGP is similar to the percentage of patients with disease control in the subpopulations: i.e.: 33% of patients had disease control vs 47% (CI95 23-67%) had 1 AGP and considerably more patients had disease control and AGP in the subgroup with immune response to 2 TUMAPs 75% vs 90% (CI95 70, 97%), respectively. These results suggest that only those patients are likely to experience clinical benefit, who have immune response against at least one expressed tumor antigen. Moreover, the percentage of patients with 1 AGP in our RCC model population is similar to the disease control rate of the phase I and phase II trials conducted with IMA901 vaccine (Table 12).

TABLE 13

Correlation between clinical benefit and AGP

| Subpopulation | % of pts with DC in the clinical subpopulation | % pts with 1 AGP in the model subpopulation (CI95) |
|---|---|---|
| No IR | 14% | 5% (0%, 18%) |
| IR to 1TUMAP | 33% | 47% (23%, 67%) |
| IR to ≥ 2 TUMAPs | 75% | 90% (70%, 97%) |
| Phase I | 40% | 49% (35%, 61%) |
| Phase II | 31% | |

Analysis of IMA901 Vaccine Potency in Multiple Populations

As shown in Table 14, AG50 value of 4.7 was observed for IMA901 vaccine, suggesting high potency based on target antigen selection. However, AP50 for IMA901 in both the unselected general population and HLA-A*02 selected subjects were only 0.75 and 1.12, respectively. Similar results were obtained for unselected RCC model population and HLA-A*02 selected populations. This results demonstrate that HLA-A*02 enrichment improved the antigenicity of IMA901, however did not ensure the immunogenicity of the vaccine. Consequently, the AGP50 values describing the potency of the vaccine are low in each population.

TABLE 14

Potency of IMA901 vaccine in in unselected population and HLA-A*02 selected subjects

| Model Population | AG50 | AP50 | AGP50 |
|---|---|---|---|
| All Subjects (n = 433) | 4.7 | 0.75 | 0.49 |
| HLA-A*02 Subjects (n = 180) | 4.7 | 1.12 | 0.81 |
| RCC population (n = 129) | 4.7 | 0.61 | 0.70 |
| RCC subpopulation A*02 (n = 51) | 4.7 | 1.06 | 1.10 |

Example 11—in Silico Trials Based on the Identification of Multiple HLA Binding Epitopes Predict the Reported T Cell Response Rates of Clinical Trials The objective of this study was to determine whether a model population, such as the one described in Example 9, may be used to predict CTL reactivity rates of vaccines, i.e. used in an in silico efficacy trial and to determine the correlation between the clinical outcome of vaccine trials and PEPI.

Published clinical trial results were collected from studies with therapeutic vaccines, which included 1,790 subjects in 64 clinical studies, treated with 42 therapeutic vaccines covering 61 different antigens (Table 15). The same vaccines used in those clinical trials were used to perform in silico trials with the model population of 433 human leukocyte antigen (HLA)-genotyped subjects (described in Example 9). No subjects were excluded for reasons other than data availability. IRR was defined as the proportion of subjects in the study population with T cell responses induced by the study vaccine. ORR was defined as the proportion of subjects in the study population with objective response (complete and partial response) after vaccination. The proportion of subjects with PEPIs (personal epitopes that bind to 3 HLA alleles of a subject), multiple PEPIs, and PEPIs in multiple antigens were computed in the in silico trials to obtain the PEPI Score, MultiPEPI Score, and MultiAgPEPI Score, respectively. The immune and objective response rates (TRR and ORR) from the published clinical trials were compared with the PEPI Score, MultiPEPI Score, and MultiAgPEPI Score. All reported and calculated scores are summarized in Table 16.

TABLE 15

Summary of patient demographics in the published clinical trials

| Characteristic | Count | Percentage |
|---|---|---|
| Total subjects | 1,790 | |
| Total studies | 64 | |
| Subjects with HIV infection | 12 | 1% |
| Subjects with neoplasia or dysplasia | 172 | 9% |
| Subjects with cancer | 1606 | 90% |
| Subjects with solid tumors | 1503 | 84% |
| Subjects with liquid tumors | 103 | 6% |
| Subjects with metastatic tumors | 788 | 44% |
| Subjects with non-metastatic tumors | 818 | 46% |
| HLA selected subjects | 918 | 51% |
| Non-HLA selected subjects | 872 | 49% |
| Trials with HLA selected subjects | 32 | 50% |
| Trials without HLA selected subjects | 32 | 50% |

TABLE 16

Response rates and PEPI Scores

| Immunotherapy | IRR | ORR | PEPI Score | Multi PEPI Score | MultiAg PEPI Score |
|---|---|---|---|---|---|
| PSMA-Survivin pulsed DC vaccine | — | 18% | 3% | 0% | 0% |
| Peptide vaccine | — | 3% | 10% | 0% | 0% |
| HPV-SLP | 83% | 60% | 73% | 70% | 34% |
|  | 100% | 60% | 73% | 70% | 34% |
| VGX-3100 | 78% | 50% | 87% | 56% | 64% |
| Melanoma peptide vaccine | 52% | 12% | 42% | 6% | 6% |
| GAA peptides vaccine | 55% | 15% | 18% | 0% | 0% |
| KRM-20 peptide vaccine | 40% | 13% | 36% | 15% | 15% |
| Peptide vaccine | 100% | 25% | 81% | 3% | 1% |
| S-288310 peptide vaccine | 67% | 17% | 44% | 8% | 8% |
| KIF20A-66 peptide | 70% | 26% | 38% | 7% | — |
| PepCan | 65% | 52% | 62% | 26% | — |
| Iplilimumab (NYESO-1 specific response) | 72% | 25% | 84% | 65% | — |
| p53 SLP70-248 | 88% | 0% | 77% | 52% | — |
|  | 100% | 0% | 77% | 52% | — |
|  | 0% | — | 77% | 52% | — |
| p53 SLP70-235 | 21% | — | 75% | 52% | — |
| GVX301 | 64% | 0% | 65% | 7% | — |
| TroVax vaccine (OXB-301) | 65% | 0% | 94% | 83% | — |
|  | 57% | 0% | 94% | 83% | — |
| StimuVax | 21% | — | 2% | — | — |
| IMA901 | 74% | — | 48% | 27% | 27% |
|  | 64% | — | 48% | 27% | 27% |
| ICT107 | 33% | — | 52% | — | — |
| ProstVac | 67% | — | 50% | 23% | — |
|  | 45% | — | 50% | 23% | — |
|  | 76% | — | 50% | 23% | — |
|  | 67% | — | 50% | 23% | — |
|  | 50% | — | 50% | 23% | — |
|  | 72% | — | 50% | 23% | — |
| Synchrotope TA2M | 46% | — | 24% | 7% | — |
| MELITAC 12 · 1 | 49% | — | 47% | 19% | — |
| HIVIS | 50% | — | 88% | — | — |
|  | 80% | — | 93% | — | — |
| ImMucin | 90% | — | 95% | 70% | — |
|  | 100% | 47% | 95% | 70% | — |
| NY-ESO-1 OLP | 71% | — | 84% | 65% | — |
|  | 82% | 0% | 84% | 65% | — |
| WT1 vaccine | 83% | — | 80% | 77% | — |
| WT1 peptide vaccine | 72% | 6% | 86% | — | — |
| RHAMM-R3 peptide vaccine | 44% | 0% | 0% | — | — |
| GMMG-MM5 peptides | 35% | — | 86% | 21% | 21% |
| INGN-225 p53 vaccine | 58% | 4% | 82% | 61% | — |
| HR2822 | 8% | — | 3% | — | — |
| GV1001 | 17% | — | 3% | — | — |
|  | 45% | — | 3% | — | — |
| Vx-001 | 51% | — | 33% | — | — |
|  | 66% | 7% | 33% | — | — |
|  | 58% | 4% | 33% | — | — |
|  | 71% | 0% | 33% | — | — |
| NY-ESO-1f | 90% | 0% | 55% | 18% | — |
| GL-0817 | 33% | — | 29% | 3% | — |
| (MAGE-A3 Trojan) | 57% | 0% | 29% | 3% | — |
|  | 0% | 0% | 29% | 3% | — |
| DPX0907 (per peptide) | 0% | — | 22% | — | — |
|  | 11% | — | 18% | — | — |
|  | 11% | — | 7% | — | — |
|  | 11% | — | 39% | — | — |
|  | 17% | — | 12% | — | — |
|  | 17% | — | 5% | — | — |
|  | 22% | — | 31% | — | — |
| CV9103 mRNA vaccine | 80% | — | 100% | — | — |

TABLE 16-continued

Response rates and PEPI Scores

| Immunotherapy | IRR | ORR | PEPI Score | Multi PEPI Score | MultiAg PEPI Score |
|---|---|---|---|---|---|
| TG4010 vaccine | 38% | 13% | 43% | 6% | — |
|  | 26% | 0% | 43% | 6% | — |
|  | 21% | — | 43% | 6% | — |
|  | — | 0% | — | — | — |
| SVN-2B peptide vaccine | 60% | — | 35% | — | — |
| TSPP peptide vaccine | — | 5% | 72% | 31% | — |
| Her2/neu peptide vaccine (p369) | 62% | — | 4% | — | — |
| Her2/neu peptide vaccine (p688) | 31% | — | 1% | — | — |
| Her2/neu peptide vaccine (p971) | 54% | — | 0% | — | — |
| MART-1 Peptide Vaccine | 15% | — | 0% | — | — |

Figure 10:
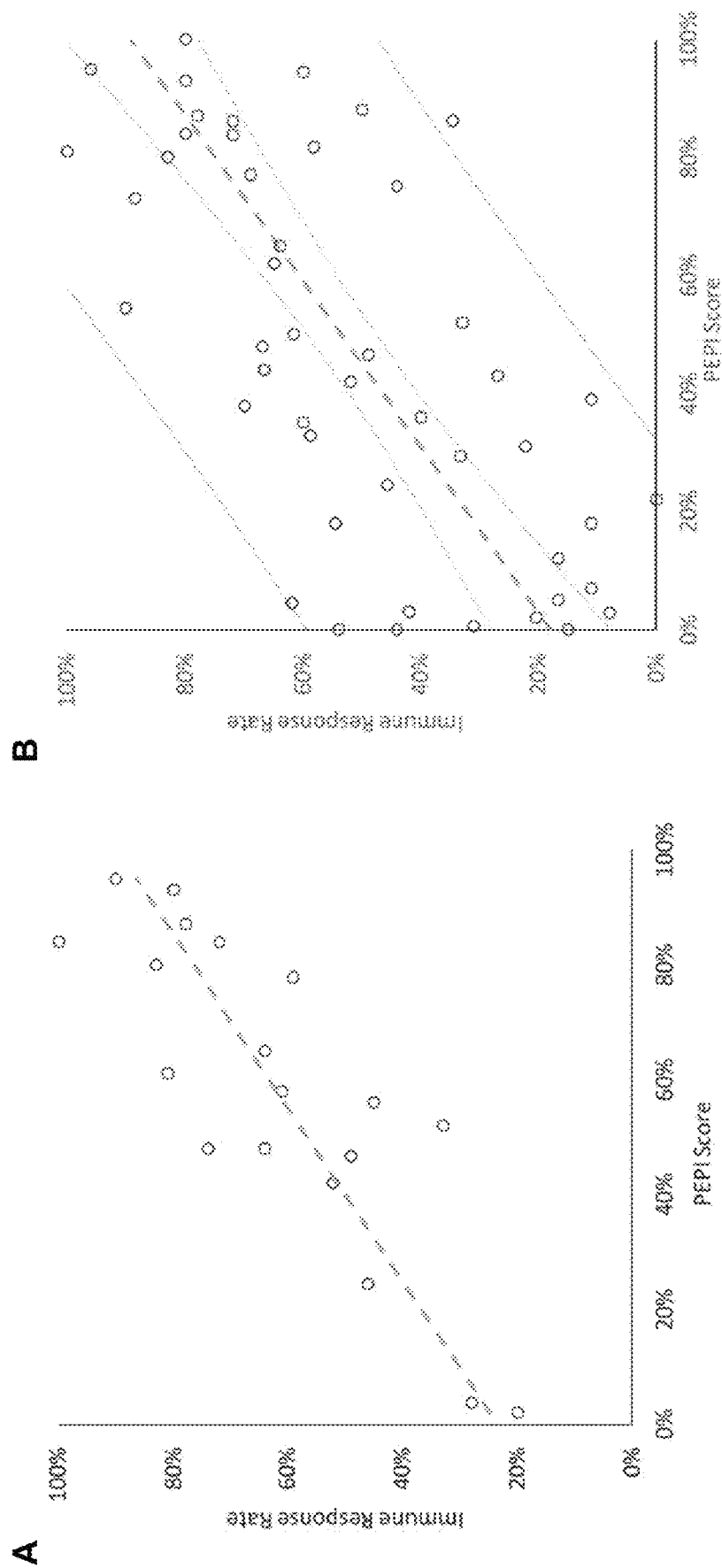
Figure 10:
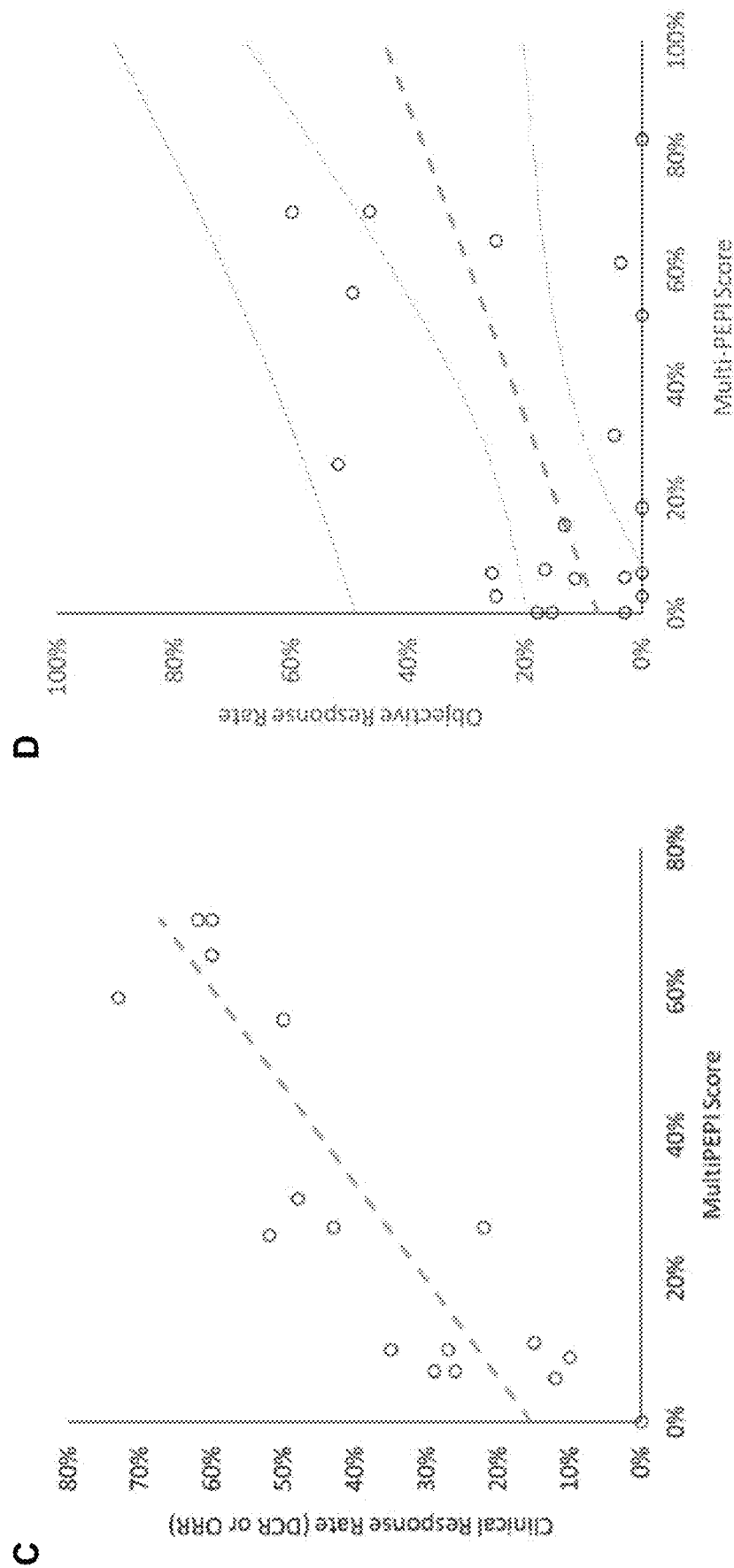
Figure 10:
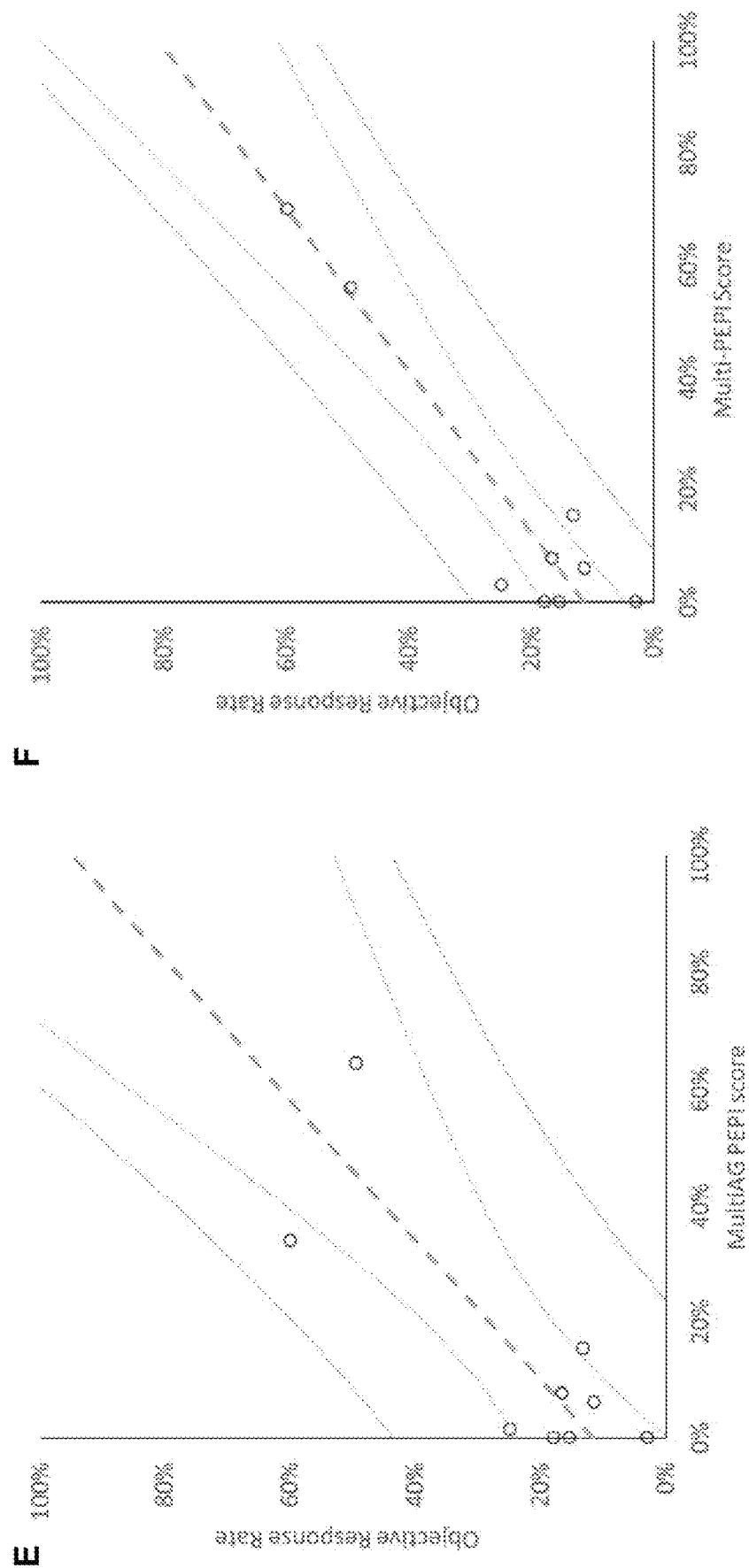
Figure 10:
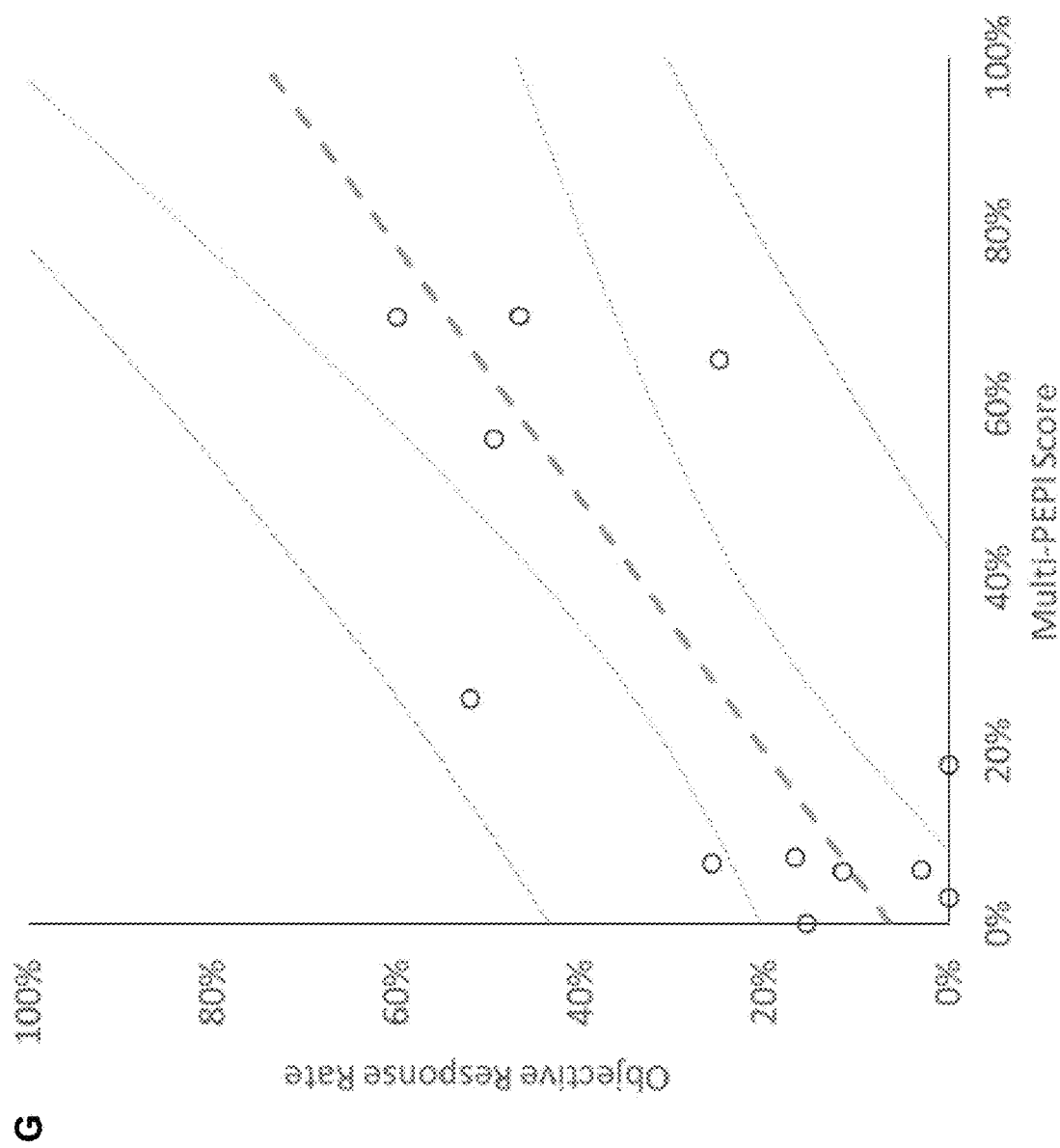

We investigated the correlation between ≥1 PEPI3+ Score and immune response rate in a previous study of 12 peptide vaccines derived from cancer antigens that induced T cell responses in a subpopulation of 172 subjects from 19 clinical trials, that were identified from peer reviewed publications. The experimentally determined response rates reported from the trials were compared with the ≥1 PEPI3+ Scores and linear correlation between ≥1 PEPI3+ Score and response rate ($R^2=0.70$) was found (p=0.001) (FIG. 10A). The correlation between ≥1 PEPI3+ Score and immune response rate was then confirmed by the analysis of 59 clinical trials involving 1,343 subjects who were treated with 40 different vaccines. Each vaccine was analyzed by comparing the published IRR from the clinical trial to the PEPI Score from the model population. (FIG. 10B). The correlation between the IRR and PEPI Score was significant ($r^2=0.465$ and p=0.001). This result demonstrated that the PEPI Score determined by in silico trials in the MP accurately predicts the IRRs observed in clinical trials.

To test whether polyclonal T cell response increases the likelihood of tumor shrinkage, ORR and MultiPEPI Score were compared. Preliminary experiments analyzed the relationship between clinical response (either ORR or DCR) and MultiPEPI Score in 17 clinical trials conducted with peptide- and DNA-based immunotherapy vaccines. The results from these experiments demonstrated a significant correlation between clinical response rate and MultiPEPI Score ($r^2=0.75$, p<0.001). To confirm these findings, ORR data from 27 clinical trials with 21 different vaccines, involving 600 subjects, were collected and analyzed (FIG. 10C). The MultiPEPI Score was calculated as the percentage of subjects in the model population with multiple PEPIs from the study vaccine. The results from this experiment demonstrated that ORR does not correlate with MultiPEPI Score (FIG. 10D).

Results from previous studies suggested that T cell responses against multiple antigens were associated with longer progression free- and overall survival. Consequently, we hypothesized that the induction of T cell responses against multiple tumor antigens increases the likelihood of tumor shrinkage. To test this hypothesis, ORR data from 10 clinical trials conducted with 9 different vaccines, involving 263 subjects, that were treated with multiantigen-targeting vaccine were collected and analyzed. The MultiAg PEPI Score was calculated as the percentage of subjects with vaccine-specific PEPIs on at least two antigens. The results from this experiment demonstrated a significant correlation between ORR and MultiAg PEPI Score ($r^2=0.64$; p=0.01), and ORR and MultiPEPI Score ($r^2=0.88$ and p=0.001) (FIGS. 10E and F, respectively). These results suggest that T cell responses against multiple tumor antigens may recognize a larger tumor cell population, thereby increasing the likelihood of tumor shrinkage.

The next analysis explored whether PEPI-specific T cell responses against antigens expressed in the tumor of interest, increase the likelihood of tumor shrinkage. A total of 15 clinical trials enrolled subjects with target antigen positive disease and 11 clinical trials had no subject preselection based on antigen expression. The proportion of subjects with objective response was significantly higher in CTs with target antigen-positive subjects compared with CTs without target pre-selection (21.0% vs 3.6%, respectively, p=0.03).

The correlation between ORR and MultiPEPI Score was statistically significant in subjects with confirmed expression of target antigens ($r^2=0.56$, p=0.005) (FIG. 10G). These results emphasize the importance of the presence of cognate PEPI in the tumor, and also that the presence of the cognate PEPI in the tumor increases the likelihood of tumor shrinkage.

This study demonstrated that the link between a subject's HLA genotype and PEPI is the most important factor in predicting clinical response to a vaccine. This study also showed that the PEPI Score can predict the clinical outcome of therapeutic vaccines.

Figure 11:
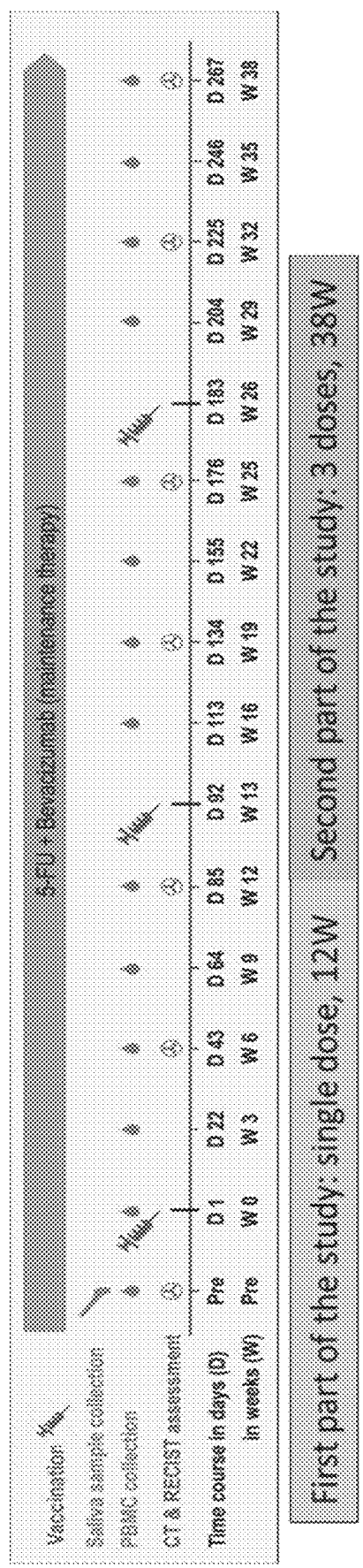

Example 12—Study Design of OBERTO Phase I/II Clinical Trial and Preliminary Safety Data OBERTO trial is a Phase I/II trial of PolyPEPI1018 Vaccine and CDx for the Treatment of Metastatic Colorectal Cancer (NCT03391232). Study design is shown in FIG. 11.

Enrollment Criteria
  Histologically confirmed metastatic adenocarcinoma originating from the colon or the rectum
  Presence of at least 1 measurable reference lesion according to RECIST 1.1
  PR or stable disease during first-line treatment with a systemic chemotherapy regimen and 1 biological therapy regimen
  Maintenance therapy with a fluoropyrimidine (5-fluorouracil or capecitabine) plus the same biologic agent (bevacizumab, cetuximab or panitumumab) used during induction, scheduled to initiate prior to the first day of treatment with the study drug
  Last CT scan at 3 weeks or less before the first day of treatment Subject Withdrawal and Discontinuation.
  During the initial study period (12 W), if a patient experiences disease progression and needs to start a second-line therapy, the patient will be withdrawn from the study.
  During the second part of the study (after 2nd dose) if a patient experiences disease progression and needs to start a second-line therapy, the patient will remain in the study, receive the third vaccination as scheduled and complete follow-up.
  Transient local erythema and edema at the site of vaccination were observed as expected, as well as a flu-like syndrome with minor fever and fatigue. These reactions are already well-known for peptide vaccination and usually are associated with the mechanism of action, because fever and flu-like syndrome might be the consequence and sign for the induction of immune responses (this is known as typical vaccine reactions for childhood vaccinations).

Only one serious adverse event (SAE) "possibly related" to the vaccine was recorded (Table 17).

One dose limiting toxicity (DLT) not related to the vaccine occurred (syncope).

Safety results are summarized in Table 17.

TABLE 17

Serious adverse events reported in the OBERTO clinical trial.
No related SAE occurred (only 1 "possibly related").

| Patient ID | SAE | Relatedness |
|---|---|---|
| 010001 | Death due to disease progression | Unrelated |
| 010004 | Embolism | Unlikely Related |
| 010004 | Abdominal pain | Unrelated |
| 010007 | Bowel Obstruction | Unrelated |
| 020004 | Non-Infectious Acute Encephalitis | Possibly Related |

Example 13—Expression Frequency Based Target Antigen Selection During Vaccine Design and It's Clinical Validation for mCRC Shared tumor antigens enable precise targeting of all tumor types—including the ones with low mutational burden. Population expression data collected previously from 2,391 CRC biopsies represents the variability of antigen expression in CRC patients worldwide (FIG. 12A).

PolyPEPI1018 is a peptide vaccine we designed to contain 12 unique epitopes derived from 7 conserved testis specific antigens (TSAs) frequently expressed in mCRC. In our model we supposed, that by selecting the TSA frequently expressed in CRC, the target identification will be correct and will eliminate the need for tumor biopsy. We have calculated that the probability of 3 out of 7 TSAs being expressed in each tumor is greater than 95%. (FIG. 12B)

In a phase I study we evaluated the safety, tolerability and immunogenicity of PolyPEPI1018 as an add-on to maintenance therapy in subjects with metastatic colorectal cancer (mCRC) (NCT03391232) (See also in Example 4).

Immunogenicity measurements proved pre-existing immune responses and indirectly confirmed target antigen expression in the patients. Immunogenicity was measured with enriched Fluorospot assay (ELISPOT) from PBMC samples isolated prior to vaccination and in different time points following a following single immunization with Poly-PEPI1018 to confirm vaccine-induced T cell responses; PBMC samples were in vitro stimulated with vaccine-specific peptides (9mers and 30mers) to determine vaccine-induced T cell responses above baseline. In average 4, at least 2 patients had pre-existing CD8 T cell responses against each target antigen (FIG. 12C). 7 out of 10 patients had pre-existing immune responses against at least 1 antigen (average 3) (FIG. 12D). These results provide proof for the proper target selection, because CD8+ T cell response for a CRC specific target TSA prior to vaccination with Poly-PEPI1018 vaccine confirms the expression of that target antigen in the analyzed patient. Targeting the real (expressed) TSAs is the prerequisite for an effective tumor vaccine.

Example 14—Pre-Clinical and Clinical Immunogenicity of PolyPEPI1018 Vaccine Proves Proper Peptide Selection PolyPEPI1018 vaccine contains six 30mer peptides, each designed by joining two immunogenic 15mer fragments (each involving a 9mer PEPI, consequently there are 2 PEPIs in each 30mer by design) derived from 7 TSAs (FIG. 13). These antigens are frequently expressed in CRC tumors based on analysis of 2,391 biopsies (FIG. 12).

Preclinical immunogenicity results calculated for the Model Population (n=433) and for a CRC cohort (n=37) resulted in 98% and 100% predicted immunogenicity based on PEPI test predictions and this was clinically proved in the OBERTO trial (n=10), with immune responses measured for at least one antigen in 90% of patients. More interestingly, 90% of patients had vaccine peptide specific immune responses against at least 2 antigens and 80% had CD8+ T cell response against 3 or more different vaccine antigens, showing evidence for appropriate target antigen selection during the design of PolyPEPI1018. CD4+ T cell specific and CD8+ T cell specific clinical immunogenicity is detailed in Table 18.

TABLE 18

Clinical immunogenicity results for PolyPEPI1018 in mCRC.

| Immunological responses | % Patients (n) |
|---|---|
| CD4+ T cell responses | 100% (10/10) |
| CD8+ T cell responses against ≥ 3 antigens | 80% (8/10) |
| Both CD8+ and CD4+ T cell responses | 90% (9/10) |
| Ex vivo detected CD8+ T cell response | 71% (5/7) |
| Ex vivo detected CD4+ T cell response | 86% (6/7) |
| Average increase of the fraction of polyfunctional (IFN-γ and TNF-α positive) CD8+ T cells compared to pre-vaccination | 0.39% |
| Average increase of the fraction of polyfunctional (IL-2 and TNF-α positive) CD4+ T cells compared to pre-vaccination | 0.066% |

High immune response rates were found for both effector and memory effector T cells, both for CD4+ and CD8+ T cells, and 9 of 10 patients' immune responses were boosted or de novo induced by the vaccine. Also, the fractions of CRC-reactive, polyfunctional CD8+ and CD4+ T cells have been increased in patient's PBMC after vaccination by 2.5- and 13-fold, respectively.

Example 15—Clinical Response for PolyPEPI1018 Treatment

Figure 14A:
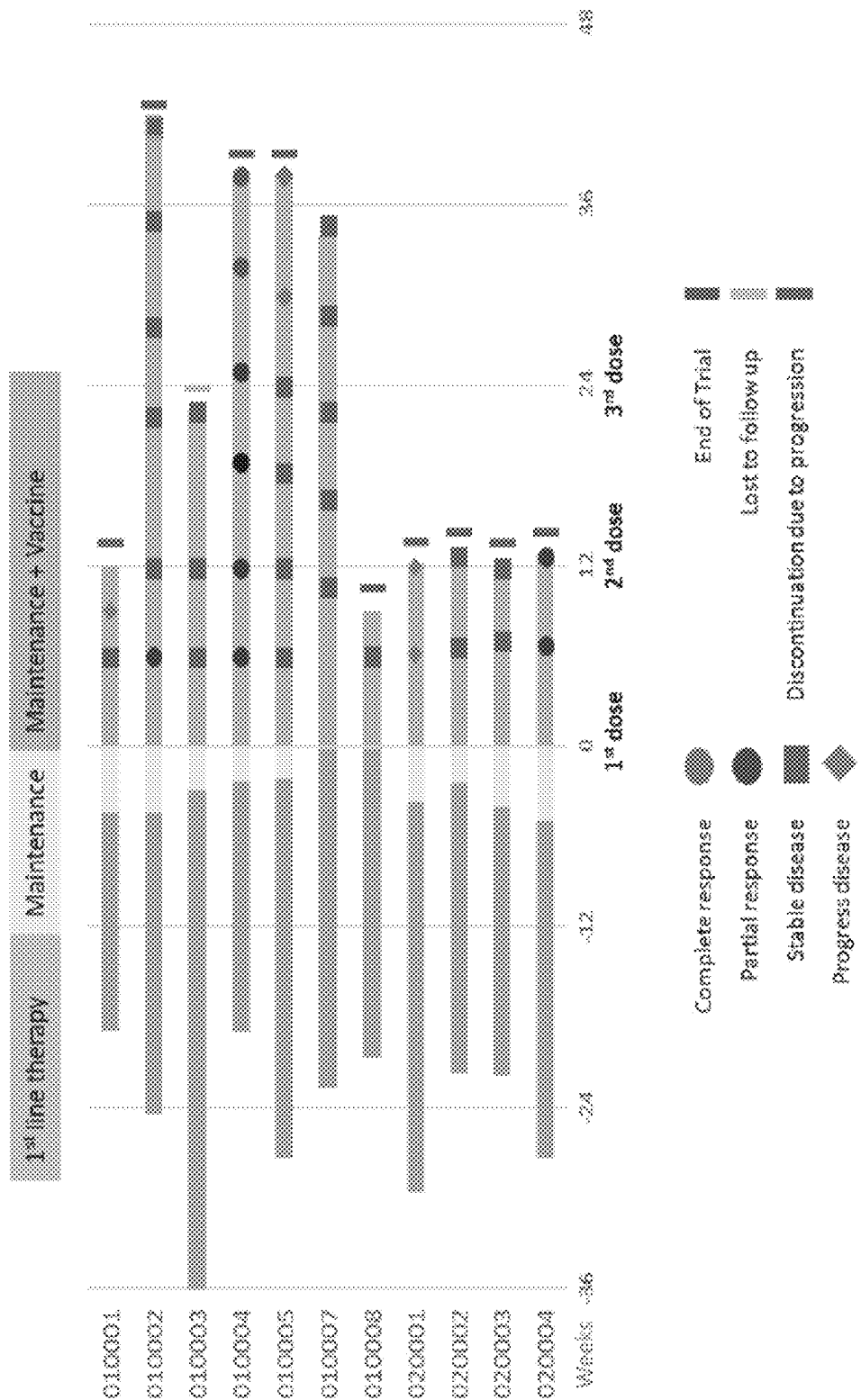
Figure 14B:
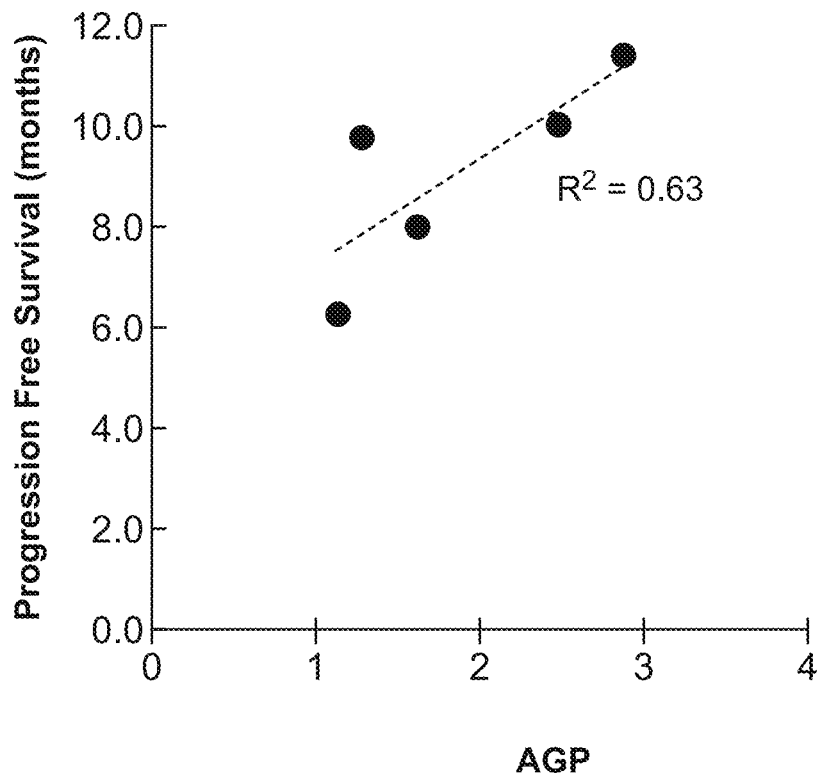
Figure 14C:
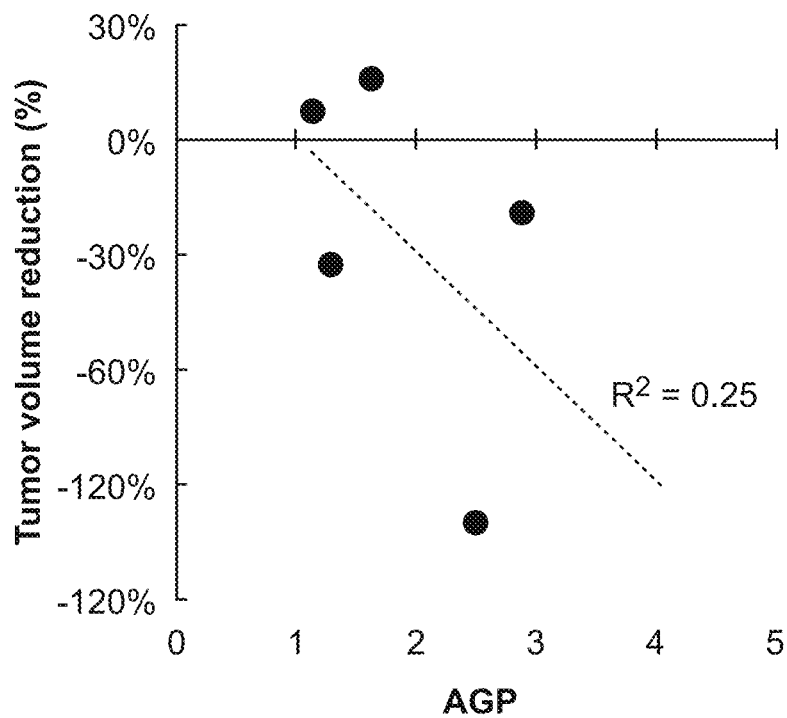

The OBERTO clinical trial (NCT03391232), that has been further described in Examples 4, 12, 13 and 14 was analyzed for preliminary objective tumor response rates (RECIST 1.1) (FIG. 14). Of the eleven vaccinated patients on maintenance therapy, 5 had stable disease (SD) at the time point of the preliminary analysis (12 weeks), 3 experienced unexpected tumor responses (partial response, PR) observed on treatment (maintenance therapy+vaccination) and 3 had progressed disease (PD) according to RECIST 1.1 criteria. Stable disease as best response was achieved in 69% of patients on maintenance therapy (capecitabine and bevacizumab). Patient 020004 had durable treatment effect after 12 weeks, and patient 010004 had long lasting treatment effect, qualified for curative surgery. Following the $3^{rd}$ vaccination this patient had no evidence of disease thus being complete responder, as shown on the swimmer plot on FIG. 14.

After one vaccination, ORR was 27%, DCR was 63%, and in patients receiving at least 2 doses (out of the 3 doses), 2 of 5 had ORR (40%) and DCR was as high as 80% (SD+PR+CR in 4 out of 5 patients) (Table 19).

TABLE 19

Clinical response for PolyPEPI1018 treatment after ≥ 1 and ≥ 2 vaccination dose

| Number of vaccination dose | Objective Response Rate (CR + PR) | Disease Control Rate (SD + PR + CR) |
|---|---|---|
| ≥1 | 27% (3/11) | 63% (7/11) |
| ≥2 | 40% (2/5) | 80% (4/5) |

Based on the data of the 5 patients receiving multiple doses of PolyPEPI1018 vaccine in the OBERTO-101 clinical trial, preliminary data suggests that higher AGP count (>2) is associated with longer PFS and elevated tumor size reduction (FIGS. 14B and C).

Example 16—Gastric Cancer Peptide Vaccine Design for Large Population

The PEPI3+ Test described above was used to design peptides for use in gastric cancer vaccines that are effective in a large percentage of patients, taking into account the heterogeneities of both tumour antigens and patients' HLAs.

Gastric cancer CTAs were identified and ranked based on the overall expression frequencies of antigens found in gastric cancer tumor samples as reported in peer reviewed publications.

Figure 16:
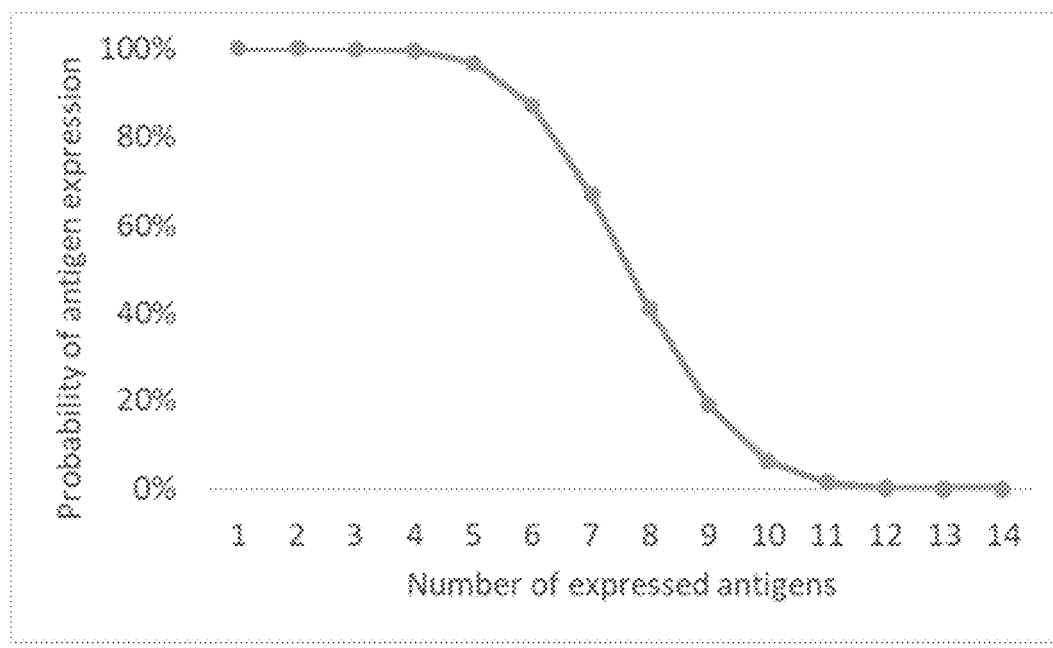

Based on the ranked expression rate the most frequently expressed CTA were selected as target antigens for gastric cancer vaccine. The expression rates of the selected gastric cancer, specific CTAs are illustrated in FIG. 16.

Figure 15:
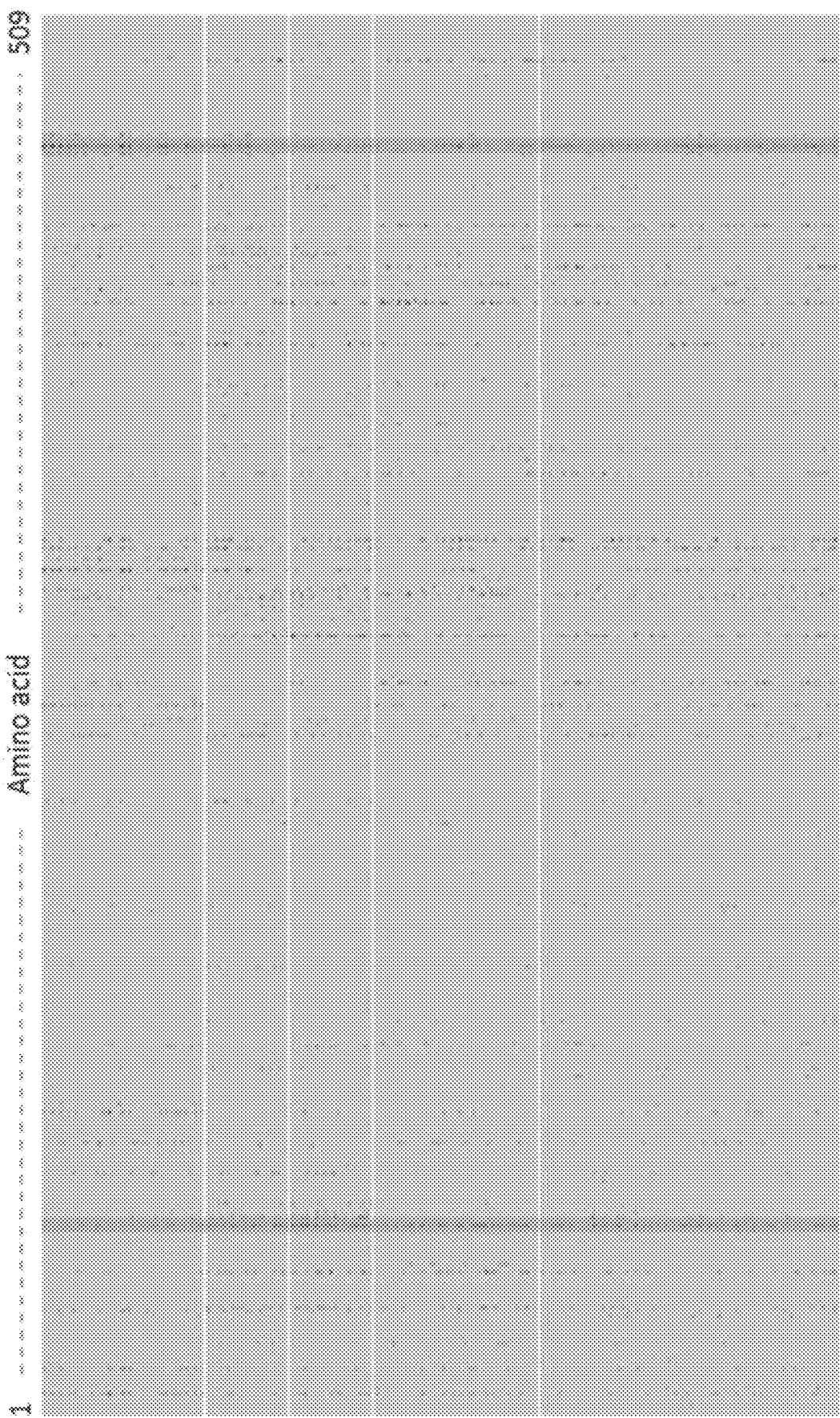

To select immunogenic peptides from the target CTAs, the PEPI3+ Test and the Model Population described in Example 8 were used to identify the 9 mer epitopes (PEPI3+ s) that are most frequently presented by at least 3 HLAs of the individuals in the Model Population. These epitopes are referred to herein as "bestEPIs". An illustrative example of the "PEPI3+ hotspot" analysis and bestEPI identification is shown in FIG. 15 for the PRAME antigen.

The reported expression frequency for each CTA was multiplied by the frequency of the PEPI3+ hotspots in the Model Population to identify the T cell epitopes (9 mers) that will induce a cytotoxic T cell response against gastric cancer antigens in the highest proportion of individuals (Table 20a). 15 mers were then selected encompassing each of the selected 9 mers (Table 20a). The 15 mers were selected to bind to most HLA class II alleles of most subjects. These 15 mers can induce both CTL and T helper responses in the highest proportion of subjects.

TABLE 20a

BestEPI list (9-mers underlined) for selecting gastric cancer peptides for vaccine composition.

| SEQ ID NO. 9 mer | SEQ ID NO. 15 mer | Antigen | N % | Opt. 15 mer | Opt. Position | B % | HLAII** (CD4) B % | * N % |
|---|---|---|---|---|---|---|---|---|
| 1 | 31 | DPPA2 | 100% | KRNKKMMKRLMTVEK | 284 | 43% | 12% | 43% |
| 2 | 32 | CAGE-1 | 77% | ASQLASKMHSLLALM | 610 | 42% | 94% | 33% |
| 3 | 33 | TSP50 | 57% | GFSYEQDPTLRDPEA | 105 | 51% | 0% | 29% |
| 4 | 34 | DPPA2 | 100% | KIEVYLRLHRHAYPE | 115 | 28% | 98% | 28% |
| 5 | 35 | HIWI | 76% | GFTTSILQYENSIML | 251 | 37% | 86% | 28% |
| 6 | 36 | SURVIVIN | 100% | AKKVRRAIEQLAAMD | 128 | 26% | 25% | 26% |
| 7 | 37 | HIWI | 76% | SIAGFVASINEGMTR | 643 | 28% | 44% | 21% |
| 8 | 38 | TSP50 | 57% | STTMETQFPVSEGKV | 84 | 36% | 0% | 21% |
| 9 | 39 | 5T4 | 52% | RLELASNHFLYLPRD | 214 | 40% | 97% | 21% |
| 10 | 40 | 5T4 | 52% | SNHFLYLPRDVLAQL | 219 | 40% | 100% | 21% |
| 11 | 41 | 5T4 | 52% | SSASSFSSSAPFLAS | 36 | 33% | 88% | 17% |
| 12 | 42 | MAGE-A2 | 31% | REDSVFAHPRKLLMQ | 234 | 55% | 74% | 17% |
| 13 | 43 | KK-LC-1 | 80% | RNTGEMSSNSTALAL | 26 | 21% | 0% | 17% |
| 14 | 44 | CAGE-1 | 77% | NIENYSTNALIQPVD | 97 | 21% | 14% | 16% |
| 15 | 45 | SURVIVIN | 100% | KDHRISTFKNWPFLE | 15 | 15% | 83% | 15% |
| 16 | 46 | MAGE-A2 | 31% | SFSTTINYTLWRQSD | 70 | 37% | 65% | 12% |
| 17 | 47 | KK-LC-1 | 80% | SRDILNNFPHSIARQ | 63 | 13% | 11% | 11% |
| 18 | 48 | MAGE-A3 | 37% | LTQHFVQENYLEYRQ | 246 | 27% | 56% | 10% |
| 19 | 49 | LAGE-1 | 14% | ITMPFSSPMEAELVR | 92 | 65% | 8% | 9% |
| 20 | 50 | MAGE-A3 | 37% | KASSSLQLVFGIELM | 153 | 23% | 58% | 9% |

TABLE 20a-continued

BestEPI list (9-mers underlined) for selecting gastric cancer peptides for vaccine composition.

| SEQ ID NO. 9 mer | SEQ ID NO. 15 mer | Antigen | N % | BestEPIs and Optimized 15 mer Opt. 15 mer | Opt. Position | B % | HLAII** (CD4) | B % * N % |
|---|---|---|---|---|---|---|---|---|
| 21 | 51 | MAGE-A10 | 30% | RNYEDHFPLLFSEAS | 166 | 27% | 26% | 8% |
| 22 | 52 | MAGE-A1 | 31% | ETSYVKVLEYVIKVS | 273 | 26% | 85% | 8% |
| 23 | 53 | MAGE-A3 | 37% | QAALSRKVAELVHFL | 106 | 21% | 45% | 8% |
| 24 | 54 | KK-LC-1 | 80% | SNTDNNLAVYDLSRD | 51 | 10% | 0% | 8% |
| 25 | 55 | PRAME | 20% | RHSQTLKAMVQAWPF | 64 | 37% | 38% | 7% |
| 26 | 56 | MAGE-A2 | 31% | SKASEYLQLVFGIEV | 152 | 24% | 69% | 7% |
| 27 | 57 | MAGE-A1 | 31% | SAFPTTINFTRQRQP | 62 | 24% | 0% | 7% |
| 28 | 58 | SSX1 | 13% | QVEHPQMTFGRLHRI | 93 | 55% | 20% | 7% |
| 29 | 59 | MAGE-A1 | 31% | PRALAETSYVKVLEY | 268 | 16% | 39% | 5% |
| 30 | 60 | PRAME | 20% | DQLLRHVMNPLETLS | 314 | 22% | 63% | 4% |

N %: Antigen expression frequency in gastric cancers;
B %: bestEPI frequency, ie the percentage of individuals with epitopes binding to at least 3 HLA class I of subjects in the model population (433 subjects);
HLAII**: Percentage of individuals having CD4+ T cell specific PEPI4+ within normal donors (n = 400);
N % * B %: N % multiplied by B %.

Fifteen 30 mer peptides were then designed (Table 21a). The 30 mers may each consist of two optimized 15 mer fragments, generally from different frequent CTAs, arranged end to end, each fragment comprising one of the 9 mers (BestEPIs) from Table 2-a.

TABLE 21a 30 mer gastric cancer vaccine peptides of composition PolyPEPI1311

| SEQID | TREOSID | Source Antigen | Peptide (30 mer) | HLAI* (CD8) | HLAH** (CD4) |
|---|---|---|---|---|---|
| 61 | GC1311-01 | CAGE-1/DPPA2 | ASQLASKMHSLLALMKRNKKMMKRLMTVEK | 64% | 94% |
| 62 | GC1311-02 | HIWI/MAGE-A10 | GFTTSILQYENSIMLRNYEDHFPLLFSEAS | 62% | 86% |
| 63 | GC1311-03 | MAGE-A2/SURVIVIN | SFSTTINYTLWRQSDAKKVRRAIEQLAAMD | 49% | 69% |
| 64 | GC1311-04 | KK-LC-1/SURVMN | RNTGEMSSNSTALALKDHRISTFKNWPFLE | 39% | 83% |
| 65 | GC1311-05 | KK-LC-1/HIWI | SRDILNNFPHSIARQSIAGFVASINEGMTR | 36% | 45% |
| 66 | GC1311-06 | MAGE-A2/PRAME | REDSVFAHPRKLLMQDQLLRHVMNPLETLS | 64% | 91% |
| 67 | GC1311-07 | 5T4/5T4 | RLELASNHFLYLPRDSNHFLYLPRDVLAQL | 65% | 100% |
| 68 | GC1311-08 | 5T4/TSP50 | SSASSFSSSAPFLASSTTMETQFPVSEGKV | 55% | 88% |
| 69 | GC1311-09 | TSP50/MAGE-A1 | GFSYEQDPTLRDPEAPRALAETSYVKVLEY | 67% | 39% |
| 70 | GC1311-10 | KK-LC-1/SSX1 | SNTDNNLAVYDLSRDQVEHPQMTFGRLHRI | 58% | 20% |
| 71 | GC1311-11 | DPPA2/LAGE-1 | KIEVYLRLHRHAYPEITMPFSSPMEAELVR | 82% | 99% |
| 72 | GC1311-12 | MAGE-A1/MAGE-A3 | ETSYVKVLEYVIKVSLTQHFVQENYLEYRQ | 41% | 91% |
| 73 | GC1311-13 | MAGE-A3/CAGE-1 | QAALSRKVAELVHFLNIENYSTNALIQPVD | 30% | 49% |

TABLE 21a-continued 30 mer gastric cancer vaccine peptides of composition PolyPEPI1311

| SEQID | TREOSID | Source Antigen | Peptide (30 mer) | HLAI* (CD8) | HLAH** (CD4) |
|---|---|---|---|---|---|
| 74 | GC1311-14 | PRAME/MAGE-A3 | RHSQTLKAMVQAWPFKASSSLQLVFGIELM | 53% | 77% |
| 75 | GC1311-15 | MAGE-A2/MAGE-A1 | SKASEYLQLVFGIEVSAFPTTINFTRQRQP | 41% | 69% |

*Percentage of individuals having CD8+ T cell specific PEPI3+ within the HLA class I Model Population (n = 433).
**Percentage of individuals having CD4+ T cell specific PEPI4+ within the normal donors (n = 400).

Characterization of PolyPEPI131

Tumor heterogeneity can be addressed by including peptide sequences that target multiple CTAs in a vaccine or immunotherapy regime. The PolyPEPI1311, composition targets 14 different CTAs. Based on the antigen expression rates for these 14 CTAs, we modelled the predicted average number of expressed antigens (AG50) and the minimum number of expressed antigens with 95% likelihood (AG95) in the cancer cells. 95% of individuals expressed minimum 5 of the 14 target antigens (AG95=5) as shown by the antigen expression curve in FIG. 17.

The AG values described above characterize a vaccine independently from the target patient population. They can be used to predict the likelihood that a specific cancer (e.g. gastric cancer) expresses antigens targeted by a specific vaccine or immunotherapy composition. AG values are based on known tumor heterogeneity, but do not take HLA heterogeneity into account.

HLA heterogeneity of a certain population can be characterised from the viewpoint of an immunotherapy or vaccine composition by the number of antigens representing PEPI3+. These are the vaccine-specific CTA antigens for which ≥1 PEPI3+ is predicted, referred to herein as the "AP". The average number of antigens with PEPI3+ (AP50) shows how the vaccine can induce immune response against the antigens targeted by the composition (gastric cancer vaccine specific immune response). The PolyPEPI1311 composition can induce immune response against an average of 8 vaccine antigens (AP50=7.98) and 95% of the Model Population can induce immune response against at least three vaccine antigens (AP95=3)(FIG. 18).

Vaccines can be further characterized by AGP values that refers to antigens with PEPIs". This parameter is the combination of the previous two parameters: (1) AG is depending on the antigen expression frequencies in the specific tumor type but not on the HLA genotype of individuals in the population, and (2) AP is depending on the HLA genotype of individuals in a population without taking account the expression frequencies of the antigen. The AGP is depending on both, the expression frequencies of vaccine antigens in the disease and the HLA genotype of individuals in a population.

Combining the data of AG of gastric cancer and AP in the Model Population we determined the AGP value of PolyPEPI1311 that represents the probability distribution of vaccine antigens that induce immune responses against antigens expressed in gastric tumors. For PolyPEPI1311, the AGP50 value in the Model Population is 3.86. The AGP95=1, means that 95% of the subjects in the Model Population induce immune responses against at least one expressed vaccine antigen (FIG. 19).

Example 17—Patient Selection Using Companion Diagnostic for Gastric Cancer, Lung Cancer, Melanoma and Bladder Cancer Vaccine The likelihood that a specific patient will have an immune response or a clinical response to treatment with one or more cancer vaccine peptides, for example as described above, can be determined based on (i) the identification of PEPI3+ within the vaccine peptide(s) (9 mer epitopes capable of binding at least three HLA of the patient); and/or (ii) a determination of target antigen expression in cancer cells of the patient, for example as measured in a tumour biopsy. Ideally both parameters are determined and the optimal combination of vaccine peptides is selected for use in treatment of the patient. However, PEPI3+ analysis alone may be used if a determination of the expressed tumour antigens, for example by biopsy, is not possible, not advised, or unreliable due to biopsy error (i.e. biopsy tissue samples taken from a small portion of the tumor or metastasised tumors do not represent the complete repertoire of CTAs expressed in the patient).

Example 18—Lung Cancer Peptide Vaccine Design for Large Population

Figure 20:
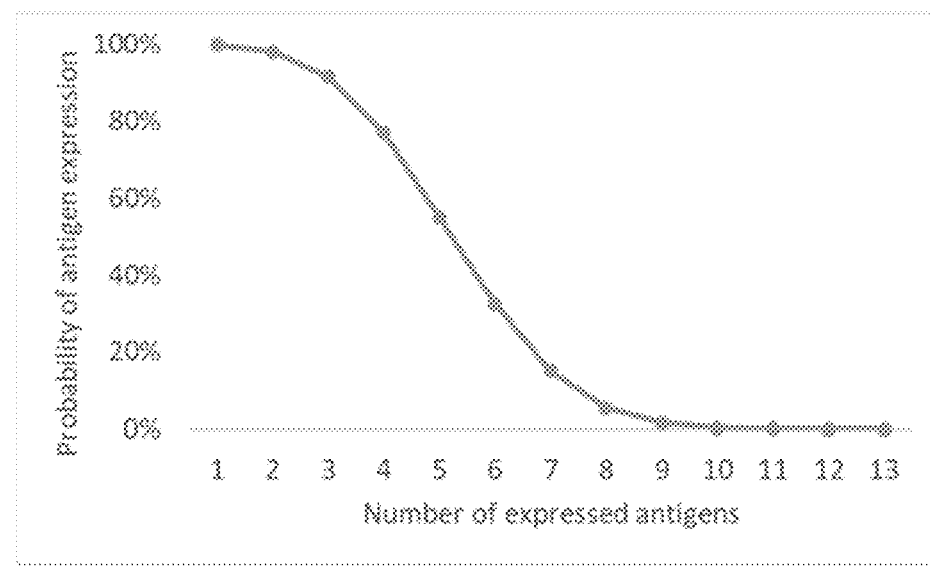

The PEPI3+ Test described above was used to design 9-mer and 15-mer peptides for use in lung cancer vaccines, using the same method described in Example 16 above for gastric cancer (Tables 20b, 21b). The expression rates of the selected gastric cancer, specific CTAs are illustrated in FIG. 20.

TABLE 20b

BestEPI list (9-mers underlined) for selecting lung cancer peptides for vaccine composition.

| SEQ ID NO. 9 mer | SEQ ID NO. 15 mer | Antigen | N % Antigen | BestEPIs and Optimized 15 mer | | | | |
|---|---|---|---|---|---|---|---|---|
| | | | | Antigen | N % | Antigen | N % | Antigen |
| 90 | 120 | BRDT | 48% | DAYKFAADVRLMFMN | 333 | 58% | 100% | 28% |
| 91 | 121 | PRAME | 63% | RHSQTLKAMVQAWPF | 64 | 37% | 38% | 23% |

TABLE 20b-continued

BestEPI list (9-mers underlined) for
selecting lung cancer peptides for vaccine composition.

| SEQ ID NO. 9 mer | SEQ ID NO. 15 mer | Antigen | Antigen N % | BestEPIs and Optimized 15 mer Antigen | N % | N % | Antigen |
|---|---|---|---|---|---|---|---|
| 92 | 122 | BRDT | 48% | DLWKHS<u>FSWPFQRPV</u> | 42 | 43% | 88% | 21% |
| 93 | 123 | NALP4 | 38% | QSTTSV<u>YSSFVFNLF</u> | 366 | 50% | 75% | 19% |
| 94 | 124 | NALP4 | 38% | K<u>RAMEAFNLV</u>RESEQ | 319 | 48% | 67% | 18% |
| 95 | 125 | NALP4 | 38% | <u>FVIDSFEEL</u>QGGLNE | 228 | 46% | 47% | 17% |
| 96 | 126 | MAGE-A12 | 36% | QVALSR<u>KMAELVHFL</u> | 106 | 48% | 63% | 17% |
| 97 | 127 | MAGE-A2 | 27% | REDSV<u>FAHPRKLLM</u>Q | 234 | 55% | 74% | 15% |
| 98 | 128 | SURVIVIN | 57% | AKKVR<u>RAIEQLAAM</u>D | 128 | 26% | 25% | 15% |
| 99 | 129 | PRAME | 63% | <u>KEEQYIAQF</u>TSQFLS | 280 | 23% | 99% | 14% |
| 100 | 130 | PRAME | 63% | DQLL<u>RHVMNPLET</u>LS | 314 | 22% | 63% | 14% |
| 101 | 131 | MAGE-A12 | 36% | RN<u>FQDFFPVIF</u>SKAS | 141 | 37% | 90% | 13% |
| 102 | 132 | PRAME | 63% | RGRLD<u>QLLRHVMNPL</u> | 310 | 21% | 65% | 13% |
| 103 | 133 | DPPA2 | 30% | KRNK<u>KMMKRLMT</u>VEK | 284 | 43% | 12% | 13% |
| 104 | 134 | NY-SAR-35 | 28% | SSY<u>FVLANGHIL</u>PNS | 94 | 42% | 85% | 12% |
| 105 | 135 | BRDT | 48% | ILKE<u>MLAKKHFSY</u>AW | 279 | 23% | 55% | 11% |
| 106 | 136 | LDHC | 29% | <u>SVMDLVGSI</u>LKNLRR | 255 | 38% | 85% | 11% |
| 107 | 137 | LDHC | 29% | KLKGE<u>MMDLQHGSL</u>F | 57 | 37% | 1% | 11% |
| 108 | 138 | MAGE-A2 | 27% | SS<u>FSTTINYTL</u>WRQS | 69 | 37% | 74% | 10% |
| 109 | 139 | MAGE-C2 | 24% | <u>MASESLSVM</u>SSNVSF | 357 | 40% | 15% | 10% |
| 110 | 140 | MAGE-C2 | 24% | EH<u>FVYGEPREL</u>LTKV | 263 | 40% | 60% | 10% |
| 111 | 141 | MAGE-C2 | 24% | SESL<u>SVMSSNVSF</u>SE | 359 | 38% | 33% | 9% |
| 112 | 142 | MAGE-A3 | 33% | LTQH<u>FVQENYLEY</u>RQ | 246 | 27% | 56% | 9% |
| 113 | 143 | MAGE-A12 | 36% | S<u>KASEYLQLV</u>FGIEV | 152 | 24% | 69% | 9% |
| 114 | 144 | SURVIVIN | 57% | KDHRI<u>STFKNWPFL</u>E | 15 | 15% | 83% | 9% |
| 115 | 145 | DPPA2 | 30% | KIEV<u>YLRLHRHAY</u>PE | 115 | 28% | 98% | 9% |
| 116 | 146 | MAGE-A3 | 33% | KASSS<u>LQLVFGIEL</u>M | 153 | 23% | 58% | 8% |
| 117 | 147 | KK-LC-1 | 35% | RNTGEM<u>SSNSTALAL</u> | 26 | 21% | 0% | 7% |
| 118 | 148 | MAGE-C2 | 24% | SS<u>FSTSSSLIL</u>GGPE | 53 | 30% | 44% | 7% |
| 119 | 149 | MAGE-A1 | 28% | P<u>RALAETSYV</u>KVLEY | 268 | 16% | 39% | 5% |

N %: Antigen expression frequency in lung cancers;
B %: bestEPI frequency, i.e. the percentage of individuals with epitopes binding to at least 3 HLA class 1 of subjects in the model population (433 subjects);
HLAII**: Percentage of individuals having CD4+ T cell specific PEPI4+ within normal donors (n = 400);
N % * B %: N % multiplied by B %.

TABLE 21b 30 mer lung cancer vaccine peptides of composition PolyPEPI821

| SEQID | TREOSID | Source Antigen | Peptide (30 mer) | HLAI* (CD8) | HLAH** (CD4) |
|---|---|---|---|---|---|
| 150 | LC821-01 | BRDT/SURVIVIN | DAYKFAADVRLMFMNAKKVRRAIEQLAAMD | 64% | 100% |
| 151 | LC821-02 | PRAME/MAGE-A2 | RHSQTLKAMVQAWPFREDSVFAHPRKLLMQ | 67% | 78% |
| 152 | LC821-03 | BRDT/MAGE-A12 | DLWKHSFSWPFQRPVSKASEYLQLVFGIEV | 57% | 91% |
| 153 | LC821-04 | PRAME/LDHC | DQLLRHVMNPLETLSSVMDLVGSILKNLRR | 53% | 94% |
| 154 | LC821-05 | NALP4/SURVIVIN | QSTTSVYSSFVFNLFKDHRISTFKNWPFLE | 55% | 92% |
| 155 | LC821-06 | MAGE-C2/NALP4 | SSFSTSSSLILGGPEFVIDSFEELQGGLNE | 60% | 80% |
| 156 | LC821-07 | MAGE-A2/NALP4 | SSFSTTINYTLWRQSKRAMEAFNLVRESEQ | 70% | 90% |
| 157 | LC821-08 | NY-SAR-35/MAGE-A12 | SSYFVLANGHILPNSRNFQDFFPVIESKAS | 67% | 98% |
| 158 | LC821-09 | MAGE-C2/PRAME | MASESLSVMSSNVSFKEEQYIAQFTSQFLS | 51% | 99% |
| 159 | LC821-10 | PRAME/MAGE-A3 | RGRLDQLLRHVMNPLLTQHFVQENYLEYRQ | 42% | 85% |
| 160 | LC821-11 | MAGE-C2/LDHC | SESLSVMSSNVSFSEKLKGEMMDLQHGSLF | 67% | 33% |
| 161 | LC821-12 | MAGE-A12/MAGE-A1 | QVALSRKMAELVHFLPRALAETSYVKVLEY | 63% | 72% |
| 162 | LC821-13 | MAGE-C2/BRDT | EHFVYGEPRELLTKVILKEMLAKKHFSYAW | 59% | 75% |
| 163 | LC821-14 | DPPA2/MAGE-A3 | KIEVYLRLHRHAYPEKASSSLQLVFGIELM | 53% | 99% |
| 164 | LC821-15 | KK-LC-1/DPPA2 | RNTGEMSSNSTALALKRNKKMMKRLMTVEK | 60% | 12% |

*Percentage of individuals having CD8+ T cell specific PEPI3+ within the HLA class I Model Population (n = 433).
**Percentage of individuals having CD4+ T cell specific PEPI4+ within the normal donors (n = 400).

Characterization of PolyPEPI821

The PolyPEPI821 composition targets 13 different CTAs. Based on the antigen expression rates for these 13 CTAs, we modelled the predicted average number of expressed antigens (AG50) and the minimum number of expressed antigens with 95% likelihood (AG95) in the cancer cells. 95% of individuals expressed minimum 2 of the 10 target antigens (AG95=2) as shown by the antigen expression curve in FIG. 21.

The PolyPEPI821 composition can induce immune response against an average of approaching 8 vaccine antigens (AP50=7.60) and 9500 of the Model Population can induce immune response against at least two vaccine antigens (AP95=2)(FIG. 22).

For PolyPEPI821, the AGP50 value in the Model Population is 2.77. The AGP91=1, means that 91% of the subjects in the Model Population induce immune responses against at least one expressed vaccine antigen (FIG. 23).

Example 19—Melanoma Peptide Vaccine Design for Large Population

Figure 24:
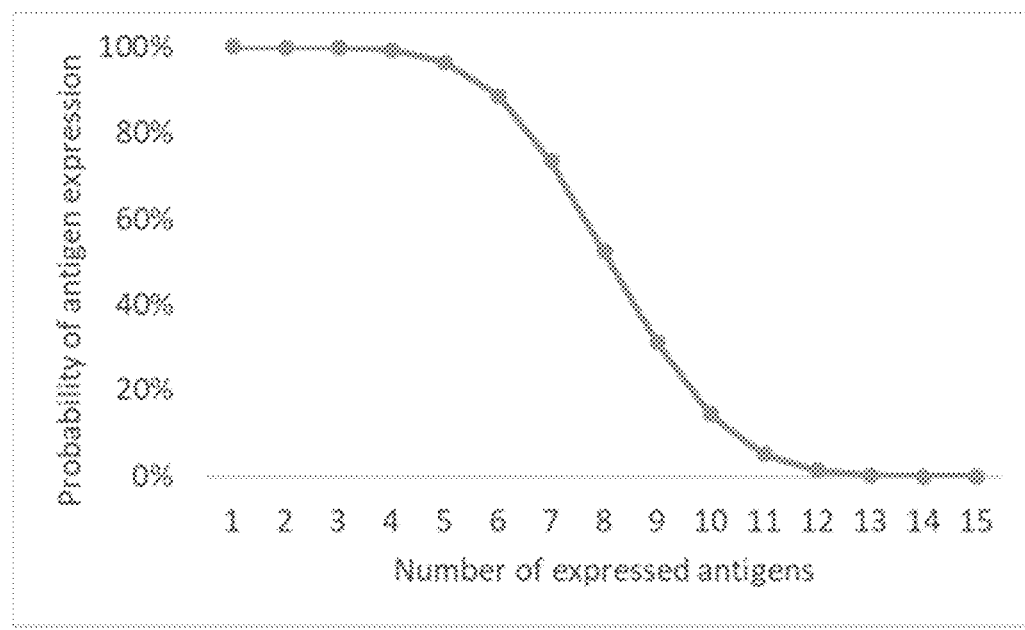

The PEPI3+ Test described above was used to design 9-mer and 15-mer peptides for use in melanoma vaccines, using the same method described in Example 16 above for gastric cancer (Tables 20c, 21c). The expression rates of the selected gastric cancer, specific CTAs are illustrated in FIG. 24.

TABLE 20c

BestEPI list (9-mers underlined) for selecting melanoma peptides for vaccine composition.

| SEQ ID NO. 9 mer | SEQ ID NO. 15 mer | Antigen | N % | Opt. 15 mer | Opt. Position | B % | HLAII** (CD4) | B % * N % |
|---|---|---|---|---|---|---|---|---|
| 178 | 208 | PRAME | 90% | LERLAYLHARLRELL | 457 | 52% | 100% | 47% |
| 179 | 209 | MAGE-A2 | 61% | EDSVFAHPRKLLMQD | 235 | 55% | 43% | 34% |
| 180 | 210 | PRAME | 90% | RHSQTLKAMVQAWPF | 64 | 37% | 38% | 33% |
| 181 | 211 | MAGE-C1 | 45% | SFSYTLLSLFQSSPE | 450 | 57% | 99% | 26% |
| 182 | 212 | Survivin | 96% | TAKKVRRAIEQLAAM | 127 | 26% | 26% | 25% |

TABLE 20c-continued

BestEPI list (9-mers underlined) for selecting melanoma peptides for vaccine composition.

| SEQ ID NO. 9 mer | SEQ ID NO. 15 mer | Antigen | N % | BestEPIs and Optimized 15 mer Opt. 15 mer | Opt. Position | B % | HLAII** (CD4) | B % * N % |
|---|---|---|---|---|---|---|---|---|
| 183 | 213 | MAGE-C1 | 45% | SPS<u>FSSTLVSLF</u>QSS | 273 | 53% | 97% | 24% |
| 184 | 214 | MAGE-A2 | 61% | SS<u>FSTTINYTL</u>WRQS | 69 | 37% | 74% | 23% |
| 185 | 215 | MAGE-A12 | 45% | QVALSR<u>KMAELVHFL</u> | 106 | 48% | 63% | 22% |
| 186 | 216 | MAGE-C1 | 45% | DDS<u>YVFVNTLDL</u>TSE | 971 | 48% | 99% | 22% |
| 187 | 217 | MAGE-C1 | 45% | <u>FSYTLASLL</u>QSSHES | 783 | 47% | 100% | 21% |
| 188 | 218 | PRAME | 90% | KEE<u>QYIAQFTSQ</u>FLS | 280 | 23% | 99% | 20% |
| 189 | 219 | MAGE-C1 | 45% | QIP<u>MTSSFSST</u>LLSI | 339 | 45% | 65% | 20% |
| 190 | 220 | PRAME | 90% | DQLL<u>RHVMNPLET</u>LS | 314 | 22% | 63% | 20% |
| 191 | 221 | Ny-ESO-1 | 38% | RGPES<u>RLLEFYLAM</u>P | 81 | 52% | 65% | 20% |
| 192 | 222 | MAGE-C2 | 45% | <u>MASESLSVM</u>SSNVSF | 357 | 40% | 15% | 18% |
| 193 | 223 | MAGE-C2 | 45% | REH<u>FVYGEPREL</u>LTK | 262 | 40% | 74% | 18% |
| 194 | 224 | MAGE-A6 | 62% | Q<u>YFVQENYLEY</u>RQVP | 248 | 27% | 93% | 17% |
| 195 | 225 | BORIS | 27% | M<u>FTSSRMSSF</u>NRHMK | 263 | 57% | 66% | 15% |
| 196 | 226 | LAGE-1 | 35% | D<u>FTVSGNLLF</u>MSVRD | 125 | 43% | 82% | 15% |
| 197 | 227 | MAGE-A2 | 61% | S<u>KASEYLQLV</u>FGIEV | 152 | 24% | 69% | 15% |
| 198 | 228 | Survivin | 96% | KDHRI<u>STFKNWPFL</u>E | 15 | 15% | 83% | 14% |
| 199 | 229 | MAGE-A11 | 54% | <u>SHSYVLVTSL</u>NLSYD | 286 | 26% | 100% | 14% |
| 200 | 230 | SSX-1 | 25% | QVEHPQ<u>MTFGRLHRI</u> | 93 | 55% | 20% | 14% |
| 201 | 231 | MAGE-A3 | 59% | <u>KASSSLQLV</u>FGIELM | 153 | 23% | 58% | 14% |
| 202 | 232 | MAGE-C2 | 45% | SS<u>FSTSSSLIL</u>GGPE | 53 | 30% | 44% | 13% |
| 203 | 233 | MAGE-A3 | 59% | QAALSR<u>KVAELVHFL</u> | 106 | 21% | 45% | 12% |
| 204 | 234 | MAGE-A11 | 54% | SPT<u>AMDAIFGSL</u>SDE | 181 | 23% | 0% | 12% |
| 205 | 235 | MAGE-A10 | 44% | RN<u>YEDHFPLLF</u>SEAS | 166 | 27% | 26% | 12% |
| 206 | 236 | MAGE-A11 | 54% | <u>YAGREHFLF</u>GEPKRL | 344 | 18% | 71% | 9% |
| 207 | 237 | MAGE-A1 | 37% | P<u>RALAETSYV</u>KVLEY | 268 | 16% | 39% | 6% |

N %: Antigen expression frequency in melanomas;
B %: bestEPI frequency, i.e. the percentage of individuals with epitopes binding to at least 3 HLA class 1 of subjects in the model population (433 subjects);
HLAII**: Percentage of individuals having CD4+ T cell specific PEPI4+ within normal donors (n = 400);
N % * B %: N % multiplied by B %.

Fifteen 30 mer peptides were then designed (Table 21c). The 30 mers may each consist of two optimized 15 mer fragments, generally from different frequent CTAs, arranged end to end, each fragment comprising one of the 9 mers (BestEPIs) from Table 20c.

PEPI621 that represents the probability distribution of vaccine antigens that induce immune responses against antigens expressed in gastric tumors. For PolyPEPI621, the AGP50 value in the Model Population is 2.77. The AGP95=1, means that 95% of the subjects in the Model Population induce immune responses against at least one expressed vaccine antigen (FIG. 27).

TABLE 21c 30 mer melanoma vaccine peptides of composition PolyPEPI621

| SEQID | TREOSID | Source Antigen | Peptide (30 mer) | HLAI* (CD8) | HLAI** (CD4) |
|---|---|---|---|---|---|
| 238 | MC621-01 | PRAME/PRAME | LERLAYLHARLRELLDQLLRHVMNPLETLS | 58% | 100% |
| 239 | MC621-02 | Survivin/MAGE-A2 | TAKKVRRAIEQLAAMEDSVFAHPRKLLMQD | 65% | 54% |
| 240 | MC621-03 | PRAME/MAGE-A3 | RHSQTLKAMVQAWPFKASSSLQLVFGIELM | 53% | 77% |
| 241 | MC621-04 | MAGE-C1/MAGE-A2 | DDSYVFVNTLDLTSESSFSTTINYTLWRQS | 70% | 99% |
| 242 | MC621-05 | MAGE-C1/MAGE-A2 | SFSYTLLSLFQSSPESKASEYLQLVFGIEV | 64% | 99% |
| 243 | MC621-06 | MAGE-A11/MAGE-C1 | SHSYVLVTSLNLSYDSPSFSSTLVSLFQSS | 73% | 100% |
| 244 | MC621-07 | LAGE-1/MAGE-C2 | DFTVSGNLLFMSVRDMASESLSVMSSNVSF | 60% | 83% |
| 245 | MC621-08 | BORIS/MAGE-A12 | MFTSSRMSSFNRHMKQVALSRKMAELVHFL | 74% | 81% |
| 246 | MC621-09 | MAGE-C2/MAGE-C1 | SSFSTSSSLILGGPEFSYTLASLLQSSHES | 54% | 100% |
| 247 | MC621-10 | Survivin/MAGE-C1 | KDHRISTFKNWPFLEQIPMTSSFSSTLLSI | 51% | 89% |
| 248 | MC621-11 | Ny-ESO-1/MAGE-A10 | RGPESRLLEFYLAMPRNYEDHFPLLFSEAS | 73% | 66% |
| 249 | MC621-12 | MAGE-A3/MAGE-A6 | QAALSRKVAELVHFLQYFVQENYLEYRQVP | 48% | 97% |
| 250 | MC621-13 | MAGE-A11/MAGE-A1 | SPTAMDAIFGSLSDEPRALAETSYVKVLEY | 53% | 39% |
| 251 | MC621-14 | MAGE-C2/MAGE-A11 | REHFVYGEPRELLTKYAGREHFLFGEPKRL | 57% | 83% |
| 252 | MC621-15 | SSX-1/PRAME | QVEHPQMTFGRLHRIKEEQYIAQFTSQFLS | 67% | 99% |

*Percentage of individuals having CD8+ T cell specific PEPI3+ within the HLA class I Model Population (n = 433).
**Percentage of individuals having CD4+ T cell specific PEPI4+ within the normal donors (n = 400)

Characterization of PolyPEPI621

The PolyPEPI621 composition targets 15 different CTAs. Based on the antigen expression rates for these 15 CTAs, we modelled the predicted average number of expressed antigens (AG50) and the minimum number of expressed antigens with 95% likelihood (AG95) in the cancer cells. 95% of individuals expressed minimum 5 of the 15 target antigens (AG95=5) as shown by the antigen expression curve in FIG. 25.

The PolyPEPI621 composition can induce immune response against an average of 8 vaccine antigens (AP50=8.29) and 95% of the Model Population can induce immune response against at least three vaccine antigens (AP95=2)(FIG. 26).

Figure 28:
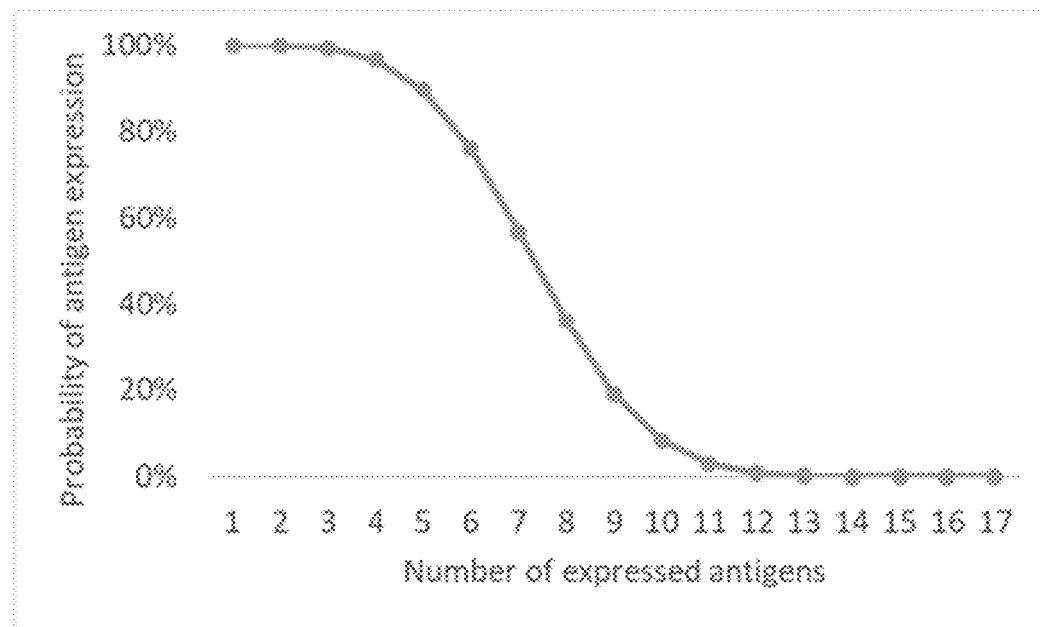

Combining the data of AG of melanoma and AP in the Model Population we determined the AGP value of Poly- Example 20—Bladder Cancer Peptide Vaccine Design for Large Population The PEPI3+ Test described above was used to design 9-mer and 15-mer peptides for use in bladder cancer vaccines, using the same method described in Example 16 above for gastric cancer (Tables 120d, 21d). The expression rates of the selected gastric cancer, specific CTAs are illustrated in FIG. 28.

TABLE 20d

BestEPI list (9-mers underlined) for selecting bladder cancer peptides for vaccine composition.

| SEQ ID NO. 9 mer | SEQ ID NO. 15 mer | Antigen | N % | BestEPIs and Optimized 15 mer Opt. 15 mer | Opt. Position | B % | HLAI** (CD4) | B % * N % |
|---|---|---|---|---|---|---|---|---|
| 268 | 298 | PIWIL2 | 82% | FVASINLTLTKWYSR | 760 | 67% | 93% | 55% |
| 269 | 299 | PIWIL2 | 82% | RNFYDPTSAMVLQQH | 341 | 60% | 49% | 49% |
| 270 | 300 | PIWIL2 | 82% | YSRVVFQMPHQEIVD | 772 | 40% | 77% | 33% |
| 271 | 301 | CTAGE1 | 53% | QNYIDQFLLTSFPTF | 33 | 59% | 90% | 31% |
| 272 | 302 | MAGE-A9 | 61% | EFMFQEALKLKVAEL | 101 | 49% | 100% | 30% |
| 273 | 303 | EpCAM | 54% | RTYWIIIELKHKARE | 140 | 51% | 100% | 28% |
| 274 | 304 | OY-TES-1 | 28% | ESTPMIMENIQELIR | 276 | 67% | 82% | 19% |
| 275 | 305 | MAGE-A9 | 61% | SSISVYYTLWSQFDE | 67 | 30% | 97% | 19% |
| 276 | 306 | NY-ESO-1 | 31% | RGPESRLLEFYLAMP | 81 | 52% | 65% | 16% |
| 277 | 307 | SURVIVIN | 62% | AKKVRRAIEQLAAMD | 128 | 26% | 25% | 16% |
| 278 | 308 | MAGE-C1 | 27% | SSFSYTLLSLFQSSP | 449 | 57% | 98% | 16% |
| 279 | 309 | CTAGE1 | 53% | SFVLFLFGGNNFIQN | 14 | 29% | 85% | 15% |
| 280 | 310 | EpCAM | 54% | QTLIYYVDEKAPEFS | 246 | 28% | 34% | 15% |
| 281 | 311 | MAGE-A2 | 25% | REDSVFAHPRKLLMQ | 234 | 55% | 74% | 14% |
| 282 | 312 | MAGE-C1 | 27% | DDSYVFVNTLDLTSE | 971 | 48% | 99% | 13% |
| 283 | 313 | LAGE-1 | 30% | DFTVSGNLLFMSVRD | 125 | 43% | 82% | 13% |
| 284 | 314 | MAGE-A3 | 42% | LTQHFVQENYLEYRQ | 246 | 27% | 56% | 11% |
| 285 | 315 | MAGE-A8 | 57% | EEAIWEALSVMGLYD | 221 | 20% | 78% | 11% |
| 286 | 316 | HAGE | 24% | NDLQMSNFVNLKNIT | 377 | 43% | 67% | 10% |
| 287 | 317 | MAGE-A8 | 57% | EKVAELVRFLLRKYQ | 114 | 18% | 99% | 10% |
| 288 | 318 | MAGE-A3 | 42% | KASSSLQLVFGIELM | 153 | 23% | 58% | 10% |
| 289 | 319 | SURVIVIN | 62% | KDHRISTFKNWPFLE | 15 | 15% | 83% | 9% |
| 290 | 320 | MAGE-A2 | 25% | SSFSTTINYTLWRQS | 69 | 37% | 74% | 9% |
| 291 | 321 | MAGE-A3 | 42% | QAALSRKVAELVHFL | 106 | 21% | 45% | 9% |
| 292 | 322 | MAGE-A1 | 34% | ETSYVKVLEYVIKVS | 273 | 26% | 85% | 9% |
| 293 | 323 | MAGE-C2 | 19% | MASESLSVMSSNVSF | 357 | 40% | 15% | 8% |
| 294 | 324 | MAGE-C2 | 19% | REHFVYGEPRELLTK | 262 | 40% | 74% | 8% |
| 295 | 325 | MAGE-A10 | 28% | RNYEDHFPLLFSEAS | 166 | 27% | 26% | 7% |
| 296 | 326 | MAGE-A12 | 29% | KASEYLQLVFGIEW | 153 | 24% | 83% | 7% |
| 297 | 327 | LAGE-1 | 30% | DSRLLQLHITMPFSS | 84 | 20% | 99% | 6% |

N %: Antigen expression frequency in bladder cancers;
B %: bestEPI frequency, ie the percentage of individuals with epitopes binding to at least 3 HLA class I of subjects in the model population (433 subjects);
HLAII**: Percentage of individuals having CD4+ T cell specific PEPI4+ within normal donors (n = 400);
N % * B %: N % multiplied by B %.

Fifteen 30 mer peptides were then designed (Table 21d). The 30 mers may each consist of two optimized 15 mer fragments, generally from different frequent CTAs, arranged end to end, each fragment comprising one of the 9 mers (BestEPIs) from Table 20d.

notherapy vaccine compositions to support the principals of binding of epitopes by multiple HLAs of a subject to induce cytotoxic T cell responses, on which the present disclosure is partly based on.

TABLE 21d 30 mer bladder cancer vaccine peptides of composition PolyPEPI1411

| SEQID | TREOSID | Source Antigen | Peptide (30 mer) | HLAI* (CD8) | HLAH** (CD4) |
|---|---|---|---|---|---|
| 328 | BLV1411-01 | MAGE-C1/PIWIL2 | DDSYVFVNTLDLTSERNFYDPTSAMVLQQH | 81% | 99% |
| 329 | BLV1411-02 | MAGE-A9/OY-TES-1 | EFMFQEALKLKVAELESTPMIMENIQELIR | 77% | 100% |
| 330 | BLV1411-03 | PIWIL2/MAGE-A1 | YSRVVFQMPHQEIVDETSYVKVLEYVIKVS | 54% | 93% |
| 331 | BLV1411-04 | CTAGE1/MAGE-A2 | QNYIDQFLLTSFPTFREDSVFAHPRKLLMQ | 82% | 100% |
| 332 | BLV1411-05 | HAGE/EpCAM | NDLQMSNFVNLKNITRTYWIIIELKHKARE | 66% | 100% |
| 333 | BLV1411-06 | MAGE-A9/MAGE-A8 | SSISVYYTLWSQFDEEKVAELVRFLLRKYQ | 42% | 100% |
| 334 | BLV1411-07 | NY-ESO-1/MAGE-A10 | RGPESRLLEFYLAMPRNYEDHFPLLFSEAS | 73% | 66% |
| 335 | BLV1411-08 | CTAGE1/MAGE-A8 | SFVLFLFGGNNFIQNEEAIWEALSVMGLYD | 46% | 94% |
| 336 | BLV1411-09 | EpCAM/MAGE-C2 | QTLIYYVDEKAPEFSREHFVYGEPRELLTK | 64% | 80% |
| 337 | BLV1411-10 | MAGE-C1/MAGE-A12 | SSFSYTLLSLFQSSPKASEYLQLVFGIEVV | 64% | 98% |
| 338 | BLV1411-11 | PIWIL2/LAGE-1 | FVASINLTLTKWYSRDFTVSGNLLFMSVRD | 76% | 94% |
| 339 | BLV1411-12 | MAGE-A3/MAGE-A3 | LTQHFVQENYLEYRQKASSSLQLVFGIELM | 47% | 71% |
| 340 | BLV1411-13 | MAGE-A2/LAGE-1 | SSFSTTINYTLWRQSDSRLLQLHITMPFSS | 61% | 99% |
| 341 | BLV1411-14 | SURVIVIN/MAGE-C2 | AKKVRRAIEQLAAMDMASESLSVMSSNVSF | 52% | 28% |
| 342 | BLV1411-15 | MAGE-A3/SURVIVIN | QAALSRKVAELVHFLKDHRISTFKNWPFLE | 30% | 90% |

*Percentage of individuals having CD8+ T cell specific PEPI3+ within the HLA class I Model Population (n = 433).
**Percentage of individuals having CD4+ T cell specific PEPI4+ within the normal donors (n=400).

Characterization of PolyPEPI1411

The PolyPEPI1411 composition targets 17 different CTAs. Based on the antigen expression rates for these 17 CTAs, we modelled the predicted average number of expressed antigens (AG50) and the minimum number of expressed antigens with 950% likelihood (AG95) in the cancer cells. 95% of individuals expressed minimum 4 of the 17 target antigens (AG95=4) as shown by the antigen expression curve in FIG. 29.

The PolyPEPI1411 composition can induce immune response against an average of 9 vaccine antigens (AP50=9.44) and 9500 of the Model Population can induce immune response against at least three vaccine antigens (AP95=3)(FIG. 30).

Combining the data of AG of bladder cancer and AP in the Model Population we determined the AGP value of PolyPEPI1411 that represents the probability distribution of vaccine antigens that induce immune responses against antigens expressed in bladder tumors. For PolyPEPI1411, the AGP50 value in the Model Population is 3.90. The AGP95=1, means that 9500 of the subjects in the Model Population induce immune responses against at least one expressed vaccine antigen (FIG. 31).

Example 21—Personalised Immunotherapy (PIT) Design and Treatment for Ovarian-, Breast- and Colorectal Cancer This Example provides proof of concept data from 4 metastatic cancer patients treated with personalized immu- Composition for Treatment of Ovarian Cancer with POC01—PIT (Patient A)

This example describes the treatment of an ovarian cancer patient with a personalised immunotherapy composition, wherein the composition was specifically designed for the patient based on her HLA genotype based on the disclosure described herein.

The HLA class I and class II genotype of a metastatic ovarian adenocarcinoma cancer patient (Patient-A) was determined from a saliva sample.

To make a personalized pharmaceutical composition for Patient-A thirteen peptides were selected, each of which met the following two criteria: (i) derived from an antigen that is expressed in ovarian cancers, as reported in peer reviewed scientific publications; and (ii) comprises a fragment that is a T cell epitope capable of binding to at least three HLA class I of Patient-A (Table 22). In addition, each peptide is optimized to bind the maximum number of HLA class II of the patient.

TABLE 22

Personalized vaccine of Patient-A.

| POC01 vaccine for Patient-A | Target Antigen | Antigen Expression | 20 mer peptides | MAX HLA class I | MAX HLA class II |
|---|---|---|---|---|---|
| POC01_P1 | AKAP4 | 89% | NSLQKQLQAVLQWIAASQFN | 3 | 5 |
| POC01_P2 | BORIS | 82% | SGDERSDEIVLTVSNSNVEE | 4 | 2 |
| POC01_P3 | SPAG9 | 76% | VQKEDGRVQAFGWSLPQKYK | 3 | 3 |
| POC01_P4 | OY-TES-1 | 75% | EVESTPMIMENIQELIRSAQ | 3 | 4 |
| POC01_P5 | SP17 | 69% | AYFESLLEKREKTNFDPAEW | 3 | 1 |
| POC01_P6 | WT1 | 63% | PSQASSGQARMFPNAPYLPS | 4 | 1 |
| POC01_P7 | HIWI | 63% | RRSIAGFVASINEGMTRWFS | 3 | 4 |
| POC01_P8 | PRAME | 60% | MQDIKMILKMVQLDSIEDLE | 3 | 4 |
| POC01_P9 | AKAP-3 | 58% | ANSVVSDMMVSIMKTLKIQV | 3 | 4 |
| POC01_P10 | MAGE-A4 | 37% | REALSNKVDELAHFLLRKYR | 3 | 2 |
| POC01_P11 | MAGE-A9 | 37% | ETSYEKVINYLVMLNAREPI | 3 | 4 |
| POC01_P12a | MAGE-A10 | 52% | DVKEVDPTGHSFVLVTSLGL | 3 | 4 |
| POC01_P12b | BAGE | 30% | SAQLLQARLMKEESPVVSWR | 3 | 2 |

Eleven PEPI3 peptides in this immunotherapy composition can induce T cell responses in Patient-A with 84% probability and the two PEPI4 peptides (POC01-P2 and POC01-P5) with 98% probability, according to the validation of the PEPI test shown in Table 3. T cell responses target 13 antigens expressed in ovarian cancers. Expression of these cancer antigens in patient-A was not tested. Instead the probability of successful killing of cancer cells was determined based on the probability of antigen expression in the patient's cancer cells and the positive predictive value of the ≥1 PEPI3+ test (AGP count). AGP count predicts the effectiveness of a vaccine in a subject: Number of vaccine antigens expressed in the patient's tumor (ovarian adenocarcinoma) with PEPI. The AGP count indicates the number of tumor antigens that the vaccine recognizes and induces a T cell response against the patient's tumor (hit the target). The AGP count depends on the vaccine-antigen expression rate in the subject's tumor and the HLA genotype of the subject. The correct value is between 0 (no PEPI presented by any expressed antigen) and maximum number of antigens (all antigens are expressed and present a PEPI).

The probability that Patient-A will express one or more of the 13 antigens is shown in FIG. 32. AGP95 (AGP with 95% probability)=5, AGP50 (the mean-expected value-of the discrete probability distribution)=7.9, mAGP (probability that AGP is at least 2)=100%, AP=13.

A pharmaceutical composition for Patient-A may be comprised of at least 2 from the 13 peptides (Table 22), because the presence in a vaccine or immunotherapy composition of at least two polypeptide fragments (epitopes) that can bind to at least three HLAs of an individual (≥2 PEPI3+) was determined to be predictive for a clinical response. The peptides are synthetized, dissolved in a pharmaceutically acceptable solvent and mixed with an adjuvant prior to injection. It is desirable for the patient to receive personalized immunotherapy with at least two peptide vaccines, but preferable more to increase the probability of killing cancer cells and decrease the chance of relapse.

For treatment of Patient-A the 13 peptides were formulated as 4×3 or 4 peptide (POC01/1, POC01/2, POC01/3, POC01/4). One treatment cycle is defined as administration of all 13 peptides within 30 days.

Patient History:
Diagnosis: Metastatic ovarian adenocarcinoma
Age: 51
Family anamnesis: colon and ovary cancer (mother) breast cancer (grandmother)
Tumor pathology:
2011: first diagnosis of ovarian adenocarcinoma; Wertheim operation and chemotherapy; lymph node removal
2015: metastasis in pericardial adipose tissue, excised
2016: hepatic metastases
2017: retroperitoneal and mesenteric lymph nodes have progressed; incipient peritoneal carcinosis with small accompanying ascites
Prior Therapy:
2012: Paclitaxel-carboplatin (6×)
2014: Caelyx-carboplatin (1×)
2016-2017 (9 months): Lymparza (Olaparib) 2×400 mg/day, oral
2017: Hycamtin inf. 5×2.5 mg (3× one seria/month)

Figure 33:
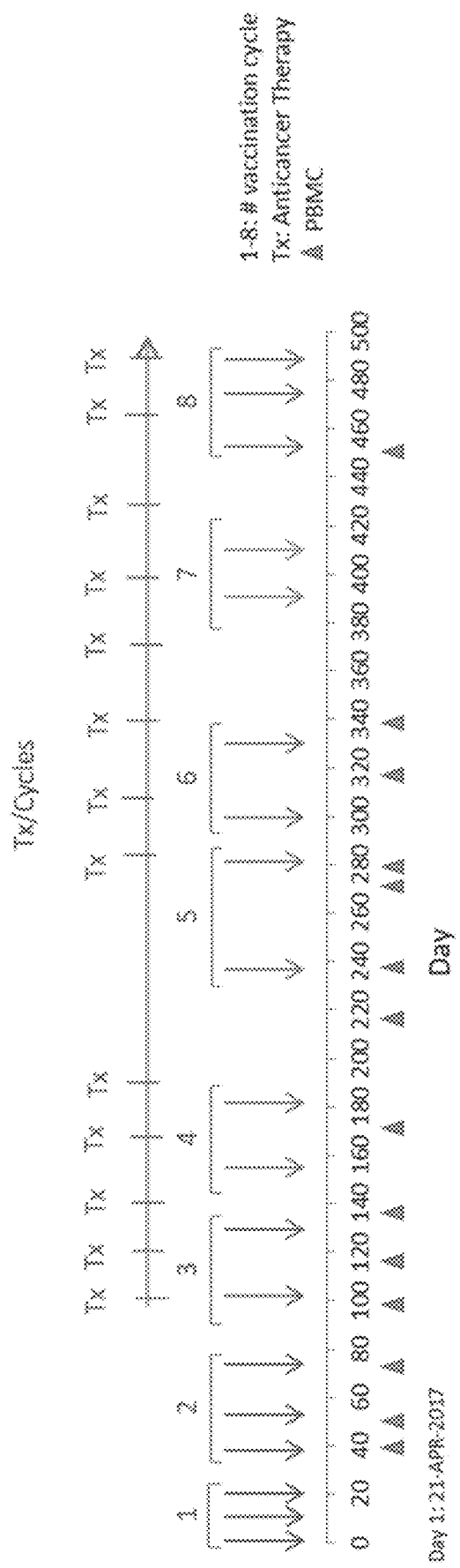

PIT vaccine treatment began on 21 Apr. 2017. FIG. 33. 2017-2018: Patient-A received 8 cycles of vaccination as add-on therapy, and lived 17 months (528 days) after start of the treatment. During this interval, after the $3^{rd}$ and $4^{th}$ vaccine treatment she experienced partial response as best response. She died in October 2018.

Figure 34:
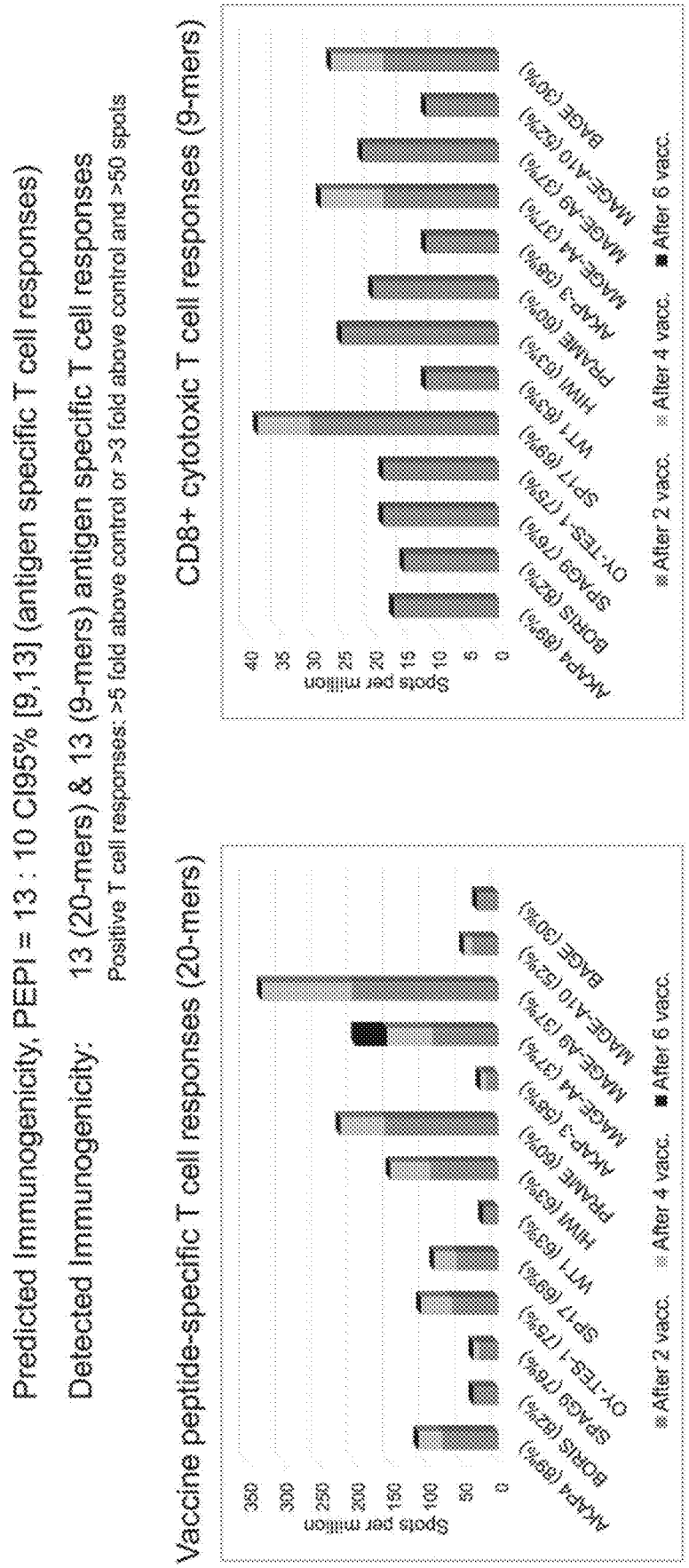

An interferon (IFN)-γ ELISPOT bioassay confirmed the predicted T cell responses of Patient-A to the 13 peptides. Positive T cell responses (defined as >5 fold above control, or >3 fold above control and >50 spots) were detected for all 13 20-mer peptides and all 13 9-mer peptides having the sequence of the PEPI of each peptide capable of binding to the maximum HLA class I alleles of Patient-A (FIG. 34). Patient's tumor MRI findings (Baseline Apr. 15, 2016) (BL: baseline for tumor response evaluation on FIG. 35)

Disease was confined primarily to liver and lymph nodes. The use of MRI limits detection of lung (pulmonary) metastasis May 2016-January 2017: Olaparib treatment (FU1: follow up 1 on FIG. 35)

Figure 35:
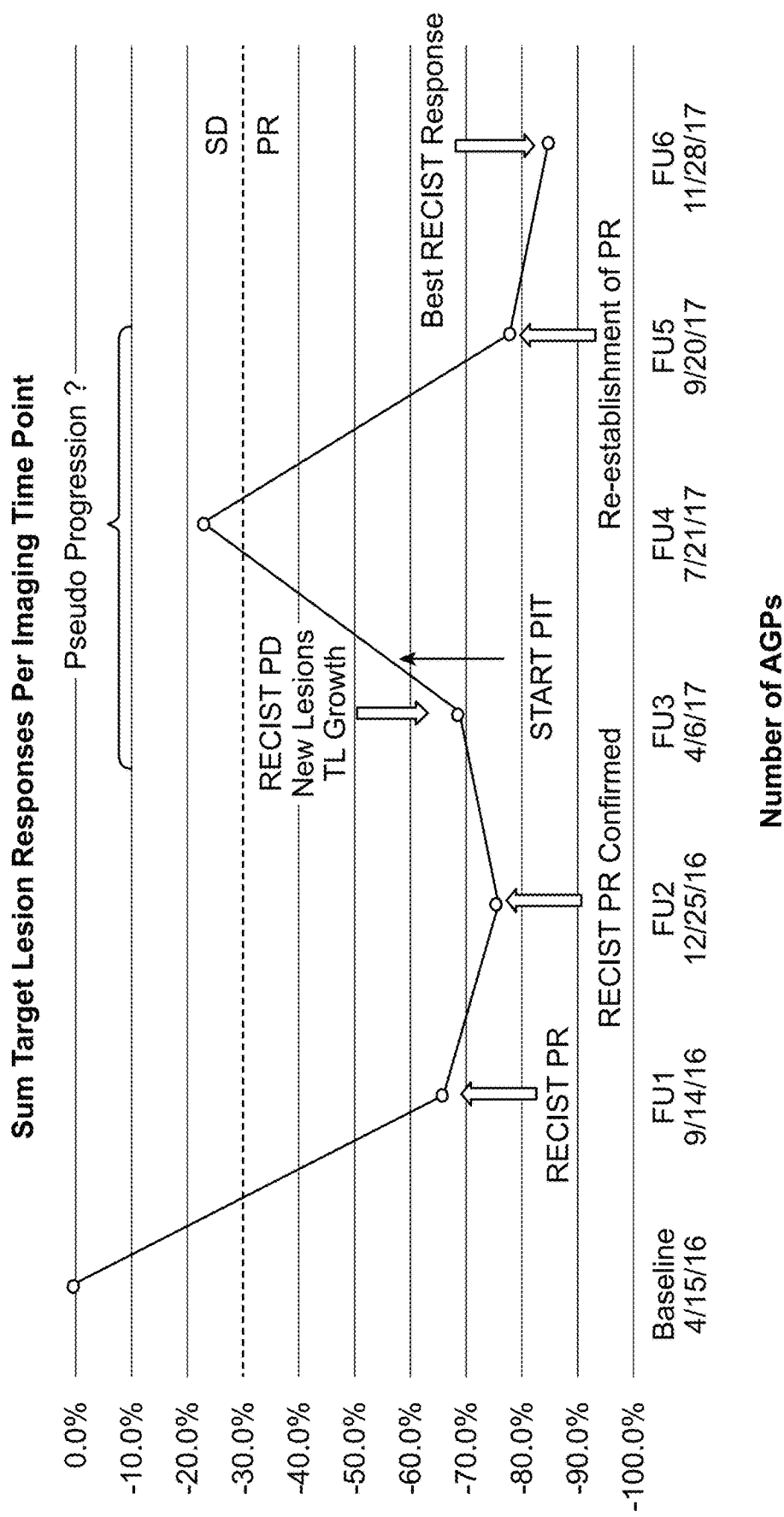

Dec. 25, 2016 (before PIT vaccine treatment) There was dramatic reduction in tumor burden with confirmation of response obtained at (FU2: follow up 2 on FIG. 35)

January-March 2017—TOPO protocol (topoisomerase)

Apr. 6, 2017 (FU3 on FIG. 35) demonstrated regrowth of existing lesions and appearance of new lesions leading to disease progression. Peritoneal carcinomatosis with increased amount of ascites. Progressive hepatic tumor and lymph node Apr. 21, 2017 Start Pit Jul. 26, 2017 (after the $2^{nd}$ Cycle of PIT): (FU4 on FIG. 35) Progression/Pseudo-Progression Rapid progression in lymph nodes, hepatic, retroperitoneal and thoracic areas, significant pleural fluid and ascites. Initiate Carboplatin, Gemcitabine, Avastin.

Sep. 20, 2017 (after 3 Cycles of PIT): (FU5 on FIG. 35) Partial Response

Complete remission in the pleural region/fluid and ascites

Remission in hepatic, retroperitoneal area and lymph nodes

The findings suggest pseudo progression.

Nov. 28, 2017 (after 4 Cycles of PIT): (FU6 on FIG. 35) Partial Response

Complete remission in the thoracic region. Remission in hepatic, retroperitoneal area and lymph nodes Apr. 13, 2018: Progression Complete remission in the thoracic and retroperitoneal regions. Progression in hepatic centers and lymph nodes Jun. 12, 2018: Stable disease Complete remission in the thoracic and retroperitoneal regions. Minimal regression in hepatic centers and lymph nodes July 2018: Progression October 2018: Patient-A died Partial MRI data for Patient-A is shown in Table 23 and FIG. 35.

TABLE 23

Summary Table of Lesions Responses

| Lesion/ Time Point | Baseline (% Δ from BL) | FU1 (% Δ from BL) | FU2 (% Δ from BL) | FU3 (% Δ from BL) | FU4 (% Δ from BL) | FU5 (% Δ from BL) | FU6 (% Δ from BL) | Best Response Cycle | PD Time Point |
|---|---|---|---|---|---|---|---|---|---|
| TL1 | NA | −56.1 | −44.4 | −44.8 | +109.3 | −47.8 | −67.3 | FU6 | FU4 |
| TL2 | NA | −100.0 | −100.0 | −47.1 | −13.1 | −100.0 | −100.0 | FU1 | FU3 |
| TL3 | NA | −59.4 | −62.3 | −62.0 | −30.9 | −66.7 | −75.9 | FU6 | FU4 |
| TL4 | NA | −65.8 | −100.0 | −100.0 | −100.0 | −100.0 | −100.0 | FU2 | NA |
| SUM | NA | −66.3 | −76.0 | −68.9 | −23.5 | −78.2 | −85.2 | FU6 | FU4 |

Design, Safety and Immunogenicity of Personalised Immunotherapy Composition (PBRC01) for Treatment of Metastatic Breast Cancer (Patient-B) PT9

Figure 36:
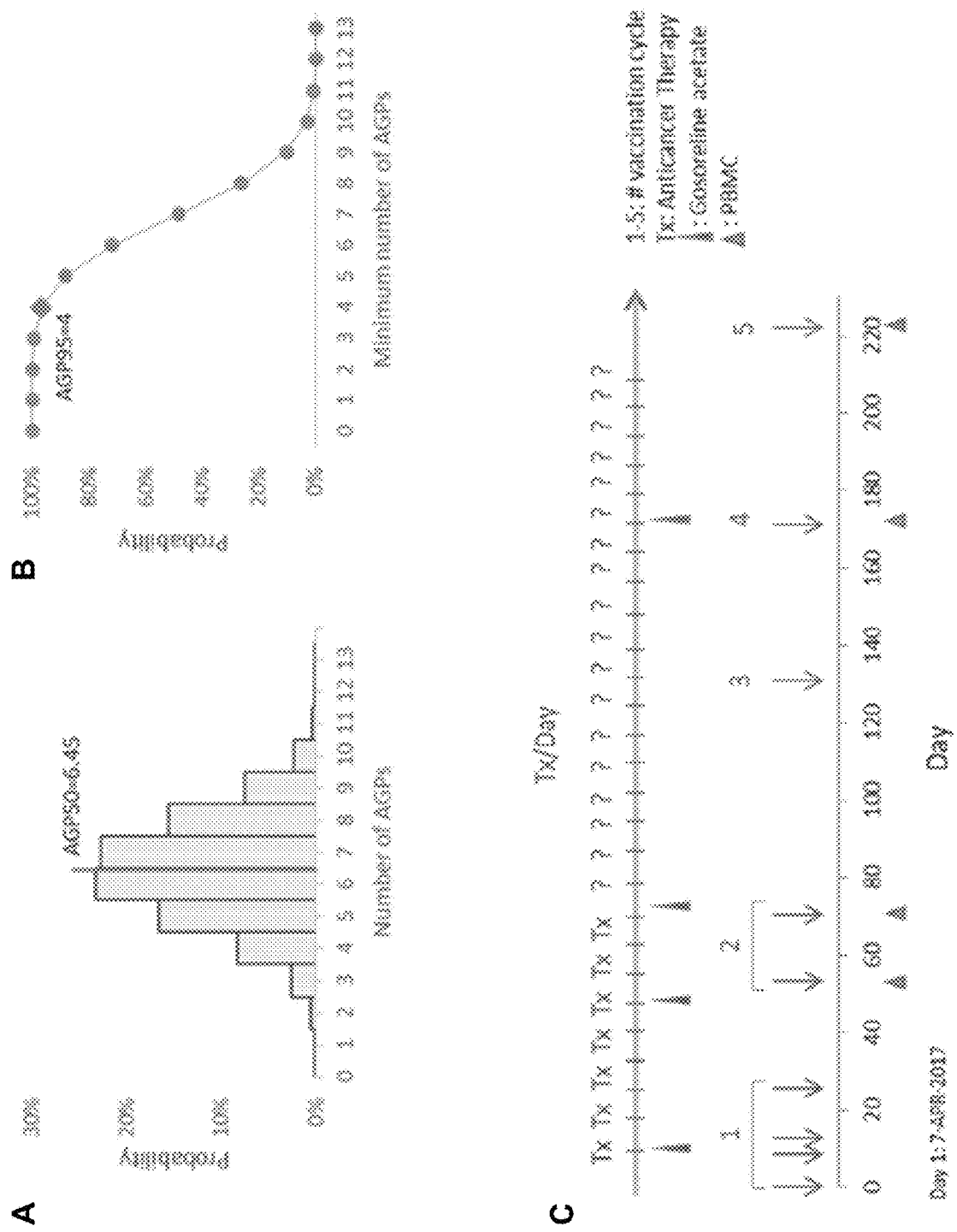

The HLA class I and class II genotype of metastatic breast cancer Patient-B was determined from a saliva sample. To make a personalized pharmaceutical composition for Patient-B twelve peptides were selected, each of which met the following two criteria: (i) derived from an antigen that is expressed in breast cancers, as reported in peer reviewed scientific publications; and (ii) comprises a fragment that is a T cell epitope capable of binding to at least three HLA class I of Patient-B (Table 24). In addition, each peptide is optimized to bind the maximum number of HLA class II of the patient. The twelve peptides target twelve breast cancer antigens. The probability that Patient-B will express one or more of the 12 antigens is shown in FIG. 36.

TABLE 24

12 peptides for Patient-B breast cancer patient

| BRC01 vaccine peptides | Target Antigen | Antigen Expression | 20 mer peptide | MAX HLA Class I | MAX HLA Class II |
|---|---|---|---|---|---|
| PBRC01_cP1 | FSIP1 | 49% | ISDTKDYFMSKTLGIGRLKR | 3 | 6 |
| PBRC01_cP2 | SPAG9 | 88% | FDRNTESLFEELSSAGSGLI | 3 | 2 |
| PBRC01_cP3 | AKAP4 | 85% | SQKMDMSNIVLMLIQKLLNE | 3 | 6 |
| PBRC01_cP4 | BORIS | 71% | SAVFHERYALIQHQKTHKNE | 3 | 6 |
| PBRC01_cP5 | MAGE-A11 | 59% | DVKEVDPTSHSYVLVTSLNL | 3 | 4 |

TABLE 24-continued 12 peptides for Patient-B breast cancer patient

| BRC01 vaccine peptides | Target Antigen | Antigen Expression | 20 mer peptide | MAX HLA Class I | MAX HLA Class II |
|---|---|---|---|---|---|
| PBRC01_cP6 | NY-SAR-35 | 49% | ENAHGQSLEEDSALEALLNF | 3 | 2 |
| PBRC01_cP7 | HOM-TES-85 | 47% | MASFRKLTLSEKVPPNHPSR | 3 | 5 |
| PBRC01_cP8 | NY-BR-1 | 47% | KRASQYSGQLKVLIAENTML | 3 | 6 |
| PBRC01_cP9 | MAGE-A9 | 44% | VDPAQLEFMFQEALKLKVAE | 3 | 8 |
| PBRC01_cP10 | SCP-1 | 38% | EYEREETRQVYMDLNNNIEK | 3 | 3 |
| PBRC01_cP11 | MAGE-A1 | 37% | PEIFGKASESLQLVFGIDVK | 3 | 3 |
| PBRC01_cP12 | MAGE-C2 | 21% | DSESSFTYTLDEKVAELVEF | 4 | 2 |

Predicted efficacy: AGP95=4; 95% likelihood that the PIT Vaccine induces CTL responses against 4 TSAs expressed in the breast cancer cells of BRC09. Additional efficacy parameters: AGP50=6.45, mAGP=100%, AP=12.

For treatment of Patient-B the 12 peptides were formulated as 4×3 peptide (PBR01/1, PBR01/2, PBR01/3, PBR01/4). One treatment cycle is defined as administration of all 12 different peptide vaccines within 30 days (FIG. 36C).

Patient History:
2013: Diagnosis: breast carcinoma diagnosis CT scan and bone scan ruled out metastatic disease,
2014: bilateral mastectomy, postoperative chemotherapy
2016: extensive metastatic disease with nodal involvement both above and below the diaphragm.
Multiple liver and pulmonary metastases.
Therapy:
2013-2014: Adriamycin-Cyclophosphamide and Paclitaxel
2017: Letrozole Palbociclib and Gosorelin and PIT vaccine
2018: Worsening conditions, patient died in January PIT vaccine treatment began on 7 Apr. 2017. Patient-B's treatment schedule and main characteristics of disease are shown in Table 25.

TABLE 25

Treatment and response of Patient-B

| | Date (2017) | | | | | |
|---|---|---|---|---|---|---|
| | Mar. | May | Jun. | Sep. | Nov. | Dec. |
| | | PIT Vaccine | | | | |
| Treatment regimen | Palbociclib Letrozole Gosorelin | | | Anticancer drug treatment interruption | | |
| Neutrophils (1.7-3.5/mm³) | ND | 1.1 | 4.5 | 3.4 | 2.4 | 3 |
| CEA (<5.0 ng/ml) | 99 | 65 | 23 | 32 | 128 | 430 |
| CA 15-3 (<31.3 U/ml) | 322 | 333 | 138 | 76 | 272 | 230 |
| T1: Right axillar lymph node | 15 mm & 11.6 $SUV_{max}$ | 9 mm & 2.0 $SUV_{max}$ | nd* | nd | nd | 6 mm & 0 SUVmax |
| T2: Right lung metastasis | 10 mm & 4.8 $SUV_{max}$ | 7 mm & 0 $SUV_{max}$ | nd | nd | nd | 4 mm & 0 $SUV_{max}$ |
| Left iliac bone metastasis | Non measurable &4.0 $SUV_{max}$ | Regression &O $SUV_{max}$ | nd | nd | nd | Regression & 0 $SUV_{max}$ |

TABLE 25-continued

Treatment and response of Patient-B

| | Date (2017) | | | | | |
|---|---|---|---|---|---|---|
| | Mar. | May | Jun. | Sep. | Nov. | Dec. |
| | | PIT Vaccine | | | | |
| Treatment regimen | Palbociclib Letrozole Gosorelin | | | Anticancer drug treatment interruption | | |
| Multiple liver metastases | Non measurable & 11.5 $SUV_{max}$ | Partial regression &6.1 $SUV_{max}$ | nd | nd | nd | Progression & 16.8 $SUV_{max}$ |

*no data

Figure 37:
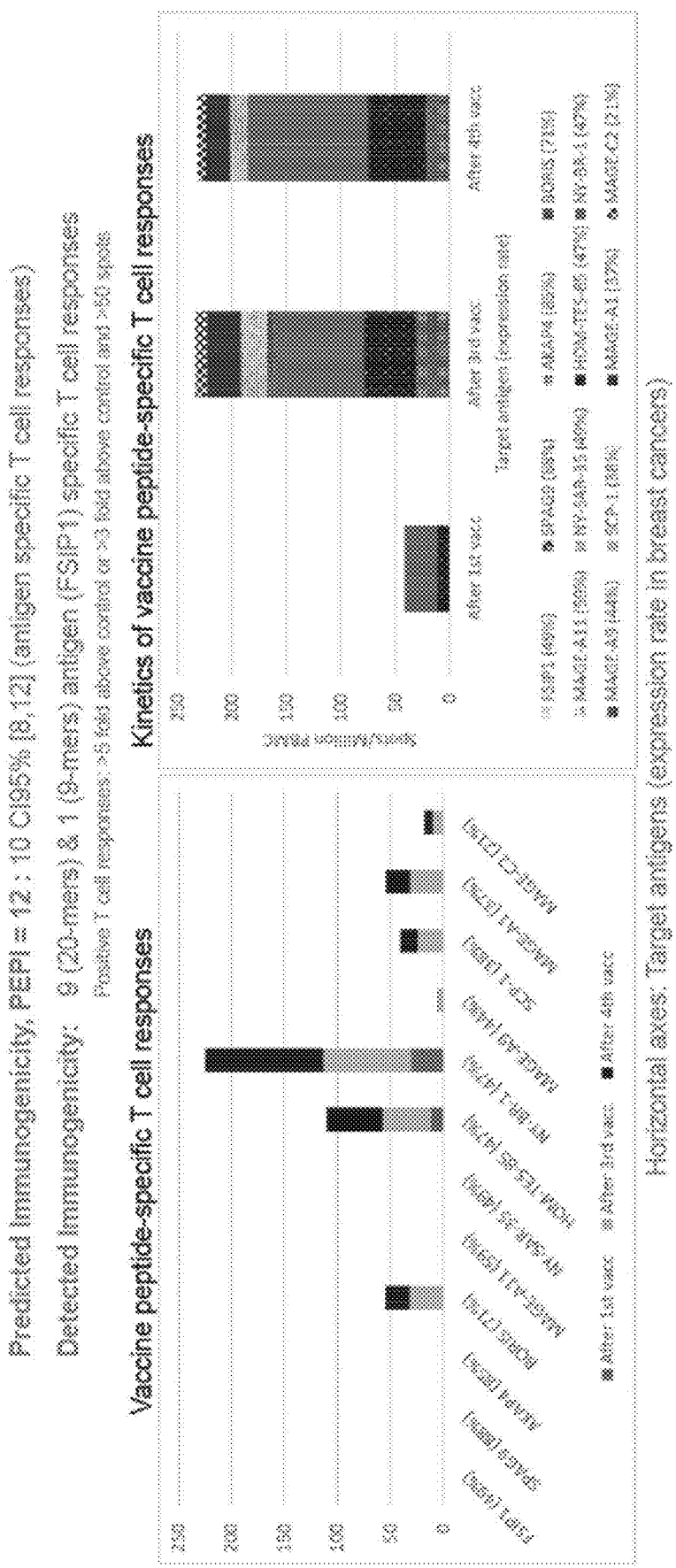

It was predicted with 95% confidence that 8-12 vaccine peptides would induce T cell responses in Patient-B. Peptide-specific T cell responses were measured in all available PBMC samples using an interferon (IFN)-γ ELISPOT bioassay (FIG. 37). The results confirmed the prediction: Nine peptides reacted positive demonstrating that T cells can recognize Patient-B's tumor cells expressing FISP1, BORIS, MAGE-A11, HOM-TES-85, NY-BR-1, MAGE-A9, SCP1, MAGE-A1 and MAGE-C2 antigens. Some tumor specific T cells were present after the 1$^{st}$ vaccination and boosted with additional treatments (e.g. MAGE-A1) others induced after boosting (e.g. MAGE-A9). Such broad tumor specific T cell responses are remarkable in a late stage cancer patient.

Patient-B History and Results
Mar. 7, 2017: Prior PIT Vaccine treatment
Hepatic multi-metastatic disease with truly extrinsic compression of the origin of the choledochal duct and massive dilatation of the entire intrahepatic biliary tract. Celiac, hepatic hilar and retroperitoneal adenopathy
March 2017: Treatment initiation—Letrozole, Palbociclib, Gosorelin & PIT Vaccine
May 2017: Drug interruption
May 26, 2017: After 1 cycle of PIT
83% reduction of tumor metabolic activity (PET CT) liver, lung lymphnodes and other metastases.
June 2017: Normalized Neutrophils values indicate Palbociclib interruption as affirmed by the patient
4 Months Delayed Rebound of Tumor Markers
March to May 2017: CEA and CA remained elevated consistently with the outcome of her anti-cancer treatment (Ban, Future Oncol 2018)

June to September 2017: CEA and CA decreased consistently with the delayed responses to immunotherapies
Quality of Life
February to March 2017: Poor, hospitalized with jaundice
April to October 2017: Excellent
November 2017: (Worsening conditions (tumor escape?)
January 2018: Patient-B died.
Immunogenicity results are summarized in FIG. 37.

Clinical outcome measurements of the patient: One month prior to the initiation of PIT vaccine treatment PET CT documented extensive DFG avid disease with nodal involvement both above and below the diaphragm (Table 25). She had progressive multiple hepatic, multifocal osseous and pulmonary metastases and retroperitoneal adenopathy. Her intrahepatic enzymes were elevated consistent with the damage caused by her liver metastases with elevated bilirubin and jaundice. She accepted Letrozole, Palbociclib and Gosorelin as anti-cancer treatment. Two month after initiation of PIT vaccinations the patient felt very well and her quality of life normalized. In fact, her PET CT showed a significant morphometabolic regression in the liver, lung, bone and lymph node metastases. No metabolic adenopathy was identifiable at the supra-diaphragmatic stage.

The combination of Pablocyclib and the personalised vaccine was likely to have been responsible for the remarkable early response observed following administration of the vaccine. Palbocyclib has been shown to improve the activity of immunotherapies by increases CTA presentation by HLAs and decreasing the proliferation of Tregs: (Goel et al. Nature. 2017:471-475). The results of Patient-B's treatment suggest that PIT vaccine may be used as add-on to the state-of-art therapy to obtain maximal efficacy.

Patient-B's tumor biomarkers were followed to disentangle the effects of state-of-art therapy from those of PIT vaccine. Tumor markers were unchanged during the initial 2-3 months of treatment then sharply dropped suggesting of a delayed effect, typical of immunotherapies (Table 25). Moreover, at the time the tumor biomarkers dropped the patient had already voluntarily interrupted treatment and confirmed by the increase in neutrophil counts.

After the 5$^{th}$ PIT treatment the patient experienced symptoms. The levels of tumor markers and liver enzymes were increased again. 33 days after the last PIT vaccination, her PET CT showed significant metabolic progression in the liver, peritoneal, skeletal and left adrenal site confirming the laboratory findings. The discrete relapse in the distant metastases could be due to potential immune resistance; perhaps caused by downregulation of both HLA expression that impairs the recognition of the tumor by PIT induced T cells. However, the PET CT had detected complete regression of the metabolic activity of all axillary and mediastinal axillary supra-diaphragmatic targets (Table 25). These localized tumor responses may be accounted to the known delayed and durable responses to immunotherapy, as it is unlikely that after anti-cancer drug treatment interruption these tumor sites would not relapse.

Personalised Immunotherapy Composition for Treatment of Patient with Metastatic Breast Carcinoma (Patient-C) PT13

Figure 38:
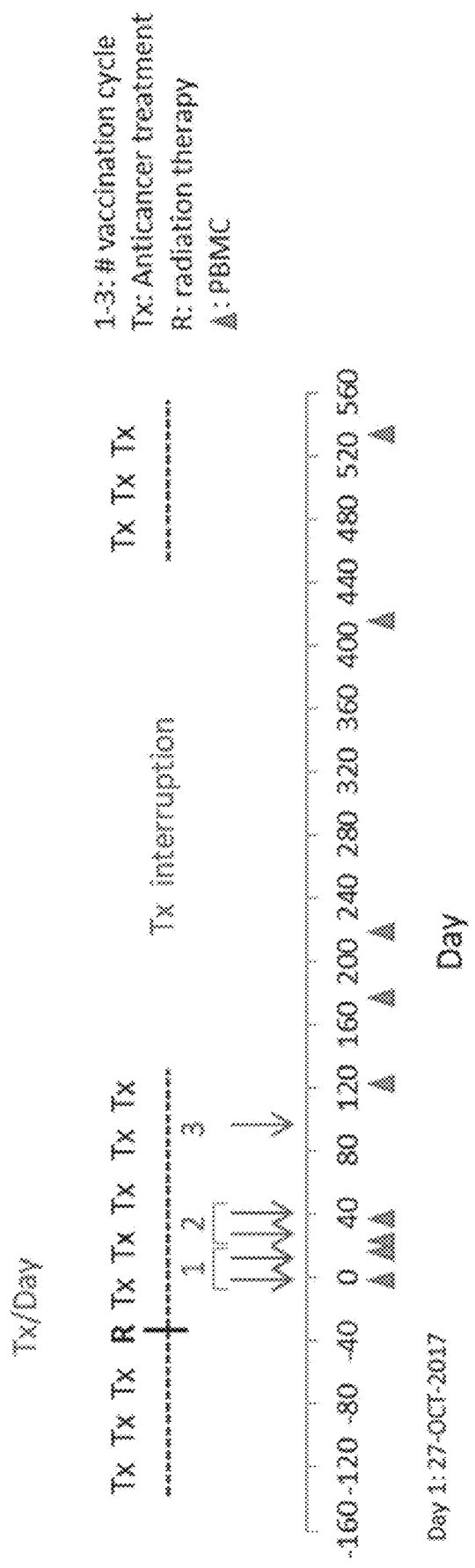
Figure 39:
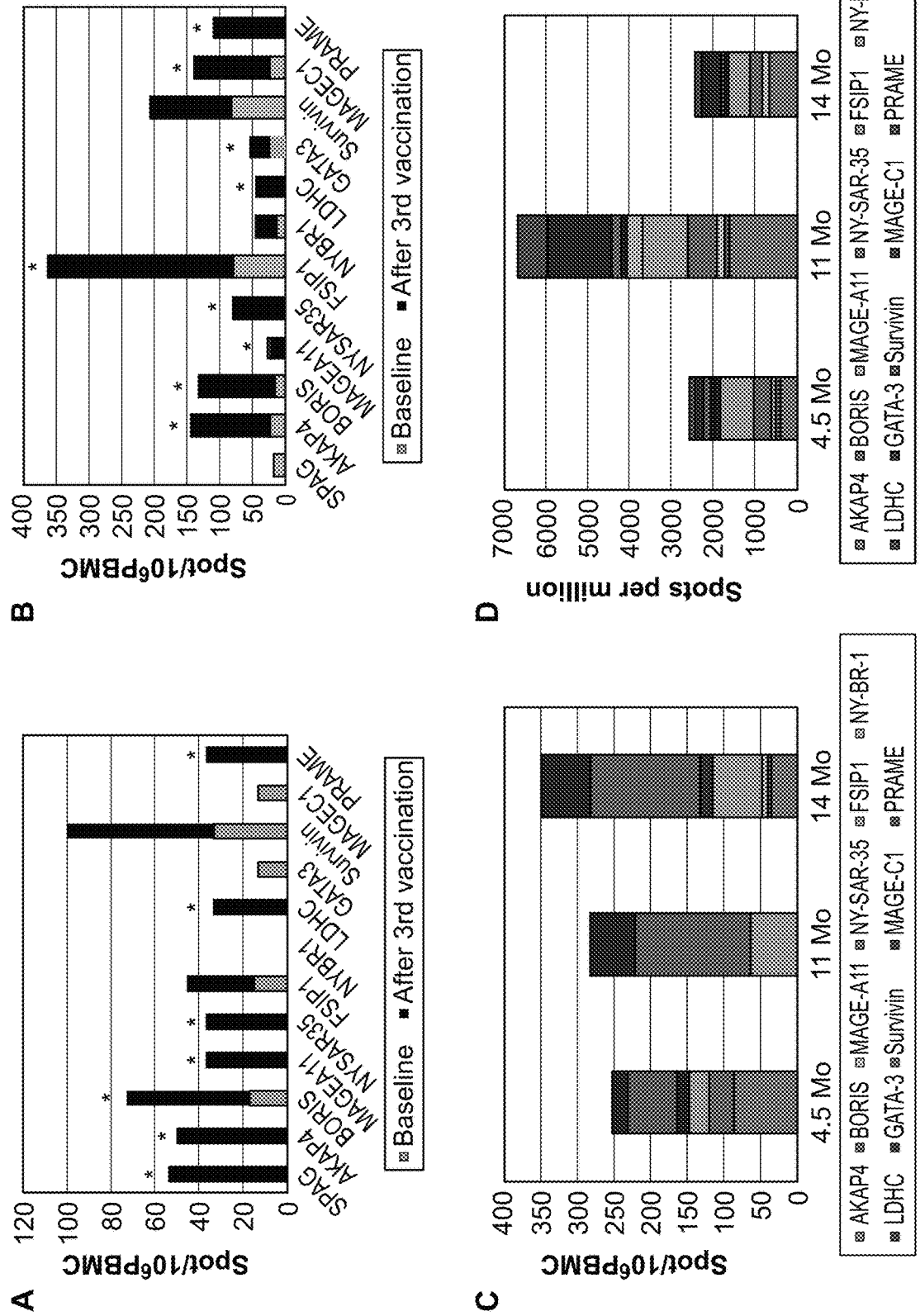

PIT vaccine similar in design to that described for Patient-A and Patient-B was prepared for the treatment of a patient (Patient-C) with metastatic breast carcinoma. PIT vaccine contained 12 PEPIs. The PIT vaccine has a predicted efficacy of AGP=4. The patient's treatment schedule is shown in FIG. 38.
Tumor Pathology
2011 Original tumor: HER2-, ER+, sentinel lymph node negative
2017 Multiple bone metastases: ER+, cytokeratin 7+, cytokeratin 20-, CA125-, TTF1-, CDX2-
Treatments
2011 Wide local resection, sentinel lymph nodes negative; radiotherapy
2017—Anti-cancer therapy (Tx): Letrozole (2.5 mg/day), Denosumab;
   Radiation (Rx): one bone
   PIT vaccine (3 cycles) as add-on to standard of care
   Bioassay confirmed positive T cell responses (defined as >5 fold above control, or >3 fold above control and >50 spots) to 11 out of the 12 20-mer peptides of the PIT vaccine and 11 out of 12 9-mer peptides having the sequence of the PEPI of each peptide capable of binding to the maximum HLA class I alleles of the patient (FIG. 39).

Long-lasting memory T-cell responses were detected after 14 months of the last vaccination (FIG. 24C-D).
Treatment Outcome
Clinical results of treatment of Patient-C are shown in Table 26. Patient-C has partial response and signs of healing bone metastases.

TABLE 26

Clinical results of treatment of breast cancer Patient-C

|  | Before PIT | +70 days * (10 w) | +150 days * (21 w) | +388 days* (55 w) |
|---|---|---|---|---|
| Bone Biopsy | Met. breast Cancer DCIS | Not done | RIB5 is negative | Not done |
| PET CT | Multiple metastases | Only RIB5 is DFG avid | Not done | Not done |
| CT | Multiple metastases | Not done | Not done | Healing bone mets (sclerotic foci) |
| CA-15-3 | 87 | 50 | 32 | 24 |

* After 3rd cycle of PIT vaccination

Immune responses are shown on FIG. 39. Predicted Immunogenicity, PEPI=12 (CI95% [8, 12] Detected Immunogenicity: 11 (20-mers) & 11 (9-mers) antigen specific T cell responses following 3 PIT vaccinations (FIG. 39A, B). After 4.5, 11 or 14 months of the last vaccination, PIT vaccine-specific immune response could still be detected (FIG. 39C, D).

Figure 40:
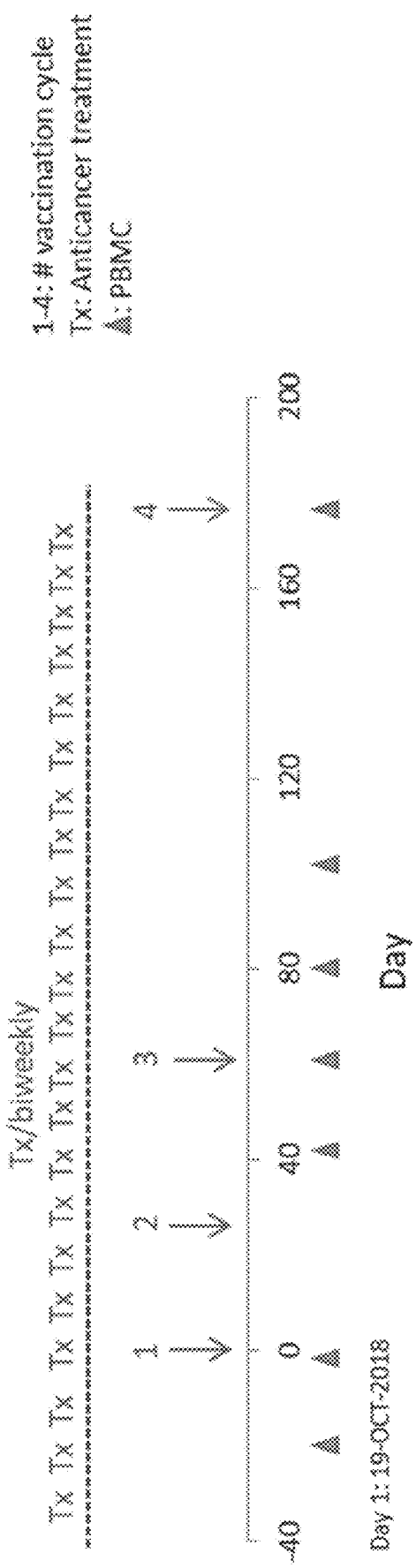

Personalised Immunotherapy Composition for Treatment of Patient with Metastatic Colorectal Cancer (Patient-D) PT16
Tumor Pathology
2017 (February) mCRC (MSS) with liver metastases, surgery of primer tumor (in sigmoid colon). pT3 pN2b (8/16) M1. KRAS G12D, TP53-C135Y, KDR-Q472H, MET-T1010I mutations. SATB2 expression. EGFR wt, PIK3CA-1391M (non-driver).
2017 (June) Partial liver resection: KRAS-G12D (35G>A) NRAS wt,
2018 (May) 2$^{nd}$ resection: SATB2 expression, lung metastases 3→21
Treatments
2017 FOLFOX-4 (oxaliplatin, Ca-folinate, 5-FU)→allergic reaction during 2$^{nd}$ treatment
   DeGramont (5-FU+Ca-folinate)
2018 (June)→FOLFIRI plus ramucirumab, biweekly; chemoembolization
2018 (October) PIT vaccination (13 patient-specific peptides, 4 doses) as add-on to standard of care.
The patient's treatment schedule is shown in FIG. 40.

Treatment Outcome

Patient in good overall condition, disease progression in lungs after 8 months confirmed by CT.

Figure 41:
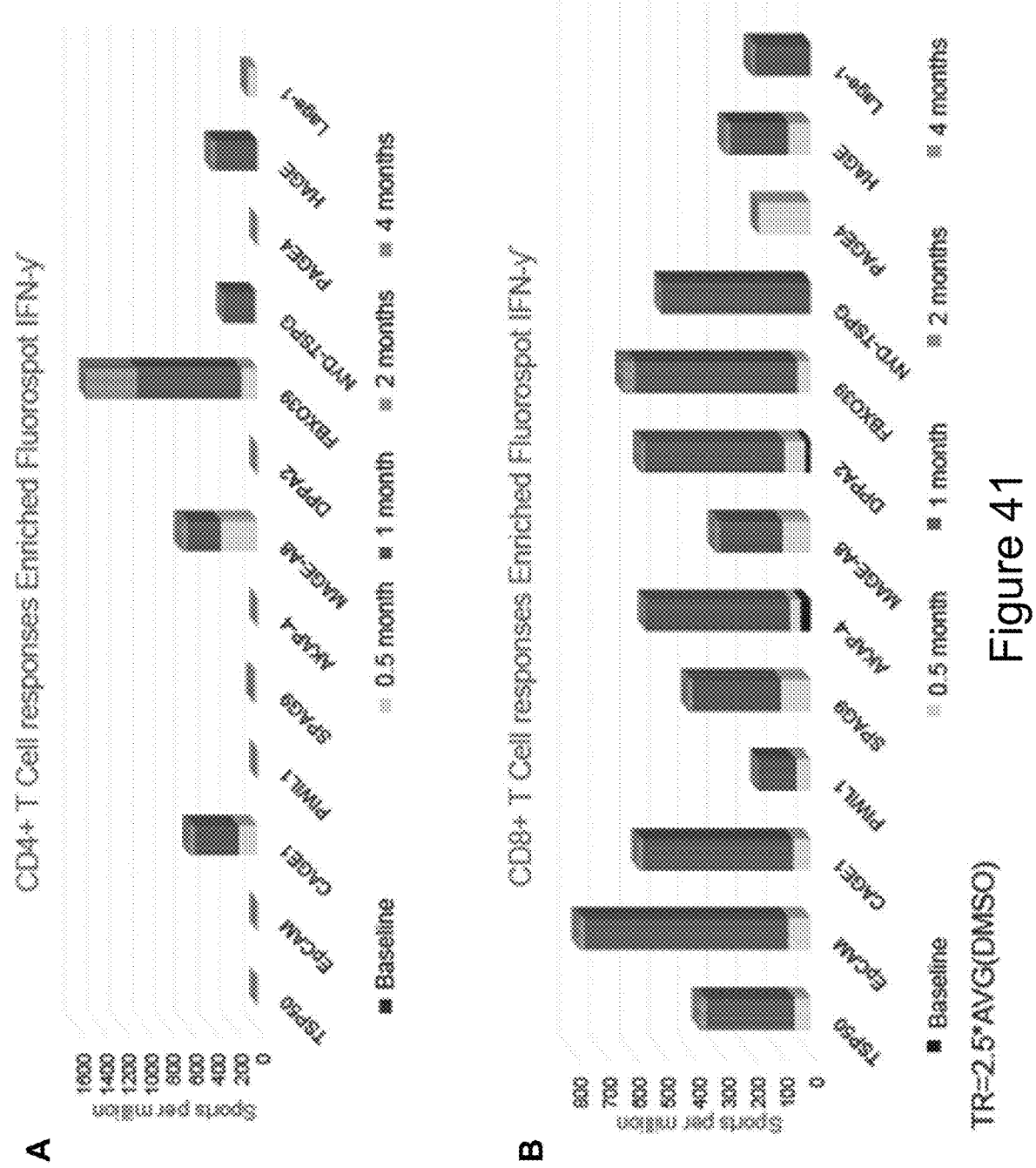

Both PIT induced and pre-existing T cell responses were measured by enriched Fluorospot from PBMC, using 9mer and 20mer peptides for stimulation (FIG. 41).

Summary of immune response rate and immunogenicity results prove the proper design for target antigen selection as well as for the induction of multi-peptide targeting immune responses, both CD4+ and CD8+ specific ones.

TABLE 27

Summary table of immunological analysis of Patient A-D

| Patient ID | Measured immunogenicity for the different vaccine peptides* | |
|---|---|---|
| | CD4+ T cells | CD8+ T cells |
| Patient-A | 13/13 (100%) | 13/13 (100%) |
| Patient-B | 9/12 (75%) | 1/12 (8%) |
| Patient-C | 11/12 (92%) | 11/12 (92%) |
| Patient-D | 7/13 (54%) | 13/13 (100%) |
| IRR (ratio of immune responder patients) | 4/4 | 4/4 |
| Ratio of immunogenic peptides (median) | 10/12-13 | 10/12-13 |

*Following 1-3 cycles of vaccination

The invention claimed is:

1. A composition comprising: (i) a peptide having an amino acid sequence comprising any one of the sequences set forth in SEQ ID NOs: 61-75; and (ii) an adjuvant.

2. The composition of claim 1, further comprising at least one additional peptide, having an amino acid sequence comprising any one of the sequences set forth in SEQ ID NOs: 61-75.

3. The composition of claim 1, further comprising at least two additional peptides, each having an amino acid sequence comprising any one of the sequences set forth in SEQ ID NOs: 61-75.

4. The composition of claim 1, further comprising at least 14 additional peptides, each having an amino acid sequence comprising any one of the sequences set forth in SEQ ID NOs: 61-75.

5. A method of treating gastric cancer using immunotherapy in an individual in need thereof, the method comprising administering to the individual a composition comprising: (i) a peptide having an amino acid sequence comprising any one of the sequences set forth in SEQ ID NOs: 61-75; and (ii) an adjuvant.

6. The method of claim 5, wherein the method further comprises administering at least one additional peptide having at least 15 consecutive amino acids from a gastric cancer antigen or fragment thereof selected from: DPPA2, CAGE-1, TSP50, HIWI, SURVIVIN, 5T4, PRAME, KK-LC-1, MAGE-A2, MAGE-A3, LAGE-1, MAGE-A10, MAGE-A1, SSX1, and combinations thereof.

7. The method of claim 5, further comprising administering at least one checkpoint inhibitor, wherein the checkpoint inhibitor is administered prior to, concomitant with, or after administration of the composition.

8. The method of claim 5, wherein the method further comprises administering at least one additional peptide having an amino acid sequence comprising any one of the sequences set forth in SEQ ID NOs: 61-75.

9. The method of claim 5, wherein the method further comprises administering at least two additional peptides each having an amino acid sequence comprising any one of the sequences set forth in SEQ ID NOs: 61-75.

10. The method of claim 5, wherein the method further comprises administering at least 14 additional peptides each having an amino acid sequence comprising any one of the sequences set forth in SEQ ID NOs: 61-75.

11. A method of treating gastric cancer using immunotherapy in an individual in need thereof, the method comprising administering to the individual: (a)(i) a first peptide having an amino acid sequence consisting of SEQ ID NO: 34; and (ii) at least one additional peptide having an amino acid sequence comprising any one of the sequences set forth in SEQ ID NOs: 31, 32, 33, 35, 36, 37, 38, 39, 40, 41, 42, 43, 44, 45, 46, 47, 48, 49, 50, 51, 52, 53, 54, 55, 56, 57, 58, 59, or 60; and (b) an adjuvant.

12. The method of claim 11, wherein the method further comprises administering at least one additional peptide having an amino acid sequence comprising at least 15 consecutive amino acids from the sequence of a gastric cancer antigen or fragment thereof selected from: DPPA2, CAGE-1, TSP50, HIWI, SURVIVIN, 5T4, PRAME, KK-LC-1, MAGE-A2, MAGE-A3, LAGE-1, MAGE-A10, MAGE-A1, SSX1, and combinations thereof.

13. The method of claim 11, further comprising administering at least one checkpoint inhibitor, wherein the checkpoint inhibitor is administered prior to, concomitant with, or after administration of the composition.

14. A method of treating gastric cancer using immunotherapy in an individual in need thereof, comprising administering to the individual a composition comprising: (a) (i) a first peptide having an amino acid sequence consisting of SEQ ID NO: 34 and (ii) at least one additional peptide having an amino acid sequence comprising at least 15 consecutive amino acids from the sequence of a gastric cancer antigen or fragment thereof selected from DPPA2, CAGE-1, TSP50, HIWI, SURVIVIN, 5T4, PRAME, KK-LC-1, MAGE-A2, MAGE-A3, LAGE-1, MAGE-A10, MAGE-A1, SSX1, or combinations thereof; and (b) an adjuvant.

15. The method of claim 14, further comprising administering at least one checkpoint inhibitor, wherein the checkpoint inhibitor is administered prior to, concomitant with, or after administration of the composition.

16. A method of treating gastric cancer using immunotherapy in an individual in need thereof, comprising administering to the individual the composition of claim 1.

17. The method of claim 16, further comprising administering at least one checkpoint inhibitor, wherein the checkpoint inhibitor is administered prior to, concomitant with, or after administration of the composition.

18. A method of treating gastric cancer using immunotherapy in an individual in need thereof, comprising administering to the individual the composition of claim 2.

19. The method of claim 18, further comprising administering at least one checkpoint inhibitor, wherein the checkpoint inhibitor is administered prior to, concomitant with, or after administration of the composition.

20. A method of treating gastric cancer using immunotherapy in an individual in need thereof, comprising administering to the individual the composition of claim 3.

21. The method of claim 20, further comprising administering at least one checkpoint inhibitor, wherein the checkpoint inhibitor is administered prior to, concomitant with, or after administration of the composition.

22. A method of treating gastric cancer using immunotherapy in an individual in need thereof, comprising administering to the individual the composition of claim 4.

23. The method of claim 22, further comprising administering at least one checkpoint inhibitor, wherein the checkpoint inhibitor is administered prior to, concomitant with, or after administration of the composition.

* * * * *